(12) United States Patent
Heffron et al.

(10) Patent No.: US 9,090,628 B2
(45) Date of Patent: *Jul. 28, 2015

(54) BENZOXAZEPIN COMPOUNDS SELECTIVE FOR PI3K P110 DELTA AND METHODS OF USE

(75) Inventors: Timothy Heffron, Burlingame, CA (US); Brian Safina, San Francisco, CA (US); Steven Staben, San Francisco, CA (US); Daniel P. Sutherlin, Burlingame, CA (US); BinQing Wei, Belmont, CA (US); Richard Elliott, Harlow (GB); Robert Heald, Harlow (GB); Eileen M. Seward, Harlow (GB); Emanuela Gancia, Harlow (GB); Bohdan Waszkowycz, Harlow (GB)

(73) Assignee: GENENTECH, INC., South San Francisco, CA (US)

( * ) Notice: Subject to any disclaimer, the term of this patent is extended or adjusted under 35 U.S.C. 154(b) by 231 days.

This patent is subject to a terminal disclaimer.

(21) Appl. No.: 13/424,500

(22) Filed: Mar. 20, 2012

(65) Prior Publication Data

US 2012/0245144 A1 Sep. 27, 2012

Related U.S. Application Data

(60) Provisional application No. 61/454,672, filed on Mar. 21, 2011.

(51) Int. Cl.
*A61K 31/553* (2006.01)
*C07D 498/04* (2006.01)
*C07D 498/14* (2006.01)
*C07D 519/00* (2006.01)

(52) U.S. Cl.
CPC ............ *C07D 498/14* (2013.01); *C07D 498/04* (2013.01); *C07D 519/00* (2013.01)

(58) Field of Classification Search
CPC ........................... A61K 31/553; C07D 498/04
USPC ........................... 514/211.1, 211.12; 540/548
See application file for complete search history.

(56) References Cited

U.S. PATENT DOCUMENTS

| | | | |
|---|---|---|---|
| 4,797,414 A | 1/1989 | Rimbault | |
| 5,314,889 A | 5/1994 | Boigegrain et al. | |
| 5,612,356 A | 3/1997 | Yoshimura et al. | |
| 5,985,799 A | 11/1999 | Tseng | |
| 6,187,801 B1 | 2/2001 | Jaehne et al. | |
| 6,251,922 B1 | 6/2001 | Jaehne et al. | |
| 6,329,407 B1 | 12/2001 | Jaehne et al. | |
| 6,476,059 B1 | 11/2002 | Jaehne et al. | |
| 7,273,880 B2 | 9/2007 | Marzabadi et al. | |
| 7,928,248 B2 | 4/2011 | Do et al. | |
| 8,242,104 B2 | 8/2012 | Blaquiere et al. | |
| 8,263,633 B2 | 9/2012 | Blaquiere et al. | |
| 8,343,955 B2 * | 1/2013 | Blaquiere et al. | 514/211.1 |
| 8,586,574 B2 * | 11/2013 | Blaquiere et al. | 514/211.1 |
| 2004/0082602 A1 | 4/2004 | Hagen et al. | |
| 2004/0198791 A1 | 10/2004 | Sato et al. | |
| 2005/0239767 A1 | 10/2005 | Chan et al. | |
| 2006/0100254 A1 | 5/2006 | Betzemeier et al. | |
| 2006/0106013 A1 | 5/2006 | Breitfelder et al. | |
| 2008/0132513 A1 | 6/2008 | Che et al. | |

FOREIGN PATENT DOCUMENTS

| | | |
|---|---|---|
| WO | 01/64675 A1 | 9/2001 |
| WO | 2008/019139 A2 | 2/2008 |
| WO | 2009/123971 A1 | 10/2009 |
| WO | 2011/036280 A1 | 3/2011 |
| WO | 2011/036284 A1 | 3/2011 |

OTHER PUBLICATIONS

Banaszak et al. et al., "New and efficient RCM in pyridinic series: synthesis of 2H-dihydropyrano- or 2,3H-dihydrooxepino[3,2-b]pyridines" Tetrahedron Lett 47(35):6235-6238 ( 2006).

Heffron et al., "Identification of GNE-477, a potent and efficacious dual PI3K/mTOR inhibitor" Bioorg Med Chem Lett.:2408-11 ( 2010).

Heffron et al., "Rational design of phosphoinositide 3-kinase α inhibitors that exhibit selectivity over the phosphoinositide 3-kinase β isoform" J Med Chem. 54:7815-33 ( 2011).

Heffron et al., "The design and identification of brain penetrant inhibitors of phosphoinositide 3-kinase α" J Med Chem. 55:8007-20 ( 2012).

(Continued)

*Primary Examiner* — Brenda Coleman
(74) *Attorney, Agent, or Firm* — Alex Andrus; Genentech, Inc.

(57) ABSTRACT

Benzoxazepin Formula I compounds, including stereoisomers, geometric isomers, tautomers, metabolites and pharmaceutically acceptable salts thereof, are useful for inhibiting the delta isoform of PI3K, and for treating disorders mediated by lipid kinases such as inflammation, immunological disorders, and cancer. Methods of using compounds of Formula I for in vitro, in situ, and in vivo diagnosis, prevention or treatment of such disorders in mammalian cells, or associated pathological conditions, are disclosed.

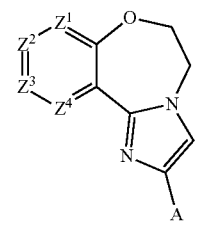

6 Claims, 8 Drawing Sheets

(56) References Cited

OTHER PUBLICATIONS

Heindel et al., "Salicylidene-thiolactone rearrangement. A direct synthesis of 4H-2-arylthieno[3,2-c][1]Benzopyran-4-ones" J Org Chem 42(8):1465-1466 (1977).

Katsura et al., "Anti-*Helicobacter pylori* Agents. 4. 2-(substituted guanidine)-4-phenylthiazoles and some structurally rigid derivatives" J Med Chem 43(17):3315-3321 (2000).

Majumdar et al., "Regioselective synthesis of thieno[3,2-c][1]benzopyran-4-ones by thio-Claisen rearrangement" Monatsh Chem 135(8):1001-1007 (2004).

Meier et al., "Intramolekulare 1,3-Dipolar Cycloadditions of Diaryl-nitrile-imines Generated from 2,5-Diaryl-tetrazoles" Helvetica Chimica Acta 68:1283-1300 (1985).

Navarro et al., "Synthesis of 1H-[1]Benzopyrano[4,3-b]pyrrole and 4H-thieeno[3,2-c]Benzopyran derivatives, functionalisation by aromatic electrophilic substitution" Heterocycles 55(12):2369-2386 (2001).

PCT ISR and Written Opinion of the ISA for PCT/EP2012/054849, Jun. 6, 2012.

Potts et al., "Carbon—carbon bond formation via intramolecular cycloadditions: Use of the thiocarbonyl ylide dipole in anhydro-4-hydroxythiazolium hydroxides" J Org Chem 54:1077-1088 (1989).

Potts et al., "Intramolecular 1,3-dipolar cycloadditions with thiocarbonyl ylides" J Chem Soc Chem Commun 7:561-3 (1986).

Reiter et al., "Pyrimidine benzamide-based thrombopoietin receptor agonists" Bioorganic & Medicinal Chemistry Letters 17(19):5447-5454 (2007).

Rueeger et al., "Discovery and SAR of potent, orally available and brain-penetrable 5,6-dihydro-4H-3-thio-1-aza-benzo[e]azulen derivatives as neuropeptide Y Y5 receptor antagonists" Bioorganic Medicinal Chem Letters 14(10):2451-2457 (2004).

Salphati et al., "Targeting the PI3K Pathway in the Brain—Efficacy of a PI3K Inhibitor Optimized to Cross the Blood-Brain Barrier" Clin Cancer Res. 18:6239-48 (2012).

Sekhar et al., "A simple and convenient method for the synthesis of condensed thiophene derivatives starting from heterocyclic chloro aldehydes. Part II" Sulfur Letters 9(6):271-277 (1989).

Staben et al., "Structure-based design of thienobenzoxepin inhibitors of PI3-kinase" Bioorg Med Chem Lett. 21:4054-8 (2011).

Trieu et al., "Condensation of (beta-chlorovinyl)carbonyl compounds with alpha-mercaptocarboxylic acids (translated from German)" Zeitschrift Fuer Chemie (translated from German), 13(2):57-8 (1973).

Wang et al., "A Facial Synthesis of the Neutral [1,2,4]Triazolo[3,2-d][1,5]Benzoxazepines and Their Chalcogen-Analogues" Synthetic Communications 32(9):1327-1335 (2002).

* cited by examiner

BENZOXAZEPIN COMPOUNDS SELECTIVE FOR PI3K P110 DELTA AND METHODS OF USE

CROSS REFERENCE TO RELATED APPLICATIONS

This non-provisional application filed under 37 CFR §1.53 (b), claims the benefit under 35 USC §119(e) of U.S. Provisional Application Ser. No. 61/454,672 filed on 21 Mar. 2011, which is incorporated by reference in entirety.

FIELD OF THE INVENTION

The invention relates generally to compounds for treating disorders mediated by lipid kinases such as inflammation, immunological, and cancer, and more specifically to compounds which inhibit PI3 kinase activity. The invention also relates to methods of using the compounds for in vitro, in situ, and in vivo diagnosis or treatment of mammalian cells, or associated pathological conditions.

BACKGROUND OF THE INVENTION

Phosphatidylinositol (PI), a phospholipid found in cell membranes, plays an important role in intracellular signal transduction. Cell signaling via 3'-phosphorylated phosphoinositides has been implicated in a variety of cellular processes, e.g., malignant transformation, growth factor signaling, inflammation, and immunity (Rameh et al (1999) J. Biol Chem, 274:8347-8350). The enzyme responsible for generating these phosphorylated signaling products, phosphatidylinositol 3-kinase (also referred to as PI 3-kinase or PI3K), was originally identified as an activity associated with viral oncoproteins and growth factor receptor tyrosine kinases that phosphorylate phosphatidylinositol (PI) and its phosphorylated derivatives at the 3'-hydroxyl of the inositol ring (Panayotou et al (1992) Trends Cell Biol 2:358-60).

Phosphoinositide 3-kinases (PI3K) are lipid kinases that phosphorylate lipids at the 3-hydroxyl residue of the inositol ring of phosphoinositols (Whitman et al (1988) Nature, 332:664). The 3'-phosphorylated phospholipids (PIP3s) generated by PI3-kinases act as second messengers recruiting kinases with lipid binding domains (including plekstrin homology (PH) regions), such as Akt and phosphoinositide-dependent kinase-1 (PDK1). Binding of Akt to membrane PIP3s causes the translocation of Akt to the plasma membrane, bringing Akt into contact with PDK1, which is responsible for activating Akt. The tumor-suppressor phosphatase, PTEN, dephosphorylates PIP3 and therefore acts as a negative regulator of Akt activation. The PI3-kinases Akt and PDK1 are important in the regulation of many cellular processes including cell cycle regulation, proliferation, survival, apoptosis and motility and are significant components of the molecular mechanisms of diseases such as cancer, diabetes and immune inflammation (Vivanco et al (2002) Nature Rev. Cancer 2:489; Phillips et al (1998) Cancer 83:41).

PI3 kinase is a heterodimer consisting of p85 and p110 subunits (Otsu et al (1991) Cell 65:91-104; Hiles et al (1992) Cell 70:419-29). Four distinct Class I PI3Ks have been identified, designated PI3K α (alpha), β (beta), δ (delta), and γ (gamma), each consisting of a distinct 110 kDa catalytic subunit and a regulatory subunit. More specifically, three of the catalytic subunits, i.e., p110 alpha, p110 beta and p110 delta, each interact with the same regulatory subunit, p85; whereas p110 gamma interacts with a distinct regulatory subunit, p101. The patterns of expression of each of these PI3Ks in human cells and tissues are also distinct.

The p110 delta isoform has been implicated in biological functions related to immune-inflammatory diseases, including signaling from the B-cell receptor, T cell receptor, FcR signaling of mast cells and monocyte/macrophage, and osteoclast function/RANKL signaling (Berndt et al (2010) Nature Chemical Biology; Williams et al (2010) Chem. & Biol. 17:123-134; Chantry et al (1997) Jour. of Biol. Chem. 272 (31):19236-19241; Deane J and Fruman D A (2004) Annu Rev. Immunol. 2004. 22:563-98; Janas et al. (2008) The Journal of Immunology, 180:739-746; Marone R et al. (2007) Biochim. Biophy. Acta, 1784:159-185. Deletion of the PI3K delta gene or selective introduction of a catalytically inactive mutant of PI3K delta causes a nearly complete ablation of B cell proliferation and signaling, and impairment of signaling through T cells as well.

SUMMARY OF THE INVENTION

The invention relates to benzoxazepine compounds of Formula I with PI3 kinase inhibitory activity and selective binding to the p110 delta isoform relative to binding to the p110 alpha isoform.

Formula I compounds have the structures:

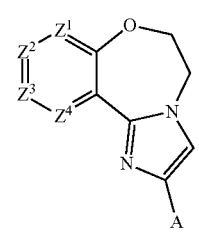

I and stereoisomers, geometric isomers, tautomers, and pharmaceutically acceptable salts thereof. The various substituents are as defined herein.

The IC50 binding activity of Formula I compounds to p110 delta is ten or more times lower than the binding activity to p110 alpha.

Another aspect of the invention provides a pharmaceutical composition comprising a Formula I compound and a pharmaceutically acceptable carrier, glidant, diluent, or excipient.

Another aspect of the invention provides the use of a Formula I compound in the manufacture of a medicament for treating a disease or disorder selected from cancer, immune disorders, cardiovascular disease, viral infection, inflammation, metabolism/endocrine function disorders and neurological disorders, and mediated by PI3 kinase including by selective inhibition of the p110 delta isoform.

The invention also relates to methods of using the Formula I compounds for in vitro, in situ, and in vivo diagnosis or treatment of mammalian cells, organisms, or associated pathological conditions, such as cancer, systemic and local inflammation, immune-inflammatory diseases such as rheumatoid arthritis, immune suppression, organ transplant rejection, allergies, ulcerative colitis, Crohn's disease, dermatitis, asthma, systemic lupus erythematosus, Sjögren's Syndrome, multiple sclerosis, scleroderma/systemic sclerosis, idiopathic thrombocytopenic purpura (ITP), anti-neutrophil cytoplasmic antibodies (ANCA) vasculitis, chronic obstructive pulmonary disease (COPD), psoriasis, and for general joint protective effects.

Another aspect of the invention provides a method of treating a disease or disorder which method comprises administering a Formula I compound to a patient with a disease or disorder selected from cancer, immune disorders, cardiovascular disease, viral infection, inflammation, metabolism/endocrine function disorders and neurological disorders, and mediated by the p110 delta, beta, or alpha isoform of PI3 kinase. The method may further comprise administering an additional therapeutic agent selected from a chemotherapeutic agent, an anti-inflammatory agent, an immunomodulatory agent, a neurotropic factor, an agent for treating cardiovascular disease, an agent for treating liver disease, an anti-viral agent, an agent for treating blood disorders, an agent for treating diabetes, and an agent for treating immunodeficiency disorders.

The methods of treating cancer include where the cancer is breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, pancreatic, myeloid disorders, lymphoma, hairy cells, buccal cavity, naso-pharyngeal, pharynx, lip, tongue, mouth, small intestine, colon-rectum, large intestine, rectum, brain and central nervous system, Hodgkin's, leukemia, bronchus, thyroid, liver and intrahepatic bile duct, hepatocellular, gastric, glioma/glioblastoma, endometrial, melanoma, kidney and renal pelvis, urinary bladder, uterine corpus, uterine cervix, multiple myeloma, acute myelogenous leukemia, chronic lymphoid leukemia, chronic myelogenous leukemia, lymphocytic leukemia, myeloid leukemia, oral cavity and pharynx, non-Hodgkin lymphoma, melanoma, or villous colon adenoma.

Another aspect of the invention provides a kit for treating a condition mediated by the p110 delta isoform of PI3 kinase, comprising a first pharmaceutical composition comprising a Formula I compound; and instructions for use.

Other aspects of the invention include: (i) method for preventing or treating conditions, disorders or diseases mediated by the activation of the PI3K kinase enzyme, in a subject in need of such treatment, which method comprises administering to said subject an effective amount of a compound of Formula I or a pharmaceutically acceptable salt thereof, in free form or in a pharmaceutically acceptable salt form as a pharmaceutical, in any of the methods as indicated herein; (ii) a compound of the Formula I in free form or in pharmaceutically acceptable salt form for use as a pharmaceutical in any of the methods described herein, in particular for the use in one or more phosphatidylinositol 3-kinase (PI3K) mediated diseases; (iii) the use of a compound of Formula I in free form or in pharmaceutically acceptable salt form in any of the methods as indicated herein, in particular for the treatment of one or more phosphatidylinositol 3-kinase mediated diseases; (iv) the use of a compound of Formula I in free form or in pharmaceutically acceptable salt form in any of the methods as indicated herein, in particular for the manufacture of a medicament for the treatment of one or more phosphatidylinositol 3-kinase mediated diseases.

DETAILED DESCRIPTION OF EXEMPLARY EMBODIMENTS

Figure 1:
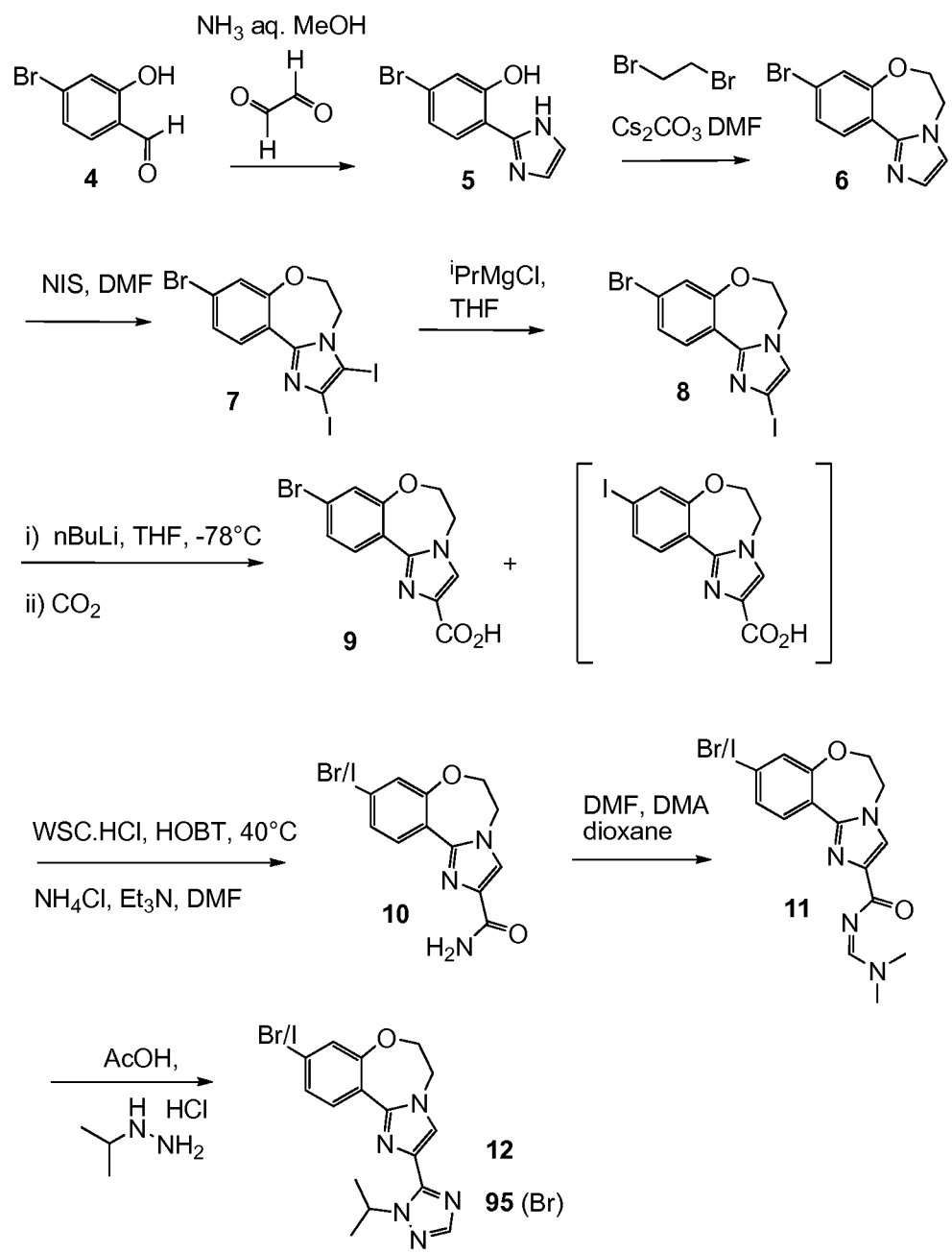
FIG. 1 shows a synthetic route to 9-halo-2-(1-isopropyl-1H-1,2,4-triazol-5-yl)-5,6-dihydrobenzo[f]imidazo[1,2-d][1,4]oxazepine compounds 12 from 4-bromo-2-hydroxybenzaldehyde 4.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

DEFINITIONS

The term "alkyl" as used herein refers to a saturated linear or branched-chain monovalent hydrocarbon radical of one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), 1-heptyl, 1-octyl, and the like.

The term "alkylene" as used herein refers to a saturated linear or branched-chain divalent hydrocarbon radical of one to twelve carbon atoms (C$_1$-C$_{12}$), wherein the alkylene radical may be optionally substituted independently with one or more substituents described below. In another embodiment, an alkylene radical is one to eight carbon atoms (C$_1$-C$_8$), or one to six carbon atoms (C$_1$-C$_6$). Examples of alkylene groups include, but are not limited to, methylene (—CH$_2$—), ethylene (—CH$_2$CH$_2$—), propylene (—CH$_2$CH$_2$CH$_2$—), and the like.

The term "alkenyl" refers to linear or branched-chain monovalent hydrocarbon radical of two to eight carbon atoms (C$_2$-C$_8$) with at least one site of unsaturation, i.e., a carbon-carbon, sp$^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH═CH$_2$), allyl (—CH$_2$CH═CH$_2$), and the like.

The term "alkenylene" refers to linear or branched-chain divalent hydrocarbon radical of two to eight carbon atoms (C$_2$-C$_8$) with at least one site of unsaturation, i.e., a carbon-carbon, sp$^2$ double bond, wherein the alkenyl radical may be optionally substituted, and includes radicals having "cis" and "trans" orientations, or alternatively, "E" and "Z" orientations. Examples include, but are not limited to, ethylenylene or vinylene (—CH═CH—), allyl (—CH$_2$CH═CH—), and the like.

The term "alkynyl" refers to a linear or branched monovalent hydrocarbon radical of two to eight carbon atoms (C$_2$-C$_8$) with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —CH$_2$C≡CH), and the like.

The term "alkynylene" refers to a linear or branched divalent hydrocarbon radical of two to eight carbon atoms (C$_2$-C$_8$) with at least one site of unsaturation, i.e., a carbon-carbon, sp triple bond, wherein the alkynyl radical may be optionally. Examples include, but are not limited to, ethynylene (—C≡C—), propynylene (propargylene, —CH$_2$C≡C—), and the like.

The terms "carbocycle", "carbocyclyl", "carbocyclic ring" and "cycloalkyl" refer to a monovalent non-aromatic, saturated or partially unsaturated ring having 3 to 12 carbon atoms (C$_3$-C$_{12}$) as a monocyclic ring or 7 to 12 carbon atoms as a bicyclic ring. Bicyclic carbocycles having 7 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Spiro carbocycles including one or more quaternary carbon atoms are also included within the scope of this definition. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, adamantanyl, and the like.

"Aryl" means a monovalent aromatic hydrocarbon radical of 6-20 carbon atoms (C$_6$-C$_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

"Arylene" means a divalent aromatic hydrocarbon radical of 6-20 carbon atoms (C$_6$-C$_{20}$) derived by the removal of two hydrogen atom from a two carbon atoms of a parent aromatic ring system. Some arylene groups are represented in the exemplary structures as "Ar". Arylene includes bicyclic radicals comprising an aromatic ring fused to a saturated, partially unsaturated ring, or aromatic carbocyclic ring. Typical arylene groups include, but are not limited to, radicals derived from benzene (phenylene), substituted benzenes, naphthalene, anthracene, biphenylene, indenylene, indanylene, 1,2-dihydronaphthalene, 1,2,3,4-tetrahydronaphthyl, and the like. Arylene groups are optionally substituted.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo[4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, piperidonyl, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, dihydroisoquinolinyl, tetrahydroisoquinolinyl, pyrazolidinylimidazolinyl, imidazolidinyl, 2-oxa-5-azabicyclo[2.2.2]octane, 3-oxa-8-azabicyclo[3.2.1]octane, 8-oxa-3-azabicyclo[3.2.1]octane, 6-oxa-3-azabicyclo[3.1.1]heptane, 2-oxa-5-azabicyclo[2.2.1]heptane, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. Spiro heterocyclyl radicals include 1,7-diazaspiro[4.5]decan-1-yl. Examples of a heterocyclic group wherein 2 ring carbon atoms are substituted with oxo (=O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Ring nitrogen atoms of the heterocycle or heteroaryl groups may be bonded with oxygen to form N-oxides.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, benzimidazole, position 2 of a isoindole, or isoindoline, position 4 of a morpholine, and position 9 of a carbazole, or β-carboline.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

"Inflammatory disorder" as used herein can refer to any disease, disorder, or syndrome in which an excessive or unregulated inflammatory response leads to excessive inflammatory symptoms, host tissue damage, or loss of tissue function. "Inflammatory disorder" also refers to a pathological state mediated by influx of leukocytes and/or neutrophil chemotaxis.

"Inflammation" as used herein refers to a localized, protective response elicited by injury or destruction of tissues, which serves to destroy, dilute, or wall off (sequester) both the injurious agent and the injured tissue. Inflammation is notably associated with influx of leukocytes and/or neutrophil chemotaxis. Inflammation can result from infection with pathogenic organisms and viruses and from noninfectious means such as trauma or reperfusion following myocardial infarction or stroke, immune response to foreign antigen, and autoimmune responses. Accordingly, inflammatory disorders amenable to treatment with Formula I compounds encompass disorders associated with reactions of the specific defense system as well as with reactions of the nonspecific defense system.

"Specific defense system" refers to the component of the immune system that reacts to the presence of specific antigens. Examples of inflammation resulting from a response of the specific defense system include the classical response to foreign antigens, autoimmune diseases, and delayed type hypersensitivity response mediated by T-cells. Chronic inflammatory diseases, the rejection of solid transplanted tissue and organs, e.g., kidney and bone marrow transplants, and graft versus host disease (GVHD), are further examples of inflammatory reactions of the specific defense system.

The term "nonspecific defense system" as used herein refers to inflammatory disorders that are mediated by leukocytes that are incapable of immunological memory (e.g., granulocytes, and macrophages). Examples of inflammation that result, at least in part, from a reaction of the nonspecific defense system include inflammation associated with conditions such as adult (acute) respiratory distress syndrome (ARDS) or multiple organ injury syndromes; reperfusion injury; acute glomerulonephritis; reactive arthritis; dermatoses with acute inflammatory components; acute purulent meningitis or other central nervous system inflammatory disorders such as stroke; thermal injury; inflammatory bowel disease; granulocyte transfusion associated syndromes; and cytokine-induced toxicity.

"Autoimmune disease" as used herein refers to any group of disorders in which tissue injury is associated with humoral or cell-mediated responses to the body's own constituents.

"Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies. "Transplant rejection" as used herein refers to any immune reaction directed against grafted tissue, such as organs or cells (e.g., bone marrow), characterized by a loss of function of the grafted and surrounding tissues, pain, swelling, leukocytosis, and thrombocytopenia. The therapeutic methods of the present invention include methods for the treatment of disorders associated with inflammatory cell activation.

"Inflammatory cell activation" refers to the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatability antigens or cell adhesion molecules) in inflammatory cells (including but not limited to monocytes, macrophages, T lymphocytes, B lymphocytes, granulocytes (i.e., polymorphonuclear leukocytes such as neutrophils, basophils, and eosinophils), mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory disorder.

The term "NSAID" is an acronym for "non-steroidal anti-inflammatory drug" and is a therapeutic agent with analgesic, antipyretic (lowering an elevated body temperature and relieving pain without impairing consciousness) and, in higher doses, with anti-inflammatory effects (reducing inflammation). The term "non-steroidal" is used to distinguish these drugs from steroids, which (among a broad range of other effects) have a similar eicosanoid-depressing, anti-inflammatory action. As analgesics, NSAIDs are unusual in that they are non-narcotic. NSAIDs include aspirin, ibuprofen, and naproxen. NSAIDs are usually indicated for the treatment of acute or chronic conditions where pain and inflammation are present. NSAIDs are generally indicated for the symptomatic relief of the following conditions: rheumatoid arthritis, osteoarthritis, inflammatory arthropathies (e.g. ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic. Most NSAIDs act as non-selective inhibitors of the enzyme cyclooxygenase, inhibiting both the cyclooxygenase-1 (COX-1) and cyclooxygenase-2 (COX-2) isoenzymes. Cyclooxygenase catalyzes the formation of prostaglandins and thromboxane from arachidonic acid (itself derived from the cellular phospholipid bilayer by phospholipase $A_2$). Prostaglandins act (among other things) as messenger molecules in the process of inflammation. COX-2 inhibitors include celecoxib, etoricoxib, lumiracoxib, parecoxib, rofecoxib, rofecoxib, and valdecoxib.

The terms "cancer" refers to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, head and neck cancer, multiple myeloma, acute myelogenous leukemia, chronic lymphoid leukemia, chronic myelogenous leukemia, lymphocytic leukemia, myeloid leukemia, oral cavity and pharynx, non-Hodgkin lymphoma, melanoma, and villous colon adenoma A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIBO, SU11248, Pfizer), letrozole (FEMARA®, Novartis), imatinib mesylate (GLEEVECO, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNEO, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, II), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gamma1I, calicheamicin omega1I (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the PI3K inhibitors of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

The term "hematopoietic malignancy" refers to a cancer or hyperproliferative disorder generated during hematopoiesis involving cells such as leukocytes, lymphocytes, natural killer cells, plasma cells, and myeloid cells such as neutrophils and monocytes. Hematopoietic Malignancies include the diseases listed in the WHO classification of Human Hematopoietic Malignancies; Tumors of Hematopoietic and Lymphoid Tissues (Jaffe E. S., Harris N. L., Stein H., Vardiman J. W. (Eds.) (2001): World Health Organization Classification of Tumours. Pathology and Genetics of Tumours of Hematopoietic and Lymphoid Tissues. IARC Press: Lyon) with the morphology code of the International Classification of Diseases (ICD-O). Behavior is coded /3 for malignant tumors and /1 for lesions of low or uncertain malignant potential.

Hematopoietic malignancies include:

I. Chronic Myeloproliferative Diseases
Chronic myelogenous leukemia—ICD-O 9875/3
Chronic neutrophilic leukemia—ICD-O 9963/3
Chronic eosinophilic leukemia/hypereosinophilic syndrome—ICD-O 9964/3
Polycythemia vera—ICD-O 9950/3
Chronic idiopathic myelofibrosis—ICD-O 9961/3
Essential thrombocytemia—ICD-O 9962/3
Chronic Myeloproliferative disease, unclassifiable—ICD-O 9975/3

II. Myelodysplastic/Myeloproliferative Diseases
Chronic myelomonocytic leukemia—ICD-O 9980/3
Atypical chronic myelogenous leukemia—ICD-O 9876/3
Juvenile myelomonocytic leukemia—ICD-O 9946/3
Myelodysplastic/myeloproliferative diseases, unclassifiable—ICD-O 9975/3

III. Myelodysplastic Syndromes
Refractory anemia—ICD-O 9980/3
Refractory anemia with ringed sideroblasts—ICD-O 9982/3
Refractory cytopenia with multilineage dysplasia—ICD-O 9985/3
Refractory anemia with excess blasts—ICD-O 9983/3
Myelodysplastic syndrome associated with isolated del (5q) chromosome abnormality—ICD-O 9986/3
Myelodysplastic syndrome, unclassifiable 9989/3

IV. Acute Myeloid Leukemias
Acute myeloid leukemias with recurrent cytogenetic abnormalities
AML with t(8;21)(q22;q22), AML1/ETO—ICD-O 9896/3
AML with inv(16)(p13q22) or t(16;16)(p13;q22), CBFb/MYH11—ICD-O 9871/3
Acute promyelocytic leukemia (AML with t(15;17)(q22;q12), PML-RARa and variants)—ICD-O 9866/3
AML with 11q23 (MLL) abnormalities—ICD-O 9897/3
Acute myeloid leukemia multilineage dysplasia—ICD-O 9895/3
Acute myeloid leukemia and myelodysplastic syndrome, therapy related—ICD-O 9920/3
Acute myeloid leukemia not otherwise categorised
Acute myeloid leukemia, minimally differentiated—ICD-O 9872/3
Acute myeloid leukemia, without maturation—ICD-O 9873/3
Acute myeloid leukemia, with maturation—ICD-O 9874/3
Acute myelomonocytic leukemia—ICD-O 9867/3
Acute monoblastic and monocytic leukemia—ICD-O 9891/3
Acute erythroid leukemia—ICD-O 9840/3
Acute megakaryoblastic leukemia—ICD-O 9910/3
Acute basophilic leukemia—ICD-O 9870/3
Acute panmyelosis with myelofibrosis—ICD-O 9931/3
Myeloid sarcoma—ICD-O 9930/3
Acute leukemia of ambiguous lineage—ICD-O 9805/3

V. B-Cell Neoplasms
Precursor hematopoietic neoplasm
Precursor B lymphoblastic leukemia/—ICD-O 9835/3
lymphoma—ICD-O 9728/3
Mature hematopoietic neoplasm
Chronic lymphocytic leukemia/—ICD-O 9823/3
small lymphocytic lymphoma—ICD-O 9670/3
hematopoietic prolymphocytic leukemia—ICD-O 9833/3
Lymphoplasmacytic lymphoma—ICD-O 9671/3
Splenic marginal zone lymphoma—ICD-O 9689/3
Hairy cell leukemia—ICD-O 9940/3
Plasma cell myeloma—ICD-O 9732/3
Solitary plasmacytoma of bone—ICD-O 9731/3
Extraosseous plasmacytoma—ICD-O 9734/3
Extranodal marginal zone hematopoietic lymphoma of mucosa-associated lymphoid tissue (MALT-lymphoma)—ICD-O 9699/3
Nodal marginal zone hematopoietic lymphoma—ICD-O 9699/3
Follicular lymphoma—ICD-O 9690/3
Mantle cell lymphoma—ICD-O 9673/3
Diffuse large hematopoietic lymphoma—ICD-O 9680/3
Mediastinal (thymic) large cell lymphoma—ICD-O 9679/3
Intravascular large hematopoietic lymphoma—ICD-O 9680/3
Primary effusion lymphoma—ICD-O 9678/3
Burkitt lymphoma/—ICD-O 9687/3
leukemia—ICD-O 9826/3
hematopoietic proliferations of uncertain malignant potential
Lymphomatoid granulomatosis—ICD-O 9766/1
Post-transplant lymphoproliferative disorder, pleomorphic—ICD-O 9970/1

VI. T-Cell and NK-Cell Neoplasms
Precursor T-cell neoplasms
Precursor T lymphoblastic leukemia/—ICD-O 9837/3
lymphoma—ICD-O 9729/3
Blastic NK cell lymphoma—ICD-O 9727/3
Mature T-cell and NK-cell neoplasms
T-cell prolymphocytic leukemia—ICD-O 9834/3
T-cell large granular lymphocytic leukemia—ICD-O 9831/3
Aggressive NK cell leukemia—ICD-O 9948/3
Adult T-cell leukemia/lymphoma—ICD-O 9827/3
Extranodal NK/T cell lymphoma, nasal type—ICD-O 9719/3
Enteropathy type T-cell lymphoma—ICD-O 9717/3
Hepatosplenic T-cell lymphoma—ICD-O 9716/3
Subcutaneous panniculitis-like T-cell lymphoma—ICD-O 9708/3
Mycosis fungoides—ICD-O 9700/3
Sezary Syndrome—ICD-O 9701/3
Primary cutaneous anaplastic large cell lymphoma—ICD-O 9718/3
Peripheral T-cell lymphoma, unspecified—ICD-O 9702/3
Angioimmunoblastic T-cell lymphoma—ICD-O 9705/3
Anaplastic large cell lymphoma—ICD-O 9714/3
T-cell proliferation of uncertain malignant potential
Lymphomatoid papulosis—ICD-O 9718/1

VII. Hodgkin Lymphoma
Nodular lymphocyte predominant Hodgkin lymphoma—ICD-O 9659/3
Classical Hodgkin lymphoma—ICD-O 9650/3
Nodular sclerosis classical Hodgkin lymphoma—ICD-O 9663/3

Lymphocyte-rich classical Hodgkin lymphoma—ICD-O 9651/3
Mixed cellularity classical Hodgkin lymphoma—ICD-O 9652/3
Lymphocyte-depleted classical Hodgkin lymphoma—ICD-O 9653/3
VIII. Histiocytic and Dendritic-Cell Neoplasms
Macrophage/histiocytic neoplasm
Histiocytic sarcoma—ICD-O 9755/3
Dendritic cell neoplasms
Langerhans cell histiocytosis—ICD-O 9751/1
Langerhans cell sarcoma—ICD-O 9756/3
Interdigitating dendritic cell sarcoma/tumor—ICD-O 9757/3/1
Follicular dendritic cell sarcoma/tumor—ICD-O 9758/3/1
Dendritic cell sarcoma, not otherwise specified—ICD-O 9757/3
IX. Mastocytosis
Cutaneous mastocytosis
Indolent systemic mastocytosis—ICD-O 9741/1
Systemic mastocytosis with associated clonal, hematological non-mast cell lineage disease—ICD-O 9741/3
Aggressive systemic mastocytosis—ICD-O 9741/3
Mast cell leukemia—ICD-O 9742/3
Mast cell sarcoma—ICD-O 9740/3
Extracutaneous mastocytoma—ICD-O 9740/1

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space. Stereoisomers include enantiomers and diastereomers.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography. Diastereomers include geometric isomers, cis/trans and E/Z isomers, and atropisomers.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt" as used herein, refers to pharmaceutically acceptable organic or inorganic salts of a compound of the invention. Exemplary salts include, but are not limited to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethylacetate, acetic acid, and ethanolamine.

The terms "compound of this invention," and "compounds of the present invention" and "compounds of Formula I" include compounds of Formulas I and stereoisomers, tautomers, solvates, metabolites, and pharmaceutically acceptable salts and prodrugs thereof.

Any formula or structure given herein, including Formula I compounds, is also intended to represent hydrates, solvates, and polymorphs of such compounds, and mixtures thereof.

Any formula or structure given herein, including Formula I compounds, is also intended to represent isotopically labeled forms of the compounds as well as unlabeled forms. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as, but not limited to 2H (deuterium, D), 3H (tritium), 11C, 13C, 14C, 15N, 18F, 31P, 32P, 35S, 36Cl, and 125I. Various isotopically labeled compounds of the present invention, for example those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the formula (I). The concentration of such a heavier isotope, specifically deuterium, may be defined by an isotopic enrichment factor. In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition.

Benzoxazepin Compounds of the Invention

Formula I compounds include compounds having the formula:

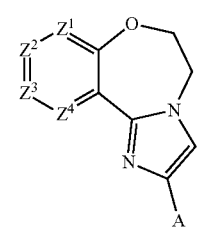

and stereoisomers, geometric isomers, tautomers, and pharmaceutically acceptable salts thereof, wherein:

$Z^1$ is $CR^1$ or N;
$Z^2$ is $CR^2$ or N;
$Z^3$ is $CR^3$ or N;
$Z^4$ is $CR^4$ or N;
where none, one, or two of $Z^1$, $Z^2$, $Z^3$ and $Z^4$ are N;
$R^1$ and $R^4$ are independently selected from H, F, Cl, and $C_1$-$C_{12}$ alkyl;
$R^2$ and $R^3$ are independently selected from H, F, Cl, Br, I, —CN, —$COR^{10}$, —$CO_2R^{10}$, —$C(=O)N(R^{10})OR^{11}$, —$C(=NR^{10})NR^{10}R^{11}$, —$C(=O)NR^{10}R^{11}$, $NO_2$, —$NR^{10}R^{11}$, —$NR^{12}C(O)R^{10}$, —$NR^{12}C(=O)OR^{11}$, —$NR^{12}C(=O)NR^{10}R^{11}$, —$NR^{12}C(=O)(C_1$-$C_{12}$ alkylene)$NR^{10}R^{11}$, —$NR^{12}(C_1$-$C_{12}$ alkylene)$NR^{10}R^{11}$, —$NR^{12}(C_1$-$C_{12}$ alkylene)$OR^{10}$, —$NR^{12}(C_1$-$C_{12}$ alkylene)$C(=O)NR^{10}R^{11}$, —$OR^{10}$, —SR , —$S(O)R^{10}$, —$S(O)_2R^{10}$, —$S(O)_2NR^{10}R^{11}$,
—S(O)—($C_2$-$C_{20}$ heterocyclyl),
—$S(O)_2$—($C_2$-$C_{20}$ heterocyclyl),
—$S(O)_2$—($C_2$-$C_{20}$ heterocyclyl)-($C_1$-$C_{12}$ alkyl)-($C_2$-$C_{20}$ heterocyclyl),
—O—($C_1$-$C_{12}$ alkylene)-($C_2$-$C_{20}$ heterocyclyl),
—O—($C_1$-$C_{12}$ alkylene)-($C_1$-$C_{20}$ heteroaryl),
—O—($C_1$-$C_{12}$ alkylene)-($C_6$-$C_{20}$ aryl),
—O—($C_1$-$C_{12}$ alkylene)-C(=O)—($C_2$-$C_{20}$ heterocyclyl),
—O—($C_2$-$C_{20}$ heterocyclyl),
—O—($C_2$-$C_{20}$ heterocyclyl)-($C_1$-$C_{12}$ alkylene)-($C_2$-$C_{20}$ heterocyclyl),
—C(=O)—($C_2$-$C_{20}$ heterocyclyl),
—C(=O)—($C_2$-$C_{20}$ heterocyclyl)-($C_2$-$C_{20}$ heterocyclyl),
—C(=O)$NR^{10}(C_1$-$C_{12}$ alkylene)$NR^{10}R^{11}$,
—C(=O)$NR^{10}(C_1$-$C_{12}$ alkylene)$NR^{10}C(=O)OR^{11}$,
—C(=O)$NR^{10}(C_1$-$C_{12}$ alkylene)$NR^{10}C(=O)R^{11}$,
—C(=O)$NR^{10}(C_1$-$C_{12}$ alkylene)$R^{10}$,
$C_1$-$C_{12}$ alkyl,
$C_2$-$C_8$ alkenyl,
$C_2$-$C_8$ alkynyl, $C_3$-$C_{12}$ carbocyclyl,
$C_2$-$C_{20}$ heterocyclyl,
$C_6$-$C_{20}$ aryl,
$C_1$-$C_{20}$ heteroaryl,
—($C_3$-$C_{12}$ carbocyclyl)-($C_1$-$C_{12}$ alkyl),
—($C_2$-$C_{20}$ heterocyclyl)-($C_1$-$C_{12}$ alkylene)-($C_2$-$C_{20}$ heterocyclyl),
—($C_2$-$C_{20}$ heterocyclyl)-($C_1$-$C_{12}$ alkyl),
—($C_2$-$C_{20}$ heterocyclyl)-($C_2$-$C_{20}$ heterocyclyl),
—($C_2$-$C_{20}$ heterocyclyl)-($C_2$-$C_{20}$ heterocyclyl)-($C_2$-$C_{20}$ heterocyclyl),
—($C_6$-$C_{20}$ aryl)-($C_1$-$C_{12}$ alkyl),
—($C_1$-$C_{20}$ heteroaryl)-($C_1$-$C_{12}$ alkyl),
—($C_1$-$C_{20}$ heteroaryl)-($C_1$-$C_{12}$ alkylene)-($C_2$-$C_{20}$ heterocyclyl),
—($C_1$-$C_{20}$ heteroaryl)-($C_2$-$C_{20}$ heterocyclyl),
—($C_1$-$C_{20}$ heteroaryl)-($C_2$-$C_{20}$ heterocyclyl)-($C_1$-$C_{12}$ alkyl),
—($C_1$-$C_{20}$ heteroaryl)-($C_2$-$C_{20}$ heterocyclyl)-($C_1$-$C_{12}$ alkyl)-($C_6$-$C_{20}$ aryl),
—($C_1$-$C_{20}$ heteroaryl)-($C_2$-$C_{20}$ heterocyclyl)-($C_2$-$C_{20}$ heterocyclyl),
—($C_1$-$C_{12}$ alkylene)-($C_3$-$C_{12}$ carbocyclyl),
—($C_1$-$C_{12}$ alkylene)-($C_2$-$C_{20}$ heterocyclyl),
—($C_1$-$C_{12}$ alkylene)-($C_2$-$C_{20}$ heterocyclyl)-($C_2$-$C_{20}$ heterocyclyl),
—($C_1$-$C_{12}$ alkylene)-($C_2$-$C_{20}$ heterocyclyl)-($C_3$-$C_{12}$ carbocyclyl),
—($C_1$-$C_{12}$ alkylene)-($C_2$-$C_{20}$ heterocyclyl)—C(=O)—($C_2$-$C_{20}$ heterocyclyl),
—($C_1$-$C_{12}$ alkylene)-($C_1$-$C_{20}$ heteroaryl),
—($C_1$-$C_{12}$ alkylene)-($C_2$-$C_{20}$ heterocyclyl)-($C_1$-$C_{12}$ alkyl),
—($C_1$-$C_{12}$ alkylene)-($C_6$-$C_{20}$ aryl)-($C_1$-$C_{12}$ alkyl),
—($C_1$-$C_{12}$ alkylene)-($C_1$-$C_{20}$ heteroaryl)-($C_1$-$C_{12}$ alkyl),
—($C_1$-$C_{12}$ alkylene)-C(=O)—($C_2$-$C_{20}$ heterocyclyl),
—($C_1$-$C_{12}$ alkylene)C(=O)OR$^{10}$,
—($C_1$-$C_{12}$ alkylene)C(=O)NR$^{10}$R$^{11}$,
—($C_1$-$C_{12}$ alkylene)-NR$^{10}$R$^{11}$,
—($C_1$-$C_{12}$ alkylene)NR$^{12}$C(=O)R$^{10}$,
—($C_1$-$C_{12}$ alkylene)OR$^{10}$,
—($C_1$-$C_{12}$ alkylene)-NR$^{10}$—($C_1$-$C_{12}$ alkylene)-($C_1$-$C_{20}$ heteroaryl),
—($C_1$-$C_{12}$ alkylene)-NR$^{10}$—($C_1$-$C_{12}$ alkylene)-($C_1$-$C_{20}$ heterocyclyl),
—($C_1$-$C_{12}$ alkylene)-NR$^{10}$—($C_1$-$C_{12}$ alkylene)-NHC(=O)—($C_1$-$C_{20}$ heteroaryl),
—($C_1$-$C_{12}$ alkylene)-($C_2$-$C_{20}$ heterocyclyl)-NR$^{10}$R$^{11}$, and
—($C_1$-$C_{12}$ alkylene)-($C_2$-$C_{20}$ heterocyclyl)-($C_1$-$C_{12}$ alkyl)-NR$^{10}$R$^{11}$,
where at least one of R$^2$ and R$^3$ are not H;
A is $C_1$-$C_{20}$ heteroaryl;
R$^{10}$, R$^{11}$ and R$^{12}$ are independently selected from H, $C_1$-$C_{12}$ alkyl, —($C_1$-$C_{12}$ alkylene)-($C_2$-$C_{20}$ heterocyclyl), —($C_1$-$C_{12}$ alkylene)-($C_6$-$C_{20}$ aryl), —($C_1$-$C_{12}$ alkylene)-($C_3$-$C_{12}$ carbocyclyl), $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl, each of which are optionally substituted with one or more groups independently selected from F, Cl, Br, I, —CH$_3$, —CH$_2$CH$_3$, —CH(CH$_3$)$_2$, —CH$_2$OH, —CH$_2$OCH$_3$, —CH$_2$CH$_2$OH, —C(CH$_3$)$_2$OH, —CH$_2$C(CH$_3$)$_2$OH, —CH$_2$CH(CH$_3$)OH, —CH$_2$CO$_2$H, —CH$_2$CO$_2$CH$_3$, —CH$_2$NH$_2$, —(CH$_2$)$_2$N(CH$_3$)$_2$, —CH$_2$C$_6$H$_5$, —CN, —CF$_3$, —CO$_2$H, —C(O)CH$_3$, —C(O)CH(OH)CH$_3$, —CO$_2$CH$_3$, —CONH$_2$, —CONHCH$_3$, —CON(CH$_3$)$_2$, —C(CH$_3$)$_2$CONH$_2$, —NH$_2$, —NO$_2$, —N(CH$_3$)$_2$, —N(CH$_3$)C(CH$_3$)$_2$CONH$_2$, —N(CH$_3$)CH$_2$CH$_2$S(O)$_2$CH$_3$, —NHCOCH$_3$, —NHS(O)$_2$CH$_3$, =O (oxo), —OH, —OCH$_3$, —OCH$_2$CH$_3$, —OCH$_2$CH$_2$OH, —OP(O)(OH)$_2$, —SCH$_3$, —S(O)$_2$CH$_3$, —S(O)$_2$NH$_2$, —S(O)$_2$N(CH$_3$)$_2$, —CH$_2$S(O)$_2$NHCH$_3$, —CH$_2$S(O)$_2$CH$_2$CH$_3$, —S(O)$_2$NHCH$_3$, —S(O)$_2$CH$_2$CH$_3$, pyrrolidin-1-yl, 2-oxopyrrolidin-1-yl, cyclopropyl, cyclopentyl, oxetanyl, 4-methylpiperazin-1-yl, and 4-morpholinyl;

or R$^{10}$ and R$^{11}$ together with the nitrogen atom to which they are attached form a $C_2$-$C_{20}$ heterocyclyl ring or $C_1$-$C_{20}$ heteroaryl each of which are optionally substituted with one or more groups independently selected from F, Cl, Br, I, —CH$_3$, —CH$_2$OH, —CH$_2$C$_6$H$_5$, —CN, —CF$_3$, —CO$_2$H, —CONH$_2$, —CONHCH$_3$, —NO$_2$, —N(CH$_3$)$_2$, —NHCOCH$_3$, —NHS(O)$_2$CH$_3$, —OH, oxo, —OCH$_3$, —OCH$_2$CH$_3$, —S(O)$_2$NH$_2$, —S(O)$_2$CH$_3$, —CH(CH$_3$)$_2$, —CH$_2$CF$_3$, —CH$_2$CH$_2$OH and —C(CH$_3$)$_2$OH; and where alkyl, alkenyl, alkynyl, alkylene, carbocyclyl, heterocyclyl, aryl, and heteroaryl are optionally substituted with one or more groups independently selected from F, Cl, Br, I, R$^{10}$, —SR$^{10}$, —S(O)$_2$R$^{10}$, —S(O)$_2$NR$^{10}$R$^{11}$, —NR$^{10}$R$^{11}$, —NR$^{12}$C(O)R$^{10}$, —CO$_2$R$^{10}$, —C(O)R$^{10}$, —CONR$^{10}$R$^{11}$, oxo, and —OR$^{10}$;

wherein the IC50 binding activity to p110 delta is ten or more times lower than the binding activity to p110 alpha.

Exemplary embodiments of Formula I compounds include wherein:
(i) Z$^1$ is CR$^1$, Z$^2$ is CR$^2$, Z$^3$ is CR$^3$, and Z$^4$ is CR$^4$;
(ii) Z$^1$ is N, Z$^2$ is CR$^2$, Z$^3$ is CR$^3$, and Z$^4$ is CR$^4$;
(iii) Z$^1$ is CR$^1$, Z$^2$ is N, Z$^3$ is CR$^3$, and Z$^4$ is CR$^4$;
(iv) Z$^1$ is CR$^1$, Z$^2$ is CR$^2$, Z$^3$ is N, and Z$^4$ is CR$^4$; or
(v) Z$^1$ is CR$^1$, Z$^2$ is CR$^2$, Z$^3$ is CR$^3$, and Z$^4$ is N.

Exemplary embodiments of Formula I compounds include wherein Z$^1$ and Z$^4$ are CH.

Exemplary embodiments of Formula I compounds include R$^2$ and R$^3$ are independently selected from $C_2$-$C_{20}$ heterocyclyl, —($C_2$-$C_{20}$ heterocyclyl)-($C_2$-$C_{20}$ heterocyclyl) and —($C_2$-$C_{20}$ heterocyclyl)-($C_1$-$C_{12}$ alkylene)-($C_2$-$C_{20}$ heterocyclyl) where heterocyclyl is optionally substituted pyrrolidinyl, piperidinyl, azetidinyl, piperazinyl, azepanyl, piperazin-2-one, morpholinyl, tetrahydropyranyl, or oxetanyl.

Exemplary embodiments of Formula I compounds include wherein R$^2$ and R$^3$ are independently selected from —SR$^{10}$, S(O)R$^{10}$, —S(O)$_2$R$^{10}$, —S(O)$_2$NR$^{10}$R$^{11}$, —S(O)—($C_2$-$C_{20}$ heterocyclyl), —S(O)$_2$—($C_2$-$C_{20}$ heterocyclyl), and —S(O)$_2$—($C_2$-$C_{20}$ heterocyclyl)-($C_1$-$C_{12}$ alkyl)-($C_2$-$C_{20}$ heterocyclyl).

Exemplary embodiments of Formula I compounds include wherein R$^2$ and R$^3$ are independently selected from OR$^{10}$, —O—($C_1$-$C_{12}$ alkylene)-($C_2$-$C_{20}$ heterocyclyl), —O—($C_1$-$C_{12}$ alkylene)-($C_1$-$C_{20}$ heteroaryl), —O—($C_1$-$C_{12}$ alkylene)-($C_6$-$C_{20}$ aryl), —O—($C_1$-$C_{12}$ alkylene)-C(=O)—($C_2$-$C_{20}$ heterocyclyl), —O—($C_2$-$C_{20}$ heterocyclyl), and —O—($C_2$-$C_{20}$ heterocyclyl)-($C_1$-$C_{12}$ alkylene)-($C_2$-$C_{20}$ heterocyclyl).

Exemplary embodiments of Formula I compounds include wherein A is selected from pyridyl, isoxazolyl, imidazolyl, pyrazolyl, pyrrolyl, thiazolyl, pyridazinyl, pyrimidinyl, pyrazinyl, oxazolyl, oxadiazolyl, 1,3,4-oxadiazol-2(3H)-one, furanyl, thienyl, 1,2,3-triazolyl, 1,2,4-triazolyl, 1,2,4-triazol-5(4H)-one, 4,5-dihydro-1,2,4-triazin-6(1H)-one, tetrazolyl, pyrrolo[2,3-b]pyridinyl, indazolyl, 3,4-dihydroquinolinyl, and benzo[d]thiazole.

Exemplary embodiments of Formula I compounds include wherein A is selected from the structures:

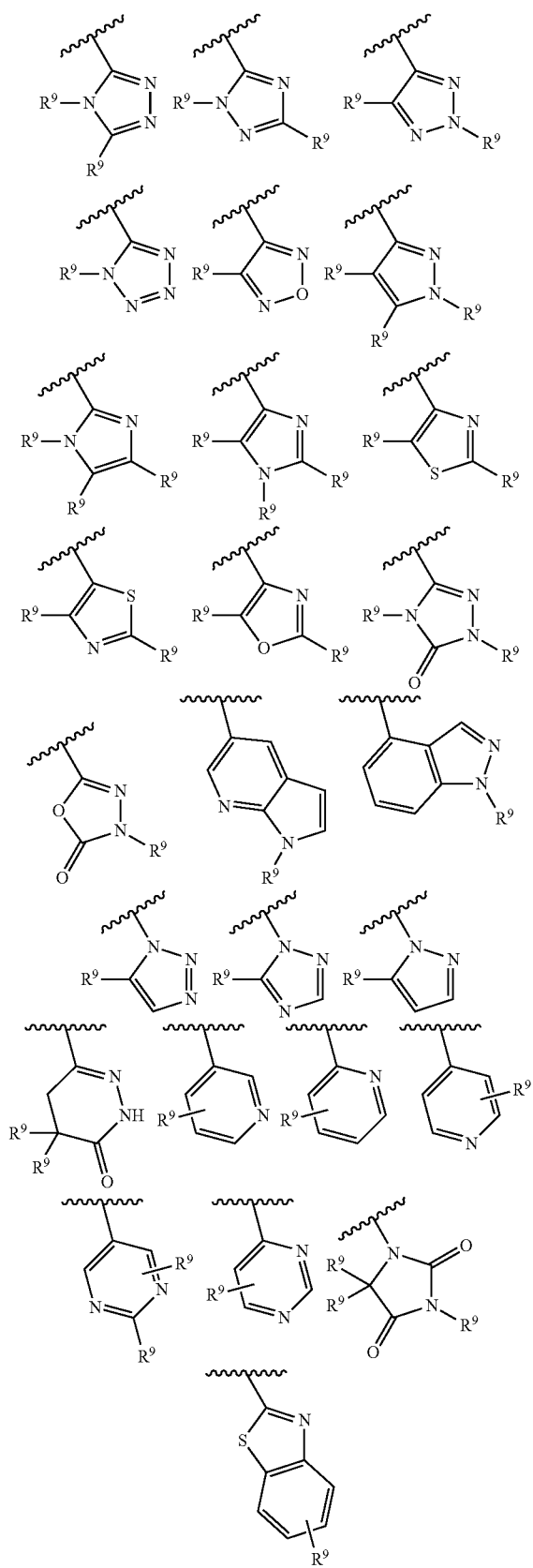

where R⁹ is independently selected from H, F, —CHF, —CHF, —CF₃, —CH₃, —CH(CH₃)₂, —CH₂CH (CH₃)₂, —CH₂CHF₂, —CH₂CH₂F, —CH₂CF₃, —CH₂OH, —CH₂CH₂OH, —CH₂CH(CH₃)OH, —CH₂CH(CH₃)OCH₃, —CH₂CO₂H, —CH(CH₃) CH₂OCH₃, —C(=O)CH₃, —C(=O)NHCH₃, —C(=O)N(CH₃)₂, —CO₂H, —CO₂CH₃, —CH₂CO₂CH₃, —NH₂, —NHC(=O)CH₃, —OH, —OCH₃, —S(O)₂CH₃, 1-methylpiperid-4-yl, 4-methylpiperazin-1-yl, 4-morpholinyl, (4-methylpiperazin-1yl)carboxamide, —CH₂(1H-1,2,4-triazol-5-yl), cyclopropyl, cyclopropylmethyl, cyclobutyl, and tetrahydrofuranyl; and where the wavy line indicates the site of attachment.

Exemplary embodiments of Formula I compounds include wherein R⁹ is —CH(CH₃)₂.

Exemplary embodiments of Formula I compounds include wherein A is optionally substituted 1H-1,2,4-triazol-5-yl.

Exemplary embodiments of Formula I compounds include wherein A is optionally substituted pyrid-2-yl or pyrid-3-yl.

The Formula I compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention.

In addition, the present invention embraces all geometric and positional isomers. For example, if a Formula I compound incorporates a double bond or a fused ring, the cis- and trans-forms, as well as mixtures thereof, are embraced within the scope of the invention. Both the single positional isomers and mixture of positional isomers are also within the scope of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embrace both solvated and unsolvated forms.

The compounds of the present invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The present invention also embraces isotopically-labeled compounds of the present invention which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Certain isotopically-labeled compounds of the present invention (e.g., those labeled with $^{3}H$ and $^{14}C$) are useful in compound and/or substrate tissue distribution assays. Tritiated ($^3$H) and carbon-14 ($^{14}$C) isotopes are useful for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C and $^{18}$F are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Biological Evaluation

The relative efficacies of Formula I compounds as inhibitors of an enzyme activity (or other biological activity) can be established by determining the concentrations at which each compound inhibits the activity to a predefined extent and then comparing the results. Typically, the preferred determination is the concentration that inhibits 50% of the activity in a biochemical assay, i.e., the 50% inhibitory concentration or "IC$_{50}$". Determination of IC$_{50}$ values can be accomplished using conventional techniques known in the art. In general, an IC$_{50}$ can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the IC$_{50}$ value. Analogously, other inhibitory concentrations can be defined through appropriate determinations of activity. For example, in some settings it can be desirable to establish a 90% inhibitory concentration, i.e., IC$_{90}$, etc.

Accordingly, a "selective PI3K delta inhibitor" can be understood to refer to a compound that exhibits a 50% inhibitory concentration (IC$_{50}$) with respect to PI3K delta that is at least at least 10-fold lower than the IC50 value with respect to any or all of the other Class I PI3K family members.

Determination of the activity of PI3 kinase activity of Formula I compounds is possible by a number of direct and indirect detection methods. Certain exemplary compounds described herein were assayed for their ability to inhibit PI3K alpha, beta, gamma, and delta isoforms (Example 901). The range of IC50 values for inhibition of PI3K delta was less than 1 nM (nanomolar) to about 10 µM (micromolar). Certain exemplary compounds of the invention had PI3K delta inhibitory IC$_{50}$ values less than 10 nM. The compounds are selective for the p110δ (delta) isoform, which is a class Ia PI3 kinase, over other class Ia PI3 kinases, and are thus selective for the p110δ isoform over both the p110α (alpha) isoform and the p110β (beta) isoform. In particular, they are selective for p110δ (delta) over p110α (alpha). The compounds are also selective for the p110δ isoform over p110γ (gamma), which is a class Ib kinase. The selectivity exhibited by Formula I compounds of the invention for p110δ (delta) over the p110α (alpha) isoform of PI3 kinase is at least 10 fold, as exemplified by the ratios of biochemical IC$_{50}$ values (Example 901).

Certain Formula I compounds may have antiproliferative activity to treat hyperproliferative disorders such as cancer. The Formula I compounds may inhibit tumor growth in mammals and may be useful for treating human cancer patients. Formula I compounds may be tested for in vitro cell proliferation activity and in vivo tumor growth inhibition according to the methods in WO 2006/046031; US 2008/0039459; US 2008/0076768; US 2008/0076758; WO 2008/070740; WO 2008/073785, which are incorporated by reference herein.

Evaluation of drug-induced immunosuppression by the compounds of the invention may be performed using in vivo functional tests, such as rodent models of induced arthritis and therapeutic or prophylactic treatment to assess disease score, T cell-dependent antibody response (TDAR), and delayed-type hypersensitivity (DTH). Other in vivo systems including murine models of host defense against infections or tumor resistance (Burleson G R, Dean J H, and Munson A E. *Methods in Immunotoxicology*, Vol. 1. Wiley-Liss, New York, 1995) may be considered to elucidate the nature or mechanisms of observed immunosuppression. The in vivo test systems can be complemented by well-established in vitro or ex vivo functional assays for the assessment of immune competence. These assays may comprise B or T cell proliferation in response to mitogens or specific antigens, measurement of signaling through the PI3K pathway in B or T cells or immortalized B or T cell lines, measurement of cell surface markers in response to B or T cell signaling, natural killer (NK) cell activity, mast cell activity, mast cell degranulation, macrophage phagocytosis or kill activity, and neutrophil oxidative burst and/or chemotaxis. In each of these tests determination of cytokine production by particular effector cells (e.g., lymphocytes, NK, monocytes/macrophages, neutrophils) may be included. The in vitro and ex vivo assays can be applied in both preclinical and clinical testing using lymphoid tissues and/or peripheral blood (House R V. "Theory and practice of cytokine assessment in immunotoxicology" (1999) Methods 19:17-27; Hubbard A K. "Effects of xenobiotics on macrophage function: evaluation in vitro" (1999) Methods; 19:8-16; Lebrec H, et al (2001) Toxicology 158:25-29).

Collagen-Induced Arthritis (CIA) 6-week detailed study using an autoimmune mechanism to mimic human arthritis; rat and mouse models (Example 902). Collagen-induced arthritis (CIA) is one of the most commonly used animal models of human rheumatoid arthritis (RA). Joint inflammation, which develops in animals with CIA, strongly resembles inflammation observed in patients with RA. Blocking tumor necrosis factor (TNT) is an efficacious treatment of CIA, just as it is a highly efficacious therapy in treatment of RA patients. CIA is mediated by both T-cells and antibodies (B-cells). Macrophages are believed to play an important role in mediating tissue damage during disease development. CIA is induced by immunizing animals with collagen emulsified in Complete Freund's Adjuvant (CFA). It is most commonly induced in the DBA/1 mouse strain, but the disease can also be induced in Lewis rats.

There is good evidence that B-cells play a key role in the pathogenesis of autoimmune and/or inflammatory disease. Protein-based therapeutics that deplete B cells such as Rituxan are effective against autoantibody-driven inflammatory diseases such as rheumatoid arthritis (Rastetter et al. (2004) Annu Rev Med 55:477). CD69 is the early activation marker in leukocytes including T cells, thymocytes, B cells, NK cells, neutrophils, and eosinophils. The CD69 human whole blood assay (Example 903) determines the ability of compounds to inhibit the production of CD69 by B lymphocytes in human whole blood activated by crosslinking surface IgM with goat F(ab')2 anti-human IgM.

The T-cell Dependent Antibody Response (TDAR) is a predictive assay for immune function testing when potential immunotoxic effects of compounds need to be studied. The IgM-Plaque Forming Cell (PFC) assay, using Sheep Red Blood Cells (SRBC) as the antigen, is currently a widely accepted and validated standard test. TDAR has proven to be a highly predictable assay for adult exposure immunotoxicity detection in mice based on the US National Toxicology Program (NTP) database (M. I. Luster et al (1992) Fundam. Appl. Toxicol. 18:200-210). The utility of this assay stems from the fact that it is a holistic measurement involving several important components of an immune response. A TDAR is dependent on functions of the following cellular compartments: (1) antigen-presenting cells, such as macrophages or dendritic cells; (2) T-helper cells, which are critical players in the genesis of the response, as well as in isotype switching; and (3) B-cells, which are the ultimate effector cells and are responsible for antibody production. Chemically-induced changes in any one compartment can cause significant changes in the overall TDAR (M. P. Holsapple In: G. R. Burleson, J. H. Dean and A. E. Munson, Editors, *Modern Methods in Immunotoxicology*, Volume 1, Wiley-Liss Publishers, New York, N.Y. (1995), pp. 71-108). Usually, this assay is performed either as an ELISA for measurement of soluble antibody (R. J. Smialowizc et al (2001) Toxicol. Sci. 61:164-175) or as a plaque (or antibody) forming cell assay (L. Guo et al (2002) Toxicol. Appl. Pharmacol. 181:219-227) to detect plasma cells secreting antigen specific antibodies. The antigen of choice is either whole cells (e.g. sheep erythrocytes) or soluble protein antigens (T. Miller et al (1998) Toxicol. Sci. 42:129-135).

Exemplary Formula I compounds in Table 1 were made, characterized, and tested for inhibition of PI3K delta and selectivity according to the methods of this invention, and have the following structures and corresponding names (ChemBioDraw Ultra, Version 11.0, CambridgeSoft Corp., Cambridge Mass.).

TABLE 1

| No. | Structure | Name | p110 delta IC50 (μM) | IC50 p110 alpha/ IC50 p110 delta |
|---|---|---|---|---|
| 101 | 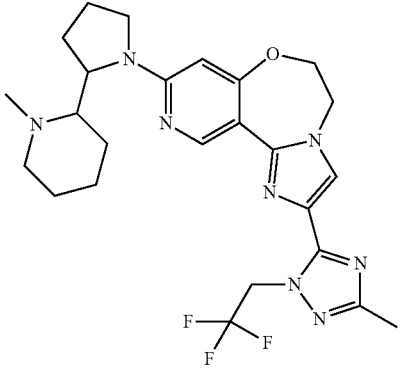 | 2-(3-methyl-1-(2,2,2-trifluoroethyl)-1H-1,2,4-triazol-5-yl)-9-(2-(1-methylpiperidin-2-yl)pyrrolidin-1-yl)-5,6-dihydroimidazo[1,2-d]pyrido[3,4-f][1,4]oxazepine | 0.000102 | 18.6 |
| 102 | 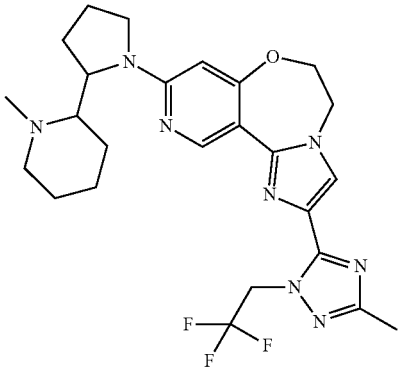 | 2-(3-methyl-1-(2,2,2-trifluoroethyl)-1H-1,2,4-triazol-5-yl)-9-(2-(1-methylpiperidin-2-yl)pyrrolidin-1-yl)-5,6-dihydroimidazo[1,2-d]pyrido[3,4-f][1,4]oxazepine | 0.000107 | 17.3 |

TABLE 1-continued

| No. | Structure | Name | p110 delta IC50 (μM) | IC50 p110 alpha/ IC50 p110 delta |
|---|---|---|---|---|
| 103 | 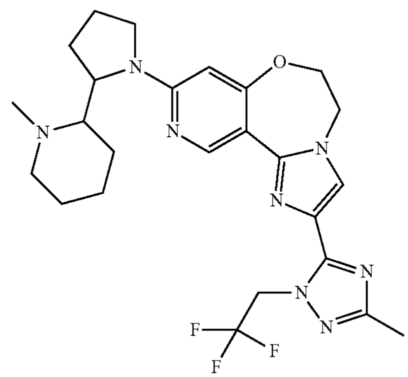 | (cis)-2-(3-methyl-1-(2,2,2-trifluoroethyl)-1H-1,2,4-triazol-5-yl)-9-(2-(1-methylpiperidin-2-yl)pyrrolidin-1-yl)-5,6-dihydroimidazo[1,2-d]pyrido[3,4-f][1,4]oxazepine | 0.000106 | 34.2 |
| 104 | 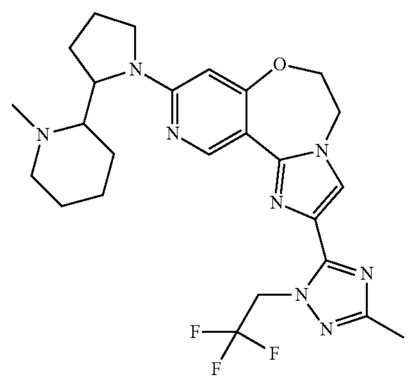 | (trans)-2-(3-methyl-1-(2,2,2-trifluoroethyl)-1H-1,2,4-triazol-5-yl)-9-(2-(1-methylpiperidin-2-yl)pyrrolidin-1-yl)-5,6-dihydroimidazo[1,2-d]pyrido[3,4-f][1,4]oxazepine | 0.000587 | 12.4 |
| 105 | 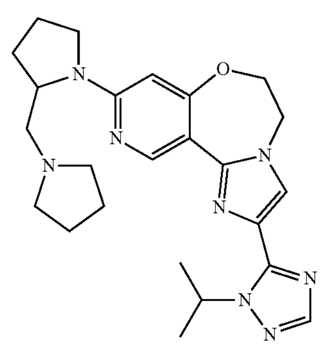 [SMILES: CC(C)n1ncnc1-c1cn2c(n1)-c1cnc(N3CCCC3CN3CCCC3)cc1OCC2] | 2-(1-isopropyl-1H-1,2,4-triazol-5-yl)-9-(2-(pyrrolidin-1-ylmethyl)pyrrolidin-1-yl)-5,6-dihydroimidazo[1,2-d]pyrido[3,4-f][1,4]oxazepine | 0.000707 | 18.3 |
| 106 | 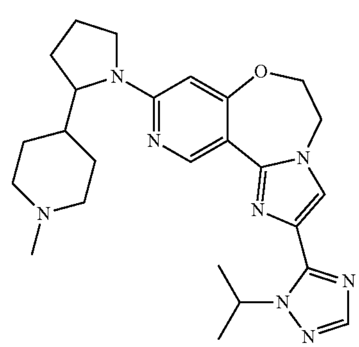 [SMILES: CC(C)n1ncnc1-c1cn2c(n1)-c1cnc(N3CCCC3C3CCN(C)CC3)cc1OCC2] | 2-(1-isopropyl-1H-1,2,4-triazol-5-yl)-9-(2-(1-methylpiperidin-4-yl)pyrrolidin-1-yl)-5,6-dihydroimidazo[1,2-d]pyrido[3,4-f][1,4]oxazepine | 0.000541 | 25.7 |

TABLE 1-continued

| No. | Structure | Name | p110 delta IC50 (μM) | IC50 p110 alpha/ IC50 p110 delta |
|---|---|---|---|---|
| 107 | | | | |
| 108 | 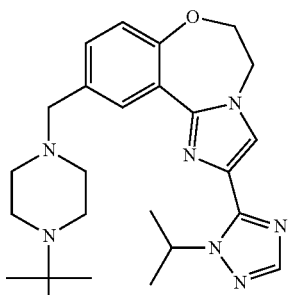 | 10-((4-tert-butylpiperazin-1-yl)methyl)-2-(1-isopropyl-1H-1,2,4-triazol-5-yl)-5,6-dihydrobenzo[f]imidazo[1,2-d][1,4]oxazepine | 0.00246 | 21.8 |
| 109 | 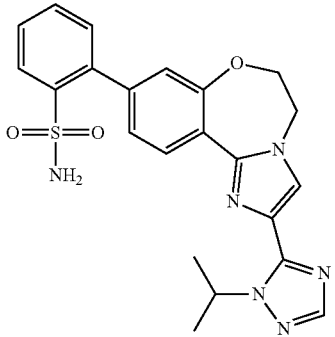 [SMILES: CC(C)n1ncnc1-c1cn2c(n1)-c1ccc(-c3ccccc3S(N)(=O)=O)cc1OCC2] | 2-(2-(1-isopropyl-1H-1,2,4-triazol-5-yl)-5,6-dihydrobenzo[f]imidazo[1,2-d][1,4]oxazepin-9-yl)benzenesulfonamide | 0.014 | 17.3 |
| 110 | 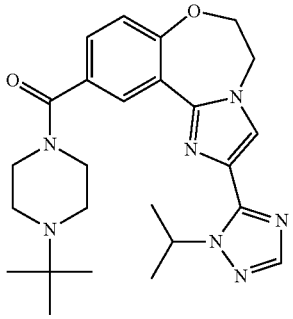 [SMILES: CC(C)n1ncnc1-c1cn2c(n1)-c1cc(C(=O)N3CCN(C(C)(C)C)CC3)ccc1OCC2] | (4-tert-butylpiperazin-1-yl)(2-(1-isopropyl-1H-1,2,4-triazol-5-yl)-5,6-dihydrobenzo[f]imidazo[1,2-d][1,4]oxazepin-10-yl)methanone | 0.000919 | 27.1 |
| 111 | 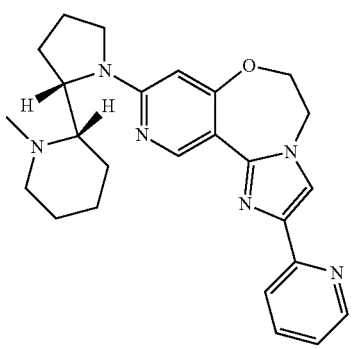 [SMILES: CN1CCCC[C@H]1[C@@H]1CCCN1c1cc2c(cn1)-c1nc(-c3ccccn3)cn1CCO2] | 9-((S)-2-((S)-1-methylpiperidin-2-yl)pyrrolidin-1-yl)-2-(pyridin-2-yl)-5,6-dihydroimidazo[1,2-d]pyrido[3,4-f][1,4]oxazepine | | |

TABLE 1-continued

| No. | Structure | Name | p110 delta IC50 (μM) | IC50 p110 alpha/ IC50 p110 delta |
|---|---|---|---|---|
| 112 | | | | |
| 113 | 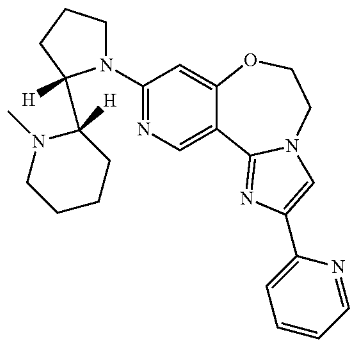 [SMILES: CN1CCCC[C@H]1[C@@H]1CCCN1c1cc2c(cn1)-c1nc(-c3ccccn3)cn1CCO2] | 9-((S)-2-((S)-1-methylpiperidin-2-yl)pyrrolidin-1-yl)-2-(pyridin-2-yl)-5,6-dihydroimidazo[1,2-d]pyrido[3,4-f][1,4]oxazepine | | |
| 114 | 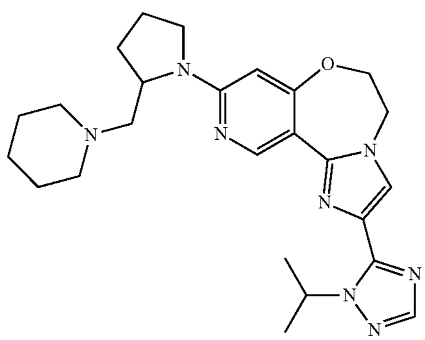 [SMILES: CC(C)n1ncnc1-c1cn2c(n1)-c1cnc(N3CCCC3CN3CCCCC3)cc1OCC2] | 2-(1-isopropyl-1H-1,2,4-triazol-5-yl)-9-(2-(piperidin-1-ylmethyl)pyrrolidin-1-yl)-5,6-dihydroimidazo[1,2-d]pyrido[3,4-f][1,4]oxazepine | | |
| 115 | 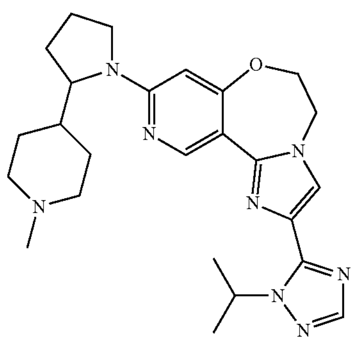 [SMILES: CC(C)n1ncnc1-c1cn2c(n1)-c1cnc(N3CCCC3C3CCN(C)CC3)cc1OCC2] | 2-(1-isopropyl-1H-1,2,4-triazol-5-yl)-9-(2-(1-methylpiperidin-4-yl)pyrrolidin-1-yl)-5,6-dihydroimidazo[1,2-d]pyrido[3,4-f][1,4]oxazepine | | |
| 116 | | | | |
| 117 | 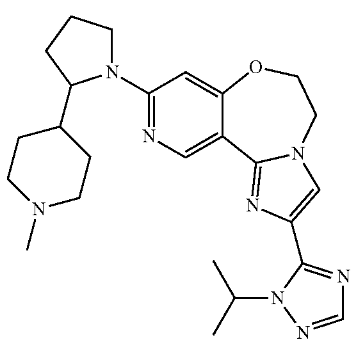 | 2-(1-isopropyl-1H-1,2,4-triazol-5-yl)-9-(2-(1-methylpiperidin-4-yl)pyrrolidin-1-yl)-5,6-dihydroimidazo[1,2-d]pyrido[3,4-f][1,4]oxazepine | | |

TABLE 1-continued

| No. | Structure | Name | p110 delta IC50 (μM) | IC50 p110 alpha/ IC50 p110 delta |
|---|---|---|---|---|
| 118 | 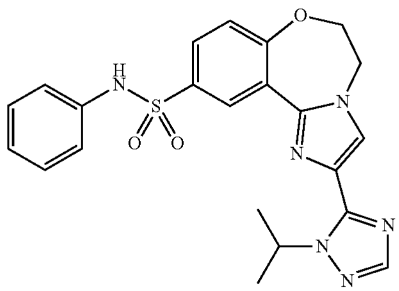 [SMILES: CC(C)n1ncnc1-c1cn2c(n1)-c1cc(S(=O)(=O)Nc3ccccc3)ccc1OCC2] | 2-(1-isopropyl-1H-1,2,4-triazol-5-yl)-N-phenyl-5,6-dihydrobenzo[f]imidazo[1,2-d][1,4]oxazepine-10-sulfonamide | | |
| 119 | 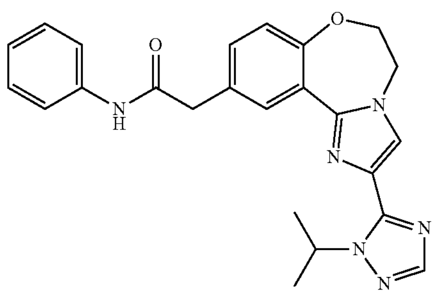 [SMILES: CC(C)n1ncnc1-c1cn2c(n1)-c1cc(CC(=O)Nc3ccccc3)ccc1OCC2] | 2-(2-(1-isopropyl-1H-1,2,4-triazol-5-yl)-5,6-dihydrobenzo[f]imidazo[1,2-d][1,4]oxazepin-10-yl)-N-phenylacetamide | | |
| 120 | 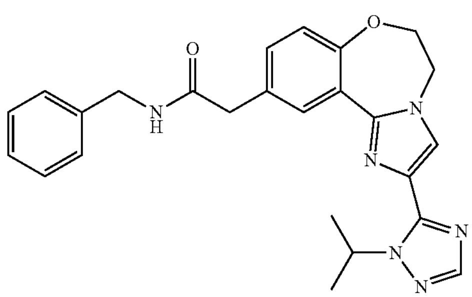 [SMILES: CC(C)n1ncnc1-c1cn2c(n1)-c1cc(CC(=O)NCc3ccccc3)ccc1OCC2] | N-benzyl-2-(2-(1-isopropyl-1H-1,2,4-triazol-5-yl)-5,6-dihydrobenzo[f]imidazo[1,2-d][1,4]oxazepin-10-yl)acetamide | | |
| 121 | 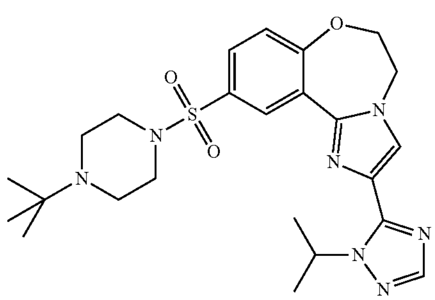 [SMILES: CC(C)n1ncnc1-c1cn2c(n1)-c1cc(S(=O)(=O)N3CCN(C(C)(C)C)CC3)ccc1OCC2] | 10-(4-tert-butylpiperazin-1-ylsulfonyl)-2-(1-isopropyl-1H-1,2,4-triazol-5-yl)-5,6-dihydrobenzo[f]imidazo[1,2-d][1,4]oxazepine | | |
| 122 | 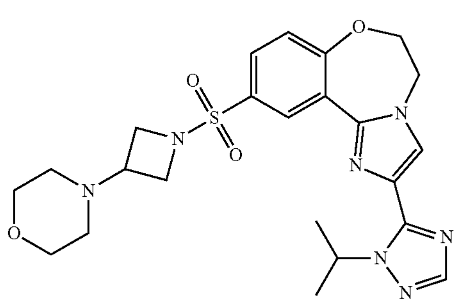 [SMILES: CC(C)n1ncnc1-c1cn2c(n1)-c1cc(S(=O)(=O)N3CC(N4CCOCC4)C3)ccc1OCC2] | 2-(1-isopropyl-1H-1,2,4-triazol-5-yl)-10-(3-morpholinoazetidin-1-ylsulfonyl)-5,6-dihydrobenzo[f]imidazo[1,2-d][1,4]oxazepine | | |

TABLE 1-continued

| No. | Structure | Name | p110 delta IC50 (μM) | IC50 p110 alpha/ IC50 p110 delta |
|---|---|---|---|---|
| 123 | 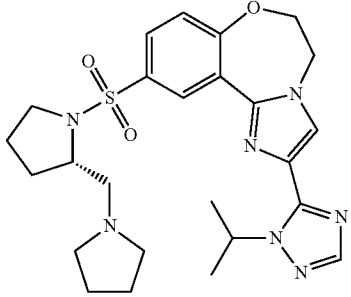 [SMILES: CC(C)n1ncnc1-c1cn2c(n1)-c1cc(S(=O)(=O)N3CCC[C@H]3CN3CCCC3)ccc1OCC2] | (S)-2-(1-isopropyl-1H-1,2,4-triazol-5-yl)-10-(2-(pyrrolidin-1-ylmethyl)pyrrolidin-1-ylsulfonyl)-5,6-dihydrobenzo[f]imidazo[1,2-d][1,4]oxazepine | | |
| 124 | 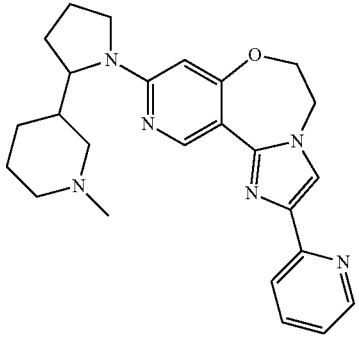 [SMILES: CN1CCCC(C2CCCN2c2cc3c(cn2)-c2nc(-c4ccccn4)cn2CCO3)C1] | 9-(2-(1-methylpiperidin-3-yl)pyrrolidin-1-yl)-2-(pyridin-2-yl)-5,6-dihydroimidazo[1,2-d]pyrido[3,4-f][1,4]oxazepine | | |
| 125 | 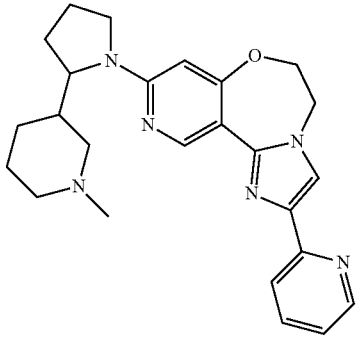 [SMILES: CN1CCCC(C2CCCN2c2cc3c(cn2)-c2nc(-c4ccccn4)cn2CCO3)C1] | 9-(2-(1-methylpiperidin-3-yl)pyrrolidin-1-yl)-2-(pyridin-2-yl)-5,6-dihydroimidazo[1,2-d]pyrido[3,4-f][1,4]oxazepine | | |
| 126 | 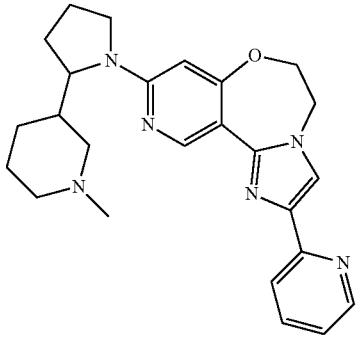 [SMILES: CN1CCCC(C2CCCN2c2cc3c(cn2)-c2nc(-c4ccccn4)cn2CCO3)C1] | 9-(2-(1-methylpiperidin-3-yl)pyrrolidin-1-yl)-2-(pyridin-2-yl)-5,6-dihydroimidazo[1,2-d]pyrido[3,4-f][1,4]oxazepine | | |

TABLE 1-continued

| No. | Structure | Name | p110 delta IC50 (μM) | IC50 p110 alpha/ IC50 p110 delta |
|---|---|---|---|---|
| 127 | 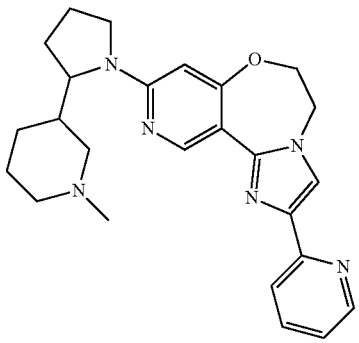 [SMILES: CN1CCCC(C2CCCN2c2cc3c(cn2)-c2nc(-c4ccccn4)cn2CCO3)C1] | 9-(2-(1-methylpiperidin-3-yl)pyrrolidin-1-yl)-2-(pyridin-2-yl)-5,6-dihydroimidazo[1,2-d]pyrido[3,4-f][1,4]oxazepine | | |
| 128 | 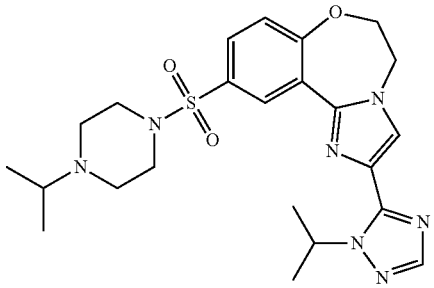 [SMILES: CC(C)N1CCN(S(=O)(=O)c2ccc3c(c2)-c2nc(-c4ncnn4C(C)C)cn2CCO3)CC1] | 2-(1-isopropyl-1H-1,2,4-triazol-5-yl)-10-(4-isopropylpiperazin-1-ylsulfonyl)-5,6-dihydrobenzo[f]imidazo[1,2-d][1,4]oxazepine | | |
| 129 | 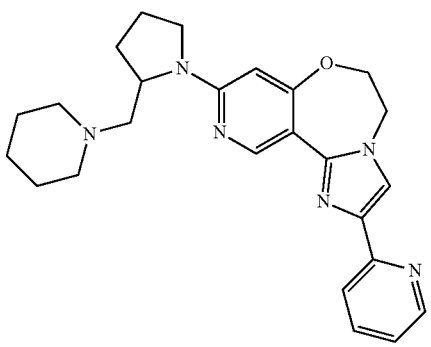 [SMILES: c1ccc(-c2cn3c(n2)-c2cnc(N4CCCC4CN4CCCCC4)cc2OCC3)nc1] | 9-(2-(piperidin-1-ylmethyl)pyrrolidin-1-yl)-2-(pyridin-2-yl)-5,6-dihydroimidazo[1,2-d]pyrido[3,4-f][1,4]oxazepine | | |
| 130 | | | | |
| 131 | 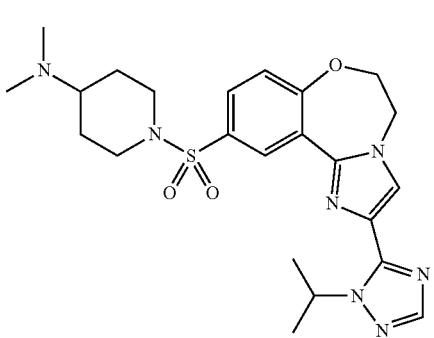 [SMILES: CC(C)n1ncnc1-c1cn2c(n1)-c1cc(S(=O)(=O)N3CCC(N(C)C)CC3)ccc1OCC2] | 1-(2-(1-isopropyl-1H-1,2,4-triazol-5-yl)-5,6-dihydrobenzo[f]imidazo[1,2-d][1,4]oxazepin-10-ylsulfonyl)-N,N-dimethylpiperidin-4-amine | | |

TABLE 1-continued

| No. | Structure | Name | p110 delta IC50 (μM) | IC50 p110 alpha/ IC50 p110 delta |
|---|---|---|---|---|
| 132 | 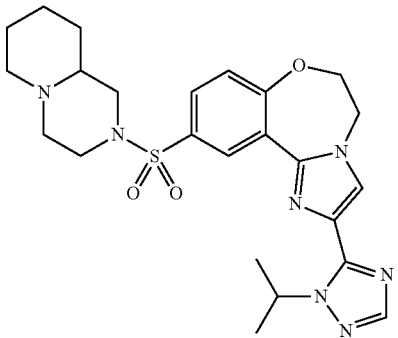 [SMILES: CC(C)n1ncnc1-c1cn2c(n1)-c1cc(S(=O)(=O)N3CCN4CCCCC4C3)ccc1OCC2] | 10-(dihydro-1H-pyrido[1,2-a]pyrazin-2(6H,7H,8H,9H,9aH)-ylsulfonyl)-2-(1-isopropyl-1H-1,2,4-triazol-5-yl)-5,6-dihydrobenzo[f]imidazo[1,2-d][1,4]oxazepine | | |
| 133 | 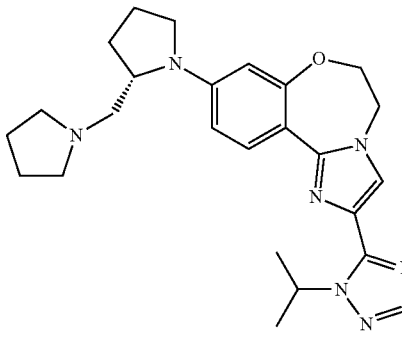 | (S)-2-(1-isopropyl-1H-1,2,4-triazol-5-yl)-9-(2-(pyrrolidin-1-ylmethyl)pyrrolidin-1-yl)-5,6-dihydrobenzo[f]imidazo[1,2-d][1,4]oxazepine | | |
| 134 | 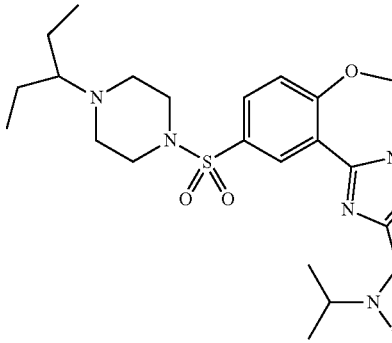 | 2-(1-isopropyl-1H-1,2,4-triazol-5-yl)-10-(4-(pentan-3-yl)piperazin-1-ylsulfonyl)-5,6-dihydrobenzo[f]imidazo[1,2-d][1,4]oxazepine | | |
| 135 | | | | |
| 136 | 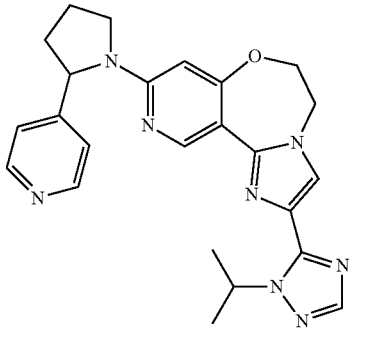 [SMILES: CC(C)n1ncnc1-c1cn2c(n1)-c1cnc(N3CCCC3c3ccncc3)cc1OCC2] | 2-(1-isopropyl-1H-1,2,4-triazol-5-yl)-9-(2-(pyridin-4-yl)pyrrolidin-1-yl)-5,6-dihydroimidazo[1,2-d]pyrido[3,4-f][1,4]oxazepine | | |

TABLE 1-continued

| No. | Structure | Name | p110 delta IC50 (μM) | IC50 p110 alpha/ IC50 p110 delta |
|---|---|---|---|---|
| 137 | 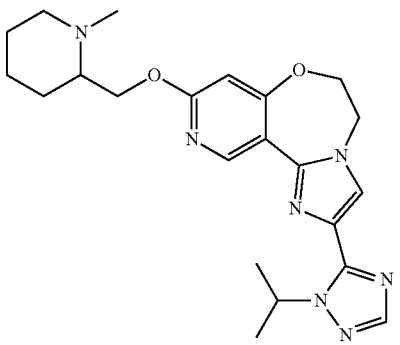 [SMILES: CC(C)n1ncnc1-c1cn2c(n1)-c1cnc(OCC3CCCCN3C)cc1OCC2] | 2-(1-isopropyl-1H-1,2,4-triazol-5-yl)-9-((1-methylpiperidin-2-yl)methoxy)-5,6-dihydroimidazo[1,2-d]pyrido[3,4-f][1,4]oxazepine | | |
| 138 | 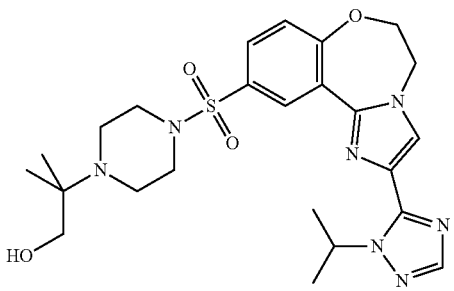 [SMILES: CC(C)n1ncnc1-c1cn2c(n1)-c1cc(S(=O)(=O)N3CCN(C(C)(C)CO)CC3)ccc1OCC2] | 2-(4-(2-(1-isopropyl-1H-1,2,4-triazol-5-yl)-5,6-dihydrobenzo[f]imidazo[1,2-d][1,4]oxazepin-10-ylsulfonyl)piperazin-1-yl)-2-methylpropan-1-ol | | |
| 139 | 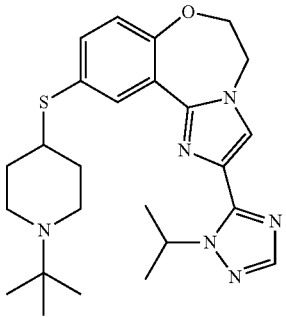 [SMILES: CC(C)n1ncnc1-c1cn2c(n1)-c1cc(SC3CCN(C(C)(C)C)CC3)ccc1OCC2] | 10-(1-tert-butylpiperidin-4-ylthio)-2-(1-isopropyl-1H-1,2,4-triazol-5-yl)-5,6-dihydrobenzo[f]imidazo[1,2-d][1,4]oxazepine | | |
| 140 | 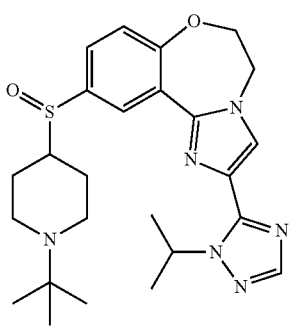 [SMILES: CC(C)n1ncnc1-c1cn2c(n1)-c1cc(S(=O)C3CCN(C(C)(C)C)CC3)ccc1OCC2] | 10-(1-tert-butylpiperidin-4-ylsulfinyl)-2-(1-isopropyl-1H-1,2,4-triazol-5-yl)-5,6-dihydrobenzo[f]imidazo[1,2-d][1,4]oxazepine | | |

TABLE 1-continued

| No. | Structure | Name | p110 delta IC50 (μM) | IC50 p110 alpha/ IC50 p110 delta |
|---|---|---|---|---|
| 141 | 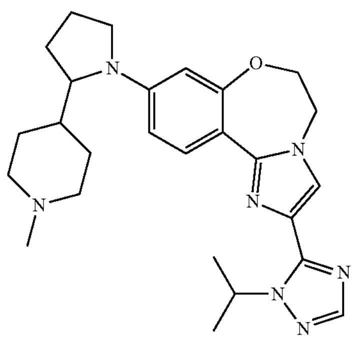 [SMILES: CC(C)n1ncnc1-c1cn2c(n1)-c1ccc(N3CCCC3C3CCN(C)CC3)cc1OCC2] | 2-(1-isopropyl-1H-1,2,4-triazol-5-yl)-9-(2-(1-methylpiperidin-4-yl)pyrrolidin-1-yl)-5,6-dihydrobenzo[f]imidazo[1,2-d][1,4]oxazepine | | |
| 142 | 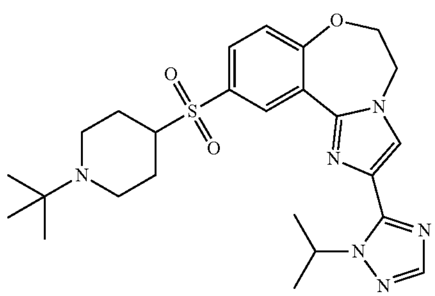 [SMILES: CC(C)n1ncnc1-c1cn2c(n1)-c1cc(S(=O)(=O)C3CCN(C(C)(C)C)CC3)ccc1OCC2] | 10-(1-tert-butylpiperidin-4-ylsulfonyl)-2-(1-isopropyl-1H-1,2,4-triazol-5-yl)-5,6-dihydrobenzo[f]imidazo[1,2-d][1,4]oxazepine | | |
| 143 | 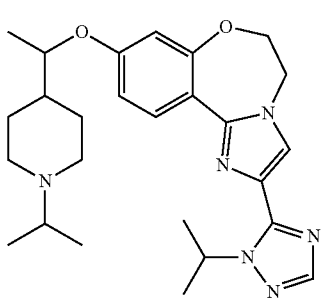 [SMILES: CC(Oc1ccc2c(c1)OCCn1cc(-c3ncnn3C(C)C)nc1-2)C1CCN(C(C)C)CC1] | 2-(1-isopropyl-1H-1,2,4-triazol-5-yl)-9-(1-(1-isopropylpiperidin-4-yl)ethoxy)-5,6-dihydrobenzo[f]imidazo[1,2-d][1,4]oxazepine | 0.000442 | 14.4 |
| 144 | 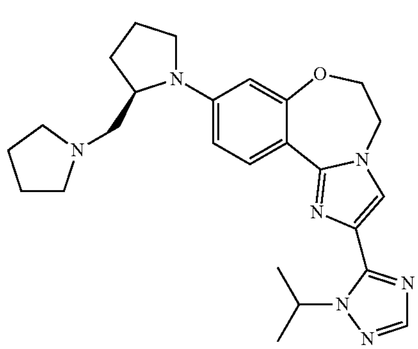 [SMILES: CC(C)n1ncnc1-c1cn2c(n1)-c1ccc(N3CCC[C@@H]3CN3CCCC3)cc1OCC2] | (R)-2-(1-isopropyl-1H-1,2,4-triazol-5-yl)-9-(2-(pyrrolidin-1-ylmethyl)pyrrolidin-1-yl)-5,6-dihydrobenzo[f]imidazo[1,2-d][1,4]oxazepine | | |

TABLE 1-continued

| No. | Structure | Name | p110 delta IC50 (μM) | IC50 p110 alpha/ IC50 p110 delta |
|---|---|---|---|---|
| 145 | 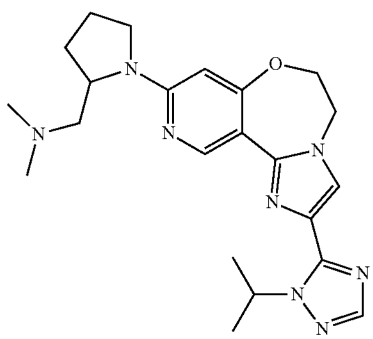 [SMILES: CC(C)n1ncnc1-c1cn2c(n1)-c1cnc(N3CCCC3CN(C)C)cc1OCC2] | 1-(1-(2-(1-isopropyl-1H-1,2,4-triazol-5-yl)-5,6-dihydroimidazo[1,2-d]pyrido[3,4-f][1,4]oxazepin-9-yl)pyrrolidin-2-yl)-N,N-dimethylmethanamine | | |
| 146 | 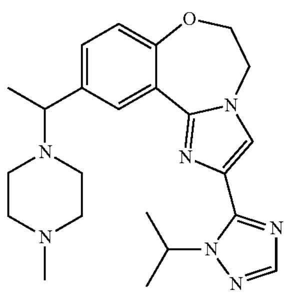 [SMILES: CC(c1ccc2c(c1)-c1nc(-c3ncnn3C(C)C)cn1CCO2)N1CCN(C)CC1] | 2-(1-isopropyl-1H-1,2,4-triazol-5-yl)-10-(1-(4-methylpiperazin-1-yl)ethyl)-5,6-dihydrobenzo[f]imidazo[1,2-d][1,4]oxazepine | | |
| 147 | 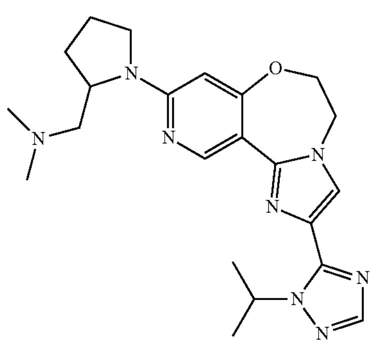 [SMILES: CC(C)n1ncnc1-c1cn2c(n1)-c1cnc(N3CCCC3CN(C)C)cc1OCC2] | 1-(1-(2-(1-isopropyl-1H-1,2,4-triazol-5-yl)-5,6-dihydroimidazo[1,2-d]pyrido[3,4-f][1,4]oxazepin-9-yl)pyrrolidin-2-yl)-N,N-dimethylmethanamine | | |
| 148 | 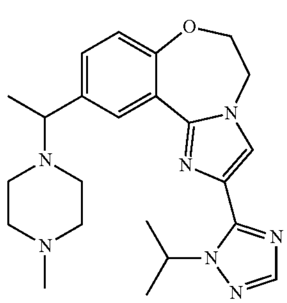 [SMILES: CC(c1ccc2c(c1)-c1nc(-c3ncnn3C(C)C)cn1CCO2)N1CCN(C)CC1] | 2-(1-isopropyl-1H-1,2,4-triazol-5-yl)-10-(1-(4-methylpiperazin-1-yl)ethyl)-5,6-dihydrobenzo[f]imidazo[1,2-d][1,4]oxazepine | | |

TABLE 1-continued

| No. | Structure | Name | p110 delta IC50 (μM) | IC50 p110 alpha/ IC50 p110 delta |
|---|---|---|---|---|
| 149 | 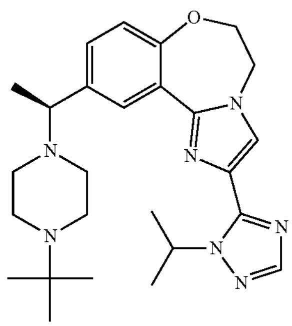 [SMILES: CC(C)n1ncnc1-c1cn2c(n1)-c1cc([C@H](C)N3CCN(C(C)(C)C)CC3)ccc1OCC2] | (S)-10-(1-(4-tert-butylpiperazin-1-yl)ethyl)-2-(1-isopropyl-1H-1,2,4-triazol-5-yl)-5,6-dihydrobenzo[f]imidazo[1,2-d][1,4]oxazepine | | |
| 150 | 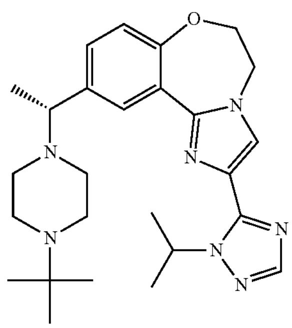 [SMILES: CC(C)n1ncnc1-c1cn2c(n1)-c1cc([C@@H](C)N3CCN(C(C)(C)C)CC3)ccc1OCC2] | (R)-10-(1-(4-tert-butylpiperazin-1-yl)ethyl)-2-(1-isopropyl-1H-1,2,4-triazol-5-yl)-5,6-dihydrobenzo[f]imidazo[1,2-d][1,4]oxazepine | | |
| 151 | | | | |
| 152 | 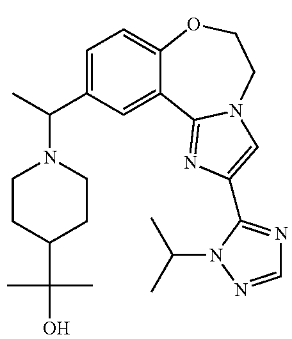 [SMILES: CC(c1ccc2c(c1)-c1nc(-c3ncnn3C(C)C)cn1CCO2)N1CCC(C(C)(C)O)CC1] | 2-(1-(1-(2-(1-isopropyl-1H-1,2,4-triazol-5-yl)-5,6-dihydrobenzo[f]imidazo[1,2-d][1,4]oxazepin-10-yl)ethyl)piperidin-4-yl)propan-2-ol | | |
| 153 | 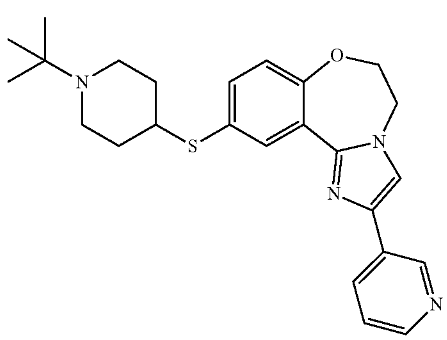 [SMILES: CC(C)(C)N1CCC(Sc2ccc3c(c2)-c2nc(-c4cccnc4)cn2CCO3)CC1] | 10-(1-tert-butylpiperidin-4-ylthio)-2-(pyridin-3-yl)-5,6-dihydrobenzo[f]imidazo[1,2-d][1,4]oxazepine | | |

TABLE 1-continued

| No. | Structure | Name | p110 delta IC50 (μM) | IC50 p110 alpha/ IC50 p110 delta |
|---|---|---|---|---|
| 154 | 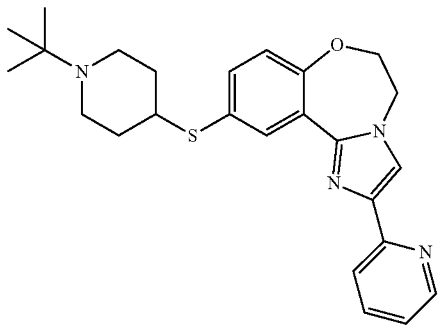 [SMILES: CC(C)(C)N1CCC(Sc2ccc3c(c2)-c2nc(-c4ccccn4)cn2CCO3)CC1] | 10-(1-tert-butylpiperidin-4-ylthio)-2-(pyridin-2-yl)-5,6-dihydrobenzo[f]imidazo[1,2-d][1,4]oxazepine | | |
| 155 | 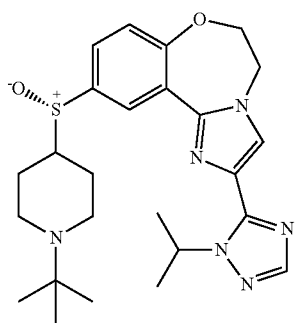 | (S)-10-(1-tert-butylpiperidin-4-ylsulfinyl)-2-(1-isopropyl-1H-1,2,4-triazol-5-yl)-5,6-dihydrobenzo[f]imidazo[1,2-d][1,4]oxazepine | | |
| 156 | | | | |
| 157 | 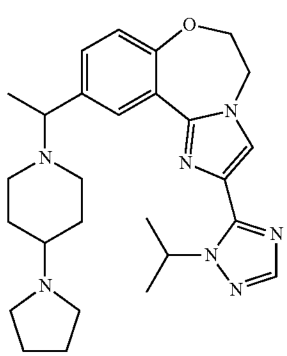 [SMILES: CC(c1ccc2c(c1)-c1nc(-c3ncnn3C(C)C)cn1CCO2)N1CCC(N2CCCC2)CC1] | 2-(1-isopropyl-1H-1,2,4-triazol-5-yl)-10-(1-(4-(pyrrolidin-1-yl)piperidin-1-yl)ethyl)-5,6-dihydrobenzo[f]imidazo[1,2-d][1,4]oxazepine | | |
| 158 | 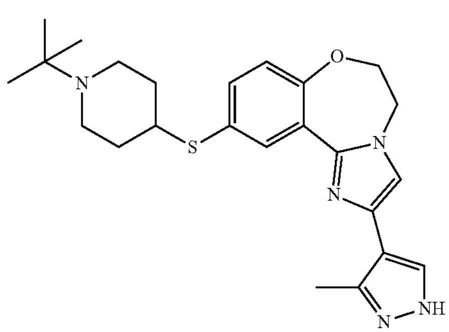 [SMILES: Cc1n[nH]cc1-c1cn2c(n1)-c1cc(SC3CCN(C(C)(C)C)CC3)ccc1OCC2] | 10-(1-tert-butylpiperidin-4-ylthio)-2-(3-methyl-1H-pyrazol-4-yl)-5,6-dihydrobenzo[f]imidazo[1,2-d][1,4]oxazepine | | |

TABLE 1-continued

| No. | Structure | Name | p110 delta IC50 (μM) | IC50 p110 alpha/ IC50 p110 delta |
|---|---|---|---|---|
| 159 | 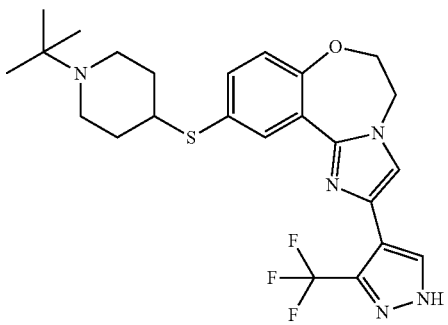 [SMILES: CC(C)(C)N1CCC(Sc2ccc3c(c2)-c2nc(-c4c[nH]nc4C(F)(F)F)cn2CCO3)CC1] | 10-(1-tert-butylpiperidin-4-ylthio)-2-(3-(trifluoromethyl)-1H-pyrazol-4-yl)-5,6-dihydrobenzo[f]imidazo[1,2-d][1,4]oxazepine | | |
| 160 | 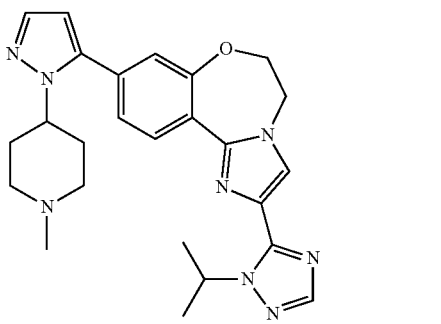 [SMILES: CC(C)n1ncnc1-c1cn2c(n1)-c1ccc(-c3ccnn3C3CCN(C)CC3)cc1OCC2] | 2-(1-isopropyl-1H-1,2,4-triazol-5-yl)-9-(1-(1-methylpiperidin-4-yl)-1H-pyrazol-5-yl)-5,6-dihydrobenzo[f]imidazo[1,2-d][1,4]oxazepine | | |
| 161 | 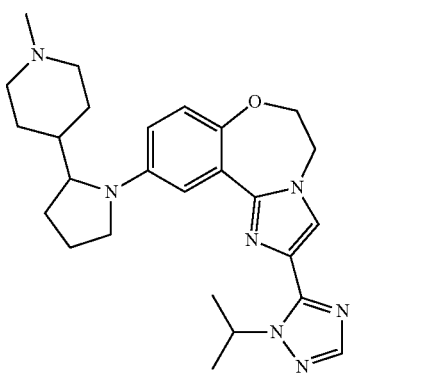 [SMILES: CC(C)n1ncnc1-c1cn2c(n1)-c1cc(N3CCCC3C3CCN(C)CC3)ccc1OCC2] | 2-(1-isopropyl-1H-1,2,4-triazol-5-yl)-10-(2-(1-methylpiperidin-4-yl)pyrrolidin-1-yl)-5,6-dihydrobenzo[f]imidazo[1,2-d][1,4]oxazepine | | |
| 162 | | | | |
| 163 | 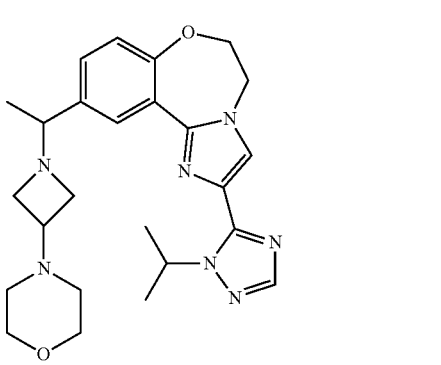 [SMILES: CC(c1ccc2c(c1)-c1nc(-c3ncnn3C(C)C)cn1CCO2)N1CC(N2CCOCC2)C1] | 2-(1-isopropyl-1H-1,2,4-triazol-5-yl)-10-(1-(3-morpholinoazetidin-1-yl)ethyl)-5,6-dihydrobenzo[f]imidazo[1,2-d][1,4]oxazepine | | |
| 164 | | | | |
| 165 | | | | |

TABLE 1-continued

| No. | Structure | Name | p110 delta IC50 (μM) | IC50 p110 alpha/ IC50 p110 delta |
|-----|-----------|------|----------------------|----------------------------------|
| 166 | 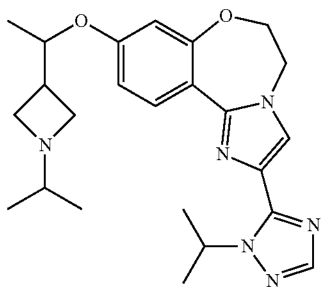 [SMILES: CC(Oc1ccc2c(c1)OCCn1cc(-c3ncnn3C(C)C)nc1-2)C1CN(C(C)C)C1] | 2-(1-isopropyl-1H-1,2,4-triazol-5-yl)-9-(1-(1-isopropylazetidin-3-yl)ethoxy)-5,6-dihydrobenzo[f]imidazo[1,2-d][1,4]oxazepine | | |
| 167 | 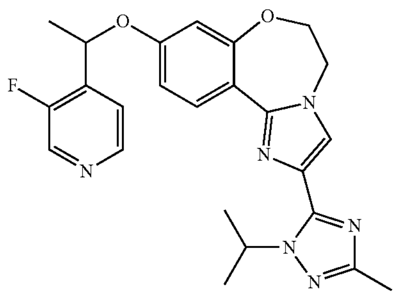 [SMILES: Cc1nc(-c2cn3c(n2)-c2ccc(OC(C)c4ccncc4F)cc2OCC3)n(C(C)C)n1] | 9-(1-(3-fluoropyridin-4-yl)ethoxy)-2-(1-isopropyl-3-methyl-1H-1,2,4-triazol-5-yl)-5,6-dihydrobenzo[f]imidazo[1,2-d][1,4]oxazepine | | |
| 168 | 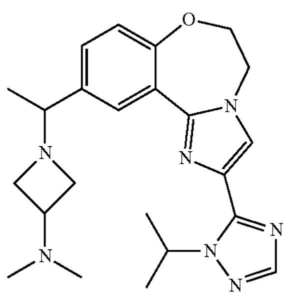 [SMILES: CC(c1ccc2c(c1)-c1nc(-c3ncnn3C(C)C)cn1CCO2)N1CC(N(C)C)C1] | 1-(1-(2-(1-isopropyl-1H-1,2,4-triazol-5-yl)-5,6-dihydrobenzo[f]imidazo[1,2-d][1,4]oxazepin-10-yl)ethyl)-N,N-dimethylazetidin-3-amine | | |
| 169 | | | | |
| 170 | 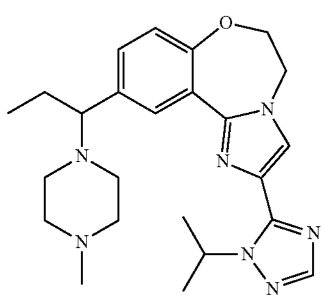 [SMILES: CCC(c1ccc2c(c1)-c1nc(-c3ncnn3C(C)C)cn1CCO2)N1CCN(C)CC1] | 2-(1-isopropyl-1H-1,2,4-triazol-5-yl)-10-(1-(4-methylpiperazin-1-yl)propyl)-5,6-dihydrobenzo[f]imidazo[1,2-d][1,4]oxazepine | | |
| 171 | 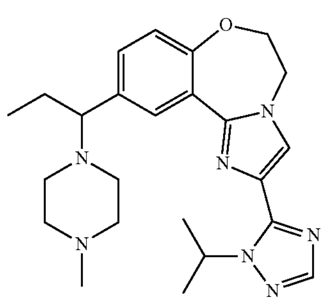 [SMILES: CCC(c1ccc2c(c1)-c1nc(-c3ncnn3C(C)C)cn1CCO2)N1CCN(C)CC1] | 2-(1-isopropyl-1H-1,2,4-triazol-5-yl)-10-(1-(4-methylpiperazin-1-yl)propyl)-5,6-dihydrobenzo[f]imidazo[1,2-d][1,4]oxazepine | | |

TABLE 1-continued

| No. | Structure | Name | p110 delta IC50 (μM) | IC50 p110 alpha/ IC50 p110 delta |
|---|---|---|---|---|
| 172 | 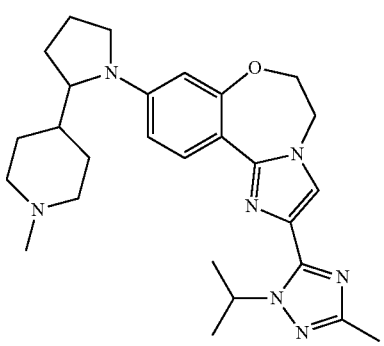 | 2-(1-isopropyl-3-methyl-1H-1,2,4-triazol-5-yl)-9-(2-(1-methylpiperidin-4-yl)pyrrolidin-1-yl)-5,6-dihydrobenzo[f]imidazo[1,2-d][1,4]oxazepine | | |
| 173 | 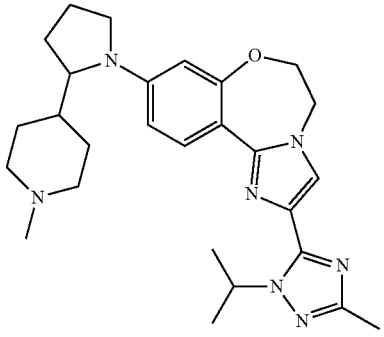 [SMILES: Cc1nc(-c2cn3c(n2)-c2ccc(N4CCCC4C4CCN(C)CC4)cc2OCC3)n(C(C)C)n1] | 2-(1-isopropyl-3-methyl-1H-1,2,4-triazol-5-yl)-9-(2-(1-methylpiperidin-4-yl)pyrrolidin-1-yl)-5,6-dihydrobenzo[f]imidazo[1,2-d][1,4]oxazepine | | |
| 174 | | | | |
| 175 | 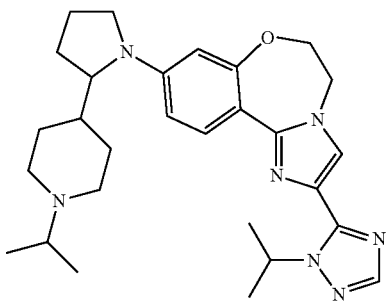 [SMILES: CC(C)N1CCC(C2CCCN2c2ccc3c(c2)OCCn2cc(-c4ncnn4C(C)C)nc2-3)CC1] | 2-(1-isopropyl-1H-1,2,4-triazol-5-yl)-9-(2-(1-isopropylpiperidin-4-yl)pyrrolidin-1-yl)-5,6-dihydrobenzo[f]imidazo[1,2-d][1,4]oxazepine | | |
| 176 | 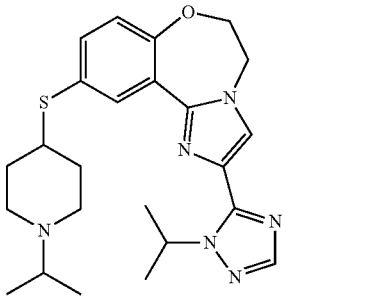 [SMILES: CC(C)N1CCC(Sc2ccc3c(c2)-c2nc(-c4ncnn4C(C)C)cn2CCO3)CC1] | 2-(1-isopropyl-1H-1,2,4-triazol-5-yl)-10-(1-isopropylpiperidin-4-ylthio)-5,6-dihydrobenzo[f]imidazo[1,2-d][1,4]oxazepine | | |

TABLE 1-continued

| No. | Structure | Name | p110 delta IC50 (μM) | IC50 p110 alpha/ IC50 p110 delta |
|---|---|---|---|---|
| 177 | 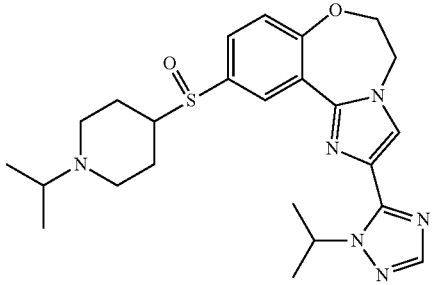 [SMILES: CC(C)N1CCC(S(=O)c2ccc3c(c2)-c2nc(-c4ncnn4C(C)C)cn2CCO3)CC1] | 2-(1-isopropyl-1H-1,2,4-triazol-5-yl)-10-(1-isopropylpiperidin-4-ylsulfinyl)-5,6-dihydrobenzo[f]imidazo[1,2-d][1,4]oxazepine | | |
| 178 | 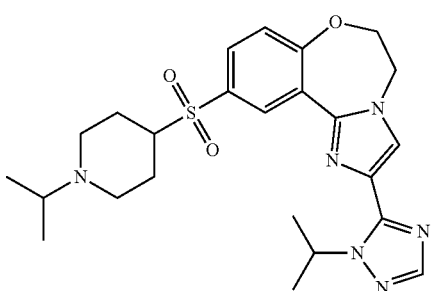 | 2-(1-isopropyl-1H-1,2,4-triazol-5-yl)-10-(1-isopropylpiperidin-4-ylsulfonyl)-5,6-dihydrobenzo[f]imidazo[1,2-d][1,4]oxazepine | | |
| 179 | 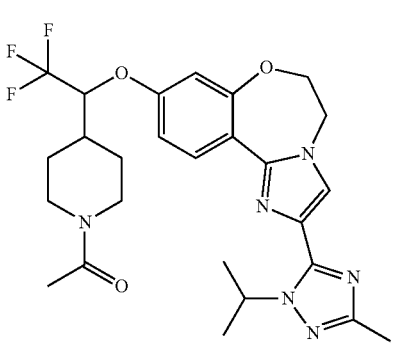 [SMILES: CC(=O)N1CCC(C(Oc2ccc3c(c2)OCCn2cc(-c4nc(C)nn4C(C)C)nc2-3)C(F)(F)F)CC1] | 1-(4-(2,2,2-trifluoro-1-(2-(1-isopropyl-3-methyl-1H-1,2,4-triazol-5-yl)-5,6-dihydrobenzo[f]imidazo[1,2-d][1,4]oxazepin-9-yloxy)ethyl)piperidin-1-yl)ethanone | | |
| 180 | 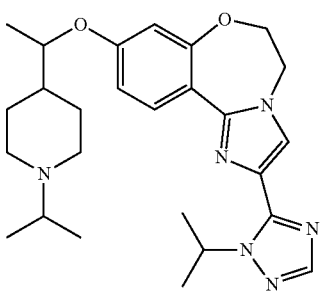 [SMILES: CC(Oc1ccc2c(c1)OCCn1cc(-c3ncnn3C(C)C)nc1-2)C1CCN(C(C)C)CC1] | 2-(1-isopropyl-1H-1,2,4-triazol-5-yl)-9-(1-(1-isopropylpiperidin-4-yl)ethoxy)-5,6-dihydrobenzo[f]imidazo[1,2-d][1,4]oxazepine | | |
| 181 | | | | |
| 182 | | | | |
| 183 | | | | |

TABLE 1-continued

| No. | Structure | Name | p110 delta IC50 (μM) | IC50 p110 alpha/ IC50 p110 delta |
|---|---|---|---|---|
| 184 | 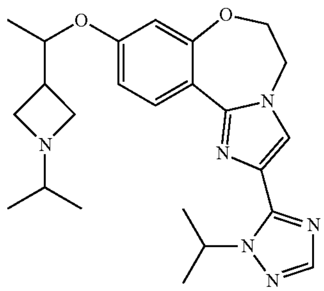 [SMILES: CC(Oc1ccc2c(c1)OCCn1cc(-c3ncnn3C(C)C)nc1-2)C1CN(C(C)C)C1] | 2-(1-isopropyl-1H-1,2,4-triazol-5-yl)-9-(1-(1-isopropylazetidin-3-yl)ethoxy)-5,6-dihydrobenzo[f]imidazo[1,2-d][1,4]oxazepine | | |
| 185 | 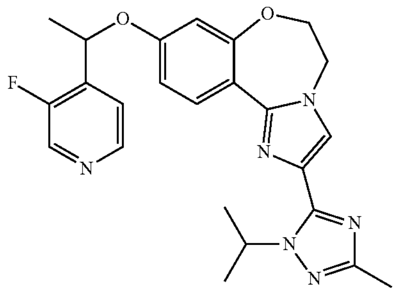 [SMILES: Cc1nc(-c2cn3c(n2)-c2ccc(OC(C)c4ccncc4F)cc2OCC3)n(C(C)C)n1] | 9-(1-(3-fluoropyridin-4-yl)ethoxy)-2-(1-isopropyl-3-methyl-1H-1,2,4-triazol-5-yl)-5,6-dihydrobenzo[f]imidazo[1,2-d][1,4]oxazepine | | |
| 186 | 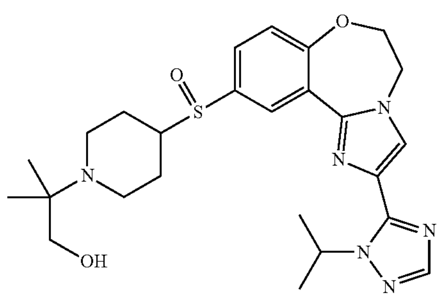 [SMILES: CC(C)n1ncnc1-c1cn2c(n1)-c1cc(S(=O)C3CCN(C(C)(C)CO)CC3)ccc1OCC2] | 2-(4-(2-(1-isopropyl-1H-1,2,4-triazol-5-yl)-5,6-dihydrobenzo[f]imidazo[1,2-d][1,4]oxazepin-10-ylsulfinyl)piperidin-1-yl)-2-methylpropan-1-ol | | |
| 187 | 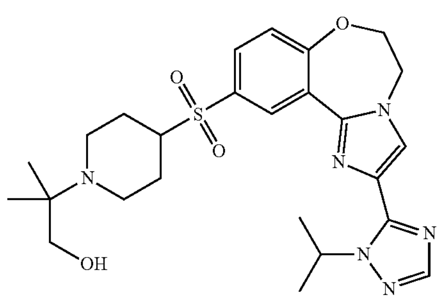 [SMILES: CC(C)n1ncnc1-c1cn2c(n1)-c1cc(S(=O)(=O)C3CCN(C(C)(C)CO)CC3)ccc1OCC2] | 2-(4-(2-(1-isopropyl-1H-1,2,4-triazol-5-yl)-5,6-dihydrobenzo[f]imidazo[1,2-d][1,4]oxazepin-10-ylsulfonyl)piperidin-1-yl)-2-methylpropan-1-ol | | |
| 188 | 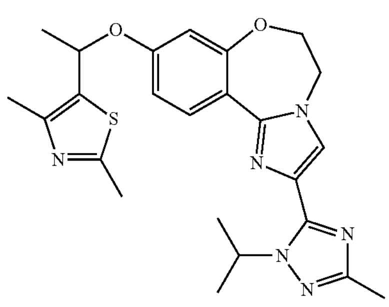 | 9-(1-(2,4-dimethylthiazol-5-yl)ethoxy)-2-(1-isopropyl-3-methyl-1H-1,2,4-triazol-5-yl)-5,6-dihydrobenzo[f]imidazo[1,2-d][1,4]oxazepine | | |

TABLE 1-continued

| No. | Structure | Name | p110 delta IC50 (μM) | IC50 p110 alpha/ IC50 p110 delta |
|---|---|---|---|---|
| 189 | 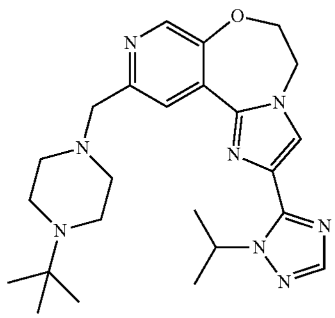 [SMILES: CC(C)n1ncnc1-c1cn2c(n1)-c1cc(CN3CCN(C(C)(C)C)CC3)ncc1OCC2] | 10-((4-tert-butylpiperazin-1-yl)methyl)-2-(1-isopropyl-1H-1,2,4-triazol-5-yl)-5,6-dihydroimidazo[1,2-d]pyrido[4,3-f][1,4]oxazepine | | |
| 190 | 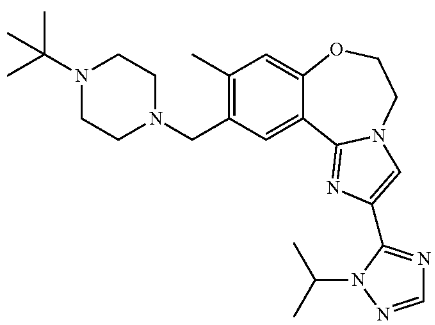 [SMILES: Cc1cc2c(cc1CN1CCN(C(C)(C)C)CC1)-c1nc(-c3ncnn3C(C)C)cn1CCO2] | 10-((4-tert-butylpiperazin-1-yl)methyl)-2-(1-isopropyl-1H-1,2,4-triazol-5-yl)-9-methyl-5,6-dihydrobenzo[f]imidazo[1,2-d][1,4]oxazepine | | |
| 191 | 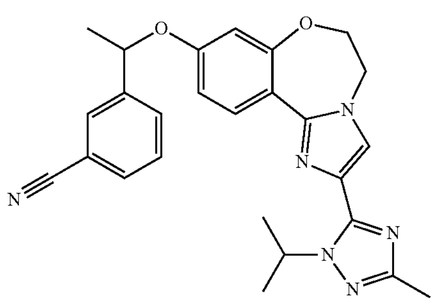 [SMILES: Cc1nc(-c2cn3c(n2)-c2ccc(OC(C)c4cccc(C#N)c4)cc2OCC3)n(C(C)C)n1] | 3-(1-(2-(1-isopropyl-3-methyl-1H-1,2,4-triazol-5-yl)-5,6-dihydrobenzo[f]imidazo[1,2-d][1,4]oxazepin-9-yloxy)ethyl)benzonitrile | | |
| 192 | 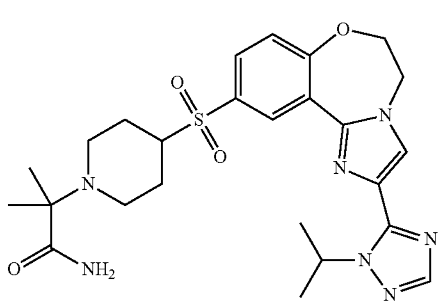 [SMILES: CC(C)n1ncnc1-c1cn2c(n1)-c1cc(S(=O)(=O)C3CCN(C(C)(C)C(N)=O)CC3)ccc1OCC2] | 2-(4-(2-(1-isopropyl-1H-1,2,4-triazol-5-yl)-5,6-dihydrobenzo[f]imidazo[1,2-d][1,4]oxazepin-10-ylsulfonyl)piperidin-1-yl)-2-methylpropanamide | | |

TABLE 1-continued

| No. | Structure | Name | p110 delta IC50 (μM) | IC50 p110 alpha/ IC50 p110 delta |
|---|---|---|---|---|
| 193 | 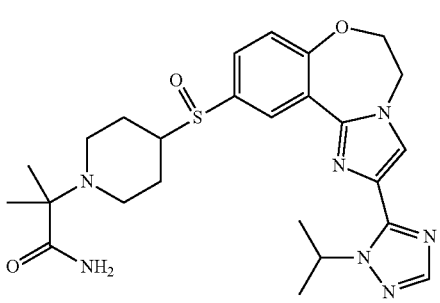 [SMILES: CC(C)n1ncnc1-c1cn2c(n1)-c1cc(S(=O)C3CCN(C(C)(C)C(N)=O)CC3)ccc1OCC2] | 2-(4-(2-(1-isopropyl-1H-1,2,4-triazol-5-yl)-5,6-dihydrobenzo[f]imidazo[1,2-d][1,4]oxazepin-10-ylsulfinyl)piperidin-1-yl)-2-methylpropanamide | | |
| 194 | 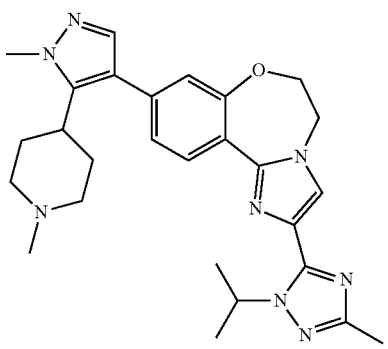 | 2-(1-isopropyl-3-methyl-1H-1,2,4-triazol-5-yl)-9-(1-methyl-5-(1-methylpiperidin-4-yl)-1H-pyrazol-4-yl)-5,6-dihydrobenzo[f]imidazo[1,2-d][1,4]oxazepine | | |
| 195 | 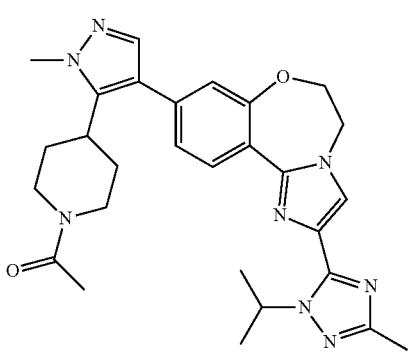 [SMILES: CC(=O)N1CCC(c2c(-c3ccc4c(c3)OCCn3cc(-c5nc(C)nn5C(C)C)nc3-4)cnn2C)CC1] | 1-(4-(4-(2-(1-isopropyl-3-methyl-1H-1,2,4-triazol-5-yl)-5,6-dihydrobenzo[f]imidazo[1,2-d][1,4]oxazepin-9-yl)-1-methyl-1H-pyrazol-5-yl)piperidin-1-yl)ethanone | | |
| 196 | 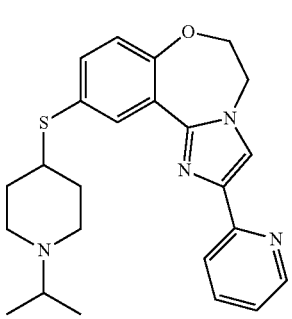 [SMILES: CC(C)N1CCC(Sc2ccc3c(c2)-c2nc(-c4ccccn4)cn2CCO3)CC1] | 10-(1-isopropylpiperidin-4-ylthio)-2-(pyridin-2-yl)-5,6-dihydrobenzo[f]imidazo[1,2-d][1,4]oxazepine | | |

TABLE 1-continued

| No. | Structure | Name | p110 delta IC50 (μM) | IC50 p110 alpha/ IC50 p110 delta |
|---|---|---|---|---|
| 197 | 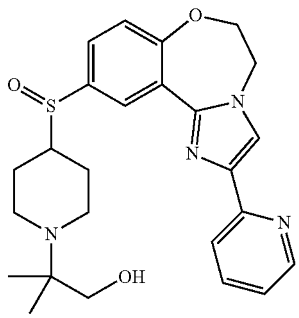 [SMILES: CC(C)(CO)N1CCC(S(=O)c2ccc3c(c2)-c2nc(-c4ccccn4)cn2CCO3)CC1] | 2-methyl-2-(4-(2-(pyridin-2-yl)-5,6-dihydrobenzo[f]imidazo[1,2-d][1,4]oxazepin-10-ylsulfinyl)piperidin-1-yl)propan-1-ol | | |
| 198 | 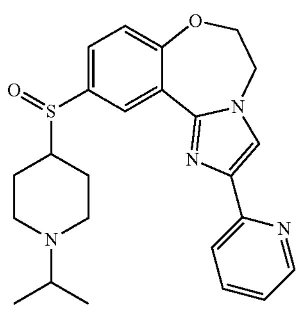 [SMILES: CC(C)N1CCC(S(=O)c2ccc3c(c2)-c2nc(-c4ccccn4)cn2CCO3)CC1] | 10-(1-isopropylpiperidin-4-ylsulfinyl)-2-(pyridin-2-yl)-5,6-dihydrobenzo[f]imidazo[1,2-d][1,4]oxazepine | | |
| 199 | 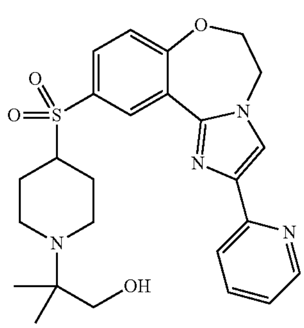 [SMILES: CC(C)(CO)N1CCC(S(=O)(=O)c2ccc3c(c2)-c2nc(-c4ccccn4)cn2CCO3)CC1] | 2-methyl-2-(4-(2-(pyridin-2-yl)-5,6-dihydrobenzo[f]imidazo[1,2-d][1,4]oxazepin-10-ylsulfonyl)piperidin-1-yl)propan-1-ol | | |
| 200 | 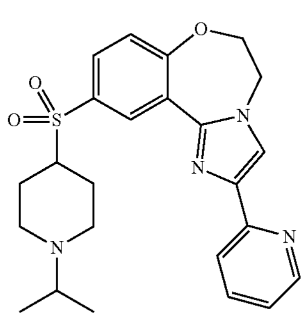 [SMILES: CC(C)N1CCC(S(=O)(=O)c2ccc3c(c2)-c2nc(-c4ccccn4)cn2CCO3)CC1] | 10-(1-isopropylpiperidin-4-ylsulfonyl)-2-(pyridin-2-yl)-5,6-dihydrobenzo[f]imidazo[1,2-d][1,4]oxazepine | | |

TABLE 1-continued

| No. | Structure | Name | p110 delta IC50 (μM) | IC50 p110 alpha/ IC50 p110 delta |
|---|---|---|---|---|
| 201 | 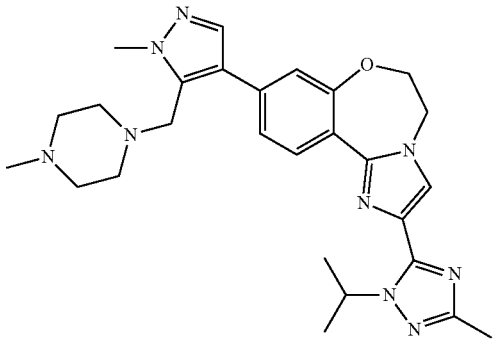 | 2-(1-isopropyl-3-methyl-1H-1,2,4-triazol-5-yl)-9-(1-methyl-5-((4-methylpiperazin-1-yl)methyl)-1H-pyrazol-4-yl)-5,6-dihydrobenzo[f]imidazo[1,2-d][1,4]oxazepine | | |
| 202 | 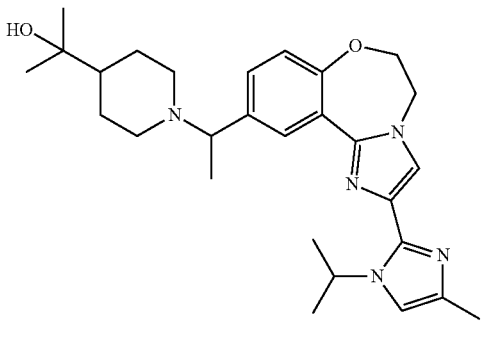 [SMILES: Cc1cn(C(C)C)c(-c2cn3c(n2)-c2cc(C(C)N4CCC(C(C)(C)O)CC4)ccc2OCC3)n1] | 2-(1-(1-(2-(1-isopropyl-4-methyl-1H-imidazol-2-yl)-5,6-dihydrobenzo[f]imidazo[1,2-d][1,4]oxazepin-10-yl)ethyl)piperidin-4-yl)propan-2-ol | | |
| 203 | 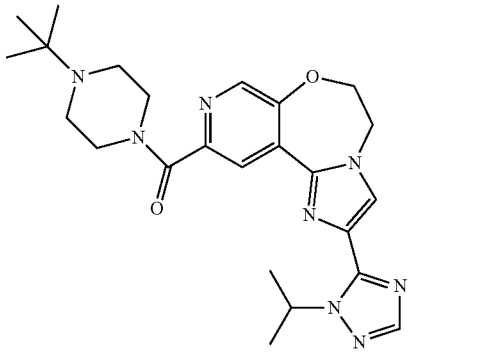 [SMILES: CC(C)n1ncnc1-c1cn2c(n1)-c1cc(C(=O)N3CCN(C(C)(C)C)CC3)ncc1OCC2] | (4-tert-butylpiperazin-1-yl)(2-(1-isopropyl-1H-1,2,4-triazol-5-yl)-5,6-dihydroimidazo[1,2-d]pyrido[4,3-f][1,4]oxazepin-10-yl)methanone | | |
| 204 | 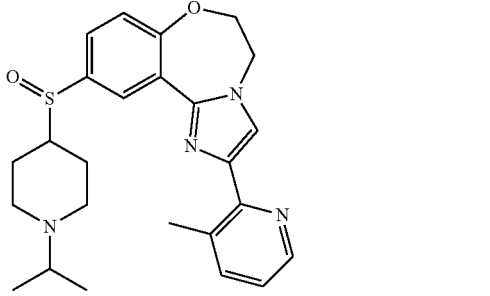 [SMILES: Cc1cccnc1-c1cn2c(n1)-c1cc(S(=O)C3CCN(C(C)C)CC3)ccc1OCC2] | 10-(1-isopropylpiperidin-4-ylsulfinyl)-2-(3-methylpyridin-2-yl)-5,6-dihydrobenzo[f]imidazo[1,2-d][1,4]oxazepine | | |

TABLE 1-continued

| No. | Structure | Name | p110 delta IC50 (μM) | IC50 p110 alpha/ IC50 p110 delta |
|---|---|---|---|---|
| 205 | 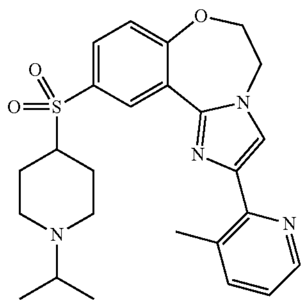 [SMILES: Cc1cccnc1-c1cn2c(n1)-c1cc(S(=O)(=O)C3CCN(C(C)C)CC3)ccc1OCC2] | 10-(1-isopropylpiperidin-4-ylsulfonyl)-2-(3-methylpyridin-2-yl)-5,6-dihydrobenzo[f]imidazo[1,2-d][1,4]oxazepine | | |
| 206 | 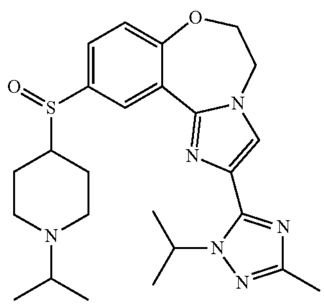 [SMILES: Cc1nc(-c2cn3c(n2)-c2cc(S(=O)C4CCN(C(C)C)CC4)ccc2OCC3)n(C(C)C)n1] | 2-(1-isopropyl-3-methyl-1H-1,2,4-triazol-5-yl)-10-(1-isopropylpiperidin-4-ylsulfinyl)-5,6-dihydrobenzo[f]imidazo[1,2-d][1,4]oxazepine | | |
| 207 | 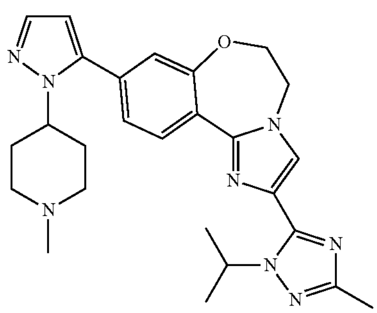 [SMILES: Cc1nc(-c2cn3c(n2)-c2ccc(-c4ccnn4C4CCN(C)CC4)cc2OCC3)n(C(C)C)n1] | 2-(1-isopropyl-3-methyl-1H-1,2,4-triazol-5-yl)-9-(1-(1-methylpiperidin-4-yl)-1H-pyrazol-5-yl)-5,6-dihydrobenzo[f]imidazo[1,2-d][1,4]oxazepine | | |
| 208 | 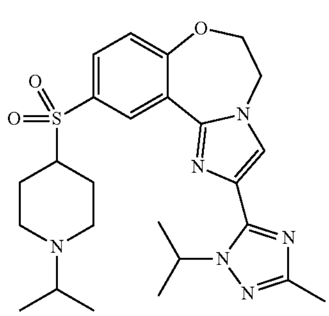 [SMILES: Cc1nc(-c2cn3c(n2)-c2cc(S(=O)(=O)C4CCN(C(C)C)CC4)ccc2OCC3)n(C(C)C)n1] | 2-(1-isopropyl-3-methyl-1H-1,2,4-triazol-5-yl)-10-(1-isopropylpiperidin-4-ylsulfonyl)-5,6-dihydrobenzo[f]imidazo[1,2-d][1,4]oxazepine | | |

TABLE 1-continued

| No. | Structure | Name | p110 delta IC50 (μM) | IC50 p110 alpha/ IC50 p110 delta |
|---|---|---|---|---|
| 209 | 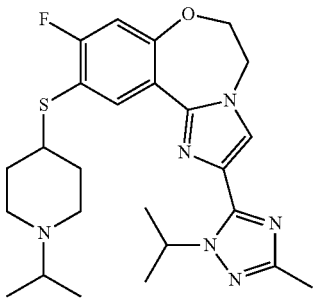 | 9-fluoro-2-(1-isopropyl-3-methyl-1H-1,2,4-triazol-5-yl)-10-(1-isopropylpiperidin-4-ylthio)-5,6-dihydrobenzo[f]imidazo[1,2-d][1,4]oxazepine | | |
| 210 | 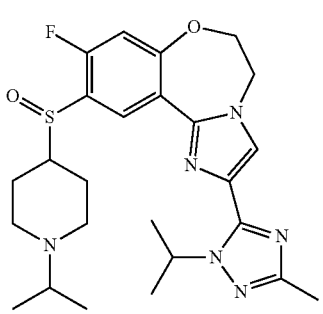 [SMILES: Cc1nc(-c2cn3c(n2)-c2cc(S(=O)C4CCN(C(C)C)CC4)c(F)cc2OCC3)n(C(C)C)n1] | 9-fluoro-2-(1-isopropyl-3-methyl-1H-1,2,4-triazol-5-yl)-10-(1-isopropylpiperidin-4-ylsulfinyl)-5,6-dihydrobenzo[f]imidazo[1,2-d][1,4]oxazepine | | |
| 211 | 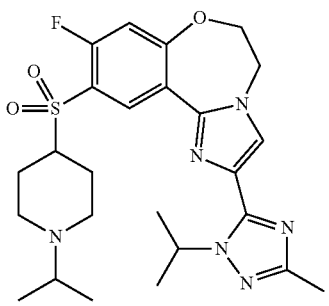 [SMILES: Cc1nc(-c2cn3c(n2)-c2cc(S(=O)(=O)C4CCN(C(C)C)CC4)c(F)cc2OCC3)n(C(C)C)n1] | 9-fluoro-2-(1-isopropyl-3-methyl-1H-1,2,4-triazol-5-yl)-10-((1-isopropylpiperidin-4-ylsulfonyl)-5,6-dihydrobenzo[f]imidazo[1,2-d][1,4]oxazepine | | |
| 212 | 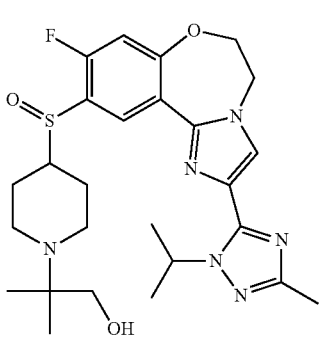 [SMILES: Cc1nc(-c2cn3c(n2)-c2cc(S(=O)C4CCN(C(C)(C)CO)CC4)c(F)cc2OCC3)n(C(C)C)n1] | 2-(4-(9-fluoro-2-(1-isopropyl-3-methyl-1H-1,2,4-triazol-5-yl)-5,6-dihydrobenzo[f]imidazo[1,2-d][1,4]oxazepin-10-ylsulfinyl)piperidin-1-yl)-2-methylpropan-1-ol | | |

TABLE 1-continued

| No. | Structure | Name | p110 delta IC50 (μM) | IC50 p110 alpha/ IC50 p110 delta |
|---|---|---|---|---|
| 213 | 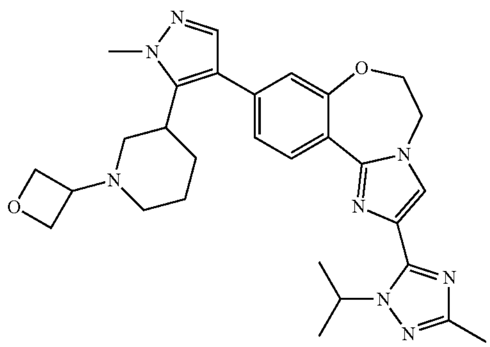 [SMILES: Cc1nc(-c2cn3c(n2)-c2ccc(-c4cnn(C)c4C4CCCN(C5COC5)C4)cc2OCC3)n(C(C)C)n1] | 2-(1-isopropyl-3-methyl-1H-1,2,4-triazol-5-yl)-9-(1-methyl-5-(1-(oxetan-3-yl)piperidin-3-yl)-1H-pyrazol-4-yl)-5,6-dihydrobenzo[f]imidazo[1,2-d][1,4]oxazepine | | |
| 214 | 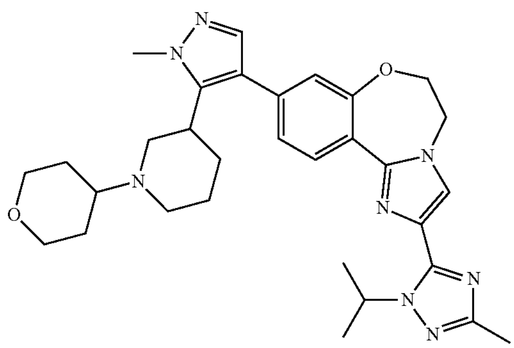 [SMILES: Cc1nc(-c2cn3c(n2)-c2ccc(-c4cnn(C)c4C4CCCN(C5CCOCC5)C4)cc2OCC3)n(C(C)C)n1] | 2-(1-isopropyl-3-methyl-1H-1,2,4-triazol-5-yl)-9-(1-methyl-5-(1-(tetrahydro-2H-pyran-4-yl)piperidin-3-yl)-1H-pyrazol-4-yl)-5,6-dihydrobenzo[f]imidazo[1,2-d][1,4]oxazepine | | |
| 215 | 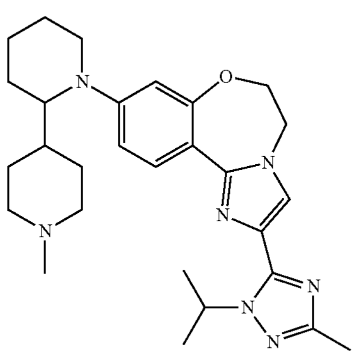 [SMILES: Cc1nc(-c2cn3c(n2)-c2ccc(N4CCCCC4C4CCN(C)CC4)cc2OCC3)n(C(C)C)n1] | 2-(1-isopropyl-3-methyl-1H-1,2,4-triazol-5-yl)-9-(1'-methyl-2,4'-bipiperidin-1-yl)-5,6-dihydrobenzo[f]imidazo[1,2-d][1,4]oxazepine | | |
| 216 | 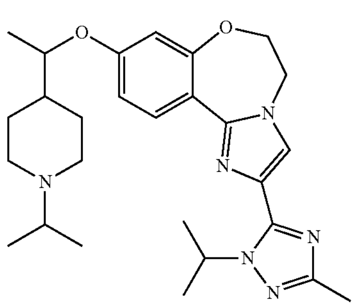 [SMILES: Cc1nc(-c2cn3c(n2)-c2ccc(OC(C)C4CCN(C(C)C)CC4)cc2OCC3)n(C(C)C)n1] | 2-(1-isopropyl-3-methyl-1H-1,2,4-triazol-5-yl)-9-(1-(1-isopropylpiperidin-4-yl)ethoxy)-5,6-dihydrobenzo[f]imidazo[1,2-d][1,4]oxazepine | | |

TABLE 1-continued

| No. | Structure | Name | p110 delta IC50 (μM) | IC50 p110 alpha/ IC50 p110 delta |
|---|---|---|---|---|
| 217 | 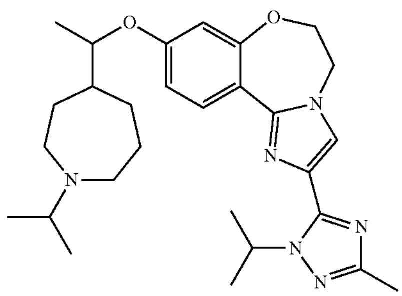 [SMILES: Cc1nc(-c2cn3c(n2)-c2ccc(OC(C)C4CCCN(C(C)C)CC4)cc2OCC3)n(C(C)C)n1] | 2-(1-isopropyl-3-methyl-1H-1,2,4-triazol-5-yl)-9-(1-(1-isopropylazepan-4-yl)ethoxy)-5,6-dihydrobenzo[f]imidazo[1,2-d][1,4]oxazepine | | |
| 218 | 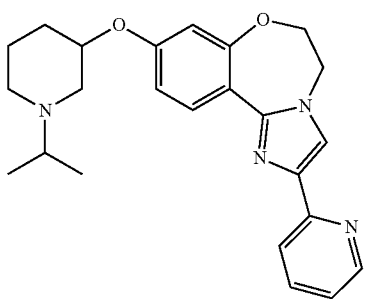 [SMILES: CC(C)N1CCCC(Oc2ccc3c(c2)OCCn2cc(-c4ccccn4)nc2-3)C1] | 9-(1-isopropylpiperidin-3-yloxy)-2-(pyridin-2-yl)-5,6-dihydrobenzo[f]imidazo[1,2-d][1,4]oxazepine | | |
| 219 | 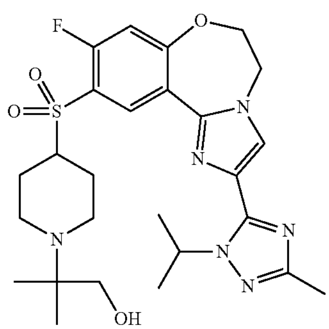 [SMILES: Cc1nc(-c2cn3c(n2)-c2cc(S(=O)(=O)C4CCN(C(C)(C)CO)CC4)c(F)cc2OCC3)n(C(C)C)n1] | 2-(4-(9-fluoro-2-(1-isopropyl-3-methyl-1H-1,2,4-triazol-5-yl)-5,6-dihydrobenzo[f]imidazo[1,2-d][1,4]oxazepin-10-ylsulfonyl)piperidin-1-yl)-2-methylpropan-1-ol | | |
| 220 | 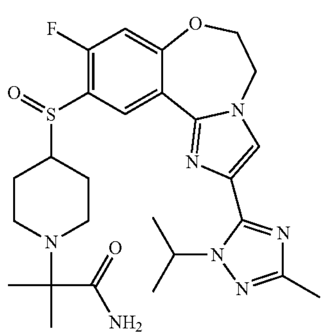 [SMILES: Cc1nc(-c2cn3c(n2)-c2cc(S(=O)C4CCN(C(C)(C)C(N)=O)CC4)c(F)cc2OCC3)n(C(C)C)n1] | 2-(4-(9-fluoro-2-(1-isopropyl-3-methyl-1H-1,2,4-triazol-5-yl)-5,6-dihydrobenzo[f]imidazo[1,2-d][1,4]oxazepin-10-ylsulfinyl)piperidin-1-yl)-2-methylpropanamide | | |

TABLE 1-continued

| No. | Structure | Name | p110 delta IC50 (μM) | IC50 p110 alpha/ IC50 p110 delta |
|---|---|---|---|---|
| 221 | 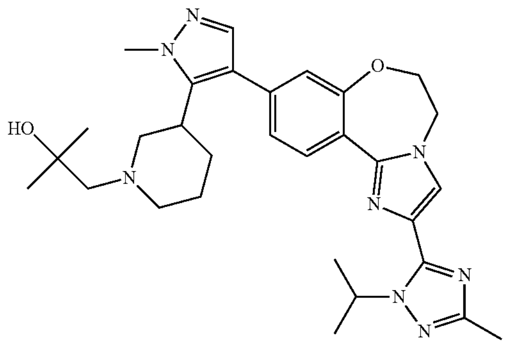 [SMILES: Cc1nc(-c2cn3c(n2)-c2ccc(-c4cnn(C)c4C4CCCN(CC(C)(C)O)C4)cc2OCC3)n(C(C)C)n1] | 1-(3-(4-(2-(1-isopropyl-3-methyl-1H-1,2,4-triazol-5-yl)-5,6-dihydrobenzo[f]imidazo[1,2-d][1,4]oxazepin-9-yl)-1-methyl-1H-pyrazol-5-yl)piperidin-1-yl)-2-methylpropan-2-ol | | |
| 222 | 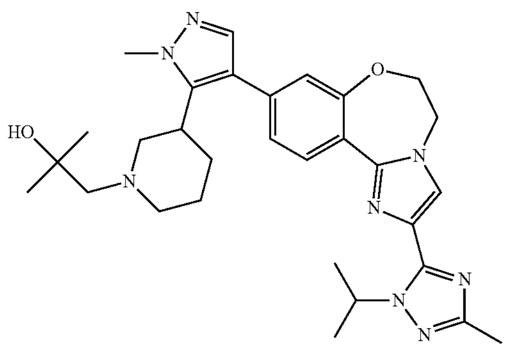 [SMILES: Cc1nc(-c2cn3c(n2)-c2ccc(-c4cnn(C)c4C4CCCN(CC(C)(C)O)C4)cc2OCC3)n(C(C)C)n1] | 1-(3-(4-(2-(1-isopropyl-3-methyl-1H-1,2,4-triazol-5-yl)-5,6-dihydrobenzo[f]imidazo[1,2-d][1,4]oxazepin-9-yl)-1-methyl-1H-pyrazol-5-yl)piperidin-1-yl)-2-methylpropan-2-ol | | |
| 223 | 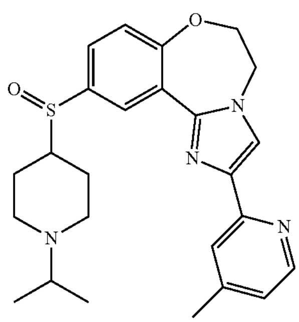 [SMILES: Cc1ccnc(-c2cn3c(n2)-c2cc(S(=O)C4CCN(C(C)C)CC4)ccc2OCC3)c1] | 10-(1-isopropylpiperidin-4-ylsulfinyl)-2-(4-methylpyridin-2-yl)-5,6-dihydrobenzo[f]imidazo[1,2-d][1,4]oxazepine | | |
| 224 | 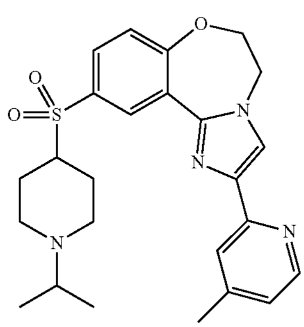 [SMILES: Cc1ccnc(-c2cn3c(n2)-c2cc(S(=O)(=O)C4CCN(C(C)C)CC4)ccc2OCC3)c1] | 10-(1-isopropylpiperidin-4-ylsulfonyl)-2-(4-methylpyridin-2-yl)-5,6-dihydrobenzo[f]imidazo[1,2-d][1,4]oxazepine | | |

US 9,090,628 B2
TABLE 1-continued

| No. | Structure | Name | p110 delta IC50 (μM) | IC50 p110 alpha/ IC50 p110 delta |
|---|---|---|---|---|
| 225 | 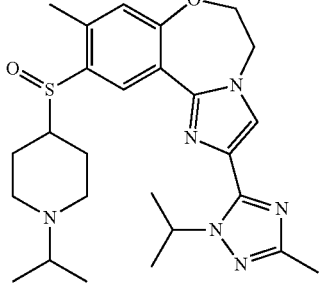 | 2-(1-isopropyl-3-methyl-1H-1,2,4-triazol-5-yl)-10-(1-isopropylpiperidin-4-ylsulfinyl)-9-methyl-5,6-dihydrobenzo[f]imidazo[1,2-d][1,4]oxazepine | | |
| 226 | 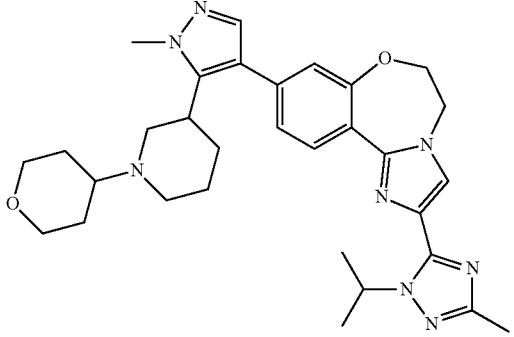 [SMILES: Cc1nc(-c2cn3c(n2)-c2ccc(-c4cnn(C)c4C4CCCN(C5CCOCC5)C4)cc2OCC3)n(C(C)C)n1] | 2-(1-isopropyl-3-methyl-1H-1,2,4-triazol-5-yl)-9-(1-methyl-5-(1-(tetrahydro-2H-pyran-4-yl)piperidin-3-yl)-1H-pyrazol-4-yl)-5,6-dihydrobenzo[f]imidazo[1,2-d][1,4]oxazepine | | |
| 227 | 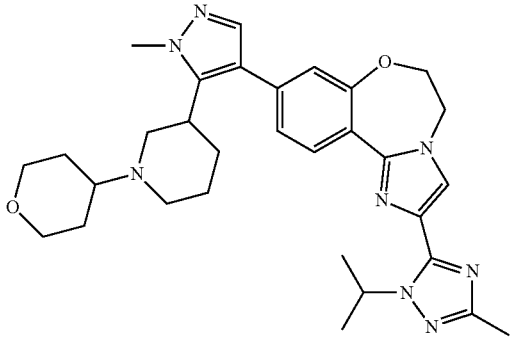 [SMILES: Cc1nc(-c2cn3c(n2)-c2ccc(-c4cnn(C)c4C4CCCN(C5CCOCC5)C4)cc2OCC3)n(C(C)C)n1] | 2-(1-isopropyl-3-methyl-1H-1,2,4-triazol-5-yl)-9-(1-methyl-5-(1-(tetrahydro-2H-pyran-4-yl)piperidin-3-yl)-1H-pyrazol-4-yl)-5,6-dihydrobenzo[f]imidazo[1,2-d][1,4]oxazepine | | |
| 228 | | | | |
| 229 | | | | |
| 230 | 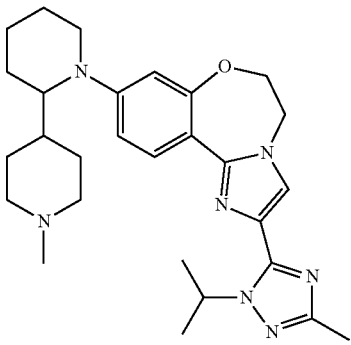 [SMILES: Cc1nc(-c2cn3c(n2)-c2ccc(N4CCCCC4C4CCN(C)CC4)cc2OCC3)n(C(C)C)n1] | 2-(1-isopropyl-3-methyl-1H-1,2,4-triazol-5-yl)-9-(1'-methyl-2,4'-bipiperidin-1-yl)-5,6-dihydrobenzo[f]imidazo[1,2-d][1,4]oxazepine | | |

TABLE 1-continued

| No. | Structure | Name | p110 delta IC50 (μM) | IC50 p110 alpha/ IC50 p110 delta |
|---|---|---|---|---|
| 231 | 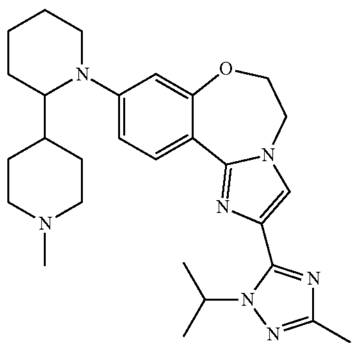 [SMILES: Cc1nc(-c2cn3c(n2)-c2ccc(N4CCCCC4C4CCN(C)CC4)cc2OCC3)n(C(C)C)n1] | 2-(1-isopropyl-3-methyl-1H-1,2,4-triazol-5-yl)-9-(1'-methyl-2,4'-bipiperidin-1-yl)-5,6-dihydrobenzo[f]imidazo[1,2-d][1,4]oxazepine | | |
| 232 | 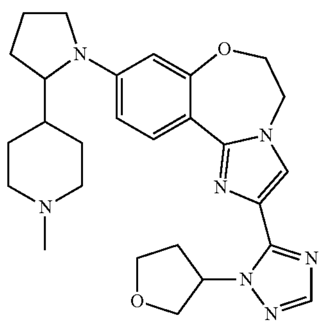 [SMILES: CN1CCC(C2CCCN2c2ccc3c(c2)OCCn2cc(-c4ncnn4C4CCOC4)nc2-3)CC1] | 9-(2-(1-methylpiperidin-4-yl)pyrrolidin-1-yl)-2-(1-(tetrahydrofuran-3-yl)-1H-1,2,4-triazol-5-yl)-5,6-dihydrobenzo[f]imidazo[1,2-d][1,4]oxazepine | | |
| 233 | 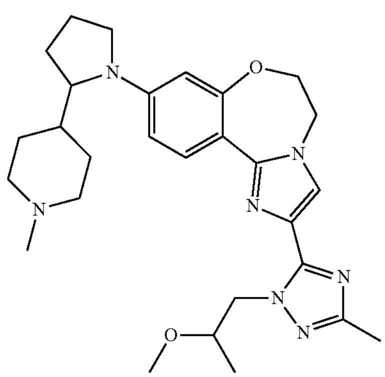 [SMILES: COC(C)Cn1nc(C)nc1-c1cn2c(n1)-c1ccc(N3CCCC3C3CCN(C)CC3)cc1OCC2] | 2-(1-(2-methoxypropyl)-3-methyl-1H-1,2,4-triazol-5-yl)-9-(2-(1-methylpiperidin-4-yl)pyrrolidin-1-yl)-5,6-dihydrobenzo[f]imidazo[1,2-d][1,4]oxazepine | | |
| 234 | 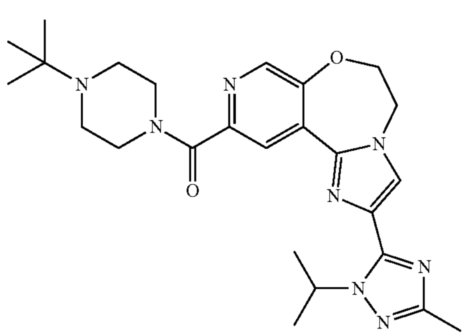 [SMILES: Cc1nc(-c2cn3c(n2)-c2cc(C(=O)N4CCN(C(C)(C)C)CC4)ncc2OCC3)n(C(C)C)n1] | (4-tert-butylpiperazin-1-yl)(2-(1-isopropyl-3-methyl-1H-1,2,4-triazol-5-yl)-5,6-dihydroimidazo[1,2-d]pyrido[4,3-f][1,4]oxazepin-10-yl)methanone | | |

TABLE 1-continued

| No. | Structure | Name | p110 delta IC50 (μM) | IC50 p110 alpha/ IC50 p110 delta |
|---|---|---|---|---|
| 235 | 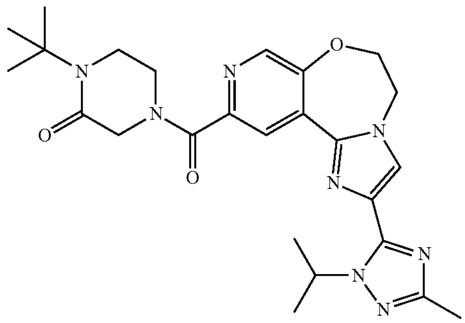 [SMILES: Cc1nc(-c2cn3c(n2)-c2cc(C(=O)N4CCN(C(C)(C)C)C(=O)C4)ncc2OCC3)n(C(C)C)n1] | 1-tert-butyl-4-(2-(1-isopropyl-3-methyl-1H-1,2,4-triazol-5-yl)-5,6-dihydroimidazo[1,2-d]pyrido[4,3-f][1,4]oxazepine-10-carbonyl)piperazin-2-one | | |
| 236 | 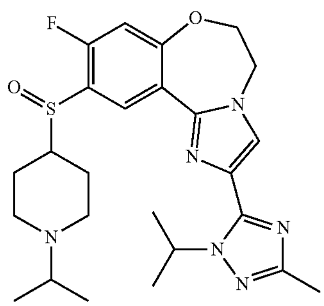 [SMILES: Cc1nc(-c2cn3c(n2)-c2cc(S(=O)C4CCN(C(C)C)CC4)c(F)cc2OCC3)n(C(C)C)n1] | 9-fluoro-2-(1-isopropyl-3-methyl-1H-1,2,4-triazol-5-yl)-10-(1-isopropylpiperidin-4-ylsulfinyl)-5,6-dihydrobenzo[f]imidazo[1,2-d][1,4]oxazepine | | |
| 237 | 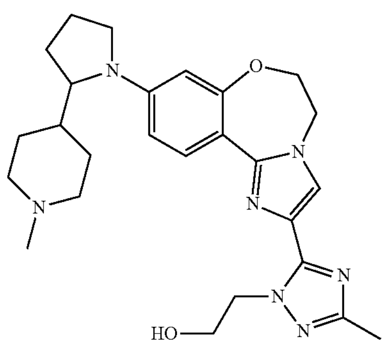 [SMILES: Cc1nc(-c2cn3c(n2)-c2ccc(N4CCCC4C4CCN(C)CC4)cc2OCC3)n(CCO)n1] | 2-(3-methyl-5-(9-(2-(1-methylpiperidin-4-yl)pyrrolidin-1-yl)-5,6-dihydrobenzo[f]imidazo[1,2-d][1,4]oxazepin-2-yl)-1H-1,2,4-triazol-1-yl)ethanol | | |
| 238 | 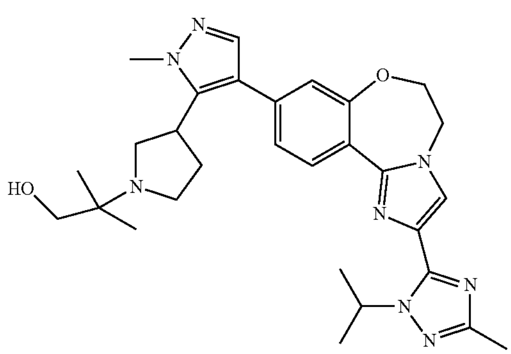 [SMILES: Cc1nc(-c2cn3c(n2)-c2ccc(-c4cnn(C)c4C4CCN(C(C)(C)CO)C4)cc2OCC3)n(C(C)C)n1] | 2-(3-(4-(2-(1-isopropyl-3-methyl-1H-1,2,4-triazol-5-yl)-5,6-dihydrobenzo[f]imidazo[1,2-d][1,4]oxazepin-9-yl)-1-methyl-1H-pyrazol-5-yl)pyrrolidin-1-yl)-2-methylpropan-1-ol | | |

TABLE 1-continued

| No. | Structure | Name | p110 delta IC50 (μM) | IC50 p110 alpha/ IC50 p110 delta |
|---|---|---|---|---|
| 239 | 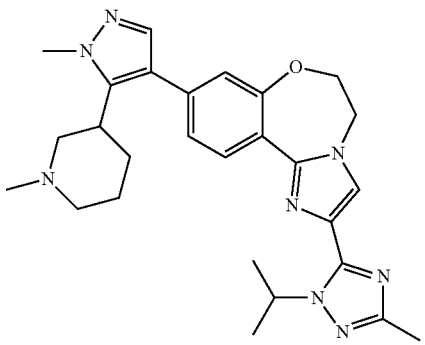 | 2-(1-isopropyl-3-methyl-1H-1,2,4-triazol-5-yl)-9-(1-methyl-5-(1-methylpiperidin-3-yl)-1H-pyrazol-4-yl)-5,6-dihydrobenzo[f]imidazo[1,2-d][1,4]oxazepine | | |
| 240 | 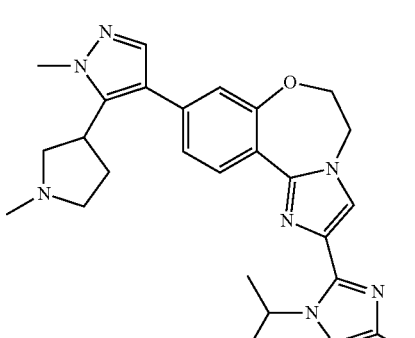 | 2-(1-isopropyl-3-methyl-1H-1,2,4-triazol-5-yl)-9-(1-methyl-5-(1-methylpyrrolidin-3-yl)-1H-pyrazol-4-yl)-5,6-dihydrobenzo[f]imidazo[1,2-d][1,4]oxazepine | | |
| 241 | 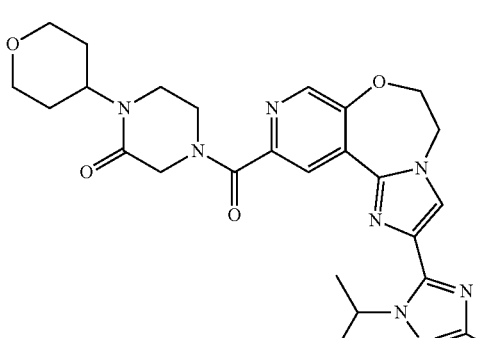 | 4-(2-(1-isopropyl-3-methyl-1H-1,2,4-triazol-5-yl)-5,6-dihydroimidazo[1,2-d]pyrido[4,3-f][1,4]oxazepine-10-carbonyl)-1-(tetrahydro-2H-pyran-4-yl)piperazin-2-one | | |
| 242 | 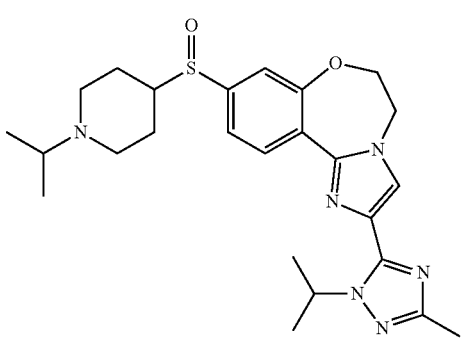 [SMILES: Cc1nc(-c2cn3c(n2)-c2ccc(S(=O)C4CCN(C(C)C)CC4)cc2OCC3)n(C(C)C)n1] | 2-(1-isopropyl-3-methyl-1H-1,2,4-triazol-5-yl)-9-(1-isopropylpiperidin-4-ylsulfinyl)-5,6-dihydrobenzo[f]imidazo[1,2-d][1,4]oxazepine | | |

TABLE 1-continued

| No. | Structure | Name | p110 delta IC50 (μM) | IC50 p110 alpha/ IC50 p110 delta |
|---|---|---|---|---|
| 243 | 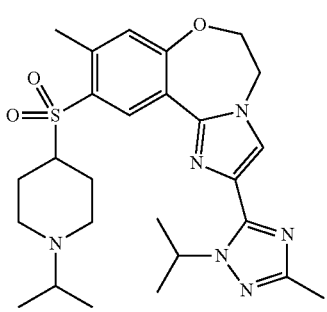 [SMILES: Cc1nc(-c2cn3c(n2)-c2cc(S(=O)(=O)C4CCN(C(C)C)CC4)c(C)cc2OCC3)n(C(C)C)n1] | 2-(1-isopropyl-3-methyl-1H-1,2,4-triazol-5-yl)-10-(1-isopropylpiperidin-4-ylsulfonyl)-9-methyl-5,6-dihydrobenzo[f]imidazo[1,2-d][1,4]oxazepine | | |
| 244 | 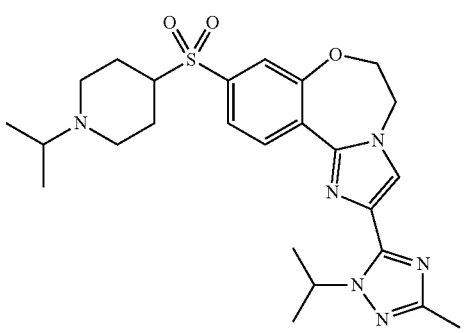 [SMILES: Cc1nc(-c2cn3c(n2)-c2ccc(S(=O)(=O)C4CCN(C(C)C)CC4)cc2OCC3)n(C(C)C)n1] | 2-(1-isopropyl-3-methyl-1H-1,2,4-triazol-5-yl)-9-(1-isopropylpiperidin-4-ylsulfonyl)-5,6-dihydrobenzo[f]imidazo[1,2-d][1,4]oxazepine | | |
| 245 | | | | |
| 246 | 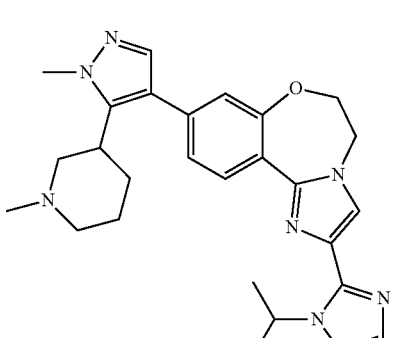 | 2-(1-isopropyl-3-methyl-1H-1,2,4-triazol-5-yl)-9-(1-methyl-5-(1-methylpiperidin-3-yl)-1H-pyrazol-4-yl)-5,6-dihydrobenzo[f]imidazo[1,2-d][1,4]oxazepine | | |
| 247 | 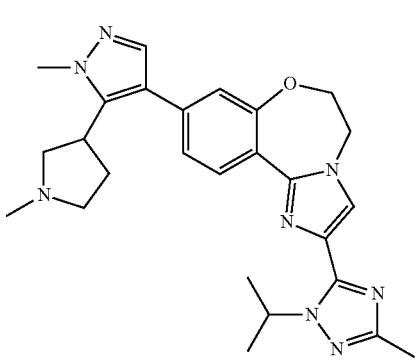 | 2-(1-isopropyl-3-methyl-1H-1,2,4-triazol-5-yl)-9-(1-methyl-5-(1-methylpyrrolidin-3-yl)-1H-pyrazol-4-yl)-5,6-dihydrobenzo[f]imidazo[1,2-d][1,4]oxazepine | | |

TABLE 1-continued

| No. | Structure | Name | p110 delta IC50 (μM) | IC50 p110 alpha/ IC50 p110 delta |
|---|---|---|---|---|
| 248 | 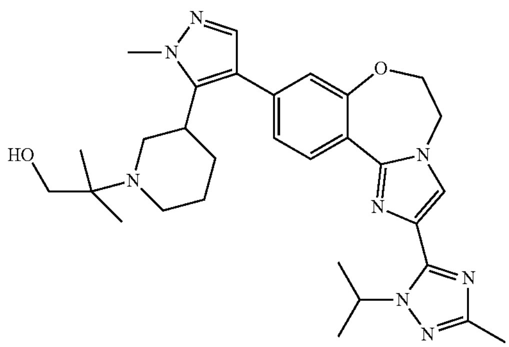 [SMILES: Cc1nc(-c2cn3c(n2)-c2ccc(-c4cnn(C)c4C4CCCN(C(C)(C)CO)C4)cc2OCC3)n(C(C)C)n1] | 2-(3-(4-(2-(1-isopropyl-3-methyl-1H-1,2,4-triazol-5-yl)-5,6-dihydrobenzo[f]imidazo[1,2-d][1,4]oxazepin-9-yl)-1-methyl-1H-pyrazol-5-yl)piperidin-1-yl)-2-methylpropan-1-ol | 0.000445 | 69.5 |
| 249 | 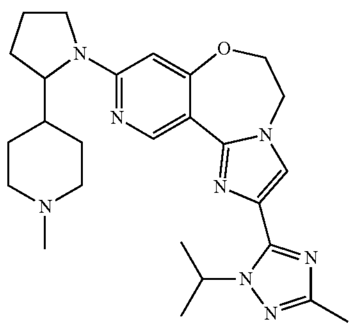 [SMILES: Cc1nc(-c2cn3c(n2)-c2cnc(N4CCCC4C4CCN(C)CC4)cc2OCC3)n(C(C)C)n1] | 2-(1-isopropyl-3-methyl-1H-1,2,4-triazol-5-yl)-9-(2-(1-methylpiperidin-4-yl)pyrrolidin-1-yl)-5,6-dihydroimidazo[1,2-d]pyrido[3,4-f][1,4]oxazepine | | |
| 250 | 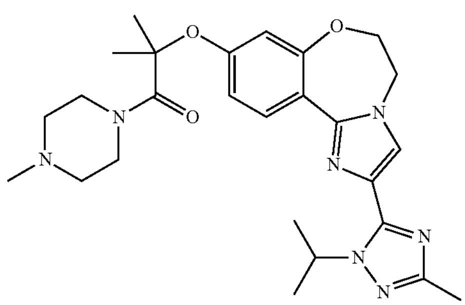 | 2-(2-(1-isopropyl-3-methyl-1H-1,2,4-triazol-5-yl)-5,6-dihydrobenzo[f]imidazo[1,2-d][1,4]oxazepin-9-yloxy)-2-methyl-1-(4-methylpiperazin-1-yl)propan-1-one | | |
| 251 | 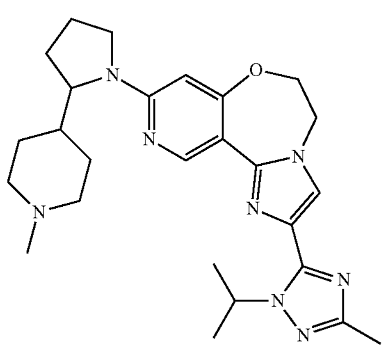 | 2-(1-isopropyl-3-methyl-1H-1,2,4-triazol-5-yl)-9-(2-(1-methylpiperidin-4-yl)pyrrolidin-1-yl)-5,6-dihydroimidazo[1,2-d]pyrido[3,4-f][1,4]oxazepine | | |

TABLE 1-continued

| No. | Structure | Name | p110 delta IC50 (μM) | IC50 p110 alpha/ IC50 p110 delta |
|---|---|---|---|---|
| 252 | 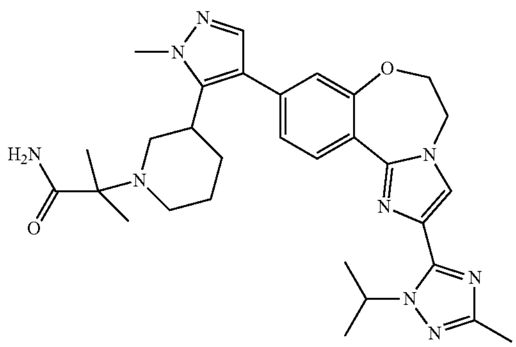 [SMILES: Cc1nc(-c2cn3c(n2)-c2ccc(-c4cnn(C)c4C4CCCN(C(C)(C)C(N)=O)C4)cc2OCC3)n(C(C)C)n1] | 2-(3-(4-(2-(1-isopropyl-3-methyl-1H-1,2,4-triazol-5-yl)-5,6-dihydrobenzo[f]imidazo[1,2-d][1,4]oxazepin-9-yl)-1-methyl-1H-pyrazol-5-yl)piperidin-1-yl)-2-methylpropanamide | | |
| 253 | 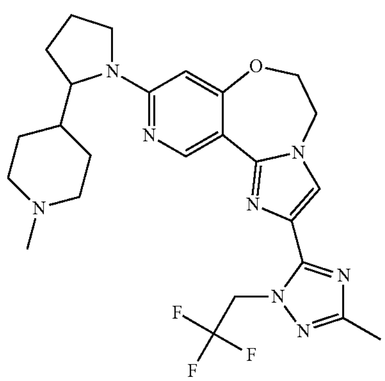 [SMILES: Cc1nc(-c2cn3c(n2)-c2cnc(N4CCCC4C4CCN(C)CC4)cc2OCC3)n(CC(F)(F)F)n1] | 2-(3-methyl-1-(2,2,2-trifluoroethyl)-1H-1,2,4-triazol-5-yl)-9-(2-(1-methylpiperidin-4-yl)pyrrolidin-1-yl)-5,6-dihydroimidazo[1,2-d]pyrido[3,4-f][1,4]oxazepine | | |
| 254 | 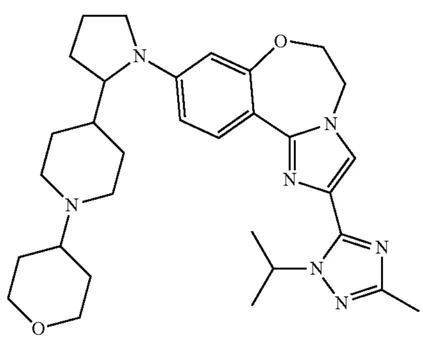 [SMILES: Cc1nc(-c2cn3c(n2)-c2ccc(N4CCCC4C4CCN(C5CCOCC5)CC4)cc2OCC3)n(C(C)C)n1] | 2-(1-isopropyl-3-methyl-1H-1,2,4-triazol-5-yl)-9-(2-(1-(tetrahydro-2H-pyran-4-yl)piperidin-4-yl)pyrrolidin-1-yl)-5,6-dihydrobenzo[f]imidazo[1,2-d][1,4]oxazepine | | |
| 255 | 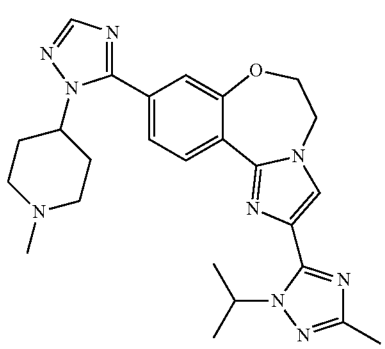 [SMILES: Cc1nc(-c2cn3c(n2)-c2ccc(-c4ncnn4C4CCN(C)CC4)cc2OCC3)n(C(C)C)n1] | 2-(1-isopropyl-3-methyl-1H-1,2,4-triazol-5-yl)-9-(1-(1-methylpiperidin-4-yl)-1H-1,2,4-triazol-5-yl)-5,6-dihydrobenzo[f]imidazo[1,2-d][1,4]oxazepine | | |

TABLE 1-continued

| No. | Structure | Name | p110 delta IC50 (μM) | IC50 p110 alpha/ IC50 p110 delta |
|-----|-----------|------|----------------------|----------------------------------|
| 256 | 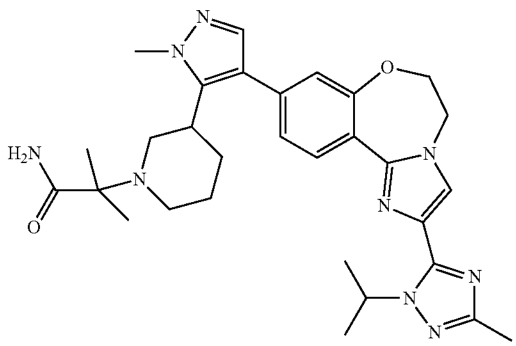 [SMILES: Cc1nc(-c2cn3c(n2)-c2ccc(-c4cnn(C)c4C4CCCN(C(C)(C)C(N)=O)C4)cc2OCC3)n(C(C)C)n1] | 2-(3-(4-(2-(1-isopropyl-3-methyl-1H-1,2,4-triazol-5-yl)-5,6-dihydrobenzo[f]imidazo[1,2-d][1,4]oxazepin-9-yl)-1-methyl-1H-pyrazol-5-yl)piperidin-1-yl)-2-methylpropanamide | | |
| 257 | 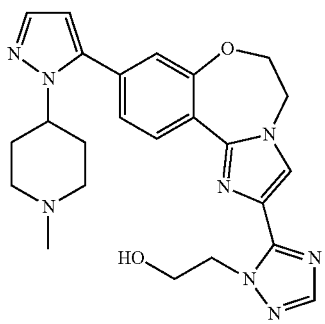 [SMILES: CN1CCC(n2nccc2-c2ccc3c(c2)OCCn2cc(-c4ncnn4CCO)nc2-3)CC1] | 2-(5-(9-(1-(1-methylpiperidin-4-yl)-1H-pyrazol-5-yl)-5,6-dihydrobenzo[f]imidazo[1,2-d][1,4]oxazepin-2-yl)-1H-1,2,4-triazol-1-yl)ethanol | | |
| 258 | 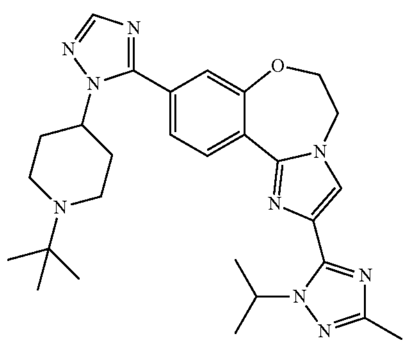 [SMILES: Cc1nc(-c2cn3c(n2)-c2ccc(-c4ncnn4C4CCN(C(C)(C)C)CC4)cc2OCC3)n(C(C)C)n1] | 9-(1-(1-tert-butylpiperidin-4-yl)-1H-1,2,4-triazol-5-yl)-2-(1-isopropyl-3-methyl-1H-1,2,4-triazol-5-yl)-5,6-dihydrobenzo[f]imidazo[1,2-d][1,4]oxazepine | 0.0821 | 10.2 |
| 259 | 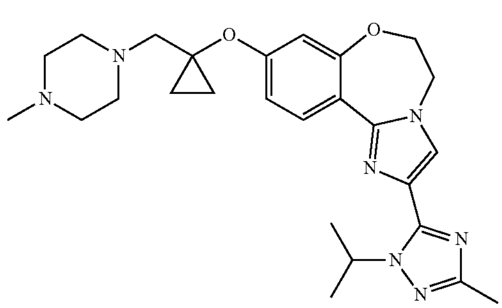 | 2-(1-isopropyl-3-methyl-1H-1,2,4-triazol-5-yl)-9-(1-((4-methylpiperazin-1-yl)methyl)cyclopropoxy)-5,6-dihydrobenzo[f]imidazo[1,2-d][1,4]oxazepine | 0.00331 | 26.1 |

TABLE 1-continued

| No. | Structure | Name | p110 delta IC50 (μM) | IC50 p110 alpha/ IC50 p110 delta |
|---|---|---|---|---|
| 260 | 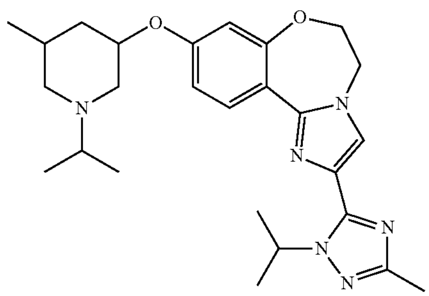 | 2-(1-isopropyl-3-methyl-1H-1,2,4-triazol-5-yl)-9-(1-isopropyl-5-methylpiperidin-3-yloxy)-5,6-dihydrobenzo[f]imidazo[1,2-d][1,4]oxazepine | 0.00256 | 12.8 |
| 261 | 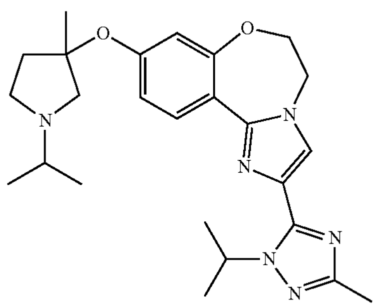 [SMILES: Cc1nc(-c2cn3c(n2)-c2ccc(OC4(C)CCN(C(C)C)C4)cc2OCC3)n(C(C)C)n1] | 2-(1-isopropyl-3-methyl-1H-1,2,4-triazol-5-yl)-9-(1-isopropyl-3-methylpyrrolidin-3-yloxy)-5,6-dihydrobenzo[f]imidazo[1,2-d][1,4]oxazepine | 0.000638 | 14.4 |
| 262 | 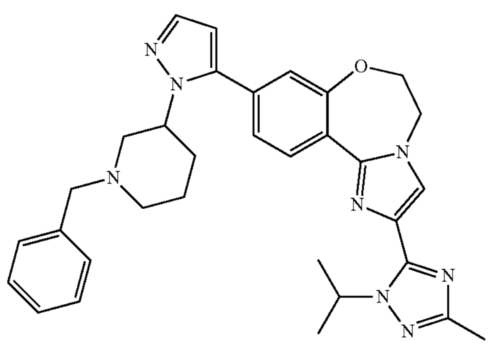 [SMILES: Cc1nc(-c2cn3c(n2)-c2ccc(-c4ccnn4C4CCCN(Cc5ccccc5)C4)cc2OCC3)n(C(C)C)n1] | 9-(1-(1-benzylpiperidin-3-yl)-1H-pyrazol-5-yl)-2-(1-isopropyl-3-methyl-1H-1,2,4-triazol-5-yl)-5,6-dihydrobenzo[f]imidazo[1,2-d][1,4]oxazepine | 0.00853 | 21.8 |
| 263 | 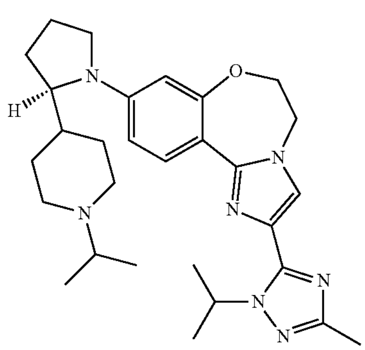 [SMILES: Cc1nc(-c2cn3c(n2)-c2ccc(N4CCC[C@@H]4C4CCN(C(C)C)CC4)cc2OCC3)n(C(C)C)n1] | (R)-2-(1-isopropyl-3-methyl-1H-1,2,4-triazol-5-yl)-9-(2-(1-isopropylpiperidin-4-yl)pyrrolidin-1-yl)-5,6-dihydrobenzo[f]imidazo[1,2-d][1,4]oxazepine | 0.000584 | 37.5 |

TABLE 1-continued

| No. | Structure | Name | p110 delta IC50 (μM) | IC50 p110 alpha/ IC50 p110 delta |
|---|---|---|---|---|
| 264 | 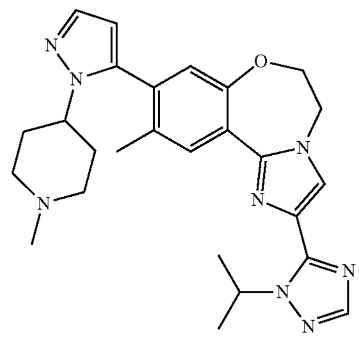 [SMILES: Cc1cc2c(cc1-c1ccnn1C1CCN(C)CC1)OCCn1cc(-c3ncnn3C(C)C)nc1-2] | 2-(1-isopropyl-1H-1,2,4-triazol-5-yl)-10-methyl-9-(1-(1-methylpiperidin-4-yl)-1H-pyrazol-5-yl)-5,6-dihydrobenzo[f]imidazo[1,2-d][1,4]oxazepine | 0.0173 | 10 |
| 265 | 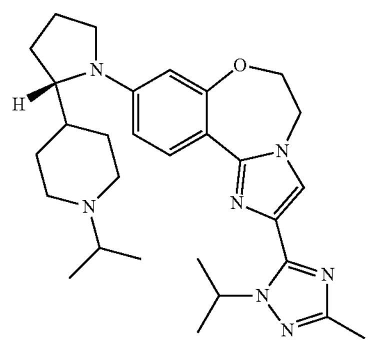 [SMILES: Cc1nc(-c2cn3c(n2)-c2ccc(N4CCC[C@H]4C4CCN(C(C)C)CC4)cc2OCC3)n(C(C)C)n1] | (S)-2-(1-isopropyl-3-methyl-1H-1,2,4-triazol-5-yl)-9-(2-(1-isopropylpiperidin-4-yl)pyrrolidin-1-yl)-5,6-dihydrobenzo[f]imidazo[1,2-d][1,4]oxazepine | 0.00051 | 39.8 |
| 266 | 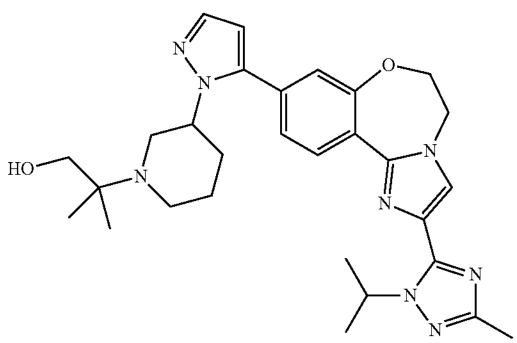 [SMILES: Cc1nc(-c2cn3c(n2)-c2ccc(-c4ccnn4C4CCCN(C(C)(C)CO)C4)cc2OCC3)n(C(C)C)n1] | 2-(3-(5-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)piperidin-1-yl)-2-methylpropan-1-ol | 0.000596 | 24.2 |
| 267 | 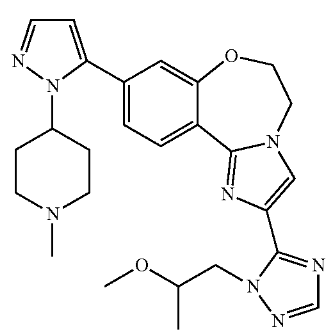 [SMILES: COC(C)Cn1ncnc1-c1cn2c(n1)-c1ccc(-c3ccnn3C3CCN(C)CC3)cc1OCC2] | 2-(1-(2-methoxypropyl)-1H-1,2,4-triazol-5-yl)-9-(1-(1-methylpiperidin-4-yl)-1H-pyrazol-5-yl)-5,6-dihydrobenzo[f]imidazo[1,2-d][1,4]oxazepine | | |

TABLE 1-continued

| No. | Structure | Name | p110 delta IC50 (µM) | IC50 p110 alpha/ IC50 p110 delta |
|---|---|---|---|---|
| 268 | 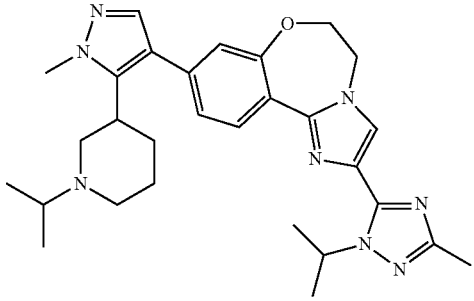 [SMILES: Cc1nc(-c2cn3c(n2)-c2ccc(-c4cnn(C)c4C4CCCN(C(C)C)C4)cc2OCC3)n(C(C)C)n1] | 2-(1-isopropyl-3-methyl-1H-1,2,4-triazol-5-yl)-9-(5-(1-isopropylpiperidin-3-yl)-1-methyl-1H-pyrazol-4-yl)-5,6-dihydrobenzo[f]imidazo[1,2-d][1,4]oxazepine | | |

TABLE 2

| No. | Structure | IUPAC_Name | p110 delta IC50 (µM) | IC50 p110 alpha/ IC50 p110 delta |
|---|---|---|---|---|
| 269 | 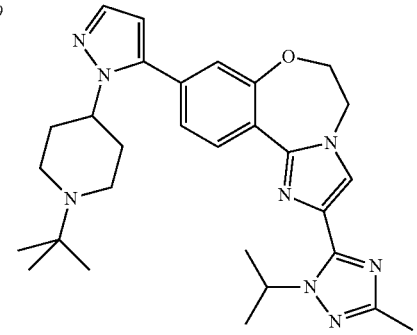 | 9-[2-(1-tert-butyl-4-piperidyl)pyrazol-3-yl]-2-(2-isopropyl-5-methyl-1,2,4-triazol-3-yl)-5,6-dihydroimidazo[1,2-d][1,4]benzoxazepine | 0.00457 | 9.8 |
| 270 | 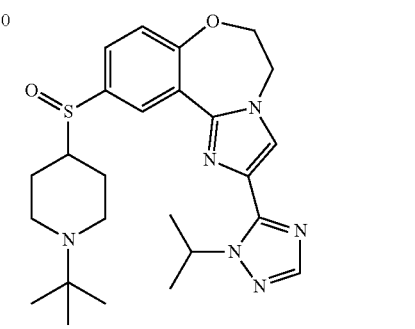 | 10-(1-tert-butylpiperidin-4-ylsulfinyl)-2-(1-isopropyl-1H-1,2,4-triazol-5-yl)-5,6-dihydrobenzo[f]imidazo[1,2-d][1,4]oxazepine | 0.000811 | 184 |
| 271 | 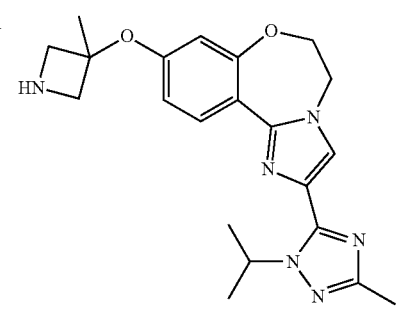 | 2-(2-isopropyl-5-methyl-1,2,4-triazol-3-yl)-9-(3-methylazetidin-3-yl)oxy-5,6-dihydroimidazo[1,2-d][1,4]benzoxazepine | 0.000633 | 9.8 |

TABLE 2-continued

| No. | Structure | IUPAC_Name | p110 delta IC50 (μM) | IC50 p110 alpha/ IC50 p110 delta |
|-----|-----------|------------|----------------------|----------------------------------|
| 272 | 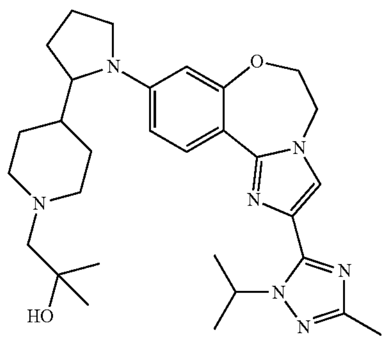 [SMILES: Cc1nc(-c2cn3c(n2)-c2ccc(N4CCCC4C4CCN(CC(C)(C)O)CC4)cc2OCC3)n(C(C)C)n1] | 1-[4-[1-[2-(2-isopropyl-5-methyl-1,2,4-triazol-3-yl)-5,6-dihydroimidazo[1,2-d][1,4]benzoxazepin-9-yl]pyrrolidin-2-yl]-1-piperidyl]-2-methyl-propan-2-ol | 0.000986 | 49.9 |
| 273 | 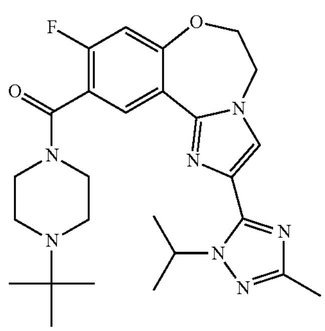 [SMILES: Cc1nc(-c2cn3c(n2)-c2cc(C(=O)N4CCN(C(C)(C)C)CC4)c(F)cc2OCC3)n(C(C)C)n1] | (4-tert-butylpiperazin-1-yl)-[9-fluoro-2-(2-isopropyl-5-methyl-1,2,4-triazol-3-yl)-5,6-dihydroimidazo[1,2-d][1,4]benzoxazepin-10-yl]methanone | 0.00273 | 69.9 |
| 274 | 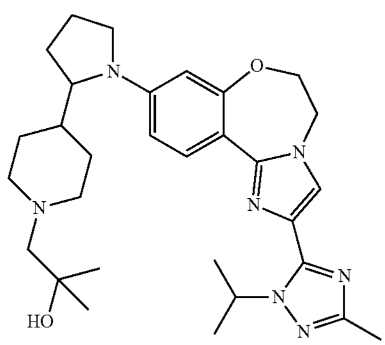 [SMILES: Cc1nc(-c2cn3c(n2)-c2ccc(N4CCCC4C4CCN(CC(C)(C)O)CC4)cc2OCC3)n(C(C)C)n1] | 1-[4-[1-[2-(2-isopropyl-5-methyl-1,2,4-triazol-3-yl)-5,6-dihydroimidazo[1,2-d][1,4]benzoxazepin-9-yl]pyrrolidin-2-yl]-1-piperidyl]-2-methyl-propan-2-ol | 0.0022 | 34 |
| 275 | 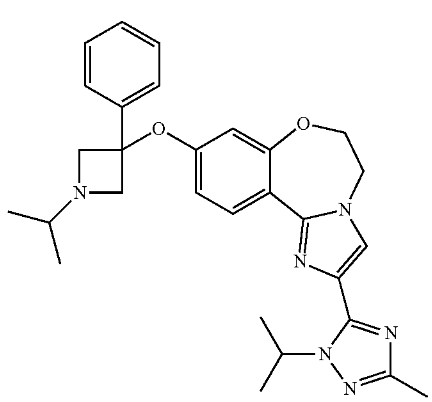 [SMILES: Cc1nc(-c2cn3c(n2)-c2ccc(OC4(c5ccccc5)CN(C(C)C)C4)cc2OCC3)n(C(C)C)n1] | 2-(2-isopropyl-5-methyl-1,2,4-triazol-3-yl)-9-(1-isopropyl-3-phenyl-azetidin-3-yl)oxy-5,6-dihydroimidazo[1,2-d][1,4]benzoxazepine | 0.0062 | 17 |

TABLE 2-continued

| No. | Structure | IUPAC_Name | p110 delta IC50 (μM) | IC50 p110 alpha/ IC50 p110 delta |
|---|---|---|---|---|
| 276 | 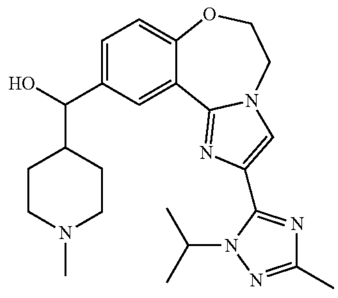 [SMILES: Cc1nc(-c2cn3c(n2)-c2cc(C(O)C4CCN(C)CC4)ccc2OCC3)n(C(C)C)n1] | [2-(2-isopropyl-5-methyl-1,2,4-triazol-3-yl)-5,6-dihydroimidazo[1,2-d][1,4]benzoxazepin-10-yl]-(1-methyl-4-piperidyl)methanol | 0.0179 | 10.8 |
| 277 | 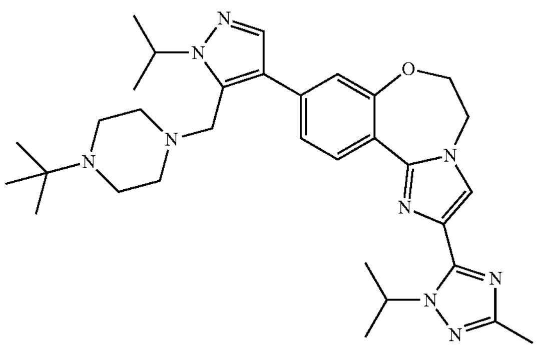 [SMILES: Cc1nc(-c2cn3c(n2)-c2ccc(-c4cnn(C(C)C)c4CN4CCN(C(C)(C)C)CC4)cc2OCC3)n(C(C)C)n1] | 9-[5-[(4-tert-butylpiperazin-1-yl)methyl]-1-isopropyl-pyrazol-4-yl]-2-(2-isopropyl-5-methyl-1,2,4-triazol-3-yl)-5,6-dihydroimidazo[1,2-d][1,4]benzoxazepine | 0.004 | 27.8 |
| 278 | 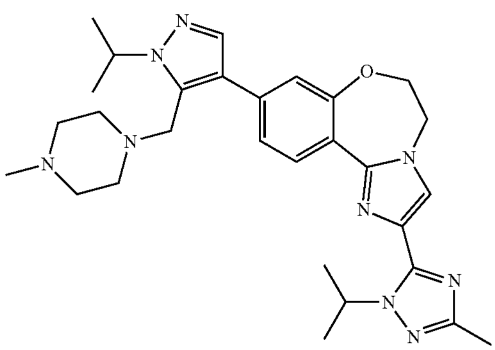 | 9-[1-isopropyl-5-[(4-methylpiperazin-1-yl)methyl]pyrazol-4-yl]-2-(2-isopropyl-5-methyl-1,2,4-triazol-3-yl)-5,6-dihydroimidazo[1,2-d][1,4]benzoxazepine | 0.00334 | 33.4 |
| 279 | 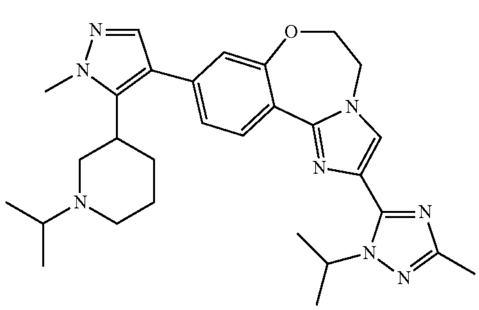 | 2-(2-isopropyl-5-methyl-1,2,4-triazol-3-yl)-9-[5-(1-isopropyl-3-piperidyl)-1-methyl-pyrazol-4-yl]-5,6-dihydroimidazo[1,2-d][1,4]benzoxazepine | 0.000324 | 178 |

| No. | Structure | IUPAC_Name | p110 delta IC50 (μM) | IC50 p110 alpha/ IC50 p110 delta |
|---|---|---|---|---|
| 280 | 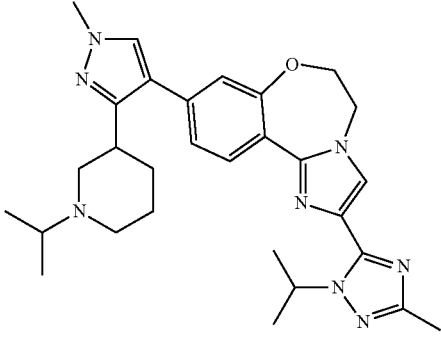 [SMILES: Cc1nc(-c2cn3c(n2)-c2ccc(-c4cn(C)nc4C4CCCN(C(C)C)C4)cc2OCC3)n(C(C)C)n1] | 2-(2-isopropyl-5-methyl-1,2,4-triazol-3-yl)-9-[3-(1-isopropyl-3-piperidyl)-1-methyl-pyrazol-4-yl]-5,6-dihydroimidazo[1,2-d][1,4]benzoxazepine | 0.000878 | 32.7 |
| 281 | 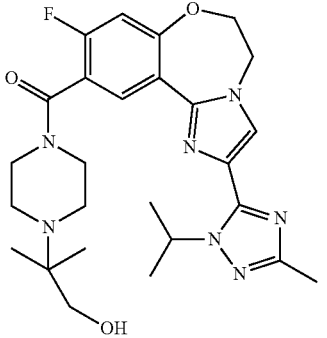 [SMILES: Cc1nc(-c2cn3c(n2)-c2cc(C(=O)N4CCN(C(C)(C)CO)CC4)c(F)cc2OCC3)n(C(C)C)n1] | [9-fluoro-2-(2-isopropyl-5-methyl-1,2,4-triazol-3-yl)-5,6-dihydroimidazo[1,2-d][1,4]benzoxazepin-10-yl]-[4-(2-hydroxy-1,1-dimethyl-ethyl)piperazin-1-yl]methanone | 0.00563 | 30.6 |
| 282 | 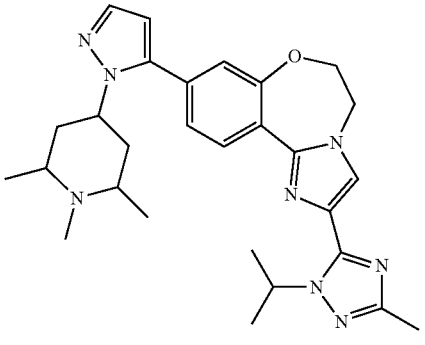 | 2-(2-isopropyl-5-methyl-1,2,4-triazol-3-yl)-9-[2-(1,2,6-trimethyl-4-piperidyl)pyrazol-3-yl]-5,6-dihydroimidazo[1,2-d][1,4]benzoxazepine | 0.0013 | 76.9 |
| 283 | 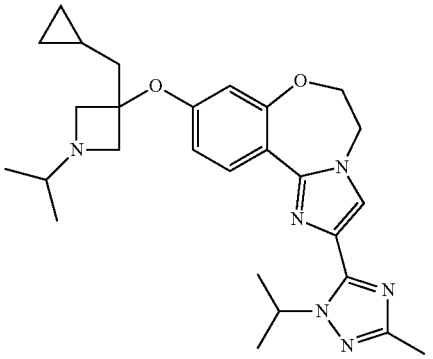 [SMILES: Cc1nc(-c2cn3c(n2)-c2ccc(OC4(CC5CC5)CN(C(C)C)C4)cc2OCC3)n(C(C)C)n1] | 9-[3-(cyclopropylmethyl)-1-isopropyl-azetidin-3-yl]oxy-2-(2-isopropyl-5-methyl-1,2,4-triazol-3-yl)-5,6-dihydroimidazo[1,2-d][1,4]benzoxazepine | 0.000936 | 75.5 |

TABLE 2-continued

| No. | Structure | IUPAC_Name | p110 delta IC50 (µM) | IC50 p110 alpha/ IC50 p110 delta |
|---|---|---|---|---|
| 284 | 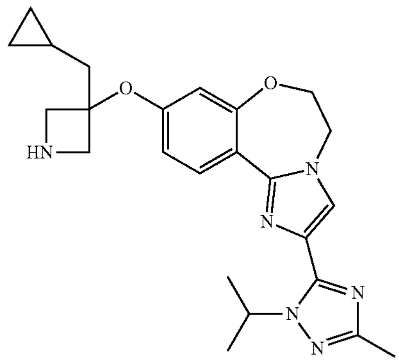 [SMILES: Cc1nc(-c2cn3c(n2)-c2ccc(OC4(CC5CC5)CNC4)cc2OCC3)n(C(C)C)n1] | 9-[3-(cyclopropylmethyl)azetidin-3-yl]oxy-2-(2-isopropyl-5-methyl-1,2,4-triazol-3-yl)-5,6-dihydroimidazo[1,2-d][1,4]benzoxazepine | 0.0029 | 23.9 |
| 285 | 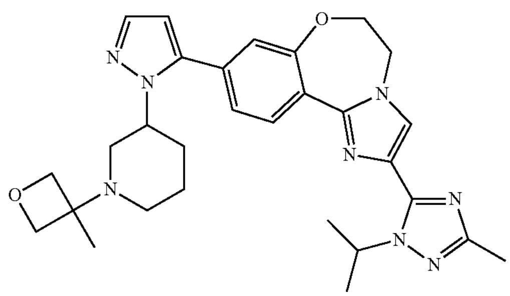 [SMILES: Cc1nc(-c2cn3c(n2)-c2ccc(-c4ccnn4C4CCCN(C5(C)COC5)C4)cc2OCC3)n(C(C)C)n1] | 2-(2-isopropyl-5-methyl-1,2,4-triazol-3-yl)-9-[2-[1-(3-methyloxetan-3-yl)-3-piperidyl]pyrazol-3-yl]-5,6-dihydroimidazo[1,2-d][1,4]benzoxazepine | 0.00139 | 31.9 |
| 286 | 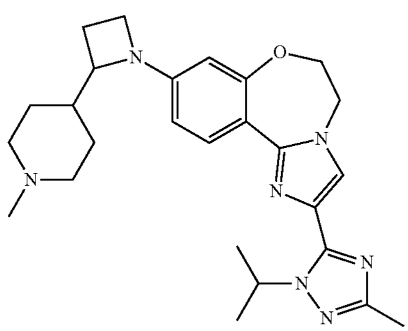 [SMILES: Cc1nc(-c2cn3c(n2)-c2ccc(N4CCC4C4CCN(C)CC4)cc2OCC3)n(C(C)C)n1] | 2-(2-isopropyl-5-methyl-1,2,4-triazol-3-yl)-9-[2-(1-methyl-4-piperidyl)azetidin-1-yl]-5,6-dihydroimidazo[1,2-d][1,4]benzoxazepine | 0.000529 | 40.7 |
| 287 | 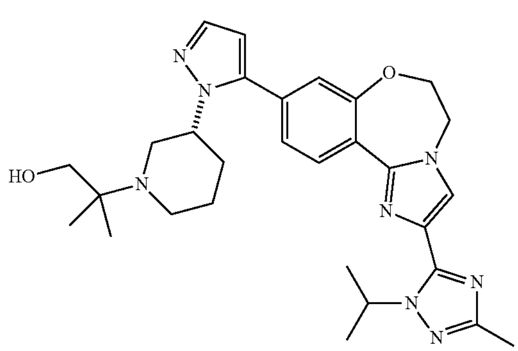 | (R)-2-(3-(5-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)piperidin-1-yl)-2-methylpropan-1-ol | 0.000292 | 37 |

TABLE 2-continued

| No. | Structure | IUPAC_Name | p110 delta IC50 (µM) | IC50 p110 alpha/ IC50 p110 delta |
|---|---|---|---|---|
| 288 | 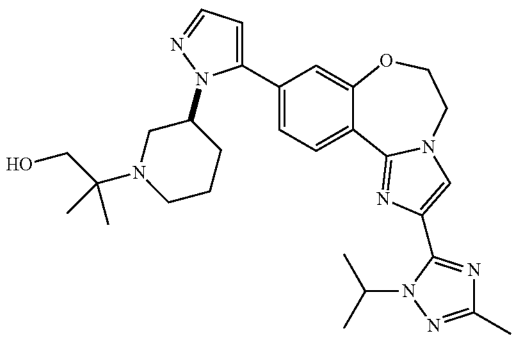 | (S)-2-(3-(5-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)piperidin-1-yl)-2-methylpropan-1-ol | 0.00201 | 21.4 |
| 289 | 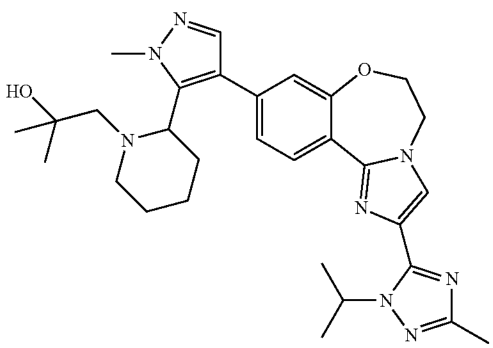 [SMILES: Cc1nc(-c2cn3c(n2)-c2ccc(-c4cnn(C)c4C4CCCCN4CC(C)(C)O)cc2OCC3)n(C(C)C)n1] | 1-[2-[4-[2-(2-isopropyl-5-methyl-1,2,4-triazol-3-yl)-5,6-dihydroimidazo[1,2-d][1,4]benzoxazepin-9-yl]-2-methyl-pyrazol-3-yl]-1-piperidyl]-2-methyl-propan-2-ol | 0.000852 | 13.1 |
| 290 | 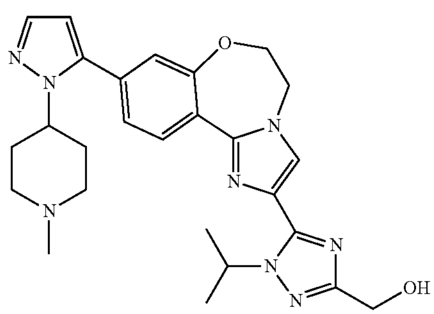 [SMILES: CC(C)n1nc(CO)nc1-c1cn2c(n1)-c1ccc(-c3ccnn3C3CCN(C)CC3)cc1OCC2] | [1-isopropyl-5-[9-[2-(1-methyl-4-piperidyl)pyrazol-3-yl]-5,6-dihydroimidazo[1,2-d][1,4]benzoxazepin-2-yl]-1,2,4-triazol-3-yl]methanol | 0.00242 | 15.9 |
| 291 | 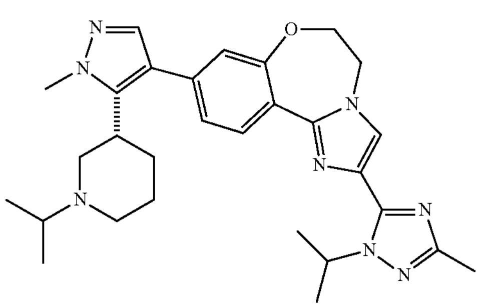 | (R)-2-(1-isopropyl-3-methyl-1H-1,2,4-triazol-5-yl)-9-(5-(1-isopropylpiperidin-3-yl)-1-methyl-1H-pyrazol-4-yl)-5,6-dihydrobenzo[f]imidazo[1,2-d][1,4]oxazepine | 0.000494 | 119 |

TABLE 2-continued

| No. | Structure | IUPAC_Name | p110 delta IC50 (μM) | IC50 p110 alpha/ IC50 p110 delta |
|---|---|---|---|---|
| 292 | 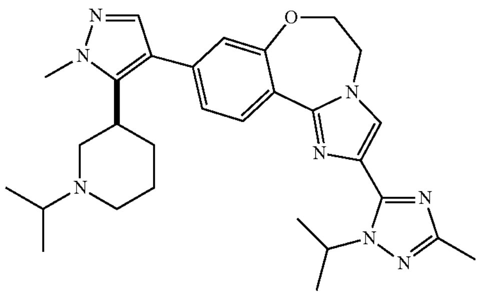 | (S)-2-(1-isopropyl-3-methyl-1H-1,2,4-triazol-5-yl)-9-(5-(1-isopropylpiperidin-3-yl)-1-methyl-1H-pyrazol-4-yl)-5,6-dihydrobenzo[f]imidazo[1,2-d][1,4]oxazepine | 0.000293 | 70.6 |
| 293 | 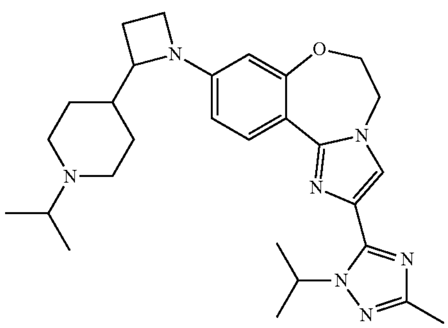 [SMILES: Cc1nc(-c2cn3c(n2)-c2ccc(N4CCC4C4CCN(C(C)C)CC4)cc2OCC3)n(C(C)C)n1] | 2-(2-isopropyl-5-methyl-1,2,4-triazol-3-yl)-9-[2-(1-isopropyl-4-piperidyl)azetidin-1-yl]-5,6-dihydroimidazo[1,2-d][1,4]benzoxazepine | 0.00147 | 10.3 |
| 294 | 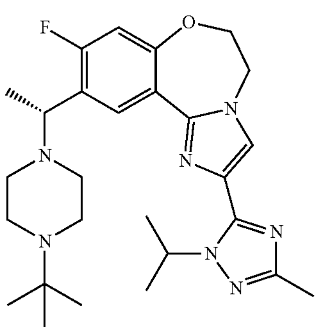 [SMILES: Cc1nc(-c2cn3c(n2)-c2cc([C@@H](C)N4CCN(C(C)(C)C)CC4)c(F)cc2OCC3)n(C(C)C)n1] | (R)-10-(1-(4-tert-butylpiperazin-1-yl)ethyl)-9-fluoro-2-(1-isopropyl-3-methyl-1H-1,2,4-triazol-5-yl)-5,6-dihydrobenzo[f]imidazo[1,2-d][1,4]oxazepine | 0.000777 | 479 |
| 295 | 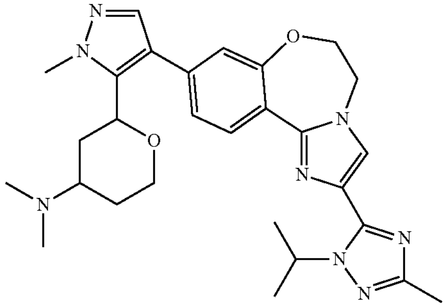 | 2-[4-[2-(2-isopropyl-5-methyl-1,2,4-triazol-3-yl)-5,6-dihydroimidazo[1,2-d][1,4]benzoxazepin-9-yl]-2-methyl-pyrazol-3-yl]-N,N-dimethyl-tetrahydropyran-4-amine | 0.000721 | 81.2 |

TABLE 2-continued

| No. | Structure | IUPAC_Name | p110 delta IC50 (μM) | IC50 p110 alpha/ IC50 p110 delta |
|---|---|---|---|---|
| 296 | 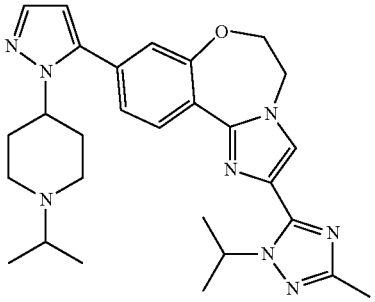 [SMILES: Cc1nc(-c2cn3c(n2)-c2ccc(-c4ccnn4C4CCN(C(C)C)CC4)cc2OCC3)n(C(C)C)n1] | 2-(2-isopropyl-5-methyl-1,2,4-triazol-3-yl)-9-[2-(1-isopropyl-4-piperidyl)pyrazol-3-yl]-5,6-dihydroimidazo[1,2-d][1,4]benzoxazepine | 0.00106 | 31.5 |
| 297 | 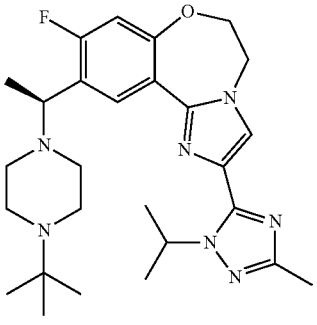 | (S)-10-(1-(4-tert-butylpiperazin-1-yl)ethyl)-9-fluoro-2-(1-isopropyl-3-methyl-1H-1,2,4-triazol-5-yl)-5,6-dihydrobenzo[f]imidazo[1,2-d][1,4]oxazepine | 0.00242 | 102 |
| 298 | 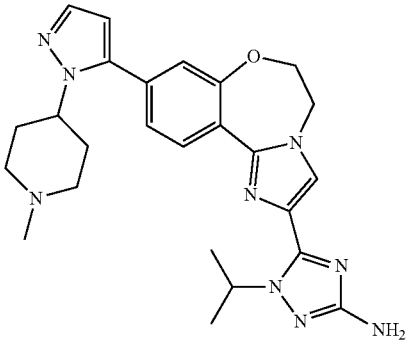 [SMILES: CC(C)n1nc(N)nc1-c1cn2c(n1)-c1ccc(-c3ccnn3C3CCN(C)CC3)cc1OCC2] | 1-isopropyl-5-[9-[2-(1-methyl-4-piperidyl)pyrazol-3-yl]-5,6-dihydroimidazo[1,2-d][1,4]benzoxazepin-2-yl]-1,2,4-triazol-3-amine | 0.000705 | 54.6 |
| 299 | 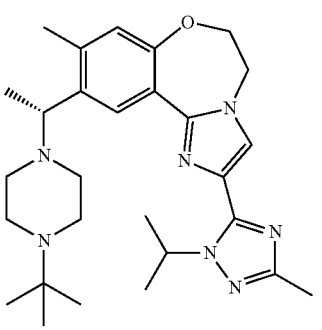 [SMILES: Cc1nc(-c2cn3c(n2)-c2cc([C@@H](C)N4CCN(C(C)(C)C)CC4)c(C)cc2OCC3)n(C(C)C)n1] | (R)-10-(1-(4-tert-butylpiperazin-1-yl)ethyl)-2-(1-isopropyl-3-methyl-1H-1,2,4-triazol-5-yl)-9-methyl-5,6-dihydrobenzo[f]imidazo[1,2-d][1,4]oxazepine | 0.000479 | 109 |

TABLE 2-continued

| No. | Structure | IUPAC_Name | p110 delta IC50 (μM) | IC50 p110 alpha/ IC50 p110 delta |
|---|---|---|---|---|
| 300 | 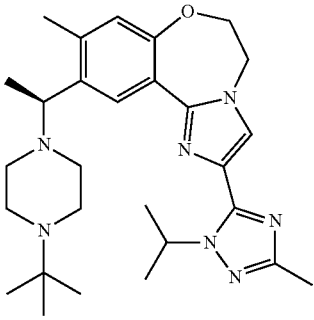 [SMILES: Cc1nc(-c2cn3c(n2)-c2cc([C@H](C)N4CCN(C(C)(C)C)CC4)c(C)cc2OCC3)n(C(C)C)n1] | (S)-10-(1-(4-tert-butylpiperazin-1-yl)ethyl)-2-(1-isopropyl-3-methyl-1H-1,2,4-triazol-5-yl)-9-methyl-5,6-dihydrobenzo[f]imidazo[1,2-d][1,4]oxazepine | 0.000881 | 27.3 |
| 301 | 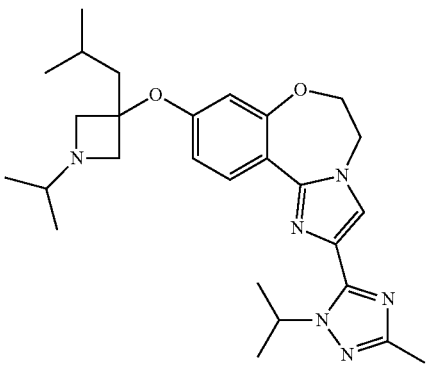 [SMILES: Cc1nc(-c2cn3c(n2)-c2ccc(OC4(CC(C)C)CN(C(C)C)C4)cc2OCC3)n(C(C)C)n1] | 9-(3-isobutyl-1-isopropyl-azetidin-3-yl)oxy-2-(2-isopropyl-5-methyl-1,2,4-triazol-3-yl)-5,6-dihydroimidazo[1,2-d][1,4]benzoxazepine | 0.00867 | 32.1 |
| 302 | 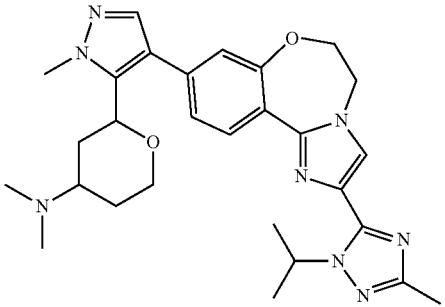 | 2-[4-[2-(2-isopropyl-5-methyl-1,2,4-triazol-3-yl)-5,6-dihydroimidazo[1,2-d][1,4]benzoxazepin-9-yl]-2-methyl-pyrazol-3-yl]-N,N-dimethyl-tetrahydropyran-4-amine | 0.00165 | 57.2 |
| 303 | 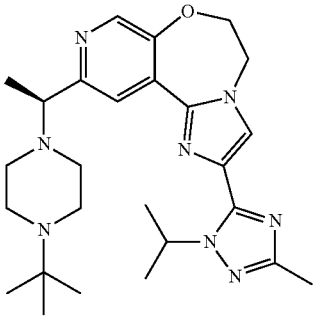 | (S)-10-(1-(4-tert-butylpiperazin-1-yl)ethyl)-2-(1-isopropyl-3-methyl-1H-1,2,4-triazol-5-yl)-5,6-dihydroimidazo[1,2-d]pyrido[4,3-f][1,4]oxazepine | 0.00192 | 113 |

TABLE 2-continued

| No. | Structure | IUPAC_Name | p110 delta IC50 (μM) | IC50 p110 alpha/ IC50 p110 delta |
|---|---|---|---|---|
| 304 | 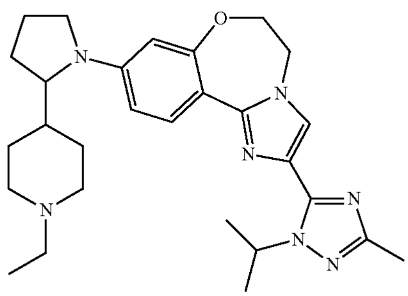 [SMILES: CCN1CCC(C2CCCN2c2ccc3c(c2)OCCn2cc(-c4nc(C)nn4C(C)C)nc2-3)CC1] | 9-[2-(1-ethyl-4-piperidyl)pyrrolidin-1-yl]-2-(2-isopropyl-5-methyl-1,2,4-triazol-3-yl)-5,6-dihydroimidazo[1,2-d][1,4]benzoxazepine | 0.00052 | 36.4 |
| 305 | 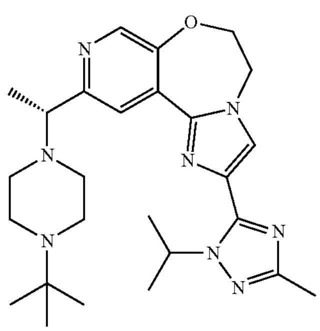 [SMILES: Cc1nc(-c2cn3c(n2)-c2cc([C@@H](C)N4CCN(C(C)(C)C)CC4)ncc2OCC3)n(C(C)C)n1] | (R)-10-(1-(4-tert-butylpiperazin-1-yl)ethyl)-2-(1-isopropyl-3-methyl-1H-1,2,4-triazol-5-yl)-5,6-dihydroimidazo[1,2-d]pyrido[4,3-f][1,4]oxazepine | 0.00281 | 28.6 |
| 306 | 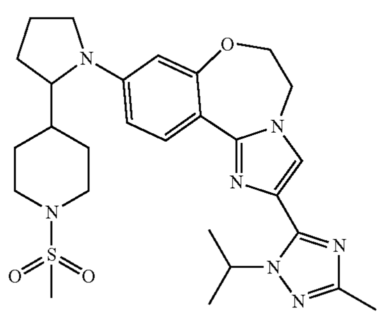 [SMILES: Cc1nc(-c2cn3c(n2)-c2ccc(N4CCCC4C4CCN(S(C)(=O)=O)CC4)cc2OCC3)n(C(C)C)n1] | 2-(2-isopropyl-5-methyl-1,2,4-triazol-3-yl)-9-[2-(1-methylsulfonyl-4-piperidyl)pyrrolidin-1-yl]-5,6-dihydroimidazo[1,2-d][1,4]benzoxazepine | 0.00118 | 12.4 |
| 307 | 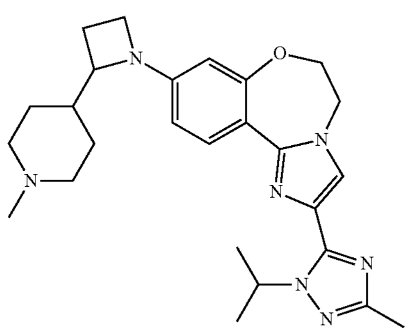 [SMILES: Cc1nc(-c2cn3c(n2)-c2ccc(N4CCC4C4CCN(C)CC4)cc2OCC3)n(C(C)C)n1] | 2-(2-isopropyl-5-methyl-1,2,4-triazol-3-yl)-9-[2-(1-methyl-4-piperidyl)azetidin-1-yl]-5,6-dihydroimidazo[1,2-d][1,4]benzoxazepine | 0.000708 | 64.1 |

TABLE 2-continued

| No. | Structure | IUPAC_Name | p110 delta IC50 (µM) | IC50 p110 alpha/ IC50 p110 delta |
|---|---|---|---|---|
| 308 | 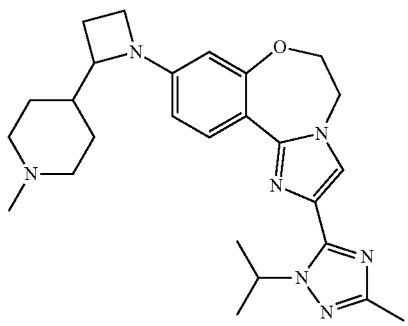 [SMILES: Cc1nc(-c2cn3c(n2)-c2ccc(N4CCC4C4CCN(C)CC4)cc2OCC3)n(C(C)C)n1] | 2-(2-isopropyl-5-methyl-1,2,4-triazol-3-yl)-9-[2-(1-methyl-4-piperidyl)azetidin-1-yl]-5,6-dihydroimidazo[1,2-d][1,4]benzoxazepine | 0.000419 | 28.2 |
| 309 | 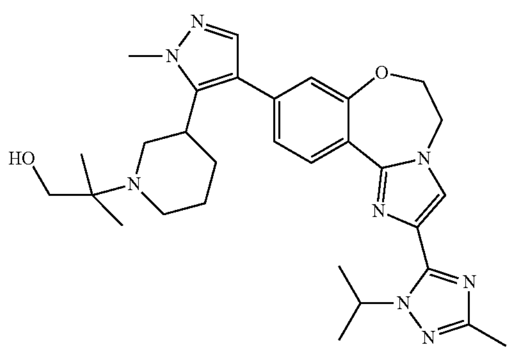 [SMILES: Cc1nc(-c2cn3c(n2)-c2ccc(-c4cnn(C)c4C4CCCN(C(C)(C)CO)C4)cc2OCC3)n(C(C)C)n1] | 2-[3-[4-[2-(2-isopropyl-5-methyl-1,2,4-triazol-3-yl)-5,6-dihydroimidazo[1,2-d][1,4]benzoxazepin-9-yl]-2-methyl-pyrazol-3-yl]-1-piperidyl]-2-methyl-propan-1-ol | 0.000485 | 190 |
| 310 | 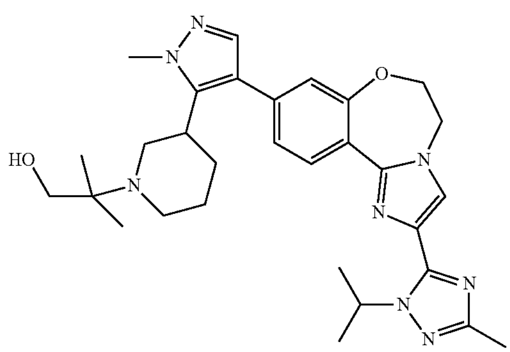 [SMILES: Cc1nc(-c2cn3c(n2)-c2ccc(-c4cnn(C)c4C4CCCN(C(C)(C)CO)C4)cc2OCC3)n(C(C)C)n1] | 2-[3-[4-[2-(2-isopropyl-5-methyl-1,2,4-triazol-3-yl)-5,6-dihydroimidazo[1,2-d][1,4]benzoxazepin-9-yl]-2-methyl-pyrazol-3-yl]-1-piperidyl]-2-methyl-propan-1-ol | 0.000262 | 122 |
| 311 | 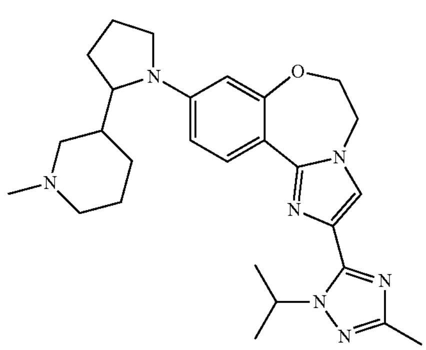 | 2-(2-isopropyl-5-methyl-1,2,4-triazol-3-yl)-9-[2-(1-methyl-3-piperidyl)pyrrolidin-1-yl]-5,6-dihydroimidazo[1,2-d][1,4]benzoxazepine | 0.00135 | 46.8 |

TABLE 2-continued

| No. | Structure | IUPAC_Name | p110 delta IC50 (μM) | IC50 p110 alpha/ IC50 p110 delta |
|---|---|---|---|---|
| 312 | 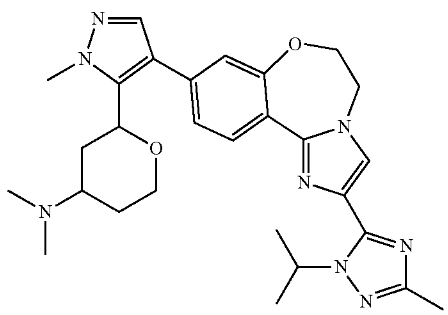 | 2-[4-[2-(2-isopropyl-5-methyl-1,2,4-triazol-3-yl)-5,6-dihydroimidazo[1,2-d][1,4]benzoxazepin-9-yl]-2-methyl-pyrazol-3-yl]-N,N-dimethyl-tetrahydropyran-4-amine | 0.000735 | 179 |
| 313 | 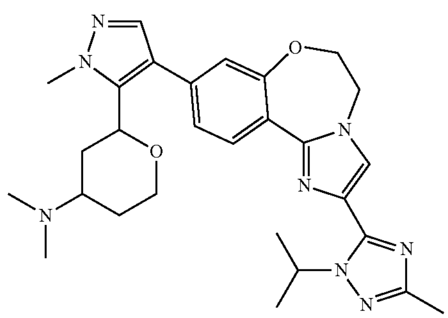 | 2-[4-[2-(2-isopropyl-5-methyl-1,2,4-triazol-3-yl)-5,6-dihydroimidazo[1,2-d][1,4]benzoxazepin-9-yl]-2-methyl-pyrazol-3-yl]-N,N-dimethyl-tetrahydropyran-4-amine | 0.000951 | 83.8 |
| 314 | 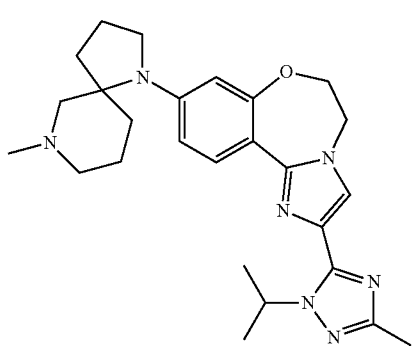 | 2-(2-isopropyl-5-methyl-1,2,4-triazol-3-yl)-9-(7-methyl-1,7-diazaspiro[4.5]decan-1-yl)-5,6-dihydroimidazo[1,2-d][1,4]benzoxazepine | 0.000335 | 50.1 |
| 315 | 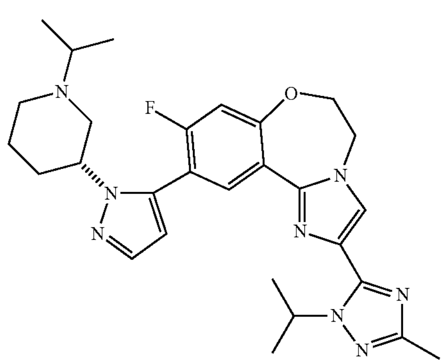 | (R)-9-fluoro-2-(1-isopropyl-3-methyl-1H-1,2,4-triazol-5-yl)-10-(1-(1-isopropylpiperidin-3-yl)-1H-pyrazol-5-yl)-5,6-dihydrobenzo[f]imidazo[1,2-d][1,4]oxazepine | 0.00044 | 25.8 |

TABLE 2-continued

| No. | Structure | IUPAC_Name | p110 delta IC50 (μM) | IC50 p110 alpha/ IC50 p110 delta |
|---|---|---|---|---|
| 316 | 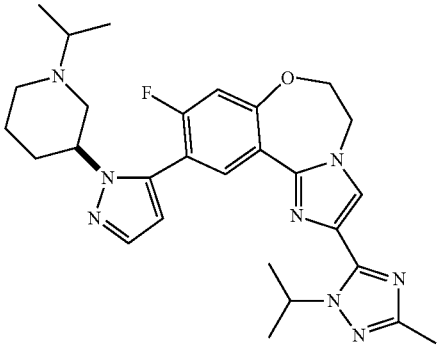 | (S)-9-fluoro-2-(1-isopropyl-3-methyl-1H-1,2,4-triazol-5-yl)-10-(1-(1-isopropylpiperidin-3-yl)-1H-pyrazol-5-yl)-5,6-dihydrobenzo[f]imidazo[1,2-d][1,4]oxazepine | <0.000035 | 214 |
| 317 | 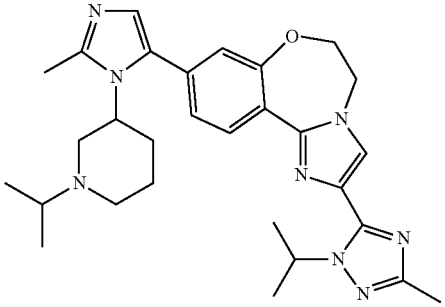 [SMILES: Cc1nc(-c2cn3c(n2)-c2ccc(-c4cnc(C)n4C4CCCN(C(C)C)C4)cc2OCC3)n(C(C)C)n1] | 2-(2-isopropyl-5-methyl-1,2,4-triazol-3-yl)-9-[3-(1-isopropyl-3-piperidyl)-2-methyl-imidazol-4-yl]-5,6-dihydroimidazo[1,2-d][1,4]benzoxazepine | 0.00651 | 22.3 |
| 318 | 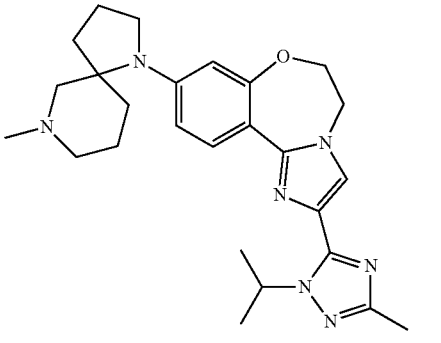 | 2-(2-isopropyl-5-methyl-1,2,4-triazol-3-yl)-9-(7-methyl-1,7-diazaspiro[4.5]decan-1-yl)-5,6-dihydroimidazo[1,2-d][1,4]benzoxazepine | 0.000178 | 29.4 |
| 319 | 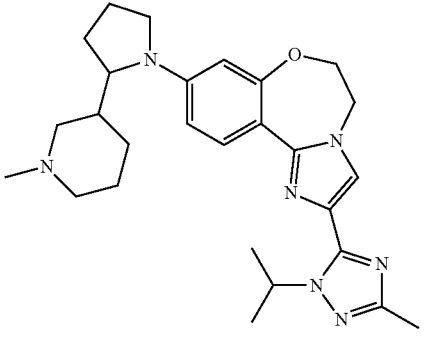 | 2-(2-isopropyl-5-methyl-1,2,4-triazol-3-yl)-9-[2-(1-methyl-3-piperidyl)pyrrolidin-1-yl]-5,6-dihydroimidazo[1,2-d][1,4]benzoxazepine | 0.00281 | 26.3 |

TABLE 2-continued

| No. | Structure | IUPAC_Name | p110 delta IC50 (μM) | IC50 p110 alpha/ IC50 p110 delta |
|---|---|---|---|---|
| 320 | 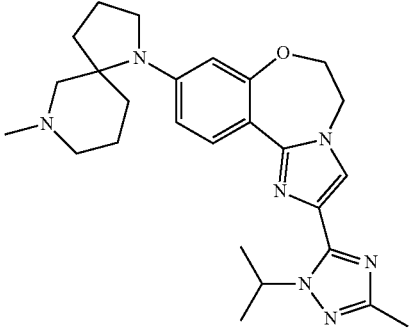 | 2-(2-isopropyl-5-methyl-1,2,4-triazol-3-yl)-9-(7-methyl-1,7-diazaspiro[4.5]decan-1-yl)-5,6-dihydroimidazo[1,2-d][1,4]benzoxazepine | 0.000236 | 54.6 |
| 321 | 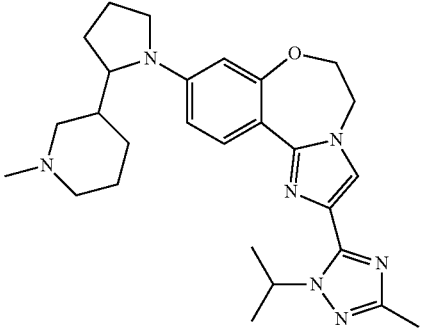 | 2-(2-isopropyl-5-methyl-1,2,4-triazol-3-yl)-9-[2-(1-methyl-3-piperidyl)pyrrolidin-1-yl]-5,6-dihydroimidazo[1,2-d][1,4]benzoxazepine | 0.00252 | 22.1 |
| 322 | 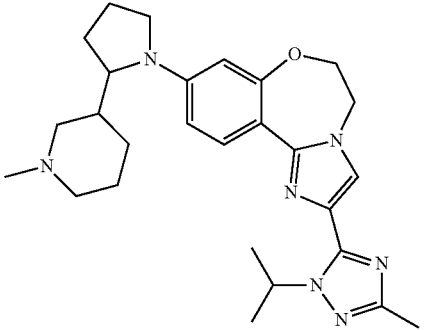 | 2-(2-isopropyl-5-methyl-1,2,4-triazol-3-yl)-9-[2-(1-methyl-3-piperidyl)pyrrolidin-1-yl]-5,6-dihydroimidazo[1,2-d][1,4]benzoxazepine | 0.00568 | 31.9 |
| 323 | 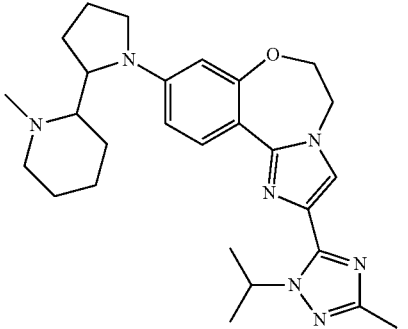 | 2-(2-isopropyl-5-methyl-1,2,4-triazol-3-yl)-9-[2-(1-methyl-2-piperidyl)pyrrolidin-1-yl]-5,6-dihydroimidazo[1,2-d][1,4]benzoxazepine | 0.00194 | 11.7 |

TABLE 2-continued

| No. | Structure | IUPAC_Name | p110 delta IC50 (μM) | IC50 p110 alpha/ IC50 p110 delta |
|---|---|---|---|---|
| 324 | 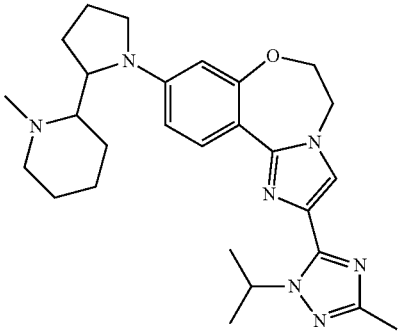 | 2-(2-isopropyl-5-methyl-1,2,4-triazol-3-yl)-9-[2-(1-methyl-2-piperidyl)pyrrolidin-1-yl]-5,6-dihydroimidazo[1,2-d][1,4]benzoxazepine | 0.139 | 15 |
| 325 | 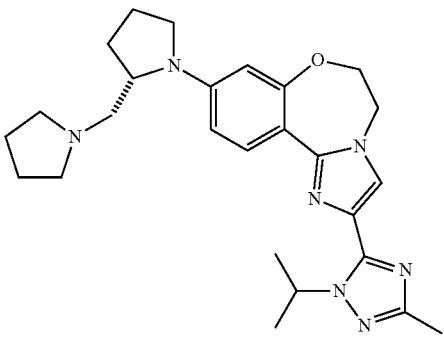 [SMILES: Cc1nc(-c2cn3c(n2)-c2ccc(N4CCC[C@H]4CN4CCCC4)cc2OCC3)n(C(C)C)n1] | (S)-2-(1-isopropyl-3-methyl-1H-1,2,4-triazol-5-yl)-9-(2-(pyrrolidin-1-ylmethyl)pyrrolidin-1-yl)-5,6-dihydrobenzo[f]imidazo[1,2-d][1,4]oxazepine | 0.000313 | 20.2 |
| 326 | 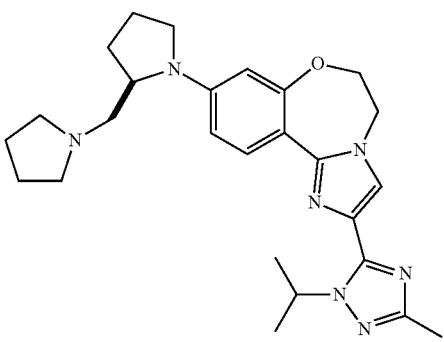 [SMILES: Cc1nc(-c2cn3c(n2)-c2ccc(N4CCC[C@@H]4CN4CCCC4)cc2OCC3)n(C(C)C)n1] | (R)-2-(1-isopropyl-3-methyl-1H-1,2,4-triazol-5-yl)-9-(2-(pyrrolidin-1-ylmethyl)pyrrolidin-1-yl)-5,6-dihydrobenzo[f]imidazo[1,2-d][1,4]oxazepine | 0.000416 | 52.9 |
| 327 | 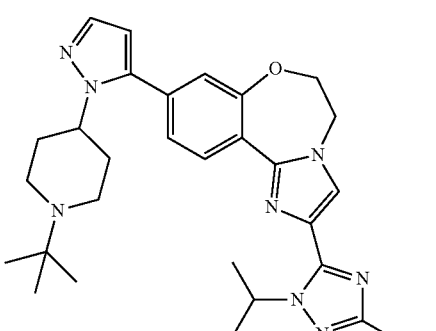 | 5-[9-[2-(1-tert-butyl-4-piperidyl)pyrazol-3-yl]-5,6-dihydroimidazo[1,2-d][1,4]benzoxazepin-2-yl]-1-isopropyl-1,2,4-triazol-3-amine | 0.00389 | 20.8 |

TABLE 2-continued

| No. | Structure | IUPAC_Name | p110 delta IC50 (μM) | IC50 p110 alpha/ IC50 p110 delta |
|-----|-----------|------------|----------------------|----------------------------------|
| 328 | 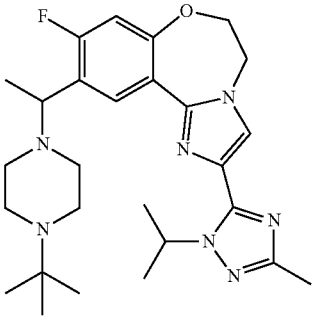 [SMILES: Cc1nc(-c2cn3c(n2)-c2cc(C(C)N4CCN(C(C)(C)C)CC4)c(F)cc2OCC3)n(C(C)C)n1] | 10-[1-(4-tert-butylpiperazin-1-yl)ethyl]-9-fluoro-2-(2-isopropyl-5-methyl-1,2,4-triazol-3-yl)-5,6-dihydroimidazo[1,2-d][1,4]benzoxazepine | 0.00229 | 109 |
| 329 | 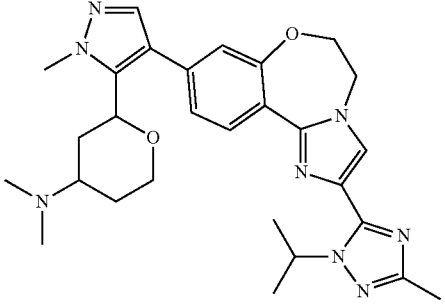 | 2-[4-[2-(2-isopropyl-5-methyl-1,2,4-triazol-3-yl)-5,6-dihydroimidazo[1,2-d][1,4]benzoxazepin-9-yl]-2-methyl-pyrazol-3-yl]-N,N-dimethyl-tetrahydropyran-4-amine | 0.000864 | 30.4 |
| 330 | 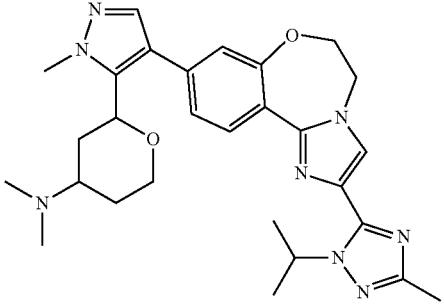 | 2-[4-[2-(2-isopropyl-5-methyl-1,2,4-triazol-3-yl)-5,6-dihydroimidazo[1,2-d][1,4]benzoxazepin-9-yl]-2-methyl-pyrazol-3-yl]-N,N-dimethyl-tetrahydropyran-4-amine | 0.00063 | 37 |
| 331 | 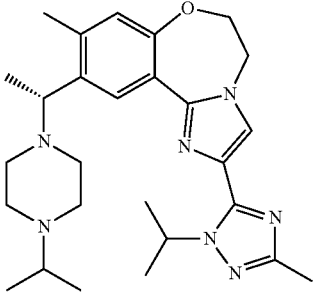 | (R)-2-(1-isopropyl-3-methyl-1H-1,2,4-triazol-5-yl)-10-(1-(4-isopropylpiperazin-1-yl)ethyl)-9-methyl-5,6-dihydrobenzo[f]imidazo[1,2-d][1,4]oxazepine | 0.000865 | 104 |

TABLE 2-continued

| No. | Structure | IUPAC_Name | p110 delta IC50 (μM) | IC50 p110 alpha/ IC50 p110 delta |
|---|---|---|---|---|
| 332 | 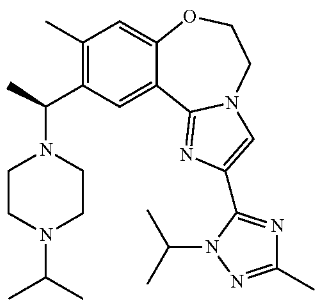 [SMILES: Cc1nc(-c2cn3c(n2)-c2cc([C@H](C)N4CCN(C(C)C)CC4)c(C)cc2OCC3)n(C(C)C)n1] | (S)-2-(1-isopropyl-3-methyl-1H-1,2,4-triazol-5-yl)-10-(1-(4-isopropylpiperazin-1-yl)ethyl)-9-methyl-5,6-dihydrobenzo[f]imidazo[1,2-d][1,4]oxazepine | 0.000678 | 13 |
| 333 | 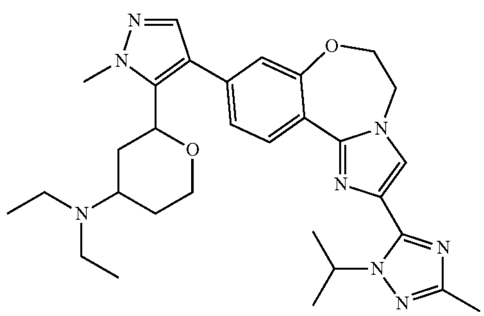 [SMILES: CCN(CC)C1CCOC(c2c(-c3ccc4c(c3)OCCn3cc(-c5nc(C)nn5C(C)C)nc3-4)cnn2C)C1] | N,N-diethyl-2-[4-[2-(2-isopropyl-5-methyl-1,2,4-triazol-3-yl)-5,6-dihydroimidazo[1,2-d][1,4]benzoxazepin-9-yl]-2-methyl-pyrazol-3-yl]tetrahydropyran-4-amine | 0.00237 | 27.2 |
| 334 | 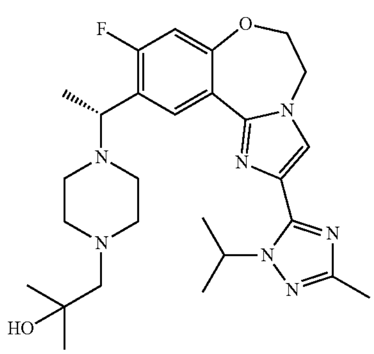 [SMILES: Cc1nc(-c2cn3c(n2)-c2cc([C@@H](C)N4CCN(CC(C)(C)O)CC4)c(F)cc2OCC3)n(C(C)C)n1] | (R)-1-(4-(1-(9-fluoro-2-(1-isopropyl-3-methyl-1H-1,2,4-triazol-5-yl)-5,6-dihydrobenzo[f]imidazo[1,2-d][1,4]oxazepin-10-yl)ethyl)piperizan-1-yl)-2-methylpropan-2-ol | 0.0105 | 17.3 |
| 335 | 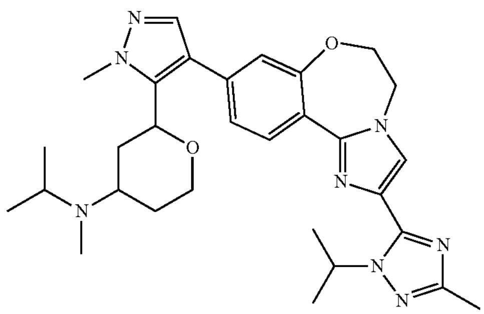 [SMILES: Cc1nc(-c2cn3c(n2)-c2ccc(-c4cnn(C)c4C4CC(N(C)C(C)C)CCO4)cc2OCC3)n(C(C)C)n1] | N-isopropyl-2-[4-[2-(2-isopropyl-5-methyl-1,2,4-triazol-3-yl)-5,6-dihydroimidazo[1,2-d][1,4]benzoxazepin-9-yl]-2-methyl-pyrazol-3-yl]-N-methyl-tetrahydropyran-4-amine | 0.00227 | 96.5 |

TABLE 2-continued

| No. | Structure | IUPAC_Name | p110 delta IC50 (μM) | IC50 p110 alpha/ IC50 p110 delta |
|---|---|---|---|---|
| 336 | 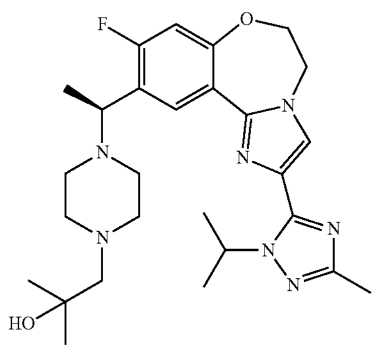 [SMILES: Cc1nc(-c2cn3c(n2)-c2cc([C@H](C)N4CCN(CC(C)(C)O)CC4)c(F)cc2OCC3)n(C(C)C)n1] | (S)-1-(4-(1-(9-fluoro-2-(1-isopropyl-3-methyl-1H-1,2,4-triazol-5-yl)-5,6-dihydrobenzo[f]imidazo[1,2-d][1,4]oxazepin-10-yl)ethyl)piperazin-1-yl)-2-methylpropan-2-ol | 0.0268 | 27 |
| 337 | 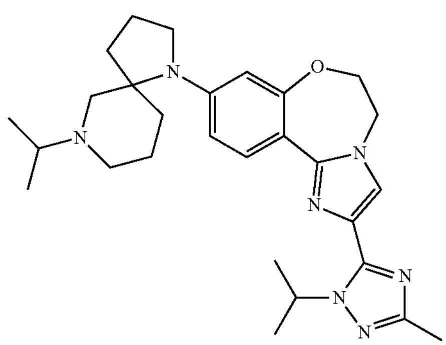 [SMILES: Cc1nc(-c2cn3c(n2)-c2ccc(N4CCCC45CCCN(C(C)C)C5)cc2OCC3)n(C(C)C)n1] | 9-(7-isopropyl-1,7-diazaspiro[4.5]decan-1-yl)-2-(2-isopropyl-5-methyl-1,2,4-triazol-3-yl)-5,6-dihydroimidazo[1,2-d][1,4]benzoxazepine | 0.00152 | 47.9 |
| 338 | 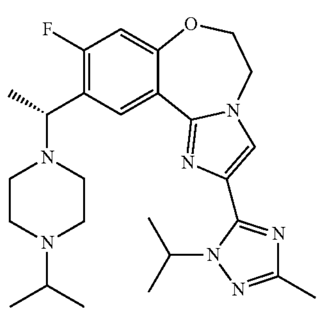 [SMILES: Cc1nc(-c2cn3c(n2)-c2cc([C@@H](C)N4CCN(C(C)C)CC4)c(F)cc2OCC3)n(C(C)C)n1] | (R)-9-fluoro-2-(1-isopropyl-3-methyl-1H-1,2,4-triazol-5-yl)-10-(1-(4-isopropylpiperazin-1-yl)ethyl)-5,6-dihydrobenzo[f]imidazo[1,2-d][1,4]oxazepine | 0.00148 | 114 |
| 339 | 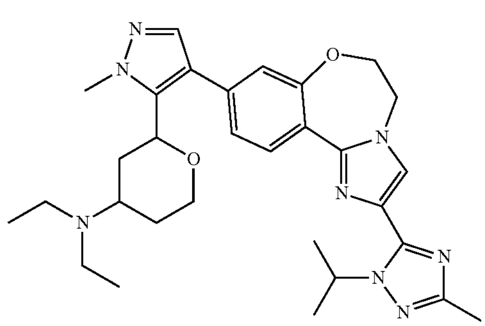 [SMILES: CCN(CC)C1CCOC(c2c(-c3ccc4c(c3)OCCn3cc(-c5nc(C)nn5C(C)C)nc3-4)cnn2C)C1] | N,N-diethyl-2-[4-[2-(2-isopropyl-5-methyl-1,2,4-triazol-3-yl)-5,6-dihydroimidazo[1,2-d][1,4]benzoxazepin-9-yl]-2-methyl-pyrazol-3-yl]tetrahydropyran-4-amine | 0.00107 | 61.5 |

TABLE 2-continued

| No. | Structure | IUPAC_Name | p110 delta IC50 (µM) | IC50 p110 alpha/ IC50 p110 delta |
|---|---|---|---|---|
| 340 | 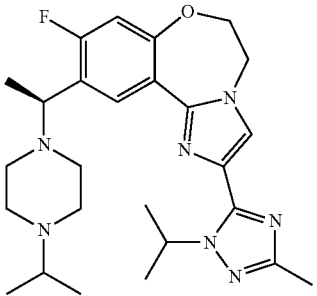 | (S)-9-fluoro-2-(1-isopropyl-3-methyl-1H-1,2,4-triazol-5-yl)-10-(1-(4-isopropylpiperazin-1-yl)ethyl)-5,6-dihydrobenzo[f]imidazo[1,2-d][1,4]oxazepine | 0.00232 | 25.8 |
| 341 | 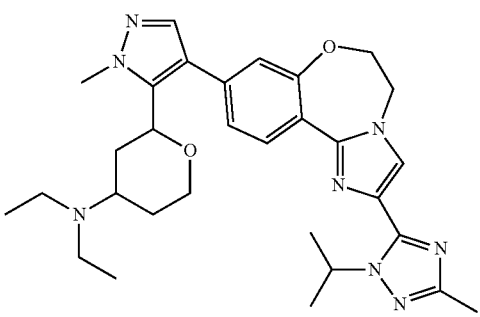 [SMILES: CCN(CC)C1CCOC(c2c(-c3ccc4c(c3)OCCn3cc(-c5nc(C)nn5C(C)C)nc3-4)cnn2C)C1] | N,N-diethyl-2-[4-[2-(2-isopropyl-5-methyl-1,2,4-triazol-3-yl)-5,6-dihydroimidazo[1,2-d][1,4]benzoxazepin-9-yl]-2-methyl-pyrazol-3-yl]tetrahydropyran-4-amine | 0.000771 | 71.1 |
| 342 | 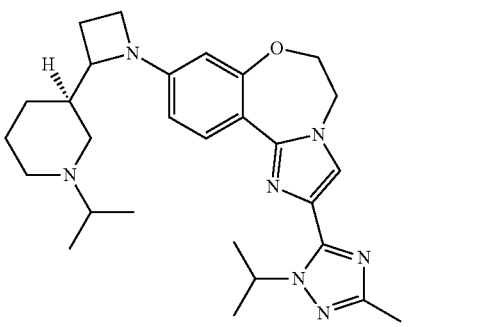 [SMILES: Cc1nc(-c2cn3c(n2)-c2ccc(N4CCC4[C@@H]4CCCN(C(C)C)C4)cc2OCC3)n(C(C)C)n1] | 2-(1-isopropyl-3-methyl-1H-1,2,4-triazol-5-yl)-9-(2-((R)-1-isopropylpiperidin-3-yl)azetidin-1-yl)-5,6-dihydrobenzo[f]imidazo[1,2-d][1,4]oxazepine | 0.00016 | 21.3 |
| 343 | 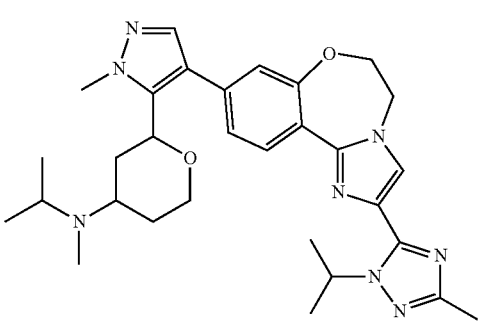 [SMILES: Cc1nc(-c2cn3c(n2)-c2ccc(-c4cnn(C)c4C4CC(N(C)C(C)C)CCO4)cc2OCC3)n(C(C)C)n1] | N-isopropyl-2-[4-[2-(2-isopropyl-5-methyl-1,2,4-triazol-3-yl)-5,6-dihydroimidazo[1,2-d][1,4]benzoxazepin-9-yl]-2-methyl-pyrazol-3-yl]-N-methyl-tetrahydropyran-4-amine | 0.000939 | 53 |

TABLE 2-continued

| No. | Structure | IUPAC_Name | p110 delta IC50 (μM) | IC50 p110 alpha/ IC50 p110 delta |
|---|---|---|---|---|
| 344 | 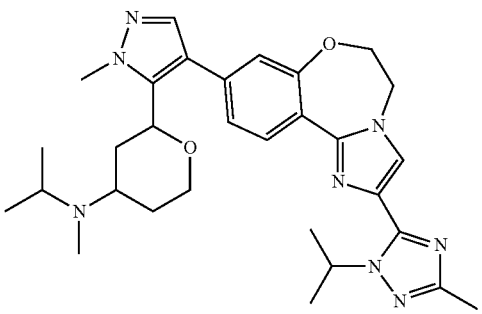 [SMILES: Cc1nc(-c2cn3c(n2)-c2ccc(-c4cnn(C)c4C4CC(N(C)C(C)C)CCO4)cc2OCC3)n(C(C)C)n1] | N-isopropyl-2-[4-[2-(2-isopropyl-5-methyl-1,2,4-triazol-3-yl)-5,6-dihydroimidazo[1,2-d][1,4]benzoxazepin-9-yl]-2-methyl-pyrazol-3-yl]-N-methyl-tetrahydropyran-4-amine | 0.00123 | 66 |
| 345 | 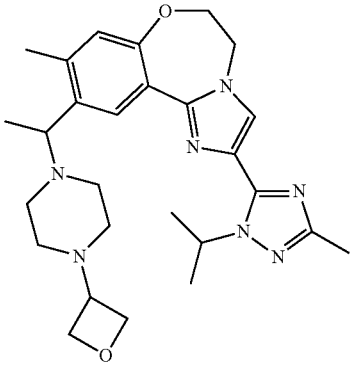 [SMILES: Cc1nc(-c2cn3c(n2)-c2cc(C(C)N4CCN(C5COC5)CC4)c(C)cc2OCC3)n(C(C)C)n1] | 2-(2-isopropyl-5-methyl-1,2,4-triazol-3-yl)-9-methyl-10-[1-[4-(oxetan-3-yl)piperazin-1-yl]ethyl]-5,6-dihydroimidazo[1,2-d][1,4]benzoxazepine | 0.00882 | 14.3 |
| 346 | 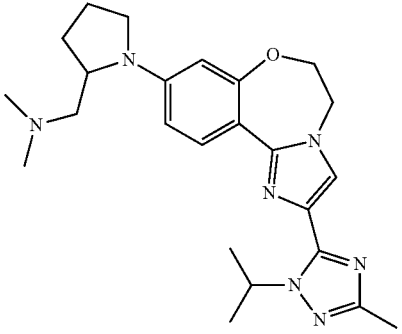 | 1-[1-[2-(2-isopropyl-5-methyl-1,2,4-triazol-3-yl)-5,6-dihydroimidazo[1,2-d][1,4]benzoxazepin-9-yl]pyrrolidin-2-yl]-N,N-dimethyl-methanamine | 0.000288 | 23 |
| 347 | 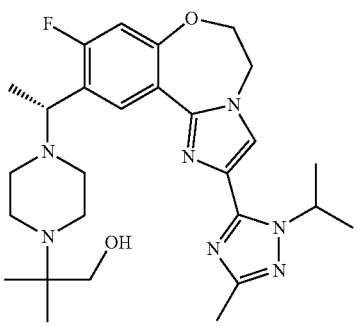 [SMILES: Cc1nc(-c2cn3c(n2)-c2cc([C@@H](C)N4CCN(C(C)(C)CO)CC4)c(F)cc2OCC3)n(C(C)C)n1] | (R)-2-(4-(1-(9-fluoro-2-(1-isopropyl-3-methyl-1H-1,2,4-triazol-5-yl)-5,6-dihydrobenzo[f]imidazo[1,2-d][1,4]oxazepin-10-yl)ethyl)piperazin-1-yl)-2-methylpropan-1-ol | 0.00553 | 47.5 |

TABLE 2-continued

| No. | Structure | IUPAC_Name | p110 delta IC50 (μM) | IC50 p110 alpha/ IC50 p110 delta |
|---|---|---|---|---|
| 348 | 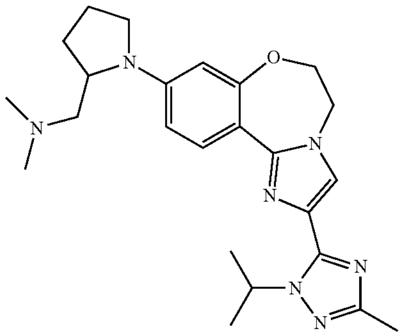 | 1-[1-[2-(2-isopropyl-5-methyl-1,2,4-triazol-3-yl)-5,6-dihydroimidazo[1,2-d][1,4]benzoxazepin-9-yl]pyrrolidin-2-yl]-N,N-dimethyl-methanamine | 0.000445 | 31.4 |
| 349 | 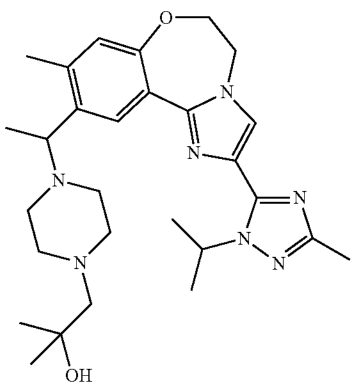 [SMILES: Cc1nc(-c2cn3c(n2)-c2cc(C(C)N4CCN(CC(C)(C)O)CC4)c(C)cc2OCC3)n(C(C)C)n1] | 1-[4-[1-[2-(2-isopropyl-5-methyl-1,2,4-triazol-3-yl)-9-methyl-5,6-dihydroimidazo[1,2-d][1,4]benzoxazepin-l0-yl]ethyl]piperazin-1-yl]-2-methyl-propan-2-ol | 0.00421 | 18.1 |
| 350 | 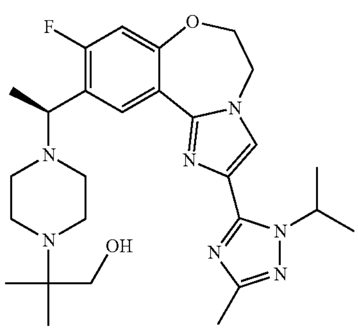 [SMILES: Cc1nc(-c2cn3c(n2)-c2cc([C@H](C)N4CCN(C(C)(C)CO)CC4)c(F)cc2OCC3)n(C(C)C)n1] | (S)-2-(4-(1-(9-fluoro-2-(1-isopropyl-3-methyl-1H-1,2,4-triazol-5-yl)-5,6-dihydrobenzo[f]imidazo[1,2-d][1,4]oxazepin-10-yl)ethyl)piperazin-1-yl)-2-methylpropan-1-ol | 0.00199 | 212 |
| 351 | 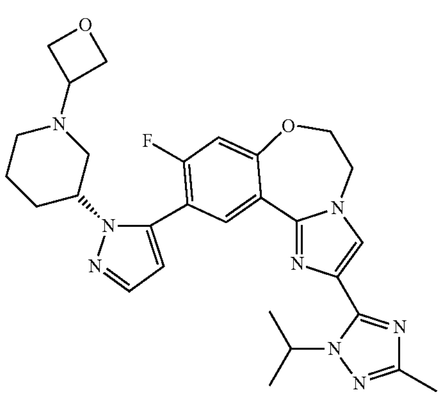 | (R)-9-fluoro-2-(1-isopropyl-3-methyl-1H-1,2,4-triazol-5-yl)-10-(1-(1-(oxetan-3-yl)piperidin-3-yl)-1H-pyrazol-5-yl)-5,6-dihydrobenzo[f]imidazo[1,2-d][1,4]oxazepine | 0.00221 | 16.6 |

TABLE 2-continued

| No. | Structure | IUPAC_Name | p110 delta IC50 (µM) | IC50 p110 alpha/ IC50 p110 delta |
|---|---|---|---|---|
| 352 | 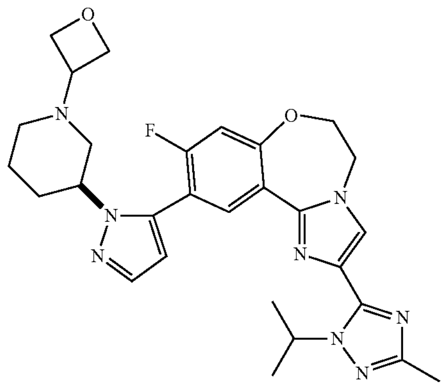 | (S)-9-fluoro-2-(1-isopropyl-3-methyl-1H-1,2,4-triazol-5-yl)-10-(1-(1-(oxetan-3-yl)piperidin-3-yl)-1H-pyrazol-5-yl)-5,6-dihydrobenzo[f]imidazo[1,2-d][1,4]oxazepine | 0.0115 | 18 |
| 353 | 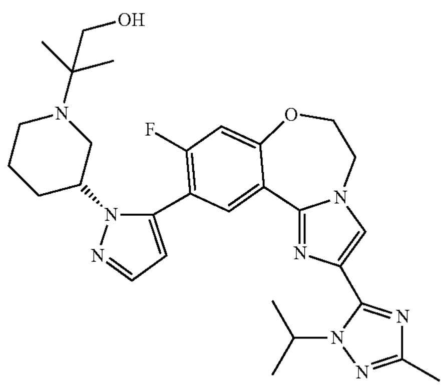 | (R)-2-(3-(5-(9-fluoro-2-(1-isopropyl-3-methyl-1H-1,2,4-triazol-5-yl)-5,6-dihydrobenzo[f]imidazo[1,2-d][1,4]oxazepin-10-yl)-1H-pyrazol-1-yl)piperidin-1-yl)-2-methylpropan-1-ol | 0.000314 | 151 |
| 354 | 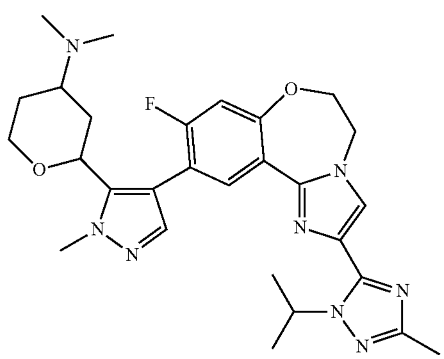 [SMILES: Cc1nc(-c2cn3c(n2)-c2cc(-c4cnn(C)c4C4CC(N(C)C)CCO4)c(F)cc2OCC3)n(C(C)C)n1] | 2-[4-[9-fluoro-2-(2-isopropyl-5-methyl-1,2,4-triazol-3-yl)-5,6-dihydroimidazo[1,2-d][1,4]benzoxazepin-10-yl]-2-methyl-pyrazol-3-yl]-N,N-dimethyl-tetrahydropyran-4-amine | 0.00066 | 14.5 |
| 355 | 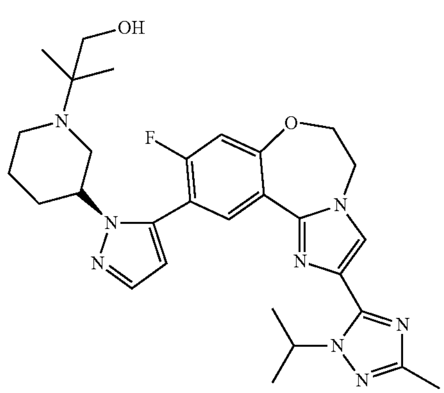 | (R)-2-(3-(5-(9-fluoro-2-(1-isopropyl-3-methyl-1H-1,2,4-triazol-5-yl)-5,6-dihydrobenzo[f]imidazo[1,2-d][1,4]oxazepin-10-yl)-1H-pyrazol-1-yl)piperidin-1-yl)-2-methylpropan-1-ol | 0.000415 | 46.4 |

TABLE 2-continued

| No. | Structure | IUPAC_Name | p110 delta IC50 (μM) | IC50 p110 alpha/ IC50 p110 delta |
|---|---|---|---|---|
| 356 | 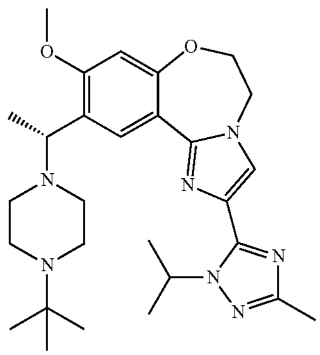 [SMILES: COc1cc2c(cc1[C@@H](C)N1CCN(C(C)(C)C)CC1)-c1nc(-c3nc(C)nn3C(C)C)cn1CCO2] | (R)-10-(1-(4-tert-butylpiperazin-1-yl)ethyl)-2-(1-isopropyl-3-methyl-1H-1,2,4-triazol-5-yl)-9-methoxy-5,6-dihydrobenzo[f]imidazo[1,2-d][1,4]oxazepine | 0.00105 | 45.5 |
| 357 | 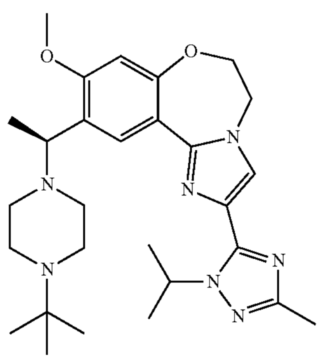 [SMILES: COc1cc2c(cc1[C@H](C)N1CCN(C(C)(C)C)CC1)-c1nc(-c3nc(C)nn3C(C)C)cn1CCO2] | (S)-10-(1-(4-tert-butylpiperazin-1-yl)ethyl)-2-(1-isopropyl-3-methyl-1H-1,2,4-triazol-5-yl)-9-methoxy-5,6-dihydrobenzo[f]imidazo[1,2-d][1,4]oxazepine | 0.000784 | 116 |
| 358 | 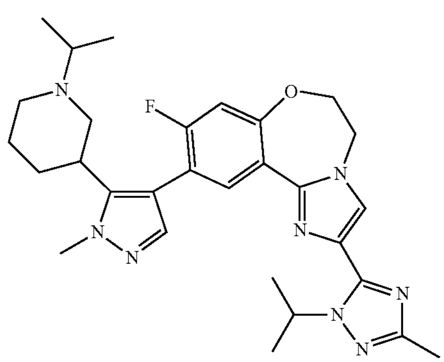 | 9-fluoro-2-(2-isopropyl-5-methyl-1,2,4-triazol-3-yl)-10-[5-(1-isopropyl-3-piperidyl)-1-methyl-pyrazol-4-yl]-5,6-dihydroimidazo[1,2-d][1,4]benzoxazepine | 0.00156 | 67.1 |
| 359 | 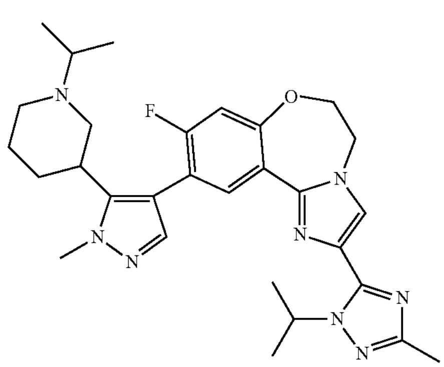 | 9-fluoro-2-(2-isopropyl-5-methyl-1,2,4-triazol-3-yl)-10-[5-(1-isopropyl-3-piperidyl)-1-methyl-pyrazol-4-yl]-5,6-dihydroimidazo[1,2-d][1,4]benzoxazepine | 0.00037 | 54.1 |

TABLE 2-continued

| No. | Structure | IUPAC_Name | p110 delta IC50 (µM) | IC50 p110 alpha/ IC50 p110 delta |
|---|---|---|---|---|
| 360 | 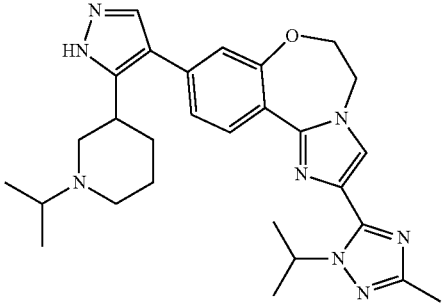 [SMILES: Cc1nc(-c2cn3c(n2)-c2ccc(-c4cn[nH]c4C4CCCN(C(C)C)C4)cc2OCC3)n(C(C)C)n1] | 2-(2-isopropyl-5-methyl-1,2,4-triazol-3-yl)-9-[5-(1-isopropyl-3-piperidyl)-1H-pyrazol-4-yl]-5,6-dihydroimidazo[1,2-d][1,4]benzoxazepine | 0.000311 | 24 |
| 361 | 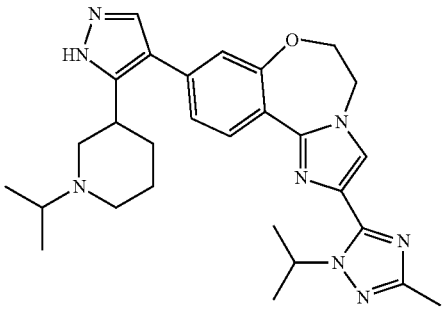 [SMILES: Cc1nc(-c2cn3c(n2)-c2ccc(-c4cn[nH]c4C4CCCN(C(C)C)C4)cc2OCC3)n(C(C)C)n1] | 2-(2-isopropyl-5-methyl-1,2,4-triazol-3-yl)-9-[5-(1-isopropyl-3-piperidyl)-1H-pyrazol-4-yl]-5,6-dihydroimidazo[1,2-d][1,4]benzoxazepine | 0.000972 | 23.6 |
| 362 | 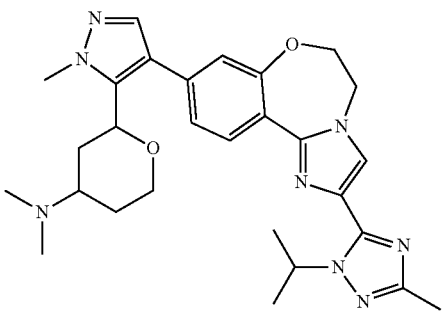 | 2-[4-[2-(2-isopropyl-5-methyl-1,2,4-triazol-3-yl)-5,6-dihydroimidazo[1,2-d][1,4]benzoxazepin-9-yl]-2-methyl-pyrazol-3-yl]-N,N-dimethyl-tetrahydropyran-4-amine | 0.00108 | 38.4 |
| 363 | 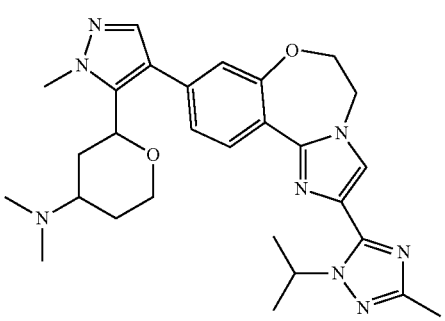 | 2-[4-[2-(2-isopropyl-5-methyl-1,2,4-triazol-3-yl)-5,6-dihydroimidazo[1,2-d][1,4]benzoxazepin-9-yl]-2-methyl-pyrazol-3-yl]-N,N-dimethyl-tetrahydropyran-4-amine | 0.0012 | 89.4 |

TABLE 2-continued

| No. | Structure | IUPAC_Name | p110 delta IC50 (µM) | IC50 p110 alpha/ IC50 p110 delta |
|---|---|---|---|---|
| 364 | 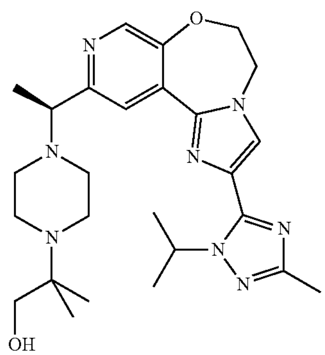 [SMILES: Cc1nc(-c2cn3c(n2)-c2cc([C@H](C)N4CCN(C(C)(C)CO)CC4)ncc2OCC3)n(C(C)C)n1] | (S)-2-(4-(1-(2-(1-isopropyl-3-methyl-1H-1,2,4-triazol-5-yl)-5,6-dihydroimidazo[1,2-d]pyrido[4,3-f][1,4]oxazepin-10-yl)ethyl)piperazin-1-yl)-2-methylpropan-1-ol | 0.0021 | 85.9 |
| 365 | 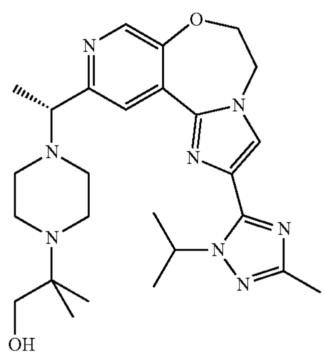 [SMILES: Cc1nc(-c2cn3c(n2)-c2cc([C@@H](C)N4CCN(C(C)(C)CO)CC4)ncc2OCC3)n(C(C)C)n1] | (R)-2-(4-(1-(2-(1-isopropyl-3-methyl-1H-1,2,4-triazol-5-yl)-5,6-dihydroimidazo[1,2-d]pyrido[4,3-f][1,4]oxazepin-10-yl)ethyl)piperazin-1-yl)-2-methylpropan-1-ol | 0.00263 | 83.2 |
| 366 | 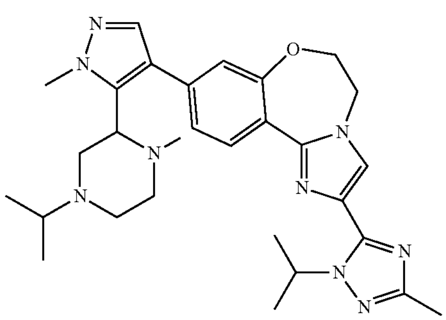 [SMILES: Cc1nc(-c2cn3c(n2)-c2ccc(-c4cnn(C)c4C4CN(C(C)C)CCN4C)cc2OCC3)n(C(C)C)n1] | 9-[5-(4-isopropyl-1-methyl-piperazin-2-yl)-1-methyl-pyrazol-4-yl]-2-(2-isopropyl-5-methyl-1,2,4-triazol-3-yl)-5,6-dihydroimidazo[1,2-d][1,4]benzoxazepine | <0.000035 | 172 |
| 367 | 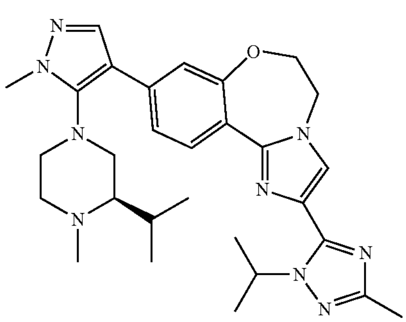 | 9-[5-[(3R)-3-isopropyl-4-methyl-piperazin-1-yl]-1-methyl-pyrazol-4-yl]-2-(2-isopropyl-5-methyl-1,2,4-triazol-3-yl)-5,6-dihydroimidazo[1,2-d][1,4]benzoxazepine | 0.000048 | 48.8 |

TABLE 2-continued

| No. | Structure | IUPAC_Name | p110 delta IC50 (μM) | IC50 p110 alpha/ IC50 p110 delta |
|---|---|---|---|---|
| 368 | 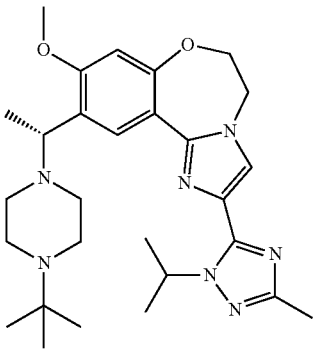 [SMILES: COc1cc2c(cc1[C@@H](C)N1CCN(C(C)(C)C)CC1)-c1nc(-c3nc(C)nn3C(C)C)cn1CCO2] | 10-[(1R)-1-(4-tert-butylpiperazin-1-yl)ethyl]-2-(2-isopropyl-5-methyl-1,2,4-triazol-3-yl)-9-methoxy-5,6-dihydroimidazo[1,2-d][1,4]benzoxazepine | 0.00106 | 92.4 |
| 369 | 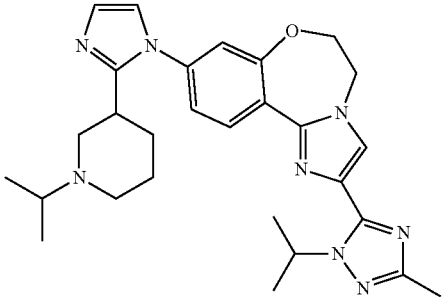 [SMILES: Cc1nc(-c2cn3c(n2)-c2ccc(-n4ccnc4C4CCCN(C(C)C)C4)cc2OCC3)n(C(C)C)n1] | 2-(2-isopropyl-5-methyl-1,2,4-triazol-3-yl)-9-[2-(1-isopropyl-3-piperidyl)imidazol-1-yl]-5,6-dihydroimidazo[1,2-d][1,4]benzoxazepine | 0.00309 | 40.4 |
| 370 | 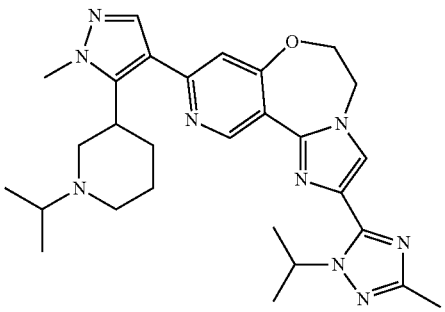 | 2-(1-isopropyl-3-methyl-1H-1,2,4-triazol-5-yl)-9-(5-(1-isopropylpiperidin-3-yl)-1-methyl-1H-pyrazol-4-yl)-5,6-dihydroimidazo[1,2-d]pyrido[3,4-f][1,4]oxazepine | 0.000571 | 16.1 |
| 371 | 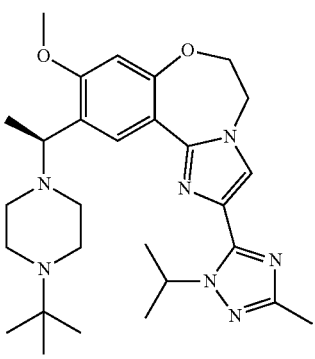 [SMILES: COc1cc2c(cc1[C@H](C)N1CCN(C(C)(C)C)CC1)-c1nc(-c3nc(C)nn3C(C)C)cn1CCO2] | 10-[(1S)-1-(4-tert-butylpiperazin-1-yl)ethyl]-2-(2-isopropyl-5-methyl-1,2,4-triazol-3-yl)-9-methoxy-5,6-dihydroimidazo[1,2-d][1,4]benzoxazepine | 0.0053 | 11.7 |

TABLE 2-continued

| No. | Structure | IUPAC_Name | p110 delta IC50 (µM) | IC50 p110 alpha/ IC50 p110 delta |
|---|---|---|---|---|
| 372 | 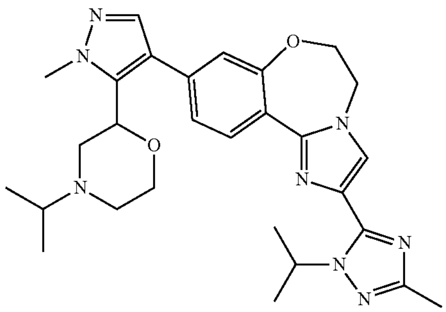 | 2-(2-isopropyl-5-methyl-1,2,4-triazol-3-yl)-9-[5-(4-isopropylmorpholin-2-yl)-1-methyl-pyrazol-4-yl]-5,6-dihydroimidazo[1,2-d][1,4]benzoxazepine | 0.000992 | 18 |
| 373 | 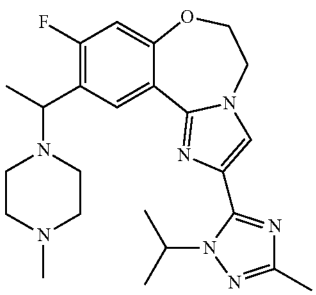 [SMILES: Cc1nc(-c2cn3c(n2)-c2cc(C(C)N4CCN(C)CC4)c(F)cc2OCC3)n(C(C)C)n1] | 9-fluoro-2-(2-isopropyl-5-methyl-1,2,4-triazol-3-yl)-10-[1-(4-methylpiperazin-1-yl)ethyl]-5,6-dihydroimidazo[1,2-d][1,4]benzoxazepine | 0.00313 | 15.7 |
| 374 | 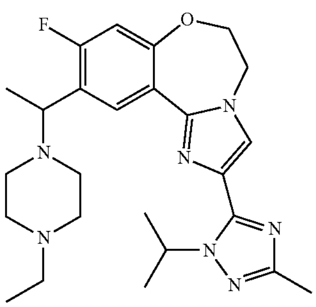 [SMILES: CCN1CCN(C(C)c2cc3c(cc2F)OCCn2cc(-c4nc(C)nn4C(C)C)nc2-3)CC1] | 10-[1-(4-ethylpiperazin-1-yl)ethyl]-9-fluoro-2-(2-isopropyl-5-methyl-1,2,4-triazol-3-yl)-5,6-dihydroimidazo[1,2-d][1,4]benzoxazepine | 0.00485 | 17.9 |

Administration of Formula I Compounds

The Formula I compounds of the invention may be administered by a route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds may be administered by intralesional administration, including perfusing or otherwise contacting the graft with the inhibitor before transplantation. The administered route may vary with the condition of the recipient, i.e. the human patient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

A dose to treat human patients may range from about 10 mg to about 1000 mg of Formula I compound. A typical dose may be about 100 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Methods of Treatment with Formula I Compounds

Formula I compounds of the present invention are useful for treating a human or animal patient suffering from a disease or disorder arising from abnormal cell growth, function or behavior associated with PI3 kinase, in particular with the p110δ (delta) isoform of PI3 kinase such as an immune disorder, cardiovascular disease, viral infection, inflammation, a metabolism/endocrine disorder or a neurological disorder, may thus be treated by a method comprising the administration thereto of a compound of the present invention as defined above. A human or animal patient suffering from cancer may also be treated by a method comprising the administration thereto of a compound of the present invention as defined above. The condition of the patient may thereby be improved or ameliorated.

Formula I compounds may be useful for in vitro, in situ, and in vivo diagnosis or treatment of mammalian cells, organisms, or associated pathological conditions, such as systemic and local inflammation, immune-inflammatory diseases such as rheumatoid arthritis, immune suppression, organ transplant rejection, allergies, ulcerative colitis, Crohn's disease, dermatitis, asthma, systemic lupus erythematosus, Sjögren's Syndrome, multiple sclerosis, scleroderma/systemic sclerosis, idiopathic thrombocytopenic purpura (ITP), anti-neutrophil cytoplasmic antibodies (ANCA) vasculitis, chronic obstructive pulmonary disease (COPD), psoriasis, and for general joint protective effects.

Formula I compounds may be useful for treating such diseases as arthritic diseases, such as rheumatoid arthritis, monoarticular arthritis, osteoarthritis, gouty arthritis, spondylitis; Behcet disease; sepsis, septic shock, endotoxic shock, gram negative sepsis, gram positive sepsis, and toxic shock syndrome; multiple organ injury syndrome secondary to septicemia, trauma, or hemorrhage; ophthalmic disorders such as allergic conjunctivitis, vernal conjunctivitis, uveitis, and thyroid-associated ophthalmopathy; eosinophilic granuloma; pulmonary or respiratory disorders such as asthma, chronic bronchitis, allergic rhinitis, ARDS, chronic pulmonary inflammatory disease (e.g., chronic obstructive pulmonary disease), silicosis, pulmonary sarcoidosis, pleurisy, alveolitis, vasculitis, emphysema, pneumonia, bronchiectasis, and pulmonary oxygen toxicity; reperfusion injury of the myocardium, brain, or extremities; fibrosis such as cystic fibrosis; keloid formation or scar tissue formation; atherosclerosis; autoimmune diseases, such as systemic lupus erythematosus (SLE), autoimmune thyroiditis, multiple sclerosis, some forms of diabetes, and Reynaud's syndrome; and transplant rejection disorders such as GVHD and allograft rejection; chronic glomerulonephritis; inflammatory bowel diseases such as chronic inflammatory bowel disease (CIBDi), Crohn's disease, ulcerative colitis, and necrotizing enterocolitis; inflammatory dermatoses such as contact dermatitis, atopic dermatitis, psoriasis, or urticaria; fever and myalgias due to infection; central or peripheral nervous system inflammatory disorders such as meningitis, encephalitis, and brain or spinal cord injury due to minor trauma; Sjogren's syndrome; diseases involving leukocyte diapedesis; alcoholic hepatitis; bacterial pneumonia; antigen-antibody complex mediated diseases; hypovolemic shock; Type I diabetes mellitus; acute and delayed hypersensitivity; disease states due to leukocyte dyscrasia and metastasis; thermal injury; granulocyte transfusion-associated syndromes; and cytokine-induced toxicity.

The methods of the invention can have utility in treating subjects who are or can be subject to reperfusion injury, i.e., injury resulting from situations in which a tissue or organ experiences a period of ischemia followed by reperfusion. The term "ischemia" refers to localized tissue anemia due to obstruction of the inflow of arterial blood. Transient ischemia followed by reperfusion characteristically results in neutrophil activation and transmigration through the endothelium of the blood vessels in the affected area. Accumulation of activated neutrophils in turn results in generation of reactive oxygen metabolites, which damage components of the involved tissue or organ. This phenomenon of "reperfusion injury" is commonly associated with conditions such as vascular stroke (including global and focal ischemia), hemorrhagic shock, myocardial ischemia or infarction, organ transplantation, and cerebral vasospasm. To illustrate, reperfusion injury occurs at the termination of cardiac bypass procedures or during cardiac arrest when the heart, once prevented from receiving blood, begins to reperfuse. It is expected that inhibition of PI3K delta activity may result in reduced amounts of reperfusion injury in such situations.

Methods of the invention include treating cancer with Formula I compounds where the cancer is breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, pancreatic, myeloid disorders, lymphoma, hairy cells, buccal cavity, naso-pharyngeal, pharynx, lip, tongue, mouth, small intestine, colon-rectum, large intestine, rectum, brain and central nervous system, Hodgkin's, leukemia, bronchus, thyroid, liver and intrahepatic bile duct, hepatocellular, gastric, glioma/glioblastoma, endometrial, melanoma, kidney and renal pelvis, urinary bladder, uterine corpus, uterine cervix, multiple myeloma, acute myelogenous leukemia, chronic lymphoid leukemia, chronic myelogenous leukemia, lymphocytic leukemia, myeloid leukemia, oral cavity and pharynx, non-Hodgkin lymphoma, melanoma, and villous colon adenoma.

Methods of the invention include administering a Formula I compound to treat a hematopoietic malignancy selected from leukemia, non-Hodgkin's lymphoma, diffuse large hematopoietic lymphoma, follicular lymphoma, mantle cell lymphoma, chronic lymphocytic leukemia (CLL), multiple myeloma, acute myeloid leukemia (AML), and myeloid cell leukemia (MCL).

Pharmaceutical Formulations

In order to use a Formula I compound for the therapeutic treatment (including prophylactic treatment) of mammals including humans, it is normally formulated in accordance with standard pharmaceutical practice as a pharmaceutical composition. According to this aspect of the invention there is provided a pharmaceutical composition comprising a compound of this invention in association with a pharmaceutically acceptable diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a compound of Formula I having the desired degree of purity may optionally be mixed with pharmaceutically acceptable diluents, carriers, excipients or stabilizers (Remington's Pharmaceutical Sciences (1980) $16^{th}$ edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound ordinarily can be stored as a solid composition, a lyophilized formulation or as an aqueous solution.

The pharmaceutical compositions of the invention will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the hyperproliferative disorder.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences $16^{th}$ edition, Osol, A. Ed. (1980).

Sustained-release preparations of compounds of Formula I may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I suitable for oral administration may be prepared as discrete units such as pills, capsules, cachets or tablets each containing a predetermined amount of a compound of Formula I. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom. Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula I intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations may be applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs. The oily phase of the emulsions of this invention may be constituted from known ingredients in a known manner, including a mixture of at least one emulsifier with a fat or an oil, or with both a fat and an oil. A hydrophilic emulsifier included together with a lipophilic emulsifier acts as a stabilizer. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of Formula I compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., poly-oxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula I may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formula I may be employed alone or in combination with other therapeutic agents for the treatment of a disease or disorder described herein, such as inflammation or a hyperproliferative disorder (e.g., cancer). In certain embodiments, a compound of Formula I is combined in a pharmaceutical combination formulation, or dosing regimen as combination therapy, with a second therapeutic compound that has anti-inflammatory or anti-hyperproliferative properties or that is useful for treating an inflammation, immune-response disorder, or hyperproliferative disorder (e.g., cancer). The second therapeutic agent may be an NSAID anti-inflammatory agent. The second therapeutic agent may be a chemotherapeutic agent. The second compound of the pharmaceutical combination formulation or dosing regimen preferably has complementary activities to the compound of Formula I such that they do not adversely affect each other. Such compounds are suitably present in combination in amounts that are effective for the purpose intended. In one embodiment, a composition of this invention comprises a compound of Formula I, or a stereoisomer, tautomer, or pharmaceutically acceptable salt or prodrug thereof, in combination with a therapeutic agent such as an NSAID.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other therapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of therapy, a compound of Formula I, or a stereoisomer, tautomer, or pharmaceutically acceptable salt or prodrug thereof, may be combined with other therapeutic, hormonal or antibody agents such as those described herein, as well as combined with surgical therapy and radiotherapy. Combination therapies according to the present invention thus comprise the administration of at least one compound of Formula I, or a stereoisomer, tautomer, or pharmaceutically acceptable salt or prodrug thereof, and the use of at least one other cancer treatment method. The amounts of the compound(s) of Formula I and the other pharmaceutically active chemotherapeutic agent(s) and the relative timings of administration will be selected in order to achieve the desired combined therapeutic effect.

Metabolites of Compounds of Formula I

Also falling within the scope of this invention are the in vivo metabolic products of Formula I described herein. Such products may result for example from the oxidation, reduction, hydrolysis, amidation, deamidation, esterification, deesterification, enzymatic cleavage, and the like, of the administered compound. Accordingly, the invention includes metabolites of compounds of Formula I, including compounds produced by a process comprising contacting a compound of this invention with a mammal for a period of time sufficient to yield a metabolic product thereof.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Articles of Manufacture

In another embodiment of the invention, an article of manufacture, or "kit", containing materials useful for the treatment of the diseases and disorders described above is provided. In one embodiment, the kit comprises a container comprising a compound of Formula I. The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula I or a formulation thereof which is effective for treating the condition and may have a sterile access port (for example, the container may be an intravenous solution bag or a vial having a stopper pierceable by a hypodermic injection needle). At least one active agent in the composition is a compound of Formula I. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a compound of Formula I can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I and, if present, the second pharmaceutical formulation. For example, if the kit comprises a first composition comprising a compound of Formula I and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of Formula I contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula I and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Preparation of Formula I Compounds

Benzoxazepin compounds of Formula I may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie*, 4, Aufl. ed. Springer-Verlag, Berlin, including supplements (also available via the Beilstein online database).

In certain embodiments, compounds of Formula I may be readily prepared using well-known procedures to prepare benzoxepin compounds (Sekhar et al (1989) Sulfur Letters 9(6):271-277; Katsura et al (2000 J. Med. Chem. 43:3315-3321; Rueeger et al (2004) Biorganic & Med. Chem. Letters 14:2451-2457; Reiter et al (2007) Biorganic & Med. Chem. Letters 17:5447-5454; Banaszak et al (2006) Tetrahedron Letters 47:6235-6238); and other heterocycles, which are described in: Comprehensive Heterocyclic Chemistry II, Editors Katritzky and Rees, Elsevier, 1997, e.g. Volume 3; Liebigs Annalen der Chemie, (9):1910-16, (1985); Helvetica Chimica Acta, 41:1052-60, (1958); Arzneimittel-Forschung, 40(12):1328-31, (1990).

Compounds of Formula I may be prepared singly or as compound libraries comprising at least 2, e.g. 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds, or pharmaceutically acceptable salts thereof.

For illustrative purposes, the General Procedures show general methods which may be applied for preparation of Formula I compounds, as well as key intermediates. The Figures and Examples sections contain more detailed description of individual reaction steps. Those skilled in the art will appreciate that other synthetic routes may be used to synthesize the inventive compounds. Although certain starting materials and routes are depicted in the Schemes, General Procedures and Examples, other similar starting materials and routes can be substituted to provide a variety of derivatives and/or reaction conditions. In addition, many of the compounds prepared by the methods described below can be further modified in light of this disclosure using conventional chemistry well known to those skilled in the art.

In preparing compounds of Formulas I, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, Third Ed., 1999.

Synthetic chemistry transformations and protecting group methodologies (protection and deprotection) useful in synthesizing Formula I compounds and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, $3^{rd}$ Ed., John Wiley and Sons (1999); and L. Paquette, ed., Encyclopedia of Reagents for Organic Synthesis, John Wiley and Sons (1995) and subsequent editions thereof.

For illustrative purposes, FIGS. 1-8 show general methods for preparing Formula I benzoxazepine compounds, as well as key intermediates. For a more detailed description of the individual reaction steps, see the General Procedures and Examples sections. Those skilled in the art will appreciate that other synthetic routes may be used to synthesize the inventive compounds. Although specific starting materials and reagents are depicted and discussed in the General Procedures, Examples, and Schemes, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

Methods of Separation

In the methods of preparing Formula I compounds, it may be advantageous to separate reaction products from one another and/or from starting materials. The desired products of each step or series of steps is separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like. Selection of appropriate methods of separation depends on the nature of the materials involved, such as, boiling point and molecular weight in distillation and sublimation, presence or absence of polar functional groups in chromatography, stability of materials in acidic and basic media in multiphase extraction, and the like.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. J. Org. Chem. (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

EXAMPLES

The chemical reactions described in the Examples may be readily adapted to prepare a number of other PI3K inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting reactive functional groups, by utilizing other suitable reagents known in the art other than those described, and/or by making routine modifications of reaction conditions. Alternatively, other reactions disclosed herein or known in the art will be recognized as having applicability for preparing other compounds of the invention.

$^1$H NMR spectra were recorded at ambient temperature using an NMR spectrometer, including a Varian Unity Inova (400 MHz) spectrometer with a triple resonance 5 mm probe. Chemical shifts are expressed in ppm relative to tetramethylsilane. The following abbreviations have been used: br=broad signal, s=singlet, d=doublet, dd=double doublet, t=triplet, q=quartet, m=multiplet.

High Pressure Liquid Chromatography/Mass Spectrometry (LCMS) experiments to determine retention times ($R_T$) and associated mass ions may be performed. The spectrometers may have an electrospray source operating in positive and negative ion mode. Additional detection is achieved using a evaporative light scattering detector.

Chiral SFC (supercritical fluid chromatography) may be used to separate enantiomers (Liu et al (2003) Chromatographia 58(11/12):775-779).

Microwave experiments were carried out using a CEM Explorer, Smith Synthesizer or a Biotage Initiator™, which uses a single-mode resonator and dynamic field tuning, both of which give reproducibility and control. Temperatures from 40-250° C. can be achieved and pressures of up to 20 bar can be reached.

Unless otherwise stated, all reactions were performed under an inert, i.e. argon or nitrogen, atmosphere.
General Preparative Procedures FIG. 1 shows a synthetic route to 9-halo-2-(1-isopropyl-1H-1,2,4-triazol-5-yl)-5,6-dihydrobenzo[f]imidazo[1,2-d][1,4]oxazepine compounds 12 from 4-bromo-2-hydroxybenzaldehyde 4.

Figure 2:
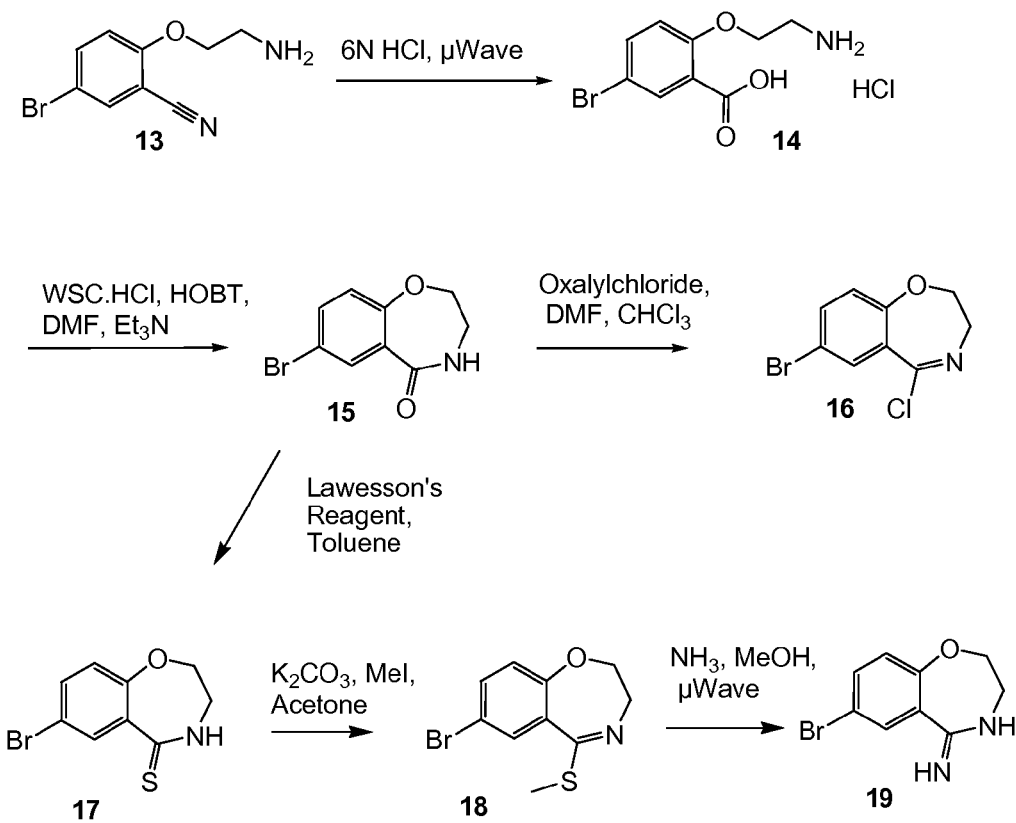
FIG. 2 shows a synthetic route to 7-bromo-5-chloro-2,3-dihydrobenzo[f][1,4]oxazepine 16 and 7-bromo-3,4-dihydrobenzo[f][1,4]oxazepin-5(2H)-imine 19

FIG. 2 shows a synthetic route to 7-bromo-5-chloro-2,3-dihydrobenzo[f][1,4]oxazepine 16 and 7-bromo-3,4-dihydrobenzo[f][1,4]oxazepin-5(2H)-imine 19

Figure 3:
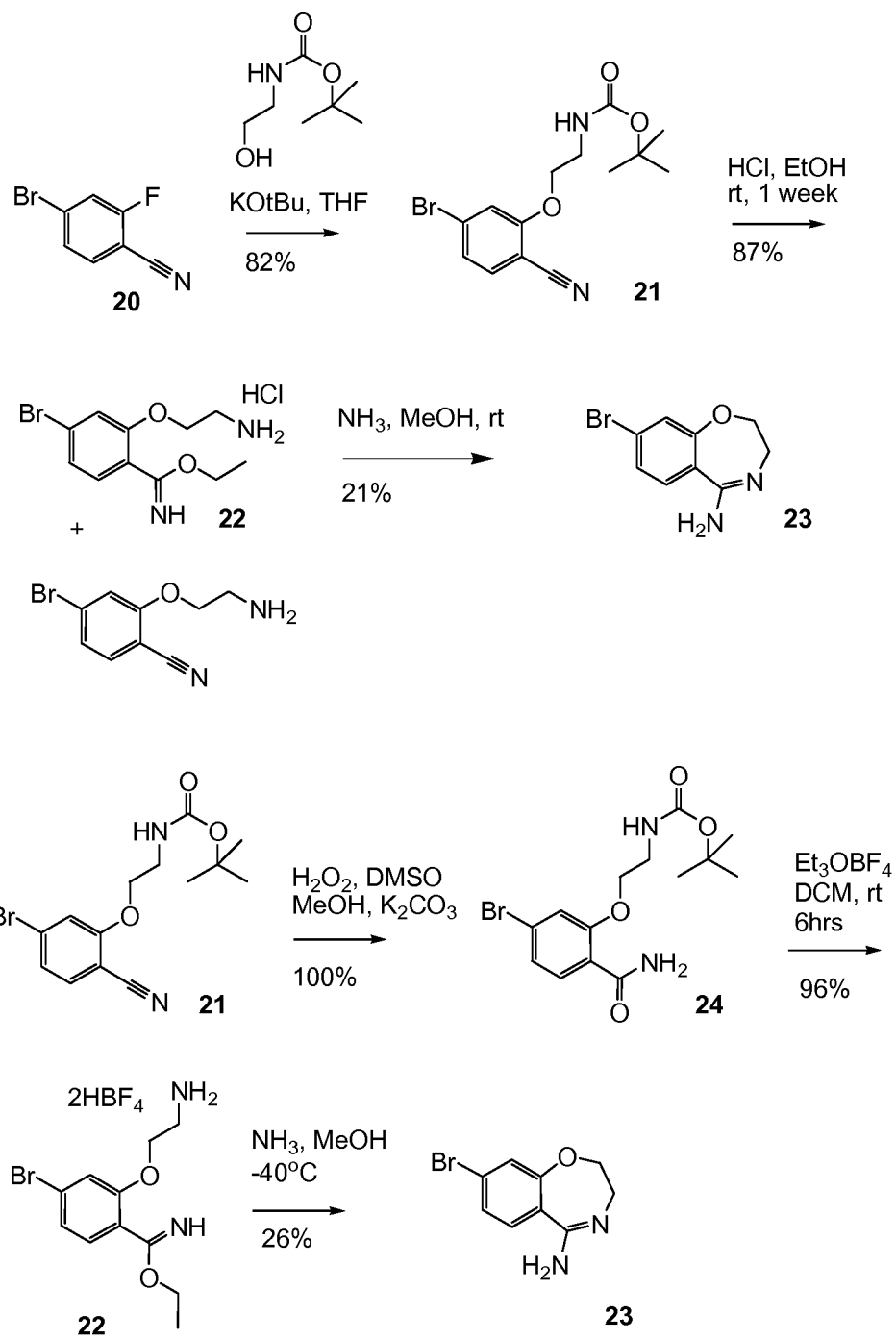
FIG. 3 shows synthetic routes to (E)-8-bromo-2,3-dihydrobenzo[f][1,4]oxazepin-5-amine 23

FIG. 3 shows synthetic routes to (E)-8-bromo-2,3-dihydrobenzo[f][1,4]oxazepin-5-amine 23

Figure 4:
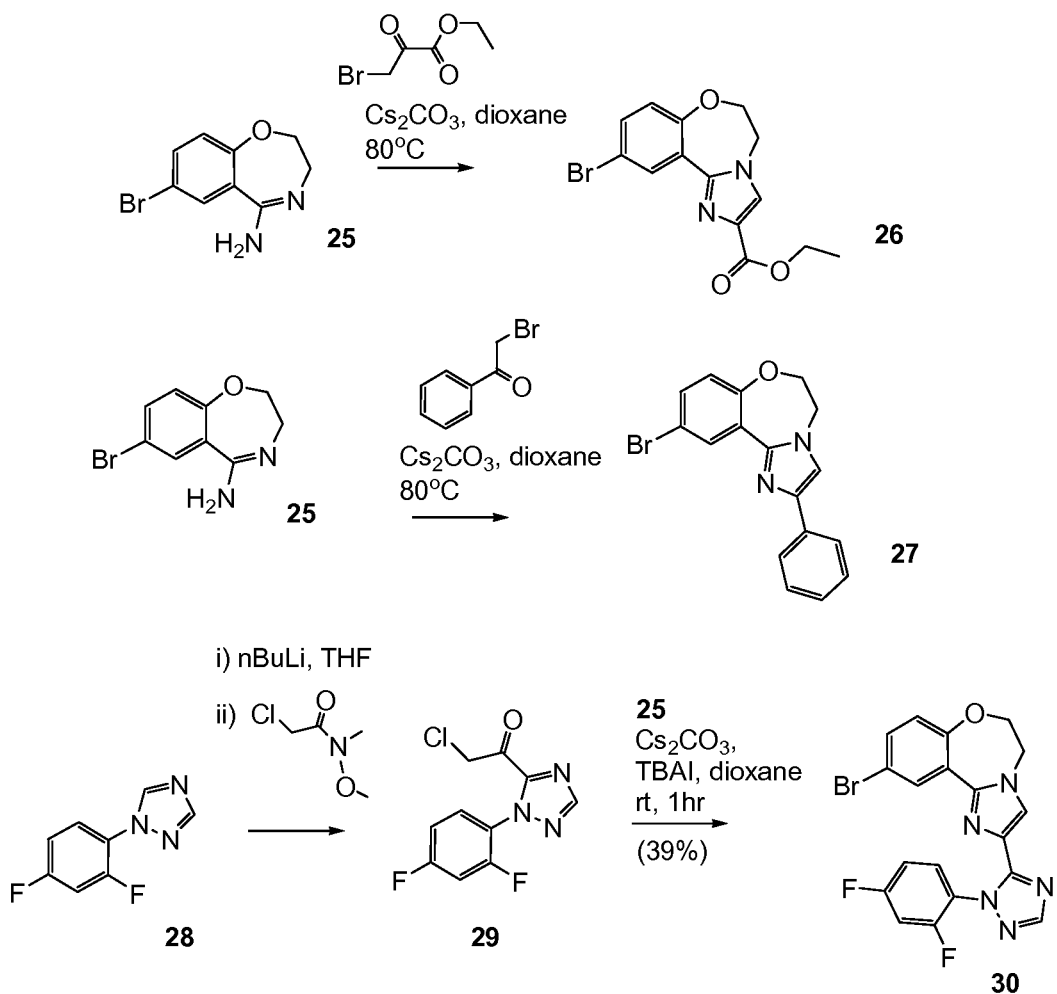
FIG. 4 shows synthetic routes to 10-bromo-2-phenyl-5,6-dihydrobenzo[f]imidazo[1,2-d][1,4]oxazepine 27 and 10-bromo-2-(1-(2,4-difluorophenyl)-1H-1,2,4-triazol-5-yl)-5,6-dihydrobenzo[f]imidazo[1,2-d][1,4]oxazepine 30

FIG. 4 shows synthetic routes to 10-bromo-2-phenyl-5,6-dihydrobenzo[f]imidazo[1,2-d][1,4]oxazepine 27 and 10-bromo-2-(1-(2,4-difluorophenyl)-1H-1,2,4-triazol-5-yl)-5,6-dihydrobenzo[f]imidazo[1,2-d][1,4]oxazepine 30

Figure 5:
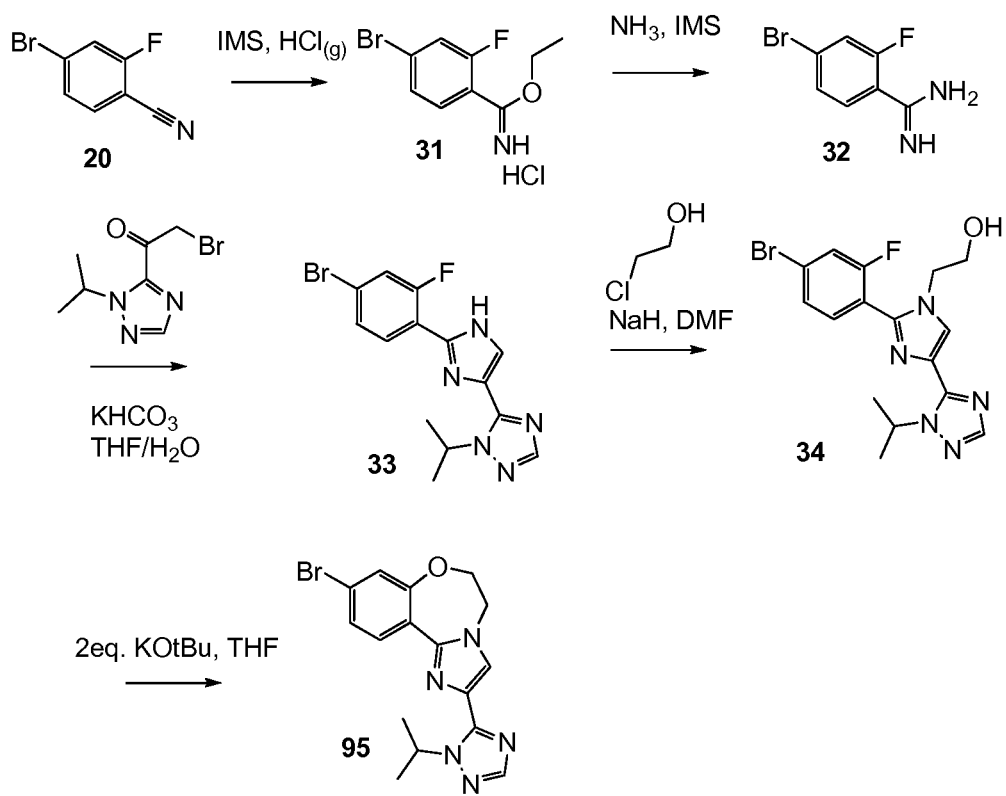
FIG. 5 shows a synthetic route to 9-halo-2-(1-isopropyl-1H-1,2,4-triazol-5-yl)-5,6-dihydrobenzo[f]imidazo[1,2-d][1,4]oxazepine compounds 95 from 4-bromo-2-fluorobenzonitrile 20.

FIG. 5 shows a synthetic route to 9-halo-2-(1-isopropyl-1H-1,2,4-triazol-5-yl)-5,6-dihydrobenzo[f]imidazo[1,2-d][1,4]oxazepine compounds 95 from 4-bromo-2-fluorobenzonitrile 20.

Figure 6:
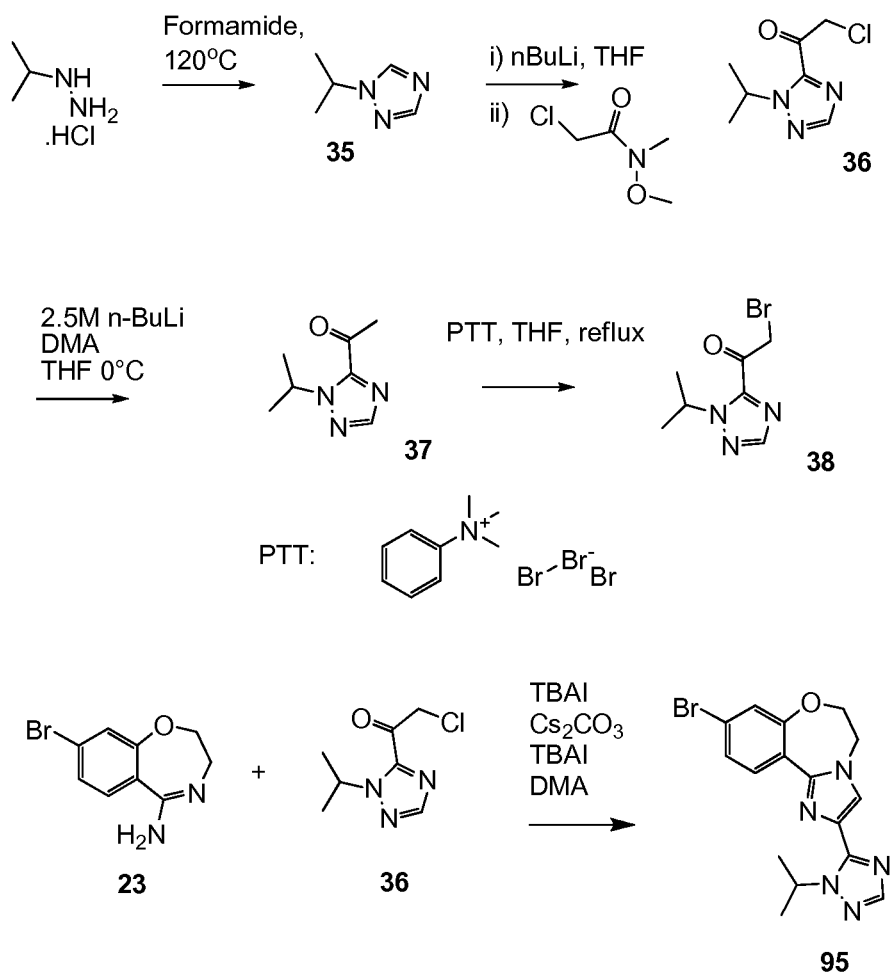
FIG. 6 shows a synthetic route to 9-halo-2-(1-isopropyl-1H-1,2,4-triazol-5-yl)-5,6-dihydrobenzo[f]imidazo[1,2-d][1,4]oxazepine compounds 95 from the reaction of (E)-8-bromo-2,3-dihydrobenzo[f][1,4]oxazepin-5-amine 23 and 2-chloro-1-(1-isopropyl-1H-1,2,4-triazol-5-yl)ethanone 36.

FIG. 6 shows a synthetic route to 9-halo-2-(1-isopropyl-1H-1,2,4-triazol-5-yl)-5,6-dihydrobenzo[f]imidazo[1,2-d][1,4]oxazepine compounds 95 from the reaction of (E)-8-bromo-2,3-dihydrobenzo[f][1,4]oxazepin-5-amine 23 and 2-chloro-1-(1-isopropyl-1H-1,2,4-triazol-5-yl)ethanone 36.

Figure 7:
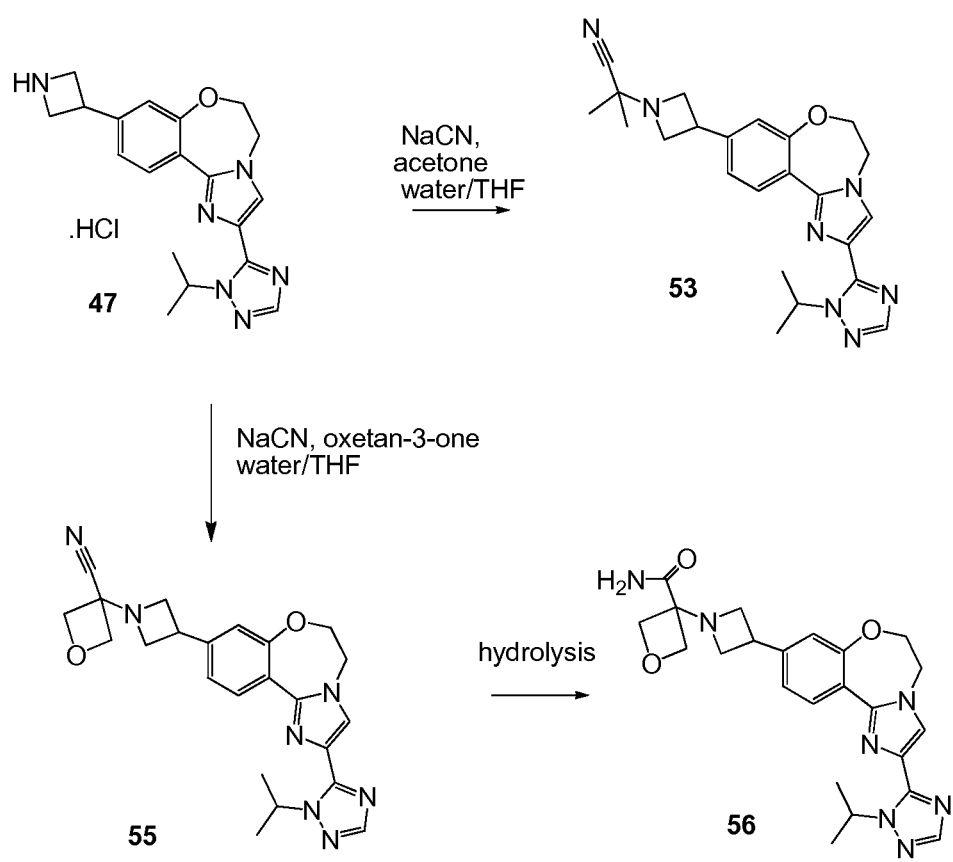
FIG. 7 shows a synthetic route to 3-(3-(2-(1-isopropyl-1H-1,2,4-triazol-5-yl)-5,6-dihydrobenzo[f]imidazo[1,2-d][1,4]oxazepin-9-yl)azetidin-1-yl)oxetane-3-carboxamide 56 from 8-azetidin-3-yl-2-(2-isopropyl-2H-[1,2,4]triazol-3-yl)-4,5-dihydro-6-oxa-1,3a-diaza-benzo[e]azulene hydrochloride 47.

FIG. 7 shows a synthetic route to 3-(3-(2-(1-isopropyl-1H-1,2,4-triazol-5-yl)-5,6-dihydrobenzo[f]imidazo[1,2-d][1,4]oxazepin-9-yl)azetidin-1-yl)oxetane-3-carboxamide 56 from 8-azetidin-3-yl-2-(2-isopropyl-2H-[1,2,4]triazol-3-yl)-4,5-dihydro-6-oxa-1,3a-diaza-benzo[e]azulene hydrochloride 47.

Figure 8:
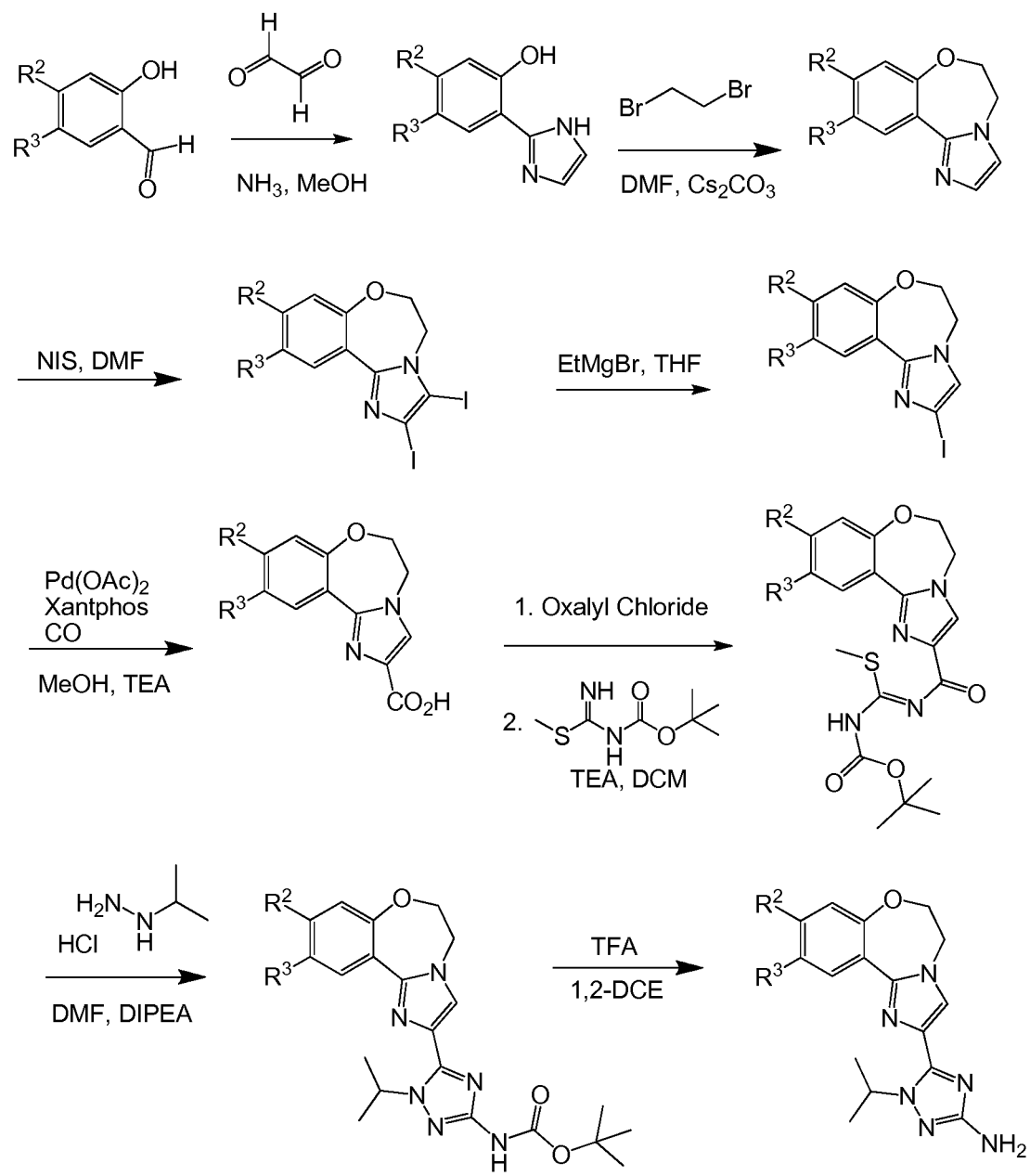
FIG. 8 shows a synthetic route to 9-substituted- and 1-substituted 5,6-dihydrobenzo[f]imidazo[1,2-d][1,4]oxazepin-2-yl)-1-isopropyl-1H-1,2,4-triazol-3-ylcarbamate compounds from 4-substituted- and 5-substituted-2-hydroxybenzaldehyde intermediates.

FIG. 8 shows a synthetic route to 9-substituted- and 1-substituted 5,6-dihydrobenzo[f]imidazo[1,2-d][1,4]oxazepin-2-yl)-1-isopropyl-1H-1,2,4-triazol-3-ylcarbamate compounds from 4-substituted- and 5-substituted-2-hydroxybenzaldehyde intermediates.

ABBREVIATIONS

AcOH: Acetic acid; BINAP: 2,2'-Bis(diphenylphosphino)-1,1'-binaphthalene; CH$_3$CN: Acetonitrile; Cs$_2$CO$_3$: Cesium carbonate; CuI: Copper iodide; DBU: 1,8-Diazabicyclo[5.4.0]undec-7-ene; DCE: Dichloroethane; DIBAL-H: Diisobutylaluminum hydride; DCM: Dichloromethane; DIPEA: Diisopropylethylamine; DMAP: 4-Dimethylaminopyridine; DME: Dimethoxyethane; DMF: Dimethylformamide; DMSO: Dimethylsulfoxide; EDCI: 1-Ethyl-3-(3'-dimethylaminopropyl)carbodiimide; EtOAc: Ethyl acetate; Et$_3$N: Triethylamine; h or hr: Hour(s); HATU: (2-(7-Aza-1H-benzotriazole-1-yl)-1,1,3,3-tetramethyluronium hexafluorophosphate); HCl: Hydrochloric acid; HCO$_2$H: Formic acid; HOAt: 1-Hydroxy-7-azabenzotriazole; HOBt: Hydroxybenzotriazole; HM-N: Isolute®HM-N is a modified form of diatomaceous earth that can efficiently absorb aqueous samples; HPLC: High-performance liquid chromatography; IMS: Industrial methylated spirits; LCMS: Liquid chromatography mass spectrometry; LiHMDS: Lithium bis(trimethylsilyl)amide; M: Molar; min: Minute(s); mL: Milliliter; mCPBA: 3-Chloroperbenzoic acid; MeOH: Methanol; MgSO$_4$: Magnesium sulphate; NaHCO$_3$: Sodium bicarbonate; NaOH: Sodium hydroxide; Na$_2$SO$_4$: Sodium sulphate; NBS: N-Bromosuccinimide; NH$_3$: Ammonia; NH$_4$Cl: Ammonium chloride; NMP: N-methylpyrrolidone; NMR: Nuclear magnetic resonance; Pd/C: Palladium on carbon; Pd$_2$dba$_3$: Tris(dibenzylideneacetone)dipalladium(0); Pd(OAc)$_2$: Palladium(II) acetate; Pd(PPh$_3$)$_4$: Tetrakis(triphenylphosphine)palladium(0); PdCl$_2${P$^t$Bu$_2$(Ph-p-NMe$_2$)}$_2$: Bis(di-tert-butyl(4-dimethylaminophenyl)phosphine)dichloropalladium(II); PTFE: Polytetrafluoro ethylene; PtO$_2$: Platinum Oxide; RT: Room temperature; Si-PPC: Pre-packed silica flash chromatography cartridge: Isolute® SPE, Biotage SNAP® or ISCO Redisep®; SCX-2 cartridge: Strong cation exchange cartridge; TBME: Tertbutyl methyl ether; TFA: Trifluoroacetic acid; THF: Tetrahydrofuran; Xantphos: 9,9-Dimethyl-4,5-bis(diphenylphosphino)xanthene Example 1

2-{4-[2-(2-Isopropyl-2H-[1,2,4]triazol-3-yl)-4,5-dihydro-6-oxa-1,3a-diazabenzo[e]azulen-9-ylsulfanyl]piperidin-1-yl}-2-methylpropan-1-ol

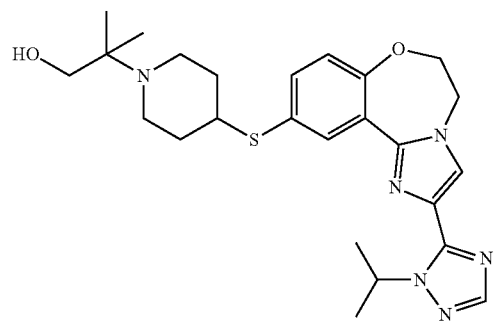 [SMILES: CC(C)n1ncnc1-c1cn2c(n1)-c1cc(SC3CCN(C(C)(C)CO)CC3)ccc1OCC2]

Step 1:
2-(4-Mercaptopiperidin-1-yl)-2-methylpropionic acid methyl ester

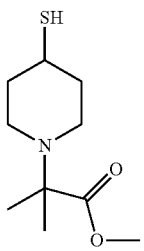

H₂S gas was bubbled into a solution of 2-methyl-2-(4-oxopiperidin-1-yl)propionic acid methyl ester (1.28 g, 6.42 mmol) in isopropanol (13 mL) for 10 min. The reaction mixture was then sealed, stirred at RT for 18 h and then left standing for 8 days at RT. After this period of time, nitrogen was bubbled into the solution for 10 min, then NaBH₄ (364 mg, 9.63 mmol) was added. The reaction mixture was stirred at RT for 10 min and then heated at 80° C. for 2 h. After cooling to RT, volatiles were removed under reduced pressure and the resulting residue was partitioned between diethyl ether and water. The aqueous layer was further extracted with diethyl ether and the combined organic phases were washed with water, followed by brine, then dried over Na₂SO₄ and concentrated in vacuo. 2-(4-Mercaptopiperidin-1-yl)-2-methylpropionic acid methyl ester (1.497 g, quantitative yield) was obtained as a colorless oil. ¹H NMR (CDCl₃, 300 MHz): δ 3.71 (3H, s), 3.01-2.85 (2H, m), 2.82-2.64 (1H, m), 2.33-2.14 (2H, m), 2.06-1.94 (2H, m), 1.71-1.58 (2H, m), 1.53-1.48 (1H, m), 1.29 (6H, s).

Step 2: 2-{4-[2-(2-Isopropyl-2H-[1,2,4]triazol-3-yl)-4,5-dihydro-6-oxa-1,3a-diazabenzo[e]azulen-9-ylsulfanyl]piperidin-1-yl}-2-methylpropionic acid methyl ester

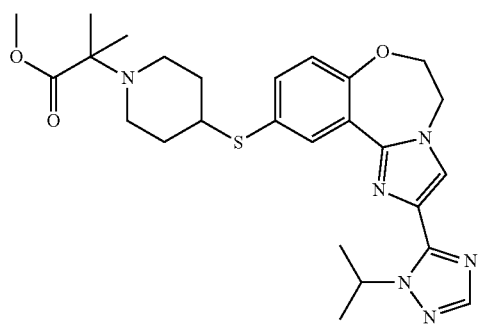 [SMILES: COC(=O)C(C)(C)N1CCC(Sc2ccc3c(c2)-c2nc(-c4ncnn4C(C)C)cn2CCO3)CC1]

A mixture of 9-bromo-2-(2-isopropyl-2H-[1,2,4]triazol-3-yl)-4,5-dihydro-6-oxa-1,3a-diazabenzo[e]azulene (326 mg, 0.871 mmol), 2-(4-mercaptopiperidin-1-yl)-2-methylpropionic acid methyl ester (284 mg, 1.307 mmol), Pd₂(dba)₃ (40 mg, 5 mol %), XantPhos (50 mg, 10 mol %) and DIPEA (0.60 mL, 3.48 mmol) in dioxane (8 mL) was purged with nitrogen and then heated at 120° C. for 1 h using microwave irradiation. After cooling to RT, the reaction mixture was diluted with DCM (200 mL) and purified by column chromatography (Si-PCC, gradient 0-20% MeOH in DCM) affording 2-{4-[2-(2-Isopropyl-2H-[1,2,4]triazol-3-yl)-4,5-dihydro-6-oxa-1,3a-diazabenzo[e]azulen-9-ylsulfanyl]piperidin-1-yl}-2-methylpropionic acid methyl ester as an orange oil (614 mg, quantitative yield). LCMS: R_T 2.23/2.28 min [M+H]⁺ 511.3.

Step 3

To an ice-cooled solution of 2-{4-[2-(2-isopropyl-2H-[1,2,4]triazol-3-yl)-4,5-dihydro-6-oxa-1,3a-diazabenzo[e]azulen-9-ylsulfanyl]piperidin-1-yl}-2-methylpropionic acid methyl ester (0.485 mmol) in THF (20 mL) was added LiAlH₄ (1.0M in THF, 1.5 mL) and the mixture was stirred at 0° C. for 1 h. To the reaction mixture was added EtOAc (0.5 mL) and stirring was continued for 10 min. Volatiles were then removed under reduced pressure and the resulting residue was partitioned between DCM and 10% aq. solution of Rochelle's salt. The suspension was stirred for 20 min and then filtered through a pad of Celite®. The filtrate was extracted with DCM and the combined organic phases were washed with water, followed by brine, then dried and concentrated in vacuo. The resulting residue was purified by column chromatography (Si-PCC, gradient 2-13% 2M NH₃/MeOH in DCM) affording 2-{4-[2-(2-Isopropyl-2H-[1,2,4]triazol-3-yl)-4,5-dihydro-6-oxa-1,3a-diazabenzo[e]azulen-9-ylsulfanyl]piperidin-1-yl}-2-methylpropan-1-ol (229 mg, 98% over two steps). LCMS: R_T 2.13/2.19 min [M+H]⁺ 483.2

Example 2

2-(2-Isopropyl-2H-[1,2,4]triazol-3-yl)-9-(piperidin-4-ylsulfanyl)-4,5-dihydro-6-oxa-1,3a-diazabenzo[e]azulene

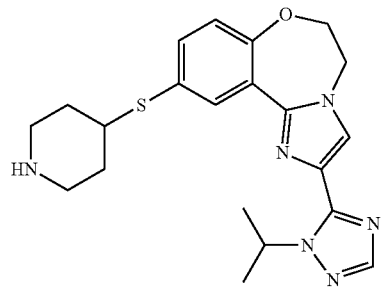 [SMILES: CC(C)n1ncnc1-c1cn2c(n1)-c1cc(SC3CCNCC3)ccc1OCC2]

Step 1: 4-[2-(2-Isopropyl-2H-[1,2,4]triazol-3-yl)-4,5-dihydro-6-oxa-1,3a-diazabenzo[e]azulen-9-ylsulfanyl]piperidine-1-carboxylic acid tertbutyl ester

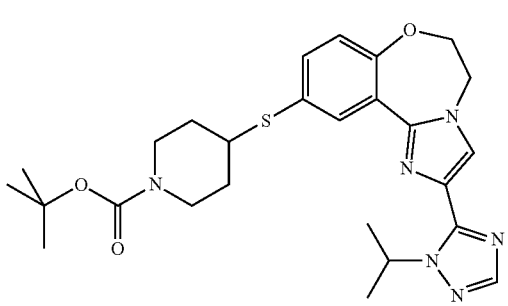 [SMILES: CC(C)n1ncnc1-c1cn2c(n1)-c1cc(SC3CCN(C(=O)OC(C)(C)C)CC3)ccc1OCC2]

A mixture of 9-bromo-2-(2-isopropyl-2H-[1,2,4]triazol-3-yl)-4,5-dihydro-6-oxa-1,3a-diazabenzo[e]azulene from Example 1 (100 mg, 0.267 mmol), 4-mercaptopiperidine-1-carboxylic acid tertbutyl ester (87 mg, 0.401 mmol), Pd$_2$(dba)$_3$ (13 mg, 5 mol %), XantPhos (15 mg, 10 mol %) and DIPEA (0.19 mL) in dioxane (3 mL) was purged with nitrogen and then heated at 120° C. for 1 h using microwave irradiation. The same process was repeated using a mixture of 9-bromo-2-(2-isopropyl-2H-[1,2,4]triazol-3-yl)-4,5-dihydro-6-oxa-1,3a-diazabenzo[e]azulene (400 mg, 1.068 mmol), 4-mercaptopiperidine-1-carboxylic acid tertbutyl ester (348 mg, 1.604 mmol), Pd$_2$(dba)$_3$ (50 mg, 5 mol %), XantPhos (61 mg, 10 mol %) and DIPEA (0.745 mL) in dioxane (10 mL). The two crude reaction mixtures were combined into DCM (200 mL) and purified by column chromatography (Si-PCC, gradient 0-7% MeOH in DCM) affording the title compound as an orange gum (1.27 g, quantitative). LCMS: R$_T$ 4.15 min [M+H]$^+$ 511.3. (110174852)

Step 2: 2-{4-[2-(2-Isopropyl-2H-[1,2,4]triazol-3-yl)-4,5-dihydro-6-oxa-1,3a-diazabenzo[e]azulen-9-ylsulfanyl]piperidin-1-yl}-2-methylpropionic acid

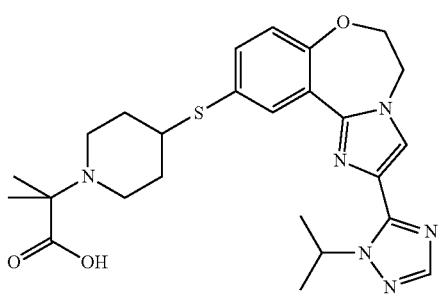 [SMILES: CC(C)n1ncnc1-c1cn2c(n1)-c1cc(SC3CCN(C(C)(C)C(=O)O)CC3)ccc1OCC2]

To a solution of 2-{4-[2-(2-isopropyl-2H-[1,2,4]triazol-3-yl)-4,5-dihydro-6-oxa-1,3a-diazabenzo[e]azulen-9-ylsulfanyl]piperidin-1-yl}-2-methylpropionic acid methyl ester (50 mg, 0.0979 mmol) in THF (4 mL) was added 1.0M LiOH in water (0.5 mL). The reaction mixture was first stirred at RT for 6 h, then left at RT for 7 days, and then heated at 120° C. for 1 h using microwave irradiation. Volatiles were removed under reduced pressure and the resulting residue was purified by column chromatography (C$_{18}$, gradient 2-80% MeOH in H$_2$O) and then loaded onto an Isolute® SCX-2 cartridge. The cartridge was washed with MeOH and the product eluted with 2M NH$_3$/MeOH affording the title compound as a white solid (20 mg, 42%). LCMS: R$_T$ 2.45 min [M–H]$^+$ 495.0.

Step 3

An ice-cooled solution of 4-[2-(2-isopropyl-2H-[1,2,4]triazol-3-yl)-4,5-dihydro-6-oxa-1,3a-diazabenzo[e]azulen-9-ylsulfanyl]piperidine-1-carboxylic acid tertbutyl ester (0.722 g) in DCM (10 mL) was treated with TFA (2 mL) and stirred at RT for 2 h. Volatiles were removed under reduced pressure and the resulting residue was purified by column chromatography (C$_{18}$, gradient 20-50% MeOH in 0.5% TFA/H$_2$O) and then loaded onto an Isolute® SCX-2 cartridge. The cartridge was washed with MeOH and the product eluted with 0.5M NH$_3$/MeOH affording 2-(2-Isopropyl-2H-[1,2,4]triazol-3-yl)-9-(piperidin-4-ylsulfanyl)-4,5-dihydro-6-oxa-1,3a-diazabenzo[e]azulene (0.368 g). LCMS: R$_T$ 2.08/2.14 min [M+H]$^+$ 411.2

Example 3

2-Methyl-2-[4-(2-pyridin-2-yl-4,5-dihydro-6-oxa-1,3a-diazabenzo[e]azulen-9-ylsulfanyl)piperidin-1-yl]propan-1-ol

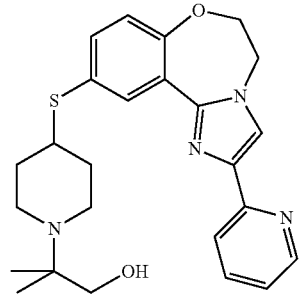 [SMILES: CC(C)(CO)N1CCC(Sc2ccc3c(c2)-c2nc(-c4ccccn4)cn2CCO3)CC1]

Step 1: 9-Bromo-2-pyridin-2-yl-4,5-dihydro-6-oxa-1,3a-diazabenzo[e]azulene

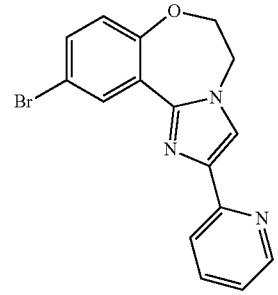 [SMILES: Brc1ccc2c(c1)-c1nc(-c3ccccn3)cn1CCO2]

A mixture of 9-bromo-2-iodo-4,5-dihydro-6-oxa-1,3a-diazabenzo[e]azulene (200 mg, 0.512 mmol), 2-tributylstannanylpyridine (226 g, 0.614 mmol), Pd$_2$(PPh$_3$)$_2$Cl$_2$ (36 mg, 0.05 mmol) and copper iodide (29 mg, 0.15 mmol) in DMF (4 mL) was purged with nitrogen and then heated at 100° C. for 1 h using microwave irradiation. The reaction mixture was diluted with MeOH (20 mL) and then loaded onto an Isolute® SCX-2 cartridge which was washed with MeOH and the product eluted with 0.5M NH$_3$/MeOH. The product containing fractions were combined and concentrated in vacuo. The resulting residue was purified by column chromatography (Si-PCC, gradient 0-8% MeOH in DCM followed by Si-PCC, gradient 0-7% MeOH in EtOAc) affording the title compound as a cream solid (140 mg, 80%). LCMS: R$_T$ 2.52 min [M+H]$^+$ 341.8/343.8.

Step 2: 2-Methyl-2-[4-(2-pyridin-2-yl-4,5-dihydro-6-oxa-1,3a-diazabenzo[e]azulen-9-ylsulfanyl)piperidin-1-yl]propionic acid methyl ester

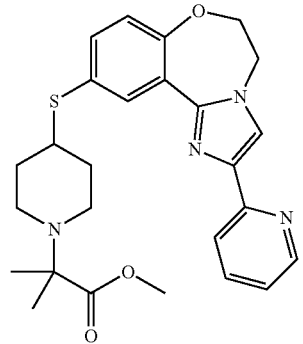 [SMILES: COC(=O)C(C)(C)N1CCC(Sc2ccc3c(c2)-c2nc(-c4ccccn4)cn2CCO3)CC1]

A mixture of 9-bromo-2-pyridin-2-yl-4,5-dihydro-6-oxa-1,3a-diazabenzo[e]azulene (300 mg, 0.877 mmol), 2-(4-mercaptopiperidin-1-yl)-2-methylpropionic acid methyl ester (286 mg, 1.315 mmol), Pd$_2$(dba)$_3$ (40 mg, 5 mol %), XantPhos (51 mg, 10 mol %) and DIPEA (0.61 mL, 3.5 mmol) in dioxane (10 mL) was purged with nitrogen and then heated at 120° C. for 1 h using microwave irradiation. The crude reaction mixture was diluted with DCM (150 mL) and purified by column chromatography (Si-PCC, gradient 0-8% 2M NH$_3$/MeOH in DCM) affording 2-Methyl-2-[4-(2-pyridin-2-yl-4,5-dihydro-6-oxa-1,3a-diazabenzo[e]azulen-9-ylsulfanyl)piperidin-1-yl]propionic acid methyl ester as an orange oil (0.674 g, quantitative). LCMS: R$_T$ 1.88 min [M+H]$^+$ 479.1.

Step 3

To an ice-cooled solution of 2-methyl-2-[4-(2-pyridin-2-yl-4,5-dihydro-6-oxa-1,3a-diazabenzo[e]azulen-9-ylsulfanyl)piperidin-1-yl]propionic acid methyl ester (0.438 mmol) in THF (20 mL) was added LiAlH$_4$ (1.0M in THF, 1.32 mL) and the mixture was stirred at 0° C. for 30 min. To the reaction mixture was added EtOAc (0.5 mL) and stirring was continued for 10 min. Volatiles were removed under reduced pressure and the resulting residue was partitioned between DCM and 10% aq. solution of Rochelle's salt. The suspension was then filtered through a pad of Celite®. The filtrate was extracted with additional DCM and the combined organic phases were washed with water, then brine, dried and concentrated in vacuo. The resulting residue was purified by column chromatography (Si-PCC, gradient 2-13% 2M NH$_3$/MeOH in DCM) affording 2-Methyl-2-[4-(2-pyridin-2-yl-4,5-dihydro-6-oxa-1,3a-diazabenzo[e]azulen-9-ylsulfanyl)piperidin-1-yl]propan-1-ol as a colorless gum (190 mg, 96% over two steps). LCMS: R$_T$ 1.799 min [M+H]$^+$ 451.1

Example 4

4-{1-[2-(2-Isopropyl-5-methyl-2H-[1,2,4]triazol-3-yl)-4,5-dihydro-6-oxa-1,3a-diazabenzo[e]azulen-8-yloxy]propyl}piperidine-1-carboxylic acid benzylester

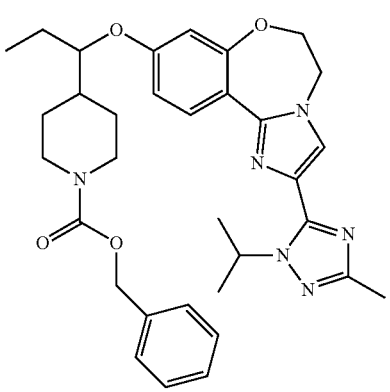 [SMILES: CCC(Oc1ccc2c(c1)OCCn1cc(-c3nc(C)nn3C(C)C)nc1-2)C1CCN(C(=O)OCc2ccccc2)CC1]

Step 1: 4-(1-Hydroxypropyl)piperidine-1-carboxylic acid benzyl ester

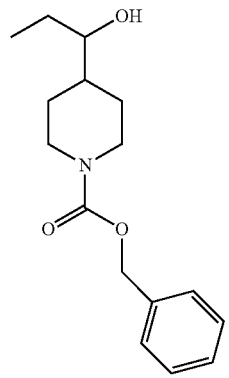 [SMILES: CCC(O)C1CCN(C(=O)OCc2ccccc2)CC1]

To a solution of 4-formylpiperidine-1-carboxylic acid benzyl ester (1.0 g, 4.04 mmol) in THF (15 mL) at 0° C. was added ethylmagnesium bromide (1.0M in THF, 8.1 mL, 8.08 mmol) and the mixture was stirred at 0° for 1 h. The reaction mixture was then quenched with water and extracted with EtOAc. The organic phase was washed with brine, dried (MgSO$_4$) and then concentrated in vacuo. The resulting residue was purified by column chromatography (Si-PCC, gradient 0-100% EtOAc in hexane) affording 4-(1-Hydroxypropyl)piperidine-1-carboxylic acid benzyl ester (690 mg, 62%). $^1$H NMR (CDCl$_3$, 400 MHz): δ 7.38-7.27 (5H, m), 5.13 (2H, bs), 4.25 (2H, s), 3.36-3.29 (1H, m), 2.83-2.66 (2H, m), 1.85-1.77 (1H, bd, J=13.16 Hz), 1.64-1.19 (7H, m), 0.97 (3H, t, J=7.41 Hz).

Step 2

To a suspension of 2-(2-isopropyl-5-methyl-2H-[1,2,4]triazol-3-yl)-4,5-dihydro-6-oxa-1,3a-diazabenzo[e]azulen-8-ol (300 mg, 0.92 mmol), 4-(1-hydroxypropyl)piperidine-1-carboxylic acid benzyl ester (308 mg, 1.11 mmol) and triphenylphosphine (411 mg, 1.38 mmol) in dioxane (5 mL) was added dropwise DEAD (217 ul, 1.38 mmol) and the reaction mixture was stirred at RT for 4 h. The mixture was then diluted with EtOAc and washed with NaOH aq. (1N). The organic phase was washed with brine, then dried (MgSO$_4$) and concentrated in vacuo. The resulting residue was purified by column chromatography (Si-PCC, gradient 0-10% MeOH in EtOAc) affording 4-{1-[2-(2-Isopropyl-5-methyl-2H-[1,2,4]triazol-3-yl)-4,5-dihydro-6-oxa-1,3a-diazabenzo[e]azulen-8-yloxy]propyl}piperidine-1-carboxylic acid benzylester (280 mg, 51%). $^1$H NMR (CDCl$_3$, 400 MHz): δ 8.40 (1H, d, J=8.97 Hz), 7.59 (1H, s), 7.37-7.28 (5H, m), 6.73 (1H, dd, J=8.99, 2.56 Hz), 6.54 (1H, d, J=2.52 Hz), 5.98-5.87 (1H, m), 5.14 (2H, s), 4.51-4.45 (2H, m), 4.44-4.37 (2H, m), 4.34-4.19 (2H, bs), 4.09-4.03 (1H, m), 2.83-2.68 (2H, m), 2.43 (3H, s), 1.88-1.78 (1H, m), 1.75-1.61 (5H, m), 1.58 (6H, d, J=6.65 Hz), 1.38-1.30 (1H, m), 0.97 (3H, t, J=7.37 Hz).

Example 5

4-{2,2,2-Trifluoro-1-[2-(2-isopropyl-5-methyl-2H-[1,2,4]triazol-3-yl)-4,5-dihydro-6-oxa-1,3a-diazabenzo[e]azulen-8-yloxy]ethyl}piperidine-1-carboxylic acid benzyl ester

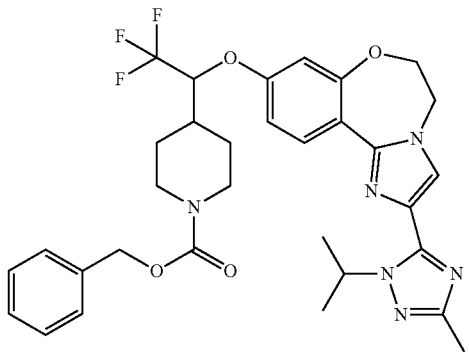 [SMILES: Cc1nc(-c2cn3c(n2)-c2ccc(OC(C4CCN(C(=O)OCc5ccccc5)CC4)C(F)(F)F)cc2OCC3)n(C(C)C)n1]

Step 1: 4-(2,2,2-Trifluoro-1-trifluoromethanesulfonyloxyethyl)piperidine-1-carboxylic acid benzyl ester

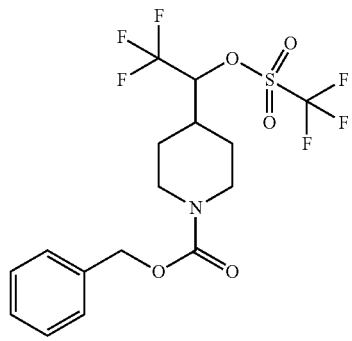 [SMILES: O=C(OCc1ccccc1)N1CCC(C(OS(=O)(=O)C(F)(F)F)C(F)(F)F)CC1]

A solution of 4-(2,2,2-trifluoro-1-hydroxyethyl)piperidine-1-carboxylic acid benzyl ester (650 mg, 2.05 mmol) in DCM (10 mL) was cooled to 0° C. and pyridine (0.199 mL, 2.46 mmol) was added followed by trifluoromethanesulfonic anhydride (0.38 mL, 2.26 mmol). The reaction mixture was stirred at 0° C. for 1 h and then quenched with water. The organic phase was washed with water and extracted with DCM (×3). The combined organic layers were washed with brine, dried over MgSO$_4$ and concentrated in vacuo affording the title compound (870 mg, 94%). $^1$H NMR (CDCl$_3$, 400 MHz): δ 7.43-7.29 (5H, m), 5.14 (2H, s), 4.87 (1H, m), 4.32 (2H, bs), 2.80 (2H, bs), 2.24-2.12 (1H, m), 1.91-1.75 (2H, m), 1.56-1.39 (2H, m).

Step 2

2-(2-Isopropyl-5-methyl-2H-[1,2,4]triazol-3-yl)-4,5-dihydro-6-oxa-1,3a-diazabenzo[e]azulen-8-ol from Example 4 (300 mg, 0.92 mmol), 4-(2,2,2-trifluoro-1-trifluoromethanesulfonyloxyethyl)piperidine-1-carboxylic acid benzyl ester (870 mg, 2.1 mmol) and Cs$_2$CO$_3$ (680 mg, 2.1 mmol) were suspended in DMF (5 mL), stirred at RT for 2 h and then heated at 80° C. for 18 h. The reaction mixture was then quenched with water and extracted with EtOAc. The organic phase was washed with brine, dried over MgSO$_4$ and concentrated in vacuo. The resulting residue was purified by column chromatography (Si-PCC, gradient 0-10% MeOH in EtOAc) affording the title compound (210 mg, 37%). LCMS: R$_T$ 4.04 min [M+H]$^+$ 625.0.

Example 6

2-(2-Isopropyl-5-methyl-2H-[1,2,4]triazol-3-yl)-9-(1-isopropylpiperidin-4-ylsulfanyl)-4,5-dihydro-6-oxa-1,3a-diazabenzo[e]azulene

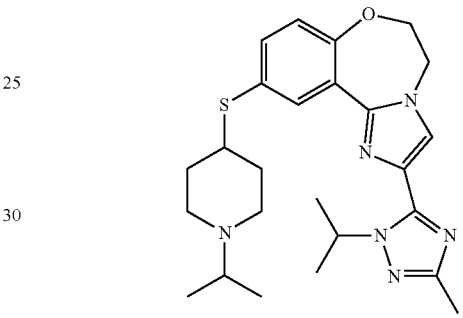

Step 1: 9-Bromo-2-(2-isopropyl-5-methyl-2H-[1,2,4]triazol-3-yl)-4,5-dihydro-6-oxa-1,3a-diazabenzo[e]azulene

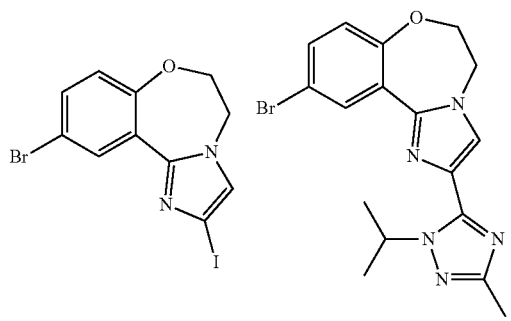

A solution of 1-isopropyl-3-methyl-1H-[1,2,4]triazole (in a 6:4 mixture with 1-isopropyl-5-methyl-1H-[1,2,4]triazole, 0.75 g, 3.6 mmol) in THF (10 mL) was cooled to −25° C. and treated with n-butyllithium (2.5M in hexanes, 1.45 mL, 3.63 mmol) over 5 min under a nitrogen atmosphere and then stirred at this temperature for 1 h. The mixture was then cooled to −30° C. and a solution of zinc chloride (0.5M in THF, 4.22 mL, 2.11 mmol) was added over 5 min. The reaction mixture was stirred between −20° C. and −25° C. for 30 min, then slowly warmed to RT and stirred at this temperature for 30 min. A solution of 9-bromo-2-iodo-4,5-dihydro-6-oxa-1,3a-diazabenzo[e]azulene (1.0 g, 2.557 mmol) in THF (2 mL) was then added followed by Pd(PPh$_3$)$_4$ (148 mg, 0.128 mmol) and the reaction mixture was stirred at 60° C. under a nitrogen atmosphere for 18 h. After cooling to RT, volatiles were removed under reduced pressure and the residue was partitioned between EtOAc and water. The aqueous layer was further washed with EtOAc and the combined organic phases were washed with water, followed by brine, then dried (Na$_2$SO$_4$) and concentrated in vacuo. The resulting residue was purified by column chromatography (Si-PCC, gradient 2-10% MeOH in DCM followed by Si-PCC, eluent 100% methyl acetate) affording the title compound as a white solid (214 mg, 22%). LCMS: R$_T$ 3.50 min [M+H]$^+$ 387.8/389.9.

Step 2

A mixture of 9-bromo-2-(2-isopropyl-5-methyl-2H-[1,2,4]triazol-3-yl)-4,5-dihydro-6-oxa-1,3a-diazabenzo[e]azulene (210 mg, 0.541 mmol), 1-isopropylpiperidine-4-thiol (129 mg, 0.812 mmol), Pd$_2$(dba)$_3$ (25 mg, 5 mol %), Xant-Phos (31 mg, 10 mol %) and DIPEA (380 µl, 2.16 mmol) in dioxane (5 mL) was purged with nitrogen and then heated at 120° C. for 1 h using microwave irradiation. The reaction mixture was then diluted with DCM (75 mL) and purified by column chromatography (Si-PCC, gradient 2-15% MeOH in DCM followed by C$_{18}$, gradient 15-50% MeOH in 0.5% TFA/H$_2$O). The product containing fractions were combined and concentrated in vacuo. The resulting residue was loaded onto an Isolute® SCX-2 cartridge which was washed with MeOH and the product eluted with 0.5M NH$_3$/MeOH. The basic fractions were concentrated under reduced pressure affording 2-(2-Isopropyl-5-methyl-2H-[1,2,4]triazol-3-yl)-9-(1-isopropylpiperidin-4-ylsulfanyl)-4,5-dihydro-6-oxa-1,3a-diazabenzo[e]azulene as a white solid/gum (146 mg, 58%). LCMS: R$_T$ 2.20 min [M+H]$^+$ 467.0

Example 7

9-(1-Isopropylpiperidin-4-ylsulfanyl)-2-(3-methylpyridin-2-yl)-4,5-dihydro-6-oxa-1,3a-diazabenzo[e]azulene

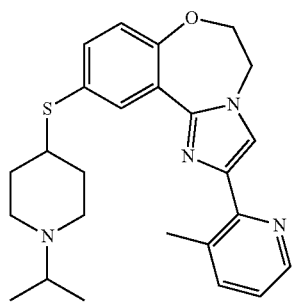 [SMILES: Cc1cccnc1-c1cn2c(n1)-c1cc(SC3CCN(C(C)C)CC3)ccc1OCC2]

Step 1: 9-Bromo-2-(3-methylpyridin-2-yl)-4,5-dihydro-6-oxa-1,3a-diazabenzo[e]azulene

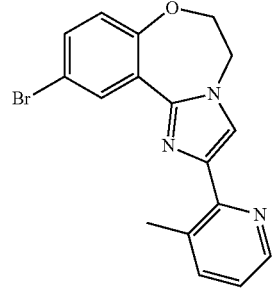 [SMILES: Cc1cccnc1-c1cn2c(n1)-c1cc(Br)ccc1OCC2]

A mixture of 9-bromo-2-iodo-4,5-dihydro-6-oxa-1,3a-diazabenzo[e]azulene (200 mg, 0.512 mmol), 3-methyl-2-tributylstannanylpyridine (235 mg, 0.614 mmol), Pd$_2$(PPh$_3$)$_2$Cl$_2$ (36 mg, 0.051 mmol) and copper iodide (29 mg, 0.153 mmol) in DMF (4 mL) was purged with nitrogen and then heated at 100° C. for 1 h using microwave irradiation. The reaction mixture was diluted with MeOH (30 mL) and then loaded onto an Isolute® SCX-2 cartridge which was washed with MeOH and the product eluted with 0.5M NH$_3$/MeOH. The product containing fractions were combined and concentrated in vacuo and the resulting residue was purified by column chromatography (Si-PCC, gradient 0-5% MeOH in EtOAc) affording the title compound as a white solid (135 mg, 74%). LCMS: R$_T$ 3.22 min [M+H]$^+$ 355.9/357.9

Step 2

A mixture of 9-bromo-2-(3-methylpyridin-2-yl)-4,5-dihydro-6-oxa-1,3a-diazabenzo[e]azulene (107 mg, 0.30 mmol), 1-isopropylpiperidine-4-thiol (72 mg, 0.45 mmol), Pd$_2$(dba)$_3$ (14 mg, 0.015 mmol, 5 mol %), XantPhos (17 mg, 0.030 mmol, 10 mol %) and DIPEA (210 µl, 1.20 mmol) in dioxane (4 mL) was purged with nitrogen and then heated at 120° C. for 1 h using microwave irradiation. The reaction mixture was diluted with DCM (75 mL) and purified by column chromatography (Si-PCC, gradient 0-10% 2M NH$_3$/MeOH in DCM followed by C$_{18}$, gradient 5-45% MeOH in 0.5% TFA/H$_2$O). The product containing fractions were combined and concentrated in vacuo and the resulting residue was loaded onto an Isolute® SCX-2 cartridge which was washed with MeOH and the product eluted with 0.5M NH$_3$/MeOH. The basic fractions were concentrated under reduced pressure affording 9-(1-Isopropylpiperidin-4-ylsulfanyl)-2-(3-methylpyridin-2-yl)-4,5-dihydro-6-oxa-1,3a-diazabenzo[e]azulene as a colorless gum (70 mg, 54%). LCMS: R$_T$ 1.83 min [M+H]$^+$ 435.1

Example 8

2-{4-[8-Fluoro-2-(2-isopropyl-5-methyl-2H-[1,2,4]triazol-3-yl)-4,5-dihydro-6-oxa-1,3a-diazabenzo[e]azulen-9-ylsulfanyl]piperidin-1-yl}-2-methylpropan-1-ol

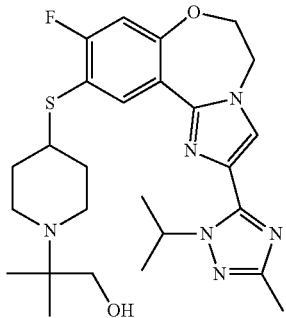 [SMILES: Cc1nc(-c2cn3c(n2)-c2cc(SC4CCN(C(C)(C)CO)CC4)c(F)cc2OCC3)n(C(C)C)n1]

Step 1: 9-Bromo-8-fluoro-2-iodo-4,5-dihydro-6-oxa-1,3a-diazabenzo[e]azulene

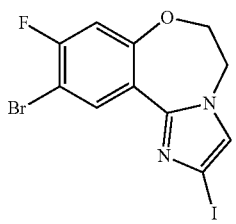 [SMILES: Fc1cc2c(cc1Br)-c1nc(I)cn1CCO2]

Step 2: 9-Bromo-8-fluoro-2-(2-isopropyl-5-methyl-2H-[1,2,4]triazol-3-yl)-4,5-dihydro-6-oxa-1,3a-diazabenzo[e]azulene

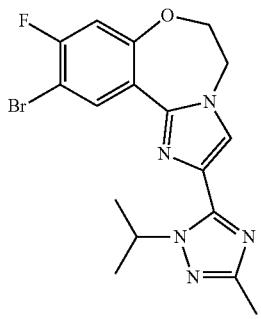 [SMILES: Cc1nc(-c2cn3c(n2)-c2cc(Br)c(F)cc2OCC3)n(C(C)C)n1]

A solution of 1-isopropyl-3-methyl-1H-[1,2,4]triazole (in a 6:4 mixture with 1-isopropyl-5-methyl-1H-[1,2,4]triazole, 0.75 g, 3.6 mmol) in THF (10 mL) was cooled to −35° C. and treated with n-butyllithium (2.5M in hexanes, 1.45 mL, 3.63 mmol). Stirring was continued for 1 h maintaining the internal temperature of between −30° C. and −20° C. The mixture was then cooled to −30° C. and a solution of zinc chloride (0.5M in THF, 4.22 mL, 2.11 mmol) was added over 5 min. The reaction mixture was stirred at −25° C. for 30 min, then slowly warmed to RT and stirred at this temperature for 1 h. A suspension of 9-bromo-8-fluoro-2-iodo-4,5-dihydro-6-oxa-1,3a-diazabenzo[e]azulene (1.046 g, 2.557 mmol) in THF (20 mL) was added followed by Pd(PPh$_3$)$_4$ (148 mg, 0.128 mmol) and the reaction mixture was stirred at 60° C. under a nitrogen atmosphere for 18 h. After cooling to RT, volatiles were removed in vacuo and the residue was partitioned between EtOAc (300 mL) and water. The aqueous phase was extracted with EtOAc (300 mL) and the combined organic layers were washed with water followed by brine, then dried (Na$_2$SO$_4$) and concentrated in vacuo. The resulting residue was purified by column chromatography (Si-PCC, eluent 100% EtOAc followed by gradient 0-8% MeOH in methyl acetate) affording 9-Bromo-8-fluoro-2-(2-isopropyl-5-methyl-2H-[1,2,4]triazol-3-yl)-4,5-dihydro-6-oxa-1,3a-diazabenzo[e]azulene as a pale yellow solid (0.66 g, 64%). LCMS: R$_T$ 4.90 min [M+H]$^+$ 405.9/407.9

Step 3: 2-{4-[8-Fluoro-2-(2-isopropyl-5-methyl-2H-[1,2,4]triazol-3-yl)-4,5-dihydro-6-oxa-1,3a-diazabenzo[e]azulen-9-ylsulfanyl]piperidin-1-yl}-2-methylpropionic acid methyl ester

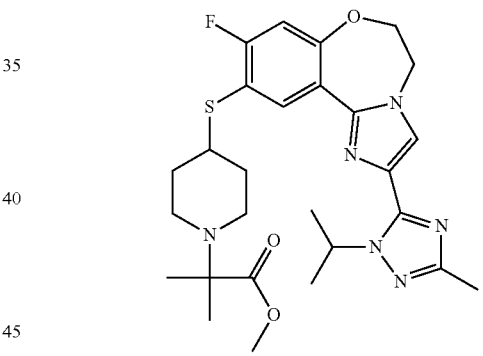

A mixture of 9-bromo-8-fluoro-2-(2-isopropyl-5-methyl-2H-[1,2,4]triazol-3-yl)-4,5-dihydro-6-oxa-1,3a-diazabenzo[e]azulene (320 mg, 0.788 mmol), 2-(4-mercaptopiperidin-1-yl)-2-methylpropionic acid methyl ester (257 mg, 1.18 mmol), Pd$_2$(dba)$_3$ (36 mg, 0.039 mmol, mol %), XantPhos (46 mg, 0.079 mmol, 10 mol %) and DIPEA (0.55 mL, 3.15 mmol) in dioxane (10 mL) was purged with nitrogen and then heated at 120° C. for 2 h using microwave irradiation. The crude reaction mixture was diluted with DCM (150 mL) and purified by column chromatography (Si-PCC, gradient 0-6% MeOH in DCM) affording 2-{4-[8-Fluoro-2-(2-isopropyl-5-methyl-2H-[1,2,4]triazol-3-yl)-4,5-dihydro-6-oxa-1,3a-diazabenzo[e]azulen-9-ylsulfanyl]piperidin-1-yl}-2-methylpropionic acid methyl ester (quantitative yield), impure but taken forward to the next step without further purification. LCMS: R$_T$ 2.29 and 2.36 min [M+H]$^+$ 543.2

Step 4: 2-{4-[8-Fluoro-2-(2-isopropyl-5-methyl-2H-[1,2,4]triazol-3-yl)-4,5-dihydro-6-oxa-1,3a-diazabenzo[e]azulen-9-ylsulfanyl]piperidin-1-yl}-2-methylpropionic acid

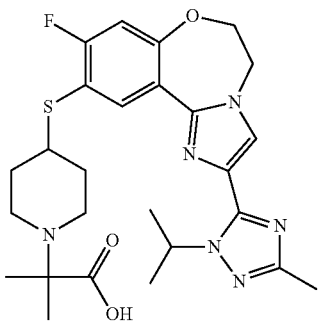 [SMILES: Cc1nc(-c2cn3c(n2)-c2cc(SC4CCN(C(C)(C)C(=O)O)CC4)c(F)cc2OCC3)n(C(C)C)n1]

To a solution of 2-{4-[8-fluoro-2-(2-isopropyl-5-methyl-2H-[1,2,4]triazol-3-yl)-4,5-dihydro-6-oxa-1,3a-diazabenzo[e]azulen-9-ylsulfanyl]piperidin-1-yl}-2-methylpropionic acid methyl ester (0.394 mmol) in MeOH (3 mL) was added 2.0M NaOH in water (1 mL). The reaction mixture was heated at 100° C. for 1 h using microwave irradiation. The crude mixture was purified by column chromatography ($C_{18}$, gradient 20-60% MeOH in 0.003M HCl/$H_2O$) then loaded onto an Isolute® SCX-2 cartridge which was washed with MeOH and the product eluted with 0.5M $NH_3$/MeOH. The product containing fractions were combined and concentrated under reduced pressure affording 2-{4-[8-Fluoro-2-(2-isopropyl-5-methyl-2H-[1,2,4]triazol-3-yl)-4,5-dihydro-6-oxa-1,3a-diazabenzo[e]azulen-9-ylsulfanyl]piperidin-1-yl}-2-methylpropionic acid as a yellow solid (177 mg, 85% over two steps). LCMS: $R_T$ 2.32, 2.37, 2.44 min [M−H]⁻ 526.8

Step 5: 2-{4-[8-Fluoro-2-(2-isopropyl-5-methyl-2H-[1,2,4]triazol-3-yl)-4,5-dihydro-6-oxa-1,3a-diazabenzo[e]azulen-9-ylsulfanyl]piperidin-1-yl}isobutyramide

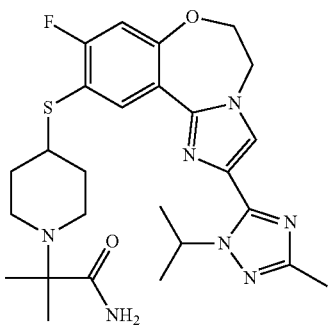 [SMILES: Cc1nc(-c2cn3c(n2)-c2cc(SC4CCN(C(C)(C)C(N)=O)CC4)c(F)cc2OCC3)n(C(C)C)n1]

To a suspension of 2-{4-[8-fluoro-2-(2-isopropyl-5-methyl-2H-[1,2,4]triazol-3-yl)-4,5-dihydro-6-oxa-1,3a-diazabenzo[e]azulen-9-ylsulfanyl]piperidin-1-yl}-2-methylpropionic acid (174 mg, 0.329 mmol) in DMF (5 mL) were added DIPEA (169 l, 0.987 mmol), HOBt.$NH_3$ (75 mg, 0.494 mmol) and EDCI (95 mg, 0.494 mmol) and the reaction mixture was stirred at RT for 18 h. The mixture was then partitioned between EtOAc and water and the aqueous phase was further extracted with EtOAc (×3). The combined organic layers were washed with water, followed by brine, then dried and concentrated in vacuo. The resulting residue was purified by column chromatography (Si-PCC, gradient 3-15% MeOH in DCM) affording the title compound as a colorless sticky solid (96 mg, 56%). LCMS: $R_T$ 2.16 min [M+H]⁺ 527.8

Step 6

To an ice-cooled solution of 2-{4-[8-fluoro-2-(2-isopropyl-5-methyl-2H-[1,2,4]triazol-3-yl)-4,5-dihydro-6-oxa-1,3a-diazabenzo[e]azulen-9-ylsulfanyl]piperidin-1-yl}-2-methylpropionic acid methyl ester (0.394 mmol) in THF (20 mL) was added LiAlH₄ (1.0M in THF, 0.79 mL) and the mixture was stirred at 0° C. for 5 min. To the reaction mixture was added EtOAc (1 mL) and stirring was continued for 10 min. Volatiles were removed under reduced pressure and the resulting residue was partitioned between DCM (40 mL) and 10% aq. solution of Rochelle's salt (50 mL). The suspension was then filtered through a pad of Celite®. The filtrate was extracted with additional DCM and the combined organic layers were washed with water, then brine, dried and concentrated in vacuo. The resulting residue was purified by column chromatography (Si-PCC, gradient 2-10% 2M $NH_3$/MeOH in DCM) affording 2-{4-[8-Fluoro-2-(2-isopropyl-5-methyl-2H-[1,2,4]triazol-3-yl)-4,5-dihydro-6-oxa-1,3a-diazabenzo[e]azulen-9-ylsulfanyl]piperidin-1-yl}-2-methylpropan-1-ol (148 mg, 73% over two steps). LCMS: $R_T$ 2.17 min [M+H]⁺ 515.0

Example 9

8-(Piperidin-3-yloxy)-2-pyridin-2-yl-4,5-dihydro-6-oxa-1,3a-diazabenzo[e]azulene

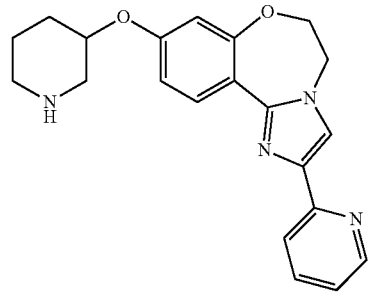 [SMILES: c1ccc(-c2cn3c(n2)-c2ccc(OC4CCCNC4)cc2OCC3)nc1]

Step 1: 8-Bromo-2-pyridin-2-yl-4,5-dihydro-6-oxa-1,3a-diazabenzo[e]azulene

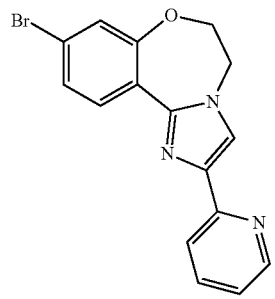

A mixture of 8-bromo-2-iodo-4,5-dihydro-6-oxa-1,3a-diazabenzo[e]azulene (300 mg, 0.767 mmol), 2-tributylstannanylpyridine (339 mg, 0.921 mmol), $Pd_2(PPh_3)_2Cl_2$ (54 mg, 0.077 mmol) and copper iodide (44 mg, 0.23 mmol) in DMF (6 mL) was purged with nitrogen and then heated at 100° C. for 1 h using microwave irradiation. The reaction mixture was loaded onto an Isolute® SCX-2 cartridge which was washed with MeOH and the product eluted with 2M NH₃/MeOH. The product containing fractions were concentrated in vacuo and the resulting residue was purified by column chromatography (Si-PCC, gradient 0-10% MeOH in DCM followed by Si-PCC, gradient 0-2% 2M NH₃/MeOH in DCM) affording the title compound as a white solid (192 mg, 73%). LCMS: $R_T$ 3.37 min [M+H]⁺ 341.9/343.9

Step 2: 3-(2-Pyridin-2-yl-4,5-dihydro-6-oxa-1,3a-diazabenzo[e]azulen-8-yloxy)piperidine-1-carboxylic acid tertbutyl ester

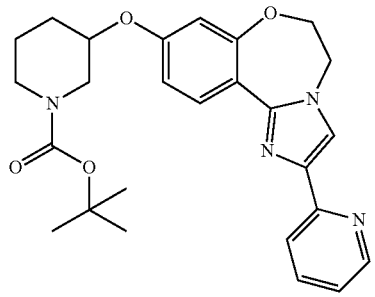 [SMILES: CC(C)(C)OC(=O)N1CCCC(Oc2ccc3c(c2)OCCn2cc(-c4ccccn4)nc2-3)C1]

To a solution of 3-hydroxypiperidine-1-carboxylic acid tertbutyl ester (176 mg, 0.88 mmol) in toluene (3 mL) was added NaH (60% in mineral oil, 35 mg, 0.88 mmol) and the mixture was heated at 70° C. for 15 min. After cooling to RT, 8-bromo-2-pyridin-2-yl-4,5-dihydro-6-oxa-1,3a-diazabenzo[e]azulene (200 mg, 0.58 mmol), Pd₂ dba₃ (11 mg, 0.001 mmol) and tertbutylXantphos (20 mg, 0.08 mmol) were added and the mixture was heated at 95° C. for 18 h. The reaction mixture was then partitioned between EtOAc and brine and the aqueous phase was further extracted with EtOAc (×3). The combined organic layers were washed with brine, then dried (Na₂SO₄) and concentrated in vacuo. The resulting residue was purified by column chromatography (Si-PCC, gradient 0-10% 2M NH₃/MeOH in DCM followed by Si-PCC, gradient 0-10% 2M NH₃/MeOH in EtOAc) affording 3-(2-Pyridin-2-yl-4,5-dihydro-6-oxa-1,3a-diazabenzo[e]azulen-8-yloxy)piperidine-1-carboxylic acid tertbutyl ester as a colorless oil, taken forward in the next step without further purification. LCMS: $R_T$ 2.68 min [M+H]⁺ 463.2

Step 3

To an ice-cooled solution of MeOH (4 mL) was added dropwise acetyl chloride (1.5 mL) and the mixture was stirred for 30 min at RT. A solution of impure 3-(2-pyridin-2-yl-4,5-dihydro-6-oxa-1,3a-diazabenzo[e]azulen-8-yloxy)piperidine-1-carboxylic acid tertbutyl ester coming from the previous step in MeOH (1 mL) was then added and the reaction mixture was stirred for 2 h at RT. A white solid was filtered off and the filtrate was concentrated in vacuo. The resulting residue was purified by HPLC (Phenomenex Gemini 5 μm C18 on a 20 min gradient 35-85% 0.1% NH₄OH in acetonitrile/water, $R_T$ 10.6 min) affording 8-(Piperidin-3-yloxy)-2-pyridin-2-yl-4,5-dihydro-6-oxa-1,3a-diazabenzo[e]azulene (13 mg, 6% over two steps).

Example 10

8-(1-Azepan-4-ylethoxy)-2-(2-isopropyl-5-methyl-2H-[1,2,4]triazol-3-yl)-4,5-dihydro-6-oxa-1,3a-diazabenzo[e]azulene

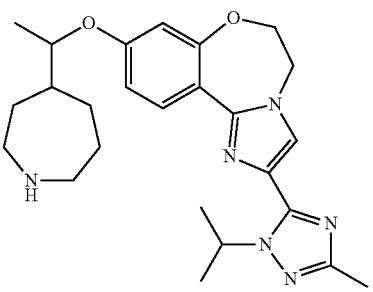 [SMILES: Cc1nc(-c2cn3c(n2)-c2ccc(OC(C)C4CCCNCC4)cc2OCC3)n(C(C)C)n1]

Step 1: 1-(1-Benzylazepan-4-yl)ethanol

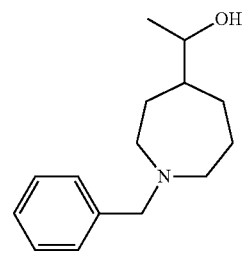 [SMILES: CC(O)C1CCCN(Cc2ccccc2)CC1]

To an ice-cooled suspension of 1-benzylazepane-4-carbaldehyde hydrochloride (1.0 g, 3.95 mmol) in THF (15 mL) was added methylmagnesium bromide (3M in diethyl ether, 4 mL) dropwise. The mixture was slowly warmed to RT and then stirred for 18 h at RT. MeOH was then added and volatiles were removed in vacuo. The resulting residue was dissolved in DMF and filtered thought a pad of silica eluting with 10% 2M NH₃/MeOH in DCM. The residue was further purified by column chromatography (Si-PCC, gradient 0-10% 2M NH₃/MeOH in DCM) and then loaded onto an Isolute® SCX-2 cartridge. The cartridge was washed with MeOH and the product eluted with 2M NH₃/MeOH. The product containing fractions were combined and concentrated in vacuo affording 1-(1-Benzylazepan-4-yl)ethanol (600 mg, 65%).
¹H NMR (CDCl₃, 400 MHz): δ 7.38-7.19 (5H, m), 3.99-3.47 (5H, m), 2.92-2.38 (4H, m), 2.01-1.51 (6H, m), 1.19 (3H, m)

Step 2: 2-(2-Isopropyl-5-methyl-2H-[1,2,4]triazol-3-yl)-4,5-dihydro-6-oxa-1,3a-diazabenzo[e]azulen-8-ol

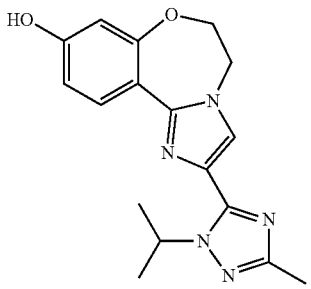 [SMILES: Cc1nc(-c2cn3c(n2)-c2ccc(O)cc2OCC3)n(C(C)C)n1]

Step 3: 4-(1-Hydroxyethyl)azepane-1-carboxylic acid tertbutyl ester

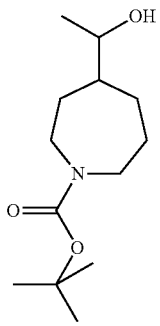 [SMILES: CC(O)C1CCCN(C(=O)OC(C)(C)C)CC1]

To a solution of 1-(1-benzylazepan-4-yl)ethanol (300 mg, 1.29 mmol) in MeOH (10 mL) were added 10% Pd/C (300 mg) and ditertbutyl dicarbonate (420 mg, 1.93 mmol). The reaction mixture was stirred at RT under a hydrogen atmosphere for 18 h. The suspension was then filtered through a pad of Celite® and the filtrate was concentrated in vacuo affording 4-(1-Hydroxyethyl)azepane-1-carboxylic acid tertbutyl ester as a colorless oil (320 mg, quantitative). $^1$H NMR (CDCl$_3$, 400 MHz): δ 3.81-3.42 (4H, m), 3.35-3.16 (2H, m), 1.98-1.76 (4H, m), 1.52-1.35 (11H, m), 1.19-1.12 (3H, m)

Step 4: 4-{1-[2-(2-Isopropyl-5-methyl-2H-[1,2,4]triazol-3-yl)-4,5-dihydro-6-oxa-1,3a-diazabenzo[e]azulen-8-yloxy]ethyl}azepane-1-carboxylic acid tertbutyl ester

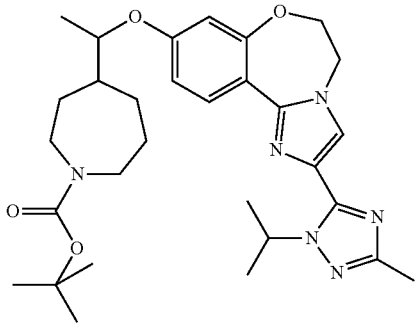 [SMILES: Cc1nc(-c2cn3c(n2)-c2ccc(OC(C)C4CCCN(C(=O)OC(C)(C)C)CC4)cc2OCC3)n(C(C)C)n1]

To a suspension of 2-(2-isopropyl-5-methyl-2H-[1,2,4]triazol-3-yl)-4,5-dihydro-6-oxa-1,3a-diazabenzo[e]azulen-8-ol from Example 4 (267 mg, 0.82 mmol), 4-(1-hydroxyethyl)azepane-1-carboxylic acid tertbutyl ester (300 mg, 1.23 mmol) and triphenylphosphine (365 mg, 1.39 mmol) in dioxane (3 mL) was added dropwise DIAD (273 ul, 1.39 mmol) and the reaction mixture was stirred at RT for 2 h. The mixture was then diluted with EtOAc and washed with aq. NaOH (1N). The aqueous phase was extracted with EtOAc (×3) and the combined organic layers were then washed with brine, dried over MgSO$_4$ and concentrated in vacuo. The resulting residue was purified by column chromatography (Si-PCC, gradient 0-10% MeOH in DCM followed by Si-PCC, gradient 0-10% MeOH in EtOAc) affording the title compound as a colorless oil (60 mg, 15%). LCMS: R$_T$ 4.08 min [M+H]$^+$ 551.2

Step 5

To a solution of 4-{1-[2-(2-isopropyl-5-methyl-2H-[1,2,4]triazol-3-yl)-4,5-dihydro-6-oxa-1,3a-diazabenzo[e]azulen-8-yloxy]ethyl}azepane-1-carboxylic acid tertbutyl ester (60 mg, 0.11 mmol) in dioxane (1 mL) was added HCl (2.5M in MeOH, 1 mL) and the reaction mixture was stirred for 1 h at RT. Volatiles were then removed in vacuo and the resulting residue was loaded onto an Isolute® SCX-2 cartridge which was washed with MeOH and the product eluted with 0.5M NH$_3$/MeOH affording 8-(1-Azepan-4-ylethoxy)-2-(2-isopropyl-5-methyl-2H-[1,2,4]triazol-3-yl)-4,5-dihydro-6-oxa-1,3a-diazabenzo[e]azulene (50 mg, quantitative). LCMS: R$_T$ 2.26 min [M+H]$^+$ 451.2

Example 11

4-{1-[2-(2-Isopropyl-5-methyl-2H-[1,2,4]triazol-3-yl)-4,5-dihydro-6-oxa-1,3a-diazabenzo[e]azulen-8-yloxy]ethyl}piperidine-1-carboxylic acid benzyl ester

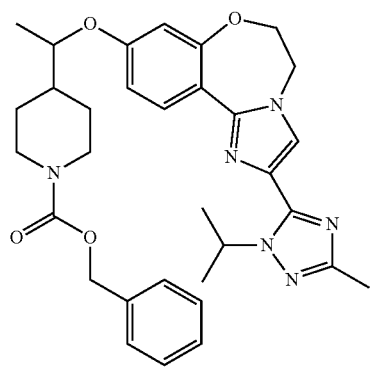 [SMILES: Cc1nc(-c2cn3c(n2)-c2ccc(OC(C)C4CCN(C(=O)OCc5ccccc5)CC4)cc2OCC3)n(C(C)C)n1]

To a suspension of 2-(2-isopropyl-5-methyl-2H-[1,2,4]triazol-3-yl)-4,5-dihydro-6-oxa-1,3a-diazabenzo[e]azulen-8-ol from Example 4 (400 mg, 1.23 mmol), 4-(1-hydroxyethyl)piperidine-1-carboxylic acid benzyl ester (487 mg, 1.85 mmol) and triphenylphosphine (548 mg, 2.09 mmol) in dioxane (7 mL) was added dropwise DIAD (410 ul, 2.09 mmol) and the reaction mixture was stirred at RT for 18 h. The mixture was then diluted with EtOAc and washed with aq. NaOH (1N). The aqueous phase was extracted with EtOAc (×3) and the combined organic layers were then washed with brine, dried over MgSO$_4$ and concentrated in vacuo. The resulting residue was purified by column chromatography (Si-PCC, gradient 0-10% MeOH in EtOAc), then suspended in DCM and filtered. The filtrate was concentrated in vacuo and purified by column chromatography (Si-PCC, gradient 0-10% MeOH in DCM) affording 4-{1-[2-(2-Isopropyl-5-methyl-2H-[1,2,4]triazol-3-yl)-4,5-dihydro-6-oxa-1,3a-diazabenzo[e]azulen-8-yloxy]ethyl}piperidine-1-carboxylic acid benzyl ester (140 mg, 20%). LCMS: $R_T$ 3.90 min [M+H]$^+$ 571.0

Example 12

9-(1-Isopropylpiperidin-4-ylsulfanyl)-2-(4-methylpyridin-2-yl)-4,5-dihydro-6-oxa-1,3a-diazabenzo[e]azulene

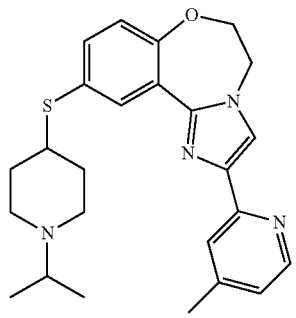 [SMILES: Cc1ccnc(-c2cn3c(n2)-c2cc(SC4CCN(C(C)C)CC4)ccc2OCC3)c1]

Step 1: 9-Bromo-2-(4-methylpyridin-2-yl)-4,5-dihydro-6-oxa-1,3a-diazabenzo[e]azulene

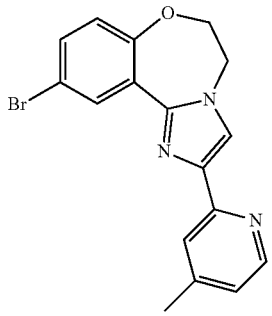 [SMILES: Cc1ccnc(-c2cn3c(n2)-c2cc(Br)ccc2OCC3)c1]

A mixture of 9-bromo-2-iodo-4,5-dihydro-6-oxa-1,3a-diazabenzo[e]azulene (200 mg, 0.512 mmol), 4-methyl-2-tributylstannanylpyridine (235 mg, 0.614 mmol), Pd$_2$(PPh$_3$)$_2$Cl$_2$ (36 mg, 0.051 mmol) and copper iodide (29 mg, 0.153 mmol) in DMF (4 mL) was purged with nitrogen and then heated at 120° C. for 45 min using microwave irradiation. The reaction mixture was diluted with MeOH (30 mL) and then loaded onto an Isolute® SCX-2 cartridge which was washed with MeOH and the product eluted with 0.5M NH$_3$/MeOH. The product containing fractions were combined and concentrated in vacuo and the resulting residue was purified by column chromatography (Si-PCC, gradient 0-10% MeOH in DCM followed by Si-PCC, gradient 0-3% MeOH in EtOAc) affording 9-Bromo-2-(4-methylpyridin-2-yl)-4,5-dihydro-6-oxa-1,3a-diazabenzo[e]azulene as a colorless solid (159 mg, 87%). LCMS: $R_T$ 2.44 min [M+H]$^+$ 355.9/357.8

Step 2

A mixture of 9-bromo-2-(4-methylpyridin-2-yl)-4,5-dihydro-6-oxa-1,3a-diazabenzo[e]azulene (147 mg, 0.411 mmol), 1-isopropylpiperidine-4-thiol (98 mg, 0.617 mmol), Pd$_2$(dba)$_3$ (19 mg, 5 mol %), XantPhos (24 mg, 10 mol %) and DIPEA (288 l, 1.64 mmol) in dioxane (5 mL) was purged with nitrogen and then heated at 120° C. for 1 h using microwave irradiation. The reaction mixture was then diluted with DCM (100 mL) and purified by column chromatography (Si-PCC, gradient 0-8% 2M NH$_3$/MeOH in DCM followed by C$_{18}$, gradient 10-50% MeOH in 0.5% TFA/H$_2$O). The product containing fractions were combined and concentrated in vacuo and the resulting residue was loaded onto an Isolute® SCX-2 cartridge which was washed with MeOH and the product eluted with 0.5M NH$_3$/MeOH. The basic fractions were concentrated under reduced pressure affording the title compound as a colorless foam (138 mg, 77%). LCMS: $R_T$ 1.79 min [M+H]$^+$ 435.2

Example 13

Methyl 2-(1-isopropyl-1H-pyrazol-5-yl)-5,6-dihydrobenzo[f]imidazo[1,2-d][1,4]oxazepine-10-carboxylate

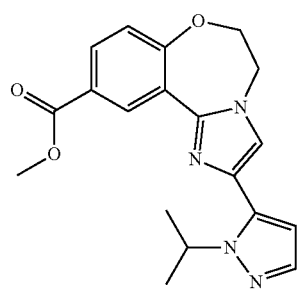 [SMILES: COC(=O)c1ccc2c(c1)-c1nc(-c3ccnn3C(C)C)cn1CCO2]

A mixture of methyl 2-iodo-5,6-dihydrobenzo[f]imidazo[1,2-d][1,4]oxazepine-10-carboxylate (370.1 mg, 1.000 mmol), 1-isopropyl-5-(4,4,5,5-tetramethyl-1,3,2-dioxaborolan-2-yl)-1H-pyrazole (354 mg, 1.50 mmol), [1,1'-Bis(diphenylphosphino)ferrocene]dichloropalladium(II), complex with dichloromethane (1:1) (40.8 mg, 0.0500 mmol) and 2.0 M of Potassium acetate in water (1.00 mL) in Acetonitrile (12 mL, 230 mmol) was degassed. The reaction was microwaved on 200 watts, 140° C. for 30 minutes. The reaction mixture was partitioned between water and ethyl acetate, filtered, the organic layer was washed with water, brine, dried over MgSO4 and concentrated in vacuum. The residue was purified on 12 g silica column eluting with 35-40% ethyl acetate in heptane. Yield 119 mg (34%). MS: (ESI+): 353.1

Example 14

2-(1-Isopropyl-1H-pyrazol-5-yl)-5,6-dihydrobenzo[f]imidazo[1,2-d][1,4]oxazepine-10-carboxylic acid

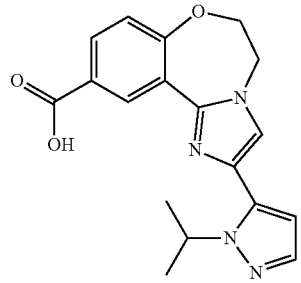 [SMILES: CC(C)n1nccc1-c1cn2c(n1)-c1cc(C(=O)O)ccc1OCC2]

Following the procedure in Example 10, methyl 2-(1-isopropyl-1H-pyrazol-5-yl)-5,6-dihydrobenzo[f]imidazo[1,2-d][1,4]oxazepine-10-carboxylate was hydrolized to give 2-(1-isopropyl-1H-pyrazol-5-yl)-5,6-dihydrobenzo[f]imidazo[1,2-d][1,4]oxazepine-10-carboxylic acid. MS(ESI+): 339.4

Example 15

Methyl 2-(4-cyano-1-isopropyl-1H-pyrazol-5-yl)-5,6-dihydrobenzo[f]imidazo[1,2-d][1,4]oxazepine-9-carboxylate

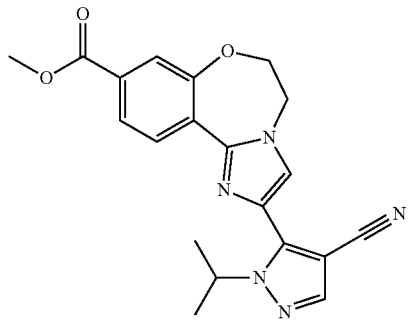 [SMILES: COC(=O)c1ccc2c(c1)OCCn1cc(-c3c(C#N)cnn3C(C)C)nc1-2]

Step 1:
5-Amino-1-isopropyl-1H-pyrazole-4-carbonitrile

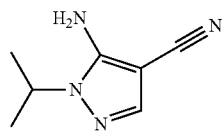

Sodium methoxide (2.139 g, 39.60 mmol) was added to a solution of ethoxymethylenemalonitrile (2.198 g, 18.00 mmol) and isopropylhydrazine hydrochloride (2.212 g, 20.00 mmol) in Ethanol (50 mL, 800 mmol). The mixture was heated under reflux for 18 hours. The solvent was removed in vacuum, the residue partitioned between ethyl acetate and water. The organic layer was washed with water, brine, dried over Na2SO4, concentrated in vacuum and purified on 25 g silica column, eluting with 25-30% of ethyl acetate in heptane, to give 5-Amino-1-isopropyl-1H-pyrazole-4-carbonitrile (yield 1.77 g, 65%). MS(ESI+): 151.2. $^1$H NMR (400 MHz, CDCl$_3$) δ 7.51 (d, J=6.4, 1H), 4.23 (ddd, J=19.8, 16.6, 9.8, 3H), 1.46 (d, J=6.6, 7H).

Step 2:
5-Iodo-1-isopropyl-1H-pyrazole-4-carbonitrile

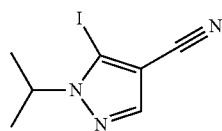

Amyl nitrite (13.00 g, 111.0 mmol) was added to a suspension of 5-amino-1-isopropyl-1H-pyrazole-4-carbonitrile (1.77 g, 11.8 mmol) in Diiodomethane (56.0 mL, 695 mmol) at −10° C. in 30 min. The mixture was stirred for 30 min at room temperature and then heated at 100° C. for 2 hours. The mixture was then cooled and concentrated in high vacuum to give a residue which was partitioned between ethyl acetate and 5% Na2S2O5. The organic layer was washed with water, 0.1% of aq HCl, water, brine, dried and concentrated in vacuum. The residue was purified on silica column eluting with 20-30% ethyl acetate in heptane. Yield 1.68 g (55%). MS(ESI+): 262.2

Step 3: Methyl 2-(tributylstannyl)-5,6-dihydrobenzo[f]imidazo[1,2-d][1,4]oxazepine-9-carboxylate

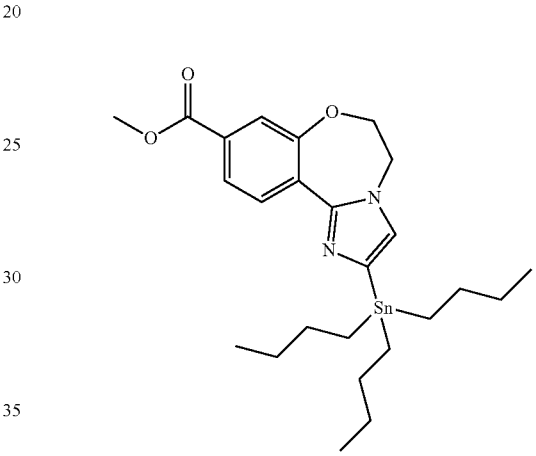

Isopropylmagnesium chloride in tetrahydrofuran (2.0 M, 1.5 mL, 3.00 mmol) was added dropwise to a solution of methyl 2-iodo-5,6-dihydrobenzo[f]imidazo[1,2-d][1,4]oxazepine-9-carboxylate (740 mg, 2.00 mmol) in Tetrahydrofuran (12 mL, 150 mmol) at room temperature. The mixture was stirred for 2.5 hours. Tributyltin chloride (0.8138 mL, 3.000 mmol) was added and the mixture was stirred for 18 hours. The mixture was mixed with sat aq. NH4Cl and extracted with ethyl acetate. The organic layer was washed with brine, dried over Na2SO4 and purified on 25 g silica column eluting with 15-20% ethyl acetate in heptane. Yield 160 mg (15%). MS(ESI+): 535.2

Step 4: Methyl 2-(4-cyano-1-isopropyl-1H-pyrazol-5-yl)-5,6-dihydrobenzo[f]imidazo[1,2-d][1,4]oxazepine-9-carboxylate A mixture of methyl 2-(tributylstannyl)-5,6-dihydrobenzo[f]imidazo[1,2-d][1,4]oxazepine-9-carboxylate (155 mg, 0.291 mmol), 5-amino-1-isopropyl-1H-pyrazole-4-carbonitrile (133 mg, 0.509 mmol) and Tetrakis(triphenylphosphine)palladium(0) (16.8 mg, 0.0145 mmol) in Toluene (6.0 mL, 56 mmol) was heated for 18 hours. The mixture was concentrating in vacuum, the residue purified on 4 g silica column eluting with 30% ethyl acetate in heptane. Yield 65 mg (59%). MS (ESI+): 378.2

Example 16

2-(4-cyano-1-isopropyl-1H-pyrazol-5-yl)-5,6-dihydrobenzo[f]imidazo[1,2-d][1,4]oxazepine-9-carboxylic acid

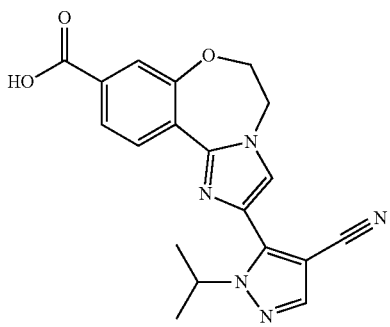 [SMILES: CC(C)n1ncc(C#N)c1-c1cn2c(n1)-c1ccc(C(=O)O)cc1OCC2]

Following the procedure in Example 10, methyl 2-(4-cyano-1-isopropyl-1H-pyrazol-5-yl)-5,6-dihydrobenzo[f]imidazo[1,2-d][1,4]oxazepine-9-carboxylate was hydrolyzed to give 2-(4-cyano-1-isopropyl-1H-pyrazol-5-yl)-5,6-dihydrobenzo[f]imidazo[1,2-d][1,4]oxazepine-9-carboxylic acid. MS (ESI+): 364.3

Example 17

10-Chloro-5,6-dihydroimidazo[1,2-d]pyrido[4,3-f][1,4]oxazepine

Step 1: 2-Chloro-5-(methoxymethoxy)pyridine

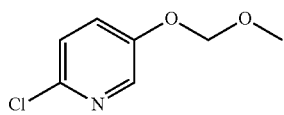

Sodium hydride, 60% dispension in mineral oil (3:2, Sodium hydride:Mineral Oil, 2.32 g) was added portion wise to a solution of 6-Chloro-pyridin-3-ol (5.00 g, 38.6 mmol) in a mixture of Tetrahydrofuran (10.0 mL, 123 mmol) and N,N-Dimethylformamide (20.0 mL, 258 mmol). The mixture formed was stirred for 15 min and Chloromethyl Methyl Ether (3.66 mL, 48.2 mmol) was added dropwise. The above mixture was stirred for 6 hours (monitored by LCMS), poured into water and extracted with ethyl acetate. The organic extracts were washed with water, brine, dried over MgSO4 and concentrated in vacuum. Purified on 40 g silica column eluting with 10-40% ethyl acetate in heptane to give 6.33 g of 2-chloro-5-(methoxymethoxy)pyridine.

Step 2: 2-Chloro-5-(methoxymethoxy)isonicotinaldehyde

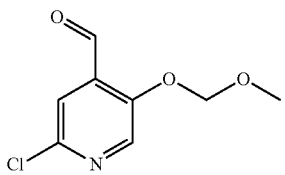

tert-Butyllithium in pentane (1.7 M, 19.0 mL) was added dropwise to a solution of 2-chloro-5-(methoxymethoxy)pyridine (4.880 g, 28.11 mmol) in 100 ml of ethyl ether at −76° C. Some precipitate appeared. The mixture was kept at −76° C. for 20 min then N,N-dimethylformamide (2.938 mL, 37.95 mmol) was added dropwise. The mixture was stirred for 10 min at −76° C. and then allowed to warm to at 0° C. for 1 h period. 10% aq NH4Cl was added and the mixture was extracted with ethyl acetate. The organic solution was washed with water, brine and dried over Na2SO4. After concentration in vacuum the yield of the crude 2-chloro-5-(methoxymethoxy)isonicotinaldehyde 5.49 g. MS: 202.0, 172.0. Without further purification was used in the next step.

Step 3: 2-chloro-4-(1H-imidazol-2-yl)-5-(methoxymethoxy)pyridine

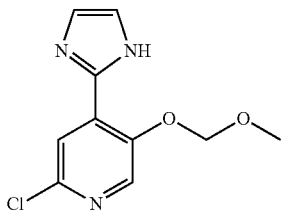 [SMILES: COCOc1cnc(Cl)cc1-c1ncc[nH]1]

Crude 2-chloro-5-(methoxymethoxy)isonicotinaldehyde (5.20 g, 25.87 mmol) was dissolved in 60 ml of methanol and mixed with 40% aqueous ethanedial (16.31 g, 112.4 mmol) and aqueous ammonia (19.15 g, 337.3 mmol). The mixture was stirred for 3 hours, concentrated in vacuum and acidified to pH <1 with 60 ml of 1 N aq HCl. The aqueous solution was extracted with ethyl acetate (3×30 ml). The organic extracts were discarded while aqueous was basified by addition of sat NaHCO3. The mixture was extracted with ethyl acetate (3×30 ml), combined organic extracts were washed with water, brine, dried and concentrated in vacuum. The residue (crude 4.185 g) was purified on 40 g silica column eluting with 60-70% of ethyl acetate in heptane to yield 2.06 g of 2-chloro-4-(1H-imidazol-2-yl)-5-(methoxymethoxy)pyridine (33%). MS (ESI+): 208 (loss of HOMe). $^1$H NMR (500 MHz, trated in vacuum, the residue purified on 4 g silica column eluting with 30% ethyl acetate in heptane. Yield 65 mg (59%). MS (ESI+): 378.2 eluting with 10-40% ethyl acetate in heptane to give 6.33 g of CDCl$_3$) δ 10.56 (s, 1H), 8.35 (s, 1H), 8.23 (s, 1H), 7.30 (s, 1H), 7.22 (s, 1H), 5.43 (s, 2H), 3.54 (d, J=14.0, 3H).

Step 4: 6-Chloro-4-(1H-imidazol-2-yl)pyridin-3-ol

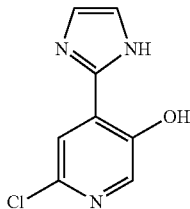 [SMILES: Oc1cnc(Cl)cc1-c1ncc[nH]1]

Hydrogen chloride in dioxane (4 M, 40 mL) was added dropwise to a solution of 2.06 g (8.60 mmol) of 2-chloro-4-(1H-imidazol-2-yl)-5-(methoxymethoxy)pyridine in Methylene chloride (40 mL, 600 mmol). The suspension was stirred for 2 hours and filtered. The solid was washed with DCM, ether and dried in vacuum. Yield of 6-chloro-4-(1H-imidazol-2-yl)pyridin-3-ol dihydrochloride 2.31 g (100%). MS (ESI+): 196.2. $^1$H NMR (400 MHz, DMSO) δ 13.20 (s, 1H), 8.14 (s, 1H), 7.96 (s, 1H), 7.42 (s, 2H).

Step 5: 10-Chloro-5,6-dihydroimidazo[1,2-d]pyrido[4,3-f][1,4]oxazepine

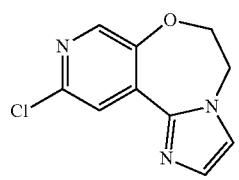 [SMILES: Clc1cc2c(cn1)OCCn1ccnc1-2]

A mixture of 2.30 g (8.55 mmol) of 6-chloro-4-(1H-imidazol-2-yl)pyridin-3-ol dihydrochloride, 1,2-dibromoethane (1.842 mL, 21.37 mmol) and Cesium Carbonate (19.46 g, 59.74 mmol) in 120 ml of N,N-Dimethylformamide was heated for 3 hours at 90° C. The mixture was filtered and concentrated in high vacuum to give 10-Chloro-5,6-dihydroimidazo[1,2-d]pyrido[4,3-f][1,4]oxazepine. Weight 1.88 g (99%) MS (ESI+): 222.2. $^1$H NMR (400 MHz, CDCl$_3$) δ 8.37 (s, 1H), 8.17 (s, 1H), 7.24 (d, J=1.0, 1H), 7.10 (d, J=0.9, 1H), 4.51-4.45 (m, 4H).

Example 18

10-chloro-2,3-diiodo-5,6-dihydroimidazo[1,2-d]pyrido[4,3-f][1,4]oxazepine

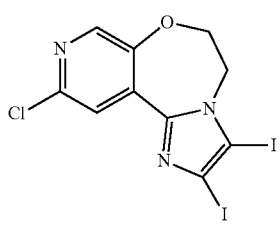 [SMILES: Clc1cc2c(cn1)OCCn1c-2nc(I)c1I]

N-Iodosuccinimide (5.771 g, 25.65 mmol) was added to 1.89 g (8.55 mmol) of 10-chloro-5,6-dihydroimidazo[1,2-d]pyrido[4,3-f][1,4]oxazepine in N,N-dimethylformamide (28 mL, 360 mmol) and the mixture was heated at 80° C. for 48 hours. A precipitate was collected, washed with DMF and ethyl ether and dried on air and then in high vacuum. Weight 2.85 g (70%). MS: 473.9. $^1$H NMR (500 MHz, CDCl$_3$) δ 8.33 (s, 1H), 8.19 (s, 1H), 4.53-4.46 (m, 2H), 4.45-4.38 (m, 2H).

Example 19

10-chloro-2-iodo-5,6-dihydroimidazo[1,2-d]pyrido[4,3-f][1,4]oxazepine

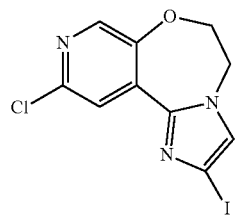 [SMILES: Clc1cc2c(cn1)OCCn1cc(I)nc1-2]

Isopropylmagnesium chloride in tetrahydrofuran (2.0 M, 3.311 mL) was added dropwise to a solution of 10-chloro-2,3-diiodo-5,6-dihydroimidazo[1,2-d]pyrido[4,3-f][1,4]oxazepine (2.850 g, 6.020 mmol) in 110 ml of tetrahydrofuran at −10° C. The mixture was allowed to warm to 10° C. in 45 min and then mixed with 250 ml of cold 10% NH4Cl. The organic layer was washed with brine and dried over Na2SO4. Concentration in vacuum afforded 2.06 g of 10-chloro-2-iodo-5,6-dihydroimidazo[1,2-d]pyrido[4,3-f][1,4]oxazepine (98.5%). MS: 348.0. $^1$H NMR (500 MHz, CDCl$_3$) δ 8.33 (d, J=10.1, 1H), 8.18 (s, 1H), 7.18 (s, 1H), 4.46 (q, J=5.8, 4H).

Example 20

10-Chloro-5,6-dihydroimidazo[1,2-d]pyrido[4,3-f][1,4]oxazepine-2-carboxamide

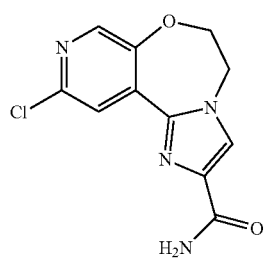 [SMILES: NC(=O)c1cn2c(n1)-c1cc(Cl)ncc1OCC2]

A mixture of 10-chloro-2-iodo-5,6-dihydroimidazo[1,2-d]pyrido[4,3-f][1,4]oxazepine (2056 mg, 5.916 mmol), bis(triphenylphosphine)palladium(II) chloride (2.10E2 mg, 0.300 mmol) and hexamethyldisilazane (7.488 mL, 35.50 mmol) in 60 ml of N,N-Dimethylformamide was subjected to carbonylation at 1 atm with CO from balloon. The reaction mixture was heated at 70° C. for 1 h. The mixture was concentrated in vacuum, the residue partitioned between ethyl acetate and 1 M aqueous sodium carbonate. The organic extracts were washed with water, brine, dried over magnesium sulfate, concentrated in vacuum and purified on a 12 g silica column eluting with 0-5% MeOH in DCM to give 1300 mg (83%). MS (ESI+): 265.0. ¹H NMR (500 MHz, DMSO) δ 8.37 (s, 1H), 8.22 (s, 1H), 7.93 (s, 1H), 7.70 (s, 1H), 7.25 (s, 1H), 4.56 (s, 4H).

Example 21

10-Chloro-N-((dimethylamino)methylene)-5,6-dihydroimidazo[1,2-d]pyrido[4,3-f][1,4]oxazepine-2-carboxamide

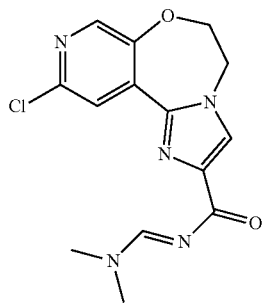 [SMILES: CN(C)/C=N/C(=O)c1cn2c(n1)-c1cc(Cl)ncc1OCC2]

A mixture of 10-chloro-5,6-dihydroimidazo[1,2-d]pyrido[4,3-f][1,4]oxazepine-2-carboxamide (1.290 g, 4.875 mmol) and 1,1-Dimethoxy-N,N-dimethylmethanamine (3.238 mL, 24.37 mmol) in 70 ml of toluene was heated under reflux for 1 hour. After cooling the product precipitated from the reaction mixture, collected, washed with ethyl ether and dried on air. Weight 0.705 g (85%). MS (ESI+): 320.1

Example 22

10-chloro-2-(1-isopropyl-1H-1,2,4-triazol-5-yl)-5,6-dihydroimidazo[1,2-d]pyrido[4,3-f][1,4]oxazepine

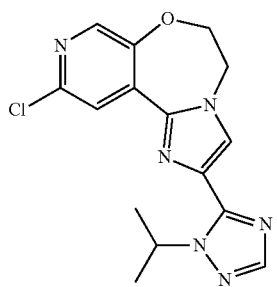 [SMILES: CC(C)n1ncnc1-c1cn2c(n1)-c1cc(Cl)ncc1OCC2]

A mixture of 660 mg (2.06 mmol) of 10-chloro-N-((dimethylamino)methylene)-5,6-dihydroimidazo[1,2-d]pyrido[4,3-f][1,4]oxazepine-2-carboxamide and isopropylhydrazine hydrochloride (0.332 g, 3.00 mmol) in 44 ml of acetic acid was heated at 85° C. for 3 hours. The mixture was cooled, filtered and mixed with 15 ml of water. A precipitate was filtered out, washed with water and dried in high vacuum. The above solid was triturated with 1 o ml of ethyl acetate, filtered out, washed with ethyl acetate, ethyl ether and dried on air. Yield 0.710 g. MS: 331.2. ¹H NMR (500 MHz, DMSO) δ 8.26 (s, 1H), 8.20 (s, 1H), 8.11 (s, 1H), 7.96 (s, 1H), 5.76 (dt, J=13.1, 6.6, 1H), 4.62 (q, J=5.6, 4H), 1.50 (d, J=6.6, 6H).

Example 23 methyl 4-hydroxy-3-(1H-imidazol-2-yl)benzoate

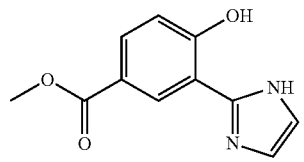 [SMILES: COC(=O)c1ccc(O)c(-c2ncc[nH]2)c1]

Following the procedure in Example 22, methyl 3-formyl-4-hydroxybenzoate was coupled with ethanal and ammonia to give methyl 4-hydroxy-3-(1H-imidazol-2-yl)benzoate. Yield 78%. MS (ESI+): 219.1

Example 24 methyl 5,6-dihydrobenzo[f]imidazo[1,2-d][1,4]oxazepine-10-carboxylate

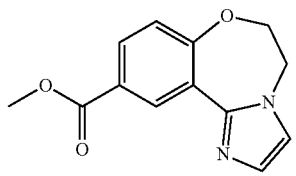 [SMILES: COC(=O)c1ccc2c(c1)-c1nccn1CCO2]

Following the procedure in Example 17, methyl 4-hydroxy-3-(1H-imidazol-2-yl)benzoate reacted with 1,2-dibromoethane to give methyl 5,6-dihydrobenzo[f]imidazo[1,2-d][1,4]oxazepine-10-carboxylate. Yield 76%. MS (ESI+): 245.0. ¹H NMR (400 MHz, CDCl₃) δ 9.21 (d, J=2.2, 1H), 7.91 (dd, J=8.6, 2.2, 1H), 7.20 (t, J=4.8, 1H), 7.05 (d, J=8.6, 1H), 7.00 (d, J=0.8, 1H), 4.53-4.48 (m, 2H), 4.43-4.39 (m, 2H), 3.91 (d, J=5.9, 3H).

Example 25 methyl 2,3-diiodo-5,6-dihydrobenzo[f]imidazo[1,2-d][1,4]oxazepine-10-carboxylate

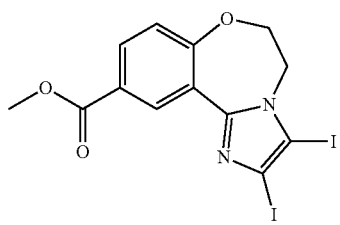 [SMILES: COC(=O)c1ccc2c(c1)-c1nc(I)c(I)n1CCO2]

A mixture of methyl 5,6-dihydrobenzo[f]imidazo[1,2-d][1,4]oxazepine-10-carboxylate (2670 mg, 9.29 mmol) and N-Iodosuccinimide (5230 mg, 23.2 mmol) in 100 ml of N,N-Dimethylformamide was heated at 80° C. for 3 hours. The mixture was mixed 300 ml of water and extracted 3×120 ml of methylene chloride. The combined organic extracts were washed with 5% aq sodium bicarbonate, 2×50 ml of 10% aq sodium thiosulfate, water, brine, dried over MgSO4 and concentrated in vacuum to a small volume. The precipitate was filtered, washed with methylene chloride and dried in vacuum. Yield 3.86 g (84%). MS 497.0. $^1$H NMR (500 MHz, CDCl$_3$) δ 9.12 (d, J=2.0, 1H), 7.93 (dd, J=8.6, 2.1, 1H), 7.05 (d, J=8.6, 1H), 4.55-4.46 (m, 2H), 4.38 (dd, J=5.0, 2.9, 2H), 3.92 (s, 3H).

Example 26 methyl 2-iodo-5,6-dihydrobenzo[f]imidazo[1,2-d][1,4]oxazepine-10-carboxylate

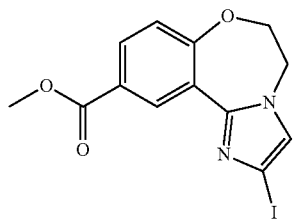 [SMILES: COC(=O)c1ccc2c(c1)-c1nc(I)cn1CCO2]

Following the procedure in Example 26, methyl 2,3-diiodo-5,6-dihydrobenzo[f]imidazo[1,2-d][1,4]oxazepine-10-carboxylate was converted to methyl 2-iodo-5,6-dihydrobenzo[f]imidazo[1,2-d][1,4]oxazepine-10-carboxylate. Yield 95%. MS(ESI+): 370.9. $^1$H NMR (400 MHz, CDCl$_3$) δ 9.15 (d, J=2.1, 1H), 7.92 (dd, J=8.6, 2.2, 1H), 7.08 (s, 1H), 7.04 (t, J=7.9, 1H), 4.48 (dd, J=9.5, 5.5, 2H), 4.40 (dd, J=9.4, 5.5, 2H), 3.92 (s, 3H).

Example 27 methyl 2-cyano-5,6-dihydrobenzo[f]imidazo[1,2-d][1,4]oxazepine-10-carboxylate

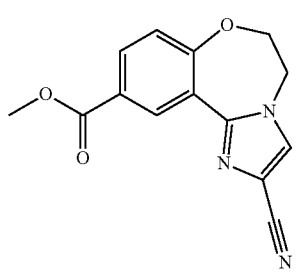 [SMILES: COC(=O)c1ccc2c(c1)-c1nc(C#N)cn1CCO2]

2-iodo-5,6-dihydrobenzo[f]imidazo[1,2-d][1,4]oxazepine-10-carboxylate (370.1 mg, 1.0 mmol) and Copper cyanide (268.6 mg, 3.000 mmol) were mixed in 8 ml of N,N-Dimethylformamide. The reaction was microwaved on 200 watts, 150° C., for 40 minutes. The reaction mixture was partitioned between 25 ml of 5% ammonia in water and 25 ml of EtOAc. The aqueous layer was additionally extracted with 3×20 ml EtOAc, combined extracts were washed with water, brine and dried over MgSO4 to afford 225 mg of methyl 2-cyano-5,6-dihydrobenzo[f]imidazo[1,2-d][1,4]oxazepine-10-carboxylate. Yield 81%. (MS: 270.0).

Example 28 methyl 2-carbamoyl-5,6-dihydrobenzo[f]imidazo[1,2-d][1,4]oxazepine-10-carboxylate

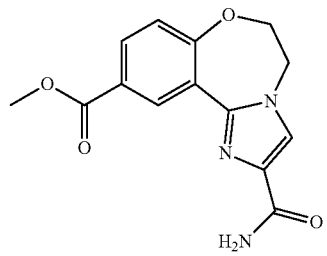 [SMILES: COC(=O)c1ccc2c(c1)-c1nc(C(N)=O)cn1CCO2]

Methyl 2-cyano-5,6-dihydrobenzo[f]imidazo[1,2-d][1,4]oxazepine-10-carboxylate (220 mg, 0.82 mmol) was dissolved in 4.0 ml of dimethyl sulfoxide and treated with a solution of potassium carbonate (136 mg, 0.980 mmol) in water (1.60 mL, 88.8 mmol). After cooling at 0° C., hydrogen peroxide (0.751 mL, 9.80 mmol) was added slowly. The mixture was stirred at room temperature for 2 hours. The mixture was diluted with 20 ml of water and extracted with ethyl acetate (3×20 ml). The organic extracts were washed with 5% sodium thiosufate, sat. NaHCO3, brine, dried over sodium sulfate and concentrated to give 180 mg (77%) of crude methyl 2-carbamoyl-5,6-dihydrobenzo[f]imidazo[1,2-d][1,4]oxazepine-10-carboxylate. MS (ESI+): 288.0.

Example 29 methyl 2-((dimethylamino)methylenecarbamoyl)-5,6-dihydrobenzo[f]imidazo[1,2-d][1,4]oxazepine-10-carboxylate

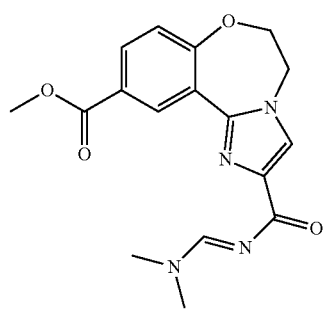 [SMILES: COC(=O)c1ccc2c(c1)-c1nc(C(=O)/N=C/N(C)C)cn1CCO2]

Following the procedure in Example 21, methyl 2-carbamoyl-5,6-dihydrobenzo[f]imidazo[1,2-d][1,4]oxazepine-10-carboxylate was converted to methyl 2-((dimethylamino)methylenecarbamoyl)-5,6-dihydrobenzo[f]imidazo[1,2-d][1,4]
oxazepine-10-carboxylate Yield 82%. MS (ESI+): 343.1

Example 30 methyl 2-(1-(2-chlorophenyl)-1H-1,2,4-triazol-5-yl)-
5,6-dihydrobenzo[f]imidazo[1,2-d][1,4]oxazepine-
10-carboxylate

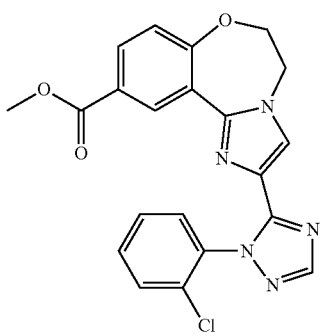 [SMILES: COC(=O)c1ccc2c(c1)-c1nc(-c3ncnn3-c3ccccc3Cl)cn1CCO2]

Following the procedure in Example 22, methyl 2-((dimethylamino)methylenecarbamoyl)-5,6-dihydrobenzo[f]imidazo[1,2-d][1,4]oxazepine-10-carboxylate was coupled with 2-chlorophenylhydrazine hydrochloride to give methyl 2-(1-(2-chlorophenyl)-1H-1,2,4-triazol-5-yl)-5,6-dihydrobenzo[f]imidazo[1,2-d][1,4]oxazepine-10-carboxylate. Yield 59%. MS (ESI+): 422.1

Example 31

2-(1-(2-chlorophenyl)-1H-1,2,4-triazol-5-yl)-5,6-
dihydrobenzo[f]imidazo[1,2-d][1,4]oxazepine-10-
carboxylic acid

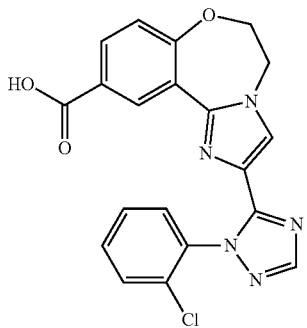 [SMILES: O=C(O)c1ccc2c(c1)-c1nc(-c3ncnn3-c3ccccc3Cl)cn1CCO2]

Following the procedure in Example 12, methyl 2-(1-(2-chlorophenyl)-1H-1,2,4-triazol-5-yl)-5,6-dihydrobenzo[f]imidazo[1,2-d][1,4]oxazepine-10-carboxylate was hydrolyzed to give 2-(1-(2-chlorophenyl)-1H-1,2,4-triazol-5-yl)-5, 6-dihydrobenzo[f]imidazo[1,2-d][1,4]oxazepine-10-
carboxylic acid. Yield 75%. MS(ESI+): 408.1

Example 32

2-(2-Isopropyl-5-methyl-2H-[1,2,4]triazol-3-yl)-9-
(1-isopropylpiperidin-4-ylsulfanyl)-8-methyl-4,5-
dihydro-6-oxa-1,3a-diazabenzo[e]azulene

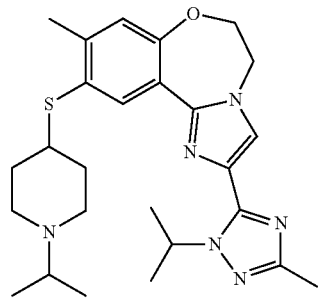 [SMILES: Cc1nc(-c2cn3c(n2)-c2cc(SC4CCN(C(C)C)CC4)c(C)cc2OCC3)n(C(C)C)n1]

Step 1: 9-Bromo-2-iodo-8-methyl-4,5-dihydro-6-
oxa-1,3a-diazabenzo[e]azulene

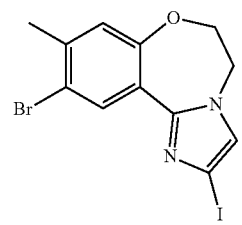 [SMILES: Cc1cc2c(cc1Br)-c1nc(I)cn1CCO2]

Step 2: 9-Bromo-2-(2-isopropyl-5-methyl-2H-[1,2,4]
triazol-3-yl)-8-methyl-4,5-dihydro-6-oxa-1,3a-diaza-
benzo[e]azulene

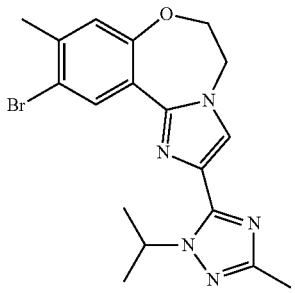 [SMILES: Cc1nc(-c2cn3c(n2)-c2cc(Br)c(C)cc2OCC3)n(C(C)C)n1]

A solution of 1-isopropyl-3-methyl-1H-[1,2,4]triazole (in a 6:4 mixture with 1-isopropyl-5-methyl-1H-[1,2,4]triazole, 0.292 g, 1.4 mmol) in THF (5 mL) was cooled to −30° C. and treated with n-butyllithium (2.5M in hexanes, 0.56 mL, 1.40 mmol). Stirring was continued for 1 h maintaining the internal temperature between −30° C. and −20° C. The mixture was then cooled to −30° C. and a solution of zinc chloride (0.5M in THF, 1.66 mL, 0.83 mmol) was added over 2 min.

The reaction mixture was then slowly warmed to RT over 1 h. A solution of 9-bromo-2-iodo-8-methyl-4,5-dihydro-6-oxa-1,3a-diazabenzo[e]azulene (404 mg, 1.0 mmol) in THF (5 mL) was added followed by Pd(PPh$_3$)$_4$ (58 mg, 0.128 mmol) and the reaction mixture was stirred at 60° C. under a nitrogen atmosphere for 18 h. After cooling to RT, volatiles were removed in vacuo and the residue was partitioned between EtOAc (300 mL) and water. The aqueous phase was further extracted with EtOAc (300 mL) and the combined organic layers were washed with water followed by brine, then dried (Na$_2$SO$_4$) and concentrated in vacuo. The resulting residue was purified by column chromatography (Si-PCC, eluent 100% EtOAc followed by gradient 1-10% MeOH in EtOAc) affording the title compound (0.168 g, 35%). LCMS: R$_T$ 3.71 min [M+H]$^+$ 402.0/404.0. 110178153

Step 3

A mixture of 9-bromo-2-(2-isopropyl-5-methyl-2H-[1,2,4]triazol-3-yl)-8-methyl-4,5-dihydro-6-oxa-1,3a-diazabenzo[e]azulene (146 mg, 0.363 mmol), 1-isopropylpiperidine-4-thiol (87 mg, 0.545 mmol), Pd$_2$(dba)$_3$ (17 mg, 5 mol %), XantPhos (21 mg, 10 mol %) and DIPEA (254 µl, 1.45 mmol) in dioxane (4 mL) was purged with nitrogen and then heated at 120° C. for 2 h using microwave irradiation. The reaction mixture was then diluted with DCM (80 mL) and purified by column chromatography (Si-PCC, gradient 0-8% 2M NH$_3$/MeOH in DCM) followed by (C$_{18}$, gradient 20-55% MeOH in 0.5% TFA/H$_2$O). The product containing fractions were combined and concentrated in vacuo. The resulting residue was loaded onto an Isolute® SCX-2 cartridge which was washed with MeOH and the product eluted with 0.5M NH$_3$/MeOH. The basic fractions were concentrated under reduced pressure affording 2-(2-Isopropyl-5-methyl-2H-[1,2,4]triazol-3-yl)-9-(1-isopropylpiperidin-4-ylsulfanyl)-8-methyl-4,5-dihydro-6-oxa-1,3a-diazabenzo[e]azulene as a colorless solid (112 mg, 64%). LCMS: R$_T$ 2.23 and 2.28 min [M+H]$^+$ 480.9

Example 33

9-bromo-5,6-dihydrobenzo[f]imidazo[1,2-d][1,4]oxazepine-2-carbaldehyde

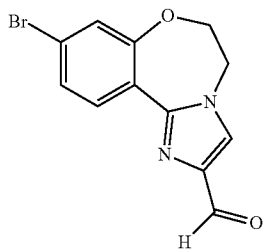 [SMILES: O=Cc1cn2c(n1)-c1ccc(Br)cc1OCC2]

Ethylmagnesium bromide in ethyl ether (3.0 M, 3.472 mL) was added dropwise to a solution of 9-bromo-2-iodo-5,6-dihydrobenzo[f]imidazo[1,2-d][1,4]oxazepine (1173 mg, 3.000 mmol) in 20 ml of tetrahydrofuran at −30° C. The mixture was stirred at this temperature for 20 min and allowed to warm to 15° C. The mixture was cooled to −25° C. again and N,N-dimethylformamide (929.2 uL, 12.00 mmol) was added. The mixture was left for 18 hours. The mixture was quenched with sat. aq. NH4Cl and extracted with ethyl acetate. The organic extracts were washed with water, brine, dried over mgSO4 and concentrated in vacuum. Yield 0.92 g. MS: 293.1

Example 34

9-bromo-2-(4-methyl-1H-imidazol-2-yl)-5,6-dihydrobenzo[f]imidazo[1,2-d][1,4]oxazepine

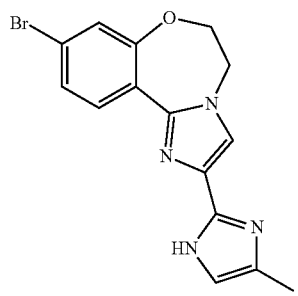 [SMILES: Cc1c[nH]c(-c2cn3c(n2)-c2ccc(Br)cc2OCC3)n1]

Ammonia in water (16.0 M, 0.819 mL) was added to a solution of 9-bromo-5,6-dihydrobenzo[f]imidazo[1,2-d][1,4]oxazepine-2-carbaldehyde (640 mg, 2.2 mmol) and pyruvaldehyde (0.787 g, 4.37 mmol) in methanol (17 mL, 420 mmol) and Tetrahydrofuran (6 mL, 70 mmol). After 1 hour the same amount of pyruvaldehyde and 16.0 M of Ammonia in water were added again. The mixture was stirred for 2 h, concentrated in vacuum and the residue partitioned between ethyl acetate and water. The organic extract was washed with water, brine, dried over MgSO4 and concentrated. The residue was purified on 4 g silica column using ethyl acetate gradient in dichloromethane. Weight 0.417 g. MS: 344.9.

Example 35

9-bromo-2-(1H-imidazol-2-yl)-5,6-dihydrobenzo[f]imidazo[1,2-d][1,4]oxazepine

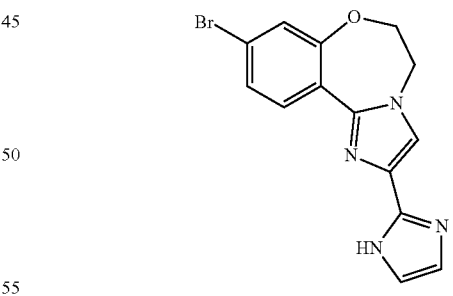

Ethanedial (0.689 mL, 6.01 mmol) and 16.0 M of Ammonia in water (1.50 mL) were added to a 9-bromo-5,6-dihydrobenzo[f]imidazo[1,2-d][1,4]oxazepine-2-carbaldehyde (550 mg, 1.5 mmol) in Methanol (30.0 mL, 742 mmol) After 1 hour, additional quantity of Ethanedial and ammonia were added and the mixture was stirred for 4 hours. The mixture then was concentrated in vacuum and partitioned between 0.5 N HCl and ethyl acetate. The organic extract was discarded, the acidic aqueous basified by careful addition of sat. NaHCO3. The mixture was extracted with ethyl acetate, the organic extracts were washed with water, brine, dried and concentrated. The residue was triturated with DCM to produce a precipitate which was collected, washed with cold DCM and dried to give 9-bromo-2-(1H-imidazol-2-yl)-5,6-dihydrobenzo[f]imidazo[1,2-d][1,4]oxazepine. MS: (ESI+)=331.2

Example 36

9-bromo-2-(1-isopropyl-1H-imidazol-2-yl)-5,6-dihydrobenzo[f]imidazo[1,2-d][1,4]oxazepine

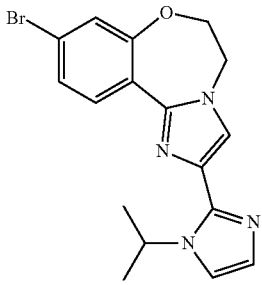 [SMILES: CC(C)n1ccnc1-c1cn2c(n1)-c1ccc(Br)cc1OCC2]

To a solution of 9-bromo-2-(1H-imidazol-2-yl)-5,6-dihydrobenzo[f]imidazo[1,2-d][1,4]oxazepine (0.237 g, 0.716 mmol) and Cesium Carbonate (0.280 g, 0.859 mmol) in N,N-Dimethylformamide (4.74 mL, 61.2 mmol) was added Isopropyl iodide (0.0859 mL, 0.859 mmol). The reaction was stirred 18 h at 50 C. The reaction was quenched with water then extracted EtOAc 2×. The crude product was purified to give 9-bromo-2-(1-isopropyl-1H-imidazol-2-yl)-5,6-dihydrobenzo[f]imidazo[1,2-d][1,4]oxazepine. MS: (ESI+)=373.1

Example 37 methyl 3-hydroxy-4-(1H-imidazol-2-yl)benzoate

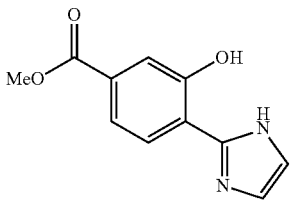 [SMILES: COC(=O)c1ccc(-c2ncc[nH]2)c(O)c1]

4-Formyl-3-hydroxybenzoic acid (5 g, 30 mmol) was suspended in methanol (70 mL), and treated with thionyl chloride (3.29 mL 45 mmol) dropwise. The mixture was heated to reflux overnight. Concentrated to dryness, and 50 mL of toluene was added, and concentrated again. The residue was recrystallized from ethyl acetate-hexane. A total of 4.8 g (85%) of methyl 4-formyl-3-hydroxybenzoate was obtained.

A mixture of methyl 4-formyl-3-hydroxybenzoate (4.8 g, 27 mmol), 40% aqueous solution of ethanedial (11.6 g, 79.93 mmol) and 50% aqueous ammonia (6.8 g, 399 mmol) in methanol (50 mL) was stirred for 2 hours or longer until the reaction is done. The solvent was removed by rotary evaporation, and the residue was partitioned between ethyl acetate and water. The mixture was filtered to remove the precipitates. pH was adjusted to 5-6 by careful addition of 1 N HCl. The aqueous layer was extracted with EtOAc three times. The combined organic layer was washed with water, brine and dried over MgSO$_4$. The residue was purified by flash chromatography to yield methyl 3-hydroxy-4-(1H-imidazol-2-yl)benzoate as a yellow solid (4 g, 71%)

Example 38 methyl 5,6-dihydrobenzo[f]imidazo[1,2-d][1,4]oxazepine-9-carboxylate

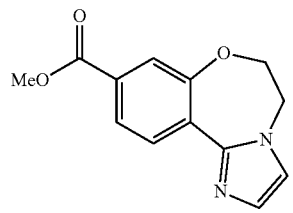 [SMILES: COC(=O)c1ccc2c(c1)OCCn1ccnc1-2]

A mixture of methyl 3-hydroxy-4-(1H-imidazol-2-yl)benzoate (2.2 g, 10 mmol), 1,2-dibromoethane (3.12 mL, 36 mmol) and cesium carbonate (13.14 g, 40 mmol) in DMF (100 mL) was heated at 90° C. for 12 hours. The mixture was filtered, the mother liquor was concentrated in vacuo, and the residue was partitioned between water and ethyl acetate. The suspension was filtered and the solid was pure byproduct. The organic layer was washed with water, brine and dried over MgSO$_4$ and concentrated to give crude methyl 5,6-dihydrobenzo[f]imidazo[1,2-d][1,4]oxazepine-9-carboxylate (2 g, 80%).

Example 38a 10-bromo-5,6-dihydrobenzo[f]imidazo[1,2-d][1,4]oxazepine

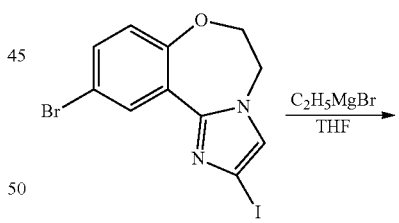

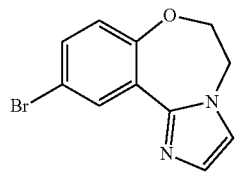

To a solution of 10-bromo-2-iodo-5,6-dihydrobenzo[f]imidazo[1,2-d][1,4]oxazepine (9 g, 20 mmol) in THF (40 mL) was added Ethylmagnesium bromide in Ethyl ether (22 mL) at −20° C. The mixture was allowed to warm to room temperature and in one and half hour the completion was showed by LCMS. The reaction mixture was poured into 10% NH$_4$Cl and extracted by EtOAc. Organic layer was washed by brine, dried by MgSO$_4$ and concentrated. The crude was purified by Isco chromatography to afford 10-bromo-5,6-dihydrobenzo[f]imidazo[1,2-d][1,4]oxazepine. LC/MS (ESI+): m/z 265 (M+H).

Example 38b 10-(2-fluoropyridin-3-yl)-5,6-dihydrobenzo[f]imidazo[1,2-d][1,4]oxazepine

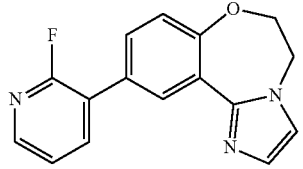 [SMILES: Fc1ncccc1-c1ccc2c(c1)-c1nccn1CCO2]

To 10-bromo-5,6-dihydrobenzo[f]imidazo[1,2-d][1,4]oxazepine (140 mg, 0.53 mmol) in DMF (20 mL) and water (2 mL) was added 2-Fluoropyridine-3-boronic acid (89 mg, 0.632 mml), Potassium acetate (207 mg, 2.11 mmol) and Tetrakis(triphenylphosphine)palladium (30 mg, 0.0264 mmol). The reaction mixture was degassed for 5 minutes, and heated at 100° C. overnight. LCMS showed desired product peak. The reaction was allowed to cool to room temperature, diluted with EtOAc, and filtered through a thin pad of celite. The filtrate was washed with water followed by brine, dried over $MgSO_4$ and concentrated. The crude residue was purified by Prep HPLC to provide 10-(2-fluoropyridin-3-yl)-5,6-dihydrobenzo[f]imidazo[1,2-d][1,4]oxazepine. LC/MS (ESI+): m/z 282 (M+H)

Example 38c 3-(5,6-dihydrobenzo[f]imidazo[1,2-d][1,4]oxazepin-10-yl)pyridin-2(1H)-one

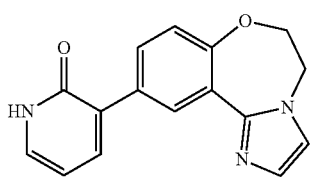 [SMILES: O=c1[nH]cccc1-c1ccc2c(c1)-c1nccn1CCO2]

To a solution of 10-(2-fluoropyridin-3-yl)-5,6-dihydrobenzo[f]imidazo[1,2-d][1,4]oxazepine (100 mg, 0.4 mmol) in DME (4 mL) was added 10% aqueous HCl (4 mL). The reaction was allowed to stir and heated at 80° C. overnight. The reaction was allowed to cool to room temperature and concentrated under reduced pressure. The crude was purified by Prep HPLC to provide 3-(5,6-dihydrobenzo[f]imidazo[1,2-d][1,4]oxazepin-10-yl)pyridin-2(1H)-one. LC/MS (ESI+): m/z 280 (M+H). $^1$H NMR (500 MHz, DMSO) δ 11.73 (s, 1H), 8.71 (d, J=2.3, 1H), 7.72-7.50 (m, 1H), 7.47-7.21 (m, 1H), 7.15-6.86 (m, 2H), 6.29 (t, J=6.6, 1H), 4.44 (d, J=6.1, 4H).

Example 38d 4-(5,6-dihydrobenzo[f]imidazo[1,2-d][1,4]oxazepin-10-yl)pyridin-2(1H)-one

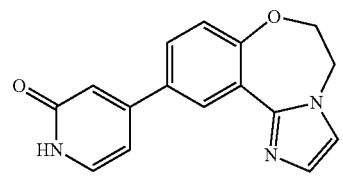 [SMILES: O=c1cc(-c2ccc3c(c2)-c2nccn2CCO3)cc[nH]1]

Following the procedures of Examples 38a-c, 4-(5,6-dihydrobenzo[f]imidazo[1,2-d][1,4]oxazepin-10-yl)pyridin-2(1H)-one was prepared. LC/MS (ESI+): m/z 280 (M+H). H NMR (500 MHz, DMSO) δ 8.70 (d, J=2.5, 1H), 7.59 (dd, J=8.5, 2.5, 1H), 7.45 (d, J=6.8, 1H), 7.35 (s, 1H), 7.09 (dd, J=16.9, 4.7, 2H), 6.57-6.36 (m, 2H), 4.47 (dd, J=11.6, 5.6, 4H).

Example 38e 5-(5,6-dihydrobenzo[f]imidazo[1,2-d][1,4]oxazepin-10-yl)pyridin-2(1H)-one

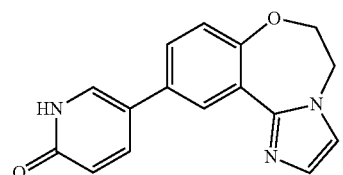

Following the procedures of Examples 38a-c, 5-(5,6-dihydrobenzo[f]imidazo[1,2-d][1,4]oxazepin-10-yl)pyridin-2(1H)-one was prepared. LC/MS (ESI+): m/z 280 (M+H). $^1$H NMR (500 MHz, DMSO) δ 8.48 (s, 1H), 8.03 (s, 1H), 7.94 (s, 1H), 7.83 (d, J=10.8, 1H), 7.77 (d, J=8.7, 1H), 7.21 (d, J=8.7, 2H), 6.46 (d, J=9.8, 1H), 4.65 (dd, J=24.3, 4.8, 4H).

Example 39 methyl 2,3-diiodo-5,6-dihydrobenzo[f]imidazo[1,2-d][1,4]oxazepine-9-carboxylate

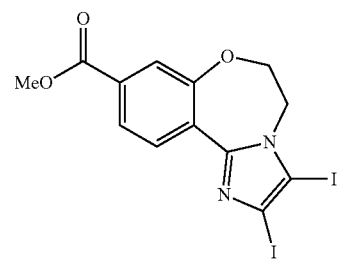 [SMILES: COC(=O)c1ccc2c(c1)OCCn1c-2nc(I)c1I]

A mixture of methyl 5,6-dihydrobenzo[f]imidazo[1,2-d][1,4]oxazepine-9-carboxylate (2 g, 8 mmol) and NIS (9.2 g, 41 mmol) in DMF was heated at 80° C. overnight. The mixture was diluted with ethyl acetate and water. The thick suspension was filtered through a glass filter. The solid was washed with ethyl acetate, then further diluted with THF, and dried over MgSO₄. LCMS indicated that this solution contained pure product. The brown solution was washed with 10% sodium thiosulfate, water, brine dried over MgSO₄ and concentrated to small volume. The precipitate was filtered and dried to give methyl 2,3-diiodo-5,6-dihydrobenzo[f]imidazo[1,2-d][1,4]oxazepine-9-carboxylate (3.4 g, 81% yield).

Example 40 methyl 2-iodo-5,6-dihydrobenzo[f]imidazo[1,2-d][1,4]oxazepine-9-carboxylate

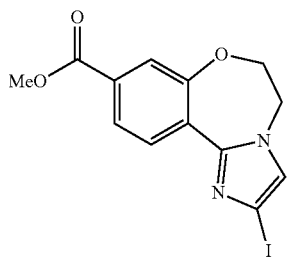 [SMILES: COC(=O)c1ccc2c(c1)OCCn1cc(I)nc1-2]

Fresh ethyl magnesium bromide in ethyl ether (3.0 M 1.1 mL) was added dropwise to a suspension of methyl 2,3-diiodo-5,6-dihydrobenzo[f]imidazo[1,2-d][1,4]oxazepine-9-carboxylate (1.1 g, 2.2 mmol) in THF at −15° C. The mixture was stirred and monitored using LC/MS. After 1 hour, there was no remaining starting material and the reaction was poured into sat. NH₄Cl and extracted with EtOAc. The organic extracts were washed with water, brine, dried over MgSO₄ and concentrated. At the end of this process, 0.7 g (80%) of methyl 2-iodo-5,6-dihydrobenzo[f]imidazo[1,2-d][1,4]oxazepine-9-carboxylate was obtained.

Example 41 methyl 2-cyano-5,6-dihydrobenzo[f]imidazo[1,2-d][1,4]oxazepine-9-carboxylate

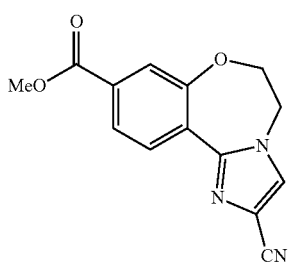 [SMILES: COC(=O)c1ccc2c(c1)OCCn1cc(C#N)nc1-2]

Methyl 2-iodo-5,6-dihydrobenzo[f]imidazo[1,2-d][1,4]oxazepine-9-carboxylate (740, 2.3 mmol) and copper cyanide (537 mg, 6.9 mmol) were mixed in DMF (8 mL). The reaction was microwaved on 200 watts, 150° C. for 40 minutes. The reaction mixture was partitioned between 15% ammonia in water and EtOAc. The aqueous layer was extracted with EtOAc three times, combined organic extracts were washed with water, brine and dried over MgSO₄ to produce 0.46 g (74% yield) of methyl 2-cyano-5,6-dihydrobenzo[f]imidazo[1,2-d][1,4]oxazepine-9-carboxylate.

Example 42 methyl 2-carbamoyl-5,6-dihydrobenzo[f]imidazo[1,2-d][1,4]oxazepine-9-carboxylate

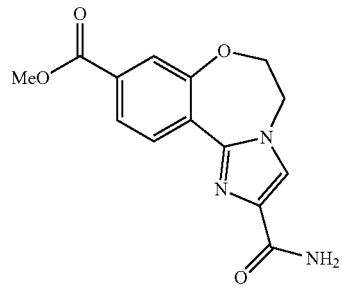 [SMILES: COC(=O)c1ccc2c(c1)OCCn1cc(C(N)=O)nc1-2]

Methyl 2-cyano-5,6-dihydrobenzo[f]imidazo[1,2-d][1,4]oxazepine-9-carboxylate (0.46 g, 1.7 mmol) was stirred with potassium carbonate (469 mg, 3.4 mmol), water (1.2 mL) and hydrogen peroxide (408 mg, 6 mmol) in DMSO (7 mL) for 4 hours. The mixture was diluted with 70 mL of water and extracted with ethyl acetate. Ethyl acetate solution was washed with water, 5% Na₂S₂O₃, water, brine, dried over MgSO₄ and concentrated under vacuum to give methyl 2-carbamoyl-5,6-dihydrobenzo[f]imidazo[1,2-d][1,4]oxazepine-9-carboxylate (0.37 g)

Example 43

9-bromo-5,6-dihydrobenzo[f]imidazo[1,2-d][1,4]oxazepine-2-carboxamide

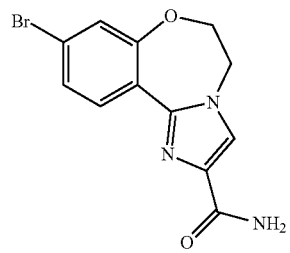 [SMILES: NC(=O)c1cn2c(n1)-c1ccc(Br)cc1OCC2]

Step 1: 5-bromo-2-(1H-imidazol-2-yl)phenol

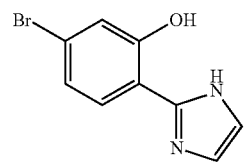 [SMILES: Oc1cc(Br)ccc1-c1ncc[nH]1]

4-Bromo-2-hydroxybenzaldehyde (1.0 g, 5 mmol), 40% aqueous solution of ethanedial (3.6 g, 24.87 mmol) and 50% aqueous ammonia (2.5 g) in methanol (20 mL) was stirred for 2 h or longer until the reaction is done. The solvent was concentrated by rotary evaporation and the residue was partitioned between EtOAc and water. The mixture was filtered to remove the precipitate. pH was adjusted to 5-6 by careful addition of 1 N HCl. The aqueous layer was extracted with EtOAc three times. The combined organic layer was washed with water, brine and dried over MgSO$_4$. Purified by ISCO chromatography (30% EtOAc/DCM) yielded 5-bromo-2-(1H-imidazol-2-yl)phenol as yellow solid 0.9 g.

Step 2: 9-bromo-5,6-dihydrobenzo[f]imidazo[1,2-d][1,4]oxazepine

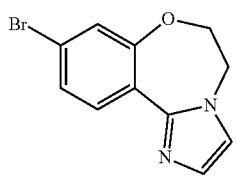 [SMILES: Brc1ccc2c(c1)OCCn1ccnc1-2]

A mixture of 5-bromo-2-(1H-imidazol-2-yl)phenol (0.9 g, 4 mmol), 1,2-dibromoethane (1.3 mL, 15 mmol) and cesium carbonate (4.9 g, 15 mmol) in DMF (20 mL) was heated to 90° C. for 12 h. The mixture was partitioned between water and ethyl acetate. The organic layer was washed with water, brine and dried over MgSO$_4$ and concentrated to give 9-bromo-5,6-dihydrobenzo[f]imidazo[1,2-d][1,4]oxazepine (0.8 g).

Step 3: 9-bromo-2,3-diiodo-5,6-dihydrobenzo[f]imidazo[1,2-d][1,4]oxazepine

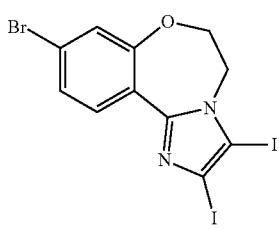 [SMILES: Brc1ccc2c(c1)OCCn1c-2nc(I)c1I]

A mixture of 9-bromo-5,6-dihydrobenzo[f]imidazo[1,2-d][1,4]oxazepine (0.8 g, 3 mmol) and NIS (1.87 g, 8.3 mmol) in DMF was stirred at room temperature for 48 h. The mixture was diluted with ethyl acetate, washed with 5% sodium bicarbonate, 10% sodium thiosulfate, water and brine and the organic layer was dried over MgSO$_4$ and concentrated to a solid residue. Purified by ISCO chromatography (30% EtOAc/Heptane) yielded 9-bromo-2,3-diiodo-5,6-dihydrobenzo[f]imidazo[1,2-d][1,4]oxazepine 1.2 g.

Step 4: 9-bromo-2-iodo-5,6-dihydrobenzo[f]imidazo[1,2-d][1,4]oxazepine

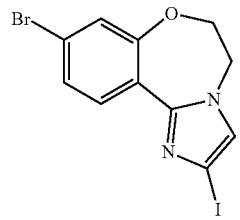 [SMILES: Brc1ccc2c(c1)OCCn1cc(I)nc1-2]

A 3.0 M solution of ethylmagnesium bromide in ethyl ether (1.1 mL) was added dropwise to a suspension of 9-bromo-2,3-diiodo-5,6-dihydrobenzo[f]imidazo[1,2-d][1,4]oxazepine (1.1 g, 2.2 mmol) in THF at −15° C. The mixture was stirred and followed by LC/MS. After 1 hour, there is no starting material left and the reaction was poured into sat. NH$_4$Cl and extracted with ethyl acetate. The organic extracts were washed with water, brine, dried over MgSO$_4$ and concentrated. The crude residue was purified by flash column chromatography to provide 9-bromo-2-iodo-5,6-dihydrobenzo[f]imidazo[1,2-d][1,4]oxazepine as white solid (0.7 g).

Step 5: 9-bromo-5,6-dihydrobenzo[f]imidazo[1,2-d][1,4]oxazepine-2-carboxamide

9-Bromo-2-iodo-5,6-dihydrobenzo[f]imidazo[1,2-d][1,4]oxazepine (1.5 g, 3.8 mmol) and bis(triphenylphosphine) palladium(II) chloride (142 mg, 0.202 mmol), DMF (45 mL) and hexamethyldisilazane (4.34 mL, 20.6 mmol) were mixed. The entire solution was purged with a CO balloon and sealed with the CO balloon attached. The reaction flask was heated at 70° C. for 2 h. LC/MS indicated clean conversion. Cooled to room temp and poured into 1 N HCl (30 mL). Stirred for 5 min and neutralized with sat. aq. NaHCO$_3$ soln. Extracted three times with EtOAc, dried over MgSO$_4$, filtered and concentrated in vacuo. Triturated with IPA and the solids were collected after filtration and EtOAc wash. This provided 734 mg (62% yield) of 9-bromo-5,6-dihydrobenzo[f]imidazo[1,2-d][1,4]oxazepine-2-carboxamide as a tan solid. LC/MS (ESI+): m/z 310 (M+H). $^1$H NMR (400 MHz, CDCl$_3$) δ 8.36 (d, J=8.5, 1H), 7.63 (s, 1H), 7.24 (dd, J=7.2, 4.2, 1H), 7.09-6.99 (m, 1H), 4.51-4.36 (m, 4H).

Example 44

9-bromo-N-formyl-5,6-dihydrobenzo[f]imidazo[1,2-d][1,4]oxazepine-2-carboxamide

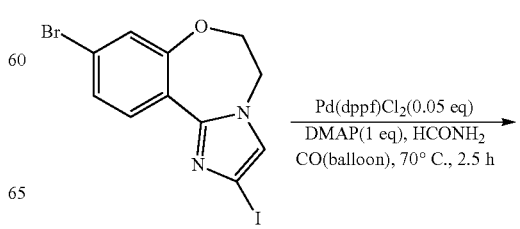

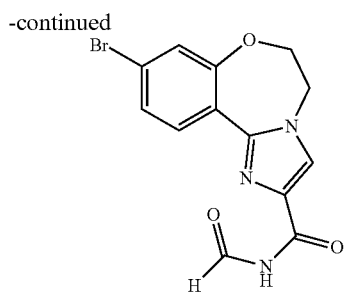

9-Bromo-2-iodo-5,6-dihydrobenzo[f]imidazo[1,2-d][1,4]oxazepine (10 g, 25.6 mmol) was heated in formamide (200 mL) with Pd(dppf)Cl$_2$ (0.94 g, 1.28 mmol) and DMAP (3.13 g, 25.6 mmol) under CO balloon at 70° C. for 2.5 h. The mixture was cooled to room temperature, diluted with EtOAc and filtered. The resulting precipitate was dried to obtain 9-bromo-N-formyl-5,6-dihydrobenzo[f]imidazo[1,2-d][1,4]oxazepine-2-carboxamide (6.7 g, 78%). $^1$H NMR (DMSO-d$_6$, 400 MHz): δ 11.10 (d, J=9.6 Hz, 1H), 9.21 (d, J=9.6 Hz, 1H), 8.53 (d, J=8.8 Hz, 1H), 8.24 (s, 1H), 7.34-7.28 (m, 2H), 4.53-4.50 (m, 4H). LC-MS: (ESI, m/z)=336 [M+H]$^+$ Example 45

2-[2-(2-Isopropyl-5-methyl-2H-[1,2,4]triazol-3-yl)-4,5-dihydro-6-oxa-1,3a-diazabenzo[e]azulen-8-yloxy]-2-methylpropionic acid

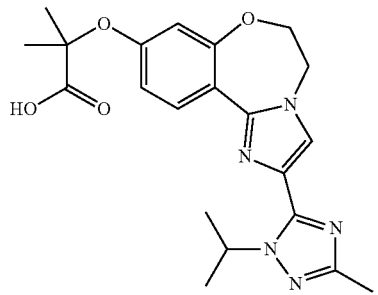 [SMILES: Cc1nc(-c2cn3c(n2)-c2ccc(OC(C)(C)C(=O)O)cc2OCC3)n(C(C)C)n1]

Step 1: 2-[2-(2-Isopropyl-5-methyl-2H-[1,2,4]triazol-3-yl)-4,5-dihydro-6-oxa-1,3a-diazabenzo[e]azulen-8-yloxy]-2-methylpropionic acid methyl ester

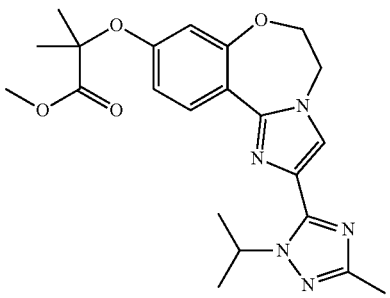

A mixture of 2-(2-isopropyl-5-methyl-2H-[1,2,4]triazol-3-yl)-4,5-dihydro-6-oxa-1,3a-diazabenzo[e]azulen-8-ol from Example 4 (30 mg, 0.0922 mmol), Cs$_2$CO$_3$ (75 mg, 0.23 mmol) and 2-bromo-2-methylpropionic acid methyl ester (36 uL, 0.277 mmol) in CH$_3$CN (2 mL) was heated at reflux temperature for 2 h. After cooling to RT, the mixture was partitioned between EtOAc and water. The aqueous layer was further extracted with EtOAc and the combined organic layers were washed with brine, then dried (Na$_2$SO$_4$) and concentrated in vacuo. The resulting residue was purified by column chromatography (Si-PCC, gradient 2-8% MeOH in DCM) affording 2-[2-(2-Isopropyl-5-methyl-2H-[1,2,4]triazol-3-yl)-4,5-dihydro-6-oxa-1,3a-diazabenzo[e]azulen-8-yloxy]-2-methylpropionic acid methyl ester as a colorless gum (40 mg, quantitative). LCMS: R$_T$ 3.25 min [M+H]$^+$ 426.1

Step 2

To a solution of 2-[2-(2-isopropyl-5-methyl-2H-[1,2,4]triazol-3-yl)-4,5-dihydro-6-oxa-1,3a-diazabenzo[e]azulen-8-yloxy]-2-methylpropionic acid methyl ester (39.2 mg, 0.0922 mmol) in MeOH (1.5 mL) was added 1M NaOH (0.46 mL) and the mixture was heated at 100° C. for 1 h using microwave irradiation. After cooling to RT, the organic solvent was removed in vacuo and the pH of the resulting mixture was adjusted to 8 by addition of 1M HCl. The mixture was then subjected to column chromatography (C$_{18}$, gradient 25-40% MeOH in H$_2$O followed by C$_{18}$, gradient 1-20% MeOH in H$_2$O) affording 2-[2-(2-Isopropyl-5-methyl-2H-[1,2,4]triazol-3-yl)-4,5-dihydro-6-oxa-1,3a-diazabenzo[e]azulen-8-yloxy]-2-methylpropionic acid (38 mg, quantitative). LCMS: R$_T$ 2.82 min [M+H]$^+$ 412.0

Example 46

8-Bromo-4,5-dihydro-6-oxa-1,3a-diaza-benzo[e]azulene-2-carboxylic acid [1-dimethylamino-eth-(E)-ylidene]-amide

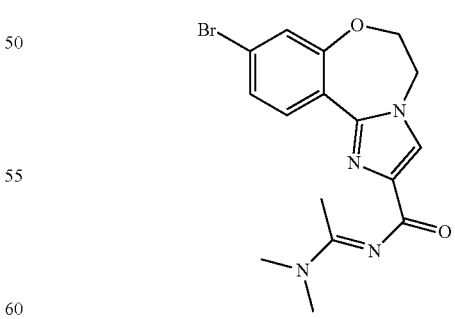

To a solution of 8-Bromo-4,5-dihydro-6-oxa-1,3a-diazabenzo[e]azulene-2-carboxylic acid amide (0.280 g, 0.000909 mol) in toluene (5 mL) was added dimethylacetamide-dimethylacetal (0.405 mL, 0.00273 mol). The solution was stirred at 95° C. for 4 h. The toluene was removed in vacuo to give 8-Bromo-4,5-dihydro-6-oxa-1,3a-diaza-benzo[e]azulene-2-carboxylic acid [1-dimethylamino-eth-(E)-ylidene]-amide. MS(ESI+) 377.1/379.1.

Example 47

[5-(8-Bromo-4,5-dihydro-6-oxa-1,3a-diaza-benzo[e]azulen-2-yl)-1-isopropyl-1H-[1,2,4]triazol-3-yl]-carbamic acid tert-butyl ester

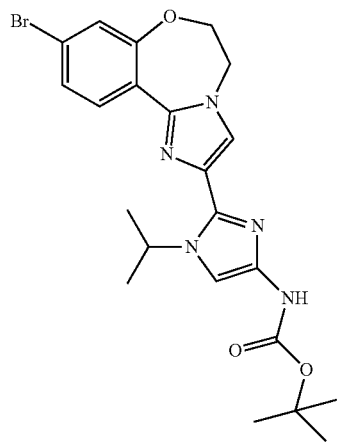 [SMILES: CC(C)n1cc(NC(=O)OC(C)(C)C)nc1-c1cn2c(n1)-c1ccc(Br)cc1OCC2]

Step 1: 8-Bromo-4,5-dihydro-6-oxa-1,3a-diaza-benzo[e]azulene-2-carboxylic acid methyl ester

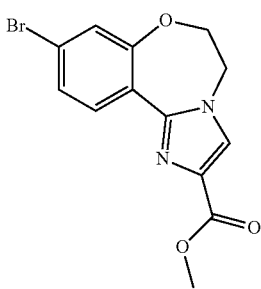 [SMILES: COC(=O)c1cn2c(n1)-c1ccc(Br)cc1OCC2]

8-Bromo-2-iodo-4,5-dihydro-6-oxa-1,3a-diaza-benzo[e]azulene (6.000 g, 0.01534 mol) followed by palladium acetate (0.1722 g, 0.7672 mmol) and 4,5-bis(diphenylphosphino)-9,9-dimethylxanthene (0.8879 g, 0.001534 mol) were added sequentially to a dry nitrogen-filled flask. Degassed triethylamine (180 mL, 1.3 mol) and methanol (60 mL) were added, and the reaction mixture was thoroughly purged with a carbon monoxide balloon for about 3 minutes. Two carbon monoxide balloons were fixed to the flask and the reaction was heated to 50° C. for 3 hours. The reaction was purged with nitrogen, concentrated in vacuo, and dry loaded onto silica gel. The crude was purified by flash chromatography (40-100% ethyl acetate in hexanes followed by 5-15% MeOH in DCM) to give 8-Bromo-4,5-dihydro-6-oxa-1,3a-diaza-benzo[e]azulene-2-carboxylic acid methyl ester (4.242 g) as a light brown solid. MS(ESI+) 323.0/325.0

Step 2: 8-Bromo-4,5-dihydro-6-oxa-1,3a-diaza-benzo[e]azulene-2-carboxylic acid

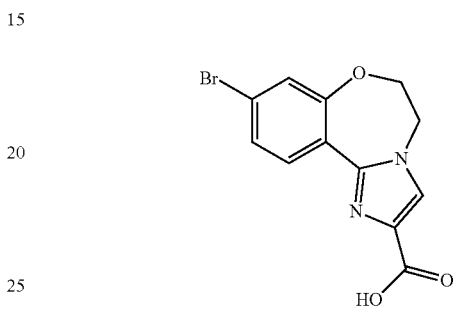

To a solution of 8-Bromo-4,5-dihydro-6-oxa-1,3a-diaza-benzo[e]azulene-2-carboxylic acid methyl ester (1.000 g, 0.003095 mol) in tetrahydrofuran (7.50 mL) and water (4.5 mL) was added lithium hydroxide (0.2964 g, 0.01238 mol). The reaction was stirred at 45° C. for 2 h. The mixture was acidified to pH=1 with 2N HCl. The resulting precipitate was filtered and rinsed with cold water to obtain 8-Bromo-4,5-dihydro-6-oxa-1,3a-diaza-benzo[e]azulene-2-carboxylic acid (860 mg) as an off-white solid. MS(ESI+) 309.0/311.0

Alternatively, to a solution of 8-bromo-2-iodo-4,5-dihydro-6-oxa-1,3a-diaza-enzo[e]azulene (10 g, 25.6 mmol) in THF (120 mL) at −78° C. was added nBuLi (19.2 mL, 1.6 M in hexanes, 30.7 mmol) at such a rate that $T_{max}$<−73° C. During the addition the purple colour faded and a tan precipitate formed. The reaction mixture was stirred at −78° C. for 20 min. $CO_2$ generated from dry-ice and passed over drying silica was bubbled through the reaction for 30 min. The temperature rose to −55° C. before dropping back to −78° C. A thick precipitate formed quickly during the addition of $CO_2$. The reaction was stirred at −78° C. for 1 h. The reaction was quenched by pouring onto 20 mL water (CARE:effervescent). The mixture was allowed to warm to RT. The pH of the mixture was adjusted to ~pH 8 by addition of saturated aqueous $NaHCO_3$ and the aqueous layer washed with ethyl acetate. The aqueous fraction was collected and the pH adjusted to ~pH 4 by addition of AcOH. The precipitate formed was collected by filtration, washed with water and dried in vacuo to give 8-Bromo-4,5-dihydro-6-oxa-1,3a-diaza-benzo[e]azulene-2-carboxylic acid as a beige solid (4.38 g, 55%). $^1$H NMR (400 MHz, $d_6$-DMSO) 8.31 (1H, d, J=8.5 Hz), 7.98 (1H, s), 7.32 (1H, dd, J=8.5, 2.2 Hz), 7.27 (1H, d, J=2.2 Hz), 4.51-4.47 (4H, m). LCMS: $R_T$=3.67 min, M+H$^+$ =309/311 (40%), M+Na$^+$ =323/325 (100%). $^1$H NMR showed product to contain ~5% 8-iodo-4,5-dihydro-6-oxa-1,3a-diaza-benzo[e]azulene-2-carboxylic acid.

Step 3: {[(E)-8-Bromo-4,5-dihydro-6-oxa-1,3a-diaza-benzo[e]azulene-2-carbonylimino]-methylthiomethyl}-carbamic acid tert-butyl ester

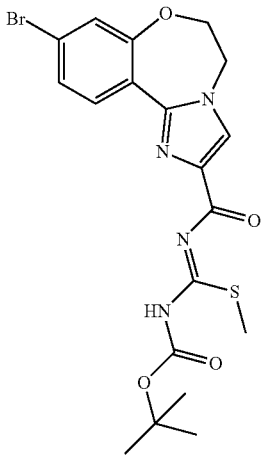 [SMILES: CS/C(=N\C(=O)c1cn2c(n1)-c1ccc(Br)cc1OCC2)NC(=O)OC(C)(C)C]

To a solution of 8-Bromo-4,5-dihydro-6-oxa-1,3a-diaza-benzo[e]azulene-2-carboxylic acid (0.839 g, 0.00271 mol) and oxalyl chloride (2M in DCM, 1.36 mL, 0.002714 mol), in methylene chloride (16.70 mL) under nitrogen atmosphere was added 1 drop of N,N-dimethylformamide. The solution was stirred at room temperature for 2 h. The reaction was concentrated in vacuo and the acid chloride was redissolved in methylene chloride (9.0 mL). The solution was added dropwise to a solution of N-tertbutoxycarbonyl-S-methylpseudothiourea (0.5164 g, 0.002714 mol) and triethylamine (1.173 mL, 0.008414 mol) in methylene chloride (9.0 mL). The reaction was stirred at room temperature for 1.5 h. Methylene chloride and water were added and the mixture was extracted 3× with methylene chloride. Saturated sodium carbonate was then added and the mixture was extracted with chloroform. The organic layers were combined and concentrated. The product was redissolved in methylene chloride and methanol and filtered. The filtrate was collected, concentrated and dry loaded onto silica gel and purified by flash chromatography (0-15% MeOH in DCM) to give {[(E)-8-Bromo-4,5-dihydro-6-oxa-1,3a-diaza-benzo[e]azulene-2-carbonylimino]-methylthiomethyl}-carbamic acid tert-butyl ester (658 mg) as an off-white solid. MS(ESI+) 481.0/483.0

Step 4: [5-(8-Bromo-4,5-dihydro-6-oxa-1,3a-diaza-benzo[e]azulen-2-yl)-1-isopropyl-1H-[1,2,4]triazol-3-yl]-carbamic acid tert-butyl ester To a solution of {[(E)-8-Bromo-4,5-dihydro-6-oxa-1,3a-diaza-benzo[e]azulene-2-carbonylimino]-methylthiomethyl}-carbamic acid tert-butyl ester (0.658 g, 0.00137 mol) in N,N-dimethylformamide (7.50 mL) was added N,N-Diisopropylethylamine (0.9524 mL, 0.005468 mol) then isopropylhydrazine hydrochloride (0.2267 g, 0.002050 mol). The reaction was stirred at room temperature for 4 h. Water and methylene chloride were added and the mixture was extracted 3× with methylene chloride. The organic layers were combined, dried with MgSO$_4$ and concentrated. The crude was purified by flash chromatography (0-10% MeOH in DCM) to give [5-(8-Bromo-4,5-dihydro-6-oxa-1,3a-diaza-benzo[e]azulen-2-yl)-1-isopropyl-1H-[1,2,4]triazol-3-yl]-carbamic acid tert-butyl ester (642 mg) a sticky light yellow solid. The material was carried forward without any further purification. MS(ESI+) 489.1/491.1

Example 48

8-Bromo-2-(2-isopropyl-5-methyl-2H-[1,2,4]triazol-3-yl)-4,5-dihydro-6-oxa-1,3a-diaza-benzo[e]azulene

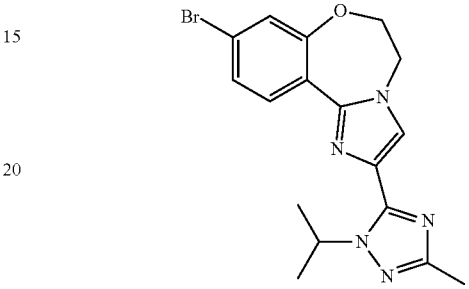

To a solution of 8-Bromo-4,5-dihydro-6-oxa-1,3a-diaza-benzo[e]azulene-2-carboxylic acid [1-dimethylamino-eth-(E)-ylidene]-amide (0.340 g, 0.000901 mol) in acetic acid (3.0 mL, 0.053 mol) was added isopropylhydrazine hydrochloride (0.1196 g, 0.001082 mol). The reaction was heated to 95° C. for 3 h. The acetic acid was removed in vacuo and the product was loaded as a solid onto silica and purified by flash chromatography (0-10% MeOH in DCM) to give 8-Bromo-2-(2-isopropyl-5-methyl-2H-[1,2,4]triazol-3-yl)-4,5-dihydro-6-oxa-1,3a-diaza-benzo[e]azulene (293 mg) as an orange solid. MS(ESI+) 388.1/390.1

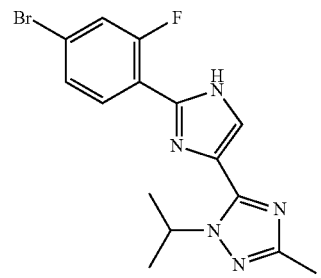 [SMILES: Cc1nc(-c2c[nH]c(-c3ccc(Br)cc3F)n2)n(C(C)C)n1]

Alternatively, 8-Bromo-2-(2-isopropyl-5-methyl-2H-[1,2,4]triazol-3-yl)-4,5-dihydro-6-oxa-1,3a-diaza-benzo[e]azulene may be prepared whereby a mixture of 4-bromo-2-fluoro-benzamidine hydrochloride (5.67 g, 22.3 mmol), potassium hydrogen carbonate (8.95 g, 89.4 mmol), THF (45 mL) and water (10 mL) was heated to reflux and a solution of 2-bromo-1-(2-isopropyl-5-methyl-2H-[1,2,4]triazol-3-yl)-ethanone (5.5 g, 22.3 mmol) in THF (15 mL) added dropwise. The reaction mixture was heated at reflux for 18 h before removal of volatile solvent in vacuo. The resultant suspension was filtered and the residue triturated in hot diethyl ether to give 5-[2-(4-Bromo-2-fluoro-phenyl)-1H-imidazol-4-yl]-1-isopropyl-3-methyl-1H-[1,2,4]triazole as an off-white solid (6.4 g, 79%). $^1$H NMR 400 MHz (DMSO-d6) δ: 7.97 (1H, t, J=8.30 Hz), 7.81 (1H, s), 7.76 (1H, dd, J=10.68, 1.92 Hz), 7.58 (1H, dd, J=8.42, 1.93 Hz), 5.79 (1H, br, m), 2.26 (3H, s), 1.44 (6H, d, J=6.60 Hz).

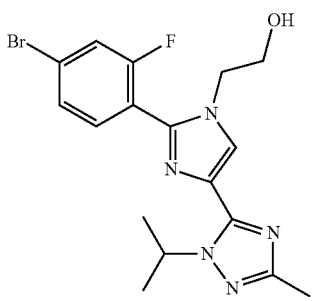 [SMILES: Cc1nc(-c2cn(CCO)c(-c3ccc(Br)cc3F)n2)n(C(C)C)n1]

A suspension of 5-[2-(4-bromo-2-fluoro-phenyl)-1H-imidazol-4-yl]-1-isopropyl-3-methyl-1H-[1,2,4]triazole (2.9 g, 7.96 mmol) in toluene (50 mL) was treated with ethylene carbonate (25 mL) and heated at reflux for 5 h. The cooled reaction mixture was diluted with DCM and passed through a pad of silica eluting with DCM then 20% methanol in DCM. Methanolic fractions were combined and concentrated in vacuo to give a pale tan solid. The solid was triturated in diethyl ether to give 2-[2-(4-Bromo-2-fluoro-phenyl)-4-(2-isopropyl-5-methyl-2H-[1,2,4]triazol-3-yl)-imidazol-1-yl]-ethanol as a white solid (2.3 g, 71%). LCMS: $R_T$=2.85 min, $[M+H]^+$ =408/410. $^1$H NMR 400 MHz (CDCl$_3$) δ: 8.16 (1H, s), 7.67-7.20 (3H, m), 5.83 (1H, m), 4.05 (2H, t, J=5.10 Hz), 3.92 (2H, t, J=5.10 Hz), 2.44 (3H, s), 1.50 (6H, d, J=6.65 Hz).

A suspension of 2-[2-(4-bromo-2-fluoro-phenyl)-4-(2-isopropyl-5-methyl-2H-[1,2,4]triazol-3-yl)-imidazol-1-yl]-ethanol (2.3 g, 5.6 mmol) in DMF (50 mL) was treated with sodium hydride (60% dispersion, 247 mg, 6.2 mmol) portionwise over 5 min and the mixture stirred at RT for 1 h. The reaction was quenched by the slow addition of water (200 mL). The precipitate formed was filtered off, washed with water to give 8-Bromo-2-(2-isopropyl-5-methyl-2H-[1,2,4]triazol-3-yl)-4,5-dihydro-6-oxa-1,3a-diaza-benzo[e]azulene as a white solid (1.64 g, 53%). LCMS: $R_T$=3.43 min, $[M+H]^+$ =388/390. $^1$H NMR 400 MHz (CDCl$_3$) δ: 8.37 (1H, d, J=8.61 Hz), 7.70 (1H, s), 7.26-7.25 (2H, m), 5.87-5.86 (1H, m), 4.50-4.48 (2H, m), 4.46-4.42 (2H, m), 2.42 (3H, s), 1.57 (6H, d, J=6.64 Hz)

Example 49

2-(2-Isopropyl-5-methyl-2H-[1,2,4]triazol-3-yl)-8-(1-isopropylpiperidin-4-ylsulfanyl)-4,5-dihydro-6-oxa-1,3a-diazabenzo[e]azulene

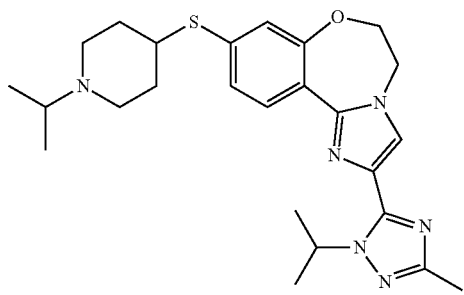 [SMILES: Cc1nc(-c2cn3c(n2)-c2ccc(SC4CCN(C(C)C)CC4)cc2OCC3)n(C(C)C)n1]

A mixture of 8-bromo-2-(2-isopropyl-5-methyl-2H-[1,2,4]triazol-3-yl)-4,5-dihydro-6-oxa-1,3a-diazabenzo[e]azulene (150 mg, 0.386 mmol), 1-isopropylpiperidine-4-thiol (92 mg, 0.579 mmol), Pd$_2$(dba)$_3$ (18 mg, 5 mol %), XantPhos (23 mg, 10 mol %) and DIPEA (0.27 mL, 1.54 mmol) in dioxane (4 mL) was purged with nitrogen and then heated at 120° C. for 1 h using microwave irradiation. After cooling to RT, the crude mixture was diluted with DCM (75 mL) and purified by column chromatography (Si-PCC, gradient 0-6% 2N NH$_3$/MeOH in DCM followed by C$_{18}$, gradient 20-50% MeOH in 0.5% TFA/H$_2$O). The product containing fractions were combined and concentrated in vacuo. The resulting residue was loaded onto an Isolute® SCX-2 cartridge which was washed with MeOH and the product eluted with 0.5M NH$_3$/MeOH. The basic fractions were concentrated under reduced pressure affording 2-(2-Isopropyl-5-methyl-2H-[1,2,4]triazol-3-yl)-8-(1-isopropylpiperidin-4-ylsulfanyl)-4,5-dihydro-6-oxa-1,3a-diazabenzo[e]azulene as a colorless solid (127 mg, 70%). LCMS: $R_T$ 3.00 min $[M+H]^+$ 467.1

Example 50

{1-[2-(2-Isopropyl-5-methyl-2H-[1,2,4]triazol-3-yl)-4,5-dihydro-6-oxa-1,3a-diazabenzo[e]azulen-8-yloxy]cyclopropyl}-(4-methylpiperazin-1-yl)methanone

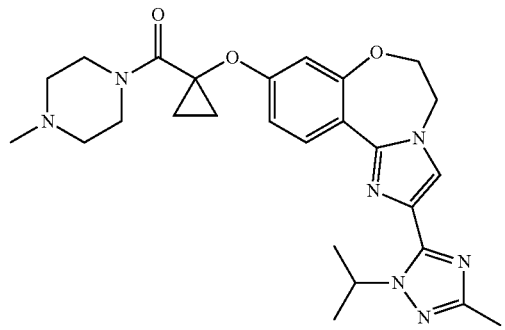

Step 1: 4-Bromo-2-[2-(2-isopropyl-5-methyl-2H-[1,2,4]triazol-3-yl)-4,5-dihydro-6-oxa-1,3a-diazabenzo[e]azulen-8-yloxy]butyric acid methyl ester

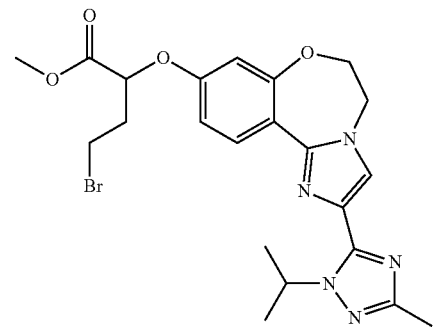

To a solution of 2-(2-isopropyl-5-methyl-2H-[1,2,4]triazol-3-yl)-4,5-dihydro-6-oxa-1,3a-diazabenzo[e]azulen-8-ol from Example 4 (2.8 g, 8.5 mmol), 4-bromo-2-hydroxybutyric acid methyl ester (2.5 g, 12.7 mmol) and triphenylphosphine (3.77 g, 14.3 mmol) in dioxane (30 mL) was added DIAD (2.8 ml, 14.3 mmol) and the reaction mixture was stirred at RT for 1 h. Additional amounts of DIAD (1.67 mL) and of triphenylphosphine (2.23 g) were added and stirring was continued for 1 h. The mixture was diluted with EtOAc and washed with aq. NaOH (1N). The aqueous phase was further extracted with EtOAc (×3). The combined organic layers were then washed with brine, dried and concentrated in vacuo. The resulting residue was purified by column chromatography (Si-PCC, gradient 0-10% MeOH in EtOAc followed by Si-PCC, gradient 0-10% MeOH in DCM) affording 4-Bromo-2-[2-(2-isopropyl-5-methyl-2H-[1,2,4]triazol-3-yl)-4,5-dihydro-6-oxa-1,3a-diazabenzo[e]azulen-8-yloxy]butyric acid methyl ester (2.5 g, 58%). $^1$H NMR (CDCl$_3$, 400 MHz): δ 8.43 (1H, d, J=9.01 Hz), 7.57 (1H, s), 6.74 (1H, d, J=9.15 Hz), 6.55 (1H, d, J=2.56 Hz), 5.95-5.83 (1H, m), 4.92 (1H, dd, J=8.80, 3.97 Hz), 4.51-4.31 (4H, m), 3.79 (3H, s), 3.65-3.53 (2H, m), 2.58-2.36 (5H, m), 1.58-1.51 (6H, m)

Step 2: 1-[2-(2-Isopropyl-5-methyl-2H-[1,2,4]triazol-3-yl)-4,5-dihydro-6-oxa-1,3a-diazabenzo[e]azulen-8-yloxy]cyclopropanecarboxylic acid methyl ester

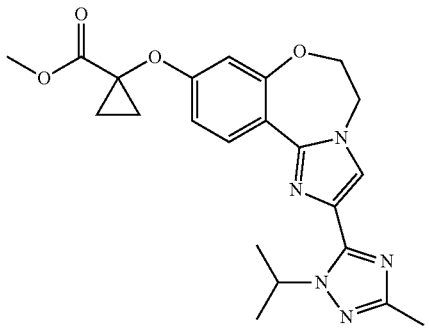

Potassium tertbutoxide (611 mg, 5.45 mmol) was added to a solution of 4-bromo-2-[2-(2-isopropyl-5-methyl-2H-[1,2,4]triazol-3-yl)-4,5-dihydro-6-oxa-1,3a-diazabenzo[e]azulen-8-yloxy]butyric acid methyl ester (2.5 g, 4.96 mmol) in THF (20 mL) and the mixture was stirred at RT for 30 min. The crude reaction mixture was diluted with water and extracted with EtOAc (×3). The combined organic layers were washed with brine, then dried and concentrated in vacuo. The resulting residue was purified by column chromatography (Si-PCC, gradient 0-7% MeOH in DCM) affording 1-[2-(2-Isopropyl-5-methyl-2H-[1,2,4]triazol-3-yl)-4,5-dihydro-6-oxa-1,3a-diazabenzo[e]azulen-8-yloxy]cyclopropanecarboxylic acid methyl ester (1.4 g, 67%). $^1$H NMR (CDCl$_3$, 400 MHz): δ 8.42 (1H, d, J=8.98 Hz), 7.56 (1H, s), 6.75 (1H, dd, J=8.97, 2.58 Hz), 6.58 (1H, d, J=2.55 Hz), 5.97-5.82 (1H, m), 4.50-4.35 (4H, m), 3.74 (3H, s), 2.40 (3H, s), 1.67-1.60 (2H, m), 1.55 (6H, d, J=6.52 Hz), 1.38-1.31 (2H, m)

Step 3: 1-[2-(2-Isopropyl-5-methyl-2H-[1,2,4]triazol-3-yl)-4,5-dihydro-6-oxa-1,3a-diazabenzo[e]azulen-8-yloxy]cyclopropanecarboxylic acid

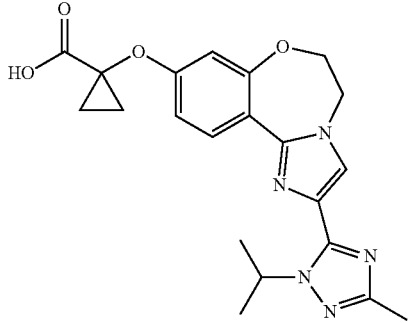 [SMILES: Cc1nc(-c2cn3c(n2)-c2ccc(OC4(C(=O)O)CC4)cc2OCC3)n(C(C)C)n1]

Lithium hydroxide monohydrate (141 mg, 3.44 mmol) was added to a solution of 1-[2-(2-isopropyl-5-methyl-2H-[1,2,4]triazol-3-yl)-4,5-dihydro-6-oxa-1,3a-diazabenzo[e]azulen-8-yloxy]cyclopropanecarboxylic acid methyl ester (730 mg, 1.72 mmol) in MeOH (10 mL) and water (2 mL) and the mixture was heated at 50° C. for 1 h. Volatiles were removed under reduced pressure and the pH of the resulting residue was adjusted to 4 by addition of 1N HCl. A precipitate formed which was collected by filtration and washed with water affording 1-[2-(2-Isopropyl-5-methyl-2H-[1,2,4]triazol-3-yl)-4,5-dihydro-6-oxa-1,3a-diazabenzo[e]azulen-8-yloxy]cyclopropanecarboxylic acid (570 mg, 81%). LCMS: R$_T$ 2.71 min [M+H]$^+$ 410.2

Step 4

A mixture of 1-[2-(2-isopropyl-5-methyl-2H-[1,2,4]triazol-3-yl)-4,5-dihydro-6-oxa-1,3a-diazabenzo[e]azulen-8-yloxy]cyclopropanecarboxylic acid (90 mg, 0.22 mmol), 1-methylpiperazine (29 uL, 0.26 mmol), HATU (108 mg, 0.29 mmol) and DIPEA (52 uL, 0.31 mmol) in DMF (3 mL) was stirred at RT for 2 h. Volatiles were removed under reduced pressure and the resulting residue was partitioned between EtOAc and water. The aqueous layer was extracted with EtOAc and the combined organic layers were washed with water, followed by brine, then dried (MgSO$_4$) and concentrated in vacuo affording {1-[2-(2-Isopropyl-5-methyl-2H-[1,2,4]triazol-3-yl)-4,5-dihydro-6-oxa-1,3a-diazabenzo[e]azulen-8-yloxy]cyclopropyl}-(4-methylpiperazin-1-yl)methanone (quantitative). LCMS: R$_T$ 2.08 min [M+H]$^+$ 492.2

Example 51

Methanesulfonic acid 3-[2-(2-isopropyl-5-methyl-2H-[1,2,4]triazol-3-yl)-4,5-dihydro-6-oxa-1,3a-diazabenzo[e]azulen-8-yloxy]-4-methanesulfonyloxy-3-methylbutyl ester

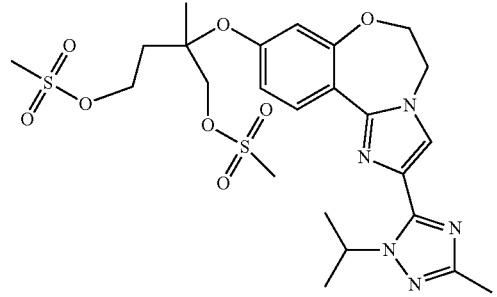

Step 1: 4-Benzyloxy-2-methylbutyric acid benzyl ester

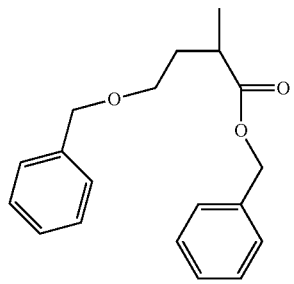 [SMILES: CC(CCOCc1ccccc1)C(=O)OCc1ccccc1]

To a solution of 3-methyldihydrofuran-2-one (2.0 g, 20.0 mmol) in dioxane (15 mL) was added a solution of KOH (1.32 g, 20.0 mmol in 5 mL of water) and the mixture was stirred at RT for 30 min, then at 90° C. for 15 min. After cooling to RT, volatiles were removed under reduced pressure and the residue was azeotroped with toluene and heated at 190° C. affording a white residue. The resulting residue was suspended in DMF (25 mL) and NaH (800 mg, 20 mmol) was added at RT over 5 min. The mixture was stirred at RT for 30 min, then bromomethylbenzene (5.94 mL, 50 mmol) was added over 5 min. Stirring at RT was continued for 18 h then the mixture was partitioned between EtOAc and water. The aqueous phase was extracted with EtOAc (×2) and the combined organic layers were washed with water, followed by brine, then dried (Na$_2$SO$_4$) and concentrated in vacuo. Half of the resulting residue was purified by column chromatography (Si-PCC, gradient 2-30% EtOAc in cyclohexane) affording 4-Benzyloxy-2-methylbutyric acid benzyl ester as a colorless oil (0.738 g, 25%). $^1$H NMR (CDCl$_3$, 400 MHz): δ 7.38-7.22 (10H, m), 5.08 (2H, s), 4.44 (2H, s), 3.51-3.44 (2H, m), 2.78-2.64 (1H, m), 2.12-1.97 (1H, m), 1.79-1.64 (1H, m), 1.19 (3H, d, J=7.06 Hz).

Step 2: 4-Benzyloxy-2-bromo-2-methylbutyric acid benzyl ester

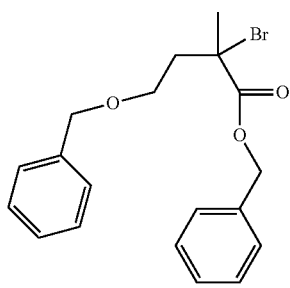 [SMILES: CC(Br)(CCOCc1ccccc1)C(=O)OCc1ccccc1]

n-Butyllithium (2.5M in hexanes, 1.01 mL, 2.54 mmol) was added to a solution of diisopropylamine (0.376 mL, 2.658 mmol) in THF (10 mL) at −30° C. under a nitrogen atmosphere. Stirring at −30° C. was continued for 45 min, and the reaction mixture was cooled to −78° C. A solution of 4-benzyloxy-2-methylbutyric acid benzyl ester (0.721 g, 2.416 mmol) in THF (8 mL) was added over 5 min and stirring at −78° C. was continued for 1 h. A solution of carbon tetrabromide (CBr$_4$) (1.20 g, 3.62 mmol) in THF (2 mL) was added and the mixture was slowly warmed to 0° C. over 3.5 h. The reaction mixture was quenched by addition of a saturated solution aqueous of NH$_4$Cl and then extracted with EtOAc (×2). The combined organic layers were washed with water, followed by brine, then dried (Na$_2$SO$_4$) and concentrated in vacuo. The resulting residue was purified by column chromatography (Si-PCC, gradient 3-18% EtOAc in cyclohexane) affording 4-benzyloxy-2-bromo-2-methylbutyric acid benzyl ester (0.434 g), used in the following step without further purification.

Step 3: 4-Benzyloxy-2-[2-(2-isopropyl-5-methyl-2H-[1,2,4]triazol-3-yl)-4,5-dihydro-6-oxa-1,3a-diazabenzo[e]azulen-8-yloxy]-2-methylbutyric acid benzyl ester

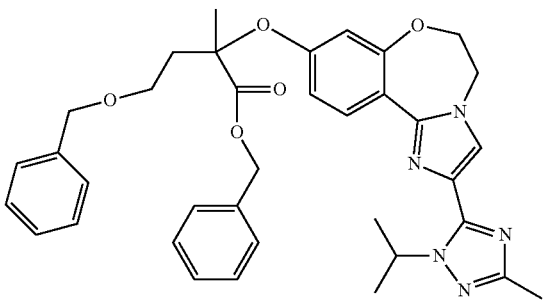 [SMILES: Cc1nc(-c2cn3c(n2)-c2ccc(OC(C)(CCOCc4ccccc4)C(=O)OCc4ccccc4)cc2OCC3)n(C(C)C)n1]

To a suspension of 2-(2-isopropyl-5-methyl-2H-[1,2,4]triazol-3-yl)-4,5-dihydro-6-oxa-1,3a-diazabenzo[e]azulen-8-ol from Example 4 (100 mg, 0.307 mmol) and Cs$_2$CO$_3$ (200 mg, 0.615 mmol) in CH$_3$CN (1 mL) was added a solution of 4-benzyloxy-2-bromo-2-methylbutyric acid benzyl ester (0.345 mmol) in CH$_3$CN (7 mL) and stirring at reflux temperature was continued for 3 h. After cooling to RT, the reaction mixture was partitioned between water and EtOAc. The aqueous phase was extracted with EtOAc and the combined organic layers were washed with water, followed by brine, then dried (Na$_2$SO$_4$) and concentrated in vacuo. The resulting residue was purified by column chromatography (Si-PCC, gradient 2-10% MeOH in DCM) affording 4-Benzyloxy-2-[2-(2-isopropyl-5-methyl-2H-[1,2,4]triazol-3-yl)-4,5-dihydro-6-oxa-1,3a-diazabenzo[e]azulen-8-yloxy]-2-methylbutyric acid benzyl ester as a pale orange gum (36 mg, 19%). LCMS: R$_T$ 4.28 min [M+H]$^+$ 622.3

Step 4: 4-Benzyloxy-2-[2-(2-isopropyl-5-methyl-2H-[1,2,4]triazol-3-yl)-4,5-dihydro-6-oxa-1,3a-diazabenzo[e]azulen-8-yloxy]-2-methylbutan-1-ol

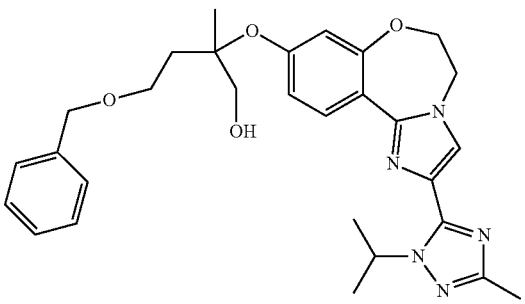 [SMILES: Cc1nc(-c2cn3c(n2)-c2ccc(OC(C)(CO)CCOCc4ccccc4)cc2OCC3)n(C(C)C)n1]

To a suspension of LiAlH$_4$ (4.4 mg, 0.116 mmol) in THF (1 mL) was added a solution of 4-benzyloxy-2-[2-(2-isopropyl-5-methyl-2H-[1,2,4]triazol-3-yl)-4,5-dihydro-6-oxa-1,3a-diazabenzo[e]azulen-8-yloxy]-2-methylbutyric acid benzyl ester (36 mg, 0.058 mmol) in THF (2 mL) and stirring at RT was continued for 2.5 h. To the reaction mixture was added EtOAc (0.5 mL) and stirring was continued for 10 min. An aqueous solution of Rochelle's salt was then added and the aqueous phase was extracted with EtOAc (×2). The combined organic phases were washed with water, followed by brine, then dried (Na$_2$SO$_4$) and concentrated in vacuo. The resulting residue was purified by column chromatography (Si-PCC, gradient 3-12% MeOH in DCM) affording 4-Benzyloxy-2-[2-(2-isopropyl-5-methyl-2H-[1,2,4]triazol-3-yl)-4,5-dihydro-6-oxa-1,3a-diazabenzo[e]azulen-8-yloxy]-2-methylbutan-1-ol (29 mg, 98%). $^1$H NMR (CDCl$_3$, 400 MHz): δ 8.41 (1H, d, J=8.83 Hz), 7.60 (1H, s), 7.39-7.27 (5H, m), 6.81 (1H, dd, J=8.83, 2.41 Hz), 6.69 (1H, d, J=2.37 Hz), 5.98-5.85 (1H, m), 4.60-4.50 (2H, m), 4.49-4.35 (4H, m), 3.83-3.69 (2H, m), 3.65-3.55 (2H, m), 3.24 (1H, s), 2.42 (3H, s), 2.20-2.12 (1H, m), 2.07-1.97 (1H, m), 1.57 (6H, d, J=6.75 Hz), 1.31 (3H, s)

Step 5: 2-[2-(2-Isopropyl-5-methyl-2H-[1,2,4]triazol-3-yl)-4,5-dihydro-6-oxa-1,3a-diazabenzo[e]azulen-8-yloxy]-2-methylbutane-1,4-diol

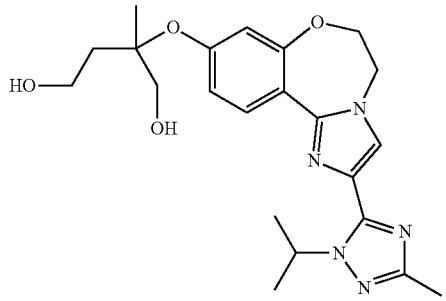 [SMILES: Cc1nc(-c2cn3c(n2)-c2ccc(OC(C)(CO)CCO)cc2OCC3)n(C(C)C)n1]

To a solution of 4-benzyloxy-2-[2-(2-isopropyl-5-methyl-2H-[1,2,4]triazol-3-yl)-4,5-dihydro-6-oxa-1,3a-diazabenzo[e]azulen-8-yloxy]-2-methylbutan-1-ol (29 mg, 0.0568 mmol) in IMS (5 mL) was added 10% Pd/C (5 mg). The reaction mixture was stirred at RT under a hydrogen atmosphere for 4 h. The suspension was then filtered through a pad of Celite® and the filtrate was concentrated in vacuo. To a solution of the residue thus obtained in IMS (5 mL) was added Pd(OH)$_2$/C (10 mg) and the reaction mixture was stirred at RT under a hydrogen atmosphere for 18 h. The suspension was then filtered through a pad of Celite® and the filtrate was concentrated in vacuo. The resulting residue was purified by column chromatography (Si-PCC, gradient 2-10% MeOH in DCM) affording 2-[2-(2-Isopropyl-5-methyl-2H-[1,2,4]triazol-3-yl)-4,5-dihydro-6-oxa-1,3a-diazabenzo[e]azulen-8-yloxy]-2-methylbutane-1,4-diol as a colorless gum (14 mg, 56%). LCMS: R$_T$ 2.39 min [M+H]$^+$ 428.3

Step 6

To a solution of 2-[2-(2-isopropyl-5-methyl-2H-[1,2,4]triazol-3-yl)-4,5-dihydro-6-oxa-1,3a-diazabenzo[e]azulen-8-yloxy]-2-methylbutane-1,4-diol (14 mg, 0.0318 mmol) and Et$_3$N (13 uL, 0.095 mmol) in DCM (2 mL) at 0° C. was added methanesulfonyl chloride (6.0 uL, 0.080 mmol) and stirring at RT was continued for 1.5 h. The mixture was diluted with DCM, washed with a saturated solution of NaHCO$_3$, followed by water, then dried (Na$_2$SO$_4$) and concentrated in vacuo affording Methanesulfonic acid 3-[2-(2-isopropyl-5-methyl-2H-[1,2,4]triazol-3-yl)-4,5-dihydro-6-oxa-1,3a-diazabenzo[e]azulen-8-yloxy]-4-methanesulfonyloxy-3-methylbutyl ester as a colorless gum (23 mg, quantitative). LCMS: R$_T$ 2.99 min [M+H]$^+$ 584.1

Example 52

Methanesulfonic acid 4-[2-(2-isopropyl-5-methyl-2H-[1,2,4]triazol-3-yl)-4,5-dihydro-6-oxa-1,3a-diazabenzo[e]azulen-8-yloxy]-5-methanesulfonyloxy-2-methylpentyl ester

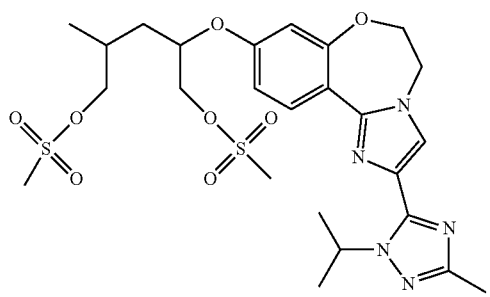 [SMILES: Cc1nc(-c2cn3c(n2)-c2ccc(OC(COS(C)(=O)=O)CC(C)COS(C)(=O)=O)cc2OCC3)n(C(C)C)n1]

Step 1: 2-Bromo-4-methylpentanedioic acid diethyl ester

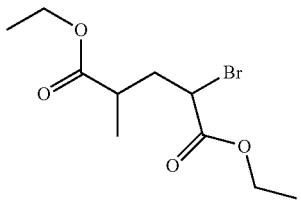

Thionyl chloride (4 mL) was added to 2-methylpentanedioic acid 5-ethyl ester (2.636 mmol) and the mixture was heated at 60° C. for 1 h under a nitrogen atmosphere. After cooling to RT, bromine (0.27 mL, 5.272 mmol) followed by 48% HBr in AcOH (1 drop) were added and the mixture was heated at 60° C. for 1 h and then at 70° C. for 2 h under a nitrogen atmosphere. After cooling to RT, volatiles were removed under reduced pressure and the resulting oil was added to ice-cooled EtOH (5 mL). Stirring at RT was continued for 3 h and then volatiles were removed in vacuo. The resulting residue was dissolved in diethyl ether and washed with a saturated solution of NaHCO$_3$, followed by brine, then dried (Na$_2$SO$_4$) and concentrated in vacuo. The resulting residue was purified by column chromatography (Si-PCC, gradient 10-30% EtOAc in cyclohexane) affording 2-bromo-4-methylpentanedioic acid diethyl ester as a colorless oil (640 mg, 86%), used in the following step without further purification.

Step 2: 2-[2-(2-Isopropyl-5-methyl-2H-[1,2,4]triazol-3-yl)-4,5-dihydro-6-oxa-1,3a-diazabenzo[e]azulen-8-yloxy]-4-methylpentanedioic acid diethyl ester

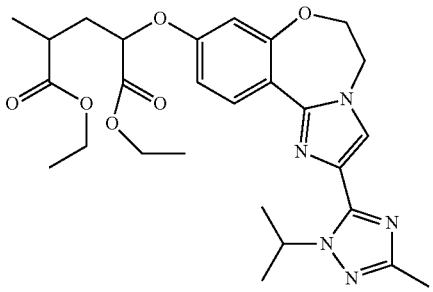 [SMILES: CCOC(=O)C(C)CC(Oc1ccc2c(c1)OCCn1cc(-c3nc(C)nn3C(C)C)nc1-2)C(=O)OCC]

To a suspension of 2-(2-isopropyl-5-methyl-2H-[1,2,4]triazol-3-yl)-4,5-dihydro-6-oxa-1,3a-diazabenzo[e]azulen-8-ol from Example 4 (330 mg, 1.013 mmol) in CH$_3$CN (18 mL) was added Cs$_2$CO$_3$ (825 mg, 2.53 mmol) followed by a solution of 2-bromo-4-methylpentanedioic acid diethyl ester (640 mg, 2.276 mmol) in CH$_3$CN (2 mL) and stirring at reflux temperature was continued for 1.5 h. After cooling to RT, the reaction mixture was partitioned between water and EtOAc. The aqueous phase was extracted with EtOAc and the combined organic layers were washed with water, followed by brine, then dried (Na$_2$SO$_4$) and concentrated in vacuo. The resulting residue was purified by column chromatography (Si-PCC, gradient 2-8% MeOH in DCM) affording 2-[2-(2-Isopropyl-5-methyl-2H-[1,2,4]triazol-3-yl)-4,5-dihydro-6-oxa-1,3a-diazabenzo[e]azulen-8-yloxy]-4-methylpentanedioic acid diethyl ester as a pale yellow gum (391 mg, 73%). LCMS: R$_T$ 3.59 min [M+H]$^+$ 526.5

Step 3: 2-[2-(2-Isopropyl-5-methyl-2H-[1,2,4]triazol-3-yl)-4,5-dihydro-6-oxa-1,3a-diazabenzo[e]azulen-8-yloxy]-4-methylpentane-1,5-diol

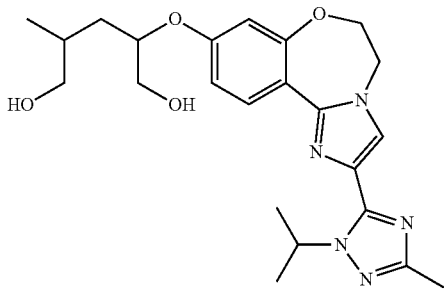 [SMILES: Cc1nc(-c2cn3c(n2)-c2ccc(OC(CO)CC(C)CO)cc2OCC3)n(C(C)C)n1]

To a suspension of LiAlH$_4$ (85 mg, 2.23 mmol) in THF (1 mL) at 0° C. was added a solution of 2-[2-(2-isopropyl-5-methyl-2H-[1,2,4]triazol-3-yl)-4,5-dihydro-6-oxa-1,3a-diazabenzo[e]azulen-8-yloxy]-4-methylpentanedioic acid diethyl ester (391 mg, 0.744 mmol) in THF (20 mL) and stirring at RT was continued for 2.5 h. To the reaction mixture was added EtOAc (2 mL) and stirring was continued for 30 min. An aqueous solution (10%) of Rochelle's salt was then added and the mixture was stirred for 5 min. Organic solvents were removed under reduced pressure and the resulting aqueous phase was extracted with EtOAc (×2). The combined organic phases were washed with water, followed by brine, then dried (Na$_2$SO$_4$) and concentrated in vacuo. The resulting residue was purified by column chromatography (Si-PCC, gradient 3-18% MeOH in DCM) affording 2-[2-(2-Isopropyl-5-methyl-2H-[1,2,4]triazol-3-yl)-4,5-dihydro-6-oxa-1,3a-diazabenzo[e]azulen-8-yloxy]-4-methylpentane-1,5-diol as a colorless gum (181 mg, 55%). LCMS: R$_T$ 2.49 min [M+H]$^+$ 442.3

Step 4

To a solution of 2-[2-(2-isopropyl-5-methyl-2H-[1,2,4]triazol-3-yl)-4,5-dihydro-6-oxa-1,3a-diazabenzo[e]azulen-8-yloxy]-4-methylpentane-1,5-diol (90 mg, 0.2038 mmol) and Et$_3$N (85 uL, 0.6114 mmol) in DCM (10 mL) cooled at 0° C. was added methanesulfonyl chloride (40 uL, 0.51 mmol) and stirring at RT was continued for 1.5 h. The mixture was diluted with DCM, washed with a saturated solution of NaHCO$_3$, followed by water, then dried (Na$_2$SO$_4$) and concentrated in vacuo affording Methanesulfonic acid 4-[2-(2-isopropyl-5-methyl-2H-[1,2,4]triazol-3-yl)-4,5-dihydro-6-oxa-1,3a-diazabenzo[e]azulen-8-yloxy]-5-methanesulfonyloxy-2-methylpentyl ester as a colorless gum (quantitative). LCMS: R$_T$ 3.07 min [M+H]$^+$ 598.1

Example 53

1-(2-(tetrahydro-2H-pyran-2-yloxy)ethyl)-4-(tributylstannyl)-1H-imidazole and 1-(2-(tetrahydro-2H-pyran-2-yloxy)ethyl)-5-(tributylstannyl)-1H-imidazole

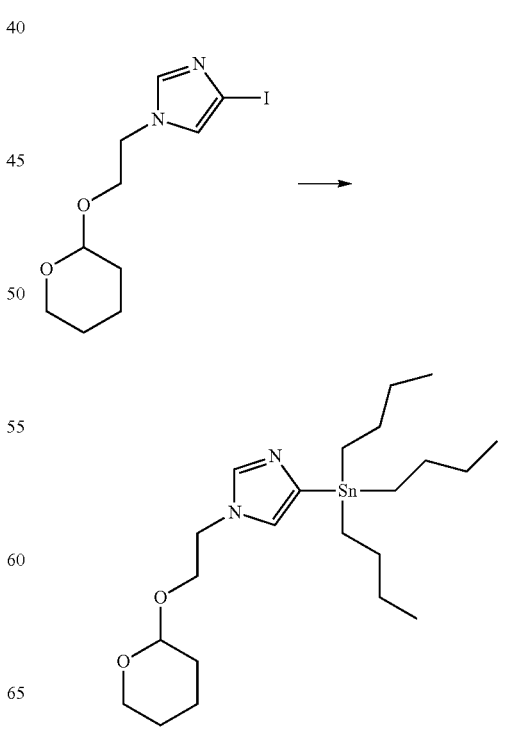

-continued

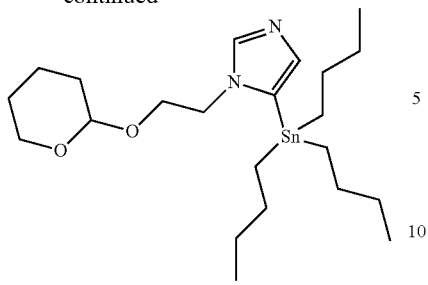

Isopropylmagnesium chloride (iPrMgCl—LiCl, 4.3 mL of 1.3 M) in THF was added dropwise to a solution of 4-iodo-1-(2-(tetrahydro-2H-pyran-2-yloxy)ethyl)-1H-imidazole (1.50 g, 4.66 mmol, mixture of regioisomers) in tetrahydrofuran (20 mL, 0.3 mol) at 0° C. The reaction mixture was stirred at 0° C. for 1 hour. Tributyltin chloride (1.64 mL, 6.05 mmol) was added and the mixture warmed to room temperature and stirred overnite. The reaction mixture was rotovapped and quenched with water, diluted with dichloromethane and filtered over celite. The aqueous layer was extracted and the crude, concentrated organic purified by flash column chromatography 50-100% ethylacetate in hexanes. NMR showed a 2:1 ratio of 1-(2-(tetrahydro-2H-pyran-2-yloxy)ethyl)-4-(tributylstannyl)-1H-imidazole and 1-(2-(tetrahydro-2H-pyran-2-yloxy)ethyl)-5-(tributylstannyl)-1H-imidazole (assumed by literature references of similar imidazole substitutions). Regioisomers were not separated.

Example 54

1-(4-bromo-1H-imidazol-1-yl)-2-methylpropan-2-ol and 1-(5-bromo-1H-imidazol-1-yl)-2-methylpropan-2-ol

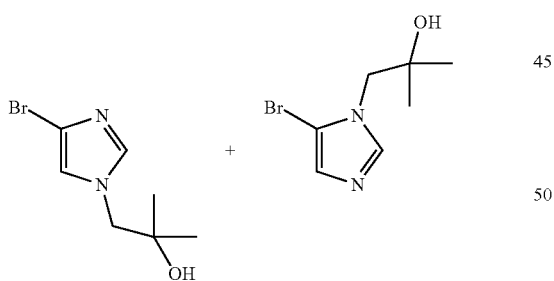

To a suspension of 4-bromo-1H-imidazole (1.0 g, 6.8 mmol) and isobutylene oxide (0.665 mL, 7.48 mmol) in methanol (0.331 mL, 8.16 mmol) was added cesium carbonate (0.63 g, 1.9 mmol). The reaction mixture was heated in a sealed vessel cautiously at 110° C. for 1.5 hrs. The reaction was cooled to room temperature, diluted with diethylether and washed 2 times with water. The organics were washed with brine, dried over magnesium sulfate and concentrated in vacuo to give a white solid which was flash purified with 100% ethyl acetate to get the two distinct intermediates. The major regioisomer was 1-(4-bromo-1H-imidazol-1-yl)-2-methylpropan-2-ol (0.8 g, 54% yield, M+1 220) while the minor regioisomer was 1-(5-bromo-1H-imidazol-1-yl)-2-methylpropan-2-ol (0.32 g, 21% yield M+1 220).

Example 55

N,N-diethyl-2-(4-(4,4,5,5-tetramethyl-1,3,2-dioxaborolan-2-yl)-1H-pyrazol-1-yl)ethanamine

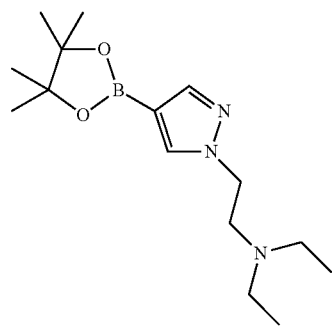 [SMILES: CCN(CC)CCn1cc(B2OC(C)(C)C(C)(C)O2)cn1]

To a solution of 4,4,5,5-tetramethyl-2-(1H-pyrazol-4-yl)-1,3,2-dioxaborolane (250 mg, 1.29 mmol) and sodium hydride (61.8 mg, 2.58 mmol) in tetrahydrofuran at 0° C. was added 2-bromo-N,N-diethylethanamine (558 mg, 2.58 mmol). The reaction was allowed to warm up to room temperature and was monitored by LCMS. After 90 minutes there was still no reaction and potassium iodide (1.71 g, 10.3 mmol) was added and the reaction was heated at 50° C. overnight. The reaction mixture was diluted with a large volume of ethyl acetate and water and partitioned. The organic layer containing the product was washed with brine and concentrated in vacuo to give clear thick oil confirmed by LCMS to be 100% pure N,N-diethyl-2-(4-(4,4,5,5-tetramethyl-1,3,2-dioxaborolan-2-yl)-1H-pyrazol-1-yl)ethanamine (340 mg, yield 90%, M+1 294.2)

Example 56

1-(2-(tert-butyldimethylsilyloxy)-2-methylpropyl)-4-(trimethylstannyl)-1H-imidazole

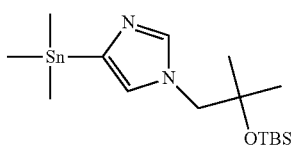 [SMILES: CC(C)(Cn1cn[c]([Sn]([CH3])([CH3])[CH3])c1)O[Si](C)(C)C(C)(C)C]

Step 1: 2,4,5-triiodo-1H-imidazole

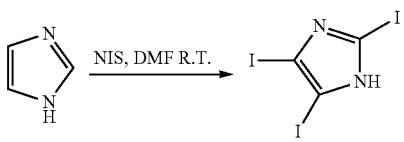 [SMILES: c1c[nH]cn1 ; Ic1nc(I)c(I)[nH]1]

To a mixture of 1H-Imidazole (50 g, 0.73 mol) in DMF (200 mL) was added NIS (328 g, 1.46 mol) portionwise, the reaction mixture was stirred at room temperature for 4 hours. The reaction mixture was poured in sat. Na₂CO₃ solution, filtered, the residue was washed with water and dried to give 150 g of 2,4,5-triiodo-1H-imidazole (Yield=46%).

Step 2: 4-iodo-1H-imidazole

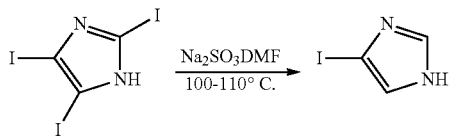

2,4,5-triiodo-1H-imidazole was reacted with Na₂SO₃ in DMF (250 mL) and stirring at 110° C. for over night under N₂ atmosphere. The reaction mixture was filtered, the filtrate was concentrated and poured into water, then extracted with EtOAc, the organic was washed with water, dried over Na₂SO₄, concentrated and purified by silica gel column to give 4-iodo-1H-imidazole (Yield=55%). LC-MS: m/z=195 [M+H⁺]

Step 3: 1-(4-iodo-1H-imidazol-1-yl)-2-methylpropan-2-ol

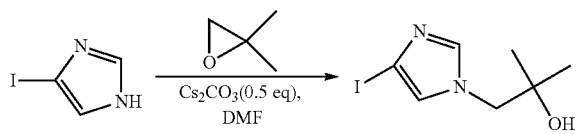

A mixture of 4-iodo-1H-imidazole, Cs₂CO₃ in 2,2-dimethyl oxirane was stirred at 120° C. for 20 min under irradiation with microwave. The reaction mixture was concentrated, and purified to give 1-(4-iodo-1H-imidazol-1-yl)-2-methylpropan-2-ol (Yield=71%). LC-MS: m/z=266 [M+H⁺] ¹H NMR (CDCl₃, 400 MHz): δ7.36 (s, 1H), 7.06 (s, 1H), 3.84 (s, 2H), 1.22 (s, 6H).

Step 4: 1-(2-(tert-butyldimethylsilyloxy)-2-methylpropyl)-4-iodo-1H-imidazole

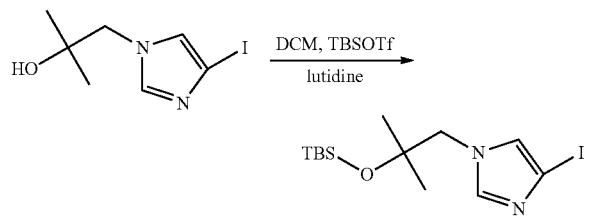

1-(4-iodo-1H-imidazol-1-yl)-2-methylpropan-2-ol was dissolved in DCm and lutidine was added dropwise at 0° C. The mixture was stirred at 0° C. for 30 min then tert-butyldimethylsilyl triflate (TBSOTf) was added dropwise. The mixture was warmed to room temperature and sat for about an hour, then quenched with 30% acetic acid, extracted ethylacetate, dried, and concentrated to give 1-(2-(tert-butyldimethylsilyloxy)-2-methylpropyl)-4-iodo-1H-imidazole (Yield=74%). LC-MS: m/z=381 [M+H⁺]

Step 5: 1-(2-(tert-butyldimethylsilyloxy)-2-methylpropyl)-4-(trimethylstannyl)-1H-imidazole

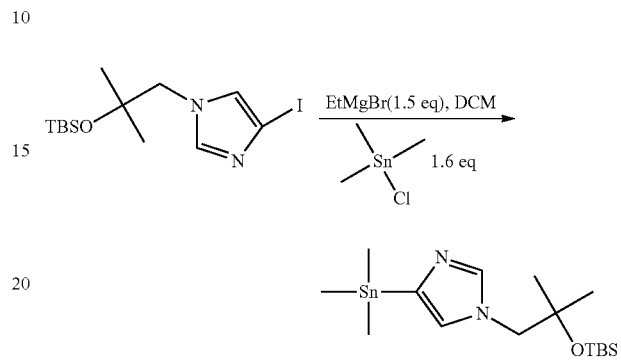

To a mixture of 1-(2-(tert-butyldimethylsilyloxy)-2-methylpropyl)-4-iodo-1H-imidazole in DCM was added ethylmagnesium bromide at −78° C. The temperature of the mixture was allowed to warm up to about 10° C. slowly and cooled again. Trimethyltin chloride was added dropwise at −78° C. After the addition, the temperature was allowed to slowly warm up to room temperature. The reaction mixture was pouted into saturate NH₄Cl solution, then extracted with DCM. The organic phase was washed with water twice, dried over anhydrous Na₂SO₄, and concentrated to give 1-(2-(tert-butyldimethylsilyloxy)-2-methylpropyl)-4-(trimethylstannyl)-1H-imidazole (Yield=74%). LC-MS: m/z=419 [M+H⁺] ¹H NMR (CDCl₃, 400 MHz): δ 7.63 (s, 1H), 7.00 (s, 1H), 3.79 (s, 2H), 1.22-1.19 (s, 6H), 0.86 (s, 9H), 0.27 (s, 6H), 0.02 (s, 6H)

Example 57

2-(1-isopropyl-3-methyl-1H-1,2,4-triazol-5-yl)-9-(4,4,5,5-tetramethyl-1,3,2-dioxaborolan-2-yl)-5,6-dihydrobenzo[f]imidazo[1,2-d][1,4]oxazepine

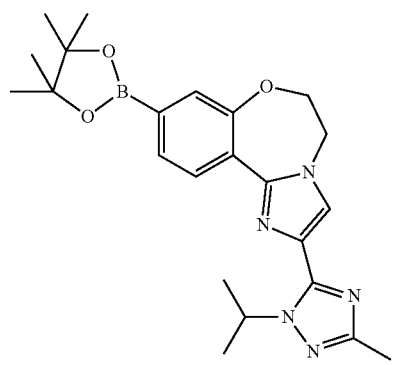

229

Step 1: 9-bromo-2-(1-isopropyl-4-methyl-1H-imidazol-2-yl)-5,6-dihydrobenzo[f]imidazo[1,2-d][1,4]oxazepine

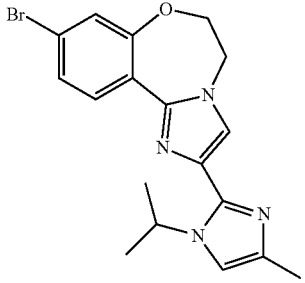 [SMILES: Cc1cn(C(C)C)c(-c2cn3c(n2)-c2ccc(Br)cc2OCC3)n1]

Isopropyl iodide (165 uL, 1.65 mmol) was added to a mixture of 417 mg (1.21 mmol) of 9-bromo-2-(4-methyl-1H-imidazol-2-yl)-5,6-dihydrobenzo[f]imidazo[1,2-d][1,4]oxazepine and cesium carbonate (538 mg, 1.65 mmol) in 3 ml of N,N-dimethylformamide. The reaction mixture was stirred at room temperature for 18 hours, mixed with water and extracted with ethyl acetate. The organic extract was washed with water, brine, dried over MgSO4, concentrated, and purified on 4 g silica column eluting with 4-5% methanol in DCM to give 210 mg of 9-bromo-2-(1-isopropyl-4-methyl-1H-imidazol-2-yl)-5,6-dihydrobenzo[f]imidazo[1,2-d][1,4]oxazepine. MS: 387.1.

Step 2: A solution of 9-bromo-2-(1-isopropyl-4-methyl-1H-imidazol-2-yl)-5,6-dihydrobenzo[f]imidazo[1,2-d][1,4]oxazepine (1.00 g, 0.00258 mol) and potassium acetate (0.758 g, 0.00773 mol) in dimethyl sulfoxide (8.5 mL, 0.12 mol); in a round bottom flask equipped with a magnetic stir bar was thoroughly purged with nitrogen. Bispinacol ester boronate (0.719 g, 0.00283 mol) and [1,1'-Bis(diphenylphosphino)ferrocene]dichloropalladium(II), complex with dichloromethane (1:1) (0.210 g, 0.258 mmol) was added and the reaction was heated to 85° C. under inert atmosphere. The reaction was monitored by LC/MS and was complete after 6 hr. The mixture was partitioned between water and methylene chloride and the mixture was extracted 3× with methylene chloride. The organic phases were combined, dried with MgSO$_4$ and concentrated. The whole was loaded onto silica and purified by flash chromatography (0-10% MeOH in DCM followed by 100% EtOAC) to give 2-(1-isopropyl-3-methyl-1H-1,2,4-triazol-5-yl)-9-(4,4,5,5-tetramethyl-1,3,2-dioxaborolan-2-yl)-5,6-dihydrobenzo[f]imidazo[1,2-d][1,4]oxazepine (488 mg) as a beige solid. MS(ESI+) 436.2.

Example 65

8-Azetidin-3-yl-2-(2-isopropyl-2H-[1,2,4]triazol-3-yl)-4,5-dihydro-6-oxa-1,3a-diaza-benzo[e]azulene hydrochloride

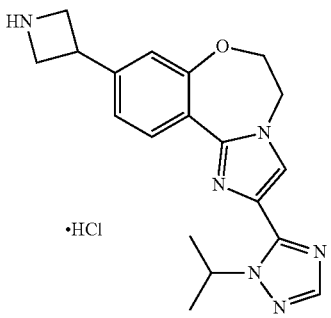 [SMILES: CC(C)n1ncnc1-c1cn2c(n1)-c1ccc(C3CNC3)cc1OCC2 ; Cl]

230

Step 1: 3-[2-(2-Isopropyl-2H-[1,2,4]triazol-3-yl)-4,5-dihydro-6-oxa-1,3a-diaza-benzo[e]azulen-8-yl]-azetidine-1-carboxylic acid tert-butyl ester

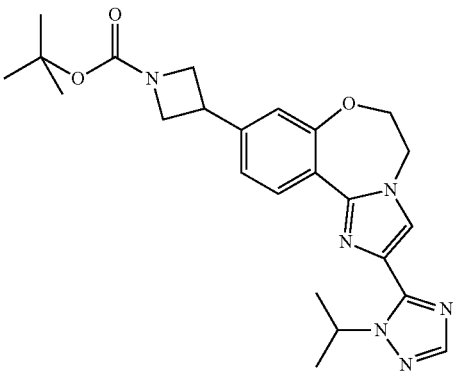 [SMILES: CC(C)n1ncnc1-c1cn2c(n1)-c1ccc(C3CN(C(=O)OC(C)(C)C)C3)cc1OCC2]

3-[2-(2-Isopropyl-2H-[1,2,4]triazol-3-yl)-4,5-dihydro-6-oxa-1,3a-diaza-benzo[[e]azulen-8-yl]-azetidine-1-carboxylic acid tert-butyl ester was prepared similarly to 3-{2-[2-(2,4-difluoro-phenyl)-2H-[1,2,4]triazol-3-yl]-4,5-dihydro-2H-6-oxa-1,2-diaza-benzo[e]azulen-8-yl}-azetidine-1-carboxylic acid tert-butyl ester from 8-bromo-2-(2-isopropyl-2H-[1,2,4]triazol-3-yl)-4,5-dihydro-6-oxa-1,3a-diaza-benzo[e]azulene and 3-azetidine-1-carboxylic acid tert-butyl ester zinc iodide. LCMS: R$_T$=4.61 min, M+H$^+$ =451.

Step 2: 8-Azetidin-3-yl-2-(2-isopropyl-2H-[1,2,4]triazol-3-yl)-4,5-dihydro-6-oxa-1,3a-diaza-benzo[e]azulene hydrochloride 8-Azetidin-3-yl-2-(2-isopropyl-2H-[1,2,4]triazol-3-yl)-4,5-dihydro-6-oxa-1,3a-diaza-benzo[e]azulene hydrochloride was prepared similarly to 8-azetidin-3-yl-2-[2-(2,4-difluoro-phenyl)-2H-[1,2,4]triazol-3-yl]-4,5-dihydro-2H-6-oxa-1,2-diaza-benzo[e]azulene hydrochloride from 3-[2-(2-isopropyl-2H-[1,2,4]triazol-3-yl)-4,5-dihydro-6-oxa-1,3a-diaza-benzo[e]azulen-8-yl]-azetidine-1-carboxylic acid tert-butyl ester. LCMS: R$_T$=2.44 min, M+H$^+$ =351

Example 66

2-(2-Isopropyl-2H-[1,2,4]triazol-3-yl)-8-piperidin-4-yl-4,5-dihydro-6-oxa-1,3a-diaza-benzo[e]azulene trifluoroacetic acid salt

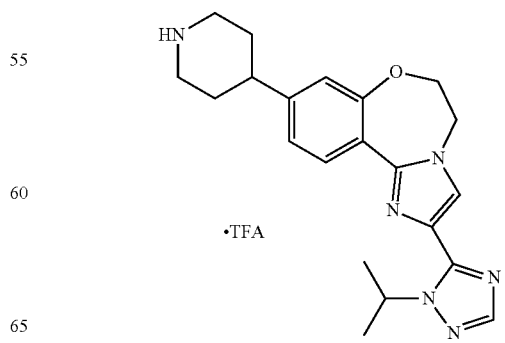

Step 1: 4-[2-(2-Isopropyl-2H-[1,2,4]triazol-3-yl)-4,5-dihydro-6-oxa-1,3a-diaza-benzo[e]azulen-8-yl]-piperidine-1-carboxylic acid tert-butyl ester

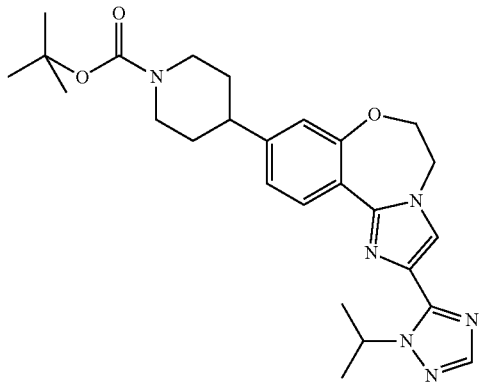 [SMILES: CC(C)n1ncnc1-c1cn2c(n1)-c1ccc(C3CCN(C(=O)OC(C)(C)C)CC3)cc1OCC2]

4-[2-(2-Isopropyl-2H-[1,2,4]triazol-3-yl)-4,5-dihydro-6-oxa-1,3a-diaza-benzo[e]azulen-8-yl]-piperidine-1-carboxylic acid tert-butyl ester was prepared similarly to 3-{2-[2-(2,4-difluoro-phenyl)-2H-[1,2,4]triazol-3-yl]-4,5-dihydro-2H-6-oxa-1,2-diaza-benzo[e]azulen-8-yl}-azetidine-1-carboxylic acid tert-butyl ester from 8-bromo-2-(2-isopropyl-2H-[1,2,4]triazol-3-yl)-4,5-dihydro-6-oxa-1,3a-diaza-benzo[e]azulene (3.0 g, 8.0 mmol) and 4-piperidine-1-carboxylic acid tert-butyl ester zinc iodide (12 mmol) (prepared similarly to 3-azetidine-1-carboxylic acid tert-butyl ester zinc iodide) to give 4-[2-(2-Isopropyl-2H-[1,2,4]triazol-3-yl)-4,5-dihydro-6-oxa-1,3a-diaza-benzo[e]azulen-8-yl]-piperidine-1-carboxylic acid tert-butyl ester (1.2 g, 31%). LCMS: $R_T$=5.06 min, M+H'=479

Step 2: 2-(2-Isopropyl-2H-[1,2,4]triazol-3-yl)-8-piperidin-4-yl-4,5-dihydro-6-oxa-1,3a-diaza-benzo[e]azulene trifluoroacetic acid salt To a solution of 4-[2-(2-isopropyl-2H-[1,2,4]triazol-3-yl)-4,5-dihydro-6-oxa-1,3a-diaza-benzo[e]azulen-8-yl]-piperidine-1-carboxylic acid tert-butyl ester (1.2 g, 2.51 mmol) in DCM (12 mL) was added TFA (8 mL) and the reaction mixture stirred at RT for 1 h. The reaction mixture was concentrated in vacuo, the residue triturated in diethyl ether to give 2-(2-Isopropyl-2H-[1,2,4]triazol-3-yl)-8-piperidin-4-yl-4,5-dihydro-6-oxa-1,3a-diaza-benzo[e]azulene trifluoroacetic acid salt as a grey solid (1.34 g, 100%). LCMS: $R_T$=2.88 min, M+H$^+$=379

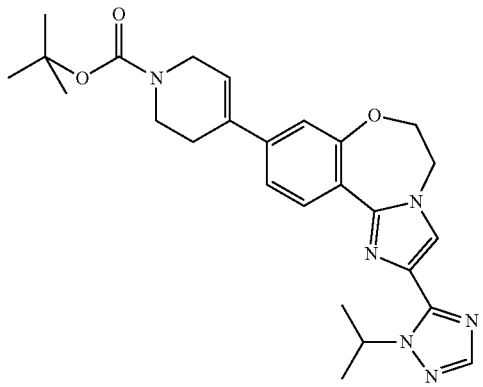

Alternatively, 2-(2-Isopropyl-2H-[1,2,4]triazol-3-yl)-8-piperidin-4-yl-4,5-dihydro-6-oxa-1,3a-diaza-benzo[e]azulene hydrochloride can be prepared whereby 8-Bromo-2-(2-isopropyl-2H-[1,2,4]triazol-3-yl)-4,5-dihydro-6-oxa-1,3a-diaza-benzo[e]azulene (2.1 g, 5.4 mmol), 3,6-dihydro-2H-pyridine-1-N-Boc-4-boronic acid pinacol ester (2.59 g, 8.3 mmol) and potassium carbonate (1.92 g, 13.9 mmol) were mixed with DMF (13 mL) and purged with argon. PdCl$_2$dppf.DCM (310 mg, 0.42 mmol) was added, purging repeated and the mixture heated to 80° C. for 18 h. After cooling the reaction mixture was filtered through Celite®, washing with ethyl acetate, and the filtrate concentrated in vacuo. The residue was partitioned between ethyl acetate and water, the organic layer separated, dried (Na$_2$SO$_4$), filtered and concentrated in vacuo. The resultant residue was subjected to flash chromatography (SiO$_2$, gradient 0 to 2% methanol in ethyl acetate) to give 4-[2-(2-Isopropyl-2H-[1,2,4]triazol-3-yl)-4,5-dihydro-6-oxa-1,3a-diaza-benzo[e]azulen-8-yl]-3,6-dihydro-2H-pyridine-1-carboxylic acid tert-butyl ester (2.56 g, 96%). LCMS $R_T$=4.79, [M+H]$^+$ =477. $^1$H NMR 400 MHz (CDCl$_3$) δ: 8.45 (1H, d, J=8.46 Hz), 7.89 (1H, s), 7.73 (1H, s), 7.19 (1H, dd, J=8.37, 1.80 Hz), 7.04 (1H, d, J=1.87 Hz), 6.15 (1H, s), 6.04-5.96 (1H, m), 4.51-4.43 (4H, m), 4.09 (2H, d, J=3.68 Hz), 3.64 (2H, t, J=5.64 Hz), 2.52 (2H, s), 1.59 (6H, d, J=6.63 Hz), 1.49 (9H, s)

4-[2-(2-Isopropyl-2H-[1,2,4]triazol-3-yl)-4,5-dihydro-6-oxa-1,3a-diaza-benzo[e]azulen-8-yl]-3,6-dihydro-2H-pyridine-1-carboxylic acid tert-butyl ester was treated with hydrochloric acid to give 2-(2-Isopropyl-2H-[1,2,4]triazol-3-yl)-8-piperidin-4-yl-4,5-dihydro-6-oxa-1,3a-diaza-benzo[e]azulene hydrochloride. $^1$H NMR 400 MHz (DMSO-d$_6$) δ: 9.08 (2H, s), 8.37 (1H, d, J=8.30 Hz), 8.18 (1H, s), 8.07 (1H, s), 7.06 (1H, dd, J=8.35, 1.80 Hz), 6.91 (1H, d, J=1.80 Hz), 5.85 (1H, m), 4.53 (4H, m), 3.35 (2H, d, J=12.46 Hz), 2.98 (2H, m), 2.87 (1H, m), 1.93 (4H, m), 1.50 (6H, d, J=6.57 Hz)

Example 72

2-(1-(2-chlorophenyl)-1H-imidazol-2-yl)-5,6-dihydrobenzo[f]imidazo[1,2-d][1,4]oxazepine-10-carboxylic acid

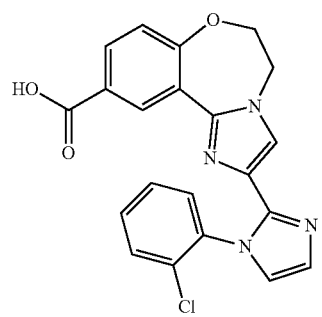 [SMILES: O=C(O)c1ccc2c(c1)-c1nc(-c3nccn3-c3ccccc3Cl)cn1CCO2]

Step 1: methyl 2-(1-(2-chlorophenyl)-1H-imidazol-2-yl)-5,6-dihydrobenzo[f]imidazo[1,2-d][1,4]oxazepine-10-carboxylate

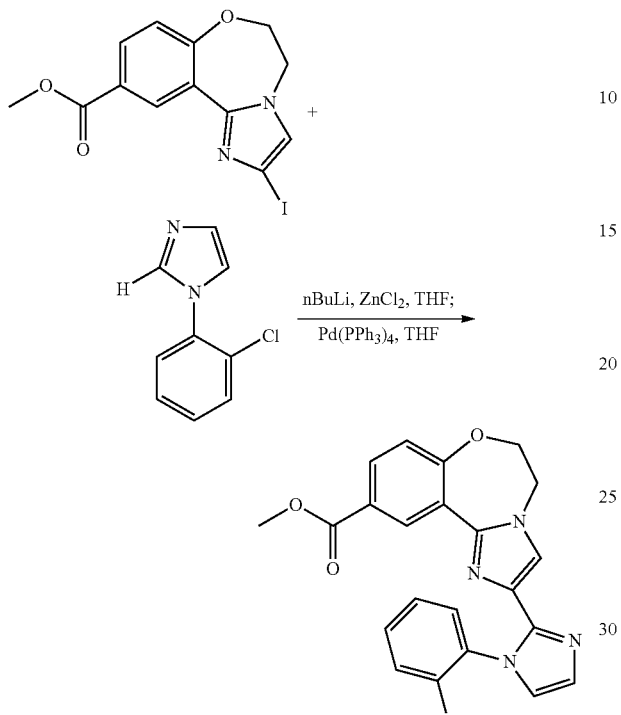

To a solution of 1-(2-chlorophenyl)-1H-imidazole (0.133 g, 0.743 mmol) in tetrahydrofuran (5.43 mL, 66.9 mmol); at −78° C. was added 1.60 M of n-Butyllithium in Hexane (0.464 mL) dropwise. The reaction mixture was stirred at −78° C. for 1 h then 0.50 M of Zinc dichloride in Tetrahydrofuran (1.48 mL) was added. The reaction mixture was warmed to RT 30 min then added Tetrakis(triphenylphosphine)palladium(0) (0.0780 g, 0.0675 mmol), solution of methyl 2-iodo-5,6-dihydrobenzo[f]imidazo[1,2-d][1,4]oxazepine-10-carboxylate (0.250 g, 0.675 mmol); in 2 ml THF. The reaction was reflux for 2 h followed by treating with additional 0.50 M of Zinc dichloride in Tetrahydrofuran 2.2 ml and refluxed 3 h. The mixture was diluted with EtOAc then washed with sat. Na2CO3, and brine. The organic layer was dried over Na$_2$SO$_4$, concentrated in vacuo. The crude product, methyl 2-(1-(2-chlorophenyl)-1H-imidazol-2-yl)-5,6-dihydrobenzo[f]imidazo[1,2-d][1,4]oxazepine-10-carboxylate, was purified by chromatography. MS: (ESI+)=421.2

Step 2: 2-(1-(2-chlorophenyl)-1H-imidazol-2-yl)-5,6-dihydrobenzo[f]imidazo[1,2-d][1,4]oxazepine-10-carboxylic acid To a solution of methyl 2-(1-(2-chlorophenyl)-1H-imidazol-2-yl)-5,6-dihydrobenzo[f]imidazo[1,2-d][1,4]oxazepine-10-carboxylate (0.100 g, 0.238 mmol) in tetrahydrofuran (5.56 mL, 68.5 mmol) and Water (5.56 mL, 308 mmol) was added Lithium hydroxide, monohydrate (0.0399 g, 0.950 mmol). The reaction mixture was stirred at rt o/n. The reaction mixture was concentrated. The reaction mixture was acidified with 1M HCl then extracted with DCM (3×). The combined organics were dried over Na2SO4, filtered and concentrated to give 2-(1-(2-chlorophenyl)-1H-imidazol-2-yl)-5,6-dihydrobenzo[f]imidazo[1,2-d][1,4]oxazepine-10-carboxylic acid. MS: (ESI+)=407.2

Example 74

10-bromo-2-(1H-imidazol-2-yl)-5,6-dihydrobenzo[f]imidazo[1,2-d][1,4]oxazepine

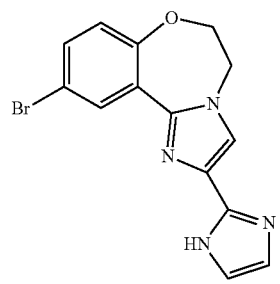 [SMILES: Brc1ccc2c(c1)-c1nc(-c3ncc[nH]3)cn1CCO2]

Step 1: 10-bromo-5,6-dihydrobenzo[f]imidazo[1,2-d][1,4]oxazepine-2-carbaldehyde

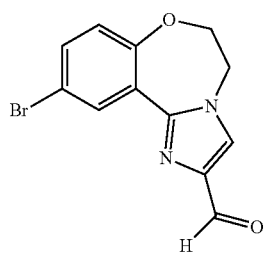 [SMILES: O=Cc1cn2c(n1)-c1cc(Br)ccc1OCC2]

10-bromo-2-iodo-5,6-dihydrobenzo[f]imidazo[1,2-d][1,4]oxazepine was formylated to give 10-bromo-5,6-dihydrobenzo[f]imidazo[1,2-d][1,4]oxazepine-2-carbaldehyde. Yield 84%. MS: 293.1

Step 2: 10-bromo-5,6-dihydrobenzo[f]imidazo[1,2-d][1,4]oxazepine-2-carbaldehyde was coupled with ethanedial in the presence of ammonia to give 10-bromo-2-(1H-imidazol-2-yl)-5,6-dihydrobenzo[f]imidazo[1,2-d][1,4]oxazepine. Yield 37%. MS: 331.0

Example 89 tert-butyl 5-(9-fluoro-5,6-dihydrobenzo[f]imidazo[1,2-d][1,4]oxazepin-2-yl)-1-isopropyl-1H-1,2,4-triazol-3-ylcarbamate

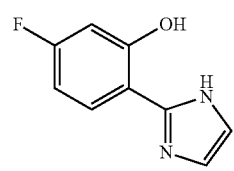 [SMILES: Oc1cc(F)ccc1-c1ncc[nH]1]

Step 1: 4-Fluoro-2-hydroxybenzaldehyde (1.918 g, 0.01369 mol), ethanedial (1.884 mL, 0.04107 mol), 14.8 M ammonium hydroxide in water (14 mL, 0.21 mol) and methanol (34 mL, 0.84 mol) were combined in a round bottom flask and the reaction mixture stirred overnight at room temperature. Complete by LCMS. Concentrated in vacuo and the crude solid was dissolved in 1 M HCl until pH was 8 with pH paper. Extracted the product with ethyl acetate, washed with brine, dried over magnesium sulfate and concentrated in vacuo again. Purified by flash chromatography in the ISCO 0% to 50% ethyl acetate in heptanes and concentrated in vacuo to give 5-fluoro-2-(1H-imidazol-2-yl)phenol (0.92 g, 37.7% yield).

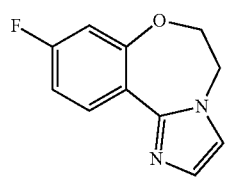 [SMILES: Fc1ccc2c(c1)OCCn1ccnc1-2]

Step 2: 5-fluoro-2-(1H-imidazole-2-yl)phenol (0.90 g, 5.0 mmol) was dissolved in N,N-Dimethylformamide (40 mL, 500 mmol). Cesium carbonate (6.6 g, 20 mmol) was added, followed by 1,2-Dibromoethane (1.7 mL, 20 mmol) and heated at 90° C. with a vigreux condensation column attached for 3 hours. Complete by LCMS. Diluted with water and extracted with ethyl acetate. Acidified the aqueous layer to pH ~5 with HCl and extracted with ethyl acetate. The combined organics were concentrated in vacuo and purified by flash chromatography on the ISCO 0-50% ethyl acetate in hexanes and concentrated in vacuo to give 9-fluoro-5,6-dihydrobenzo[f]imidazo[1,2-d][1,4]oxazepine (0.69 g, 67% yield)

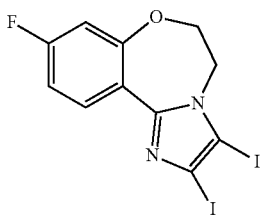 [SMILES: Fc1ccc2c(c1)OCCn1c-2nc(I)c1I]

Step 3: 9-fluoro-5,6-dihydrobenzo[f]imidazo[1,2-d][1,4] oxazepine (0.69 g, 3.4 mmol), N-Iodosuccinimide (2.83 g, 12.6 mmol), and N,N-Dimethylformamide in a round bottom flask and let stir for four days. Diluted with ethyl acetate and partitioned with Sat. Sodium bicarbonate and water (50/50). The aqueous layer was extracted once more with ethyl acetate and the combined organics were dried over magnesium sulfate and concentrated in vacuo and purified by flash chromatography on the ISCO 0-40% ethyl acetate in hexanes to give 9-fluoro-2,3-diiodo-5,6-dihydrobenzo[f]imidazo[1,2-d][1,4]oxazepine (1.25 g, 81% yield)

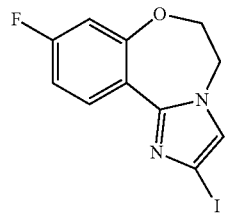 [SMILES: Fc1ccc2c(c1)OCCn1cc(I)nc1-2]

Step 4: 9-fluoro-2,3-diiodo-5,6-dihydrobenzo[f]imidazo[1,2-d][1,4]oxazepine (1.24 g, 2.74 mmol) was dissolved in tetrahydrofuran (25 mL, 310 mmol) and cooled to −78° C. in a dry ice/acetone bath. Added 3.0 Methylmagnesium bromide in ether (1.37 mL and allowed the reaction to warm up to −40° C. and stir for 4 hours. Complete by LCMS. Diluted with 100 mL of saturated ammonium chloride and extracted with ethyl acetate. Dried over magnesium sulfate, concentrated in vacuo and purified by flash chromatography on the ISCO 0-40% ethyl acetate in hexanes to give 9-fluoro-2-iodo-5,6-dihydrobenzo[f]imidazo[1,2-d][1,4]oxazepine (0.794 g, 88% yield)

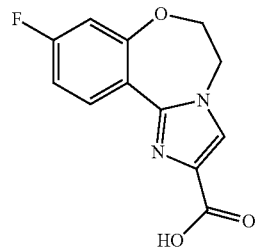 [SMILES: O=C(O)c1cn2c(n1)-c1ccc(F)cc1OCC2]

Step 5: A round bottom flask containing 9-fluoro-2-iodo-5,6-dihydrobenzo[f]imidazo[1,2-d][1,4]oxazapine (0.794 g, 2.40 mmol) was purged thoroughly with nitrogen. Palladium (II) acetate (27 mg, 0.12 mmol) and 4,5-bis(diphenylphosphino)-9,9-dimethylxanthene (139 mg, 0.24 mmol) was added sequentially with more purging. Methanol (10 mL, 200 mmol) and triethylamine (30 mL, 200 mmol) purged with nitrogen were added and the reaction mixture was purged with Carbon monoxide for 5 minutes. Two Carbon monoxide balloons were attached and the reaction mixture was heated at 50° C. for 4.5 hours. Complete formation of the methyl ester was confirmed by LCMS. Purged reaction with nitrogen and concentrated in vacuo. Purified the ester by flash chromatography on the ISCO 0 to 50% ethyl acetate in heptane and concentrated in vacuo. The ester was dissolved in tetrahydrofuran and (20 mL, 200 mmol) and 1 M Lithium hydroxide was added (7.22 mL) and the reaction was stirred for three days. Complete hydrolysis by LCMS. Adjusted to pH ~5 with 1 M HCl and extracted off the product with dichloromethane and 5% methanol to give 9-fluoro-5,6-dihydrobenzo[f]imidazo[1,2-d][1,4]oxazepine-2-carboxylic acid (0.386 g, 64.6% yield)

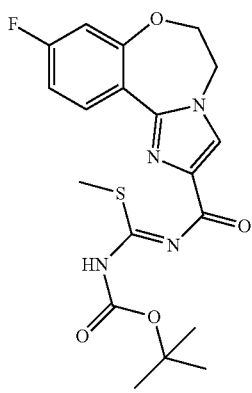 [SMILES: CS/C(=N\C(=O)c1cn2c(n1)-c1ccc(F)cc1OCC2)NC(=O)OC(C)(C)C]

Step 6: Suspended 9-fluoro-5,6-dihydrobenzo[f]imidazo[1,2-d][1,4]oxazepine-2-carboxylic acid (0.65 g, 2.6 mmol) in dichloromethane (15 mL, 230 mmol) and added 2.0 M oxalyl chloride in dichloromethane (2.0 mL) followed by N,N-Dimethylformamide (81 uL) and since the reaction still was not in solution toluene was added (15 mL, 140 mmol) and the mixture heated with a heat gun until about half was dissolved. Let stir 30 minutes and concentrated in vacuo to get the acid chloride. This was dissolved in 20 mL dichloromethane and the intermediate was added (0.50 g, 2.6 mmol) and triethylamine (1.1 mL, 7.8 mmol) in dichloromethane (50 mL, 800 mmol). The reaction mixture was stirred for 3 hours and was mostly complete by LCMS. Added water and extracted with dichloromethane 3×. Washed with brine, dried over magnesium sulfate and concentrated in vacuo and purified by flash chromatography on the ISCO 0-50% ethyl acetate in heptane to give acylthiourea intermediate (0.20 g, 18% yield).

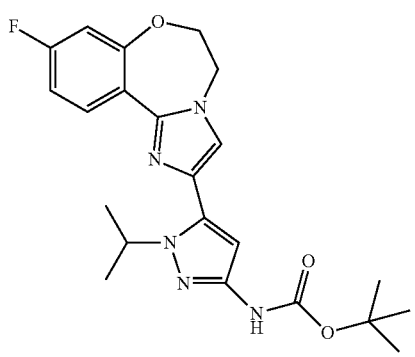 [SMILES: CC(C)n1nc(NC(=O)OC(C)(C)C)cc1-c1cn2c(n1)-c1ccc(F)cc1OCC2]

Step 7: Acylthiourea intermediate (200 mg, 0.4 mmol) was dissolved in N,N-Dimethylformamide (10 mL, 100 mmol) and N,N-Diisopropylamine (0.29 mL, 1.662 mmol) was added followed by isopropylhydrazine hydrochloride (68.92 mg, 0.62 mmol). The reaction was stirred at room temperature overnight. Complete reaction confirmed by LCMS. Diluted with water and extracted with DCM 3 times. The combined organic layers were dried over dried over magnesium sulfate and concentrated in vacuo. The product was purified by flash chromatography on the ISCO 0 to 10% methanol in dichloromethane to give tert-butyl 5-(9-fluoro-5,6-dihydrobenzo[f]imidazo[1,2-d][1,4]oxazepin-2-yl)-1-isopropyl-1H-1,2,4-triazol-3-ylcarbamate (200 mg, 100% yield)

Example 90

10-fluoro-5,6-dihydrobenzo[f]imidazo[1,2-d][1,4]oxazepine-2-carboxamide

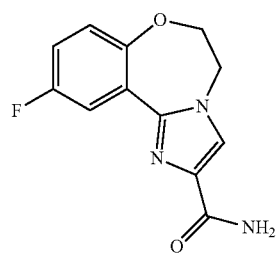 [SMILES: NC(=O)c1cn2c(n1)-c1cc(F)ccc1OCC2]

Step 1: 4-fluoro-2-(1H-imidazol-2-yl)phenol

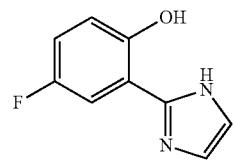 [SMILES: Oc1ccc(F)cc1-c1ncc[nH]1]

5-fluoro-2-hydroxybenzaldehyde (5.0 g, 36 mmol), ethanedial (4.912 mL, 107 mmol), 14.8 M ammonium hydroxide in water (40 mL, 600 mmol), and methanol (90 mL, 2000 mmol) were combined in a round bottom flask and let stir at room temperature overnight. Complete reaction was confirmed by LCMS. Concentrated in vacuo and added 1 M HCL until pH was ~8. Extracted with ethyl acetate, washed with brine, dried over magnesium sulfate and concentrated in vacuo. Purified by flash chromatography 0 to 50% ethyl acetate in heptane to give 4-fluoro-2-(1H-imidazol-2-yl)phenol (2.24 g, 35% yield)

Step 2

Following the procedures of Example 89, 4-fluoro-2-(1H-imidazol-2-yl)phenol was converted to 10-fluoro-5,6-dihydrobenzo[f]imidazo[1,2-d][1,4]oxazepine-2-carboxamide.

Example 91

2-Bromo-1-(2-isopropyl-5-methyl-2H-[1,2,4]triazol-3-yl)-ethanone

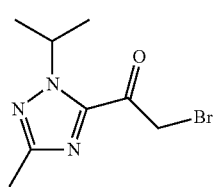

Step 1: Acetic acid hydrazide (100 g, 1.35 mol) was suspended in acetone (991 mL, 13.5 mol) and cyclohexane (1.5 L). The reaction mixture was heated at 55° C. for 16 h, during which the solids dissolved to give a colorless solution. The reaction mixture was concentrated in vacuo to give Acetic acid isopropylidenehydrazide as a white solid (153 g, 100%). $^1$H NMR 400 MHz (CDCl$_3$) δ: 8.25 (1H, br s), 2.26 (3H, s), 2.00 (3H, s), 1.83 (3H, s)

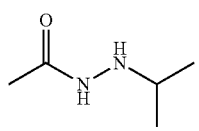

Step 2: To a solution of acetic acid isopropylidenehydrazide (153 g, 1.35 mol) in IMS (1.5 L) was added platinum oxide (0.66 g) and the reaction mixture stirred under an atmosphere of hydrogen at RT until $^1$H NMR showed complete consumption of acetic acid isopropylidenehydrazide (~48 h). The reaction mixture was filtered through a plug of Celite® and the filtrate concentrated in vacuo to give Acetic acid N'-isopropylhydrazide as a colorless oil which crystallised on standing (154.6 g). $^1$H NMR 400 MHz (CDCl$_3$) δ: 3.12 (1H, sept, J=6.3 Hz), 1.96 (3H, s), 1.04 (6H, d, J=6.3 Hz)

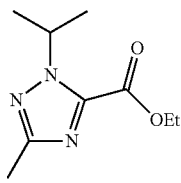

Step 3: To a solution of ethyl thiooxamate (29.6 g, 0.22 mol) in DCM (260 mL) at RT was added trimethyloxonium tetrafluoroborate (34.5 g, 0.23 mol) and the mixture stirred at RT for 2 h. During this time the yellow colour faded and a thick white precipitate was formed. Acetic acid N'-isopropylhydrazide (27.1 g, 0.23 mol) and TEA (30.9 mL, 0.22 mol) were added as a solution in DCM (75 mL) causing the precipitate to dissolve. The reaction mixture was stirred at reflux for 5 h then at RT for 10 h. The reaction mixture was washed with water, and the aqueous layer extracted with DCM (2×50 mL). The combined organic extracts were washed with brine, dried (MgSO$_4$) and concentrated in vacuo. The resultant residue was subjected to flash chromatography (SiO$_2$, gradient 0-100% ethyl acetate in cyclohexane) to give 2-Isopropyl-5-methyl-2H-[1,2,4]triazole-3-carboxylic acid ethyl ester as a pale yellow oil which crystallised on standing (15.6 g, 32%). $^1$H NMR 400 MHz (CDCl$_3$) δ: 5.49 (1H, sept, J=6.7 Hz), 4.45 (2H, t, J=7.2 Hz), 2.43 (3H, s), 1.50 (6H, d, J=6.7 Hz), 1.44 (3H, t, J=7.2 Hz)

Step 4: To a solution of 2-isopropyl-5-methyl-2H-[1,2,4]triazole-3-carboxylic acid ethyl ester (12.09 g, 61.3 mmol) and dibromomethane (8.63 mL, 122.6 mmol) in THF (500 mL) at −78° C. was added methyllithium (40.9 mL, 122.6 mmol, 3M solution in diethoxymethane) dropwise. The reaction mixture was stirred at −78° C. for 15 min. Acetic acid (3 mL) was added and the reaction mixture allowed to warm to RT. The reaction mixture was diluted with water and extracted with ethyl acetate (3×30 mL). The combined organic extracts were washed with brine, dried (MgSO$_4$) and concentrated in vacuo. The resultant residue was subjected to flash chromatography (SiO$_2$, gradient 0-100% ethyl acetate in cyclohexane) to give 2-Bromo-1-(2-isopropyl-5-methyl-2H-[1,2,4]triazol-3-yl)-ethanone as a colorless oil which crystallised on standing (11.26 g, 75%). $^1$H NMR 400 MHz (CDCl$_3$) δ: 5.41 (1H, sept, J=6.6 Hz), 4.67 (2H, s), 2.44 (3H, s), 1.49 (6H, d, J=6.6 Hz)

Example 92

2-(2-Isopropyl-5-methyl-2H-[1,2,4]triazol-3-yl)-4,5-dihydro-6-oxa-1,3a,9-triaza-benzo[e]azulen-8-ol

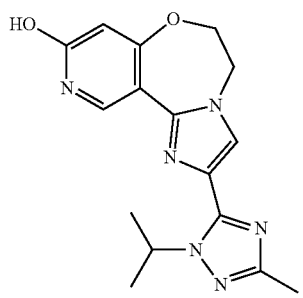 [SMILES: Cc1nc(-c2cn3c(n2)-c2cnc(O)cc2OCC3)n(C(C)C)n1]

Step 1: 4-Chloro-5-iodo-pyridin-2-ylamine

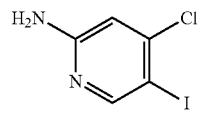

To a solution of 2-amino-4-chloropyridine (150 g, 0.78 mol) in DMF (1.5 L) was added NIS (341 g, 1.52 mol) and the reaction mixture stirred at RT for 18 h before being concentrated in vacuo to 300 mL volume. The resultant residue was poured into 10% aqueous sodium thiosulfate solution (1.2 L), stirred for 15 min and the precipitate formed collected by filtration, washed with water then dried at 35° C. in vacuo to give the title compound as a pale brown solid (185 g, 62%). $^1$H NMR 400 MHz (CDCl$_3$) δ: 8.33 (1H, s), 6.68 (1H, s), 4.52 (2H, s).

Step 2: 4-Chloro-5-iodo-2-methoxy-pyridine

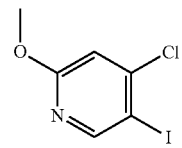

To a solution of 4-chloro-5-iodo-pyridin-2-ylamine (64.2 g, 0.25 mol) in methanol (1.1 L) and TFA (93.7 mL, 1.26 mol)

was added tert-butyl nitrite (150 mL, 1.26 mol) so as to maintain temperature less than 3° C. The resultant mixture was stirred at RT for 1 h then allowed to warm to RT and stirred for 16 h. The reaction was quenched by the careful addition of water then concentrated in vacuo to one-fourth of the volume. The resultant residue was treated with water (1 L) and the precipitate formed collected by filtration and dried in vacuo at 35° C. to give the title compound (62.3 g, 92%). Contains 16% impurity. $^1$H NMR 400 MHz (DMSO-$d_6$) δ: 8.56 (1H, s), 7.20 (1H, s), 3.86 (3H, s).

Step 3: 4-Chloro-6-methoxy-nicotinonitrile

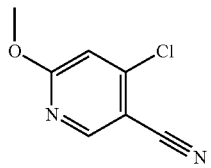

A suspension of 4-chloro-5-iodo-2-methoxy-pyridine (30.5 g, 0.11 mol), zinc (II) cyanide (7.97 g, 68 mmol), Pd(PPh$_3$)$_4$ (6.56 g, 5.66 mmol) and DMF (450 mL) was degassed and then heated at 120° C. for 1 h before being concentrated in vacuo. The resultant residue was treated with water then extracted with DCM, the organic extract dried (MgSO$_4$), filtered, then concentrated in vacuo. The resultant residue was crystallized from DCM to give the title compound (10.1 g, 54%). The mother liquors were concentrated in vacuo and the residue subjected to flash chromatography (SiO$_2$ gradient 0 to 100% ethyl acetate in cyclohexane) then crystallization from cyclohexane to give the further title compound (5.16 g, 28%, 82% total). $^1$H NMR 400 MHz (CDCl$_3$) δ: 8.45 (1H, s), 6.90 (1H, s), 4.01 (3H, s).

Step 4: 4-Chloro-6-methoxy-nicotinamidine hydrochloride

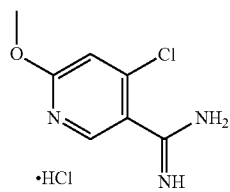

To a solution of 4-chloro-6-methoxy-nicotinonitrile (10.1 g, 59.7 mmol) in THF (300 mL) at −78° C. was added LiH-MDS (65.7 mL) dropwise and the reaction mixture stirred for 30 min before allowing to warm to RT and stirring for a further 1 h. The reaction was quenched by the addition of 1N HCl (to pH ~1) and then extracted three times with ethyl acetate. The aqueous layer was concentrated in vacuo to give brown solid which was azeotroped with toluene to give the title compound as a tan solid. Mixture with ammonium chloride, 72% title compound by weight. (15.2 g, 83%). $^1$H NMR 400 MHz (DMSO-$d_6$) δ: 9.68 (4H, d, J=15.79 Hz), 8.46 (1H, s), 7.47 (5H, t, J=50.66 Hz), 7.27 (1H, s), 3.95 (3H, s).

Step 5: 4-Chloro-5-[4-(2-isopropyl-5-methyl-2H-[1,2,4]triazol-3-yl)-1H-imidazol-2-yl]-2-methoxy-pyridine

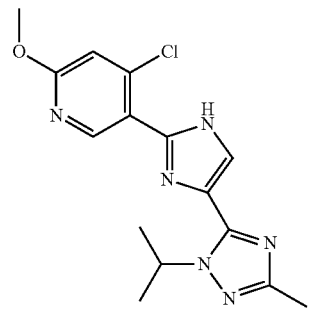 [SMILES: COc1cc(Cl)c(-c2nc(-c3nc(C)nn3C(C)C)c[nH]2)cn1]

A suspension of 4-chloro-6-methoxy-nicotinamidine hydrochloride (18.4 mmol) and potassium bicarbonate (7.37 g, 73.6 mmol) in THF (42 mL) and water (8.5 mL) was heated to reflux and treated with a solution of 2-bromo-1-(2-isopropyl-5-methyl-2H-[1,2,4]triazol-3-yl)-ethanone (4.53 g, 18.4 mmol) in THF (14 mL) added dropwise. The reaction mixture was heated at reflux for 18 h before removal of volatile solvent in vacuo. The resultant suspension was filtered and the residue washed with water then dried to give the title compound as a brown solid (5.91 g, 97%). LCMS: $R_T$=2.68 min, [M+H]$^+$ =333/335. $^1$H NMR 400 MHz (CDCl$_3$) δ: 10.41 (1H, s), 9.02 (1H, s), 7.81 (1H, s), 6.87 (1H, s), 5.91 (1H, m), 4.00 (3H, s), 2.41 (3H, s), 1.55 (6H, d, J=6.71 Hz).

Step 6: 2-[2-(4-Chloro-6-methoxy-pyridin-3-yl)-4-(2-isopropyl-5-methyl-2H-[1,2,4]triazol-3-yl)-imidazol-1-yl]-ethanol

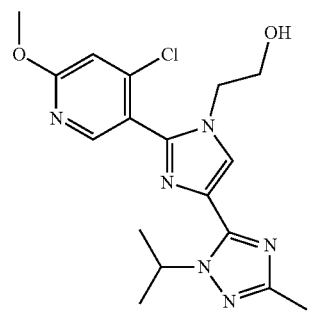 [SMILES: COc1cc(Cl)c(-c2nc(-c3nc(C)nn3C(C)C)cn2CCO)cn1]

A suspension of 4-chloro-5-[4-(2-isopropyl-5-methyl-2H-[1,2,4]triazol-3-yl)-1H-imidazol-2-yl]-2-methoxy-pyridine (5.9 g, 17.7 mmol) in toluene (20 mL) was treated with ethylene carbonate (50 mL) and heated at 130° C. for 2.5 h. The cooled reaction mixture was concentrated in vacuo then diluted with DCM and passed through a pad of silica eluting with DCM then 20% methanol in DCM. Methanolic fractions were combined and concentrated in vacuo and the resultant residue subjected to recrystallisation from acetonitrile to give the title compound as a pale tan solid (2.27 g, 34%). LCMS: $R_T$=2.53 min [M+H]$^+$ =377/379. $^1$H NMR 400 MHz (CDCl$_3$) δ: 8.25 (1H, s), 8.05 (1H, s), 6.92 (1H, s), 5.82-5.80 (1H, m), 4.00 (3H, s), 3.97 (2H, t, J=4.92 Hz), 3.88 (2H, t, J=4.92 Hz), 2.38 (3H, s), 1.48 (6H, d, J=6.63 Hz).

Step 7: 2-(2-Isopropyl-5-methyl-2H-[1,2,4]triazol-3-yl)-8-methoxy-4,5-dihydro-6-oxa-1,3a,9-triaza-benzo[e]azulene

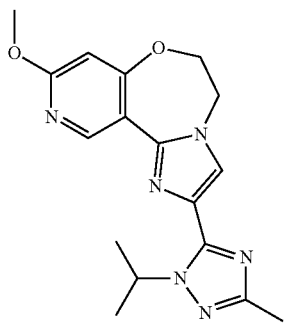 [SMILES: COc1cc2c(cn1)-c1nc(-c3nc(C)nn3C(C)C)cn1CCO2]

A solution of 2-[2-(4-chloro-6-methoxy-pyridin-3-yl)-4-(2-isopropyl-5-methyl-2H-[1,2,4]triazol-3-yl)-imidazol-1-yl]-ethanol (2.25 g, 5.97 mmol) in DMF (30 mL) was cooled to 0° C. and treated with sodium hydride (239 mg, 5.97 mmol), the reaction mixture stirred at 0° C. for 30 min then allowed to warm to RT and stirred for 2 h. The reaction mixture was re-cooled to 0° C. and treated with water (400 mL), the precipitated product filtered off and washed with water then dried in vacuo to give the title compound as a white solid (1.02 g, 50%). LCMS $R_T$=2.68 min, [M+H]$^+$ =341. $^1$H NMR 400 MHz (DMSO-d$_6$) δ: 9.15 (1H, s), 7.87 (1H, s), 6.42 (1H, s), 5.84 (1H, m), 4.57-4.56 (4H, m), 3.89 (3H, s), 2.25 (3H, s), 1.46 (6H, d, J=6.60 Hz).

Step 8

A solution of 2-(2-isopropyl-5-methyl-2H-[1,2,4]triazol-3-yl)-8-methoxy-4,5-dihydro-6-oxa-1,3a,9-triaza-benzo[e]azulene (1.0 g, 2.97 mmol) in 48% aqueous HBr (5 mL) and acetic acid (5 mL) was heated at 80° C. for 7.5 h before being concentrated in vacuo. The resultant residue was suspended in water (10 mL) and pH adjusted to about 6 using 5N aqueous NaOH. The precipitate formed was filtered off, washed with water then dried in vacuo to give 2-(2-Isopropyl-5-methyl-2H-[1,2,4]triazol-3-yl)-4,5-dihydro-6-oxa-1,3a,9-triaza-benzo[e]azulen-8-ol as a white solid (1.01 g, 100%). LCMS $R_T$=2.01 min, [M+H]$^+$ =327. $^1$H NMR 400 MHz (DMSO-d$_6$) δ: 8.42 (1H, s), 7.85 (1H, s), 5.85 (1H, s), 5.69-5.65 (1H, m), 4.55-4.54 (2H, m), 4.50-4.46 (2H, m), 2.27 (3H, s), 1.44 (6H, d, J=6.59 Hz).

Example 93

2-(2-Isopropyl-2H-[1,2,4]triazol-3-yl)-4,5-dihydro-6-oxa-1,3a,9-triaza-benzo[e]azulen-8-ol

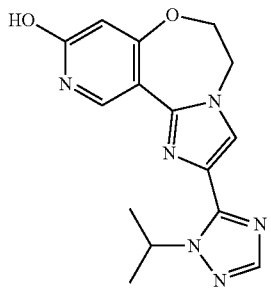 [SMILES: CC(C)n1ncnc1-c1cn2c(n1)-c1cnc(O)cc1OCC2]

Step 1: 4-Chloro-5-[4-(2-isopropyl-2H-[1,2,4]triazol-3-yl)-1H-imidazol-2-yl]-2-methoxy-pyridine

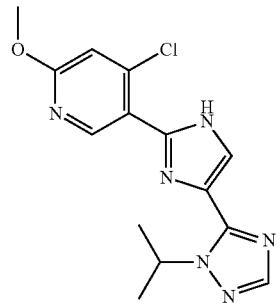 [SMILES: COc1cc(Cl)c(-c2nc(-c3ncnn3C(C)C)c[nH]2)cn1]

A suspension of 4-chloro-6-methoxy-nicotinamidine hydrochloride (50.9 mmol) and potassium bicarbonate (20.4 g, 202.5 mmol) in THF (128 mL) and water (21 mL) was heated to reflux and treated with a solution of 2-chloro-1-(2-isopropyl-2H-[1,2,4]triazol-3-yl)-ethanone (9.55 g, 50.9 mmol) in THF (25 mL) added dropwise. The reaction mixture was heated at reflux for 24 h before removal of volatile solvent in vacuo. The resultant residue was diluted with water and extracted with ethyl acetate. The combined extracts were dried (Na2SO4), treated with charcoal (15 g), filtered and concentrated in vacuo to give a solid. The solid was triturated with 10% diethyl ether in pentane then dried at 50° C. in vacuo to give 4-Chloro-5-[4-(2-isopropyl-2H-[1,2,4]triazol-3-yl)-1H-imidazol-2-yl]-2-methoxy-pyridine as a pale brown solid (8.74 g, 54%). LCMS RT=2.86 min, [M+H]$^+$ =319/321. 1H NMR 400 MHz (CDCl$_3$) δ: 9.03 (1H, s), 7.89 (1H, s), 7.83 (1H, s), 7.26 (1H, s) 6.88 (1H, s), 4.01 (3H, s), 1.58 (6H, d, J=6.63 Hz).

Step 2: 2-[2-(4-Chloro-6-methoxy-pyridin-3-yl)-4-(2-isopropyl-2H-[1,2,4]triazol-3-yl)-imidazol-1-yl]-ethanol

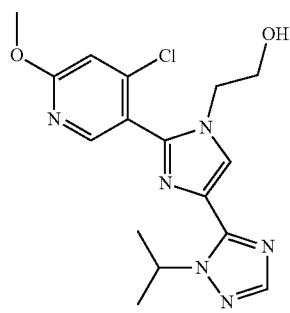 [SMILES: COc1cc(Cl)c(-c2nc(-c3ncnn3C(C)C)cn2CCO)cn1]

To warmed ethylene carbonate (34 g) was added 4-chloro-5-[4-(2-isopropyl-2H-[1,2,4]triazol-3-yl)-1H-imidazol-2-yl]-2-methoxy-pyridine (8.74 g, 27.4 mmol) and the mixture heated at 130° C. for 3 h. The cooled reaction mixture was diluted with DCM and loaded onto silica (150 g). The silica was washed with DCM then 5% methanol in DCM. Methanolic fractions were combined and concentrated in vacuo to give the title compound as a brown foam (7.52 g, 75%).

LCMS RT=2.65, [M+H]+=363/365. $^1$H NMR 400 MHz (CDCl3) δ: 8.27 (1H, s), 8.02 (1H, s), 7.85 (1H, s), 6.93 (1H, s), 5.98-5.82 (1H, m), 4.00 (5H, m), 3.88 (2H, t, J=5.11 Hz), 1.51 (6H, d, J=6.62 Hz).

Step 3: 2-(2-Isopropyl-2H-[1,2,4]triazol-3-yl)-8-methoxy-4,5-dihydro-6-oxa-1,3a,9-triaza-benzo[e]azulene

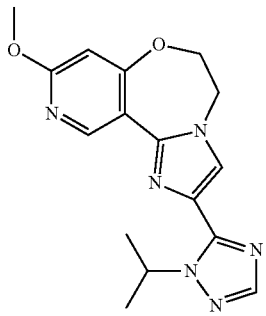 [SMILES: COc1cc2c(cn1)-c1nc(-c3ncnn3C(C)C)cn1CCO2]

A solution of 2-[2-(4-chloro-6-methoxy-pyridin-3-yl)-4-(2-isopropyl-2H-[1,2,4]triazol-3-yl)-imidazol-1-yl]-ethanol (7.52 g, 20.7 mmol) in DMF (100 mL) was cooled to 0° C. and treated with sodium hydride (804 mg, 20.1 mmol), the reaction mixture stirred at 0° C. for 10 min then allowed to warm to RT and stirred for 72 h. Further sodium hydride (150 mg) was added and stirring continued until no starting material remained before removal of solvent in vacuo. The residue was dissolved in ethyl acetate and the resultant solution washed three times with saturated brine then dried (Na2SO4), filtered and concentrated in vacuo. The resultant residue was triturated in pentane/diethyl ether (5:1) to give the title compound as a brown solid (5.38 g, 79%). LCMS RT=2.86, [M+H]$^+$=327. $^1$H NMR 400 MHz (CDCl$_3$) δ: 9.35 (1H, s), 7.87 (1H, s), 7.63 (1H, s), 6.37 (1H, s), 6.03-6.02 (1H, m), 4.54-4.53 (2H, m), 4.53-4.33 (2H, m), 3.99 (3H, s), 1.57 (6H, d, J=6.63 Hz).

Step 4

A solution of 2-(2-isopropyl-2H-[1,2,4]triazol-3-yl)-8-methoxy-4,5-dihydro-6-oxa-1,3a,9-triaza-benzo[e]azulene (1.0 g, 2.97 mmol) in acetic acid (40 mL) was treated with 48% aqueous HBr (37.7 mL) and heated at 80° C. for 5 h before being concentrated in vacuo. The resultant residue was suspended in water (60 mL) and pH adjusted to 6 using 5N aqueous NaOH. The precipitate formed was filtered off, washed with water then dried in vacuo. The resultant solid was triturated in acetone to give 2-(2-Isopropyl-2H-[1,2,4]triazol-3-yl)-4,5-dihydro-6-oxa-1,3a,9-triaza-benzo[e]azulen-8-ol as a beige solid (3.58 g, 69%). LCMS RT=2.04 min, [M+H]$^+$=313. $^1$H NMR 400 MHz (DMSO-d$_6$) δ: 8.42 (1H, s), 7.90 (1H, s), 7.83 (1H, s), 5.84 (1H, s), 5.78 (1H, m), 4.71-4.30 (4H, m), 1.45 (6H, d, J=6.60 Hz).

Example 94

2-(2-Isopropyl-2H-[1,2,4]triazol-3-yl)-8-piperidin-4-yl-4,5-dihydro-6-oxa-1,3a,9-triaza-benzo[e]azulene hydrochloride

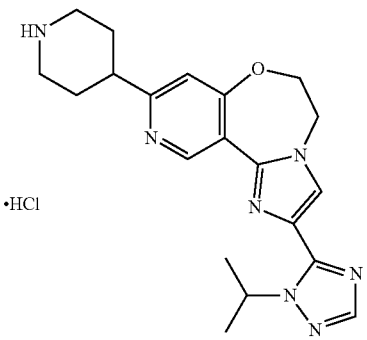 [SMILES: Cl ; CC(C)n1ncnc1-c1cn2c(n1)-c1cnc(C3CCNCC3)cc1OCC2]

Step 1: Trifluoro-methanesulfonic acid 2-(2-isopropyl-2H-[1,2,4]triazol-3-yl)-4,5-dihydro-6-oxa-1,3a,9-triaza-benzo[e]azulen-8-yl ester

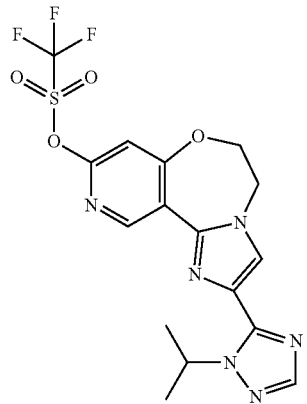 [SMILES: CC(C)n1ncnc1-c1cn2c(n1)-c1cnc(OS(=O)(=O)C(F)(F)F)cc1OCC2]

A suspension of 2-(2-isopropyl-2H-[1,2,4]triazol-3-yl)-4,5-dihydro-6-oxa-1,3a,9-triaza-benzo[e]azulen-8-ol (238 mg, 0.76 mmol) in DMF (2.2 mL) was treated with sodium hydride (65% dispersion in mineral oil, 34 mg, 0.91 mmol), the reaction mixture heated at 40° C. for 1.5 h then cooled to RT. Benzenebis(trifluoromethane) sulfonamide (327 mg, 0.91 mmol) was added and the reaction mixture stirred at RT for 24 h before being diluted with ethyl acetate (60 mL) and washed with brine (4×20 mL). The resultant solution was dried (MgSO$_4$), filtered and concentrated in vacuo to give a solid which was triturated in diethyl ether to give Trifluoro-methanesulfonic acid 2-(2-isopropyl-2H-[1,2,4]triazol-3-yl)-4,5-dihydro-6-oxa-1,3a,9-triaza-benzo[e]azulen-8-yl ester as a white solid (44 mg). The mother liquors from trituration were concentrated in vacuo, the resultant residue recrystallised from methanol to give further compound (39 mg, 25% total). LCMS R$_T$=3.27 min, [M+H]$^+$=445. $^1$H NMR 400 MHz (DMSO-d6) δ: 9.32 (1H, s), 8.04 (1H, s), 7.93 (1H, s), 7.36 (1H, s), 5.89 (1H, m), 4.74 (2H, m), 4.63 (2H, m), 1.48 (6H, d, J=6.58 Hz)

Step 2

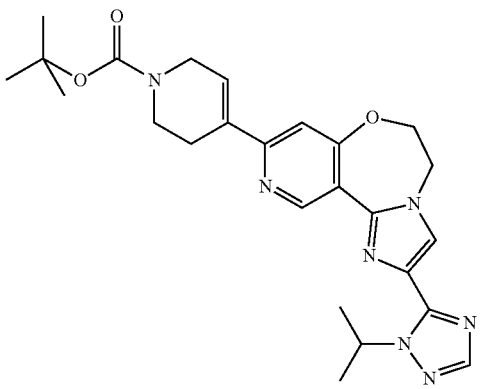 [SMILES: CC(C)n1ncnc1-c1cn2c(n1)-c1cnc(C3=CCN(C(=O)OC(C)(C)C)CC3)cc1OCC2]

To a mixture of trifluoro-methanesulfonic acid 2-(2-isopropyl-2H-[1,2,4]triazol-3-yl)-4,5-dihydro-6-oxa-1,3a,9-triaza-benzo[e]azulen-8-yl ester (83 mg, 0.19 mmol) and 2N aqueous sodium carbonate (600 uL) in DMF (1.2 mL) was added palladium bis(dibenzylideneacetone) (6 mg, 0.01 mmol), triphenylphosphine (4 mg, 0.015 mmol) and 4-(4,4,5,5-tetramethyl-[1,3,2]dioxaborolan-2-yl)-3,6-dihydro-2H-pyridine-1-carboxylic acid tert-butyl ester (75 mg, 0.24 mmol). The reaction mixture was degassed and then heated at 90° C. under an atmosphere of argon for 2 h before being concentrated in vacuo. The resultant residue was partitioned between ethyl acetate and water, the aqueous extracted with ethyl acetate (×3) and the combined organic extracts dried (MgSO$_4$), filtered and concentrated in vacuo. The resultant residue was subjected to flash chromatography (SiO$_2$, gradient 0 to 10% methanol in ethyl acetate) to give 4-[2-(2-Isopropyl-2H-[1,2,4]triazol-3-yl)-4,5-dihydro-6-oxa-1,3a,9-triaza-benzo[e]azulen-8-yl]-3,6-dihydro-2H-pyridine-1-carboxylic acid tert-butyl ester as a white solid (41 mg, 45%). LCMS (*) R$_T$=3.24 min, [M+H]$^+$ =478. $^1$H NMR 400 MHz (CDCl$_3$) δ: 9.65 (1H, s), 7.94 (1H, s), 7.89 (1H, s), 7.00 (1H, s), 6.84 (1H, s), 4.60 (2H, s), 4.50 (2H, s), 4.18 (2H, s), 3.67 (2H, s), 2.62 (2H, s), 1.59 (6H, d, J=6.62 Hz), 1.50 (9H, s)

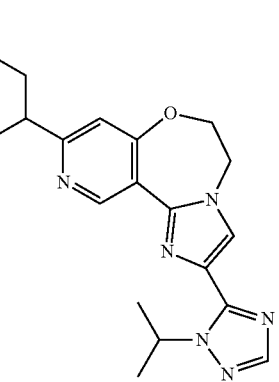

Step 3

A mixture of 4-[2-(2-isopropyl-2H-[1,2,4]triazol-3-yl)-4,5-dihydro-6-oxa-1,3a,9-triaza-benzo[e]azulen-8-yl]-3,6-dihydro-2H-pyridine-1-carboxylic acid tert-butyl ester (89 mg, 0.19 mmol) in IMS (10 mL) was treated with platinum oxide (10 mg), the reaction mixture degassed and stirred at RT under an atmosphere of hydrogen for 72 h. Further platinum oxide (10 mg) was added and stirring continued at RT for 18 h before the filtering through Celite® and concentrating in vacuo. The resultant residue was subjected to flash chromatography (SiO$_2$, gradient 0 to 5% methanol in DCM) to give 4-[2-(2-Isopropyl-2H-[1,2,4]triazol-3-yl)-4,5-dihydro-6-oxa-1,3a,9-triaza-benzo[e]azulen-8-yl]-piperidine-1-carboxylic acid tert-butyl ester (58 g, 64%). LCMS R$_T$=2.72, [M+H]$^+$ =480

Step 4: A solution of 4-[2-(2-isopropyl-2H-[1,2,4]triazol-3-yl)-4,5-dihydro-6-oxa-1,3a,9-triaza-benzo[e]azulen-8-yl]-piperidine-1-carboxylic acid tert-butyl ester (58 mg, 0.12 mmol) in DCM (0.5 mL) and methanol (0.3 mL) was treated with 4M HCl in dioxane (0.8 mL) and the reaction mixture stirred at RT for 1.5 h before being concentrated in vacuo. The resultant residue was triturated with diethyl ether to give 2-(2-Isopropyl-2H-[1,2,4]triazol-3-yl)-8-piperidin-4-yl-4,5-dihydro-6-oxa-1,3a,9-triaza-benzo[e]azulene hydrochloride (66 mg, 100%). LCMS R$_T$=1.68 min, [M+H]$^+$ =380

Example 95

9-bromo-2-(1-isopropyl-1H-1,2,4-triazol-5-yl)-5,6-dihydrobenzo[f]imidazo[1,2-d][1,4]oxazepine 95

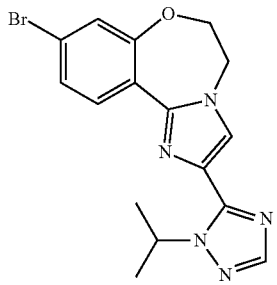

9-Bromo-5,6-dihydrobenzo[f]imidazo[1,2-d][1,4]oxazepine-2-carboxamide (4.93 g, 16.0 mmol) was taken up in 1,1-dimethoxy-N,N-dimethylmethanamine (25 mL, 0.18 mol) and 1,2-dimethoxyethane (66.5 mL, 0.640 mol). The heterogeneous mixture was stirred very vigorously and heated at 65° C. for 1 h. LC/MS showed complete consumption of starting material at the end of this period. The reaction mixture was concentrated in vacuo and carried on to the subsequent reaction with no further purification steps applied. The crude product from the previous reaction (5.8 g, 16.0 mmol) was suspended in glacial acetic acid (53.2 mL) and isopropylhydrazine hydrochloride (4.36 g, 39.4 mmol) was added. The mixture was heated at 100° C. for 2 h. The reaction vessel was cooled to room temp and the solvent was removed in vacuo. The resultant residue was dry loaded onto silica gel and purified by ISCO chromatography (120 g column, 100% EtOAc). In total, 2.3 g (39% yield) of 95 was isolated over the two steps. LC/MS (ESI+): m/z 376 (M+H, with halide isotope). $^1$H NMR (400 MHz, DMSO) δ 8.34 (d, J=8.6, 1H), 7.95 (s, 1H), 7.91 (s, 1H), 7.36 (dd, J=8.7, 2.0, 1H), 7.30 (d, J=2.0, 1H), 5.85 (dt, J=13.3, 6.6, 1H), 4.55 (d, J=15.5, 4H), 1.48 (d, J=6.6, 6H)

Alternatively, to a suspension of 8-bromo-4,5-dihydro-6-oxa-1,3a-diaza-benzo[e]azulene-2-carboxylic acid 1-dimethylamino-meth-(Z)-ylideneamide (8.52 g, 23.5 mmol) in acetic acid (50 mL) was added isopropylhydrazine hydrochloride (3.37 g, 30.5 mmol) and the reaction mixture heated at 100° C. for 1 h. The reaction mixture was allowed to cool to RT and was poured onto water (500 mL) causing the product to precipitate as an off-white solid. The product was collected by filtration, washed with water (~200 mL) and dried in vacuo at 45° C. for 16 h to yield 95 as an off-white solid (7.88 g, 86%). $^1$H NMR (400 MHz, d$_6$-DMSO) 8.43 (1H, d, J=8.6 Hz), 7.97 (1H, s), 7.92 (1H, d, J=0.6 Hz), 7.36 (1H, dd, J=8.6, 2.0 Hz), 7.30 (1H, d, J=2.0 Hz), 5.86 (1H, sept, J=6.6 Hz), 4.56-4.52 (4H, m), 1.48 (6H, d, J=6.6 Hz). LCMS: R$_T$=4.69 min, M+H$^+$ =374/376. $^1$H NMR showed product to contain ~5% 8-iodo-2-(2-isopropyl-2H-[1,2,4]triazol-3-yl)-4,5-dihydro-6-oxa-1,3a-diaza-benzo[e]azulene.

Also alternatively:

Step 1: 4-Bromo-2-fluoro-benzimidic acid ethyl ester hydrochloride

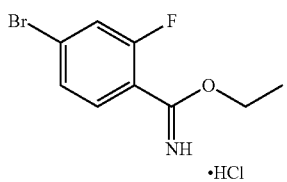

A suspension of 4-bromo-2-fluorobenzonitrile (25.0 g, 125 mmol) in IMS (88 mL) at 0-5° C. and treated dropwise with acetyl chloride (71 mL, 1 mol) maintaining the temperature below 10° C. The reaction vessel was sealed and the mixture stirred at RT for 18 h before concentrating in vacuo. The resultant residue was triturated in diethyl ether to give 4-Bromo-2-fluoro-benzimidic acid ethyl ester hydrochloride as a white solid (20.3 g, 57%). $^1$H NMR δ (ppm, DMSO-d6): 7.93-7.88 (1H, m), 7.85-7.76 (1H, m), 7.72-7.64 (1H, m), 4.60 (2H, q, J=7.02 Hz), 1.47-1.38 (3H, m).

Step 2: 4-Bromo-2-fluoro-benzamidine hydrochloride

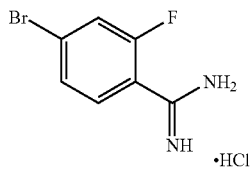 [SMILES: N=C(N)c1ccc(Br)cc1F ; Cl]

A mixture of 4-bromo-2-fluoro-benzimidic acid ethyl ester hydrochloride (20.3 g, 72 mmol) in IMS (250 mL) at 0-5° C. was saturated with NH$_3$ (gas), and the flask sealed before allowing to warm to RT and stirring for 18 h. Solvent was removed in vacuo and the residue triturated in diethyl ether to give 4-Bromo-2-fluoro-benzamidine hydrochloride as a white solid (18.1 g, 100%). $^1$H NMR δ (ppm) (DMSO-d$_6$): 9.26 (4H, s), 7.92-7.87 (1H, m), 7.71-7.62 (2H, m).

Step 3:
1-(2-Isopropyl-2H-[1,2,4]triazol-3-yl)-ethanone

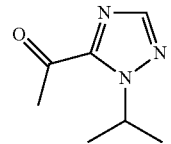

To a solution of 1-isopropyl-1H-[1,2,4]triazole (33 g, 300 mmol) in THF at −10° C. was added n-butyllithium (145 mL, 2.5M, 360 mmol) dropwise over 45 min, and then the mixture stirred at 0° C. for 30 min. DMA (35 mL) was added, the mixture allowed to warm to RT and stirred for 1 h. The resultant suspension was treated with saturated aqueous ammonium chloride (300 mL). The aqueous phase was extracted with ethyl acetate and the combined organic extracts dried (Na$_2$SO$_4$), filtered and concentrated in vacuo to give 1-(2-Isopropyl-2H-[1,2,4]triazol-3-yl)-ethanone as a pale orange oil (40.1 g, 87%). $^1$H NMR δ (ppm) (CDCl$_3$): 7.93 (1H, s), 5.58-5.46 (1H, m), 2.72 (3H, d, J=0.78 Hz), 1.49 (6H, dd, J=6.61, 0.78 Hz).

Step 4: 2-Bromo-1-(2-isopropyl-2H-[1,2,4]triazol-3-yl)-ethanone

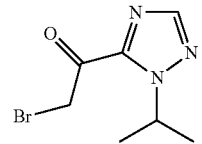

To a solution of 1-(2-isopropyl-2H-[1,2,4]triazol-3-yl)-ethanone (10 g, 65.3 mmol) in acetic acid (1 mL) and THF (100 mL) was added a solution of PTT (phenyltrimethylammonium tribromide, 24.5 g, 65.3 mmol) in THF (100 mL) over 20 min. The reaction mixture was heated at 75° C. before cooling to RT. The resultant mixture was concentrated in vacuo and the products partitioned between ethyl acetate and saturated aqueous sodium bicarbonate solution. The organic layer was separated, dried (Na$_2$SO$_4$), filtered and concentrated in vacuo to give a residue which was subjected to flash chromatography (SiO$_2$, gradient 0 to 20% ethyl acetate in cyclohexane) to give 2-Bromo-1-(2-isopropyl-2H-[1,2,4]triazol-3-yl)-ethanone as an oil (5.4 g, 36%). $^1$H NMR δ (ppm) (CDCl$_3$): 7.98 (1H, s), 5.53-5.42 (1H, m), 4.69 (2H, s), 1.52 (6H, d, J=6.63 Hz).

Step 5: 5-[2-(4-Bromo-2-fluoro-phenyl)-1H-imidazol-4-yl]-1-isopropyl-1H-[1,2,4]triazole

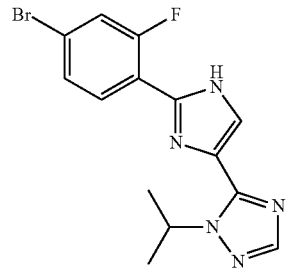 [SMILES: CC(C)n1ncnc1-c1c[nH]c(-c2ccc(Br)cc2F)n1]

To a rapidly stirred mixture of 4-bromo-2-fluoro-benzamidine hydrochloride (9.84 g, 38.8 mmol), potassium hydrogen carbonate (15.6 g, 154.8 mmol), THF (98 mL) and water (16 mL) at reflux was added a solution of 2-bromo-1-(2-isopropyl-2H-[1,2,4]triazol-3-yl)-ethanone (9.0 g, 38.8 mmol) in THF (19 mL) over 15 min. The resulting mixture was stirred for 18 h at reflux before concentrating in vacuo. The resultant residue was treated with water and the solid formed collected by filtration, washed (water, then 1:1 diethyl ether: cyclohexane then diethyl ether) to give 5-[2-(4-Bromo-2-fluoro-phenyl)-1H-imidazol-4-yl]-1-isopropyl-1H-[1,2,4]triazole as a brown solid (10.1 g, 74%). $^1$H NMR δ (ppm) (CDCl$_3$): 8.21-8.14 (1H, m), 7.90 (1H, s), 7.80 (1H, s), 7.47-7.38 (2H, m), 7.26 (1H, s), 5.91 (1H, br, s), 1.59 (6H, d, J=6.63 Hz).

A solution of 5-[2-(4-bromo-2-fluoro-phenyl)-1H-imidazol-4-yl]-1-isopropyl-1H-[1,2,4]triazole (10.0 g, 28.6 mmol) in DMF (100 mL) was treated with ethylene carbonate (5.3 g, 60.1 mmol) and cesium carbonate (13.9 g, 42.5 mmol) and then heated at 100° C. for 72 h. Further cesium carbonate (9.0 g, 27.5 mmol) and water (0.5 mL) were added and heating continued for 24 h before concentrating the reaction mixture in vacuo. The resultant residue was partitioned between DCM and water, the organic layer was isolated, washed with water then brine, dried (Na$_2$SO$_4$), filtered and concentrated in vacuo. The resultant residue was subjected to flash chromatography (SiO$_2$, 1% MeOH in DCM) to give 95 as an off-white solid (5.78 g, 58%). $^1$H NMR δ (ppm) (CDCl$_3$): 8.04 (1H, s), 7.83 (1H, s), 7.50-7.38 (3H, m), 5.93-5.84 (1H, m), 4.07-4.02 (2H, m), 3.93-3.88 (2H, m), 1.53-1.46 (6H, m)

Example 105

2-(1-isopropyl-1H-1,2,4-triazol-5-yl)-9-(2-(pyrrolidin-1-ylmethyl)pyrrolidin-1-yl)-5,6-dihydroimidazo[1,2-d]pyrido[3,4-f][1,4]oxazepine 105

A mixture of 12-chloro-4-[1-(propan-2-yl)-1H-1,2,4-triazol-5-yl]-9-oxa-3,6,13-triazatricyclo[8.4.0.0$^{2,6}$]tetradeca-1(14),2,4,10,12-pentaene from Example 135 (150 mg, 0.454 mmol), TEA (0.500 mL), and 1,2'-methylenedipyrrolidine (420 mg, 2.73 mmol) in NMP (0.500 mL) was stirred at 150° C. for 24 hr under nitrogen atmosphere. The resultant mixture was purified by reverse phase combiflash eluting with 0-50% gradient of CH$_3$CN in 0.5% NH$_4$HCO$_3$ to afford 105 (81 mg, 40% yield) as white solid. LCMS (ESI): RT=4.54 min, m/z: 449.3 [M+H$^+$]. $^1$H-NMR (500 MHz, DMSO-d$_6$): δ 9.09 (s, 1H), 7.89 (s, 1H), 7.83 (s, 1H), 5.98-5.93 (m, 2H), 4.52-4.47 (m, 4H), 4.14 (s, 1H), 3.47 (s, 1H), 3.27 (s, 1H), 2.58-2.56 (m, 2H), 2.50-2.46 (m, 4H), 2.06-1.93 (m, 2H), 1.92-1.87 (m, 2H), 1.70-1.67 (m, 4H), 1.48 (s, 6H)

Example 106

2-(1-isopropyl-1H-1,2,4-triazol-5-yl)-9-(2-(1-methylpiperidin-4-yl)pyrrolidin-1-yl)-5,6-dihydroimidazo[1,2-d]pyrido[3,4-f][1,4]oxazepine 106

A mixture of 12-chloro-4-[1-(propan-2-yl)-1H-1,2,4-triazol-5-yl]-9-oxa-3,6,13-triazatricyclo[8.4.0.0$^{2,6}$]tetradeca-1(14),2,4,10,12-pentaene from Example 135 (160 mg, 0.480 mmol), TEA (0.50 mL), and 1-methyl-4-(pyrrolidin-2-yl)piperidine (161 mg, 0.960 mmol) in NMP (0.5 mL) was stirred at 150° C. for 24 h under nitrogen atmosphere. The resultant mixture was then purified by reverse phase combiflash eluting with a 0-50% gradient of CH$_3$CN in 0.3% NH$_4$HCO$_3$ to give 106 (66 mg, 60% yield). LCMS (ESI): RT=4.11 min, m/z: 463.3 [M+H$^+$]. $^1$H NMR (500 MHz, DMSO-d$_6$): δ 9.08 (t, J=10.5 Hz, 1H), 7.90 (t, J=10.5 Hz, 1H), 7.84 (t, J=10 Hz, 1H), 5.98 (t, J=20 Hz, 2H), 4.52-4.47 (m, 4H), 4.10 (s, 1H), 3.45 (d, J=6.5 Hz, 1H), 2.78 (s, 1H), 2.11 (d, J=10 Hz, 3H), 1.93-1.66 (m, 8H), 1.50-1.39 (m, 7H), 1.31-1.27 (m, 3H)

Example 108

10-((4-tert-butylpiperazin-1-yl)methyl)-2-(1-isopropyl-1H-1,2,4-triazol-5-yl)-5,6-dihydrobenzo[f]imidazo[1,2-d][1,4]oxazepine 108

Step 1: Methyl 4-[1-(propan-2-yl)-1H-1,2,4-triazol-5-yl]-9-oxa-3,6-diazatricyclo[8.4.0.0$^{2,6}$]tetradeca1(14),2,4,10,12-pentaene-13-carboxylate

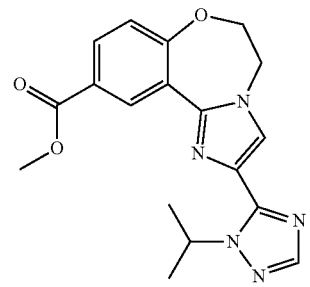 [SMILES: COC(=O)c1ccc2c(c1)-c1nc(-c3ncnn3C(C)C)cn1CCO2]

A mixture of 12-bromo-4-[1-(propan-2-yl)-1H-1,2,4-triazol-5-yl]-9-oxa-3,6-diazatricyclo[8.4.0.0$^{2,6}$]tetradeca1(14),2,4,10,12-pentaene (3.00 g, 8.04 mmol), Pd(OAc)$_2$ (0.18 g, 0.81 mmol), Xantphos (930 mg, 1.61 mmol) in MeOH (10.0 mL) and TEA (50.0 mL) was heated at 80° C. under CO (1 atm) overnight. The solid was filtered, the filtrate was concentrated and purified by silica gel chromatography eluting with a 50% gradient of EtOAc in petroleum ether to give methyl 4-[1-(propan-2-yl)-1H-1,2,4-triazol-5-yl]-9-oxa-3,6-diazatricyclo[8.4.0.0$^{2,6}$]tetradeca1(14),2,4,10,12-pentaene-13-carboxylate (1.7 g, 61% yield) as a white solid. LCMS (ESI) m/z: 354.2 [M+H$^+$].

Step 2: {4-[1-(Propan-2-yl)-1H-1,2,4-triazol-5-yl]-9-oxa-3,6-diazatricyclo[8.4.0.0$^{2,6}$]tetradeca-1(14),2,4,10,12-pentaen-13-yl}methanol

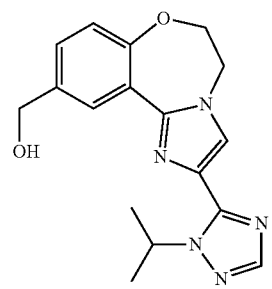 [SMILES: CC(C)n1ncnc1-c1cn2c(n1)-c1cc(CO)ccc1OCC2]

To a solution of methyl 4-[1-(propan-2-yl)-1H-1,2,4-triazol-5-yl]-9-oxa-3,6-diazatricyclo[8.4.0.0$^{2,6}$]tetradeca1(14),2,4,10,12-pentaene-13-carboxylate (1.70 g, 4.82 mmol) in THF (150 mL) was added LiAlH$_4$ (732 mg, 19.3 mmol). The reaction mixture was heated to reflux for 2 hours. After cooling down, the reaction was quenched with a piece of ice cube at 0° C. The solid was filtered off and washed with ethyl acetate (3×30 mL). The combined filtrate was concentrate to give the crude product, which was purified by column chromatography on silica gel eluting with a 50% gradient of EtOAc in petroleum ether to afford {4-[1-(propan-2-yl)-1H-1,2,4-triazol-5-yl]-9-oxa-3,6-diazatricyclo[8.4.0.0$^{2,6}$]tetradeca1(14),2,4,10,12-pentaen-13-yl}methanol (1.30 g, 83% yield) as a pale yellow solid. LCMS (ESI) m/z: 326.2 [M+H$^+$].

Step 3: 4-[1-(Propan-2-yl)-1H-1,2,4-triazol-5-yl]-9-oxa-3,6-diazatricyclo[8.4.0.0$^{2,6}$]tetradeca1(14),2,4,10,12-pentaene-13-carbaldehyde

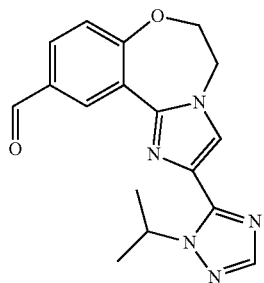 [SMILES: CC(C)n1ncnc1-c1cn2c(n1)-c1cc(C=O)ccc1OCC2]

To a solution of {4-[1-(propan-2-yl)-1H-1,2,4-triazol-5-yl]-9-oxa-3,6-diazatricyclo[8.4.0.0$^{2,6}$]tetradeca1(14),2,4,10,12-pentaen-13-yl}methanol (1.30 g, 4.00 mmol) in EtOAc (100 mL) was added 2-iodobenzoic acid (4.48 g, 16.0 mmol). The mixture was heated at 80° C. overnight. The solid was filtered, the filtrate was concentrated and purified by column chromatography on silica gel eluting with a 20% gradient of EtOAc in petroleum ether to afford 4-[1-(propan-2-yl)-1H-1,2,4-triazol-5-yl]-9-oxa-3,6-diazatricyclo[8.4.0.0$^{2,6}$]tetradeca1(14),2,4,10,12-pentaene-13-carbaldehyde (800 mg, 62% yield) as yellow solid. LCMS (ESI) m/z: 324.2 [M+H$^+$].

Step 4

To a solution of 4-[1-(propan-2-yl)-1H-1,2,4-triazol-5-yl]-9-oxa-3,6-diazatricyclo[8.4.0.0$^{2,6}$]tetradeca1(14),2,4,10,12-pentaene-13-carbaldehyde (50 mg, 0.16 mmol) in EtOH (5.0 mL) was added 1-tert-butylpiperazine (46 mg, 0.32 mmol) and Ti(Oi-Pr)$_4$ (88 mg, 0.31 mmol). The mixture was stirred at room temperature for 30 min. NaBH$_3$CN (20 mg, 0.32 mmol) was added and the reaction mixture was further stirred at room temperature for overnight. The solid was filtered, and the filtrate was concentrated and purified by reverse phase combiflash eluting with a 0-70% gradient of CH$_3$CN in 0.3% NH$_4$HCO$_3$ to give 108 (16 mg, 25% yield). LCMS (ESI): RT=4.92 min, m/z: 450.4 [M+H$^+$]. $^1$H NMR (500 MHz, CD$_3$OD): δ 8.41 (d, J=2 Hz, 1H), 7.92 (d, J=3 Hz, 1H), 7.20 (dd, J=8.5 Hz, 2.5 Hz, 1H), 7.00 (d, J=8.5 Hz, 1H), 5.90-5.85 (m, 1H), 4.43-4.51 (m, 4H), 3.47 (s, 2H), 2.51-2.39 (m, 8H), 1.51-1.46 (m, 6H), 0.98 (s, 9H)

Example 109

2-(2-(1-isopropyl-1H-1,2,4-triazol-5-yl)-5,6-dihydrobenzo[f]imidazo[1,2-d][1,4]oxazepin-9-yl)benzenesulfonamide 109

Step 1: N-tert-Butylbenzenesulfonamide

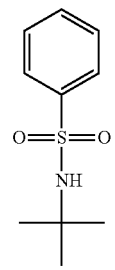

2-Methylpropan-2-amine (5.8 g, 80 mmol) and K$_2$CO$_3$ (11 g, 80 mmol) were dissolved in a mixed solvents of THF and H$_2$O (V:V=1:5, 30 ml). Benzenesulfonyl chloride (7.06 g, 40.0 mmol) was added drop wise at 0° C. to the above solution. After being stirred overnight, the resulting mixture was extracted with ethyl acetate (3×100 mL), washed with 1 N HCl (50 mL), sat. NaHCO$_3$ (50 mL), sat. NaCl (50 mL), and dried over Na$_2$SO$_4$. After concentration, the residue was purified by silica gel chromatography eluting with a 0-10% gradient of EtOAc in petroleum ether to afford N-tert-butylbenzenesulfonamide (6.0 g, 90% yield) as white solid. $^1$H NMR (500 MHz, CDCl$_3$): δ 7.93-7.91 (m, 2H), 7.54-7.47 (m, 3H), 5.06 (br, 1H), 1.22 (s, 9H)

Step 2: 2-(N-tert-Butylsulfamoyl)phenylboronic acid

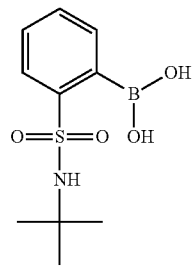 [SMILES: CC(C)(C)NS(=O)(=O)c1ccccc1B(O)O]

N-tert-Butylbenzenesulfonamide (2.00 g, 12.7 mmol) was dissolved in anhydrous THF (10 mL). After being cooled to −78° C., n-BuLi (2.5 M, 6.0 mL) was injected slowly to the above solution. After being stirred at this temperature for another 1 h, triisopropyl borate (11.9 g, 63.5 mmol) was added at −78° C. The resulting mixture was then allowed to warm to room temperature slowly for 8 h. 1N HCl (10 mL) was added to hydrolyze the borate. The organic layer was dried over Na$_2$SO$_4$. After removal of the solvent, the residue was used for the next step without further purification.

Step 3: N-tert-Butyl-2-{4-[1-(propan-2-yl)-1H-1,2,4-triazol-5-yl]-9-oxa-3,6-diazatricyclo[8.4.0.0²,⁶]tetradeca1(14),2,4,10,12-pentaen-12-yl}benzene-1-sulphonamide

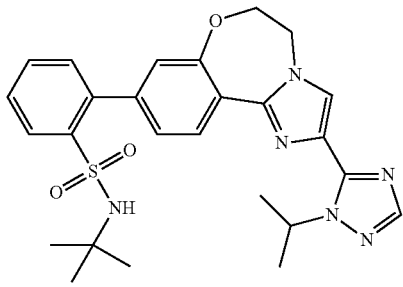 [SMILES: CC(C)n1ncnc1-c1cn2c(n1)-c1ccc(-c3ccccc3S(=O)(=O)NC(C)(C)C)cc1OCC2]

A mixture of 12-bromo-4-[1-(propan-2-yl)-1H-1,2,4-triazol-5-yl]-9-oxa-3,6-diazatricyclo[8.4.0.0²,⁶]tetradeca-1(14),2,4,10,12-pentaene (200 mg, 0.53 mmol), 2-(N-tert-butylsulfamoyl)phenylboronic acid (274 mg, 1.07 mmol), Pd(dppf)Cl₂ (38.9 mg, 0.0530 mmol), and CS₂CO₃ (350 mg, 1.07 mmol) in 1,4-dioxane (5 mL) was heated to 100° C. for 8 h. After filtration, the filtrate was purified by reverse phase combiflash eluting with a 0-70% gradient of CH₃CN in 0.3% NH₄HCO₃ to afford N-tert-butyl-2-{4-[1-(propan-2-yl)-1H-1,2,4-triazol-5-yl]-9-oxa-3,6-diazatricyclo[8.4.0.0²,⁶]tetradeca1(14),2,4,10,12-pentaen-12-yl}benzene-1-sulphonamide (250 mg, 93% yield) as white solid. LCMS (ESI) m/z: 507.2 [M+H⁺]

Step 4

A mixture of N-tert-butyl-2-{4-[1-(propan-2-yl)-1H-1,2,4-triazol-5-yl]-9-oxa-3,6-diazatricyclo[8.4.0.0²,⁶]tetradeca1(14),2,4,10,12-pentaen-12-yl}benzene-1-sulphonamide (200 mg, 0.400 mmol) in TFA (5.0 mL) was heated to 80° C. for 3 h. After concentration, the residue was adjusted to pH around 8, extracted with ethyl acetate (3×50 mL). After removal of the solvent, the residue was purified by reverse phase combiflash eluting with a 0-70% gradient of CH₃CN in 0.3% NH₄HCO₃ to give 109 (60 mg, 33% yield) as white solid. LCMS (ESI): RT=5.15 min, m/z: 451.2 [M+H⁺]. ¹H NMR (500 MHz, DMSO-d₆): δ 8.44-8.41 (m, 1H), 8.07-8.03 (m, 1H), 7.98 (d, J=7.5 Hz, 1H), 7.93 (d, J=8.0 Hz, 1H), 7.64-7.56 (m, 3H), 7.39-7.36 (m, 1H), 7.21-7.19 (m, 2H), 7.09 (d, J=5.5 Hz, 1H), 5.97-5.95 (m, 1H), 4.58-4.55 (m, 4H) 1.52-1.49 (m, 6H)

Example 110

(4-tert-butylpiperazin-1-yl)(2-(1-isopropyl-1H-1,2,4-triazol-5-yl)-5,6-dihydrobenzo[f]imidazo[1,2-d][1,4]oxazepin-10-yl)methanone 110

Step 1: 4-[1-(propan-2-yl)-1H-1,2,4-triazol-5-yl]-9-oxa-3,6-diazatricyclo[8.4.0.0²,⁶]tetradeca-1(14),2,4,10,12-pentaene-13-carboxylic acid

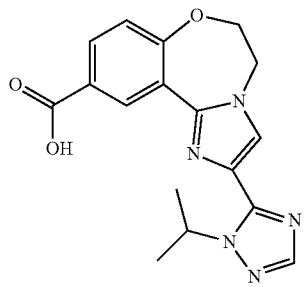 [SMILES: CC(C)n1ncnc1-c1cn2c(n1)-c1cc(C(=O)O)ccc1OCC2]

To a solution of methyl 4-[1-(propan-2-yl)-1H-1,2,4-triazol-5-yl]-9-oxa-3,6-diazatricyclo[8.4.0.0²,⁶]tetradeca1(14),2,4,10,12-pentaene-13-carboxylate (1.40 g, 3.95 mmol) in MeOH (25 ml) was added LiOH (2.0 N, 10 ml). The resulting solution was heated to reflux for overnight. The volatiles were removed in vacuo and the residue was adjusted to pH around 6-7 using 1 N HCl. The solid was collected and dried under reduce pressure to give the desired product (1.0 g, 75% yield) as a brown solid. LCMS m/z [M+H]⁺ 340.2.

Step 2

To a solution of 4-[1-(propan-2-yl)-1H-1,2,4-triazol-5-yl]-9-oxa-3,6-diazatricyclo[8.4.0.0²,⁶]tetradeca-1(14),2,4,10,12-pentaene-13-carboxylic acid (50 mg, 0.147 mmol) in DMF (2 mL) was added 1-tert-butylpiperazine (42 mg, 0.296 mmol), DIPEA (57 mg, 0.442 mmol) and HATU (112 mg, 0.295 mmol). The reaction mixture was heated at 100° C. for 2 h. The resultant mixture was purified by Combi-flash eluting with a 5-95% gradient of CH₃CN in 0.3% NH₄HCO₃ to give 110 (25 mg, 37% yield) as an off-white solid. LCMS (ESI): RT=4.95 min, m/z: 464.3 [M+H⁺]. ¹H NMR (500 MHz, DMSO-d₆) δ 8.42 (d, J=2.0 Hz, 1H), 7.98 (s, 1H), 7.93 (s, 1H), 7.38-7.36 (dd, J=2.0, 8.5 Hz, 1H), 7.12-7.11 (d, J=8.5 Hz, 1H), 5.80 (m, 1H), 4.56 (s, 4H), 3.7-3.3 (m, 4H), 2.90 (s, 1H), 2.87 (s, 1H), 1.50-1.48 (d, 6H), 1.03-1.02 (m, 11H)

Example 111

9-((S)-2-((S)-1-methylpiperidin-2-yl)pyrrolidin-1-yl)-2-(pyridin-2-yl)-5,6-dihydroimidazo[1,2-d]pyrido[3,4-f][1,4]oxazepine 111

Step 1: 12-Chloro-4-(pyridin-2-yl)-9-oxa-3,6,13-triazatricyclo[8.4.0.0²,⁶]tetradeca-1(14),2,4,10,12-pentaene

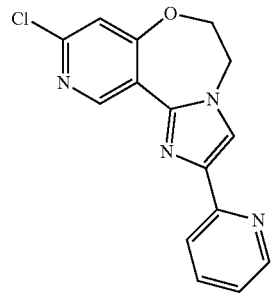 [SMILES: Clc1cc2c(cn1)-c1nc(-c3ccccn3)cn1CCO2]

A mixture of 12-chloro-4-iodo-9-oxa-3,6,13-triazatricyclo[8.4.0.0²,⁶]tetradeca-1(14),2,4,10,12-pentaene (1.00 g, 2.88 mmol), pyridin-2-ylzinc(II) bromide (0.5 M THF) (8.60 mL), Pd(PPh₃)₄ (498 mg, 0.432 mmol) in THF (30 mL) was stirred at 35° C. for 16 hr. After removal of the solvent, the residue was washed with acetone to afford 12-chloro-4-(pyridin-2-yl)-9-oxa-3,6,13-triazatricyclo[8.4.0.0²,⁶]tetradeca-1(14),2,4,10,12-pentaene (750 mg, 87% yield) as yellow solid. LCMS (ESI) m/z: 299.0 [M+H⁺].

Step 2

A mixture of 12-chloro-4-(pyridin-2-yl)-9-oxa-3,6,13-triazatricyclo[8.4.0.0²,⁶]tetradeca-1(14),2,4,10,12-pentaene (300 mg, 1.00 mmol), TEA (0.5 mL), and 1-methyl-2-(pyrrolidin-2-yl)piperidine (507 mg, 3.01 mmol) in NMP (0.5 mL) was stirred at 150° C. for 24 h under nitrogen atmosphere. After cooling down, the resultant mixture was purified directly by reverse phase Combiflash eluting with 0-50% gradient of $CH_3CN$ in 0.5% $NH_4HCO_3$ to give diastereomeric 111: 15 mg of diastereomer A and 12 mg diasteromer B (48% total yield). Diasteromer A: LCMS (ESI): RT=4.48 min, m/z: 431.3 [M+H⁺]. ¹H-NMR (500 MHz, DMSO-$d_6$): δ 9.14 (s, 1H), 8.50 (d, J=4.5 Hz, 1H), 7.96 (d, J=7.5 Hz, 1H), 7.83-7.79 (m, 2H), 7.22-7.19 (m, 1H), 6.05 (s, 1H), 4.52-4.45 (m, 4H), 4.11 (s, 1H), 3.45-3.34 (m, 2H), 2.78 (s, 1H), 2.17 (s, 3H), 2.11-2.01 (m, 2H), 1.95-1.85 (m, 4H), 1.70 (s, 1H), 1.50-1.35 (m, 3H), 1.30-1.19 (m, 2H). Diastereomer B: LCMS (ESI): RT=4.75 min, m/z: 431.3 [M+H⁺]. ¹H-NMR (500 MHz, DMSO-$d_6$): δ 9.15 (s, 1H), 8.50 (d, J=4.0 Hz, 1H), 7.96 (d, J=8.2 Hz, 1H), 7.83-7.78 (m, 2H), 7.22-7.19 (m, 1H), 5.98 (s, 1H), 4.52-4.45 (m, 5H), 3.42 (s, 2H), 2.77 (s, 1H), 2.29 (s, 3H), 2.16-2.13 (m, 2H), 2.00-1.88 (m, 4H), 1.64 (s, 1H), 1.50-1.25 (m, 3H), 1.20-0.90 (m, 2H)

Example 118

2-(1-isopropyl-1H-1,2,4-triazol-5-yl)-N-phenyl-5,6-dihydrobenzo[f]imidazo[1,2-d][1,4]oxazepine-10-sulfonamide 118

To a suspension of sodium 2-(2-isopropyl-2H-[1,2,4]triazol-3-yl)-4,5-dihydro-6-oxa-1,3a-diazabenzo[e]azulene-9-sulfonate from Example 121 (0.26 mmol) in THF (10 mL) was added oxalyl chloride (111 μL, 1.30 mmol) and the resulting mixture stirred at RT for 10 min then cooled to 0° C. before DMF (100 μL, 1.27 mmol) was added. The resulting mixture was stirred for 3 h then azeotroped with toluene. The resulting residue was suspended in DCM (10 mL) and added to a solution of phenylamine (36 μL, 0.39 mmol) and $NEt_3$ (72 μL, 0.52 mmol) in DCM (5 mL) at RT The resulting mixture was stirred for 16 h then quenched with $H_2O$. The organic phase was washed with brine then dried ($Na_2SO_4$) and concentrated in vacuo. The resulting residue was purified by column chromatography (Si-PCC, gradient 0-14% MeOH in MeOAc) then freeze-dried from MeCN and $H_2O$ affording 118 as a white solid (6 mg, 5%). LCMS: $R_T$ 4.18 [M+H]⁺ 451.2. ¹H NMR (DMSO, 400 MHz): δ 8.84 (1H, d, J=2.45 Hz), 7.95 (1H, s), 7.93 (1H, d, J=0.63 Hz), 7.65 (1H, dd, J=8.68, 2.47 Hz), 7.17-7.16 (5H, m), 6.99 (1H, t, J=7.29 Hz), 5.69-5.68 (1H, m), 4.55-4.54 (4H, m), 1.50 (6H, d, J=6.60 Hz)

Example 119

2-(2-(1-isopropyl-1H-1,2,4-triazol-5-yl)-5,6-dihydrobenzo[f]imidazo[1,2-d][1,4]oxazepin-10-yl)-N-phenylacetamide 119

To a mixture of [2-(2-isopropyl-2H-[1,2,4]triazol-3-yl)-4,5-dihydro-6-oxa-1,3a-diazabenzo[e]azulen-9-yl]acetic acid trifluoroacetic acid salt from Example 120 (100 mg, 0.21 mmol), HATU (96 mg, 0.25 mmol) and $NEt_3$ (63 mg, 0.63 mmol) in DMF (2 mL) was added a solution of phenylamine (23 mg, 0.25 mmol) in DMF (0.2 mL) and the resulting mixture stirred at RT for 16 h. The reaction mixture was loaded onto an Isolute® SCX-2 cartridge which was washed with MeOH and the product eluted with 2M $NH_3$/MeOH. The resulting residue was purified by column chromatography (Si-PCC, gradient 0-8% MeOH in DCM) affording 119 as a white solid (51 mg, 57%). LCMS: $R_T$ 4.09 min [M+H]⁺ 429.3. ¹H NMR (CDCl₃, 400 MHz): δ 8.43 (1H, d, J=2.27 Hz), 7.91 (1H, s), 7.72 (1H, s), 7.47 (2H, d, J=8.02 Hz), 7.43 (1H, s), 7.29-7.26 (2H, m), 7.09-7.06 (2H, m), 5.86-5.85 (1H, m), 4.46-4.45 (4H, m), 3.78 (2H, s), 1.55 (6H, d, J=6.61 Hz)

Example 120

N-benzyl-2-(2-(1-isopropyl-1H-1,2,4-triazol-5-yl)-5,6-dihydrobenzo[f]imidazo[1,2-d][1,4]oxazepin-10-yl)acetamide 120

Step 1: 2-(2-Isopropyl-2H-[1,2,4]triazol-3-yl)-4,5-dihydro-6-oxa-1,3a-diazabenzo[e]azulen-9-yl]acetic acid tert-butyl ester

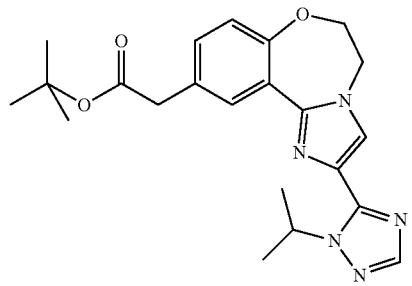 [SMILES: CC(C)n1ncnc1-c1cn2c(n1)-c1cc(CC(=O)OC(C)(C)C)ccc1OCC2]

To a mixture of 9-bromo-2-(2-isopropyl-2H-[1,2,4]triazol-3-yl)-4,5-dihydro-6-oxa-1,3a-diazabenzo[e]azulene (1.02 g, 2.73 mmol), QPhos (80 mg) and Pd(dba)₂ (70 mg, 0.12 mmol) in THF (30 mL) was added 2-tert-butoxy-2-oxoethyl zinc chloride (16 mL, 8.18 mmol, 0.5M solution in $Et_2O$) and the resulting mixture stirred at RT for 16 h. Further QPhos (60 mg), Pd(dba)₂ (50 mg, 0.09 mmol) and 2-tert-butoxy-2-oxoethyl zinc chloride (10 mL, 5.11 mmol, 0.5M solution in $Et_2O$) were added and the mixture stirred at 60° C. for 1.5 h. The reaction mixture was concentrated in vacuo and the residue partitioned between DCM and $H_2O$. The organic phase was washed with brine, dried ($Na_2SO_4$) and concentrated in vacuo. The resulting residue was purified by column chromatography (Si-PCC, gradient 0-7% MeOH in DCM) affording 2-(2-Isopropyl-2H-[1,2,4]triazol-3-yl)-4,5-dihydro-6-oxa-1,3a-diazabenzo[e]azulen-9-yl]acetic acid tert-butyl ester as a pink solid (970 mg, 87%). LCMS: $R_T$ 3.68 min [M+H]⁺ 410.4

Step 2: [2-(2-Isopropyl-2H-[1,2,4]triazol-3-yl)-4,5-dihydro-6-oxa-1,3a-diazabenzo[e]azulen-9-yl]acetic acid

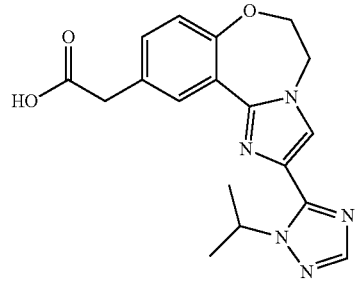 [SMILES: CC(C)n1ncnc1-c1cn2c(n1)-c1cc(CC(=O)O)ccc1OCC2]

To a solution of [2-(2-isopropyl-2H-[1,2,4]triazol-3-yl)-4,5-dihydro-6-oxa-1,3a-diazabenzo[e]azulen-9-yl]acetic acid tert-butyl ester (930 mg, 2.27 mmol) in DCM (20 mL) was added TFA (10 mL) and the resulting mixture stirred at RT for 1 h. The reaction mixture was loaded onto an Isolute® SCX-2 cartridge which was washed with MeOH and the product eluted with 2M NH$_3$/MeOH. The resulting residue was found to be acid and the corresponding methyl ester so was purified by column chromatography (Si-PCC, gradient 0-20% MeOH in DCM) affording [2-(2-Isopropyl-2H-[1,2,4]triazol-3-yl)-4,5-dihydro-6-oxa-1,3a-diazabenzo[e]azulen-9-yl]acetic acid as a white solid (164 mg, 21%). LCMS: R$_T$ 2.65 min [M+H]$^+$ 354.3

Step 3

To a mixture of [2-(2-isopropyl-2H-[1,2,4]triazol-3-yl)-4,5-dihydro-6-oxa-1,3a-diazabenzo[e]azulen-9-yl]acetic acid trifluoroacetic acid salt (100 mg, 0.21 mmol), HATU (96 mg, 0.25 mmol) and NEt$_3$ (63 mg, 0.63 mmol) in DMF (2 mL) was added a solution of benzylamine (27 mg, 0.25 mmol) in DMF (0.2 mL) and the resulting mixture stirred at RT for 3 h. The reaction mixture was loaded onto an Isolute® SCX-2 cartridge which was washed with MeOH and the product eluted with 2M NH$_3$/MeOH. The resulting residue was purified by column chromatography (Si-PCC, gradient 0-8% tMeOH in DCM) affording 120 as a white solid (78 mg, 84%). LCMS: R$_T$ 3.94 min [M+H]$^+$ 443.3. $^1$H NMR (CDCl$_3$, 400 MHz): δ 8.38 (1H, d, J=2.31 Hz), 7.91 (1H, s), 7.75 (1H, s), 7.27-7.19 (6H, m), 7.04 (1H, d, J=8.36 Hz), 5.89-5.88 (1H, m), 5.79 (1H, s), 4.46-4.43 (6H, m), 3.68 (2H, s), 1.59 (6H, d, J=6.62 Hz)

Example 121

10-(4-tert-butylpiperazin-1-ylsulfonyl)-2-(1-isopropyl-1H-1,2,4-triazol-5-yl)-5,6-dihydrobenzo[f]imidazo[1,2-d][1,4]oxazepine 121

Step 1: Sodium 2-(2-isopropyl-2H-[1,2,4]triazol-3-yl)-4,5-dihydro-6-oxa-1,3a-diazabenzo[e]azulene-9-sulfonate

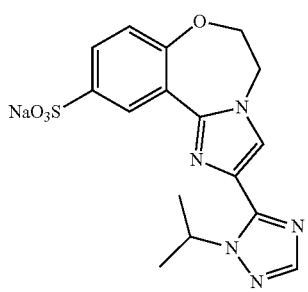

To chlorosulfonic acid (4 mL) at 0° C. was added 2-(2-isopropyl-2H-[1,2,4]triazol-3-yl)-4,5-dihydro-6-oxa-1,3a-diazabenzo[e]azulene (400 mg, 1.35 mmol) portion wise and the resulting mixture stirred for 5 min then added drop wise to ice. NaOH (7.2 g) in H$_2$O (20 mL) was added to the mixture and stirred for 1 h at RT then concentrated in vacuo. The resulting residue was purified by column chromatography (C$_{18}$, gradient 0.5-1% MeOH in H$_2$O) then extracted into hot MeOH. Upon cooling the mixture was filtered and the filtrate concentrated in vacuo affording Sodium 2-(2-isopropyl-2H-[1,2,4]triazol-3-yl)-4,5-dihydro-6-oxa-1,3a-diazabenzo[e]azulene-9-sulfonate (1.32 g) contaminated with inorganic salts. LCMS: R$_T$ 2.14 min [M+H]$^+$ 376.1

Step 2: 2-(2-Isopropyl-2H-[1,2,4]triazol-3-yl)-4,5-dihydro-6-oxa-1,3a-diazabenzo[e]azulene-9-sulfonyl chloride

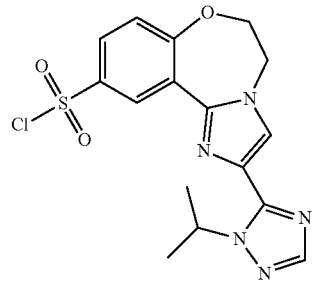 [SMILES: CC(C)n1ncnc1-c1cn2c(n1)-c1cc(S(=O)(=O)Cl)ccc1OCC2]

To a suspension of 2-(2-isopropyl-2H-[1,2,4]triazol-3-yl)-4,5-dihydro-6-oxa-1,3a-diazabenzo[e]azulene-9-sulfonic acid (228 mg, 0.61 mmol) in THF (15 mL) was added oxalyl chloride (257 μL, 3.04 mmol) and the resulting mixture stirred at RT for 15 min. The reaction mixture was cooled to 0° before DMF (126 μL, 1.69 mmol) was added and the resulting mixture warmed to RT after 10 min then stirred for a further 2 h. The reaction mixture was azeotroped with toluene affording 2-(2-Isopropyl-2H-[1,2,4]triazol-3-yl)-4,5-dihydro-6-oxa-1,3a-diazabenzo[e]azulene-9-sulfonyl chloride (500 mg).

Step 3

To a suspension of sodium 2-(2-isopropyl-2H-[1,2,4]triazol-3-yl)-4,5-dihydro-6-oxa-1,3a-diazabenzo[e]azulene-9-sulfonate (0.34 mmol) in THF (10 mL) was added oxalyl chloride (143 μL, 1.69 mmol) and the resulting mixture stirred at RT for 10 min then cooled to 0° C. before DMF (126 μL, 1.69 mmol) was added. The resulting mixture was stirred for 3 h then azeotroped with toluene. The resulting residue was suspended in DCM (15 mL) and added to a solution of tert-butylpiperazine (96 mg, 0.68 mmol) and NEt$_3$ (157 μL, 1.13 mmol) in DCM (10 mL) at RT The resulting mixture was stirred for 1 h then quenched with a saturated aqueous NaHCO$_3$ solution. The organic phase was washed with H$_2$O and brine, then dried (Na$_2$SO$_4$) and concentrated in vacuo. The resulting residue was purified by column chromatography (Si-PCC, gradient 3-20% 2M NH$_3$/MeOH in EtOAc then C18, gradient 25-45% MeOH in H$_2$O). The resulting residue was partitioned between DCM and a saturated aqueous NaHCO$_3$ solution, the organic phase dried (Na$_2$SO$_4$) and concentrated in vacuo affording 121 (25 mg, 22%). LCMS: R$_T$ 2.93 [M+H]$^+$ 500.3. $^1$H NMR (DMSO, 400 MHz): δ 8.78 (1H, d, J=2.41 Hz), 8.00 (1H, s), 7.94 (1H, s), 7.62 (1H, dd, J=8.62, 2.42 Hz), 7.28 (1H, d, J=8.62 Hz), 5.74-5.74 (1H, m), 4.64-4.60 (4H, m), 2.92-2.85 (4H, m), 2.59-2.53 (4H, m), 1.49 (6H, d, J=6.62 Hz), 0.93 (9H, s)

Example 122

2-(1-isopropyl-1H-1,2,4-triazol-5-yl)-10-(3-morpholinoazetidin-1-ylsulfonyl)-5,6-dihydrobenzo[f]imidazo[1,2-d][1,4]oxazepine 122

To a solution of 4-azetidin-3-ylmorpholine (52 mg, 0.36 mmol) and NEt$_3$ (84 μL, 0.61 mmol) in DCM (5 mL) at 0° C.

was added a suspension of 2-(2-isopropyl-2H-[1,2,4]triazol-3-yl)-4,5-dihydro-6-oxa-1,3a-diazabenzo[e]azulene-9-sulfonyl chloride from Example 121 (100 mg, 0.12 mmol) in DCM (5 mL) and the resulting mixture warmed to RT after 10 min then stirred for 16 h. The reaction mixture was diluted with DCM, washed with a saturated aqueous $NaHCO_3$ solution then dried ($Na_2SO_4$) and concentrated in vacuo. The resulting residue was purified by column chromatography (Si-PCC, gradient 2-6% 2M $NH_3$/MeOH in DCM then C18, gradient 20-50% MeOH in $H_2O$). The resulting residue was loaded onto an Isolute® SCX-2 cartridge which was washed with MeOH and the product eluted with 2M $NH_3$/MeOH affording 122 (40 mg, 65%). LCMS: $R_T$ 3.00 min [M+H]$^+$ 500.3. $^1$H NMR (DMSO, 400 MHz): δ 8.87 (1H, d, J=2.40 Hz), 8.02 (1H, s), 7.94 (1H, d, J=0.62 Hz), 7.72 (1H, dd, J=8.62, 2.42 Hz), 7.32 (1H, d, J=8.62 Hz), 5.73-5.64 (1H, m), 4.64-4.63 (4H, m), 3.78 (2H, t, J=7.73 Hz), 3.58 (2H, dd, J=8.39, 5.80 Hz), 3.42 (4H, t, J=4.34 Hz), 3.03-3.01 (1H, m), 2.15-2.09 (4H, m), 1.49 (6H, d, J=6.62 Hz)

Example 123 (S)-2-(1-isopropyl-1H-1,2,4-triazol-5-yl)-10-(2-(pyrrolidin-1-ylmethyl)pyrrolidin-1-ylsulfonyl)-5,6-dihydrobenzo[f]imidazo[1,2-d][1,4]oxazepine 123

To a solution of (S)-2-pyrrolidin-1-ylmethylpyrrolidine (36 mg, 0.23 mmol) and $NEt_3$ (54 μL, 0.39 mmol) in DCM (5 mL) at 0° C. was added a suspension of 2-(2-isopropyl-2H-[1,2,4]triazol-3-yl)-4,5-dihydro-6-oxa-1,3a-diazabenzo[e]azulene-9-sulfonyl chloride from Example 121 (64 mg, 0.08 mmol) in DCM (5 mL) and the resulting mixture warmed to RT after 10 min then stirred for 16 h. The reaction mixture was diluted with DCM, washed with a saturated aqueous $NaHCO_3$ solution then dried ($Na_2SO_4$) and concentrated in vacuo. The resulting residue was purified by column chromatography (Si-PCC, gradient 2-10% 2M $NH_3$/MeOH in DCM then C18, gradient 15-40% MeOH in $H_2O$). The resulting residue was loaded onto an Isolute® SCX-2 cartridge which was washed with MeOH and the product eluted with 2M $NH_3$/MeOH affording 123 (22 mg, 56%). LCMS: $R_T$ 2.90 min [M+H]$^+$ 512.3. $^1$H NMR (DMSO, 400 MHz): δ 9.01 (1H, d, J=2.40 Hz), 7.95 (1H, s), 7.82 (1H, s), 7.77 (1H, dd, J=8.65, 2.41 Hz), 7.26 (1H, d, J=8.65 Hz), 5.90-5.89 (1H, m), 4.61-4.60 (4H, m), 3.79-3.69 (1H, m), 3.42-3.41 (1H, m), 3.30-3.24 (1H, m), 2.76 (1H, dd, J=12.12, 4.10 Hz), 2.65-2.62 (5H, m), 1.80-1.79 (7H, m), 1.67-1.54 (1H, m). 1.59 (3H, d, J=6.62 Hz), 1.57 (3H, d, J=6.58 Hz)

Example 128

2-(1-isopropyl-1H-1,2,4-triazol-5-yl)-10-(4-isopropylpiperazin-1-ylsulfonyl)-5,6-dihydrobenzo[f]imidazo[1,2-d][1,4]oxazepine 128

To a solution of 1-isopropylpiperazine (50 mg, 0.39 mmol) and $NEt_3$ (90 μL, 0.65 mmol) in DCM (8 mL) at 0° C. was added a suspension of 2-(2-isopropyl-2H-[1,2,4]triazol-3-yl)-4,5-dihydro-6-oxa-1,3a-diazabenzo[e]azulene-9-sulfonyl chloride from Example 121 (0.13 mmol) in DCM (8 mL) and the resulting mixture warmed to RT after 10 min then stirred for 2 h. The reaction mixture was diluted with DCM, washed with a saturated aqueous $NaHCO_3$ solution then dried ($Na_2SO_4$) and concentrated in vacuo. The resulting residue was purified by column chromatography (Si-PCC, gradient 2-7% 2M $NH_3$/MeOH in DCM) affording 128 (41 mg, 65%) as a white solid. LCMS: $R_T$ 2.90 min [M+H]$^+$ 486.3. $^1$H NMR (DMSO, 400 MHz): δ 8.79 (1H, d, J=2.41 Hz), 8.00 (1H, s), 7.94 (1H, d, J=0.61 Hz), 7.63 (1H, dd, J=8.62, 2.43 Hz), 7.28 (1H, d, J=8.62 Hz), 5.76-5.69 (1H, m), 4.64-4.62 (4H, m), 2.94-2.87 (4H, m), 2.62-2.61 (1H, m), 2.54-2.43 (4H, m), 1.49 (6H, d, J=6.62 Hz), 0.89 (6H, d, J=6.53 Hz)

Example 129

9-(2-(piperidin-1-ylmethyl)pyrrolidin-1-yl)-2-(pyridin-2-yl)-5,6-dihydroimidazo[1,2-d]pyrido[3,4-f][1,4]oxazepine 129

To a solution of 12-chloro-4-(pyridin-2-yl)-9-oxa-3,6,13-triazatricyclo[8.4.0.0$^{2,6}$]tetradeca-1(14),2,4,10,12-pentaene (200 mg, 0.671 mmol) in NMP (10 mL) was added TEA (10 mL) and 1-(pyrrolidin-2-ylmethyl)piperidine (135 mg, 0.804 mmol). The reaction mixture was stirred at 160° C. for 24 h. After cooling to room temperature, the reaction mixture was purified by Combi-flash eluting with a 5-95% gradient of $CH_3CN$ in 0.3% $NH_4HCO_3$ to give 129 which was further purified by chiral HPLC (AS-H column, 10% EtOH isocratic) to separate 15.9 mg of one enantiomer and 7 mg of the other (8% total yield). LCMS (ESI): RT=4.55 min, m/z: 431.3 [M+H$^+$]. $^1$H NMR (500 MHz, DMSO-d$_6$) δ 9.14 (s, 1H), 8.50-8.49 (d, J=4.0 Hz, 1H), 7.97-7.95 (d, J=8.0 Hz, 1H), 7.82-7.78 (m, 2H), 7.22-7.19 (m, 1H), 5.95 (s, 1H), 4.49-4.44 (m, 4H), 4.17 (m, 1H), 3.46-3.44 (m, 1H), 3.28-3.25 (m, 1H), 2.54 (m, 1H), 2.45-2.33 (m, 3H), 2.21-2.16 (m, 1H), 2.01-1.97 (m, 2H), 1.94-1.86 (m, 2H), 1.53-1.50 (m, 4H), 1.39-1.38 (m, 2H)

Example 131

1-(2-(1-isopropyl-1H-1,2,4-triazol-5-yl)-5,6-dihydrobenzo[f]imidazo[1,2-d][1,4]oxazepin-10-ylsulfonyl)-N,N-dimethylpiperidin-4-amine To a solution of dimethyl-piperidin-4-yl-amine (45 mg, 0.35 mmol) and $NEt_3$ (83 μL, 0.59 mmol) in DCM (15 mL) at 0° C. was added a suspension of 2-(2-isopropyl-2H-[1,2,4]triazol-3-yl)-4,5-dihydro-6-oxa-1,3a-diazabenzo[e]azulene-9-sulfonyl chloride from Example 121 (93 mg, 0.12 mmol) in DCM (5 mL) and the resulting mixture warmed to RT after 10 min then stirred for 1 h. The reaction mixture was diluted with DCM, washed with a saturated aqueous $NaHCO_3$ solution then dried ($Na_2SO_4$) and concentrated in vacuo. The resulting residue was purified by column chromatography (Si-PCC, gradient 0-16% MeOH in EtOAc) then freeze-dried from MeCN/$H_2O$ affording 131 (29 mg, 52%) as a white solid. LCMS: $R_T$ 2.83 min [M+H]$^+$ 486.3. $^1$H NMR (DMSO, 400 MHz): δ 8.79 (1H, d, J=2.42 Hz), 8.00 (1H, s), 7.93 (1H, d, J=0.62 Hz), 7.63 (1H, dd, J=10.74, 2.40 Hz), 7.26 (1H, d, J=8.62 Hz), 5.72-5.71 (1H, m), 4.61-4.60 (4H, m), 3.60-3.57 (2H, m), 2.40-2.39 (2H, m), 2.15-2.05 (1H, m), 2.10 (6H, s), 1.77-1.73 (2H, m), 1.49 (6H, d, J=6.62 Hz), 1.46-1.37 (2H, m)

Example 132

10-(dihydro-1H-pyrido[1,2-a]pyrazin-2(6H,7H,8H,9H,9aH)-ylsulfonyl)-2-(1-isopropyl-1H-1,2,4-triazol-5-yl)-5,6-dihydrobenzo[f]imidazo[1,2-d][1,4]oxazepine 132

To a solution of octahydropyrido[1,2-a]pyrazine (50 mg, 0.38 mmol) and $NEt_3$ (83 μL, 0.59 mmol) in DCM (15 mL) at 0° C. was added a suspension of 2-(2-isopropyl-2H-[1,2,4]triazol-3-yl)-4,5-dihydro-6-oxa-1,3a-diazabenzo[e]azulene- 9-sulfonyl chloride from Example 121 (93 mg, 0.12 mmol) in DCM (5 mL) and the resulting mixture warmed to RT after 10 min then stirred for 1 h. The reaction mixture was diluted with DCM, washed with a saturated aqueous NaHCO$_3$ solution then dried (Na$_2$SO$_4$) and concentrated in vacuo. The resulting residue was purified by column chromatography (Si-PCC, gradient 0-8% MeOH in EtOAc) then freeze-dried from MeCN/H$_2$O affording 132 (36 mg, 62%) as a white solid. LCMS: R$_T$ 2.90 min [M+H]$^+$ 498.3. $^1$H NMR (DMSO, 400 MHz): δ 8.78 (1H, d, J=2.41 Hz), 8.01 (1H, s), 7.94 (1H, s), 7.63 (1H, dd, J=8.63, 2.42 Hz), 7.28 (1H, d, J=8.62 Hz), 5.73-5.72 (1H, m), 4.63-4.59 (4H, m), 3.53 (1H, d, J=11.02 Hz), 3.43 (1H, d, J=9.07 Hz), 2.70-2.68 (2H, m), 2.33-2.32 (1H, m), 2.19-2.11 (1H, m), 1.93-1.92 (3H, m), 1.62 (1H, d, J=12.59 Hz), 1.57-1.52 (2H, m), 1.49 (6H, t, J=6.30 Hz), 1.38-1.16 (2H, m), 1.01-0.87 (1H, m)

Example 133 (S)-2-(1-isopropyl-1H-1,2,4-triazol-5-yl)-9-(2-(pyrrolidin-1-ylmethyl)pyrrolidin-1-yl)-5,6-dihydrobenzo[f]imidazo[1,2-d][1,4]oxazepine 133

A mixture of 9-bromo-2-(1-isopropyl-1H-1,2,4-triazol-5-yl)-5,6-dihydrobenzo[f]imidazo[1,2-d][1,4]oxazepine 95 from Example 95 (100 mg, 0.27 mmol), (S)-pyrrolidinylmethylpyrrolidine (206 mg, 1.34 mmol), K$_3$PO$_4$ (114 mg, 0.53 mmol), trans-4-hydroxyproline (14 mg, 0.11 mmol) and CuI (10 mg, 0.05 mmol) in DMSO (0.5 mL) was heated at 90° C. for 23 h. The reaction mixture was loaded onto an Isolute® SCX-2 cartridge which was washed with MeOH and the product eluted with 2M NH$_3$/MeOH. The resulting residue was dissolved in DCM and washed with 10% citric acid, dried (Na$_2$SO$_4$) and concentrated in vacuo. The resulting residue was purified by column chromatography (Si-PCC, gradient 0-6% MeOH in DCM) then Isolute® SCX-2 cartridge which was washed with MeOH and the product eluted with 2M NH$_3$/MeOH. The resulting residue was freeze-dried from MeCN/H$_2$O to afford 133 (22 mg, 19%) as a white solid. LCMS: R$_T$ 2.81 min [M+H]$^+$ 448.4. $^1$H NMR (DMSO, 400 MHz): δ 8.19 (1H, d, J=8.93 Hz), 7.88 (1H, d, J=0.63 Hz), 7.77 (1H, s), 6.45 (1H, dd, J=9.00, 2.43 Hz), 6.13 (1H, d, J=2.38 Hz), 5.93-5.92 (1H, m), 4.48-4.36 (4H, m), 3.89-3.81 (1H, m), 3.42-3.35 (1H, m), 3.15-3.05 (1H, m), 2.64-2.57 (2H, m), 2.43-2.40 (4H, m), 2.00-1.98 (4H, m), 1.74-1.66 (4H, m), 1.47 (6H, d, J=6.61 Hz)

Example 134

2-(1-isopropyl-1H-1,2,4-triazol-5-yl)-10-(4-(pentan-3-yl)piperazin-1-ylsulfonyl)-5,6-dihydrobenzo[f]imidazo[1,2-d][1,4]oxazepine 134

Step 1: 4-[2-(2-Isopropyl-2H-[1,2,4]triazol-3-yl)-4,5-dihydro-6-oxa-1,3a-diazabenzo[e]azulene-9-sulfonyl]piperazine-1-carboxylic acid tert-butyl ester

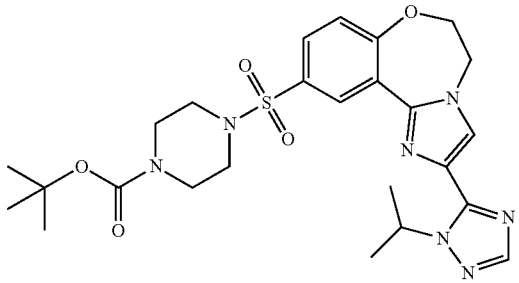 [SMILES: CC(C)n1ncnc1-c1cn2c(n1)-c1cc(S(=O)(=O)N3CCN(C(=O)OC(C)(C)C)CC3)ccc1OCC2]

To a solution of piperazine-1-carboxylic acid tert-butyl ester (216 mg, 1.16 mmol) and NEt$_3$ (272 μL, 1.93 mmol) in DCM (30 mL) at 0° C. was added a suspension of 2-(2-isopropyl-2H-[1,2,4]triazol-3-yl)-4,5-dihydro-6-oxa-1,3a-diazabenzo[e]azulene-9-sulfonyl chloride from Example 121 (270 mg, 0.39 mmol) in DCM (20 mL) and the resulting mixture warmed to RT after 10 min then stirred for 30 min. The reaction mixture was diluted with DCM, washed with a saturated aqueous NaHCO$_3$ solution then dried (Na$_2$SO$_4$) and concentrated in vacuo. The resulting residue was purified by column chromatography (Si-PCC, gradient 0-5% MeOH in DCM) affording 4-[2-(2-Isopropyl-2H-[1,2,4]triazol-3-yl)-4,5-dihydro-6-oxa-1,3a-diazabenzo[e]azulene-9-sulfonyl]piperazine-1-carboxylic acid tert-butyl ester (196 mg, 93%) as a white solid. LCMS: R$_T$ 4.72 min [M+H]$^+$ 544.3. $^1$H NMR (DMSO, 400 MHz): δ 8.77 (1H, d, J=2.43 Hz), 8.01 (1H, s), 7.94 (1H, d, J=0.61 Hz), 7.63 (1H, dd, J=8.64, 2.44 Hz), 7.28 (1H, d, J=8.64 Hz), 5.75-5.71 (1H, m), 4.67-4.57 (4H, m), 3.44-3.38 (4H, m), 2.91 (4H, t, J=4.83 Hz), 1.50 (6H, d, J=6.62 Hz), 1.32 (9H, s)

Step 2: 2-(2-Isopropyl-2H-[1,2,4]triazol-3-yl)-9-(piperazine-1-sulfonyl)-4,5-dihydro-6-oxa-1,3a-diazabenzo[e]azulene

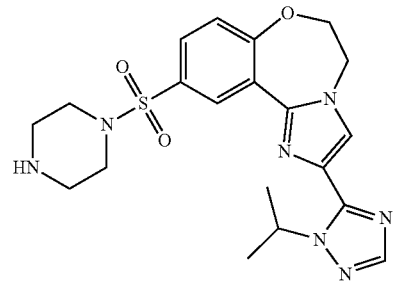 [SMILES: CC(C)n1ncnc1-c1cn2c(n1)-c1cc(S(=O)(=O)N3CCNCC3)ccc1OCC2]

A solution of 4-[2-(2-isopropyl-2H-[1,2,4]triazol-3-yl)-4,5-dihydro-6-oxa-1,3a-diazabenzo[e]azulene-9-sulfonyl]piperazine-1-carboxylic acid tert-butyl ester (175 mg, 0.32 mmol) in DCM (3 mL) was treated with TFA (3 mL) and the resulting mixture stirred at RT for 1 h then concentrated in vacuo. The resulting residues was loaded onto an Isolute® SCX-2 cartridge which was washed with MeOH and eluted with 2M NH$_3$/MeOH affording 2-(2-Isopropyl-2H-[1,2,4]triazol-3-yl)-9-(piperazine-1-sulfonyl)-4,5-dihydro-6-oxa-1,3a-diazabenzo[e]azulene (126 mg, 88%). LCMS: R$_T$ 2.20 and 0.32 min [M+H]$^+$ 444.3

Step 3

A mixture of 2-(2-isopropyl-2H-[1,2,4]triazol-3-yl)-9-(piperazine-1-sulfonyl)-4,5-dihydro-6-oxa-1,3a-diazabenzo[e]azulene (35 mg, 0.08 mmol), pentanone (25 μL, 0.24 mmol), AcOH (9 μL, 0.16 mmol) and 4 Å molecular sieves in DCE (2 mL) was stirred at RT for 1 h before the addition of sodium triacetoxyborohydride (33 mg, 0.16 mmol). The resulting mixture was stirred for 16 h before further pentanone (100 μL, 0.92 mmol) and sodium triacetoxyborohydride (198 mg, 0.96 mmol) were added. The mixture was stirred for 20 h then loaded onto an Isolute® SCX-2 cartridge which was washed with MeOH and the product eluted with 2M NH$_3$/MeOH. The resulting residue was purified by column chromatography (Si-PCC, gradient 0-10% MeOH in DCM) to afford 134 (10 mg, 25%) as a white solid. LCMS: R$_T$ 3.13 min [M+H]$^+$ 514.4. $^1$H NMR (CDCl$_3$, 400 MHz): δ 8.95 (1H, d, J=2.36 Hz), 7.88 (1H, s), 7.70 (1H, s), 7.65 (1H, dd, J=8.59, 2.37 Hz), 7.17 (1H, d, J=8.60 Hz), 5.94-5.85 (1H, m), 4.59-4.58 (2H, m), 4.52-4.51 (2H, m), 3.05 (4H, s), 2.61 (4H, s), 2.13-2.10 (1H, m), 1.60 (6H, d, J=6.64 Hz), 1.46-1.35 (2H, m), 1.29-1.27 (2H, m), 0.83 (6H, t, J=7.36 Hz)

Example 136

2-(1-isopropyl-1H-1,2,4-triazol-5-yl)-9-(2-(pyridin-4-yl)pyrrolidin-1-yl)-5,6-dihydroimidazo[1,2-d]pyrido[3,4-f][1,4]oxazepine 136

Step 1: 12-Chloro-9-oxa-3,6,13-triazatricyclo[8.4.0.0²,⁶]tetradeca-1(14),2,4,10,12-pentaene-4-carboxamide

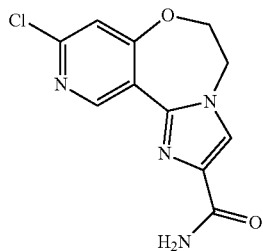 [SMILES: NC(=O)c1cn2c(n1)-c1cnc(Cl)cc1OCC2]

To a solution of 12-chloro-4-iodo-9-oxa-3,6,13-triazatricyclo[8.4.0.0²,⁶]tetradeca-1(14),2,4,10,12-pentaene (10.0 g, 28.7 mmol) in dry DMF (300 mL) was added Pd(PPh₃)₂Cl₂ (1.00 g, 1.44 mmol) and (Me₃Si)₂NH (86.1 mmol, 14.0 g). The mixture was stirred at 70° C. for 4 h under carbon monoxide atmosphere. After removal of the solvent, the residue was treated with ice-water. The solid was collected by filtration, dissolved in ethyl acetate (400 ml), dried over anhydrous Na₂SO₄, and concentrated to give 12-chloro-9-oxa-3,6,13-triazatricyclo[8.4.0.0²,⁶]tetradeca-1(14),2,4,10,12-pentaene-4-carboxamide (7.20 g, 97% yield), which was used in the next step without further purification. LCMS (ESI) m/z: 265.1 [M+H⁺]

Step 2: 12-Chloro-N-[(1E)-(dimethylamino)methylidene]-9-oxa-3,6,13-triazatricyclo[8.4.0.0²,⁶]tetradeca-1(14),2,4,10,12-pentaene-4-carboxamide

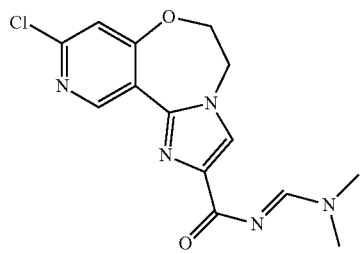 [SMILES: CN(C)/C=N/C(=O)c1cn2c(n1)-c1cnc(Cl)cc1OCC2]

To a solution of 12-chloro-9-oxa-3,6,13-triazatricyclo[8.4.0.0²,⁶]tetradeca-1(14),2,4,10,12-pentaene-4-carboxamide (0.380 mmol, 100 mg) in 1,4-dioxane (3 mL) was added DMF-DMA (1.14 mmol, 147 mg). The mixture was stirred at 100° C. for 1 hour under nitrogen atmosphere. Then solvent was evaporated under reduced pressure, the residue was washed by ether to give 12-chloro-N-[(1E)-(dimethylamino)methylidene]-9-oxa-3,6,13-triazatricyclo[8.4.0.0²,⁶]tetradeca-1(14),2,4,10,12-pentaene-4-carboxamide (80 mg, 68% yield), which was used in the next step without further purification. LCMS (ESI) m/z: 320.1 [M+H⁺]

Step 3: 12-Chloro-4-[1-(propan-2-yl)-1H-1,2,4-triazol-5-yl]-9-oxa-3,6,13-triazatricyclo[8.4.0.0²,⁶]tetradeca-1(14),2,4,10,12-pentaene

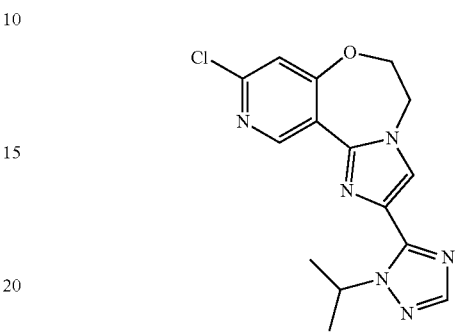

To a solution of 12-chloro-N-[(1E)-(dimethylamino)methylidene]-9-oxa-3,6,13-triazatricyclo[8.4.0.0²,⁶]tetradeca-1(14),2,4,10,12-pentaene-4-carboxamide (0.25 mmol, 80 mg) in acetic acid (3 mL) was added hydrochloric isopropylhydrazine (0.50 mmol, 5 mg). The mixture was stirred at 100° C. for 1 h under nitrogen atmosphere. After removal of the solvent, the residue was purified by reverse phase combiflash eluting with a 0-50% gradient of CH₃CN in 0.3% NH₄HCO₃ to give 12-chloro-4-[1-(propan-2-yl)-1H-1,2,4-triazol-5-yl]-9-oxa-3,6,13-triazatricyclo[8.4.0.0²,⁶]tetradeca-1(14),2,4,10,12-pentaene (50 mg, 61% yield). LCMS (ESI) m/z: 331.1 [M+H⁺]. ¹H NMR (500 MHz, DMSO-d₆): δ 9.29 (s, 1H), 8.02 (s, 1H), 7.94 (s, 1H), 7.24 (s, 1H), 5.86 (t, J=13.5 Hz, 1H), 4.68-4.65 (m, 2H), 4.61-4.59 (m, 2H), 1.49 (d, J=6.5 Hz, 6H)

Step 4

A mixture of 12-chloro-4-[1-(propan-2-yl)-1H-1,2,4-triazol-5-yl]-9-oxa-3,6,13-triazatricyclo[8.4.0.0²,⁶]tetradeca-1(14),2,4,10,12-pentaene (150 mg, 0.450 mmol), TEA (0.5 mL), and 4-(pyrrolidin-2-yl)pyridine (134 mg, 0.900 mmol) in NMP (0.5 mL) was stirred at 150° C. for 24 h under nitrogen atmosphere. The resulting mixture was purified by reverse phase combiflash eluting with a 0-50% gradient of CH₃CN in 0.3% NH₄HCO₃ to give 136, which was further purified by chiral HPLC (AD column, 30% EtOH (0.1% DEA) in n-Hexane isocratic) to separate the (R) and (S) enantiomers, 23 mg of one enantiomer and 28 mg of the other (26% total yield).

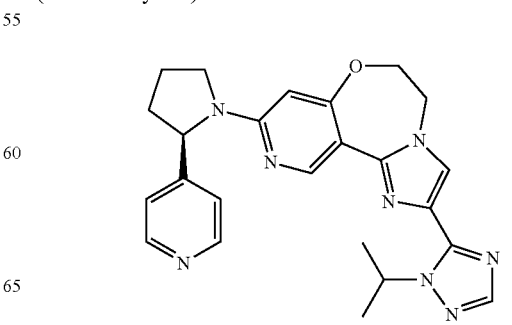

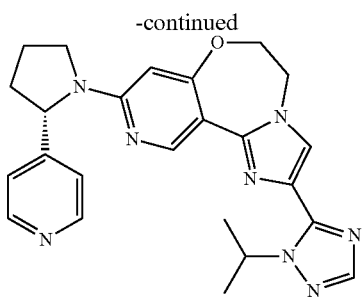

LCMS (ESI): RT=5.10 min, m/z: 443.2 [M+H⁺]. ¹H NMR (500 MHz, CDCl₃): δ 9.28 (s, 1H), 8.54-8.53 (m, 2H), 7.85 (s, 1H), 7.57 (s, 1H), 7.27 (s, 1H), 7.13 (d, J=6, 2H), 6.08-6.02 (m, 1H), 5.80 (s, 1H), 5.07 (d, J=4, 1H), 4.46 (d, J=4, 2H), 4.37-4.36 (m, 2H), 3.88 (d, J=8, 1H), 3.69 (d, J=8, 1H), 2.48 (t, J=14, 1H), 2.08-1.69 (m, 3H), 1.53 (d, J=6.5, 6H)

Example 137

2-(1-isopropyl-1H-1,2,4-triazol-5-yl)-94(1-methylpiperidin-2-yl)methoxy)-5,6-dihydroimidazo[1,2-d]pyrido[3,4-f][1,4]oxazepine 137

Step 1: (1-Methylpiperidin-2-yl)methyl 4-methylbenzenesulfonate

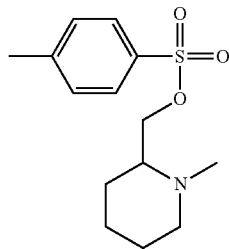 [SMILES: Cc1ccc(S(=O)(=O)OCC2CCCCN2C)cc1]

To a mixture of (1-methylpiperidin-2-yl)methanol (1.00 g, 7.75 mmol) in dry DMF (5.0 mL) at 0° C. was added NaH (620 mg, 15.5 mmol, 60% in mineral oil). After being stirred for 1 h, TsCl (2.96 g, 15.5 mmol) in DMF (1.0 mL) was added. The resulting mixture was further stirred at room temperature for 10 h and then poured into the ice-water (20 mL). The resulting mixture was extracted with EtOAc (2×50 mL). The organic layers were dried over Na₂SO₄ and evaporated to dryness to afford the crude product, which was purified by silica gel chromatography eluting with a 20% gradient of EtOAc in petroleum ether to afford (1-methylpiperidin-2-yl)methyl 4-methylbenzenesulfonate (800 mg, 36.5% yield). LCMS (ESI) m/z: 284.2 [M+H⁺]

Step 2

A mixture of 4-[1-(propan-2-yl)-1H-1,2,4-triazol-5-yl]-9-oxa-3,6,13-triazatricyclo[8.4.0.0²,⁶]tetradeca1(14),2,4,10,12-pentaen-12-ol (110 mg, 0.354 mmol), (1-methylpiperidin-2-yl)methyl 4-methylbenzenesulfonate (200 mg, 0.707 mmol), and K₂CO₃ (146 mg, 1.06 mmol) in acetonitrile (5.0 ml) was heated to reflux for 12 h. The solid was filtered off through Celite. The filtrate was concentrated to give the crude product, which was purified by prep-HPLC (Gilson GX 281, Shim-pack PRC-ODS 250 mm×20 mm×2, gradient: CH₃CN/10 mm/L NH₄HCO₃, 17 min) to afford 137 (12 mg, 8.0% yield). LCMS (ESI): RT=4.45 min, m/z: 424.4 [M+H⁺]. ¹H NMR (500 MHz, DMSO-d₆): δ 9.34 (s, 1H), 7.91 (s, 1H), 7.85 (s, 1H), 5.95-5.91 (m, 1H), 5.86 (s, 1H), 5.04-5.03 (m, 1H), 4.56-4.48 (m, 4H), 3.31 (s, 1H), 2.91-2.71 (m, 3H), 2.29-2.35 (m, 4H), 2.08-2.11 (m, 1H), 1.60-1.83 (m, 4H), 1.54-1.47 (m, 7H)

Example 138

2-(4-(2-(1-isopropyl-1H-1,2,4-triazol-5-yl)-5,6-dihydrobenzo[f]imidazo[1,2-d][1,4]oxazepin-10-ylsulfonyl)piperazin-1-yl)-2-methylpropan-1-ol 138

To a solution of 2-methyl-2-piperazin-1-ylpropan-1-ol (71 mg, 0.45 mmol) and NEt₃ (105 µL, 0.75 mmol) in DCM (10 mL) at 0° C. was added 2-(2-isopropyl-2H-[1,2,4]triazol-3-yl)-4,5-dihydro-6-oxa-1,3a-diazabenzo[e]azulene-9-sulfonyl chloride from Example 121 (97 mg, 0.15 mmol) and the resulting mixture warmed to RT after 10 min then stirred for 16 h. The reaction mixture was washed with a saturated aqueous NaHCO₃ solution then dried (Na₂SO₄) and concentrated in vacuo. The resulting residue was purified by column chromatography (Si-PCC, gradient 0-10% MeOH in DCM then C₁₈, gradient 10-40% MeOH in H₂O). The resulting residue was loaded onto an Isolute® SCX-2 cartridge which was washed with MeOH and the product eluted with 2M NH₃/MeOH then freeze-dried from MeCN/H₂O to afford 138 (20 mg, 26%) as a white solid. LCMS: R_T 2.86 min [M+H]⁺ 516.4. ¹H NMR (CDCl₃, 400 MHz): δ 8.95 (1H, d, J=2.37 Hz), 7.88 (1H, s), 7.69 (1H, s), 7.64 (1H, dd, J=8.60, 2.40 Hz), 7.19 (1H, d, J=8.61 Hz), 5.86-5.84 (1H, m), 4.62-4.57 (2H, m), 4.54-4.50 (2H, m), 3.28-3.11 (6H, m), 2.69 (4H, brd s), 1.60 (6H, d, J=6.63 Hz), 1.03 (6H, brd s)

Example 139

10-(1-tert-butylpiperidin-4-ylthio)-2-(1-isopropyl-1H-1,2,4-triazol-5-yl)-5,6-dihydrobenzo[f]imidazo[1,2-d][1,4]oxazepine 139

Step 1: 1-tert-Butylpiperidine-4-thiol

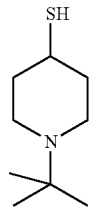

A solution of 1-tert-butylpiperidin-4-one (1.0 g, 6.44 mmol) in ⁱPrOH (10 mL) was stirred under an atmosphere of hydrogen sulfide for 65 h before sodium borohydride (367 mg, 9.70 mmol) was added and the mixture heated at 80° C. for 2 h. The reaction mixture was concentrated in vacuo and the resulting residue partitioned between Et₂O and H₂O. The aqueous phase was further extracted with EtOAc and the combined organic extracts dried (Na₂SO₄) and concentrated in vacuo to afford 1-tert-Butylpiperidine-4-thiol (907 mg, 81%) as a colourless oil. ¹H NMR (CDCl₃, 400 MHz): δ 4.03-4.01 (1H, m), 3.05-2.88 (2H, m), 2.81-2.60 (2H, m), 2.17-2.12 (2H, m), 2.09-1.92 (1H, m), 1.64-1.63 (2H, m), 1.47 (1H, s), 1.20 (3H, d, J=6.11 Hz), 1.14-0.98 (5H, m)

Step 2

A mixture of 9-bromo-2-(2-isopropyl-2H-[1,2,4]triazol-3-yl)-4,5-dihydro-6-oxa-1,3a-diazabenzo[e]azulene (100 mg, 0.27 mmol), 1-tert-butylpiperidine-4-thiol (120 mg, 0.69 mmol), $Pd_2(dba)_3$ (24 mg, 10 mol %), XantPhos (31 mg, 20 mol %) and DIPEA (186 µL, 1.07 mmol) in dioxane (3 mL) was purged with argon and heated at 120° C. for 40 min using microwave irradiation. The reaction mixture was diluted with DCM and purified by column chromatography (Si-PCC, gradient 0-20% MeOH in DCM then $C_{18}$, gradient 20-50% MeOH in $H_2O$). The resulting residue was loaded onto an Isolute® SCX-2 cartridge which was washed with MeOH and the product eluted with 2M $NH_3$/MeOH. The residue was triturated with $Et_2O$ affording 139 as a white solid (16 mg, 51%). LCMS: $R_T$ 3.11 min [M+H]$^+$ 467.4. $^1$H NMR (DMSO, 400 MHz): δ 8.54 (1H, d, J=2.35 Hz), 7.94 (1H, d, J=0.67 Hz), 7.77 (1H, s), 7.36 (1H, dd, J=8.49, 2.37 Hz), 7.02 (1H, d, J=8.48 Hz), 5.92-5.91 (1H, m), 4.55-4.49 (4H, m), 3.06-3.04 (3H, m), 2.30 (2H, t, J=11.23 Hz), 2.08-1.96 (2H, m), 1.65-1.64 (2H, m), 1.58 (6H, d, J=6.65 Hz), 1.08 (9H, s)

Example 140

10-(1-tert-butylpiperidin-4-ylsulfinyl)-2-(1-isopropyl-1H-1,2,4-triazol-5-yl)-5,6-dihydrobenzo[f]imidazo[1,2-d][1,4]oxazepine 140

To a solution of 9-(1-tert-butylpiperidin-4-ylsulfanyl)-2-(2-isopropyl-2H-[1,2,4]triazol-3-yl)-4,5-dihydro-6-oxa-1,3a-diazabenzo[e]azulene, also named as 10-(1-tert-butylpiperidin-4-ylthio)-2-(1-isopropyl-1H-1,2,4-triazol-5-yl)-5,6-dihydrobenzo[f]imidazo[1,2-d][1,4]oxazepine 139 (280 mg, 0.60 mmol) in DCM (30 mL) at 0° C. was added TFA (139 µL, 1.81 mmol) followed by a solution of m-CPBA (114 mg, 0.66 mmol) in DCM (10 mL). The resulting mixture was stirred for 30 min then washed with a saturated aqueous $NaHCO_3$ solution, dried ($Na_2SO_4$) and concentrated in vacuo. The resulting residue was purified by column chromatography (Si-PCC, gradient 0-12% 2M $NH_3$/MeOH in DCM then $C_{18}$, gradient 10-35% MeOH in $H_2O$) affording racemic 140 as a white solid (227 mg, 78%). LCMS: $R_T$ 2.55 min [M+H]$^+$ 483.4. $^1$H NMR (DMSO, 400 MHz): δ 8.77 (1H, d, J=2.30 Hz), 7.94 (1H, s), 7.81 (1H, s), 7.58 (1H, dd, J=8.59, 2.31 Hz), 7.29 (1H, d, J=8.58 Hz), 5.89-5.88 (1H, m), 4.59 (4H, s), 3.18 (2H, s), 2.23 (2H, s), 1.91 (1H, s), 1.87 (2H, s), 1.69-1.64 (2H, m), 1.56 (6H, dd, J=6.63, 3.37 Hz), 1.07 (9H, s)

Example 141

2-(1-isopropyl-1H-1,2,4-triazol-5-yl)-9-(2-(1-methylpiperidin-4-yl)pyrrolidin-1-yl)-5,6-dihydrobenzo[f]imidazo[1,2-d][1,4]oxazepine 141

A mixture of 8-bromo-2-(2-isopropyl-2H-[1,2,4]triazol-3-yl)-4,5-dihydro-6-oxa-1,3a-diazabenzo[e]azulene, also named as 9-bromo-2-(1-isopropyl-1H-1,2,4-triazol-5-yl)-5,6-dihydrobenzo[f]imidazo[1,2-d][1,4]oxazepine 95 (300 mg, 0.80 mmol), 1-methyl-4-pyrrolidin-2-ylpiperidine (338 mg, 2.00 mmol), NaO$^t$Bu (232 mg, 2.40 mmol) and Pd(P$^t$Bu$_3$)$_2$ (20 mg, 0.04 mmol) in toluene (6 mL) was heated at 110° C. for 3 h. The reaction mixture was loaded onto an Isolute® SCX-2 cartridge which was washed with MeOH and the product eluted with 2M $NH_3$/MeOH. The resulting residue was purified by column chromatography ($C_{18}$, gradient 10-65% MeOH in $H_2O$) then loaded onto an Isolute® SCX-2 cartridge which was washed with MeOH and the product eluted with 2M $NH_3$/MeOH. The resulting residue was freeze-dried from MeCN/$H_2O$ to afford 141 (20 mg, 16%) as a white solid. LCMS: $R_T$ 2.91 min [M+H]$^+$ 462.4. $^1$H NMR (DMSO, 400 MHz): δ 8.18 (1H, d, J=8.95 Hz), 7.87 (1H, s), 7.77 (1H, s), 6.49 (1H, dd, J=9.03, 2.41 Hz), 6.13 (1H, d, J=2.36 Hz), 5.94-5.93 (1H, m), 4.45-4.40 (4H, m), 3.74 (1H, s), 3.45-3.43 (1H, m), 3.14-3.11 (1H, m), 2.78 (2H, s), 2.12 (3H, s), 1.99-1.72 (5H, m), 1.71-1.51 (3H, m), 1.47 (6H, dd, J=6.60, 1.90 Hz), 1.33-1.31 (3H, m)

Example 142

10-(1-tert-butylpiperidin-4-ylsulfonyl)-2-(1-isopropyl-1H-1,2,4-triazol-5-yl)-5,6-dihydrobenzo[f]imidazo[1,2-d][1,4]oxazepine 142

To a solution of 9-(1-tert-butylpiperidin-4-ylsulfanyl)-2-(2-isopropyl-2H-[1,2,4]triazol-3-yl)-4,5-dihydro-6-oxa-1,3a-diazabenzo[e]azulene, also named as 10-(1-tert-butylpiperidin-4-ylthio)-2-(1-isopropyl-1H-1,2,4-triazol-5-yl)-5,6-dihydrobenzo[f]imidazo[1,2-d][1,4]oxazepine 139 (70 mg, 0.15 mmol) and TFA (34 µL, 0.45 mmol) in DCM (20 mL) at 0° C. was added a solution of m-CPBA (63 mg, 0.36 mmol) in DCM (6 mL) and the resulting mixture stirred for 1.5 h. The reaction mixture was washed with a saturated aqueous $NaHCO_3$ solution followed by $H_2O$, then dried ($Na_2SO_4$) and concentrated in vacuo. The resulting residue was purified by column chromatography (Si-PCC, gradient 0-25% MeOH in DCM then $C_{18}$, gradient 15-40% MeOH in $H_2O$). The resulting residue was loaded onto an Isolute® SCX-2 cartridge which was washed with MeOH and the product eluted with 2M $NH_3$/MeOH affording 142 as a white solid (39 mg, 51%). LCMS: $R_T$ 2.75 min [M+H]$^+$ 499.3. $^1$H NMR (DMSO, 400 MHz): δ 9.03 (1H, d, J=2.39 Hz), 7.94 (1H, s), 7.83 (1H, s), 7.76 (1H, dd, J=8.65, 2.40 Hz), 7.29 (1H, d, J=8.65 Hz), 5.90-5.89 (1H, m), 4.62-4.61 (4H, m), 3.12-3.10 (3H, m), 2.14 (2H, t, J=11.90 Hz), 2.07-2.03 (2H, m), 1.69-1.67 (2H, m), 1.58 (6H, d, J=6.64 Hz), 1.04 (9H, s)

Example 143

2-(1-isopropyl-1H-1,2,4-triazol-5-yl)-9-(1-(1-isopropylpiperidin-4-yl)ethoxy)-5,6-dihydrobenzo[f]imidazo[1,2-d][1,4]oxazepine 143

Step 1: 4-{1-[2-(2-Isopropyl-2H-[1,2,4]triazol-3-yl)-4,5-dihydro-6-oxa-1,3a-diazabenzo[e]azulen-8-yloxy]ethyl}piperidine-1-carboxylic acid benzyl ester

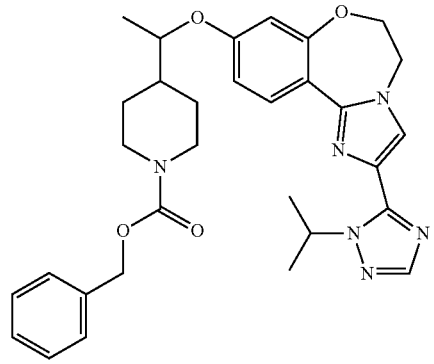 [SMILES: CC(Oc1ccc2c(c1)OCCn1cc(-c3ncnn3C(C)C)nc1-2)C1CCN(C(=O)OCc2ccccc2)CC1]

To a suspension of 2-(2-isopropyl-2H-[1,2,4]triazol-3-yl)-4,5-dihydro-6-oxa-1,3a-diazabenzo[e]azulen-8-ol (250 mg, 0.80 mmol), 4-(1-hydroxyethyl)piperidine-1-carboxylic acid benzyl ester (233 mg, 0.88 mmol) and PPh$_3$ (316 mg, 1.20 mmol) in dioxane (5 mL) was added DIAD (237 µL, 1.20 mmol) and the resulting yellow solution stirred at RT for 1 h. The reaction mixture was concentrated in vacuo and purified by column chromatography (Si-PCC, gradient 0-10% MeOH in TBME). The resulting residue was dissolved in EtOAc and washed with 1M NaOH, then dried ($Na_2SO_4$) and concentrated in vacuo affording 4-{1-[2-(2-Isopropyl-2H-[1,2,4]triazol-3-yl)-4,5-dihydro-6-oxa-1,3a-diazabenzo[e]azulen-8-yloxy]ethyl}piperidine-1-carboxylic acid benzyl ester (278 mg, 62%) as a white foam. LCMS: $R_T$ 4.08 min $[M+H]^+$ 557.5

Step 2: 2-(2-Isopropyl-2H-[1,2,4]triazol-3-yl)-8-(1-piperidin-4-ylethoxy)-4,5-dihydro-6-oxa-1,3a-diazabenzo[e]azulene

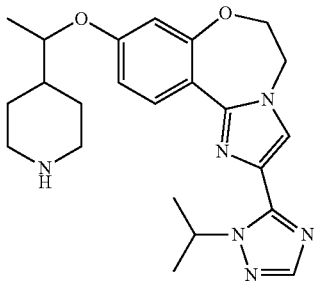 [SMILES: CC(Oc1ccc2c(c1)OCCn1cc(-c3ncnn3C(C)C)nc1-2)C1CCNCC1]

A suspension of 4-{1-[2-(2-isopropyl-2H-[1,2,4]triazol-3-yl)-4,5-dihydro-6-oxa-1,3a-diazabenzo[e]azulen-8-yloxy]ethyl}piperidine-1-carboxylic acid benzyl ester (278 mg, 0.50 mmol) and 10% Pd/C (150 mg) in EtOAc (10 mL) was stirred under an atmosphere of $H_2$ at RT for 1 h then heated at 50° C. for 3 h. The reaction mixture was filtered through Celite® and the filtrate concentrated in vacuo to afford 2-(2-Isopropyl-2H-[1,2,4]triazol-3-yl)-8-(1-piperidin-4-ylethoxy)-4,5-dihydro-6-oxa-1,3a-diazabenzo[e]azulene (211 mg, quantitative) as a colourless oil. LCMS: $R_T$ 2.26 min $[M+H]^+$ 423.4

Step 3

A mixture of 2-(2-isopropyl-2H-[1,2,4]triazol-3-yl)-8-(1-piperidin-4-ylethoxy)-4,5-dihydro-6-oxa-1,3a-diazabenzo[e]azulene (211 mg, 0.50 mmol), acetone (6 mL) and 10% Pd/C (150 mg) in MeOH (2 mL) was stirred under an atmosphere of $H_2$ at RT for 16 h. The reaction mixture was filtered through Celite® and the filtrate concentrated in vacuo. The resulting residue was purified by reverse phase HPLC (Phenomenex Gemini 5 µm C18, on a gradient 10-90%, 0.1% $HCO_2H$ acetonitrile/water) to afford 143 (161 mg, 69%). LCMS: $R_T$ 3.08 $[M+H]^+$ 465.4. $^1H$ NMR (DMSO, 400 MHz): δ 8.29 (1H, d, J=8.96 Hz), 8.23 (1H, s), 7.90 (1H, d, J=0.64 Hz), 7.85 (1H, s), 6.77 (1H, dd, J=8.99, 2.54 Hz), 6.57 (1H, d, J=2.51 Hz), 5.93-5.85 (1H, m), 4.48 (4H, s), 4.38-4.31 (1H, m), 2.97 (2H, d, J=11.01 Hz), 2.87-2.86 (1H, m), 2.30 (2H, t, J=11.50 Hz), 1.84 (1H, d, J=12.83 Hz), 1.67-1.63 (2H, m), 1.47 (6H, d, J=6.60 Hz), 1.44-1.29 (1H, m), 1.21 (3H, d, J=6.10 Hz), 1.03 (6H, d, J=6.56 Hz)

Example 144

(R)-2-(1-isopropyl-1H-1,2,4-triazol-5-yl)-9-(2-(pyrrolidin-1-ylmethyl)pyrrolidin-1-yl)-5,6-dihydrobenzo[f]imidazo[1,2-d][1,4]oxazepine 144

A mixture of 8-bromo-2-(2-isopropyl-2H-[1,2,4]triazol-3-yl)-4,5-dihydro-6-oxa-1,3a-diazabenzo[e]azulene, also named as 9-bromo-2-(1-isopropyl-1H-1,2,4-triazol-5-yl)-5,6-dihydrobenzo[f]imidazo[1,2-d][1,4]oxazepine 95 (200 mg, 0.27 mmol), (R)-pyrrolidynlmethylpyrrolidine (412 mg, 1.33 mmol), $K_3PO_4$ (228 mg, 0.53 mmol), CuI (20 mg, 0.05 mmol) and L-4-transhydroxyproline (14 mg, 0.11 mmol) in DMSO (1 mL) was heated at 100° C. for 18 h. The reaction mixture was loaded onto an Isolute® SCX-2 cartridge which was washed with MeOH and the product eluted with 2M $NH_3$/MeOH. The resulting residue was purified by column chromatography (Si-PCC, gradient 0-10% MeOH in DCM then $C_{18}$, gradient 5-45% MeOH in $H_2O$). The resulting residue was loaded onto an Isolute® SCX-2 cartridge which was washed with MeOH and the product eluted with 2M $NH_3$/MeOH. The resulting residue was freeze-dried from MeCN/$H_2O$ to afford 144 (41 mg, 34%) as a white solid. LCMS: $R_T$ 4.78 min $[M+H]^+$ 448.4. $^1H$ NMR (DMSO, 400 MHz): δ 8.19 (1H, d, J=8.92 Hz), 7.88 (1H, d, J=0.63 Hz), 7.77 (1H, s), 6.45 (1H, dd, J=9.00, 2.43 Hz), 6.13 (1H, d, J=2.38 Hz), 5.96-5.93 (1H, m), 4.47-4.36 (4H, m), 3.89-3.81 (1H, m), 3.40-3.38 (1H, m), 3.14-3.04 (1H, m), 2.64-2.57 (2H, m), 2.50-2.34 (4H, m), 1.98-1.96 (4H, m), 1.74-1.66 (4H, m), 1.47 (6H, d, J=6.61 Hz)

Example 145

1-(1-(2-(1-isopropyl-1H-1,2,4-triazol-5-yl)-5,6-dihydroimidazo[1,2-d]pyrido[3,4-f][1,4]oxazepin-9-yl)pyrrolidin-2-yl)-N,N-dimethylmethanamine 145

Step 1: 1-{4-[1-(Propan-2-yl)-1H-1,2,4-triazol-5-yl]-9-oxa-3,6,13-triazatricyclo[8.4.0.0$^{2,6}$]tetradeca-1(14),2,4,10,12-pentaen-12-yl}pyrrolidine-2-carbaldehyde

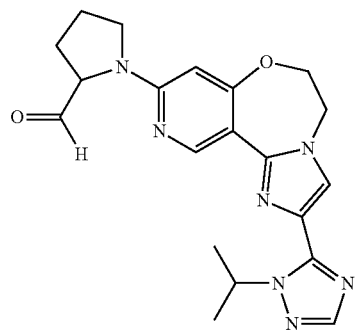 [SMILES: CC(C)n1ncnc1-c1cn2c(n1)-c1cnc(N3CCCC3C=O)cc1OCC2]

A mixture of 12-chloro-4-[1-(propan-2-yl)-1H-1,2,4-triazol-5-yl]-9-oxa-3,6,13-triazatricyclo[8.4.0.0$^{2,6}$]tetradeca-1(14),2,4,10,12-pentaene from Example 135 (500 mg, 1.51 mmol) and pyrrolidin-2-yl-methanol (1.00 g, 9.89 mmol) was stirred at 160° C. for 4 hr. The resulting mixture was poured into water and extracted with ethyl acetate, washed with brine, dried over $MgSO_4$, filtered, and evaporated to give the crude product, which was purified by reverse phase combiflash eluting with 0-50% gradient of $CH_3CN$ in 0.5% $NH_4HCO_3$ to give (1-{4-[1-(propan-2-yl)-1H-1,2,4-triazol-5-yl]-9-oxa-3,6,13-triazatricyclo[8.4.0.0$^{2,6}$]tetradeca-1(14), 2,4,10,12-pentaen-12-yl}pyrrolidin-2-yl)methanol as white solid (345 mg, 58% yield). LCMS (ESI) m/z: 396.2 [M+H$^+$].

A mixture of (1-{4-[1-(propan-2-yl)-1H-1,2,4-triazol-5-yl]-9-oxa-3,6,13-triazatricyclo[8.4.0.0$^{2,6}$]tetradeca-1(14),2,4,10,12-pentaen-12-yl}pyrrolidin-2-yl)methanol (173 mg, 0.436 mmol), 2-iodobenzoic acid (305 mg, 1.09 mmol) in ethyl acetate (10.0 mL) was refluxed for 6 hr. After filtration, the filtrated was evaporated to afford 1-{4-[1-(propan-2-yl)-1H-1,2,4-triazol-5-yl]-9-oxa-3,6,13-triazatricyclo[8.4.0.0$^{2,6}$]tetradeca-1(14),2,4,10,12-pentaen-12-yl}pyrrolidine-2-carbaldehyde (160 mg, 92% yield) as pale yellow solid. LCMS (ESI) m/z: 394.3 [M+H$^+$].

Step 2

A mixture of 8-(2-carbaldehyde-1-pyrrolidin-)-2-(2-isopropyl-2H-[1,2,4]triazol-3-yl)-4,5-dihydro-6-oxa-1,3a,9-triaza-benzo[e]azulene (150 mg, 1.00 eq), dimethylamine hydrochloride (93.0 mg, 1.14 mmol), and Ti(Oi-Pr)$_4$ (325 mg, 1.14 mmol) in EtOH was stirred at room temperature for 30 min. NaBH$_3$CN (129 mg, 1.14 mmol) was added and stirred for 16 hr. After removal of the solvent, several drops of water were added. The solid was filtered off and the filtrated was evaporated. The residue was purified by reverse phase combiflash eluting with 0-40% gradient of CH$_3$CN in 0.5% NH$_4$HCO$_3$, to give 145, which was further purified by chiral HPLC (AD column, 30% EtOH (0.1% DEA) in n-Hexane isocratic) to give (R) and (S) enantiomers, 6 mg of one enantiomer and 8 mg of the other (25% total yield).

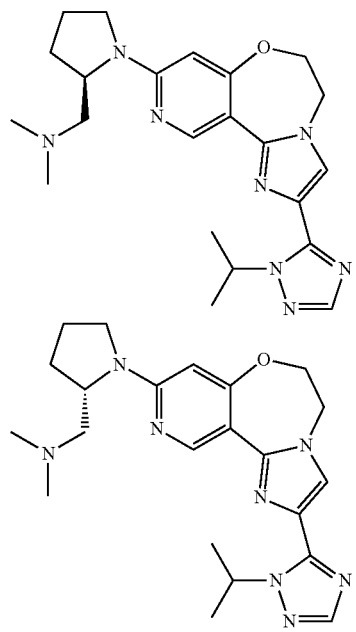

LCMS (ESI): R$_T$=4.40 min, m/z: 423.3 [M+H$^+$]. $^1$H-NMR (500 MHz, DMSO-d$_6$): δ 9.08 (s, 1H), 7.90 (s, 1H), 7.84 (s, 1H), 5.96-5.92 (m, 2H), 4.52-4.48 (m, 4H), 4.15 (s, 1H), 3.49-3.45 (m, 1H), 3.28-3.25 (m, 1H), 2.36 (s, 1H), 2.25 (m, 7H), 2.05-1.99 (m, 2H), 1.97-1.87 (m, 2H), 1.48 (s, 6H)

Example 146

2-(1-isopropyl-1H-1,2,4-triazol-5-yl)-10-(1-(4-methylpiperazin-1-yl)ethyl)-5,6-dihydrobenzo[f]imidazo[1,2-d][1,4]oxazepine 146

Step 1: 13-Bromo-9-oxa-3,6-diazatricyclo[8.4.0.0$^{2,6}$]tetradeca1(14),2,4,10,12-pentaene-4-carboxamide

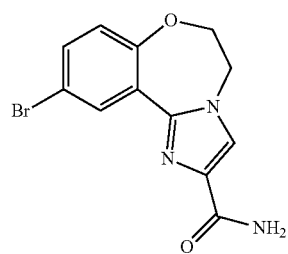 [SMILES: NC(=O)c1cn2c(n1)-c1cc(Br)ccc1OCC2]

To a solution of 13-bromo-4-iodo-9-oxa-3,6-diazatricyclo[8.4.0.0$^{2,6}$]tetradeca1(14),2,4,10,12-pentaene (5.0 g, 0.013 mol) in DMF (50 mL) was added hexamethyldisilazane (16 mL, 0.077 mol) and Pd(PPh$_3$)$_2$Cl$_2$ (0.45 g, 0.639 mmol). After being purged with CO three times, the mixture was heated at 70° C. for 3 h. After removal of the solvent, water (100 mL) was added. The solid was collected by filtration, washed with water and dried in vacuo to afford 13-Bromo-9-oxa-3,6-diazatricyclo[8.4.0.0$^{2,6}$]tetradeca1(14),2,4,10,12-pentaene-4-carboxamide (3.75 g, 95% yield) as a yellow solid. LCMS (ESI) m/z: 309.1 [M+H$^+$]

Step 2: 13-Bromo-N-[(1E)-(dimethylamino)methylidene]-9-oxa-3,6-diazatricyclo[8.4.0.0$^{2,6}$]tetradeca1(14),2,4,10,12-pentaene-4-c arboxamide

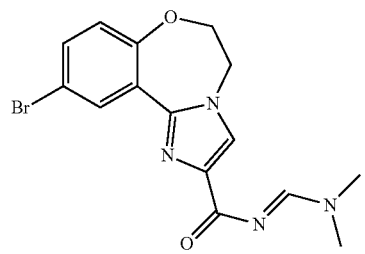

To a solution of 13-bromo-9-oxa-3,6-diazatricyclo[8.4.0.0$^{2,6}$]tetradeca1(14),2,4,10,12-pentaene-4-carboxamide (2.0 g, 6.5 mmol) in dioxane (30 mL) was added DMF-DMA (2.6 mL, 19 mmol). The reaction mixture was heated at 100° C. for 1 h. The solvent was removed under reduce pressure and the residue was triturated with hot diethyl ether. The solid was collected by filtration, washed with diethyl ether and dried in vacuo to afford 13-Bromo-N-[(1E)-(dimethylamino)methylidene]-9-oxa-3,6-diazatricyclo[8.4.0.0$^{2,}$

275

6]tetradeca1(14),2,4,10,12-pentaene-4-carboxamide (2.2 g, 93% yield) as a yellow solid. LCMS (ESI) m/z: 365.1 [M+H$^+$]

Step 3: 13-Bromo-4-[1-(propan-2-yl)-1H-1,2,4-triazol-5-yl]-9-oxa-3,6-diazatricyclo[8.4.0.0$^{2,6}$]tetradeca1(14),2,4,10,12-pentaene

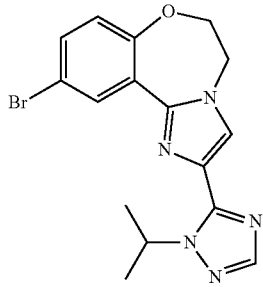 [SMILES: CC(C)n1ncnc1-c1cn2c(n1)-c1cc(Br)ccc1OCC2]

To a solution of 13-bromo-N-[(1E)-(dimethylamino)methylidene]-9-oxa-3,6-diazatricyclo[8.4.0.0$^{2,6}$]tetradeca1(14),2,4,10,12-pentaene-4-carboxamide (2.2 g, 6.1 mmol) in AcOH (20 mL) was added isopropylhydrazine hydrochloride (0.73 g, 6.6 mmol). The mixture was heated at 100° C. for 1 h. Most of the solvent was removed and water (50 mL) was added. The solid was collected by filtration, washed with water and dried in vacuo to afford 13-Bromo-4-[1-(propan-2-yl)-1H-1,2,4-triazol-5-yl]-9-oxa-3,6-diazatricyclo[8.4.0.0$^{2,6}$]tetradeca1(14),2,4,10,12-pentaene, also named as 10-bromo-2-(1-isopropyl-1H-1,2,4-triazol-5-yl)-5,6-dihydrobenzo[f]imidazo[1,2-d][1,4]oxazepine (1.8 g, 74% yield) as a yellow solid. LCMS (ESI) m/z: 376.1 [M+H$^+$].

Step 4: N-Methoxy-N-methyl-4-[1-(propan-2-yl)-1H-1,2,4-triazol-5-yl]-9-oxa-3,6-diazatricyclo[8.4.0.0$^{2,6}$]tetradeca1(14),2,4,10,12-pentaene-13-carboxamide

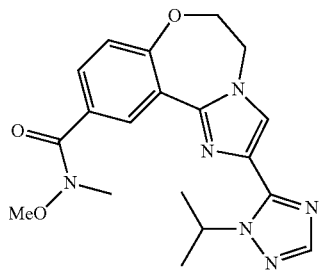 [SMILES: CON(C)C(=O)c1ccc2c(c1)-c1nc(-c3ncnn3C(C)C)cn1CCO2]

To a round bottom flask was added 13-bromo-4-[1-(propan-2-yl)-1H-1,2,4-triazol-5-yl]-9-oxa-3,6-diazatricyclo[8.4.0.0$^{2,6}$]tetradeca1(14),2,4,10,12-pentaene (1.6 g, 4.3 mmol), N,O-dimethylhydroxylamine hydrochloride (0.62 g, 6.4 mmol), Pd(OAc)$_2$ (95 mg, 0.43 mmol), Xantphos (0.49 g, 0.85 mmol), TEA (1.3 g, 13 mmol) and toluene (20 mL). After being purged with CO three times, the mixture was heated at 80° C. overnight. The solid was filtered off, the filtrate was concentrated and purified by silica gel chromatography eluting with EtOAc/petroleum ether (1:1) to give N-Methoxy-N-methyl-4-[1-(propan-2-yl)-1H-1,2,4-triazol-5-yl]-9-oxa-3,6-diazatricyclo[8.4.0.0$^{2,6}$]tetradeca1(14),2,4,10,12-

276 pentaene-13-carboxamide (800 mg, 50% yield) as a yellow solid. LCMS (ESI) m/z: 383.3 [M+H$^+$].

Step 5: 1-{4-[1-(Propan-2-yl)-1H-1,2,4-triazol-5-yl]-9-oxa-3,6-diazatricyclo[8.4.0.0$^{2,6}$]tetradeca1(14),2,4,10,12-pentaen-13-yl}ethan-1-one

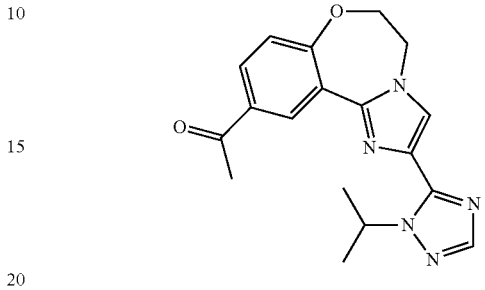

To a solution of N-methoxy-N-methyl-4-[1-(propan-2-yl)-1H-1,2,4-triazol-5-yl]-9-oxa-3,6-diazatricyclo[8.4.0.0$^{2,6}$]tetradeca1(14),2,4,10,12-pentaene-13-carboxamide (800 mg, 2.09 mmol) in THF (80 mL) was added methylmagnesium chloride (3.5 mL, 10.5 mmol) dropwise at 0° C. The mixture was further stirred at 0° C. for 1 h. After being quenched with aqueous NH$_4$Cl (20 mL), most of THF was removed by rotate evaporate. The residue was extracted with ethyl acetate (3×20 mL), washed with water (3×20 mL), and sat. NaCl (20 mL). The organic phase was dried and concentrated to give the crude product, which was purified by silica gel chromatography eluting with EtOAc/petroleum ether (1:1) to give 1-{4-[1-(Propan-2-yl)-1H-1,2,4-triazol-5-yl]-9-oxa-3,6-diazatricyclo[8.4.0.0$^{2,6}$]tetradeca1(14),2,4,10,12-pentaen-13-yl}ethan-1-one (560 mg, 80% yield) as a white solid. LCMS (ESI) m/z: 338.2 [M+H$^+$]

Step 6: 1-{4-[1-(Propan-2-yl)-1H-1,2,4-triazol-5-yl]-9-oxa-3,6-diazatricyclo[8.4.0.0$^{2,6}$]tetradeca1(14),2,4,10,12-pentaen-13-yl}ethan-1-ol

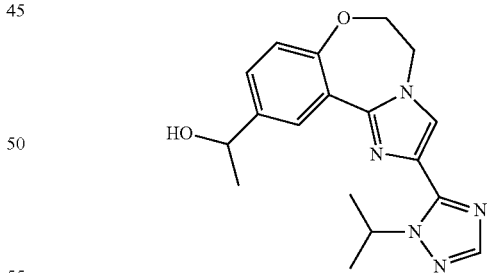

To a solution of 1-{4-[1-(propan-2-yl)-1H-1,2,4-triazol-5-yl]-9-oxa-3,6-diazatricyclo[8.4.0.0$^{2,6}$]tetradeca1(14),2,4,10,12-pentaen-13-yl}ethan-1-one (500 mg, 1.48 mmol) in THF (50 mL) was added LiAlH$_4$ (0.282 g, 7.37 mmol), then the mixture was heated at 60° C. for 1 h. After cooling to room temperature, the reaction was quenched with a piece of ice cube. The solid was filtered off and washed with ethyl acetate (3×10 mL). The combined filtrate was concentrated to give the crude product, which was purified by silica gel chromatography eluting with DCM/MeOH (50:1) to give 1-{4-[1-(Propan-2-yl)-1H-1,2,4-triazol-5-yl]-9-oxa-3,6-diazatricyclo[8.4.0.0²,⁶]tetradeca1(14),2,4,10,12-pentaen-13-yl}ethan-1-ol (420 mg, 83% yield) as a white solid. LCMS (ESI) m/z: 340.3 [M+H⁺].

Step 7: 1-{4-[1-(Propan-2-yl)-1H-1,2,4-triazol-5-yl]-9-oxa-3,6-diazatricyclo[8.4.0.0²,⁶]tetradeca1(14),2,4,10,12-pentaen-13-yl}ethyl methanesulfonate

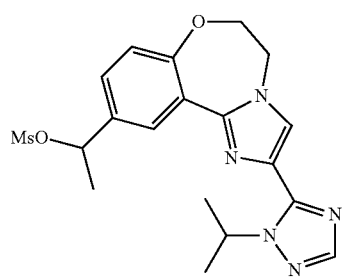 [SMILES: CC(OS(C)(=O)=O)c1ccc2c(c1)-c1nc(-c3ncnn3C(C)C)cn1CCO2]

To a solution of 1-{4-[1-(propan-2-yl)-1H-1,2,4-triazol-5-yl]-9-oxa-3,6-diazatricyclo[8.4.0.0²,⁶]tetradeca1(14),2,4,10,12-pentaen-13-yl}ethan-1-ol (200 mg, 0.590 mmol) in DCM (20 mL) at 0° C. was added TEA (296 mg, 2.93 mmol) and MsCl (136 mg, 1.19 mmol). The reaction mixture was stirred 0° C. for 2 h and then allowed to warm to room temperature. The reaction was quenched with sat. NaHCO₃ (10 mL), the resultant mixture was washed with sat. NaCl (20 mL). The organic phase was dried and concentrated to afford 1-{4-[1-(Propan-2-yl)-1H-1,2,4-triazol-5-yl]-9-oxa-3,6-diazatricyclo[8.4.0.0²,⁶]tetradeca1(14),2,4,10,12-pentaen-13-yl}ethyl methanesulfonate (246 mg, 100% yield) as a brown solid, which was directly used in next step without further purification.

Step 8

A mixture of 1-{4-[1-(propan-2-yl)-1H-1,2,4-triazol-5-yl]-9-oxa-3,6-diazatricyclo[8.4.0.0²,⁶]tetradeca-1(14),2,4,10,12-pentaen-13-yl}ethyl methanesulfonate (246 mg, 0.590 mmol) in 1-methylpiperazine (25 mL) was heated at 90° C. for 16 h. The solvent was removed and the residue was purified by Combi-flash eluting with a 5-95% gradient of CH₃CN in 0.3% NH₄HCO₃ to give 146. Separation of the enantiomers and further purification by chiral HPLC (AY-H column, 5% EtOH isocratic) gave: 44.3 mg of one enantiomer and 40.0 mg of the other (34% total yield).

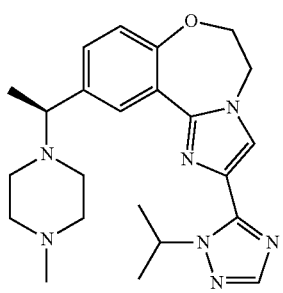

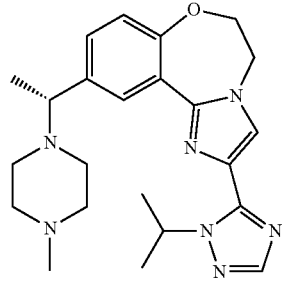

LCMS (ESI): RT=4.67 min, m/z: 422.4 [M+H⁺]. ¹H NMR (500 MHz, MeOD-d₄) δ 8.44-8.43 (d, J=2.0 Hz, 1H), 7.95 (s, 1H), 7.77 (s, 1H), 7.29-7.27 (dd, J=8.0, 2.0 Hz, 1H), 7.03-7.02 (d, J=8.0 Hz, 1H), 5.95 (m, 1H), 4.54-4.49 (m, 4H), 3.48 (m, 1H), 2.60-2.20 (m, 11H), 1.59 (d, J=6.5 Hz, 6H), 1.42 (d, J=6.5 Hz, 3H)

Example 149

(S)-10-(1-(4-tert-butylpiperazin-1-yl)ethyl)-2-(1-isopropyl-1H-1,2,4-triazol-5-yl)-5,6-dihydrobenzo[f]imidazo[1,2-d][1,4]oxazepine 149

Step 1: 13-Bromo-9-oxa-3,6-diazatricyclo[8.4.0.0²,⁶]tetradeca1(14),2,4,10,12-pentaene-4-carboxamide

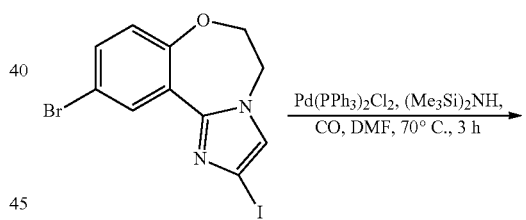

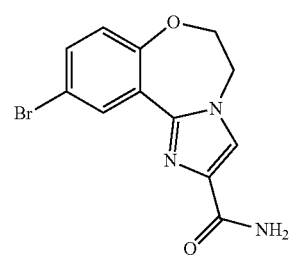

To a solution of 13-bromo-4-iodo-9-oxa-3,6-diazatricyclo[8.4.0.0²,⁶]tetradeca1(14),2,4,10,12-pentaene (5.0 g, 0.013 mol) in DMF (50 mL) was added hexamethyldisilazane (16 mL, 0.077 mol) and Pd(PPh₃)₂Cl₂ (0.45 g, 0.639 mmol). After being purged with CO three times, the mixture was heated at 70° C. for 3 h. After removal of the solvent, water (100 mL) was added. The solid was collected by filtration, washed with water, and dried in vacuo to afford the title compound (3.8 g, 95% yield) as a yellow solid. LCMS m/z [M+H]+ 309.1.

Step 2: 13-Bromo-N-[(1E)-(dimethylamino)methylidene]-9-oxa-3,6-diazatricyclo[8.4.0.0²,⁶]tetradeca1(14),2,4,10,12-pentaene-4-carboxamide

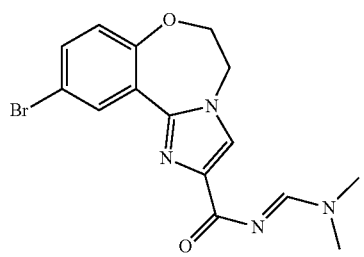 [SMILES: CN(C)/C=N/C(=O)c1cn2c(n1)-c1cc(Br)ccc1OCC2]

To a solution of 13-bromo-9-oxa-3,6-diazatricyclo[8.4.0.0²,⁶]tetradeca1(14),2,4,10,12-pentaene-4-carboxamide (2.0 g, 6.5 mmol) in dioxane (30 mL) was added DMF-DMA (2.6 mL, 19 mmol). The reaction mixture was heated at 100° C. for 1 h. The solvent was removed under reduce pressure and the residue was triturated with hot diethyl ether. The solid was collected by filtration, washed with diethyl ether, and dried in vacuo to afford the title compound (2.2 g, 93% yield) as a yellow solid. LCMS m/z [M+H]+ 365.1

Step 3: 13-Bromo-4-[1-(propan-2-yl)-1H-1,2,4-triazol-5-yl]-9-oxa-3,6-diazatricyclo[8.4.0.0²,⁶]tetradeca1(14),2,4,10,12-pentaene

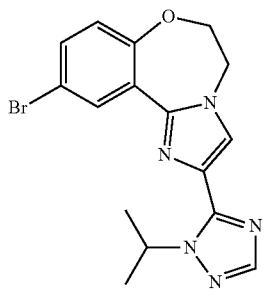 [SMILES: CC(C)n1ncnc1-c1cn2c(n1)-c1cc(Br)ccc1OCC2]

To a solution of 13-bromo-N-[(1E)-(dimethylamino)methylidene]-9-oxa-3,6-diazatricyclo[8.4.0.0²,⁶]tetradeca1(14),2,4,10,12-pentaene-4-carboxamide (2.2 g, 6.1 mmol) in AcOH (20 mL) was added isopropylhydrazine hydrochloride (0.73 g, 6.6 mmol). The mixture was heated at 100° C. for 1 h. Most of the solvent was removed and water (50 mL) was added. The solid was collected by filtration, washed with water, and dried in vacuo to afford the title compound (1.8 g, 74% yield) as a yellow solid. LCMS m/z [M+H]+ 376.1.

Step 4: N-Methoxy-N-methyl-4-[1-(propan-2-yl)-1H-1,2,4-triazol-5-yl]-9-oxa-3,6-diazatricyclo[8.4.0.0²,⁶]tetradeca1(14),2,4,10,12-pentaene-13-carboxamide

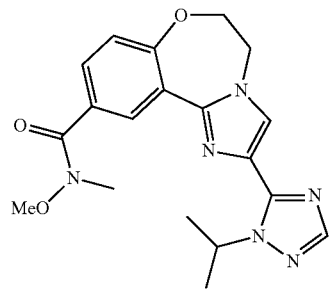 [SMILES: CON(C)C(=O)c1ccc2c(c1)-c1nc(-c3ncnn3C(C)C)cn1CCO2]

To a round bottom flask was added 13-bromo-4-[1-(propan-2-yl)-1H-1,2,4-triazol-5-yl]-9-oxa-3,6-diazatricyclo[8.4.0.0²,⁶]tetradeca1(14),2,4,10,12-pentaene (1.6 g, 4.3 mmol), N,O-dimethylhydroxylamine hydrochloride (0.62 g, 6.4 mmol), Pd(OAc)₂ (95 mg, 0.43 mmol), Xantphos (0.49 g, 0.85 mmol), TEA (1.3 g, 13 mmol) and toluene (20 mL). After being purged with CO three times, the mixture was heated at 80° C. overnight. The solid was filtered off. The filtrate was concentrated and purified by silica gel chromatography using 50% EtOAc in petroleum ether as eluant to give the desired product (800 mg, 50% yield) as a yellow solid. LCMS m/z [M+H]+ 383.3

Step 5: 1-{4-[1-(Propan-2-yl)-1H-1,2,4-triazol-5-yl]-9-oxa-3,6-diazatricyclo[8.4.0.0²,⁶]tetradeca1(14),2,4,10,12-pentaen-13-yl}ethan-1-one

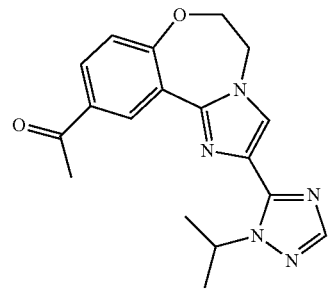 [SMILES: CC(=O)c1ccc2c(c1)-c1nc(-c3ncnn3C(C)C)cn1CCO2]

To a solution of N-methoxy-N-methyl-4-[1-(propan-2-yl)-1H-1,2,4-triazol-5-yl]-9-oxa-3,6-diazatricyclo[8.4.0.0²,⁶]tetradeca1(14),2,4,10,12-pentaene-13-carboxamide (800 mg, 2.09 mmol) in THF (80 mL) was added methylmagnesium chloride (3.50 mL, 10.5 mmol) dropwise at 0° C. The mixture was further stirred at 0° C. for 1 h. After being quenched with aqueous NH₄Cl (20 mL), most of THF was removed. The residue was extracted with ethyl acetate (3×20 mL), washed with water (3×20 mL), and brine (20 mL). The organic phase was dried and concentrated to give the crude product, which was purified by silica gel chromatography using 50% EtOAc in petroleum ether as eluant to give the desired product (560 mg, 80% yield) as a white solid. LCMS m/z [M+H]+ 338.2

Step 6: 1-{4-[1-(Propan-2-yl)-1H-1,2,4-triazol-5-yl]-9-oxa-3,6-diazatricyclo[8.4.0.0²,⁶]tetradeca1(14),2,4,10,12-pentaen-13-yl}ethan-1-ol

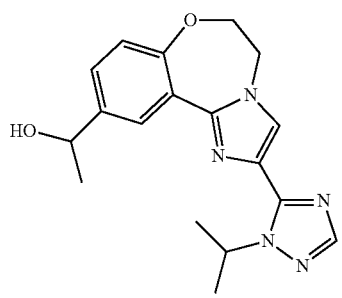 [SMILES: CC(O)c1ccc2c(c1)-c1nc(-c3ncnn3C(C)C)cn1CCO2]

To a solution of 1-{4-[1-(propan-2-yl)-1H-1,2,4-triazol-5-yl]-9-oxa-3,6-diazatricyclo[8.4.0.0²,⁶]tetradeca1(14),2,4,10,12-pentaen-13-yl}ethan-1-one (500 mg, 1.48 mmol) in THF (50 mL) was added LiAlH₄ (0.282 g, 7.37 mmol). The mixture was heated at 60° C. for 1 h. After cooling to room temperature, the reaction was quenched with a piece of ice cube. The solid was filtered off and washed with ethyl acetate (3×10 mL). The combined filtrate was concentrated to give the crude product, which was purified by silica gel chromatography using 2% MeOH in DCM as eluant to give the desired product (420 mg, 83% yield) as a white solid. LCMS m/z [M+H]+ 340.3

Step 7: 1-{4-[1-(Propan-2-yl)-1H-1,2,4-triazol-5-yl]-9-oxa-3,6-diazatricyclo[8.4.0.0²,⁶]tetradeca1(14),2,4,10,12-pentaen-13-yl}ethyl methanesulfonate

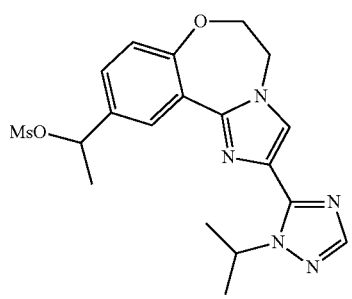 [SMILES: CC(OS(C)(=O)=O)c1ccc2c(c1)-c1nc(-c3ncnn3C(C)C)cn1CCO2]

To a solution of 1-{4-[1-(propan-2-yl)-1H-1,2,4-triazol-5-yl]-9-oxa-3,6-diazatricyclo[8.4.0.0²,⁶]tetradeca1(14),2,4,10,12-pentaen-13-yl}ethan-1-ol (200 mg, 0.590 mmol) in DCM (20 mL) at 0° C. was added TEA (296 mg, 2.93 mmol) and MsCl (136 mg, 1.19 mmol). The reaction mixture was stirred 0° C. for 2 h and then allowed to warm to room temperature. The reaction was quenched with sat. NaHCO₃ (10 mL) and the resultant mixture was further washed with brine (20 mL). The organic phase was then dried and concentrated to afford the crude product (246 mg, 100% yield) as a brown solid, which was directly used in next step without further purification.

Step 8

A mixture of 1-{4-[1-(propan-2-yl)-1H-1,2,4-triazol-5-yl]-9-oxa-3,6-diazatricyclo[8.4.0.0²,⁶]tetradeca1(14),2,4,10,12-pentaen-13-yl}ethyl methanesulfonate from Example 146 (140 mg, 0.340 mmol) and 1-tert-butylpiperazine (238 mg, 1.70 mmol) in 1,4-dioxane (4 mL) was stirred at 90° C. for 16 h under nitrogen atmosphere. After concentration, the residue was purified by reverse phase Combiflash eluting with a 0-50% gradient of CH₃CN in 0.3% NH₄HCO₃ to give racemic 10-(1-(4-tert-butylpiperazin-1-yl)ethyl)-2-(1-isopropyl-1H-1,2,4-triazol-5-yl)-5,6-dihydrobenzo[f]imidazo[1,2-d][1,4]oxazepine. Further purification and separation of enantiomers was conducted by chiral HPLC (OD-H column, 2% EtOH (0.1% DEA) in n-hexane isocratic) to give a first eluting peak, 26 mg of 149 and a second eluting peak, 27 mg of 150 (34% total yield)

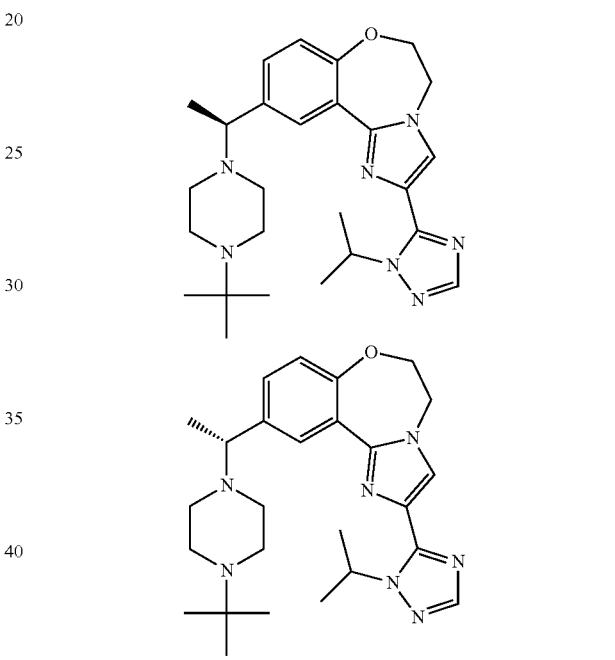

149: First eluting peak, 26 mg, 17% yield. >98% ee (15.94 min, OD-H, 2% EtOH (0.1% DEA) in n-hexane isocratic, 20 min). ¹H NMR (500 MHz, DMSO-d₆) δ 8.39 (d, J=2 Hz, 1H), 7.92 (s, 2H), 7.21 (q, J=10.5 Hz, 1H), 6.99 (d, J=8 Hz, 1H), 5.84 (t, J=13 Hz, 1H), 4.50 (q, J=20.5 Hz, 4H), 3.42 (d, J=7 Hz, 1H), 2.54-2.36 (m, 8H), 1.50 (t, J=14 Hz, 6H), 1.29 (d, J=14 Hz, 3H), 0.96 (s, 9H). LCMS m/z [M+H]+ 464.4. LCMS 10 MIN CAD GRADIENT, 1.2 ml/min on Agilent 1200/G6110 System. Purity is 100% by UV 254.

Example 150

(R)-10-(1-(4-tert-butylpiperazin-1-yl)ethyl)-2-(1-isopropyl-1H-1,2,4-triazol-5-yl)-5,6-dihydrobenzo[f]imidazo[1,2-d][1,4]oxazepine 150 Following Example 149, 150 was prepared as the second eluting peak, 27 mg, 17% yield. >93% ee (19.33 min, OD-H, 2% EtOH (0.1% DEA) in n-hexane isocratic, 22.5 min). ¹H NMR (500 MHz, DMSO-d₆) δ 8.39 (d, J=2 Hz, 1H), 7.92 (s, 2H), 7.21 (q, J=10.5 Hz, 1H), 6.99 (d, J=8 Hz, 1H), 5.84 (t, J=13 Hz, 1H), 4.50 (q, J=20.5 Hz, 4H), 3.42 (d, J=7 Hz, 1H), 2.54-2.36 (m, 8H), 1.50 (t, J=14 Hz, 6H), 1.29 (d, J=14 Hz, 3H), 0.96 (s, 9H). LCMS m/z [M+H]+

Example 152

2-(1-(1-(2-(1-isopropyl-1H-1,2,4-triazol-5-yl)-5,6-dihydrobenzo[f]imidazo[1,2-d][1,4]oxazepin-10-yl)ethyl)piperidin-4-yl)propan-2-ol 152

To a solution of 1-{4-[1-(propan-2-yl)-1H-1,2,4-triazol-5-yl]-9-oxa-3,6-diazatricyclo[8.4.0.0$^{2,6}$]tetradeca1(14),2,4,10,12-pentaen-13-yl}ethyl methanesulfonate from Example 146 (123 mg, 0.295 mmol) in dioxane (15 mL) was added 2-(piperidin-4-yl)propan-2-ol (422 mg, 2.95 mmol). The mixture was heated at 90° C. overnight. The solvent was removed and the residue was purified by Combi-flash eluting with a 5-95% gradient of CH$_3$CN in 0.3% NH$_4$HCO$_3$ to give 152. The enantiomers were separated by chiral SFC (OD-H column, 15% EtOH isocratic) to give: 17.6 mg of one enantiomer and 13.0 mg of the other (22% total yield)

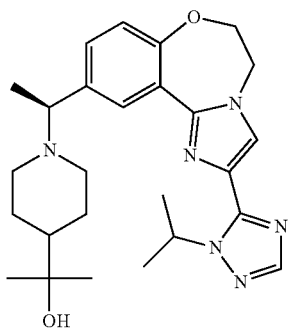

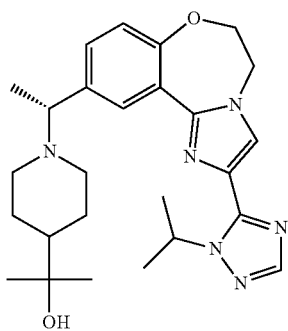

LCMS (ESI): RT=4.86 min, m/z: 465.4 [M+H$^+$]. $^1$H NMR (500 MHz, MeOH-d$_4$) δ 8.30 (d, J=2.5 Hz, 1H), 7.84 (s, 1H), 7.66 (s, 1H), 7.20-7.18 (dd, J=2.0, 8.5 Hz, 1H), 6.95-6.93 (d, J=8.5 Hz, 1H), 5.83-5.81 (m, 1H), 4.44-4.40 (m, 4H), 3.44-3.42 (m, 1H), 3.10-3.07 (m, 1H), 2.89-2.86 (m, 1H), 1.90 (m, 1H), 1.78 (m, 1H), 1.68-1.66 (m, 1H), 1.61-1.58 (m, 1H), 1.48-1.47 (d, J=6.5 Hz, 6H), 1.36-1.34 (m, 4H), 1.24-1.21 (m, 1H), 1.14-1.11 (m, 1H), 1.02 (s, 6H)

Example 153

10-(1-tert-butylpiperidin-4-ylthio)-2-(pyridin-3-yl)-5,6-dihydrobenzo[f]imidazo[1,2-d][1,4]oxazepine 153

Step 1: 9-Bromo-2-pyridin-3-yl-4,5-dihydro-6-oxa-1,3a-diazabenzo[e]azulene

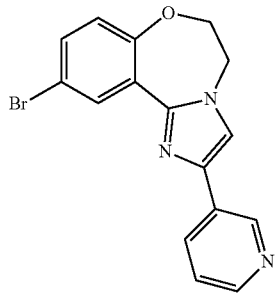 [SMILES: Brc1ccc2c(c1)-c1nc(-c3cccnc3)cn1CCO2]

A mixture of 9-bromo-2-iodo-4,5-dihydro-6-oxa-1,3a-diazabenzo[e]azulene (150 mg, 0.39 mmol), 3-pyridylboronic acid (51 mg, 0.42 mmol), bis[di-tert-butyl(4-dimethylaminophenyl)phosphine]dichloropalladium(II) (8 mg, 0.01 mmol) and KF (1 mL, 2M aqueous solution) in MeCN (1 mL) was heated at 85° C. for 30 h. Further 3-pyridylboronic acid (26 mg, 0.21 mmol), bis[di-tert-butyl(4-dimethylaminophenyl)phosphine]dichloropalladium(II) (4 mg, 0.01 mmol). The reaction mixture was loaded onto an Isolute® SCX-2 cartridge which was washed with MeOH and the product eluted with 2M NH$_3$/MeOH. The resulting residue was purified by column chromatography (Si-PCC, gradient 0-100% EtOAc in cyclohexane) then (C$_{18}$, gradient 15-60% MeOH in H$_2$O). The resulting residue was loaded onto an Isolute® SCX-2 cartridge which was washed with MeOH and the product eluted with 2M NH$_3$/MeOH affording 9-Bromo-2-pyridin-3-yl-4,5-dihydro-6-oxa-1,3a-diazabenzo[e]azulene as a white solid (17 mg, 18%). LCMS: R$_T$ 3.40 min [M+H]$^+$ 342.0 and 344.0. $^1$H NMR (CDCl$_3$, 400 MHz): δ 8.81 (1H, d, J=2.55 Hz), 8.55 (1H, ddd, J=4.87, 1.80, 0.93 Hz), 8.13 (1H, dt, J=7.96, 1.06 Hz), 7.76 (1H, td, J=7.73, 1.82 Hz), 7.68 (1H, s), 7.34 (1H, dd, J=8.68, 2.56 Hz), 7.17 (1H, ddd, J=7.49, 4.86, 1.22 Hz), 6.91 (1H, d, J=8.68 Hz), 4.50-4.44 (4H, m)

Step 2

A mixture of 9-bromo-2-pyridin-3-yl-4,5-dihydro-6-oxa-1,3a-diazabenzo[e]azulene (35 mg, 0.10 mmol), 1-tert-butylpiperidine-4-thiol (53 mg, 0.30 mmol), Pd$_2$(dba)$_3$ (9 mg, 10 mol %), XantPhos (12 mg, 20 mol %) and DIPEA (72 μL, 0.41 mmol) in dioxane (2 mL) was purged with argon and heated at 120° C. for 40 min, then 130° C. for 1 h and 140° C. for 1 h using microwave irradiation. The reaction mixture was loaded onto an Isolute® SCX-2 cartridge which was washed with MeOH and the product eluted with 2M NH$_3$/MeOH. The resulting residue was purified by column chromatography (Si-PCC, gradient 0-20% 2M NH$_3$/MeOH in EtOAc then C$_{18}$, gradient 2-20% MeOH in H$_2$O). The resulting residue was loaded onto an Isolute® SCX-2 cartridge which was washed with MeOH and the product eluted with 2M NH$_3$/MeOH affording 153 as an off-white solid (6 mg, 15%). LCMS: $R_T$ 2.42 min [M+H]⁺ 435.1. ¹H NMR (CDCl₃, 400 MHz): δ 9.03-9.02 (1H, m), 8.75-8.72 (1H, m), 8.51 (1H, dd, J=4.82, 1.67 Hz), 8.21 (1H, d, J=7.88 Hz), 7.35-7.33 (3H, m), 6.99 (1H, d, J=8.26 Hz), 4.52-4.50 (2H, m), 4.46-4.44 (2H, m), 3.03-2.98 (2H, br m), 2.20 (2H, br m), 2.06-1.94 (3H, br m), 1.66-1.62 (2H, br m), 1.06 (9H, br m)

Example 154

10-(1-tert-butylpiperidin-4-ylthio)-2-(pyridin-2-yl)-5,6-dihydrobenzo[f]imidazo[1,2-d][1,4]oxazepine 154

A mixture of 9-bromo-2-pyridin-2-yl-4,5-dihydro-6-oxa-1,3a-diazabenzo[e]azulene from Example 3 (200 mg, 0.58 mmol), 1-tert-butylpiperidine-4-thiol (202 mg, 1.69 mmol), Pd₂(dba)₃ (160 mg, 10 mol %), XantPhos (68 mg, 20 mol %) and DIPEA (410 µL, 2.34 mmol) in dioxane (5 mL) was purged with argon and heated at 140° C. for 1 h using microwave irradiation. The reaction mixture was filtered through Celite® and the filtrate concentrated in vacuo. The resulting residue was loaded onto an Isolute® SCX-2 cartridge which was washed with MeOH and the product eluted with 2M NH₃/MeOH. The resulting residue was purified by column chromatography (Si-PCC, gradient 0-20% MeOH in DCM then C₁₈, gradient 2-25% MeOH in H₂O). The resulting residue was loaded onto an Isolute® SCX-2 cartridge which was washed with MeOH and the product eluted with 2M NH₃/MeOH affording 154 as a white solid (36 mg, 15%). LCMS: $R_T$ 2.40 min [M+H]⁺ 435.1. ¹H NMR (CDC₃, 400 MHz): δ 8.15-8.14 (1H, m), 7.76 (1H, td, J=8.52, 2.20 Hz), 7.67 (1H, s), 7.33 (1H, dd, J=8.45, 3.89 Hz), 7.15-7.15 (1H, m), 6.96 (1H, d, J=8.43 Hz), 4.46-4.45 (4H, m), 3.03-2.98 (4H, m), 2.20 (2H, t, J=11.00 Hz), 2.06-1.94 (3H, m), 1.66-1.62 (2H, m), 1.06 (9H, s)

Example 155

(S)-10-(1-tert-butylpiperidin-4-ylsulfinyl)-2-(1-isopropyl-1H-1,2,4-triazol-5-yl)-5,6-dihydrobenzo[f]imidazo[1,2-d][1,4]oxazepine 155

The enantiomers of racemic 10-(1-tert-butylpiperidin-4-ylsulfinyl)-2-(1-isopropyl-1H-1,2,4-triazol-5-yl)-5,6-dihydrobenzo[f]imidazo[1,2-d][1,4]oxazepine 140 were separated by SFC chiral chromatography to give (S) enantiomer 155 and its (R) enantiomer.

Example 157

2-(1-isopropyl-1H-1,2,4-triazol-5-yl)-10-(1-(4-(pyrrolidin-1-yl)piperidin-1-yl)ethyl)-5,6-dihydrobenzo[f]imidazo[1,2-d][1,4]oxazepine 157

A mixture of 1-(2-(1-isopropyl-1H-1,2,4-triazol-5-yl)-5,6-dihydrobenzo[f]imidazo[1,2-d][1,4]oxazepin-10-yl)ethyl methanesulfonate from Example 146 (246 mg, 0.590 mmol) and 4-(pyrrolidin-1-yl)piperidine (435 mg, 2.82 mmol) in 1,4-dioxane (4 mL) was stirred at 90° C. for 16 h under nitrogen atmosphere. After concentration, the residue was purified by reverse phase Combiflash eluting with a 0-50% gradient of CH₃CN in 0.3% NH₄HCO₃ to give 157. The enantiomers were separated by chiral HPLC (OD column, 30% EtOH (0.1% DEA) in n-hexane isocratic) to give: 52 mg of one enantiomer and 49 mg of the other (42% total yield)

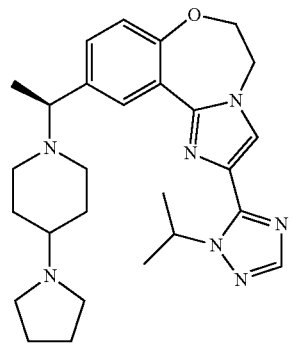

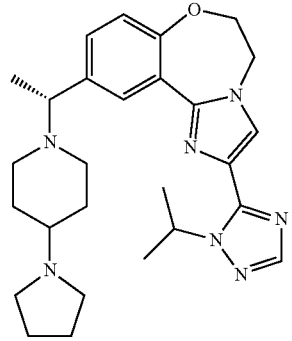

LCMS (ESI): $R_T$=5.76 min, m/z: 476.3 [M+H⁺]. ¹H NMR (500 MHz, DMSO-d₆): δ 8.45 (d, J=2 Hz, 1H), 7.92 (s, 1H), 7.22 (q, J=11 Hz, 1H), 6.99 (d, J=8.5 Hz, 1H), 5.92-5.86 (m, 1H), 4.50 (t, J=22 Hz, 4H), 3.51 (q, J=20 Hz, 1H), 2.85 (d, J=10.5 Hz, 1H), 2.77 (s, J=11 Hz, 1H), 2.42 (s, 4H), 1.98-1.96 (m, 2H), 1.87-1.76 (m, 3H), 1.63 (s, 4H), 1.51-1.49 (m, 6H), 1.38 (t, J=11 Hz, 2H), 1.29 (d, J=7 Hz, 3H)

Example 158

10-(1-tert-butylpiperidin-4-ylthio)-2-(3-methyl-1H-pyrazol-4-yl)-5,6-dihydrobenzo[f]imidazo[1,2-d][1,4]oxazepine-158

Step 1: 9-Bromo-2-(3-methyl-1H-pyrazol-4-yl)-4,5-dihydro-6-oxa-1,3a-diazabenzo[e]azulene

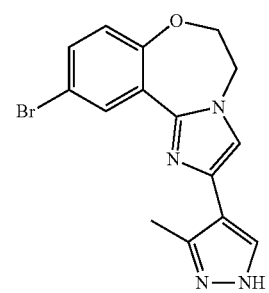 [SMILES: Cc1n[nH]cc1-c1cn2c(n1)-c1cc(Br)ccc1OCC2]

A mixture of 9-bromo-2-iodo-4,5-dihydro-6-oxa-1,3a-diazabenzo[e]azulene (200 mg, 0.51 mmol), 3-methylpyrazole-4-boronic acid pinacol ester (117 mg, 0.56 mmol), PdCl₂dppf.DCM (42 mg, 0.05 mmol) and Cs₂CO₃ (416 mg, 1.28 mmol) in dioxane (4 mL) and H₂O (1 mL) was purged with argon and heated at 80° C. for 1 h. The reaction mixture was loaded onto an Isolute® SCX-2 cartridge which was washed with MeOH and the product eluted with 2M NH₃/MeOH. The resulting residue was purified by column chromatography (Si-PCC, gradient 0-3% MeOH in DCM) affording 9-Bromo-2-(3-methyl-1H-pyrazol-4-yl)-4,5-dihydro-6-oxa-1,3a-diazabenzo[e]azulene (53 mg, 30%). LCMS: R$_T$ 2.21 min [M+H]⁺ 345.3

Step 2

A mixture of 9-bromo-2-(3-methyl-1H-pyrazol-4-yl)-4,5-dihydro-6-oxa-1,3a-diazabenzo[e]azulene (53 mg, 0.15 mmol), 1-tert-butylpiperidine-4-thiol (53 mg, 0.31 mmol), Pd₂(dba)₃ (46 mg, 0.05 mmol), Xantphos (29 mg, 0.05 mmol) and DIPEA (105 µL, 0.62 mmol) in dioxane (3 mL) was purged with argon and heated at 100° C. for 2 h. The reaction mixture was loaded onto an Isolute® SCX-2 cartridge which was washed with MeOH and the product eluted with 2M NH₃/MeOH. The resulting residue was purified by column chromatography (Si-PCC, gradient 0-10% MeOH in DCM) followed by reverse phase HPLC (Phenomenex Gemini 5 µm C₁₈, on a gradient 5-95%, 0.1% HCO₂H in acetonitrile/water) affording 158 (25 mg, 37%). LCMS: R$_T$ 2.32 min [M+H]⁺ 428.2. ¹H NMR (CDCl₃, 400 MHz): δ 8.50 (1H, d, J=2.40 Hz), 8.23 (2H, s), 7.75 (1H, s), 7.40 (1H, s), 7.29 (1H, dd, J=8.45, 2.42 Hz), 7.00 (1H, d, J=8.44 Hz), 4.45-4.44 (4H, m), 3.05-3.01 (3H, m), 2.43 (3H, s), 2.27 (2H, t, J=11.14 Hz), 1.94 (2H, d, J=12.76 Hz), 1.50-1.48 (2H, m), 1.03 (9H, s)

Example 159

10-(1-tert-butylpiperidin-4-ylthio)-2-(3-(trifluoromethyl)-1H-pyrazol-4-yl)-5,6-dihydrobenzo[f]imidazo[1,2-d][1,4]oxazepine 159

Step 1: 9-Bromo-2-(3-trifluoromethyl-1H-pyrazol-4-yl)-4,5-dihydro-6-oxa-1,3a-diazabenzo[e]azulene

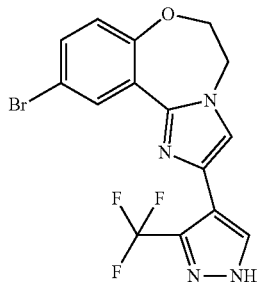 [SMILES: FC(F)(F)c1n[nH]cc1-c1cn2c(n1)-c1cc(Br)ccc1OCC2]

A mixture of 9-bromo-2-iodo-4,5-dihydro-6-oxa-1,3a-diazabenzo[e]azulene (750 mg, 1.91 mmol), 4-(4,4,5,5-tetramethyl-[1,3,2]dioxaborolan-2-yl)-3-trifluoromethyl-1H-pyrazole (550 mg, 2.10 mmol), PdCl₂dppf.DCM (156 mg, 0.19 mmol) and Cs₂CO₃ (1.55 g, 4.77 mmol) in dioxane (12 mL) and H₂O (3 mL) was purged with argon and heated at 80° C. for 18 h. Further 4-(4,4,5,5-tetramethyl-[1,3,2]dioxaborolan-2-yl)-3-trifluoromethyl-1H-pyrazole (225 mg, 1.05 mmol) and PdCl₂dppf.DCM (78 mg, 0.09 mmol) were added and the mixture heated at 85° C. for a further 24 h. The reaction mixture was loaded onto an Isolute® SCX-2 cartridge which was washed with MeOH and the product eluted with 2M NH₃/MeOH. The resulting residue was purified by column chromatography (Si-PCC, gradient 0-5% MeOH in DCM) affording 9-Bromo-2-(3-trifluoromethyl-1H-pyrazol-4-yl)-4,5-dihydro-6-oxa-1,3a-diazabenzo[e]azulene as a white solid (20 mg, 3%). LCMS: R$_T$ 4.42 min [M+H]⁺ 399.0 and 401.0. ¹H NMR (CDCl₃, 400 MHz): δ 13.65 (1H, s), 8.57 (1H, d, J=2.61 Hz), 8.30 (1H, s), 7.43-7.42 (2H, m), 7.00 (1H, d, J=8.71 Hz), 4.52-4.45 (4H, m)

Step 2

A mixture of 9-bromo-2-(3-trifluoromethyl-1H-pyrazol-4-yl)-4,5-dihydro-6-oxa-1,3a-diazabenzo[e]azulene (73 mg, 0.18 mmol), 1-tert-butylpiperidine-4-thiol (63 mg, 0.37 mmol), Pd₂(dba)₃ (55 mg, 0.06 mmol), Xantphos (35 mg, 0.06 mmol) and DIPEA (125 µL, 0.73 mmol) in dioxane (3 mL) was purged with argon and heated at 100° C. for 2 h. The reaction mixture was loaded onto an Isolute® SCX-2 cartridge which was washed with MeOH and the product eluted with 2M NH₃/MeOH. The resulting residue was purified by column chromatography (Si-PCC, gradient 0-10% MeOH in DCM) followed by reverse phase HPLC (Phenomenex Gemini 5 µm C18, on a gradient 5-95%, 0.1% HCO₂H in acetonitrile/water) affording 159 (56 mg, 31%). LCMS: R$_T$ 3.11 min [M+H]⁺ 492.1. ¹H NMR (DMSO, 400 MHz): δ 8.51 (1H, d, J=2.40 Hz), 8.26-8.25 (1H, m), 8.21 (1H, s), 7.42 (1H, s), 7.31 (1H, dd, J=8.46, 2.42 Hz), 7.01 (1H, d, J=8.46 Hz), 4.47 (4H, s), 3.12-3.01 (1H, m), 3.05-2.93 (2H, m), 2.24 (2H, t, J=11.08 Hz), 1.92 (2H, d, J=12.67 Hz), 1.48-1.47 (2H, m), 1.02 (9H, s)

Example 160

2-(1-isopropyl-1H-1,2,4-triazol-5-yl)-9-(1-(1-methylpiperidin-4-yl)-1H-pyrazol-5-yl)-5,6-dihydrobenzo[f]imidazo[1,2-d][1,4]oxazepine 160

Step 1: 1-(Tetrahydro-2H-pyran-2-yl)-1H-pyrazol-5-ylboronic acid

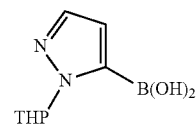

A mixture of 1H-pyrazole (6.00 g, 88.1 mmol), 3,4-dihydro-2H-pyran (9.00 g, 107 mmol), and TFA (cat. 2.00 mL) was heated to reflux for 5 hr. At the end of reaction, NaH (100 mg, 4.17 mmol) was added to quench the reaction. The resulting mixture was extracted with ethyl acetate, washed with brine, dried over MgSO₄, filtered, and evaporated. The residue was purified by silica gel chromatography eluting with EtOAc/petroleum ether (1:100) to afford 1-(tetrahydro-2H-pyran-2-yl)-1H-pyrazole (6.6 g, 49% yield) as pale yellow sold. LCMS (ESI) m/z: 153.1 [M+H⁺].

To a solution of 1-(tetrahydro-2H-pyran-2-yl)-1H-pyrazole (2.10 g, 13.8 mmol) in anhydrous THF (30.0 mL) was added n-BuLi (2.5 M in hexane, 14.0 mL) at −78° C. The mixture was kept at this temperature for 30 min. Triisopropyl borate (2.85 g, 15.2 mmol) was added over 10 min at −78° C. and held for 1 hr. The resulting mixture was allowed to reach room temperature over 4 hr. After being quenched by aq. HCl (2.00 M, 55.0 mL) with intensive stirring, the aqueous phase was added NaCl (s) and extracted with THF/EtOAc. The combined organic layer was washed with brine, sat NaHCO₃, dried over MgSO₄, filtered and evaporated to afford 1-(tetrahydro-2H-pyran-2-yl)-1H-pyrazol-5-ylboronic acid (3.6 g, 52% yield) as yellow oil. LCMS (ESI) m/z: 197.0 [M+H$^+$].

Step 2: 4-[1-(Propan-2-yl)-1H-1,2,4-triazol-5-yl]-12-(1H-pyrazol-5-yl)-9-oxa-3,6-diazatricyclo[8.4.0.0$^{2,6}$]tetradeca-1(14),2,4,10,12-pentaene

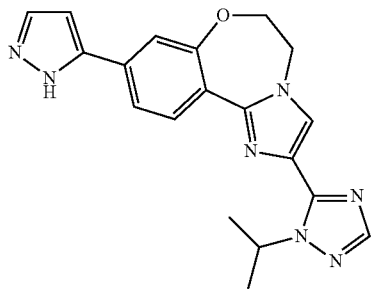 [SMILES: CC(C)n1ncnc1-c1cn2c(n1)-c1ccc(-c3ccn[nH]3)cc1OCC2]

A mixture of 12-bromo-4-[1-(propan-2-yl)-1H-1,2,4-triazol-5-yl]-9-oxa-3,6-diazatricyclo[8.4.0.0$^{2,6}$]tetradeca-1(14),2,4,10,12-pentaene (2.00 g, 5.34 mmol), 1-(tetrahydro-2H-pyran-2-yl)-1H-pyrazol-5-ylboronic acid (1.58 g, 8.01 mmol), Pd(dppf)Cl$_2$ (437 mg, 0.535 mmol), Na$_2$CO$_3$ (1.70 g, 16.0 mmol) in DME/EtOH/H$_2$O (15/3/3 mL) was stirred at 100° C. for 1 hr under microwave irradiation. The mixture was extracted with EtOAc, washed with brine, dried over MgSO$_4$, filtered, and evaporated to give crude product, which was purified by silica gel chromatography eluting with EtOAc/petroleum ether (1:5) to afford 12-[1-(oxan-2-yl)-1H-pyrazol-5-yl]-4-[1-(propan-2-yl)-1H-1,2,4-triazol-5-yl]-9-oxa-3,6-diazatricyclo[8.4.0.0$^{2,6}$]tetradeca-1(14),2,4,10,12-pentaene (2.2 g, 90% yield) as white solid. LCMS (ESI) m/z: 446.3 [M+H$^+$].

To a solution of 3N HCl in ethyl acetate at −20° C. (100 mL) was added dropwise a solution of 12-[1-(oxan-2-yl)-1H-pyrazol-5-yl]-4-[1-(propan-2-yl)-1H-1,2,4-triazol-5-yl]-9-oxa-3,6-diazatricyclo[8.4.0.0$^{2,6}$]tetradeca-1(14),2,4,10,12-pentaene (2.20 g, 6.09 mmol) in ethyl acetate (20.0 mL). After being stirred at this temperature for 1 h, the reaction mixture was warmed to room temperature and stirred for 3 hr. After removal of the solvent, the residue was treated with water and basified to pH around 10. The aqueous layer was then extracted with ethyl acetate, washed with brine, dried over MgSO$_4$, filtered, and concentrated to afford 4-[1-(propan-2-yl)-1H-1,2,4-triazol-5-yl]-12-(1H-pyrazol-5-yl)-9-oxa-3,6-diazatricyclo[8.4.0.0$^{2,6}$]tetradeca-1(14),2,4,10,12-pentaene (1.4 g, 78% yield) as pale yellow solid. LCMS (ESI) m/z: 362.0 [M+H$^+$].

Step 3: tert-Butyl 4-(methylsulfonyloxy)piperidine-1-carboxylate

A mixture of piperidin-4-ol (3.00 g, 29.6 mmol), TEA (9.00 g, 88.9 mmol), and (Boc)$_2$O (9.70 g, 44.4 mmol) in DCM (50.0 mL) was stirred at room temperature for 16 hr. At the end of reaction of reaction, the solvents were removed to afford crude product, which was purified by silica gel chromatography eluting with EtOAc/petroleum ether (1:10) to give tert-butyl 4-hydroxypiperidine-1-carboxylate (4.89 g, 82% yield) as a pale yellow oil. LCMS (ESI) m/z: 146.1 [M-56H$^+$].

To a solution of tert-butyl 4-hydroxypiperidine-1-carboxylate (4.50 g, 22.4 mmol, 1.0 eq) and TEA (11.3 g, 5.0 eq) in DCM (30.0 mL) at 0° C. was added MsCl (5.10 g, 44.5 mmol, 2.0 eq) in DCM (10.0 mL) dropwise. The resulting mixture was stirred at 0° C. for 30 min and then warmed to room temperature with stirring for 3 hr. After being quenched with water and extracted with ethyl acetate, the organic layers were combined, washed with brine, dried over MgSO$_4$, filtered, and evaporated to afford the crude product, which was purified via silica gel chromatography eluting with EtOAc/petroleum ether (1:5) to afford tert-butyl 4-(methylsulfonyloxy)piperidine-1-carboxylate (4.8 g, 77% yield) as pale yellow solid. LCMS (ESI) m/z: 224.1 [M-56+H$^+$].

Step 4

A mixture of 4-[1-(propan-2-yl)-1H-1,2,4-triazol-5-yl]-12-(1H-pyrazol-5-yl)-9-oxa-3,6-diazatricyclo[8.4.0.0$^{2,6}$]tetradeca-1(14),2,4,10,12-pentaene (1.00 g, 2.77 mmol), tert-butyl 4-(methylsulfonyloxy)piperidine-1-carboxylate (1.95 g, 6.92 mmol), and K$_2$CO$_3$ (1.90 g, 13.8 mmol) in CH$_3$CN (50.0 mL) was stirred at 100° C. for 60 hr. After removal of the solvents, the residue was treated with water and extracted with ethyl acetate. The organic layers were combined, washed with brine, dried over MgSO$_4$, filtered, and evaporated to afford the crude product, which was purified by reverse phase combiflash eluting with 0-50% gradient CH$_3$CN in 0.5% NH$_4$HCO$_3$ and followed by prep-HPLC (Gilson GX 281, Shim-pack PRC-ODS 250 mm×20 mm×2, gradient: CH$_3$CN/10 mm/L NH$_4$HCO$_3$, 17 min) to give tert-butyl-4-(5-{4-[1-(propan-2-yl)-1H-1,2,4-triazol-5-yl]-9-oxa-3,6-diazatricyclo[8.4.0.0$^{2,6}$]tetradeca-1(14),2,4,10,12-pentaen-12-yl}-1H-pyrazol-1-yl)piperidine-1-carboxylate (100 mg, 7% yield) as pale yellow solid. LCMS (ESI) m/z: 545.3 [M+H$^+$]. $^1$H-NMR (500 MHz, DMSO-d$_6$): δ 8.54 (d, J=10.5 Hz, 1H), 7.99 (s, 1H), 7.93 (s, 1H), 7.56 (s, 1H), 7.26, (dd, J=2.5 Hz, 10.5 Hz, 1H), 7.12 (s, 1H), 6.40 (s, 1H), 5.94-5.91 (m, 1H), 4.59-4.56 (m, 4H), 4.42 (s, 1H), 4.02-3.99 (m, 2H), 2.84-2.83 (m, 2H), 1.92-1.85 (m, 4H), 1.50 (s, 6H), 1.40 (s, 9H).

A mixture of tert-butyl-4-(5-{4-[1-(propan-2-yl)-1H-1,2,4-triazol-5-yl]-9-oxa-3,6-diazatricyclo[8.4.0.0$^{2,6}$]tetradeca-1(14),2,4,10,12-pentaen-12-yl}-1H-pyrazol-1-yl)piperidine-1-carboxylate (100 mg, 0.184 mmol) and LiAlH$_4$ (35.0 mg, 0.921 mmol) in THF (5.00 mL) was refluxed for 1 h. At the end of reaction, H$_2$O was added to quench reaction. After filtration, the filtrate was evaporated to afford the crude product, which was purified by reverse phase combiflash eluting with 0-50% gradient CH$_3$CN in 0.5% NH$_4$HCO$_3$ and followed by prep-HPLC (Gilson GX 281, Shim-pack PRC-ODS 250 mm×20 mm×2, gradient: CH$_3$CN/10 mm/L NH$_4$HCO$_3$, 17 min) to give 160 (23 mg, 27% yield) as white solid. LCMS (ESI): R$_T$=4.93 min, m/z: 459.4 [M+H$^+$]. $^1$H-NMR (500 MHz, DMSO-d$_6$): δ 8.53 (d, J=8.5 Hz, 1H), 7.99 (s, 1H), 7.93 (s, 1H), 7.55 (d, J=1.5 Hz, 1H), 7.24 (d, J=8.0 Hz, 1H), 7.10 (s, 1H), 6.39 (d, J=1.5 Hz, 1H), 5.94-5.91 (m, 1H), 4.57 (s, 4H), 4.15 (s, 1H), 2.84-2.82 (m, 2H), 2.16 (s, 3H), 2.15-2.12 (m, 2H), 1.94-1.89 (m, 2H), 1.10-1.79 (m, 2H), 1.50 (s, 6H)

Example 161

2-(1-isopropyl-1H-1,2,4-triazol-5-yl)-10-(2-(1-methylpiperidin-4-yl)pyrrolidin-1-yl)-5,6-dihydrobenzo[f]imidazo[1,2-d][1,4]oxazepine 161

A mixture of 13-bromo-4-[1-(propan-2-yl)-1H-1,2,4-triazol-5-yl]-9-oxa-3,6-diazatricyclo[8.4.0.0$^{2,6}$]tetradeca1(14),2,4,10,12-pentaene (200 mg, 0.540 mmol), 1-methyl-4-(pyrrolidin-2-yl)piperidine (108 mg, 0.640 mmol), Pd(P$^t$Bu$_3$)$_2$ (7 mg, 0.015 mmol), NaO$^t$Bu (155 mg, 1.62 mmol) in toluene (2 ml) in a seal tube was degassed with N$_2$ for three times. The resulting mixture was stirred at 110° C. for 1 h. The solid was filtered off through Celite. The filtrate was concentrated to give the crude product, which was purified by prep-HPLC (Gilson GX 281, Shim-pack PRC-ODS 250 mm×20 mm×2, gradient: CH₃CN/10 mm/L NH₄HCO₃, 17 min) to afford 161. The (R) and (S) enantiomers were further purified and separated by chiral HPLC (AD column, 30% EtOH (0.1% DEA) in n-Hexane isocratic) to give 6 mg of one enantiomer and 11 mg of the other (5% total yield)

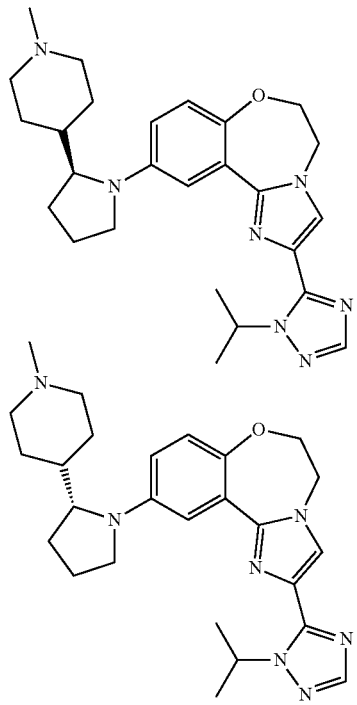

LCMS (ESI): RT=5.31, m/z: 462.4 [M+H⁺]. ¹H NMR (500 MHz, CD₃OD): δ 7.96 (s, 1H), 7.77 (s, 1H), 7.65 (d, J=3 Hz, 1H), 6.95 (d, J=9 Hz, 1H), 6.72-6.70 (m, 1H), 5.92 (t, J=13 Hz, 2H), 4.51-4.49 (m, 2H), 4.44 (t, J=6 Hz, 2H), 3.80 (d, J=2.5 Hz, 1H), 3.59 (d, J=6.5 Hz, 1H), 3.26-3.18 (m, 1H), 2.96-2.88 (m, 2H), 2.25 (s, 3H), 2.05-1.96 (m, 5H), 1.88-1.86 (m, 2H), 1.71 (d, J=12.5, 1H), 1.59-1.40 (m, 9H)

Example 163

2-(1-isopropyl-1H-1,2,4-triazol-5-yl)-10-(1-(3-morpholinoazetidin-1-yl)ethyl)-5,6-dihydrobenzo[f]imidazo[1,2-d][1,4]oxazepine 163

Step 1: 1-(1-{4-[1-(Propan-2-yl)-1H-1,2,4-triazol-5-yl]-9-oxa-3,6-diazatricyclo[8.4.0.0²,⁶]tetradeca1(14), 2,4,10,12-pentaen-13-yl}ethyl)azetidin-3-ol

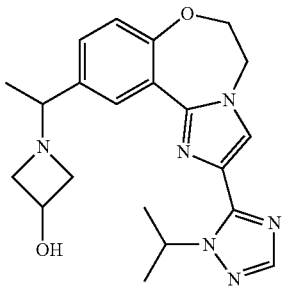 [SMILES: CC(c1ccc2c(c1)-c1nc(-c3ncnn3C(C)C)cn1CCO2)N1CC(O)C1]

To a solution of 1-{4-[1-(propan-2-yl)-1H-1,2,4-triazol-5-yl]-9-oxa-3,6-diazatricyclo[8.4.0.0²,⁶]tetradeca1(14),2,4,10, 12-pentaen-13-yl}ethylmethanesulfonate (0.19 mmol, 80 mg) in CH₃CN (10 mL) was added K₂CO₃ (0.72 mmol, 106 mg) and azetidin-3-ol (0.38 mmol, 28 mg), the mixture was stirred at 80° C. for 16 h. After concentration, the residue was purified by reverse phase Combiflash eluting with a 0-50% gradient of CH₃CN in 0.3% NH₄HCO₃ to give 1-(1-{4-[1-(propan-2-yl)-1H-1,2,4-triazol-5-yl]-9-oxa-3,6-diazatricyclo[8.4.0.0²,⁶]tetradeca-1(14),2,4,10,12-pentaen-13-yl}ethyl)azetidin-3-ol (70 mg, 92% yield). LCMS (ESI) m/z: 395.1 [M+H⁺]

Step 2: 1-(1-{4-[1-(Propan-2-yl)-1H-1,2,4-triazol-5-yl]-9-oxa-3,6-diazatricyclo[8.4.0.0²,⁶]tetradeca1(14), 2,4,10,12-pentaen-13-yl}ethyl)azetidin-3-yl methanesulfonate

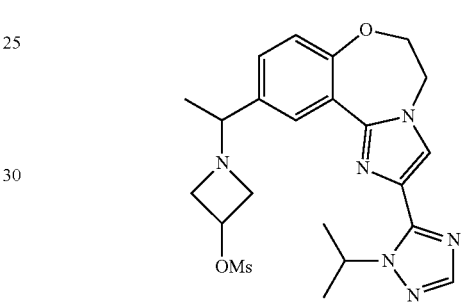

To a solution of 1-(1-{4-[1-(propan-2-yl)-1H-1,2,4-triazol-5-yl]-9-oxa-3,6-diazatricycl[8.4.0.0²,⁶]tetradeca1(14),2, 4,10,12-pentaen-13-yl}ethyl)azetidin-3-ol (0.16 mmol, 65 mg) in dry DCM (10 mL) was added TEA (0.80 mmol, 80 mg) and MsCl (0.32 mmol, 36 mg), the mixture was stirred at 20° C. for 2 h. The reaction mixture was treated with saturated NaHCO₃ solution (10 mL), extracted with ethyl acetate (3×20 mL), dried over anhydrous Na₂SO₄. Solvent was evaporated under reduced pressure to give 1-(1-{4-[1-(propan-2-yl)-1H-1,2,4-triazol-5-yl]-9-oxa-3,6-diazatricyclo[8.4.0.0²,⁶]tetradeca1(14),2,4,10,12-pentaen-13-yl}ethyl)azetidin-3-yl-methanesulfonate (70 mg, 92% yield), which was used in the next step without further purification.

Step 3

A mixture of 1-(1-{4-[1-(propan-2-yl)-1H-1,2,4-triazol-5-yl]-9-oxa-3,6-diazatricyclo[8.4.0.0²,⁶]tetradeca1(14),2,4,10, 12-pentaen-13-yl}ethyl)azetidin-3-yl methanesulfonate (70 mg, 0.15 mmol) and morpholine (20 mg, 1.5 mmol) in 1,4-dioxane (4 mL) was stirred at 80° C. for 16 h under nitrogen atmosphere. After concentration, the residue was purified by reverse phase Combiflash eluting with a 0-50% gradient of CH₃CN in 0.3% NH₄HCO₃ to give 163. The enantiomers were separated by chiral HPLC (OD column, 10% EtOH (0.1% DEA) in n-hexane isocratic) to give: 24 mg of one enantiomer and 25 mg of the other (71% total yield)

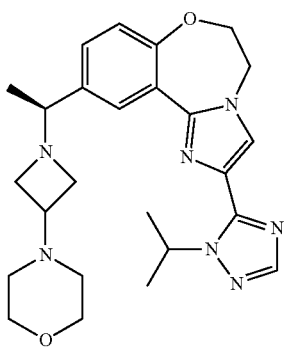

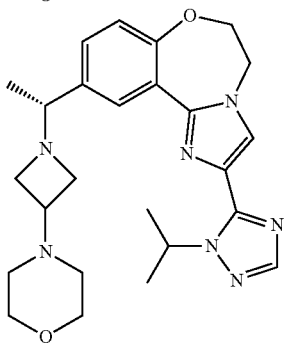

LCMS (ESI): RT=4.53 min, m/z: 464.4 [M+H⁺]. ¹H NMR (500 MHz, MeOH-d₄): δ 8.44 (d, J=1.5 Hz, 1H), 7.97 (s, 1H), 7.79 (s, 1H), 7.31 (q, J=10.5 Hz, 1H), 7.06 (d, J=9 Hz, 1H), 6.00 (t, J=13.5 Hz, 1H), 4.53 (q, J=20.5 Hz, 4H), 3.69-3.67 (m, 5H), 3.48 (d, J=6.5 Hz, 1H), 3.25-3.23 (m, 1H), 3.05 (t, J=12 Hz, 1H), 2.99-2.90 (m, 2H), 2.34 (s, 4H), 1.69 (q, J=9 Hz, 6H), 1.31 (d, J=6 Hz, 3H)

Example 166

2-(1-isopropyl-1H-1,2,4-triazol-5-yl)-9-(1-(1-isopropylazetidin-3-yl)ethoxy)-5,6-dihydrobenzo[f]imidazo[1,2-d][1,4]oxazepine 166

Step 1: 3-{1-[2-(2-Isopropyl-2H-[1,2,4]triazol-3-yl)-4,5-dihydro-6-oxa-1,3a-diazabenzo[e]azulen-8-yloxy]ethyl}azetidine-1-carboxylic acid tert-butyl ester

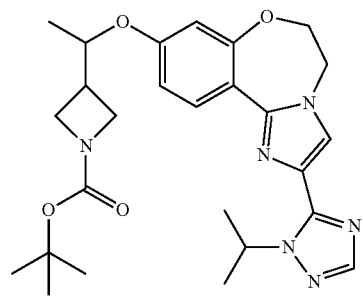 [SMILES: CC(Oc1ccc2c(c1)OCCn1cc(-c3ncnn3C(C)C)nc1-2)C1CN(C(=O)OC(C)(C)C)C1]

To a suspension of 2-(2-isopropyl-2H-[1,2,4]triazol-3-yl)-4,5-dihydro-6-oxa-1,3a-diazabenzo[e]azulen-8-ol (300 mg, 0.96 mmol), 3-(1-hydroxyethyl)azetidine-1-carboxylic acid tert-butyl ester (213 mg, 1.06 mmol) and PPh₃ (379 mg, 1.46 mmol) in dioxane (5 mL) was added DIAD (285 μL, 1.46 mmol) and the resulting yellow solution stirred at RT for 2 h. Further 3-(1-hydroxyethyl)azetidine-1-carboxylic acid tert-butyl ester (105 mg, 0.53 mmol), PPh₃ (190 mg, 0.73 mmol) and DIAD (143 μL, 0.73 mmol) were added and the resulting mixture stirred for 2 h. The reaction mixture was partitioned between EtOAc and 1M NaOH, the organic phase dried (MgSO₄) and concentrated in vacuo. The resulting residue was purified by column chromatography (Si-PCC, gradient 0-10% MeOH in EtOAc) affording 3-{1-[2-(2-Isopropyl-2H-[1,2,4]triazol-3-yl)-4,5-dihydro-6-oxa-1,3a-diazabenzo[e]azulen-8-yloxy]ethyl}azetidine-1-carboxylic acid tert-butyl ester (312 mg, 66%). LCMS: R$_T$ 3.76 min [M+H]⁺ 495.2

Step 2

A solution of 3-{1-[2-(2-isopropyl-2H-[1,2,4]triazol-3-yl)-4,5-dihydro-6-oxa-1,3a-diazabenzo[e]azulen-8-yloxy]ethyl}azetidine-1-carboxylic acid tert-butyl ester (312 mg, 0.63 mmol) in 4M HCl in dioxane (2 mL) and MeOH (5 mL) was stirred at RT for 1 h then concentrated in vacuo. The resulting residue was combined with Pd/C (150 mg) and NEt₃ (0.5 mL) in MeOH (3 mL) and acetone (5 mL) and stirred under an atmosphere of H₂ for 18 h. The reaction mixture was filtered and the filtrate partitioned between H₂O and EtOAc. The combined organic phases were dried (MgSO₄) and concentrated in vacuo. The resulting residue was purified by column chromatography (Si-PCC, gradient 0-10% MeOH in EtOAc) then reverse phase HPLC (Phenomenex Gemini 5 μm C₁₈, on a gradient 10-90%, 0.1% HCO₂H in acetonitrile/water) to afford 166 (63 mg, 23%). LCMS: R$_T$ 2.92 min [M+H]⁺ 437.3. ¹H NMR (CDCl₃, 400 MHz): δ 8.63 (1H, s), 8.45 (1H, d, J=8.95 Hz), 7.87 (1H, s), 7.60 (1H, s), 6.74 (1H, dd, J=8.97, 2.56 Hz), 6.57 (1H, d, J=2.52 Hz), 6.00-5.93 (1H, m), 4.52-4.47 (3H, m), 4.44-4.42 (2H, m), 3.95-3.92 (2H, m), 3.61 (1H, t, J=8.14 Hz), 3.44 (1H, t, J=8.17 Hz), 2.89-2.87 (1H, m), 1.59 (6H, d, J=6.64 Hz), 1.24 (3H, d, J=6.14 Hz), 1.17 (3H, d, J=6.36 Hz), 1.14 (3H, d, J=6.41 Hz)

Example 167

9-(1-(3-fluoropyridin-4-yl)ethoxy)-2-(1-isopropyl-3-methyl-1H-1,2,4-triazol-5-yl)-5,6-dihydrobenzo[f]imidazo[1,2-d][1,4]oxazepine 167

Step 1: 2-(2-Isopropyl-5-methyl-2H-[1,2,4]triazol-3-yl)-4,5-dihydro-6-oxa-1,3a-diazabenzo[e]azulen-8-ol

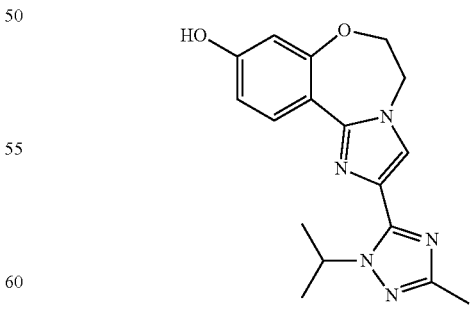

A mixture of 8-bromo-2-(2-isopropyl-5-methyl-2H-[1,2,4]triazol-3-yl)-4,5-dihydro-6-oxa-1,3a-diazabenzo[e]azulene (4.0 g, 10.3 mmol), KOH (1.73 g, 30.9 mmol), Pd₂(dba)₃ (189 mg, 0.2 mmol) and Xphos (350 mg, 0.82 mmol) in dioxane (20 mL) and H₂O (10 mL) was purged with argon and heated at 90° C. for 45 min. The cooled reaction mixture was diluted with EtOAc and H$_2$O then acidified with 1M HCl. The resulting precipitate was collected by filtration. The filtrate was separated, the aqueous phase extracted with further EtOAc and the combined organic extracts dried (MgSO$_4$) and concentrated in vacuo. The resulting solid was combined with the original precipitate and triturated with Et$_2$O. The resulting solid was collected by filtration and dried in vacuo affording 2-(2-Isopropyl-5-methyl-2H-[1,2,4]triazol-3-yl)-4,5-dihydro-6-oxa-1,3a-diazabenzo[e]azulen-8-ol as a white solid (3.01 g, 90%). LCMS: R$_T$ 2.36 min [M+H]$^+$ 326.2

Step 2

To a suspension of 2-(2-isopropyl-5-methyl-2H-[1,2,4]triazol-3-yl)-4,5-dihydro-6-oxa-1,3a-diazabenzo[e]azulen-8-ol (300 mg, 0.92 mmol), 1-(3-fluoropyridin-4-yl)ethanol (195 mg, 1.38 mmol) and PPh$_3$ (411 mg, 1.57 mmol) in dioxane (5 mL) was added DIAD (325 µL, 1.57 mmol) and the resulting yellow solution stirred at RT for 2 h. The reaction mixture was partitioned between EtOAc and 1M NaOH, the organic phase dried (MgSO$_4$) and concentrated in vacuo. The resulting residue was purified by column chromatography (Si-PCC, gradient 0-10% MeOH in EtOAc) then triturated with TBME affording 167 (220 mg, 53%). LCMS: R$_T$ 4.36 min [M+H]$^+$ 449.3. $^1$H NMR (DMSO, 400 MHz): δ 8.47 (1H, d, J=1.61 Hz), 8.39-8.36 (2H, m), 7.56 (1H, s), 7.39-7.34 (1H, m), 6.69 (1H, dd, J=8.99, 2.60 Hz), 6.46 (1H, d, J=2.57 Hz), 5.91-5.83 (1H, m), 5.66 (1H, q, J=6.47 Hz), 4.44-4.43 (2H, m), 4.39-4.35 (2H, m), 2.40 (3H, s), 1.68 (3H, d, J=6.45 Hz), 1.55 (6H, d, J=6.65 Hz)

Example 168

1-(1-(2-(1-isopropyl-1H-1,2,4-triazol-5-yl)-5,6-dihydrobenzo[f]imidazo[1,2-d][1,4]oxazepin-10-yl)ethyl)-N,N-dimethylazetidin-3-amine 168

A mixture of 1-(1-{4-[1-(propan-2-yl)-1H-1,2,4-triazol-5-yl]-9-oxa-3,6-diazatricyclo[8.4.0.0$^{2,6}$]tetradeca1(14),2,4,10,12-pentaen-13-yl}ethyl)azetidin-3-yl methanesulfonate from Example 162 (70 mg, 0.15 mmol) and dimethylamine (68 mg, 1.5 mmol) in 1,4-dioxane (4 mL) was stirred at 80° C. for 16 h under nitrogen atmosphere. After concentration, the residue was purified by reverse phase Combiflash eluting with a 0-50% gradient of CH$_3$CN in 0.3% NH$_4$HCO$_3$ to give 168. The enantiomers were separated by chiral HPLC (OJ-H column, 2% EtOH (0.1% DEA) in n-hexane isocratic) to give: 9 mg of one enantiomer and 5 mg of the other (23% total yield).

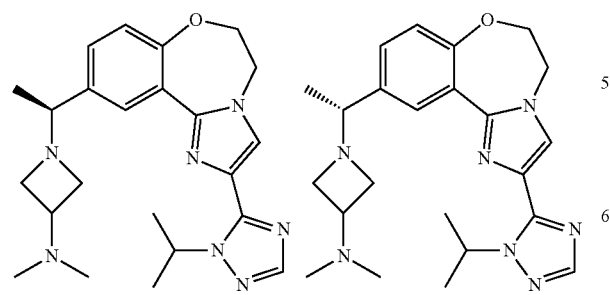

LCMS (ESI): R$_T$=4.59 min, m/z: 422.3 [M+H]$^+$. $^1$H NMR (500 MHz, MeOH-d$_4$): δ 8.43 (s, 1H), 7.96 (s, 1H), 7.79 (s, 1H), 7.31 (d, J=4 Hz, 1H), 7.06 (t, J=8.5 Hz, 1H), 6.03 (t, J=12.5 Hz, 1H), 4.52 (t, J=14 Hz, 4H), 3.69 (t, J=5.5 Hz, 1H), 3.46 (d, J=6 Hz, 1H), 3.26 (d, J=6 Hz, 1H), 3.00 (t, J=14 Hz, 1H), 2.91-2.83 (m, 2H), 2.13 (s, 6H), 1.62-1.60 (m, 6H), 1.31 (d, J=6 Hz, 3H)

Example 170

2-(1-isopropyl-1H-1,2,4-triazol-5-yl)-10-(1-(4-methylpiperazin-1-yl)propyl)-5,6-dihydrobenzo[f]imidazo[1,2-d][1,4]oxazepine 170

A mixture of 1-{4-[1-(propan-2-yl)-1H-1,2,4-triazol-5-yl]-9-oxa-3,6-diazatricyclo[8.4.0.0$^{2,6}$]tetradeca1(14),2,4,10,12-pentaen-13-yl}ethyl methanesulfonate from Example 146 (244 mg, 0.570 mmol) and 1-methylpiperazine (280 mg, 2.80 mmol) in 1,4-dioxane (4 mL) was stirred at 90° C. for 16 h under nitrogen atmosphere. After concentration, the residue was purified by reverse phase Combiflash eluting with a 0-50% gradient of CH$_3$CN in 0.3% NH$_4$HCO$_3$ to give 170. The enantiomers were separated by chiral HPLC (OD-H column, 5% EtOH (0.1% DEA) in n-hexane isocratic) to give: 20 mg of one enantiomer and 16 mg of the other (15% total yield).

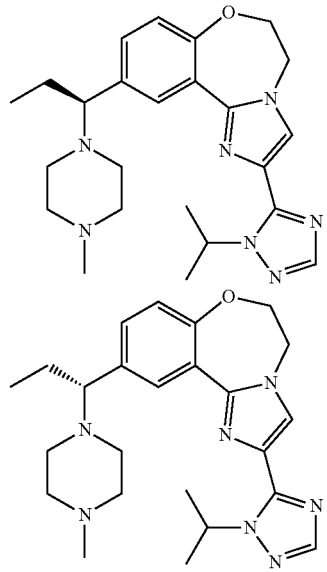

LCMS ESI): RT=5.31 min, m/z: 436.3 [M+H]$^+$. $^1$H NMR (500 MHz, MeOH-d$_4$): δ 8.40 (d, J=2.5 Hz, 1H), 7.96 (s, 1H), 7.79 (s, 1H), 7.26-7.24 (m, 1H), 7.16 (d, J=8 Hz, 1H), 5.93 (t, J=13.5 Hz, 1H), 4.53 (t, J=14.5 Hz, 4H), 2.60-2.41 (m, 7H), 2.25 (s, 6H), 2.02-1.98 (m, 1H), 1.88-1.83 (m, 1H), 1.59 (d, J=7 Hz, 6H), 0.80 (t, J=14.5 Hz, 3H)

Example 172

2-(1-isopropyl-3-methyl-1H-1,2,4-triazol-5-yl)-9-(2-(1-methylpiperidin-4-yl)pyrrolidin-1-yl)-5,6-dihydrobenzo[f]imidazo[1,2-d][1,4]oxazepine 172

A mixture of 9-bromo-2-(1-isopropyl-3-methyl-1H-1,2,4-triazol-5-yl)-5,6-dihydrobenzo[f]imidazo[1,2-d][1,4]oxazepine (300 mg, 0.773 mmol), 1-methyl-4-(pyrrolidin-2-yl)piperidine hydrochloride (395 mg, 1.93 mmol), Pd(P$^t$Bu$_3$)$_2$ (20 mg, 0.04 mmol), Na$_2$O$^t$Bu (223 mg, 2.32 mmol) in toluene (6.0 ml) in a seal tube was degassed with N$_2$ for three times. The resulting mixture was stirred at 110° C. for 120 min. The solid was filtered through Celite. The filtrate was concentrated to give the crude product, which was purified by prep-HPLC (Gilson GX 281, Shim-pack PRC-ODS 250 mm×20 mm×2, gradient: $CH_3CN/10$ mm/L $NH_4HCO_3$, 17 min) to give the racemic 172, which was separated by chiral-HPLC (AD-H column, 15% EtOH (0.1% DEA) in hexane isocratic) to give the (R)/(S) enantiomers: 29.0 mg of one enantiomer and 32.0 mg of the other (16% total yield). LCMS (ESI): RT=5.25 min, m/z: 476.4 [M+H$^+$]. $^1$H NMR (500 MHz, DMSO-d$_6$): δ 8.17 (d, J=8.5 Hz, 1H), 7.74 (s, 1H), 6.49 (d, J=8.5 Hz, 1H), 6.13 (s, 1H), 5.89-5.87 (m, 1H), 4.45-4.39 (m, 4H), 3.75 (s, 1H), 3.44 (d, J=3.5 Hz, 1H), 3.14 (d, J=8 Hz, 1H), 2.80-2.76 (m, 2H), 2.24 (s, 3H), 2.11 (s, 3H), 1.94-1.28 (m, 17H)

Example 175

2-(1-isopropyl-1H-1,2,4-triazol-5-yl)-9-(2-(1-isopropylpiperidin-4-yl)pyrrolidin-1-yl)-5,6-dihydrobenzo[f]imidazo[1,2-d][1,4]oxazepine 175

Step 1: 1-Isopropyl-4-(pyrrolidin-2-yl)piperidine hydrochloride

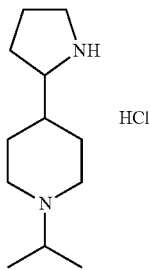

To a mixture of tert-butyl 2-(piperidin-4-yl)pyrrolidine-1-carboxylate (400 mg, 1.57 mmol) in dry DMF (2.0 mL) at 0° C., was added NaH (132 mg, 3.30 mmol, 60% in mineral oil) in small portion. The reaction mixture was then warmed to room temperature with stirring for another 1 h. 2-iodopropane (2.0 mL) was added. The resulting mixture was stirred at room temperature for 24 h and then poured into the ice-water (20 mL). The resultant mixture was extracted with EtOAc (2×50 mL). The combined organic layers were dried over $Na_2SO_4$ and evaporated to dryness. The residue was purified by silica gel chromatography eluting with a 5-10% gradient of MeOH in DCM to afford tert-butyl 2-(1-isopropylpiperidin-4-yl)pyrrolidine-1-carboxylate (302 mg, 65% yield). A solution of tert-butyl 2-(1-isopropylpiperidin-4-yl)pyrrolidine-1-carboxylate (302 mg, 1.02 mmol) in sat. HCl/dioxane (5 mL) was stirred at room temperature for 8 h. After removal of the solvent, 1-isopropyl-4-(pyrrolidin-2-yl)piperidine hydrochloride (232 mg, 100% yield) as yellow solid was obtained. LCMS (ESI) m/z: 197.2 [M+H$^+$].

Step 2

A mixture of 12-bromo-4-[1-(propan-2-yl)-1H-1,2,4-triazol-5-yl]-9-oxa-3,6-diazatricyclo[8.4.0.0$^{2,6}$]tetradeca1(14), 2,4,10,12-pentaene (300 mg, 0.800 mmol), 1-isopropyl-4-(pyrrolidin-2-yl)piperidine hydrochloride (163 mg, 0.800 mmol), Pd(P$^t$Bu$_3$)$_2$ (20 mg, 0.040 mmol), Na$_2$O$^t$Bu (232 mg, 2.40 mol) in toluene (2 mL) in a seal tube was degassed with N$_2$ for three times. The resulting mixture was stirred at 110° C. for 120 min. After the completion of the reaction, the solid was filtered off via Celite. The filtrate was concentrated and purified by prep-HPLC (Gilson GX 281, Shim-pack PRC-ODS 250 mm×20 mm×2, gradient: $CH_3CN/10$ mm/L $NH_4HCO_3$, 17 min) to give racemic 175 (40 mg, 10% yield). The (R) and (S) enantiomers were separated by chiral-HPLC (OD-H column, 10% IPA in hexane isocratic) to give 7.0 mg one enantiomer and 10 mg the other enantiomer.

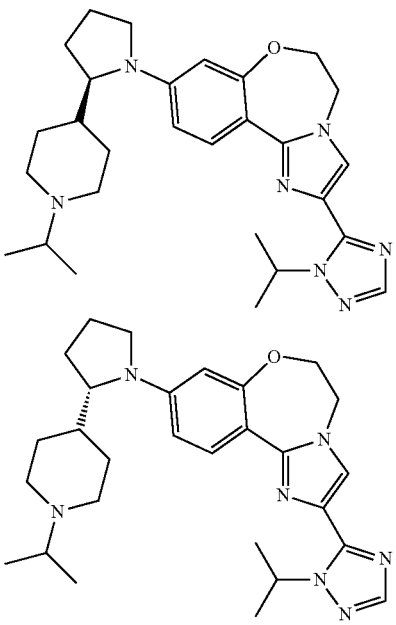

LCMS (ESI): RT=5.37 min, m/z: 490.5 [M+H$^+$]. $^1$H NMR (500 MHz, CD$_3$OD): δ 8.23 (d, J=8.5 Hz, 1H), 7.94 (s, 1H), 7.65 (s, 1H), 6.52-6.50 (m, 1H), 6.24 (d, J=2 Hz, 1H), 5.98-5.93 (m, 1H), 4.71 (s, 1H), 4.49-4.44 (m, 4H), 3.81-3.79 (m, 1H), 3.54-3.50 (m, 1H), 3.25-3.22 (m, 1H), 3.06-2.80 (m, 2H), 2.30-1.40 (m, 16H), 1.12 (d, J=6.5 Hz, 6H)

Example 176

2-(1-isopropyl-1H-1,2,4-triazol-5-yl)-10-(1-isopropylpiperidin-4-ylthio)-5,6-dihydrobenzo[f]imidazo[1,2-d][1,4]oxazepine 176

A mixture of 9-bromo-2-(2-isopropyl-2H-[1,2,4]triazol-3-yl)-4,5-dihydro-6-oxa-1,3a-diazabenzo[e]azulene from Example 1 (400 mg, 1.07 mmol), 1-isopropylpiperidine-4-thiol (340 mg, 2.14 mmol), Pd$_2$(dba)$_3$ (50 mg, 5 mol %), XantPhos (61 mg, 10 mol %) and DIPEA (0.745 mL, 4.28 mmol) in dioxane (10 mL) was purged with nitrogen and then heated at 120° C. for 1 h using microwave irradiation. The reaction mixture was diluted with DCM (200 mL) and purified by column chromatography (Si-PCC, 0-13% MeOH in DCM) then (C$_{18}$, 20-45% MeOH in 0.003M HCl/H$_2$O). The product containing fractions were combined and concentrated in vacuo and the resulting residue was loaded onto an Isolute® SCX-2 cartridge which was washed with MeOH and the product eluted with 0.5M NH$_3$/MeOH. The basic fractions were concentrated under reduced pressure affording 176 as a colorless solid (437 mg, 90%). LCMS: R$_T$ 3.01 min [M+H]$^+$ 453.3. $^1$H NMR (MeOD, 400 MHz): δ 8.54 (1H, d, J=2.36 Hz), 7.93 (1H, s), 7.77 (1H, s), 7.36 (1H, dd, J=8.49, 2.37 Hz), 7.02 (1H, d, J=8.49 Hz), 5.96-5.86 (1H, m), 4.55-4.46 (4H, m), 3.11-3.05 (1H, m), 2.94-2.84 (2H, m), 2.75-2.63 (1H, m), 2.28 (2H, t, J=11.32 Hz), 2.05-1.95 (2H, m), 1.69-1.53 (8H, m), 1.04 (6H, d, J=6.57 Hz)

Example 177

2-(1-isopropyl-1H-1,2,4-triazol-5-yl)-10-(1-isopropylpiperidin-4-ylsulfinyl)-5,6-dihydrobenzo[f]imidazo[1,2-d][1,4]oxazepine 177

To an ice-cooled solution of 9-(1-isopropylpiperidin-4-ylsulfanyl)-2-(2-isopropyl-2H-[1,2,4]triazol-3-yl)-4,5-dihydro-6-oxa-1,3a-diazabenzo[e]azulene 176 (410 mg, 0.91 mmol) in DCM (40 mL) was added TFA (210 µL, 2.72 mmol) followed by a solution of m-CPBA (172 mg, 0.997 mmol) in DCM (10 mL). The resulting mixture was stirred for 1 h at 0° C. then washed with a saturated solution of $NaHCO_3$, followed by water, then dried ($Na_2SO_4$) and concentrated in vacuo. The resulting residue was purified by column chromatography (Si-PCC, gradient 0-13% 2M $NH_3$/MeOH in DCM followed by Si-PCC, gradient 0-16% 2M $NH_3$/MeOH in EtOAc and then Si-PCC, gradient 0-10% 2M $NH_3$/MeOH in DCM) affording racemic 177 (181 mg, 43%). LCMS: $R_T$ 2.48 min [M+H]$^+$ 469.2. $^1$H NMR (MeOD, 400 MHz): δ 8.77 (1H, d, J=2.30 Hz), 7.95 (1H, s), 7.82 (1H, s), 7.59 (1H, dd, J=8.59, 2.31 Hz), 7.29 (1H, d, J=8.58 Hz), 5.95-5.87 (1H, m), 4.60 (4H, s), 3.03-2.93 (2H, m), 2.82 (1H, tt, J=11.83, 4.02 Hz), 2.75-2.67 (1H, m), 2.28-2.19 (2H, m), 1.91-1.79 (2H, m), 1.78-1.61 (2H, m), 1.57 (6H, 2d, J=6.63 Hz), 1.03 (6H, d, J=6.56 Hz)

Example 178

2-(1-isopropyl-1H-1,2,4-triazol-5-yl)-10-(1-isopropylpiperidin-4-ylsulfonyl)-5,6-dihydrobenzo[f]imidazo[1,2-d][1,4]oxazepine 178

To a solution of 9-(1-isopropylpiperidine-4-sulfinyl)-2-(2-isopropyl-2H-[1,2,4]triazol-3-yl)-4,5-dihydro-6-oxa-1,3a-diazabenzo[e]azulene 177 (214 mg, 0.456 mmol) and TFA (105 µL, 1.32 mmol) in DCM (10 mL) at 0° C. was added a solution of m-CPBA (95 mg, 0.542 mmol) in DCM (2 mL) and the resulting mixture was stirred for 2 h at RT. Volatiles were removed under reduced pressure and the crude material was purified by column chromatography ($C_{18}$, gradient 10-45% MeOH in 0.5% TFA/$H_2O$). The product containing fractions were combined and concentrated in vacuo and the resulting residue was loaded onto an Isolute® SCX-2 cartridge which was washed with MeOH and the product eluted with 0.5M $NH_3$ in MeOH affording 178 as a white solid (115 mg, 52%). LCMS: $R_T$ 2.68 min [M+H]$^+$ 485.2. $^1$H NMR (DMSO, 400 MHz): δ 8.89 (1H, d, J=2.40 Hz), 8.01 (1H, s), 7.95 (1H, d, J=0.62 Hz), 7.72 (1H, dd, J=8.63, 2.42 Hz), 7.31 (1H, d, J=8.63 Hz), 5.77-5.66 (1H, m), 4.69-4.58 (4H, m), 3.21-3.11 (1H, m), 2.85-2.77 (2H, m), 2.70-2.60 (1H, m), 2.09 (2H, bt, J=11.51 Hz), 1.92 (2H, bd, J=12.10 Hz), 1.50 (6H, d, J=6.61 Hz), 1.49-1.35 (2H, m), 0.89 (6H, d, J=6.54 Hz)

Example 179

1-(4-(2,2,2-trifluoro-1-(2-(1-isopropyl-3-methyl-1H-1,2,4-triazol-5-yl)-5,6-dihydrobenzo[f]imidazo[1,2-d][1,4]oxazepin-9-yloxy)ethyl)piperidin-1-yl)ethanone 179

To a solution of 4-{2,2,2-trifluoro-1-[2-(2-isopropyl-5-methyl-2H-[1,2,4]triazol-3-yl)-4,5-dihydro-6-oxa-1,3a-diazabenzo[e]azulen-8-yloxy]ethyl}piperidine-1-carboxylic acid benzyl ester from Example 5 (210 mg, 0.34 mmol) in a 1:10 mixture MeOH:acetone (11 mL), was added 10% Pd/C (200 mg). The reaction mixture was stirred at RT under a hydrogen atmosphere for 18 h. The suspension was then filtered through a pad of Celite® and to the filtrate fresh 10% Pd/C (200 mg) was added. The reaction mixture was stirred at RT under a hydrogen atmosphere for 48 h. The suspension was then filtered through a pad of Celite® and the filtrate was concentrated in vacuo. The resulting residue was treated with DIPEA (0.79 mL, 4.42 mmol) and acetyl chloride (0.23 mL, 4.08 mmol) and stirred at RT for 18 h. The crude material was purified by reverse phase HPLC (Phenomenex Gemini 5 µm C18 on a 25 min gradient 10-90% 0.1% $HCO_2H$ in acetonitrile/water) affording 179 (15 mg, 8%). LCMS: $R_T$ 4.23 min [M+H]$^+$ 533.2. $^1$H NMR (CDCl$_3$, 400 MHz): δ 8.47 (1H, d, J=8.99 Hz), 7.61 (1H, s), 6.80 (1H, dd, J=9.00, 2.62 Hz), 6.64 (1H, d, J=2.49 Hz), 5.92-5.85 (1H, m), 4.78-4.69 (1H, m), 4.50-4.47 (2H, m), 4.46-4.35 (3H, m), 3.93-3.85 (1H, m), 3.16-3.02 (1H, m), 2.64-2.51 (1H, m), 2.42 (3H, s), 2.27-2.15 (1H, m), 2.10 (3H, d, J=2.36 Hz), 2.05-1.93 (1H, m), 1.89-1.75 (1H, m), 1.64-1.44 (8H, m)

Example 186

2-(4-(2-(1-isopropyl-1H-1,2,4-triazol-5-yl)-5,6-dihydrobenzo[f]imidazo[1,2-d][1,4]oxazepin-10-ylsulfinyl)piperidin-1-yl)-2-methylpropan-1-ol 186

To an ice-cooled solution of 2-{4-[2-(2-isopropyl-2H-[1,2,4]triazol-3-yl)-4,5-dihydro-6-oxa-1,3a-diazabenzo[e]azulen-9-ylsulfanyl]piperidin-1-yl}-2-methylpropan-1-ol from Example 1 (229 mg, 0.474 mmol) in DCM (10 mL) was added TFA (110 µL, 1.42 mmol) followed by a solution of m-CPBA (82 mg, 0.474 mmol) in DCM (2 mL). The resulting mixture was stirred for 1 h at 0° C. then volatiles were removed under reduced pressure. The crude material was purified by column chromatography ($C_{18}$, gradient 10-35% MeOH in 0.5% TFA/$H_2O$) and then loaded onto an Isolute® SCX-2 cartridge. The cartridge was washed with MeOH and the product was eluted with 0.5M $NH_3$ in MeOH affording 186 as a white solid (177 mg, 75%). LCMS: $R_T$ 2.45 min [M+H]$^+$ 499.2. $^1$H NMR (DMSO, 400 MHz): δ 8.59 (1H, d, J=2.26 Hz), 7.97 (1H, s), 7.93 (1H, s), 7.53 (1H, dd, J=8.53, 2.28 Hz), 7.25 (1H, d, J=8.53 Hz), 5.80-5.67 (1H, m), 4.61-4.43 (4H, m), 4.22-4.16 (1H, m), 3.21 (2H, d, J=4.59 Hz), 3.06-2.96 (2H, m), 2.73-2.63 (1H, m), 2.17-2.05 (2H, m), 1.77 (1H, bd, J=12.25 Hz), 1.59 (1H, bd, J=12.59 Hz), 1.52-1.34 (8H, m), 0.88 (6H, s)

Example 187

2-(4-(2-(1-isopropyl-1H-1,2,4-triazol-5-yl)-5,6-dihydrobenzo[f]imidazo[1,2-d][1,4]oxazepin-10-ylsulfonyl)piperidin-1-yl)-2-methylpropan-1-ol 187

To an ice-cooled solution of 2-{4-[2-(2-isopropyl-2H-[1,2,4]triazol-3-yl)-4,5-dihydro-6-oxa-1,3a-diazabenzo[e]azulen-9-ylsulfanyl]piperidin-1-yl}-2-methylpropan-1-ol from Example 1 (63 mg, 0.129 mmol) in DCM (6 mL) was added TFA (30 µL, 0.388 mmol) followed by a slow addition of a solution of m-CPBA (49 mg, 0.285 mmol) in DCM (1.5 mL) and the resulting mixture was stirred for 3 h at 0° C. Volatiles were removed under reduced pressure and the resulting residue was purified by column chromatography ($C_{18}$, gradient 10-45% MeOH in 0.5% TFA/$H_2O$) and then loaded onto an Isolute® SCX-2 cartridge which was washed with MeOH and the product eluted with 0.5M NH₃ in MeOH. The basic fractions were concentrated under reduced pressure and the resulting residue was purified by column chromatography (Si-PCC, gradient 2-8% 2M NH₃/MeOH in DCM) affording 187 as a white solid (21 mg, 31%). LCMS: $R_T$ 2.67 min [M+H]⁺ 515.2. ¹H NMR (DMSO, 400 MHz): δ 8.87 (1H, d, J=2.38 Hz), 8.00 (1H, s), 7.94 (1H, s), 7.70 (1H, dd, J=8.63, 2.40 Hz), 7.29 (1H, d, J=8.63 Hz), 5.77-5.64 (1H, m), 4.67-4.74 (4H, m), 4.22 (1H, t, J=5.39 Hz), 3.22-3.07 (3H, m), 3.02 (2H, d, J=11.16 Hz), 2.09 (2H, t, J=11.54 Hz), 1.89 (2H, d, J=12.00 Hz), 1.49 (6H, d, J=6.61 Hz), 1.45-1.31 (2H, m), 0.86 (6H, s)

Example 188

9-(1-(2,4-dimethylthiazol-5-yl)ethoxy)-2-(1-isopropyl-3-methyl-1H-1,2,4-triazol-5-yl)-5,6-dihydrobenzo[f]imidazo[1,2-d][1,4]oxazepine 188

To a suspension of 2-(2-isopropyl-5-methyl-2H-[1,2,4] triazol-3-yl)-4,5-dihydro-6-oxa-1,3a-diazabenzo[e]azulen-8-ol from Example 4 (345 mg, 1.06 mmol), 1-(2,4-dimethylthiazol-5-yl)ethanol (250 mg, 1.59 mmol) and triphenylphosphine (0.84 g, 3.18 mmol) in dioxane (15 mL) was added dropwise DEAD (0.63 mL, 3.18 mmol) and the reaction mixture was stirred at RT for 18 h. Additional amounts of 1-(2,4-dimethylthiazol-5-yl)ethanol (100 mg, 0.63 mmol) and triphenylphosphine (0.42 g, 1.59 mmol) were added, followed by DEAD (0.31 mL, 1.59 mmol) and stirring at RT was continued for 72 h. Volatiles were removed under reduced pressure and the resulting residue was loaded onto an Isolute® SCX-2 cartridge which was washed with MeOH and the product eluted with 2M NH₃/MeOH. The product containing fractions were combined and concentrated in vacuo and the resulting residue was further purified by column chromatography (Si-PCC, gradient 0-6% MeOH in EtOAc then C₁₈, gradient 15-70% MeOH in H₂O) and finally loaded onto an Isolute® SCX-2 cartridge. The cartridge was washed with MeOH and the product eluted with 2M NH₃/MeOH affording 188 as a white solid (60 mg, 12%). LCMS: $R_T$ 4.42 min [M+H]⁺ 465.1. ¹H NMR (CDCl₃, 400 MHz): δ 8.33 (1H, d, J=9.33 Hz), 7.53 (1H, s), 6.65 (1H, dd, J=9.33 and 2.56 Hz), 6.46 (1H, d, J=2.71), 5.91-5.81 (1H, m), 5.54-5.48 (1H, m), 4.44-4.29 (4H, m), 2.57 (3H, s), 2.39 (3H, s), 2.37 (3H, s), 1.65 (3H, d J=6.22 Hz), 1.52 (6H, d, J=6.72 Hz)

Example 190

1044-tert-butylpiperazin-1-yl)methyl)-2-(1-isopropyl-1H-1,2,4-triazol-5-yl)-9-methyl-5,6-dihydrobenzo[f]imidazo[1,2-d][1,4]oxazepine 190

Step 1: {12-Methyl-4-[1-(propan-2-yl)-1H-1,2,4-triazol-5-yl]-9-oxa-3,6-diazatricyclo[8.4.0.0²,⁶]tetradeca-1(14),2,4,10,12-pentaen-13-yl}methanol

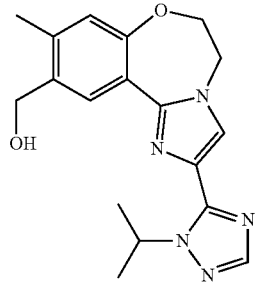 [SMILES: Cc1cc2c(cc1CO)-c1nc(-c3ncnn3C(C)C)cn1CCO2]

To a solution of methyl 12-methyl-4-[1-(propan-2-yl)-1H-1,2,4-triazol-5-yl]-9-oxa-3,6-diazatricyclo[8.4.0.0²,⁶]tetradeca-1(14),2,4,10,12-pentaene-13-carboxylate (100 mg, 0.272 mmol) in THF (10 mL) was added LiAlH₄ (52 mg, 1.37 mmol). The mixture was heated to reflux for 2 h. After cooling to room temperature, the reaction was quenched with a piece of ice cube. The solid was filtered, washed with EtOAc (3×5 mL). The combined filtrate was concentrated to give {12-methyl-4-[1-(propan-2-yl)-1H-1,2,4-triazol-5-yl]-9-oxa-3,6-diazatricyclo[8.4.0.0²,⁶]tetradeca 1(14),2,4,10,12-pentaen-13-yl}methanol (92 mg, 100% yield), which was directly used in the next step without further purification. LCMS (ESI) m/z: 340.2 [M+H⁺].

Step 2: 12-Methyl-4-[1-(propan-2-yl)-1H-1,2,4-triazol-5-yl]-9-oxa-3,6-diazatricyclo[8.4.0.0²,⁶]tetradeca-1(14),2,4,10,12-pentaene-13-carbaldehyde

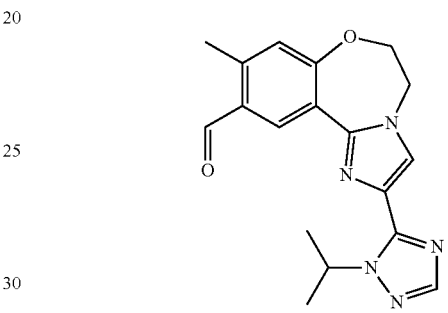

To a solution of {12-methyl-4-[1-(propan-2-yl)-1H-1,2,4-triazol-5-yl]-9-oxa-3,6-diazatricyclo[8.4.0.0²,⁶]tetradeca-1 (14),2,4,10,12-pentaen-13-yl}methanol (92 mg, 0.271 mmol) in EtOAc (10 mL) was added 2-iodobenzoic acid (304 mg, 1.086 mmol). The mixture was heated at 80° C. overnight. The solid was filtered, the filtrate was concentrated and purified by silica gel chromatography eluting with EtOAc/ petroleum ether (1:1) to give 12-methyl-4-[1-(propan-2-yl)-1H-1,2,4-triazol-5-yl]-9-oxa-3,6-diazatricyclo[8.4.0.0²,⁶] tetradeca-1(14),2,4,10,12-pentaene-13-carbaldehyde (65 mg, 71% yield) as a yellow solid. LCMS (ESI) m/z: 338.1 [M+H+].

Step 3

To a solution of 12-methyl-4-[1-(propan-2-yl)-1H-1,2,4-triazol-5-yl]-9-oxa-3,6-diazatricyclo[8.4.0.0²,⁶]tetradeca-1 (14),2,4,10,12-pentaene-13-carbaldehyde (55.0 mg, 0.163 mmol) in EtOH (10 mL) was added 1-tert-butylpiperazine (46 mg, 0.324 mmol) and tetraisopropyl titanate (93 mg, 0.327 mmol). After being stirred at room temperature for 1 h, sodium cyanoborohydride (21.0 mg, 0.333 mmol) was added. The mixture was stirred at room temperature overnight. After being quenched with water (5 mL), the resultant mixture was extracted with EtOAc (3×10 mL), washed with water (2×10 mL), and brine (10 mL). The organic phase was dried over Na₂SO₄ and concentrated to give crude product, which was purified by prep-HPLC (Gilson GX 281, Shim-pack PRC-ODS 250 mm×20 mm×2, gradient: CH₃CN/10 mm/L NH₄HCO₃, 17 min) to afford 190 (18.2 mg, 24% yield) as a white solid. LCMS (ESI): RT=5.67 min, m/z: 464.4 [M+H+]. ¹H NMR (500 MHz, MeOH-d₄) δ 8.33 (s, 1H), 7.91 (s, 1H), 7.89 (s, 1H), 6.85 (s, 1H), 5.88 (m, 1H), 4.50-4.44 (m, 4H), 3.40 (s, 2H), 2.45-2.36 (m, 7H), 2.27 (s, 3H), 1.51-1.50 (d, J=7.0 Hz, 6H), 0.99 (s, 9H)

Example 191

3-(1-(2-(1-isopropyl-3-methyl-1H-1,2,4-triazol-5-yl)-5,6-dihydrobenzo[f]imidazo[1,2-d][1,4]oxazepin-9-yloxy)ethyl)benzonitrile 191

To a suspension of 2-(2-isopropyl-5-methyl-2H-[1,2,4]triazol-3-yl)-4,5-dihydro-6-oxa-1,3a-diazabenzo[e]azulen-8-ol from Example 4 (300 mg, 0.92 mmol), 3-(1-hydroxyethyl)benzonitrile (390 mg, 2.65 mmol) and triphenylphosphine (600 mg, 2.28 mmol) in dioxane (10 mL) was added dropwise DIAD (449 ul, 2.28 mmol) and the reaction mixture was stirred at RT for 18 h under an argon atmosphere. Volatiles were removed in vacuo and the resulting residue was purified by column chromatography (Si-PCC, gradient 0-10% MeOH in EtOAc). The product containing fractions were combined and concentrated under reduced pressure. The resulting residue was stirred in aq. NaOH (2M) for 15 min and then was filtered off. The resulting residue was purified by reverse phase HPLC (Phenomenex Gemini 5 μm C18 on a 25 min gradient 50-100% 0.1% HCO$_2$H in acetonitrile/water) affording 191 (29 mg, 7%). LCMS: R$_T$ 4.81 min [M+H]$^+$ 455.2. $^1$H NMR (DMSO, 400 MHz): δ 8.26 (1H, d, J=8.97 Hz), 7.93-7.89 (1H, m), 7.82-7.74 (3H, m), 7.60 (1H, t, J=7.78 Hz), 6.80 (1H, dd, J=9.00, 2.57 Hz), 6.57 (1H, d, J=2.54 Hz), 5.87-5.75 (1H, m), 5.66 (1H, q, J=6.38 Hz), 4.49-4.40 (4H, m), 2.25 (3H, s), 1.59 (3H, d, J=6.35 Hz), 1.45 (6H, d, J=6.60 Hz)

Example 192

2-(4-(2-(1-isopropyl-1H-1,2,4-triazol-5-yl)-5,6-dihydrobenzo[f]imidazo[1,2-d][1,4]oxazepin-10-ylsulfonyl)piperidin-1-yl)-2-methylpropanamide 192

Step 1: 2-{4-[2-(2-Isopropyl-2H-[1,2,4]triazol-3-yl)-4,5-dihydro-6-oxa-1,3a-diazabenzo[e]azulen-9-ylsulfanyl]piperidin-1-yl}isobutyramide

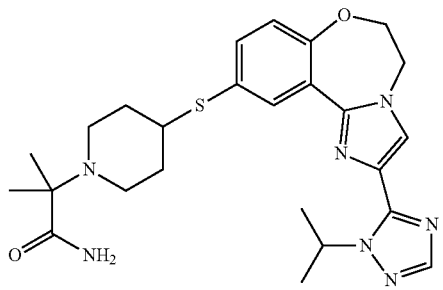 [SMILES: CC(C)n1ncnc1-c1cn2c(n1)-c1cc(SC3CCN(C(C)(C)C(N)=O)CC3)ccc1OCC2]

A mixture of 2-(2-isopropyl-2H-[1,2,4]triazol-3-yl)-9-(piperidin-4-ylsulfanyl)-4,5-dihydro-6-oxa-1,3a-diazabenzo[e]azulene from Example 2 (0.244 g, 0.594 mmol), 2-bromo-2-methylpropionamide (0.494 g, 2.976 mmol) and Cs$_2$CO$_3$ (0.774 g, 2.376 mmol) in CH$_3$CN (15 mL) was heated at 120° C. for 2 h using microwave irradiation. The crude mixture was filtered through a pad of Celite® and the filtrate was concentrated in vacuo. The resulting residue was purified by column chromatography (Si-PCC, gradient 2-8% 2M NH$_3$/MeOH in DCM) to give 0.261 g (89% yield) of 2-{4-[2-(2-Isopropyl-2H-[1,2,4]triazol-3-yl)-4,5-dihydro-6-oxa-1,3a-diazabenzo[e]azulen-9-ylsulfanyl]piperidin-1-yl}isobutyramide as a colorless foam. A portion of the resulting residue (28 mg) was further purified by column chromatography (C$_{18}$, gradient 15-55% MeOH in 0.5% TFA/H$_2$O) and then loaded onto an Isolute® SCX-2 cartridge which was washed with MeOH and the product eluted with 0.5M NH$_3$/MeOH affording the title compound (13 mg). LCMS: R$_T$ 2.92 min [M+H]$^+$ 496.1.

Method B: A mixture of 2-(2-isopropyl-2H-[1,2,4]triazol-3-yl)-9-(piperidin-4-ylsulfanyl)-4,5-dihydro-6-oxa-1,3a-diazabenzo[e]azulene from Example 2 (80 mg, 0.195 mmol), 2-bromo-2-methylpropionamide (39 mg, 0.234 mmol) and Ag$_2$O (90 mg, 0.39 mmol) in CH$_3$CN (2 mL) and water (0.1 mL) was flushed with nitrogen, then sealed and heated at 80° C. for 18 h. The crude mixture was filtered through a pad of Celite® and the filtrate was concentrated in vacuo. The resulting residue was purified by column chromatography (Si-PCC, gradient 2-10% 2M NH$_3$/MeOH in DCM) affording the title compound as a colorless gum (38 mg, 40%). LCMS: R$_T$ 2.08/2.17 min [M+H]$^+$ 496.2

Method C: To a suspension of 2-{4-[2-(2-isopropyl-2H-[1,2,4]triazol-3-yl)-4,5-dihydro-6-oxa-1,3a-diazabenzo[e]azulen-9-ylsulfanyl]piperidin-1-yl}-2-methylpropionic acid (20 mg, 0.0411 mmol) in DMF (1.5 mL) was added DIPEA (21 ul, 0.123 mmol), HOBt.NH$_3$ (9 mg, 0.0616 mmol) and EDCI (12 mg, 0.0616 mmol) and the reaction mixture was stirred at RT for 18 h. The mixture was then partitioned between EtOAc and water. The aqueous layer was further extracted with EtOAc and the combined organic layers were washed with water, followed by brine, then dried and concentrated in vacuo. The resulting residue was purified by column chromatography (Si-PCC, gradient 2-8% 2M NH$_3$/MeOH in DCM) affording 2-{4-[2-(2-Isopropyl-2H-[1,2,4]triazol-3-yl)-4,5-dihydro-6-oxa-1,3a-diazabenzo[e]azulen-9-ylsulfanyl]piperidin-1-yl}isobutyramide as a colorless gum (16 mg, 77%). LCMS: R$_T$ 2.16/2.19 min [M+H]$^+$ 496.1

Step 2

To an ice-cooled solution of 2-{4-[2-(2-isopropyl-2H-[1,2,4]triazol-3-yl)-4,5-dihydro-6-oxa-1,3a-diazabenzo[e]azulen-9-ylsulfanyl]piperidin-1-yl}isobutyramide (86 mg, 0.1735 mmol) in DCM (10 mL) was added TFA (40 μL, 0.52 mmol) followed by a slow addition of a solution of m-CPBA (66 mg, 0.382 mmol) in DCM (2 mL) and the resulting mixture was stirred for 2 h at 0° C. Volatiles were removed under reduced pressure and the resulting residue was purified by column chromatography (C$_{18}$, gradient 15-40% MeOH in 0.5% TFA/H$_2$O) and then loaded onto an Isolute® SCX-2 cartridge which was washed with MeOH and the product eluted with 0.5M NH$_3$ in MeOH affording 192 as a white solid (43 mg, 47%). LCMS: R$_T$ 2.64 min [M+H]$^+$ 528.1. $^1$H NMR (DMSO, 400 MHz): δ 8.89 (1H, d, J=2.40 Hz), 8.00 (1H, s), 7.94 (1H, d, J=0.62 Hz), 7.72 (1H, dd, J=8.64, 2.42 Hz), 7.30 (1H, d, J=8.64 Hz), 7.11 (1H, d, J=3.21 Hz), 6.84 (1H, d, J=3.15 Hz), 5.76-5.65 (1H, m), 4.67-4.56 (4H, m), 3.22-3.12 (1H, m), 2.80 (2H, bd, J=11.03 Hz), 2.06 (2H, bt, J=11.43 Hz), 1.89 (2H, bd, J=11.60 Hz), 1.68-1.55 (2H, m), 1.49 (6H, d, J=6.61 Hz), 1.01 (6H, s)

Example 193

2-(4-(2-(1-isopropyl-1H-1,2,4-triazol-5-yl)-5,6-dihydrobenzo[f]imidazo[1,2-d][1,4]oxazepin-10-ylsulfinyl)piperidin-1-yl)-2-methylpropanamide 193

To an ice-cooled solution of 2-{4-[2-(2-isopropyl-2H-[1,2,4]triazol-3-yl)-4,5-dihydro-6-oxa-1,3a-diazabenzo[e]azulen-9-ylsulfanyl]piperidin-1-yl}isobutyramide from Example 192 (233 mg, 0.470 mmol) in DCM (20 mL) was added TFA (109 μL, 1.41 mmol) followed by a solution of m-CPBA (89 mg, 0.512 mmol) in DCM (2 mL). The resulting mixture was stirred for 30 min at 0° C. then volatiles were removed under reduced pressure. The crude material was purified by column chromatography (C$_{18}$, gradient 10-40% MeOH in 0.5% TFA/H$_2$O) and then loaded onto an Isolute® SCX-2 cartridge. The cartridge was washed with MeOH and the product was eluted with 0.5M NH$_3$ in MeOH affording 193 as a colorless foam (116 mg, 48%). LCMS: R$_T$ 2.42 min [M+H]$^+$ 512.1. $^1$H NMR (DMSO, 400 MHz): δ 8.61 (1H, d, J=2.26 Hz), 7.98 (1H, s), 7.93 (1H, s), 7.55 (1H, dd, J=8.53, 2.28 Hz), 7.26 (1H, d, J=8.53 Hz), 7.09 (1H, d, J=3.29 Hz), 6.87 (1H, d, J=3.29 Hz), 5.78-5.67 (1H, m), 4.61-4.54 (4H, m), 2.80 (2H, bd, J=10.79 Hz), 2.74-2.64 (1H, m), 2.13-2.00 (2H, m), 1.78 (1H, bd, J=12.05 Hz), 1.69-1.55 (3H, m), 1.49 (3H, d, J=6.6 Hz), 1.47 (3H, d, J=6.6 Hz), 1.02 (6H, s)

Example 194

2-(1-isopropyl-3-methyl-1H-1,2,4-triazol-5-yl)-9-(1-methyl-5-(1-methylpiperidin-4-yl)-1H-pyrazol-4-yl)-5,6-dihydrobenzo[f]imidazo[1,2-d][1,4]oxazepine 194

Following the procedures in Example 266, 194 was prepared. $^1$H NMR (400 MHz, DMSO) δ 8.40 (d, J=8.3 Hz, 1H), 7.90 (s, 1H), 7.39 (s, 1H), 7.10-7.05 (m, 1H), 6.95-6.90 (m, 1H), 5.93-5.71 (m, 1H), 4.58-4.49 (m, 4H), 3.87 (s, 3H), 2.88-2.77 (m, 3H), 2.26 (s, 3H), 2.14 (s, 3H), 1.95-1.80 (m, 4H), 1.71-1.60 (m, 2H), 1.47 (d, J=6.6 Hz, 6H). LCMS: 487.3

Example 195

1-(4-(4-(2-(1-isopropyl-3-methyl-1H-1,2,4-triazol-5-yl)-5,6-dihydrobenzo[f]imidazo[1,2-d][1,4]oxazepin-9-yl)-1-methyl-1H-pyrazol-5-yl)piperidin-1-yl)ethanone 195

Following the procedures in Example 266, 195 was prepared. $^1$H NMR (400 MHz, DMSO) δ 8.43-8.37 (m, 1H), 7.89 (s, 1H), 7.42 (s, 1H), 7.12-7.05 (m, 1H), 6.93 (s, 1H), 5.89-5.79 (m, 1H), 4.56-4.43 (m, 5H), 3.93-3.82 (d, J=47.1 Hz, 4H), 3.25-3.00 (m, 2H), 2.55 (s, 1H), 2.26 (s, 3H), 1.99 (s, 3H), 1.91-1.57 (m, 4H), 1.46 (d, J=6.4 Hz, 6H). LCMS: 515.3

Example 196

(4-tert-butylpiperazin-1-yl)(2-(1-isopropyl-1H-1,2,4-triazol-5-yl)-5,6-dihydroimidazo[1,2-d]pyrido[4,3-f][1,4]oxazepin-10-yl)methanone 196

A mixture of 9-bromo-2-pyridin-2-yl-4,5-dihydro-6-oxa-1,3a-diazabenzo[e]azulene from Example 3 (40 mg, 0.117 mmol), 1-isopropylpiperidine-4-thiol (37 mg, 0.234 mmol), Pd$_2$(dba)$_3$ (5 mg, 5 mol %), XantPhos (6 mg, 10 mol %) and DIPEA (75 ul, 0.0416 mmol) in dioxane (1.5 mL) was purged with nitrogen and then heated at 120° C. for 1 h using microwave irradiation. The reaction mixture was diluted with DCM (50 mL) and purified by column chromatography (Si-PCC, gradient 0-20% MeOH in DCM; then 20-30% 2M NH$_3$/MeOH in DCM followed by C$_{18}$, gradient 5-30% MeOH in 0.003M HCl/H$_2$O). The product containing fractions were combined and concentrated in vacuo and the resulting residue was loaded onto an Isolute® SCX-2 cartridge which was washed with MeOH and the product eluted with 0.5M NH$_3$/MeOH. The product containing fractions were combined and concentrated in vacuo affording 196 as a colorless foam (17 mg, 35%). LCMS: R$_T$ 2.35 min [M+H]$^+$ 421.1. $^1$H NMR (DMSO, 400 MHz): δ 8.56 (1H, d, J=2.38 Hz), 8.52 (1H, ddd, J=4.81, 1.82, 0.93 Hz), 7.99 (1H, dt, J=7.92, 1.07 Hz), 7.91 (1H, s), 7.82 (1H, td, J=7.70, 1.85 Hz), 7.35 (1H, dd, J=8.46, 2.41 Hz), 7.23 (1H, ddd, J=7.46, 4.81, 1.23 Hz), 7.03 (1H, d, J=8.46 Hz), 4.54-4.47 (4H, m), 3.09-2.99 (1H, m), 2.78-2.70 (2H, m), 2.68-2.60 (1H, m), 2.17 (2H, bt, J=11.00 Hz), 1.88 (2H, bd, J=12.55 Hz), 1.51-1.40 (2H, m), 0.92 (6H, d, J=6.56 Hz)

Example 197

2-methyl-2-(4-(2-(pyridin-2-yl)-5,6-dihydrobenzo[f]imidazo[1,2-d][1,4]oxazepin-10-ylsulfinyl)piperidin-1-yl)propan-1-ol 197

To an ice-cooled solution of 2-methyl-2-[4-(2-pyridin-2-yl-4,5-dihydro-6-oxa-1,3a-diazabenzo[e]azulen-9-ylsulfanyl)piperidin-1-yl]propan-1-ol from Example 3 (187 mg, 0.415 mmol) in DCM (20 mL) was added TFA (160 μL, 2.075 mmol) followed by a solution of m-CPBA (79 mg, 0.456 mmol) in DCM (2 mL). The resulting mixture was stirred for 30 min at 0° C. then volatiles were removed under reduced pressure. The crude material was purified by column chromatography (C$_{18}$, gradient 10-30% MeOH in 0.5% TFA/H$_2$O) and then loaded onto an Isolute® SCX-2 cartridge. The cartridge was washed with MeOH and the product was eluted with 0.5M NH$_3$ in MeOH. Further purification by column chromatography (Si-PCC, gradient 2-17% 2M NH$_3$/MeOH in DCM) afforded 197 as a light brown foam (102 mg, 52%). LCMS: R$_T$1.87 min [M+H]$^+$ 467.1. $^1$H NMR (DMSO, 400 MHz): δ 8.71 (1H, d, J=2.27 Hz), 8.53 (1H, ddd, J=4.81, 1.82, 0.94 Hz), 8.00 (1H, dt, J=7.92, 1.08 Hz), 7.95 (1H, s), 7.83 (1H, td, J=7.70, 1.85 Hz), 7.50 (1H, dd, J=8.51, 2.30 Hz), 7.26-7.21 (2H, m), 4.58-4.52 (4H, m), 4.18 (1H, t, J=5.42 Hz), 3.21 (2H, d, J=5.19 Hz), 3.07-2.98 (2H, m), 2.72-2.62 (1H, m), 2.17-2.04 (2H, m), 1.78-1.72 (1H, m), 1.48-1.41 (3H, m), 0.89 (6H, s)

Example 198

10-(1-isopropylpiperidin-4-ylsulfinyl)-2-(pyridin-2-yl)-5,6-dihydrobenzo[f]imidazo[1,2-d][1,4]oxazepine 198

To an ice-cooled solution of 9-(1-isopropylpiperidin-4-ylsulfanyl)-2-pyridin-2-yl-4,5-dihydro-6-oxa-1,3a-diazabenzo[e]azulene 196 (242 mg, 0.574 mmol) in DCM (20 mL) was added TFA (222 μL, 2.87 mmol) followed by a solution of m-CPBA (109 mg, 0.632 mmol) in DCM (2 mL). The resulting mixture was stirred for 30 min at 0° C. then volatiles were removed under reduced pressure. The crude material was purified by column chromatography (C$_{18}$, gradient 5-30% MeOH in 0.5% TFA/H$_2$O) and then loaded onto an Isolute® SCX-2 cartridge. The cartridge was washed with MeOH and the product was eluted with 0.5M NH$_3$ in MeOH affording 198 as a light pink foam (216 mg, 86%). LCMS: R$_T$1.89 min [M+H]$^+$ 437.1. $^1$H NMR (DMSO, 400 MHz): δ 8.72 (1H, d, J=2.27 Hz), 8.53 (1H, ddd, J=4.81, 1.81, 0.94 Hz), 8.00 (1H, dt, J=7.92, 1.07 Hz), 7.95 (1H, s), 7.83 (1H, td, J=7.70, 1.85 Hz), 7.50 (1H, dd, J=8.51, 2.30 Hz), 7.26-7.20 (2H, m), 4.59-4.53 (4H, m), 2.86-2.77 (2H, m), 2.73-2.58 (2H, m), 2.09 (2H, bq, J=11.88 Hz), 1.77 (1H, bd, J=12.25 Hz), 1.59-1.41 (3H, m), 0.90 (6H, d, J=6.54 Hz)

Example 199

2-methyl-2-(4-(2-(pyridin-2-yl)-5,6-dihydrobenzo[f]imidazo[1,2-d][1,4]oxazepin-10-ylsulfonyl)piperidin-1-yl)propan-1-ol 199

To an ice-cooled solution of 2-methyl-2-[4-(2-pyridin-2-yl-4,5-dihydro-6-oxa-1,3a-diazabenzo[e]azulene-9-sulfinyl)

piperidin-1-yl]propan-1-ol 197 (30 mg, 0.064 mmol) in DCM (2 mL) was added TFA (25 µL, 0.318 mmol) followed by a slow addition of a solution of m-CPBA (13 mg, 0.076 mmol) in DCM (0.5 mL) and the resulting mixture was stirred for 1 h at RT. Volatiles were removed under reduced pressure and the resulting residue was purified by column chromatography ($C_{18}$, gradient 5-30% MeOH in 0.5% TFA/$H_2O$). To an ice-cooled solution in DCM (10 mL) of the product thus obtained was added TFA (12 µA) followed by a solution of m-CPBA (13 mg, 0.076 mmol) in DCM (0.5 mL). The mixture was stirred at RT for 1.5 h and then volatiles were removed under reduced pressure. The resulting residue was purified by column chromatography ($C_{18}$, gradient 5-30% MeOH in 0.5% TFA/$H_2O$) and then loaded onto an Isolute® SCX-2 cartridge which was washed with MeOH and the product eluted with 0.5M $NH_3$ in MeOH. Further purification by column chromatography (Si-PCC, gradient 2-8% 2M $NH_3$/MeOH in DCM) afforded 199 as a white solid (14 mg, 47%). LCMS: $R_T$ 2.03 min [M+H]$^+$ 483.1. $^1$H NMR (DMSO, 400 MHz): δ 8.95 (1H, d, J=2.41 Hz), 8.53 (1H, ddd, J=4.81, 1.80, 0.93 Hz), 8.00-7.94 (2H, m), 7.85 (1H, td, J=7.69, 1.84 Hz), 7.68 (1H, dd, J=8.62, 2.43 Hz), 7.29-7.22 (2H, m), 4.65-4.55 (4H, m), 4.21 (1H, t, J=5.42 Hz), 3.22-3.10 (3H, m), 3.07-2.99 (2H, m), 2.09 (2H, bt, J=11.55 Hz), 1.86 (2H, bd, J=12.02 Hz), 1.50-1.37 (2H, m), 0.87 (6H, s)

Example 200

10-(1-isopropylpiperidin-4-ylsulfonyl)-2-(pyridin-2-yl)-5,6-dihydrobenzo[f]imidazo[1,2-d][1,4]oxazepine 200

To an ice-cooled solution of 9-(1-isopropylpiperidine-4-sulfinyl)-2-pyridin-2-yl-4,5-dihydro-6-oxa-1,3a-diazabenzo [e]azulene 198 (50 mg, 0.1145 mmol) in DCM (10 mL) was added TFA (44 µL, 0.573 mmol) followed by a slow addition of a solution of m-CPBA (30 mg, 0.172 mmol) in DCM (1 mL). The resulting mixture was stirred for 2 h at RT. Volatiles were removed under reduced pressure and the resulting residue was purified by column chromatography ($C_{18}$, gradient 5-35% MeOH in 0.5% TFA/$H_2O$) and then loaded onto an Isolute® SCX-2 cartridge. The cartridge was washed with MeOH and the product eluted with 0.5M $NH_3$ in MeOH. Further purification by column chromatography (Si-PCC, gradient 2-8% 2M $NH_3$/MeOH in DCM) afforded 200 as a white solid (39 mg, 75%). LCMS: $R_T$ 2.05 min [M+H]$^+$ 453.1. $^1$H NMR (DMSO, 400 MHz): δ 8.95 (1H, d, J=2.41 Hz), 8.53 (1H, ddd, J=4.81, 1.80, 0.93 Hz), 8.00-7.95 (2H, m), 7.84 (1H, td, J=7.69, 1.84 Hz), 7.69 (1H, dd, J=8.62, 2.43 Hz), 7.30-7.22 (2H, m), 4.65-4.54 (4H, m), 3.23-3.13 (1H, m), 2.82 (2H, bd, J=11.14 Hz), 2.68-2.59 (1H, m), 2.08 (2H, bt, J=11.51 Hz), 1.87 (2H, bd, J=12.10 Hz), 1.51-1.40 (2H, m), 0.89 (6H, d, J=6.55 Hz)

Example 201

2-(1-isopropyl-3-methyl-1H-1,2,4-triazol-5-yl)-9-(1-methyl-5-((4-methylpiperazin-1-yl)methyl)-1H-pyrazol-4-yl)-5,6-dihydrobenzo[f]imidazo[1,2-d][1,4]oxazepine 201

Following the procedures in Example 266, 201 was prepared. $^1$H NMR (400 MHz, DMSO) δ 8.39 (d, J=8.3 Hz, 1H), 7.88 (s, 1H), 7.68 (s, 1H), 7.31-7.25 (m, 1H), 7.25-7.20 (m, 1H), 5.84 (hept, J=6.7 Hz, 1H), 4.56-4.48 (m, 4H), 3.88 (s, 3H), 3.65 (s, 2H), 2.45-2.30 (m, 8H), 2.25 (s, 3H), 2.13 (s, 3H), 1.47 (d, J=6.6 Hz, 6H). LCMS: 502.3

Example 202

2-(1-(1-(2-(1-isopropyl-4-methyl-1H-imidazol-2-yl)-5,6-dihydrobenzo[f]imidazo[1,2-d][1,4]oxazepin-10-yl)ethyl)piperidin-4-yl)propan-2-ol 202

Step 1: 1-{4-[4-Methyl-1-(propan-2-yl)-1H-imidazol-2-yl]-9-oxa-3,6-diazatricyclo[8.4.0.0$^{2,6}$]tetradeca1(14),2,4,10,12-pentaen-13-yl}ethyl methanesulfonate

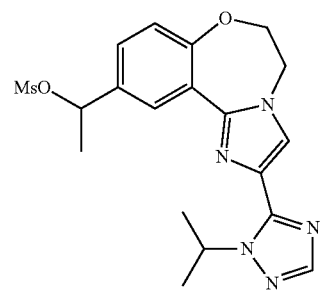 [SMILES: CC(OS(C)(=O)=O)c1ccc2c(c1)-c1nc(-c3ncnn3C(C)C)cn1CCO2]

To a solution of 1-{4-[4-methyl-1-(propan-2-yl)-1H-imidazol-2-yl]-9-oxa-3,6-diazatricyclo[8.4.0.0$^{2,6}$]tetradeca-1 (14),2,4,10,12-pentaen-13-yl}ethan-1-ol (10 mg, 0.028 mmol) in DCM (2 mL) at 0° C. was added TEA (14 mg, 0.139 mmol) and methanesulfonyl chloride (6.0 mg, 0.053 mmol). The reaction mixture was further stirred at 0° C. for 2 h. TLC showed the reaction was completed. After being quenched with aqueous NaHCO$_3$ (5 mL), the resultant mixture was extracted with DCM (3×5 mL), washed with brine (2×5 mL). The organic phase was dried over Na$_2$SO$_4$ and concentrated to give 1-{4-[4-methyl-1-(propan-2-yl)-1H-imidazol-2-yl]-9-oxa-3,6-diazatricyclo[8.4.0.0$^{2,6}$]tetradeca1(14),2,4,10,12-pentaen-13-yl}ethyl methanesulfonate (12 mg, 100% yield), which was directly used in the next step without further purification.

Step 2

To a solution of 1-{4-[4-methyl-1-(propan-2-yl)-1H-imidazol-2-yl]-9-oxa-3,6-diazatricyclo[8.4.0.0$^{2,6}$]tetradeca-1 (14),2,4,10,12-pentaen-13-yl}ethyl methanesulfonate (12 mg, 0.028 mmol) in dioxane (2 mL) was added 2-(piperidin-4-yl)propan-2-ol (40 mg, 0.280 mmol). The resulting mixture was heated at 90° C. overnight. The solvent was removed under reduce pressure and the residue was purified by prep-HPLC (Gilson GX 281, Shim-pack PRC-ODS 250 mm×20 mm×2, gradient: CH$_3$CN/10 mm/L NH$_4$HCO$_3$, 17 min) to afford 202 (2.5 mg, 18% yield) as a white solid. LCMS (ESI): RT=5.23 min, m/z: 478.4 [M+H$^+$]. $^1$H NMR (500 MHz, DMSO-d$_6$) δ 8.36 (s, 1H), 7.55 (s, 1H), 7.30-7.28 (d, J=9.0 Hz, 1H), 7.05-7.04 (d, J=8.0 Hz, 1H), 7.02 (s, 1H), 5.48 (m, 1H), 4.52 (s, 4H), 3.57 (m, 1H), 3.21-3.18 (m, 1H), 2.99 (m, 1H), 2.23 (s, 3H), 2.10-1.60 (m, 4H), 1.52-1.47 (m, 10H), 1.35-1.22 (m, 3H), 1.13 (s, 6H)

Example 203

(4-tert-butylpiperazin-1-yl)(2-(1-isopropyl-1H-1,2,4-triazol-5-yl)-5,6-dihydroimidazo[1,2-d]pyrido[4,3-f][1,4]oxazepin-10-yl)methanone 203

Step 1: 2-(1-isopropyl-1H-1,2,4-triazol-5-yl)-10-vinyl-5,6-dihydroimidazo[1,2-d]pyrido[4,3-f][1,4]oxazepine

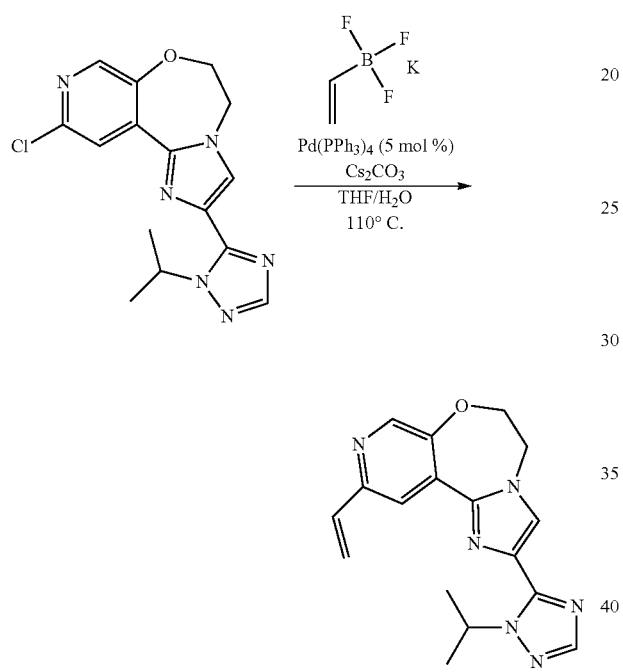

10-chloro-2-(1-isopropyl-1H-1,2,4-triazol-5-yl)-5,6-dihydroimidazo[1,2-d]pyrido[4,3-f][1,4]oxazepine from Example 22 (596 mg, 0.00180 mol) and potassium chlorotrifluoroborate (0.483 g, 0.00360 mol) were dissolved in tetrahydrofuran (7 mL, 0.09 mol) and water (1 mL, 0.08 mol). Cesium Carbonate (1.8 g, 0.0054 mol) was added and the mixture was degassed with bubbling $N_2$ for 10 minutes.

Tetrakis(triphenylphosphine)palladium(0) (0.10 g, 0.090 mmol) was added. The reaction vessel was sealed and then heated at 110° C. in a oil bath overnight. The reaction mixture was cooled at 0° C. The seal was removed. LC-MS analysis of the reaction mixture showed complete conversion to desired product. The reaction mixture was partitioned between EtOAc and $H_2O$. The aqueous layer was discarded and the org. layer was washed with brine. The organic extract was dried over sodium sulfate, filtered, and concentrated to dryness. The crude residue was purified by FCC to give 2-(1-isopropyl-1H-1,2,4-triazol-5-yl)-10-vinyl-5,6-dihydroimidazo[1,2-d]pyrido[4,3-f][1,4]oxazepine (12 g—$SiO_2$, 0-10% MeOH/DCM). LCMS 323.3

Step 2: 2-(1-isopropyl-1H-1,2,4-triazol-5-yl)-5,6-dihydroimidazo[1,2-d]pyrido[4,3-f][1,4]oxazepine-10-carbaldehyde

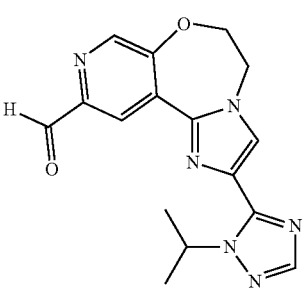 [SMILES: CC(C)n1ncnc1-c1cn2c(n1)-c1cc(C=O)ncc1OCC2]

2-(1-isopropyl-1H-1,2,4-triazol-5-yl)-10-vinyl-5,6-dihydroimidazo[1,2-d]pyrido[4,3-f][1,4]oxazepine (0.500 g, 0.00155 mol) was dissolved in Tetrahydrofuran (30 mL, 0.4 mol) and Water (20 mL, 1 mol). Osmium tetraoxide 4% (wt) in water (0.758 mL, 0.000124 mol) was added. Followed by sodium metaperiodate (0.664 g, 0.00310 mol). The reaction mixture was stirred overnight at room temperature. LC-MS analysis of the reaction mixture showed complete conversion to desired product [C]. The crude reaction mixture was quenched with saturated sodium thiosulfate, diluted with EtOAc, and extracted 3×. The combined organic layers were dried over sodium sulfate, filtered, and concentrated to dryness to give 2-(1-isopropyl-1H-1,2,4-triazol-5-yl)-5,6-dihydroimidazo[1,2-d]pyrido[4,3-f][1,4]oxazepine-10-carbaldehyde.

Step 3: 2-(1-isopropyl-1H-1,2,4-triazol-5-yl)-5,6-dihydroimidazo[1,2-d]pyrido[4,3-f][1,4]oxazepine-10-carboxylic acid

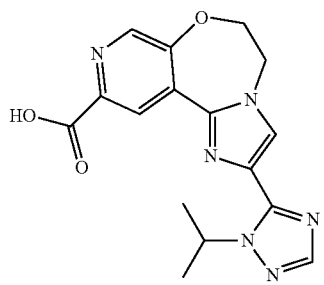 [SMILES: CC(C)n1ncnc1-c1cn2c(n1)-c1cc(C(=O)O)ncc1OCC2]

2-(1-isopropyl-1H-1,2,4-triazol-5-yl)-5,6-dihydroimidazo[1,2-d]pyrido[4,3-f][1,4]oxazepine-10-carbaldehyde (0.250 g, 0.771 mmol) was dissolved in N,N-Dimethylformamide (2 mL, 0.02 mol). Oxone® (0.569 g, 0.925 mmol) was added and the reaction mixture was stirred overnight at room temperature. A light-brown precipitate formed and was collected by filtration. LC-MS analysis verified precipitate as desired product, 2-(1-isopropyl-1H-1,2,4-triazol-5-yl)-5,6-dihydroimidazo[1,2-d]pyrido[4,3-f][1,4]oxazepine-10-carboxylic acid which was carried on without further purification.

Step 4

[2-(1-isopropyl-1H-1,2,4-triazol-5-yl)-5,6-dihydroimidazo[1,2-d]pyrido[4,3-f][1,4]oxazepine-10-carboxylic acid (0.140 g, 0.411 mmol) was dissolved in N,N-Dimethylformamide (3.18 mL, 0.0411 mol) at room temperature. N,N-Diisopropylethylamine (0.287 mL, 0.00164 mol) was added followed by N,N,N',N'-Tetramethyl-O-(7-azabenzotriazol-1-yl)uronium Hexafluorophosphate (0.172 g, 0.452 mmol). The suspension was stirred for 10 minutes. 1-tert-butylpiperazine (0.0878 g, 0.617 mmol) was added and the reaction mixture was stirred for 1 hour. LCMS shows complete conversion to product. The reaction mixture was concentrated to dryness and was purified by reversed phase HPLC to give 203. $^1$H NMR (400 MHz, DMSO) δ 8.42 (s, 1H), 8.39 (s, 1H), 8.14 (s, 1H), 8.09 (s, 1H), 7.94 (s, 1H), 7.94 (s, 1H), 5.76 (dt, J=13.2, 6.6 Hz, 1H), 4.64 (s, 4H), 3.56 (br d, J=48.6 Hz, 8H), 1.49 (d, J=6.6 Hz, 6H), 1.02 (s, 9H). LCMS 465.3.

Example 204

10-(1-isopropylpiperidin-4-ylsulfinyl)-2-(3-methylpyridin-2-yl)-5,6-dihydrobenzo[f]imidazo[1,2-d][1,4]oxazepine 204

To an ice-cooled solution of 9-(1-isopropylpiperidin-4-ylsulfanyl)-2-(3-methylpyridin-2-yl)-4,5-dihydro-6-oxa-1,3a-diazabenzo[e]azulene from Example 7 (70 mg, 0.161 mmol) in DCM (10 mL) was added TFA (62 μL, 0.805 mmol) followed by a solution of m-CPBA (31 mg, 0.177 mmol) in DCM (2 mL). The resulting mixture was stirred for 15 min at 0° C. then volatiles were removed under reduced pressure. The crude material was purified by column chromatography ($C_{18}$, gradient 5-40% MeOH in 0.5% TFA/$H_2O$) and then loaded onto an Isolute® SCX-2 cartridge. The cartridge was washed with MeOH and the product was eluted with 0.5M $NH_3$ in MeOH affording 204 as a pale orange foam (65 mg, 90%). LCMS: $R_T$ 1.92 min [M+H]$^+$ 451.1. $^1$H NMR (DMSO, 400 MHz): δ 8.66 (1H, d, J=2.27 Hz), 8.40 (1H, dd, J=4.69, 1.63 Hz), 7.89 (1H, s), 7.64 (1H, ddd, J=7.65, 1.72, 0.84 Hz), 7.49 (1H, dd, J=8.50, 2.30 Hz), 7.23 (1H, d, J=8.72 Hz), 7.18 (1H, dd, J=7.96, 4.16 Hz), 4.60-4.53 (4H, m), 2.85-2.77 (2H, m), 2.73-2.59 (5H, m), 2.13-2.02 (2H, m), 1.76 (1H, bd, J=12.29 Hz), 1.58 (1H, bd, J=12.37 Hz), 1.52-1.38 (2H, m), 0.90 (6H, d, J=6.54 Hz)

Example 205

10-(1-isopropylpiperidin-4-ylsulfonyl)-2-(3-methylpyridin-2-yl)-5,6-dihydrobenzo[f]imidazo[1,2-d][1,4]oxazepine 205

To an ice-cooled solution of 9-(1-isopropylpiperidine-4-sulfinyl)-2-(3-methylpyridin-2-yl)-4,5-dihydro-6-oxa-1,3a-diazabenzo[e]azulene 204 (40 mg, 0.088 mmol) in DCM (10 mL) was added TFA (34 μL, 0.44 mmol) followed by a slow addition of a solution of m-CPBA (23 mg, 0.132 mmol) in DCM (2 mL) and the resulting mixture was stirred for 1 h at RT. Volatiles were removed under reduced pressure and the resulting residue was purified by column chromatography ($C_{18}$, gradient 5-40% MeOH in 0.5% TFA/$H_2O$) and then loaded onto an Isolute® SCX-2 cartridge. The cartridge was washed with MeOH and the product eluted with 0.5M $NH_3$ in MeOH. Further purification by column chromatography (Si-PCC, gradient 2-8% 2M $NH_3$/MeOH in DCM) afforded 205 as a white solid (28 mg, 68%). LCMS: $R_T$ 2.04 min [M+H]$^+$ 467.1. $^1$H NMR (DMSO, 400 MHz): δ 8.94 (1H, d, J=2.41 Hz), 8.42 (1H, dd, J=4.69, 1.62 Hz), 7.93 (1H, s), 7.70-7.63 (2H, m), 7.29 (1H, d, J=8.61 Hz), 7.20 (1H, dd, J=7.64, 4.66 Hz), 4.67-4.56 (4H, m), 3.21-3.11 (1H, m), 2.86-2.78 (2H, m), 2.72 (3H, s), 2.69-2.60 (1H, m), 2.09 (2H, bt, J=11.50 Hz), 1.89 (2H, bd, J=12.09 Hz), 1.50-1.38 (2H, m), 0.90 (6H, d, J=6.55 Hz)

Example 206

2-(1-isopropyl-3-methyl-1H-1,2,4-triazol-5-yl)-10-(1-isopropylpiperidin-4-ylsulfinyl)-5,6-dihydrobenzo[f]imidazo[1,2-d][1,4]oxazepine 206

To an ice-cooled solution of 2-(2-isopropyl-5-methyl-2H-[1,2,4]triazol-3-yl)-9-(1-isopropylpiperidin-4-ylsulfanyl)-4,5-dihydro-6-oxa-1,3a-diazabenzo[e]azulene from Example 6 (146 mg, 0.313 mmol) in DCM (10 mL) was added TFA (72 μL, 0.939 mmol) followed by a solution of m-CPBA (59 mg, 0.344 mmol) in DCM (2 mL). The resulting mixture was stirred for 1 h at 0° C. then volatiles were removed under reduced pressure. The crude material was purified by column chromatography ($C_{18}$, gradient 15-40% MeOH in 0.5% TFA/$H_2O$) and then loaded onto an Isolute® SCX-2 cartridge. The cartridge was washed with MeOH and the product was eluted with 0.5M $NH_3$ in MeOH affording 206 as a colorless foam (130 mg, 86%). LCMS: $R_T$ 2.47 min [M+H]$^+$ 483.1. $^1$H NMR (DMSO, 400 MHz): δ 8.59 (1H, d, J=2.27 Hz), 7.93 (1H, s), 7.53 (1H, dd, J=8.53, 2.29 Hz), 7.25 (1H, d, J=8.53 Hz), 5.71-5.58 (1H, m), 4.62-4.50 (4H, m), 2.8-2.75 (2H, m), 2.74-2.58 (2H, m), 2.26 (3H, s), 2.13-2.03 (2H, m), 1.78 (1H, bd, J=12.31 Hz), 1.61 (1H, bd, J=12.24 Hz), 1.50-1.33 (7H, m), 0.90 (6H, d, J=6.54 Hz)

Example 208

2-(1-isopropyl-3-methyl-1H-1,2,4-triazol-5-yl)-10-(1-isopropylpiperidin-4-ylsulfonyl)-5,6-dihydrobenzo[f]imidazo[1,2-d][1,4]oxazepine 208

To an ice-cooled solution of 2-(2-isopropyl-5-methyl-2H-[1,2,4]triazol-3-yl)-9-(1-isopropylpiperidine-4-sulfinyl)-4,5-dihydro-6-oxa-1,3a-diazabenzo[e]azulene 206 (35 mg, 0.0731 mmol) in DCM (6 mL) was added TFA (17 μL, 0.306 mmol) followed by a slow addition of a solution of m-CPBA (16 mg, 0.0951 mmol) in DCM (1 mL) and the resulting mixture was stirred for 2 h at 0° C. Volatiles were removed under reduced pressure and the resulting residue was purified by column chromatography ($C_{18}$, gradient 10-40% MeOH in 0.5% TFA/$H_2O$) and then loaded onto an Isolute® SCX-2 cartridge. The cartridge was washed with MeOH and the product eluted with 0.5M $NH_3$ in MeOH affording 208 as a white solid (24 mg, 66%). LCMS: $R_T$ 2.68 min [M+H]$^+$ 499.1. $^1$H NMR (DMSO, 400 MHz): δ 8.87 (1H, d, J=2.40 Hz), 7.97 (1H, s), 7.71 (1H, dd, J=10.93, 2.38 Hz), 7.30 (1H, d, J=8.63 Hz), 5.70-5.58 (1H, m), 4.68-4.56 (4H, m), 3.20-3.10 (1H, m), 2.84-2.77 (2H, m), 2.68-2.59 (1H, m), 2.27 (3H, s), 2.09 (2H, bt, J=11.46 Hz), 1.91 (2H, bd, J=12.10 Hz), 1.54-1.34 (8H, m), 0.89 (6H, d, J=6.55 Hz)

Example 209

9-fluoro-2-(1-isopropyl-3-methyl-1H-1,2,4-triazol-5-yl)-10-(1-isopropylpiperidin-4-ylthio)-5,6-dihydrobenzo[f]imidazo[1,2-d][1,4]oxazepine 209

A mixture of 9-bromo-8-fluoro-2-(2-isopropyl-5-methyl-2H-[1,2,4]triazol-3-yl)-4,5-dihydro-6-oxa-1,3a-diazabenzo

[e]azulene from Example 8 (300 mg, 0.738 mmol), 1-isopropylpiperidine-4-thiol (176 mg, 1.107 mmol), Pd$_2$(dba)$_3$ (34 mg, 5 mol %), XantPhos (43 mg, 10 mol %) and DIPEA (0.52 mL, 2.95 mmol) in dioxane (10 mL) was purged with nitrogen and then heated at 120° C. for 1 h using microwave irradiation. The crude reaction mixture was diluted with DCM (100 mL) and purified by column chromatography (Si-PCC, gradient 0-10% MeOH in DCM followed by C$_{18}$, gradient 20-55% MeOH in 0.5% TFA/H$_2$O). The product containing fractions were combined and concentrated in vacuo and the resulting residue was loaded onto an Isolute® SCX-2 cartridge. The cartridge was washed with MeOH and the product eluted with 0.5M NH$_3$ in MeOH affording 209 as a white solid (217 mg, 61%). LCMS: R$_T$ 3.12 min [M+H]$^+$ 485.1. $^1$H NMR (DMSO, 400 MHz): δ 8.49 (1H, d, J=8.69 Hz), 7.89 (1H, s), 7.01 (1H, d, J=10.14 Hz), 5.78-5.66 (1H, m), 4.57-4.46 (4H, m), 3.10-3.00 (1H, m), 2.78-2.69 (2H, m), 2.67-2.57 (1H, m), 2.24 (3H, s), 2.15 (2H, bt, J=10.98 Hz), 1.89 (2H, bd, J=12.50 Hz), 1.52-1.39 (8H, m), 0.90 (6H, d, J=6.56 Hz)

Example 210

9-fluoro-2-(1-isopropyl-3-methyl-1H-1,2,4-triazol-5-yl)-10-(1-isopropylpiperidin-4-ylsulfinyl)-5,6-dihydrobenzo[f]imidazo[1,2-d][1,4]oxazepine 210

To an ice-cooled solution of 8-fluoro-2-(2-isopropyl-5-methyl-2H-[1,2,4]triazol-3-yl)-9-(1-isopropylpiperidin-4-ylsulfanyl)-4,5-dihydro-6-oxa-1,3a-diazabenzo[e]azulene 209 (194 mg, 0.40 mmol) in DCM (15 mL) was added TFA (93 µL, 1.20 mmol) followed by a solution of m-CPBA (76 mg, 0.440 mmol) in DCM (2 mL). The resulting mixture was stirred for 15 min at 0° C. then volatiles were removed under reduced pressure. The crude material was purified by column chromatography (C$_{18}$, gradient 20-45% MeOH in 0.5% TFA/H$_2$O) and then loaded onto an Isolute® SCX-2 cartridge. The cartridge was washed with MeOH and the product eluted with 0.5M NH$_3$ in MeOH affording 210 as a white solid (167 mg, 83%). LCMS: R$_T$ 2.61 min [M+H]$^+$ 501.1. $^1$H NMR (DMSO, 400 MHz): δ 8.71 (1H, d, J=7.99 Hz), 7.93 (1H, s), 7.15 (1H, d, J=10.69 Hz), 5.69-5.57 (1H, m), 4.66-4.51 (4H, m), 2.89-2.76 (3H, m), 2.72-2.60 (1H, m), 2.26 (3H, s), 2.20-2.06 (2H, m), 1.94-1.85 (1H, bd, J=12.30 Hz), 1.59-1.40 (9H, m), 0.91 (6H, d, J=6.53 Hz)

Example 211

9-fluoro-2-(1-isopropyl-3-methyl-1H-1,2,4-triazol-5-yl)-10-(1-isopropylpiperidin-4-ylsulfonyl)-5,6-dihydrobenzo[f]imidazo[1,2-d][1,4]oxazepine 211

To an ice-cooled solution of 8-fluoro-2-(2-isopropyl-5-methyl-2H-[1,2,4]triazol-3-yl)-9-(1-isopropylpiperidine-4-sulfinyl)-4,5-dihydro-6-oxa-1,3a-diazabenzo[e]azulene 210 (51 mg, 0.102 mmol) in DCM (8 mL) was added TFA (24 µL, 0.306 mmol) followed by a slow addition of a solution of m-CPBA (21 mg, 0.122 mmol) in DCM (1 mL) and the resulting mixture was stirred for 2.5 h at 0° C. Additional m-CPBA (9 mg) in DCM (0.5 mL) was added and the mixture was stirred for 1 h at RT. Volatiles were then removed under reduced pressure and the resulting residue was purified by column chromatography (C$_{18}$, gradient 20-50% MeOH in 0.5% TFA/H$_2$O) and then loaded onto an Isolute® SCX-2 cartridge. The cartridge was washed with MeOH and the product eluted with 0.5M NH$_3$ in MeOH. Further purification by column chromatography (Si-PCC, gradient 5-10% MeOH in DCM) afforded 211 as a white solid (22 mg, 41%). LCMS: R$_T$ 2.76 min [M+H]$^+$ 517.1. $^1$H NMR (DMSO, 400 MHz): δ 8.88 (1H, d, J=8.22 Hz), 7.94 (1H, s), 7.25 (1H, d, J=11.17 Hz), 5.67-5.55 (1H, m), 4.73-4.54 (4H, m), 3.28-3.15 (1H, m), 2.89-2.79 (2H, m), 2.72-2.60 (1H, m), 2.26 (3H, s), 2.13 (2H, bt, J=11.43 Hz), 1.89 (2H, bd, J=12.04 Hz), 1.58-1.41 (8H, m), 0.91 (6H, d, J=6.55 Hz)

Example 212

2-(4-(9-fluoro-2-(1-isopropyl-3-methyl-1H-1,2,4-triazol-5-yl)-5,6-dihydrobenzo[f]imidazo[1,2-d][1,4]oxazepin-10-ylsulfinyl)piperidin-1-yl)-2-methylpropan-1-ol 212

To an ice-cooled solution of 2-{4-[8-fluoro-2-(2-isopropyl-5-methyl-2H-[1,2,4]triazol-3-yl)-4,5-dihydro-6-oxa-1,3a-diazabenzo[e]azulen-9-ylsulfanyl]piperidin-1-yl}-2-methylpropan-1-ol from Example 8 (148 mg, 0.287 mmol) in DCM (10 mL) was added TFA (67 µL, 0.863 mmol) followed by a solution of m-CPBA (55 mg, 0.316 mmol) in DCM (2 mL). The resulting mixture was stirred for 30 min at 0° C. then volatiles were removed under reduced pressure. The crude material was purified by column chromatography (C$_{18}$, gradient 10-40% MeOH in 0.5% TFA/H$_2$O) affording 212 as a white solid (135 mg, 88%). LCMS: R$_T$ 2.58 min [M+H]$^+$ 531.1. $^1$H NMR (DMSO, 400 MHz): δ 8.69 (1H, d, J=7.99 Hz), 7.91 (1H, s), 7.13 (1H, d, J=10.67 Hz), 5.67-5.56 (1H, m), 4.65-4.50 (4H, m), 4.20 (1H, t, J=5.39 Hz), 3.20 (2H, d, J=5.03 Hz), 3.09-2.97 (2H, m), 2.84-2.73 (1H, m), 2.25 (3H, s), 2.21-2.07 (2H, m), 1.90-1.82 (1H, m), 1.56-1.38 (9H, m), 0.88 (6H, s)

Example 213

2-(1-isopropyl-3-methyl-1H-1,2,4-triazol-5-yl)-9-(1-methyl-5-(1-(oxetan-3-yl)piperidin-3-yl)-1H-pyrazol-4-yl)-5,6-dihydrobenzo[f]imidazo[1,2-d][1,4]oxazepine 213

Step 1: tert-Butyl 5-(trifluoromethylsulfonyloxy)-3,4-dihydropyridine-1(2H)-carboxylate

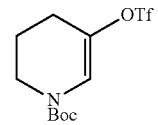

To a solution of tert-butyl 3-oxopiperidine-1-carboxylate (15 g, 75 mmol) in THF (100 mL) at −78° C., was added LDA (45 mL) dropwise. After 20 min, a solution of N-phenylbis(trifluoromethanesulphonimide) (42.0 g, 120 mmol) in THF (50 mL) was added dropwise. The reaction mixture was allowed to warm up slowly to room temperature with stirring for 18 h. After concentration, the residue was diluted with Et$_2$O, wished with 1N NaOH (3×20 mL) and brine. The organic layer was dried over Na$_2$SO$_4$, filtered, and concentrated. The crude product was purified by silica gel chromatography eluting with a 0-10% gradient of EtOAc in petroleum ether to give tert-butyl 5-(trifluoromethylsulfonyloxy)-

3,4-dihydropyridine-1(2H)-carboxylate (7.3 g, 30% yield) as a pale yellow oil. LCMS (ESI) m/z: 255.0 [M+H+].

Step 2: tert-Butyl 5-(1-methyl-1H-pyrazol-5-yl)-3,4-dihydropyridine-1(2H)-carboxylate

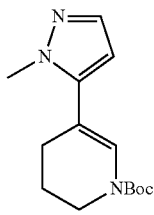 [SMILES: Cn1nccc1C1=CN(C(=O)OC(C)(C)C)CCC1]

To a solution of tert-butyl 5-(trifluoromethylsulfonyloxy)-3,4-dihydropyridine-1(2H)-carboxylate (2.0 g, 6.0 mmol) in dioxane (40 mL) was added 1-methyl-1H-pyrazol-5-ylboronic acid (0.83 g, 6.60 mmol), Na$_2$CO$_3$ (1.90 g, 18.1 mmol), and Pd(dppf)Cl$_2$ (370 mg, 0.600 mmol). The resulting mixture was stirred at 80° C. for 18 h. After concentration, the residue was purified by silica gel chromatography eluting with a 0-25% gradient of EtOAc in petroleum ether to give tert-butyl 5-(1-methyl-1H-pyrazol-5-yl)-3,4-dihydropyridine-1(2H)-carboxylate (0.80 g, 58% yield) as pale yellow oil. LCMS (ESI) m/z: 263.2 [M+H+].

Step 3: tert-Butyl 3-(1-methyl-1H-pyrazol-5-yl)piperidine-1-carboxylate

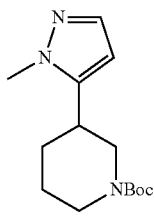 [SMILES: Cn1nccc1C1CCCN(C(=O)OC(C)(C)C)C1]

To a solution of tert-butyl 5-(1-methyl-1H-pyrazol-5-yl)-3,4-dihydropyridine-1(2H)-carboxylate (800 mg, 3.00 mmol) in MeOH (20 mL) was added 10% Pd/C (80 mg). The reaction mixture was stirred under H$_2$ (1 atm) for 16 h. After concentration, the residue was purified by silica gel chromatography eluting with a 0-30% gradient of EtOAc in petroleum ether to give tert-butyl 3-(1-methyl-1H-pyrazol-5-yl)piperidine-1-carboxylate (0.68 g, 86% yield) as pale yellow oil. LCMS (ESI) m/z: 265.2 [M+H+]

Step 4: tert-Butyl 3-(4-bromo-1-methyl-1H-pyrazol-5-yl)piperidine-1-carboxylate

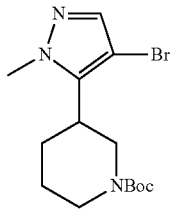 [SMILES: Cn1ncc(Br)c1C1CCCN(C(=O)OC(C)(C)C)C1]

To a solution of tert-butyl 3-(1-methyl-1H-pyrazol-5-yl)piperidine-1-carboxylate (680 mg, 2.50 mmol) in THF (20 mL) was added NBS (486 mg, 2.80 mmol). The reaction mixture was stirred for 2 h. After concentration, the residue was purified by silica gel chromatography eluting with a 0-50% gradient of EtOAc in petroleum ether to give tert-butyl 3-(4-bromo-1-methyl-1H-pyrazol-5-yl)piperidine-1-carboxylate (0.66 g, 75% yield) as pale yellow oil. LCMS (ESI) m/z: 344.1 [M+H+].

Step 5: 1-tert-Butyl-5-(1-methyl-4-{4-[3-methyl-1-(propan-2-yl)-1H-1,2,4-triazol-5-yl]-9-oxa-3,6-diazatricyclo[8.4.0.0$^{2,6}$]tetradeca1(14),2,4,10,12-pentaen-12-yl}-1H-pyrazol-5-yl)-λ$^3$,3-oxazocan-2-one

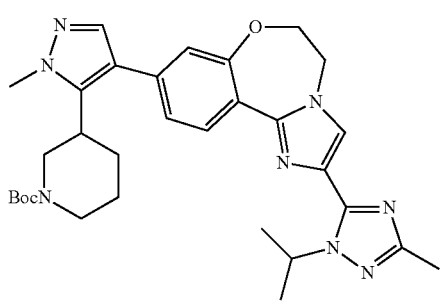

To a solution of tert-butyl 3-(4-bromo-1-methyl-1H-pyrazol-5-yl)piperidine-1-carboxylate (680 mg, 1.98 mmol) in dioxane (20.0 mL), was added {4-[3-methyl-1-(propan-2-yl)-1H-1,2,4-triazol-5-yl]-9-oxa-3,6-diazatricyclo[8.4.0.0$^{2,6}$]tetradeca1(14),2,4,10,12-pentaen-12-yl}boronic acid (660 mg, 1.87 mmol), K$_2$CO$_3$ (780 mg, 5.70 mmol), and Pd(dppf)Cl$_2$ (117 mg, 0.19 mmol). The resulting mixture was stirred at 80° C. for 18 h. After concentration, the residue was diluted with EtOAc (20 mL) and washed with brine (20 mL). The organic layer was dried over Na$_2$SO$_4$, filtered, and concentrated. The crude product was purified by silica gel chromatography eluting with a 0-20% gradient of EtOAc in petroleum ether to give 1-tert-butyl-5-(1-methyl-4-{4-[3-methyl-1-(propan-2-yl)-1H-1,2,4-triazol-5-yl]-9-oxa-3,6-diazatricyclo[8.4.0.0$^{2,6}$]tetradeca1(14),2,4,10,12-pentaen-12-yl}-1H-pyrazol-5-yl)-λ$^3$,3-oxazocan-2-one (540 mg, 50% yield) as a yellow solid. LCMS (ESI) m/z: 573.4 [M+H+].

Step 6: 4-[3-Methyl-1-(propan-2-yl)-1H-1,2,4-triazol-5-yl]-12-[1-methyl-5-(piperidin-3-yl)-1H-pyrazol-4-yl]-9-oxa-3,6-diazatricyclo[8.4.0.0$^{2,6}$]tetradeca1(14),2,4,10,12-pentaene

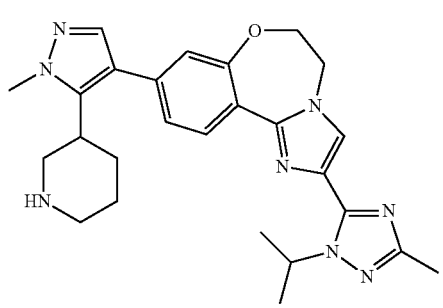

To a solution of 1-tert-butyl-5-(1-methyl-4-{4-[3-methyl-1-(propan-2-yl)-1H-1,2,4-triazol-5-yl]-9-oxa-3,6-diazatricyclo[8.4.0.0$^{2,6}$]tetradeca1(14),2,4,10,12-pentaen-12-yl}-1H-pyrazol-5-yl)-λ$^3$,3-oxazocan-2-one (540 mg, 0.94 mmol) in MeOH (10 mL) was added 4N HCl (2 mL). The reaction mixture was stirred at room temperature for 4 h. 1N K$_2$CO$_3$ (6.0 mL) was added. After concentration, the residue was purified by reverse phase Combiflash eluting with a 0-70% gradient of CH$_3$CN in 0.3% NH$_4$HCO$_3$ to afford 4-[3-methyl-1-(propan-2-yl)-1H-1,2,4-triazol-5-yl]-12-[1-methyl-5-(piperidin-3-yl)-1H-pyrazol-4-yl]-9-oxa-3,6-diazatricyclo[8.4.0.0$^{2,6}$]tetradeca1(14),2,4,10,12-pentaene (320 mg, 72% yield). LCMS (ESI) m/z: 473.4 [M+H$^+$]

Step 7

A mixture of 4-[3-methyl-1-(propan-2-yl)-1H-1,2,4-triazol-5-yl]-12-[1-methyl-5-(piperidin-3-yl)-1H-pyrazol-4-yl]-9-oxa-3,6-diazatricyclo[8.4.0.0$^{2,6}$]tetradeca1(14),2,4,10,12-pentaene (80 mg, 0.17 mmol), tetrahydropyran-4-one (25 mg, 0.25 mmol) and Ti(O-$^i$Pr)$_4$ (2 drops) in EtOH (20 mL) was stirred at room temperature for 18 h. After concentration, the residue was purified by prep-HPLC (Gilson GX 281, Shimpack PRC-ODS 250 mm×20 mm×2, gradient: CH$_3$CN/10 mm/L NH$_4$HCO$_3$, 17 min) to give 213 (16 mg, 18% yield). LCMS (ESI): RT=4.75 min, m/z: 527.3 [M+H$^+$]. $^1$H NMR (500 MHz, DMSO-d$_6$) δ 8.42 (d, J=8.0 Hz, 1H), 7.91 (s, 1H), 7.43 (s, 1H), 7.08 (d, J=1.5 Hz, 1H), 6.94 (s, 1H), 7.39-7.36 (m, 1H), 5.87-5.84 (m, 1H), 4.54-4.40 (m, 8H), 3.90 (s, 3H), 3.18 (s, 1H), 2.74-2.69 (m, 2H), 2.24 (s, 3H), 2.11-2.06 (m, 1H), 1.78-1.71 (m, 5H), 1.47 (d, J=2.0 Hz, 6H)

Example 215

2-(1-isopropyl-3-methyl-1H-1,2,4-triazol-5-yl)-9-(1'-methyl-2,4'-bipiperidin-1-yl)-5,6-dihydrobenzo[f]imidazo[1,2-d][1,4]oxazepine 215

A mixture of 9-bromo-2-(2-isopropyl-5-methyl-2H-[1,2,4]triazol-3-yl)-4,5-dihydro-6-oxa-1,3a-diazabenzo[e]azulene from Example 6 (200 mg, 0.51 mmol), l'-methyl-[2,4]bipiperidinyl (234 mg, 1.28 mmol), sodium tertbutoxide (148 mg, 1.5 mmol) and Pd(P($^t$Bu)$_3$)$_2$ (13 mg, 0.026 mmol) in dioxane was degassed with a stream of argon and then heated at 100° C. for 1 h in a sealed tube. After cooling to RT, the mixture was diluted with water and extracted with EtOAc (×3). The combined organic phases were concentrated in vacuo and then purified by column chromatography (Si-PCC, gradient 0-10% MeOH in EtOAc, and then with 20% 2M NH$_3$/MeOH in DCM) followed by HPLC purification (Phenomenex Gemini 5 µm C18 on a 25 min gradient 50-95% 0.1% NH$_4$OH in acetonitrile/water) affording 215 (30 mg, 12%). LCMS: R$_T$ 2.98 min [M+H]$^+$ 490.2. $^1$H NMR (CDCl$_3$, 400 MHz): δ 8.27 (1H, d, J=8.98 Hz), 7.51 (1H, s), 6.63 (1H, dd, J=9.25, 2.95 Hz), 6.38 (1H, d J=2.95 Hz), 6.00-5.88 (1H, m), 4.46-4.39 (2H, m), 4.38-4.30 (2H, m), 3.68-3.59 (2H, m), 3.11-3.02 (1H, m), 2.95-2.88 (1H, m), 2.85-2.78 (1H, m), 2.4 (3H, s), 2.25 (3H, s), 1.98-1.60 (11H, m), 1.56 (6H, d, J=7.15 Hz), 1.40-1.19 (2H, m)

Example 216

2-(1-isopropyl-3-methyl-1H-1,2,4-triazol-5-yl)-9-(1-(1-isopropylpiperidin-4-yl)ethoxy)-5,6-dihydrobenzo[f]imidazo[1,2-d][1,4]oxazepine 216

To a solution of 4-{1-[2-(2-isopropyl-5-methyl-2H-[1,2,4]triazol-3-yl)-4,5-dihydro-6-oxa-1,3a-diazabenzo[e]azulen-8-yloxy]ethyl}piperidine-1-carboxylic acid benzyl ester from Example 11 (60 mg, 0.10 mmol) in acetone (2 mL) and MeOH (0.5 mL) was added 10% Pd/C (50 mg). The reaction mixture was stirred at RT under a hydrogen atmosphere for 48 h. The suspension was then filtered through a pad of Celite® and the filtrate was concentrated in vacuo. The resulting residue was purified by column chromatography (Si-PCC, gradient 0-10% 2M NH$_3$/MeOH in DCM) affording 216 (20 mg, 42%). LCMS: R$_T$ 3.03 min [M+H]$^+$ 379.2. $^1$H NMR (CDCl$_3$, 400 MHz): δ 8.39 (1H, d, J=8.96 Hz), 7.56 (1H, s), 6.70 (1H, dd, J=8.98, 2.55 Hz), 6.52 (1H, d, J=2.51 Hz), 5.99-5.84 (1H, m), 4.51-4.34 (4H, m), 4.19 (1H, m), 3.00-2.78 (2H, m), 2.77-2.63 (1H, m), 2.41 (3H, s), 2.18-2.05 (3H, m), 1.95-1.85 (1H, m), 1.77-1.67 (1H, m), 1.56 (6H, d, J=8.76 Hz), 1.52-1.32 (2H, m), 1.28 (3H, d, J=8.24 Hz), 1.05 (6H, d, J=6.54 Hz)

Example 217

2-(1-isopropyl-3-methyl-1H-1,2,4-triazol-5-yl)-9-(1-(1-isopropylazepan-4-yl)ethoxy)-5,6-dihydrobenzo[f]imidazo[1,2-d][1,4]oxazepine 217

To a solution of 8-(1-azepan-4-ylethoxy)-2-(2-isopropyl-5-methyl-2H-[1,2,4]triazol-3-yl)-4,5-dihydro-6-oxa-1,3a-diazabenzo[e]azulene from Example 10 (50 mg, 0.11 mmol) in a 10:1 mixture of DCM:MeOH (2.2 mL) were added acetone (81 uL, 1.1 mmol), AcOH (0.011 mmol) and sodium triacetoxyborohydride (47 mg, 0.22 mmol). The reaction mixture was stirred for 24 h at RT, then diluted with DCM and poured into water. The aqueous layer was extracted with DCM (×3) and the combined organic phases were washed with brine, then dried (Na$_2$SO$_4$) and concentrated in vacuo. The resulting residue was purified by column chromatography (Si-PCC, gradient 0-10% 2M NH$_3$/MeOH in DCM) affording 217 as a white solid (48 mg, 81%). LCMS: R$_T$ 3.16 min [M+H]$^+$ 493.2. $^1$H NMR (CDCl$_3$, 400 MHz): δ 8.40 (1H, d, J=8.95 Hz), 7.56 (1H, s), 6.71 (1H, d, J=9.07 Hz), 6.52 (1H, s), 5.98-5.86 (1H, m), 4.52-4.44 (2H, m), 4.43-4.36 (2H, m), 4.33-4.23 (1H, m), 2.92-2.80 (1H, m), 2.76-2.48 (5H, m), 2.41 (3H, s), 2.02-1.74 (5H, m), 1.63-1.40 (7H, m), 1.30-1.23 (3H, m), 1.03-0.95 (6H, m)

Example 218

9-(1-isopropylpiperidin-3-yloxy)-2-(pyridin-2-yl)-5,6-dihydrobenzo[f]imidazo[1,2-d][1,4]oxazepine 218

To a solution of 8-(piperidin-3-yloxy)-2-pyridin-2-yl-4,5-dihydro-6-oxa-1,3a-diazabenzo[e]azulene from Example 9 (13 mg, 0.036 mmol) in DCM (1 mL) were added acetone (100 uL), AcOH (50 uL) and sodium triacetoxyborohydride (15 mg, 0.072 mmol). The resulting mixture was stirred at RT for 18 h and then diluted with EtOAc. The organic layer was poured into water and the aqueous layer basified with a saturated solution of NaHCO$_3$. The aqueous phase was extracted with EtOAc (×3) and the combined organic layers were washed with brine, then dried (Na$_2$SO$_4$) and concentrated in vacuo. The resulting residue was purified by column chromatography (Si-PCC, gradient 0-10% 2M NH$_3$/MeOH in DCM) affording 218 as a white solid (11 mg, 76%). LCMS: R$_T$ 2.05 min [M+H]$^+$ 405.1. $^1$H NMR (CDCl$_3$, 400 MHz): δ 8.57-8.51 (2H, m), 8.09 (1H, dt, J=7.95, 1.07 Hz), 7.72 (1H, td, J=7.72, 1.83 Hz), 7.61 (1H, s), 7.16-7.10 (1H, m), 6.75 (1H, dd, J=8.99, 2.58 Hz), 6.57 (1H, d, J=2.55 Hz), 4.50-4.45 (2H, m), 4.43-4.32 (3H, m), 3.13-3.07 (1H, m), 2.85-2.70 (2H, m), 2.26-2.10 (3H, m), 1.86-1.78 (1H, m), 1.48-1.36 (1H, m), 1.26 (1H, s), 1.04 (6H, d, J=6.57 Hz)

Example 219

2-(4-(9-fluoro-2-(1-isopropyl-3-methyl-1H-1,2,4-triazol-5-yl)-5,6-dihydrobenzo[f]imidazo[1,2-d][1,4]oxazepin-10-ylsulfonyl)piperidin-1-yl)-2-methylpropan-1-ol 219

To an ice-cooled solution of 2-{4-[8-fluoro-2-(2-isopropyl-5-methyl-2H-[1,2,4]triazol-3-yl)-4,5-dihydro-6-oxa-1,3a-diazabenzo[e]azulene-9-sulfinyl]piperidin-1-yl}-2-methylpropan-1-ol 212 (41 mg, 0.0767 mmol) in DCM (8 mL) was added TFA (30 µL, 0.383 mmol) followed by a slow addition of a solution of m-CPBA (17 mg, 0.10 mmol) in DCM (1.5 mL) and the resulting mixture was stirred for 3 h at 0° C. Volatiles were removed under reduced pressure and the resulting residue was purified by column chromatography ($C_{18}$, gradient 10-45% MeOH in 0.5% TFA/$H_2O$) and then loaded onto an Isolute® SCX-2 cartridge. The cartridge was washed with MeOH and the product eluted with 0.5M $NH_3$ in MeOH. Further purification by column chromatography (Si-PCC, gradient 3-15% MeOH in DCM) afforded 219 as a white solid (16 mg, 38%). LCMS: $R_T$ 2.72 min $[M+H]^+$ 547.1. $^1$H NMR (DMSO, 400 MHz): δ 8.87 (1H, d, J=8.22 Hz), 7.93 (1H, s), 7.24 (1H, d, J=11.15 Hz), 5.66-5.55 (1H, m), 4.70-4.52 (4H, m), 4.21 (1H, t, J=5.47 Hz), 3.24-3.14 (3H, m), 3.08-2.99 (2H, m), 2.25 (3H, s), 2.12 (2H, bt, J=11.72 Hz), 1.86 (2H, bd, J=11.95 Hz), 1.55-1.43 (8H, d, J=6.62 Hz), 0.88 (6H, s)

Example 220

2-(4-(9-fluoro-2-(1-isopropyl-3-methyl-1H-1,2,4-triazol-5-yl)-5,6-dihydrobenzo[f]imidazo[1,2-d][1,4]oxazepin-10-ylsulfinyl)piperidin-1-yl)-2-methylpropanamide 220

To an ice-cooled solution of 2-{4-[8-fluoro-2-(2-isopropyl-5-methyl-2H-[1,2,4]triazol-3-yl)-4,5-dihydro-6-oxa-1,3a-diazabenzo[e]azulen-9-ylsulfanyl]piperidin-1-yl}isobutyramide from Example 8 (96 mg, 0.183 mmol) in DCM (10 mL) was added TFA (42 µL, 0.548 mmol) followed by a solution of m-CPBA (35 mg, 0.201 mmol) in DCM (2 mL). The resulting mixture was stirred for 30 min at 0° C. then volatiles were removed under reduced pressure. The crude material was purified by column chromatography ($C_{18}$, gradient 10-50% MeOH in 0.5% TFA/$H_2O$) and then loaded onto an Isolute® SCX-2 cartridge. The cartridge was washed with MeOH and the product was eluted with 0.5M $NH_3$ in MeOH. The product containing fractions were concentrated in vacuo and further purified by column chromatography (Si-PCC, gradient 2-12% MeOH in DCM) affording 220 as a white solid (59 mg, 60%). LCMS: $R_T$ 2.54 min $[M+H]^+$ 544.1. $^1$H NMR (DMSO, 400 MHz): δ 8.72 (1H, d, J=7.98 Hz), 7.93 (1H, s), 7.17-7.09 (2H, m), 6.86 (1H, s), 5.68-5.56 (1H, m), 4.67-4.50 (4H, m), 2.88-2.74 (3H, m), 2.26 (3H, s), 2.19-2.04 (2H, m), 1.92-1.84 (1H, m), 1.76-1.51 (3H, m), 1.50-1.42 (6H, m), 1.03 (6H, d, J=4.44 Hz)

Example 221

1-(3-(4-(2-(1-isopropyl-3-methyl-1H-1,2,4-triazol-5-yl)-5,6-dihydrobenzo[f]imidazo[1,2-d][1,4]oxazepin-9-yl)-1-methyl-1H-pyrazol-5-yl)piperidin-1-yl)-2-methylpropan-2-ol 221

A solution of 4-[3-methyl-1-(propan-2-yl)-1H-1,2,4-triazol-5-yl]-12-[1-methyl-5-(piperidin-3-yl)-1H-pyrazol-4-yl]-9-oxa-3,6-diazatricyclo[8.4.0.0$^{2,6}$]tetradeca1(14),2,4,10,12-pentaene (38 mg, 0.08 mmol) and 2,2-dimethyloxirane (0.2 ml) in EtOH (2 ml) was stirred at room temperature for 12 h. After removal of the solvent, the residue was purified by Combiflash eluting with a 0-70% gradient of $CH_3CN$ in 0.3% $NH_4HCO_3$ to give racemic 221 (35 mg 80% yield), which was separated by chiral HPLC (AD-H column, 15% EtOH (0.1% DEA) in hexane isocratic) to afford (R)/(S) enantiomers: 6.3 mg of one enantiomer and 8.4 mg of the other (34% total yield). LCMS (ESI): RT=5.49 min, m/z: 545.3 $[M+H^+]$. $^1$H NMR (500 MHz, DMSO-$d_6$): δ 8.35 (d, J=8.0 Hz, 1H), 7.65 (s, 1H), 7.30 (s, 1H), 7.01-6.99 (m, 1H), 6.91 (d, J=2.0 Hz, 1H), 5.83-5.81 (m, 1H), 4.46-4.43 (m, 4H), 3.85 (s, 3H), 2.92-2.83 (m, 2H), 2.43-2.39 (m, 2H), 2.27 (s, 3H), 2.22 (s, 1H), 2.09-2.08 (m, 1H), 1.60-1.56 (m, 4H), 1.45 (d, J=6.5 Hz, 6H), 1.19 (s, 3H), 1.07 (d, J=7.0 Hz, 6H)

Example 223

10-(1-isopropylpiperidin-4-ylsulfinyl)-2-(4-methylpyridin-2-yl)-5,6-dihydrobenzo[f]imidazo[1,2-d][1,4]oxazepine 223

To an ice-cooled solution of 9-(1-isopropylpiperidin-4-ylsulfanyl)-2-(4-methylpyridin-2-yl)-4,5-dihydro-6-oxa-1,3a-diazabenzo[e]azulene from Example 12 (138 mg, 0.317 mmol) in DCM (20 mL) was added TFA (122 µL, 1.59 mmol) followed by a solution of m-CPBA (60 mg, 0.349 mmol) in DCM (2 mL). The resulting mixture was stirred for 15 min at 0° C. then volatiles were removed under reduced pressure. The crude material was purified by column chromatography ($C_{18}$, gradient 5-40% MeOH in 0.5% TFA/$H_2O$) and then loaded onto an Isolute® SCX-2 cartridge. The cartridge was washed with MeOH and the product eluted with 0.5M $NH_3$ in MeOH affording 223 as a colorless foam (114 mg, 80%). LCMS: $R_T$1.94 min $[M+H]^+$ 501.0. $^1$H NMR (DMSO, 400 MHz): δ 8.70 (1H, d, J=2.27 Hz), 8.38 (1H, d, J=4.97 Hz), 7.92 (1H, s), 7.81 (1H, s), 7.50 (1H, dd, J=8.51, 2.30 Hz), 7.23 (1H, d, J=8.51 Hz), 7.07 (1H, d, J=5.03 Hz), 4.59-4.50 (4H, m), 2.86-2.78 (2H, m), 2.74-2.58 (2H, m), 2.39 (3H, s), 2.15-2.01 (2H, m), 1.76 (1H, bd, J=12.05 Hz), 1.59-1.43 (3H, m), 0.90 (6H, d, J=6.53 Hz)

Example 224

10-(1-isopropylpiperidin-4-ylsulfonyl)-2-(4-methylpyridin-2-yl)-5,6-dihydrobenzo[f]imidazo[1,2-d][1,4]oxazepine 224

To an ice-cooled solution of 9-(1-isopropylpiperidine-4-sulfinyl)-2-(4-methylpyridin-2-yl)-4,5-dihydro-6-oxa-1,3a-diazabenzo[e]azulene 223 (86 mg, 0.19 mmol) in DCM (7 mL) was added TFA (74 µL, 0.953 mmol) followed by a slow addition of a solution of m-CPBA (43 mg, 0.248 mmol) in DCM (2 mL) and the resulting mixture was stirred for 3 h at 0° C. Volatiles were removed under reduced pressure and the resulting residue was purified by column chromatography ($C_{18}$, gradient 5-40% MeOH in 0.5% TFA/$H_2O$) and then loaded onto an Isolute® SCX-2 cartridge. The cartridge was washed with MeOH and the product eluted with 0.5M $NH_3$ in MeOH. Further column chromatography purification (Si-PCC, gradient 2-8% 2M $NH_3$/MeOH in DCM) afforded 224 as a white solid (69 mg, 77%). LCMS: $R_T$ 2.08 min $[M+H]^+$ 467.1. $^1$H NMR (DMSO, 400 MHz): δ 8.95 (1H, d, J=2.41 Hz), 8.40 (1H, d, J=4.98 Hz), 7.96 (1H, s), 7.80 (1H, s), 7.70

(1H, dd, J=8.62, 2.44 Hz), 7.29 (1H, d, J=8.62 Hz), 7.09 (1H, dd, J=5.05, 1.56 Hz), 4.65-4.55 (4H, m), 3.24-3.15 (1H, m), 2.83 (2H, bd, J=11.14 Hz), 2.70-2.60 (1H, m), 2.41 (3H, s), 2.09 (2H, t, J=11.51 Hz), 1.88 (2H, d, J=12.14 Hz), 1.54-1.41 (2H, m), 0.90 (6H, d, J=6.55 Hz)

Example 225

2-(1-isopropyl-3-methyl-1H-1,2,4-triazol-5-yl)-10-(1-isopropylpiperidin-4-ylsulfinyl)-9-methyl-5,6-dihydrobenzo[f]imidazo[1,2-d][1,4]oxazepine 225

To an ice-cooled solution of 2-(2-isopropyl-5-methyl-2H-[1,2,4]triazol-3-yl)-9-(1-isopropylpiperidin-4-ylsulfanyl)-8-methyl-4,5-dihydro-6-oxa-1,3a-diazabenzo[e]azulene from Example 32 (112 mg, 0.233 mmol) in DCM (10 mL) was added TFA (90 μL, 1.165 mmol) followed by a solution of m-CPBA (44 mg, 0.256 mmol) in DCM (2 mL). The resulting mixture was stirred for 20 min at 0° C. then volatiles were removed under reduced pressure. The crude material was purified by column chromatography ($C_{18}$, gradient 20-50% MeOH in 0.5% TFA/$H_2O$) and then loaded onto an Isolute® SCX-2 cartridge. The cartridge was washed with MeOH and the product eluted with 0.5M $NH_3$ in MeOH affording 225 as a white solid (100 mg, 87%). LCMS: $R_T$ 2.60 min $[M+H]^+$ 497.1. $^1$H NMR (DMSO, 400 MHz): δ 8.72 (1H, s), 7.89 (1H, s), 7.00 (1H, s), 5.72-5.60 (1H, m), 4.62-4.47 (4H, m), 2.80 (2H, t, J=11.82 Hz), 2.72-2.57 (2H, m), 2.33 (3H, s), 2.25 (3H, s), 2.18-2.00 (2H, m), 1.81 (1H, bd, J=12.17 Hz), 1.63-1.38 (9H, m), 0.89 (6H, d, J=6.54 Hz)

Example 226

2-(1-isopropyl-3-methyl-1H-1,2,4-triazol-5-yl)-9-(1-methyl-5-(1-(tetrahydro-2H-pyran-4-yl)piperidin-3-yl)-1H-pyrazol-4-yl)-5,6-dihydrobenzo[f]imidazo[1,2-d][1,4]oxazepine 226

To a solution of 4-[3-methyl-1-(propan-2-yl)-1H-1,2,4-triazol-5-yl]-12-[1-methyl-5-(piperidin-3-yl)-1H-pyrazol-4-yl]-9-oxa-3,6-diazatricyclo[8.4.0.0$^{2,6}$]tetradeca1(14), 2,4,10,12-pentaene (60 mg, 0.13 mmol) and tetrahydropyran-4-one (26 mg, 0.26 mmol) in ethanol (10 mL) was added Ti(Oi-Pr)$_4$ (74 mg, 0.26 mmol). After being stirred at 20° C. for 20 min, NaBH$_3$CN (16 mg, 0.26 mmol) was added and stirred at 20° C. for 16 h. The solvent was removed and several drops of water were added. The solid was filtered off and the filtrate was evaporated to afford the crude product, which was purified by reverse phase Combiflash eluting with a 0-50% gradient of CH$_3$CN in 0.3% NH$_4$HCO$_3$ to give 226 (35 mg, 50% yield). LCMS (ESI): RT=4.97 min, m/z: 557.4 [M+H$^+$]. $^1$H NMR (500 MHz, MeOH-d$_4$) δ 8.48 (d, J=8 Hz, 1H), 7.25 (s, 1H), 7.41 (s, 1H), 7.09 (d, J=8 Hz, 1H), 7.00 (s, 1H), 5.94 (t, J=13 Hz, 1H), 4.54 (d, J=5 Hz, 4H), 3.95 (d, J=6.5 Hz, 5H), 3.35 (t, J=25 Hz, 3H), 3.25 (s, 1H), 3.00 (d, J=6.5 Hz, 2H), 2.51-2.54 (m, 2H), 2.38 (s, 3H), 2.12 (d, J=11 Hz, 1H), 1.86-1.62 (m, 6H), 1.56-1.49 (m, 6H)

Example 232

9-(2-(1-methylpiperidin-4-yl)pyrrolidin-1-yl)-2-(1-(tetrahydrofuran-3-yl)-1H-1,2,4-triazol-5-yl)-5,6-dihydrobenzo[f]imidazo[1,2-d][1,4]oxazepine 232

Step 1: 12-Bromo-9-oxa-3,6-diazatricyclo[8.4.0.0$^{2,6}$]tetradeca1(14),2,4,10,12-pentaene-4-carboxamide

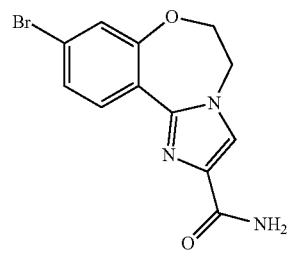 [SMILES: NC(=O)c1cn2c(n1)-c1ccc(Br)cc1OCC2]

To a solution of 12-bromo-4-iodo-9-oxa-3,6-diazatricyclo [8.4.0.0$^{2,6}$]tetradeca 1(14),2,4,10,12-pentaene (11.0 g, 28.7 mmol) in dried DMF (300 mL) was added Pd(PPh$_3$)$_2$Cl$_2$ (1.0 g, 1.4 mmol) and (Me$_3$Si)$_2$NH (14 g, 86 mmol). The mixture was stirred at 70° C. for 4 h under carbon monoxide atmosphere. After removal of the solvent, the residue was treated with ice-water, filtered, extracted with ethyl acetate (400 ml), dried over anhydrous Na$_2$SO$_4$, and concentrated to give 12-bromo-9-oxa-3,6-diazatricyclo[8.4.0.0$^{2,6}$]tetradeca1 (14),2,4,10,12-pentaene-4-carboxamide (7.2 g, 97% yield), which was used in the next step without further purification. LCMS (ESI) m/z: 308.1 [M+H$^+$].

Step 2: 12-Bromo-N-[(1E)-(dimethylamino)methylidene]-9-oxa-3,6-diazatricyclo[8.4.0.0$^{2,6}$]tetradeca1(14),2,4,10,12-pentaene-4-carboxamide

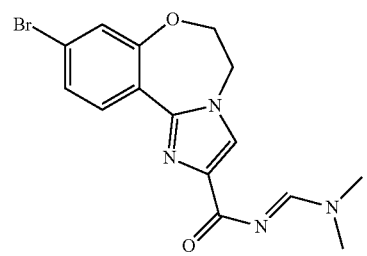

To a solution of 12-bromo-9-oxa-3,6-diazatricyclo [8.4.0.0$^{2,6}$]tetradeca1(14),2,4,10,12-pentaene-4-carboxamide (100 mg, 0.380 mmol) in 1,4-dioxane (3 mL) was added DMF-DMA (147 mg, 1.14 mmol). The resulting mixture was stirred at 100° C. for 1 h under nitrogen atmosphere. After removal of the solvent, the residue was washed with ether to afford 12-bromo-N-[(1E)-(dimethylamino)methylidene]-9-oxa-3,6-diazatricyclo[8.4.0.0$^{2,6}$]tetradeca-1(14),2,4,10,12- pentaene-4-carboxamide (80 mg, 68% yield), which was used in the next step without further purification. LCMS (ESI) m/z: 363.3 [M+H$^+$].

Step 3: 13-Bromo-4-[1-(oxolan-3-yl)-1H-1,2,4-triazol-5-yl]-9-oxa-3,6-diazatricyclo[8.4.0.0$^{2,6}$]tetradeca1(14),2,4,10,12-pentaene

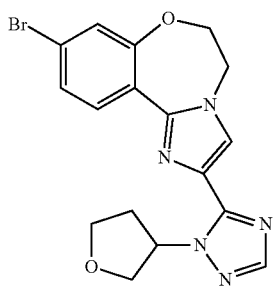 [SMILES: Brc1ccc2c(c1)OCCn1cc(-c3ncnn3C3CCOC3)nc1-2]

To a solution of 12-bromo-N-[(1E)-(dimethylamino)methylidene]-9-oxa-3,6-diazatricyclo[8.4.0.0$^{2,6}$]tetradeca1(14),2,4,10,12-pentaene-4-carboxamide (80 mg, 0.25 mmol) in acetic acid (3 ml) was added (tetrahydrofuran-3-yl)hydrazine HCl salt (69 mg, 0.5 mmol). The mixture was stirred at 100° C. for 1 h under nitrogen atmosphere. After concentration, the residue was purified by reverse phase Combiflash eluting with a 0-50% gradient of CH$_3$CN in 0.3% NH$_4$HCO$_3$ to give 13-bromo-4-[1-(oxolan-3-yl)-1H-1,2,4-triazol-5-yl]-9-oxa-3,6-diazatricyclo[8.4.0.0$^{2,6}$]tetradeca1(14),2,4,10,12-pentaene (61 mg, 61% yield). LCMS (ESI) m/z: 402.1 [M+H$^+$]

Step 4

A mixture of 12-bromo-4-[1-(oxolan-3-yl)-1H-1,2,4-triazol-5-yl]-9-oxa-3,6-diazatricyclo[8.4.0.0$^{2,6}$]tetradeca1(14),2,4,10,12-pentaene (40 mg, 0.010 mmol), 1-methyl-4-(pyrrolidin-2-yl)piperidine (3.0 mg, 0.020 mmol), Pd(P$^t$Bu$_3$)$_2$ (1.0 mg, 0.0010 mmol), NaO$^t$Bu (2.9 mg, 0.030 mmol) in toluene (2.0 ml) in a seal tube was degassed with N$_2$ for three times. The resulting mixture was stirred at 110° C. for 1 h. The solid was filtered off and the filtrate was concentrated to give the crude product, which was purified by prep-HPLC (Gilson GX 281, Shim-pack PRC-ODS 250 mm×20 mm×2, gradient: CH$_3$CN/1% formic acid, 17 min) to afford 232 (8.0 mg, 16% yield). LCMS (ESI): RT=3.39 min, m/z: 490.2 [M+H$^+$]. $^1$H NMR (500 MHz, DMSO-d$_6$) δ 8.40 (s, 1H), 7.31 (s, 1H), 8.02 (s, 1H), 7.93 (s, 1H), 6.60 (d, J=9 Hz, 1H), 6.42 (d, J=2.5 Hz, 1H), 4.54-4.52 (m, 4H), 4.29 (q, J=16 Hz, 1H), 4.16 (q, J=23 Hz, 1H), 4.03-4.01 (m, 1H), 3.97-3.95 (m, 1H), 3.86 (s, 1H), 3.55-3.53 (m, 1H), 3.24 (d, J=8 Hz, 1H), 2.98 (t, J=21 Hz, 2H), 2.56-2.48 (m, 2H), 2.29 (d, J=12 Hz, 3H), 2.04-1.93 (m, 5H), 1.78 (s, 1H), 1.69 (d, J=11.5 Hz, 1H), 1.53-1.44 (m, 3H)

Example 233

2-(1-(2-methoxypropyl)-3-methyl-1H-1,2,4-triazol-5-yl)-9-(2-(1-methylpiperidin-4-yl)pyrrolidin-1-yl)-5,6-dihydrobenzo[f]imidazo[1,2-d][1,4]oxazepine Step 1: 12-Bromo-4-[1-(2-methoxypropyl)-3-methyl-1H-1,2,4-triazol-5-yl]-9-oxa-3,6-diazatricyclo[8.4.0.0$^{2,6}$]tetradeca1(14),2,4,10,12-pentaene

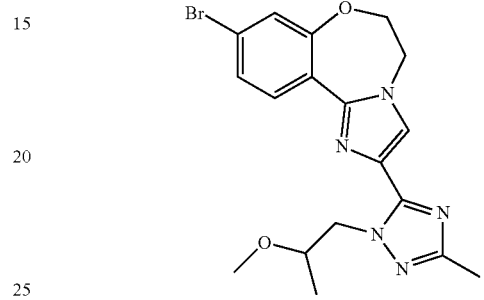

To a solution of 12-bromo-4-iodo-9-oxa-3,6-diazatricyclo[8.4.0.0$^{2,6}$]tetradeca1(14),2,4,10,12-pentaene (1.0 g, 2.6 mmol) in dry DMF (20 mL) was added hydrochloric acetimidamide (266 mg, 2.81 mmol), Pd(OAc)$_2$ (58 mg, 0.26 mmol), and Xantphos (305 mg, 0.520 mmol). The reaction mixture was stirred at 40° C. for 3 h under carbon monoxide atmosphere. LCMS indicated complete conversion. Acetic acid (40 mL) and hydrochloric (2-methoxypropyl)hydrazine (577 mg, 5.20 mmol) were added, the resultant mixture was stirred at 100° C. for 1 h. After concentration, the residue was purified by silica gel chromatography eluting with DCM/methanol (100:1) to give 12-bromo-4-[1-(2-methoxypropyl)-3-methyl-1H-1,2,4-triazol-5-yl]-9-oxa-3,6-diazatricyclo[8.4.0.0$^{2,6}$]tetradeca1(14),2,4,10,12-pentaene (707 mg, 65% yield) as white solid. LCMS (ESI) m/z: 418.3 [M+H$^+$].

Step 2

A mixture of 12-bromo-4-[1-(2-methoxypropyl)-3-methyl-1H-1,2,4-triazol-5-yl]-9-oxa-3,6-diazatricyclo[8.4.0.0$^{2,6}$]tetradeca1(14),2,4,10,12-pentaene (70 mg, 0.096 mmol), 1-methyl-4-(pyrrolidin-2-yl)piperidine (32 mg, 0.19 mmol), Pd(P$^t$Bu$_3$)$_2$ (6.0 mg, 0.0096 mmol), NaO$^t$Bu (2.8 mg, 0.029 mmol), and toluene (2 ml) in a seal tube was degassed with N$_2$ for three times. The resulting mixture was stirred at 110° C. for 1 h. The solid was filtered off and the filtrate was concentrated. The residue was purified by preparative HPLC (Gilson GX 281, Shim-pack PRC-ODS 250 mm×20 mm×2, gradient: CH$_3$CN/10 mm/L NH$_4$HCO$_3$, 17 min) to afford 233 (10 mg, 12% yield). LCMS (ESI): RT=3.42 min, m/z: 506.3 [M+H$^+$]. $^1$H NMR (500 MHz, DMSO-d$_6$) δ 8.30 (s, 1H), 8.16 (d, J=9 Hz, 1H), 7.76 (s, 1H), 6.50-6.48 (m, 1H), 6.14 (d, J=2.5 Hz, 1H), 4.90-4.81 (m, 1H), 4.69-4.60 (m, 1H), 4.43-4.38 (m, 4H), 3.86-3.84 (m, 1H), 3.75 (t, J=11 Hz, 1H), 3.45-3.43 (m, 1H), 3.14 (d, J=9 Hz, 1H), 2.87 (t, J=21 Hz, 2H), 2.23 (s, 3H), 2.20 (s, 3H), 1.96-1.83 (m, 6H), 1.64-1.58 (m, 2H), 1.43-1.33 (m, 3H), 1.11-1.09 (m, 3H)

Example 234

(4-tert-butylpiperazin-1-yl)(2-(1-isopropyl-3-methyl-1H-1,2,4-triazol-5-yl)-5,6-dihydroimidazo[1,2-d]pyrido[4,3-f][1,4]oxazepin-10-yl)methanone 234

Following the procedures in Example 266, 234 was prepared. ¹H NMR (400 MHz, DMSO) δ 8.41-8.39 (m, 1H), 8.39-8.37 (m, 1H), 8.08-7.99 (m, 1H), 5.82-5.48 (m, 1H), 4.62 (s, 4H), 3.56 (d, J=107.2 Hz, 5H), 2.57 (d, J=33.0 Hz, 3H), 2.26 (s, 3H), 1.46 (d, J=6.6 Hz, 6H), 1.02 (s, 9H). LCMS: 479.3

Example 235

1-tert-butyl-4-(2-(1-isopropyl-3-methyl-1H-1,2,4-triazol-5-yl)-5,6-dihydroimidazo[1,2-d]pyrido[4,3-f][1,4]oxazepine-10-carbonyl)piperazin-2-one 235

Following the procedures in Example 266, 235 was prepared. ¹H NMR (400 MHz, DMSO) δ 8.60-8.55 (m, 1H), 8.44-8.37 (m, 1H), 8.08-8.03 (m, 1H), 5.76-5.63 (m, 1H), 4.68-4.59 (m, 4H), 4.31-4.23 (br s, 1H), 4.19-4.06 (br s, 1H), 3.89-3.72 (m, 2H), 3.55-3.42 (m, 2H), 2.25 (d, J=23.3 Hz, 3H), 1.46 (d, J=6.6 Hz, 6H), 1.39 (s, 9H). LCMS: 493.3

Example 237

2-(3-methyl-5-(9-(2-(1-methylpiperidin-4-yl)pyrrolidin-1-yl)-5,6-dihydrobenzo[f]imidazo[1,2-d][1,4]oxazepin-2-yl)-1H-1,2,4-triazol-1-yl)ethanol 237

Step 1: (E)-tert-Butyl 2-(2-(tert-butyldimethylsilyloxy)ethylidene)hydrazinecarboxylate

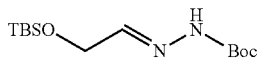

A mixture of tert-butyl hydrazinecarboxylate (2.5 g, 19 mmol), MgSO₄ (11.4 g, 95.0 mmol), and 2-(tert-butyldimethylsilyloxy)acetaldehyde (9.9 g, 57 mmol) in DCM (100 mL) was heated to reflux overnight. The solid was filtered off and the filtrate was concentrated. The residue was purified by silica gel chromatography eluting with EtOAc/petroleum ether (1:5) to give (E)-tert-butyl 2-(2-(tert-butyldimethylsilyloxy)ethylidene)hydrazinecarboxylate (5.1 g, 94% yield) as colorless oil. LCMS (ESI) m/z: 233.3 [M-56+H⁺].

Step 2: tert-Butyl 2-(2-(tert-butyldimethylsilyloxy)ethyl)hydrazinecarboxylate

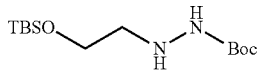

A mixture of (E)-tert-butyl 2-(2-(tert-butyldimethylsilyloxy)ethylidene)hydrazinecarboxylate (5.1 g, 17.71 mmol) and Pd/C (0.5 g, 10%) in MeOH (100 mL) was stirred under 1 atm H₂ at room temperature for 1 h. The solid was filtered off and the filtrate was concentrated. The residue was purified by silica gel chromatography eluting with EtOAc/petroleum ether (5:1) to give tert-butyl 2-(2-(tert-butyldimethylsilyloxy) ethyl)hydrazinecarboxylate (2.8 g, 55% yield) as colorless oil. LCMS (ESI) m/z: 235.3 [M-56+H⁺].

Step 3: 2-Hydrazinylethanol hydrochloride

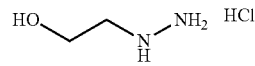

A mixture of tert-butyl 2-(2-(tert-butyldimethylsilyloxy)ethyl)hydrazinecarboxylate (100 mg, 0.345 mmol) in 4N HCl/dioxane (10 mL) was stirred at room temperature overnight. The solvent was removed under reduce pressure to give the crude product, which was used in the next step without further purification.

Step 4: 2-(5-{12-Bromo-9-oxa-3,6-diazatricyclo[8.4.0.0²,⁶]tetradeca-1(14),2,4,10,12-pentaen-4-yl}-3-methyl-1H-1,2,4-triazol-1-yl)ethan-1-ol

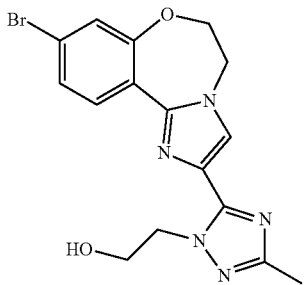 [SMILES: Cc1nc(-c2cn3c(n2)-c2ccc(Br)cc2OCC3)n(CCO)n1]

A mixture of 12-bromo-4-iodo-9-oxa-3,6-diazatricyclo[8.4.0.0²,⁶]tetradeca-1(14),2,4,10,12-pentaene (100 mg, 0.256 mmol), acetimidamide hydrochloride (26.5 mg, 0.282 mmol), Pd(OAc)₂ (2.9 mg, 0.0129 mmol), Xantphos (14.8 mg, 0.0256 mmol), and TEA (77.6 mg, 0.768 mmol) in DMF (5 mL) was heated at 40° C. under CO (1 atm) for 2 h. After cooling to room temperature, 2-hydrazinylethanol hydrochloride (57.3 mg, 0.512 mmol) and acetic acid (5 mL) were added. The resulting mixture was heated at 80° C. for 0.5 h. The solvent was removed under reduce pressure and the residue was purified by prep-HPLC (Gilson GX 281, Shim-pack PRC-ODS 250 mm×20 mm×2, gradient: CH₃CN/10 mm/L NH₄HCO₃, 17 min) to afford 2-(5-{12-bromo-9-oxa-3,6-diazatricyclo[8.4.0.0²,⁶]tetradeca-1(14),2,4,10,12-pentaen-4-yl}-3-methyl-1H-1,2,4-triazol-1-yl)ethan-1-ol (80 mg, 80% yield) as white solid. LCMS (ESI) m/z: 390.1 [M+H⁺].

Step 5

A mixture of 2-(5-{12-bromo-9-oxa-3,6-diazatricyclo[8.4.0.0²,⁶]tetradeca-1(14),2,4,10,12-pentaen-4-yl}-3-methyl-1H-1,2,4-triazol-1-yl)ethan-1-ol (80.0 mg, 0.206 mmol), 1-methyl-4-(pyrrolidin-2-yl)piperidine (41.5 mg, 0.247 mmol), Pd₂(dba)₃ (9.4 mg, 0.010 mmol), Xphos (9.8 mg, 0.021 mmol), and t-BuONa (59.3 mg, 0.618 mmol) in dioxane (10 ml) was degassed with N₂ 3 times. The resulting mixture was sealed in a microwave vial and stirred at 100° C. overnight. The solid was filtered off. The filtrate was concentrated to give the crude product, which was purified by prep-HPLC (Gilson GX 281, Shim-pack PRC-ODS 250 mm×20 mm×2, gradient: CH₃CN/10 mm/L NH₄HCO₃, 17 min) to afford 237 (3.5 mg, 4% yield) as an off white solid. LCMS (ESI): RT=4.03 min, m/z: 478.4 [M+H⁺]. ¹H NMR (500 MHz, MeOD-d₄) δ 8.40 (m, 1H), 8.10-8.09 (d, J=8.5 Hz, 1H), 7.56 (s, 1H), 6.44-6.42 (dd, J=9.0, 2.0 Hz, 1H), 6.17 (d, J=2.5 Hz, 1H), 4.68-4.66 (m, 2H), 4.37-4.32 (m, 4H), 3.93-3.91 (t, J=5.5 Hz, 2H), 3.79-3.76 (m, 1H), 3.46-3.37 (m, 3H), 3.17-3.12 (m, 1H), 2.82 (m, 1H), 2.69 (s, 3H), 2.26 (s, 3H), 1.99-1.82 (m, 6H), 1.73-1.70 (m, 1H), 1.56-1.51 (m, 2H), 1.23-1.19 (m, 2H)

Example 240

2-(1-isopropyl-3-methyl-1H-1,2,4-triazol-5-yl)-9-(1-methyl-5-(1-methylpyrrolidin-3-yl)-1H-pyrazol-4-yl)-5,6-dihydrobenzo[f]imidazo[1,2-d][1,4]oxazepine 240

Step 1: tert-Butyl 3-(N-methoxy-N-methylcarbamoyl)pyrrolidine-1-carboxylate

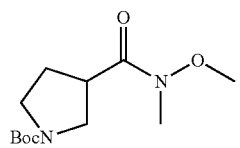

A mixture of 1-(tert-butoxycarbonyl)pyrrolidine-3-carboxylic acid (5.0 g, 23 mmol), O,N-dimethylhydroxylamine hydrochloride (4.51 g, 46.5 mmol), DIPEA (9.00 g, 69.6 mmol), and HATU (17.6 g, 46.5 mmol) in DMF (50 mL) was stirred at 15° C. for 16 h. DMF was removed, the residue was extracted with ethyl acetate, washed with brine, dried over MgSO₄, filtered, and evaporated to give the crude product, which was purified by silica gel chromatography eluting with a 0-30% gradient of EtOAc in petroleum ether to afford tert-butyl 3-(N-methoxy-N-methylcarbamoyl)pyrrolidine-1-carboxylate (6.3 g, 90% yield) as pale yellow oil. LCMS (ESI) m/z: 203.2 [M-56+H⁺].

Step 2: tert-Butyl 3-acetylpyrrolidine-1-carboxylate

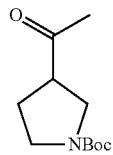

A mixture of tert-butyl 3-(N-methoxy-N-methylcarbamoyl)pyrrolidine-1-carboxylate (6.30 g, 24.3 mmol) and MeMgCl (3.0 M, 40 mL) in THF (100 mL) was stirred at 0° C. for 3 h. Sat. NH₄Cl was added to quench reaction. The resulting mixture was extracted with ethyl acetate (30 mL), washed with brine, dried over MgSO₄, filtered, and evaporated to give tert-butyl 3-acetylpyrrolidine-1-carboxylate (3.6 g, 69% yield) as yellow oil. LCMS (ESI) m/z: 158.3 [M-56+H⁺].

Step 3: tert-Butyl 34(E)-3-(dimethylamino)acryloyl)pyrrolidine-1-carboxylate

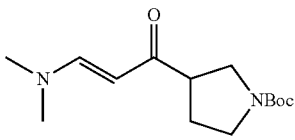 [SMILES: CN(C)/C=C/C(=O)C1CCN(C(=O)OC(C)(C)C)C1]

A mixture of tert-butyl 3-acetylpyrrolidine-1-carboxylate (3.6 g, 16 mmol), DMF (10 mL), and DMF-DMA (20 mL) was stirred at 140° C. for 16 h. The resultant mixture was extracted with ethyl acetate, washed with brine, dried over MgSO₄, filtered, and evaporated to afford tert-butyl 3-((E)-3-(dimethylamino)acryloyl)pyrro-lidine-1-carboxylate (4.44 g, 97% yield) as brown oil. LCMS (ESI) m/z: 213.3 [M-56+H⁺].

Step 4: tert-Butyl 3-(1-methyl-1H-pyrazol-5-yl)pyrrolidine-1-carboxylate

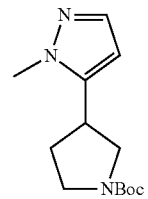

A mixture of tert-butyl 34(E)-3-(dimethylamino)acryloyl)pyrrolidine-1-carboxylate (4.44 g, 16.6 mmol) and methylhydrazine sulfuric salt (12.0 g, 83.3 mmol) in MeOH (50 mL) was stirred at room temperature for 20 h. Sat. NaHCO₃ was added to quench reaction, the resultant mixture was extracted with ethyl acetate (50 ml), washed with brine, dried over MgSO₄, filtered, and evaporated to give tert-butyl 3-(1-methyl-1H-pyrazol-5-yl)-pyrrolidine-1-carboxylate (2.3 g, 55% yield) as pale yellow oil. LCMS (ESI) m/z: 252.3 [M+H⁺].

Step 5: tert-Butyl 3-(4-bromo-1-methyl-1H-pyrazol-5-yl)pyrrolidine-1-carboxylate

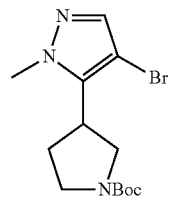 [SMILES: Cn1ncc(Br)c1C1CCN(C(=O)OC(C)(C)C)C1]

A mixture of tert-butyl 3-(1-methyl-1H-pyrazol-5-yl)-pyrrolidine-1-carboxylate (2.3 g, 7.0 mmol) and NBS (1.48 g, 8.39 mmol) in THF (50 mL) was stirred at room temperature for 1 h. Solvent was removed to afford the crude product, which was purified by reverse phase Combiflash eluting with a 0-70% gradient of CH$_3$CN in 0.3% NH$_4$HCO$_3$ to give tert-butyl 3-(4-bromo-1-methyl-1H-pyrazol-5-yl)pyrrolidine-1-carboxylate (2.28 g, 75% yield) as white solid. LCMS (ESI) m/z: 332.1 [M+H]$^+$. $^1$H-NMR (500 MHz, CDCl$_3$) δ 7.38 (s, 1H), 3.88 (s, 3H), 3.75-3.61 (m, 3H), 3.52 (s, 1H), 3.38 (s, 1H), 2.48 (s, 1H), 2.15 (s, 1H), 1.48 (s, 9H).

Step 6: 1-tert-Butyl-6-(1-methyl-4-{4-[3-methyl-1-(propan-2-yl)-1H-1,2,4-triazol-5-yl]-9-oxa-3,6-diazatricyclo[8.4.0.0$^{2,6}$]tetradeca-1(14),2,4,10,12-pentaen-12-yl}-1H-pyrazol-5-yl)-λ$^3$,3-oxazepan-2-one

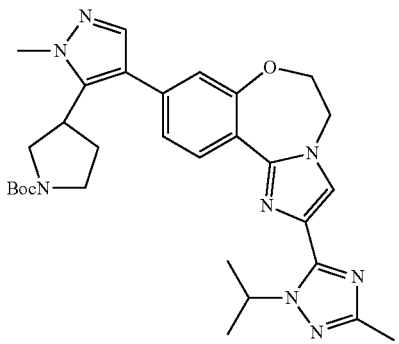

A mixture of tert-butyl 3-(4-bromo-1-methyl-1H-pyrazol-5-yl)pyrrolidine-1-carboxylate (1.0 g, 3.1 mmol), 4-[3-methyl-1-(propan-2-yl)-1H-1,2,4-triazol-5-yl]-12-(tetramethyl-1,3,2-dioxaborolan-2-yl)-9-oxa-3,6-diazatricyclo[8.4.0.0$^{2,6}$]tetradeca1 (14),2,4,10,12-pentaene (1.1 g, 2.5 mmol), Pd(dppf)Cl$_2$ (310 mg, 0.379 mmol), and Na$_2$CO$_3$ (1.34 g, 12.6 mmol) in dioxane (20 mL) was stirred at 80° C. for 16 h. The resultant mixture was extracted with ethyl acetate (50 mL), washed with brine, dried over MgSO$_4$, filtered, and evaporated to afford the crude product, which was purified by reverse phase Combiflash eluting with a 0-70% gradient of CH$_3$CN in 0.3% NH$_4$HCO$_3$ to give 1-tert-butyl-6-(1-methyl-4-{4-[3-methyl-1-(propan-2-yl)-1H-1,2,4-triazol-5-yl]-9-oxa-3,6-diazatricyclo[8.4.0.0$^{2,6}$]tetradeca1(14),2,4,10,12-pentaen-12-yl}-1H-pyrazol-5-yl)-λ$^3$,3-oxazepan-2-one (920 mg, 46% yield) as white solid. LCMS (ESI) m/z: 559.4 [M+H]$^+$. $^1$H-NMR (500 MHz, DMSO-d$_6$) δ 8.41 (d, J=8.5 Hz, 1H), 7.91 (s, 1H), 7.48 (s, 1H), 7.09 (d, J=8.5 Hz, 1H), 6.96 (s, 1H), 5.88-5.85 (m, 1H), 4.53 (s, 4H), 3.75 (s, 3H), 3.72 (s, 1H), 3.60 (s, 1H), 3.51-3.42 (m, 2H), 3.24-3.20 (m, 1H), 2.26 (s, 3H), 2.15-2.07 (m, 2H), 1.46 (s, 6H), 1.37 (s, 9H).

Step 7

A mixture of 1-tert-butyl-6-(1-methyl-4-{4-[3-methyl-1-(propan-2-yl)-1H-1,2,4-triazol-5-yl]-9-oxa-3,6-diazatricyclo[8.4.0.0$^{2,6}$]tetradeca-1(14),2,4,10,12-pentaen-12-yl}-1H-pyrazol-5-yl)-λ$^3$,3-oxazepan-2-one (150 mg, 0.269 mmol) and LiAlH$_4$ (51 mg, 1.3 mmol) in THF (5 mL) was refluxed for 1 hr. MeOH was added to quench reaction, The solid was filtered off and the filtrate was evaporated to afford the crude product, which was purified by reverse phase Combiflash eluting with a 0-70% gradient of CH$_3$CN in 0.3% NH$_4$HCO$_3$ to give racemic 240 (65 mg, 51% yield), which was separated by chiral SFC (Cellulose-2 column, 10% MeOH (0.1% DEA) isocratic) to give: 22.5 mg of one enantiomer and 35.5 mg of the other (46% total yield). LCMS (ESI): RT=4.79 min, m/z: 473.4 [M+H]$^+$. $^1$H-NMR (500 MHz, DMSO-d$_6$) δ 8.41 (d, J=8.5 Hz, 1H), 7.90 (s, 1H), 7.52 (s, 1H), 7.12 (dd, J=1.5 Hz, J=8.5 Hz, 1H), 6.99 (s, 1H), 5.77 (t, J=7.0 Hz, J=13.5 Hz, 1H), 4.53 (s, 4H), 3.97 (s, 3H), 3.74 (s, 1H), 2.80-2.74 (m, 2H), 2.65 (t, J=9.5 Hz, J=18.5 Hz, 1H), 2.49-2.46 (m, 1H), 2.30 (s, 3H), 2.26 (s, 3H), 2.19-2.17 (m, 1H), 1.96-1.93 (m, 1H), 1.46 (s, 6H)

Example 241

4-(2-(1-isopropyl-3-methyl-1H-1,2,4-triazol-5-yl)-5,6-dihydroimidazo[1,2-d]pyrido[4,3-f][1,4]oxazepine-10-carbonyl)-1-(tetrahydro-2H-pyran-4-yl)piperazin-2-one 241

Following the procedures in Example 266, 241 was prepared. $^1$H NMR (400 MHz, DMSO) δ 8.61-8.53 (m, 1H), 8.43-8.39 (m, 1H), 8.07-8.03 (m, 1H), 5.75-5.62 (m, 1H), 4.69-4.59 (m, 4H), 4.41-4.31 (m, 1H), 4.26-4.15 (m, 1H), 3.97-8.82 (m, 4H), 3.45-3.32 (m, 4H), 2.26 (s, 3H), 1.86-1.65 (m, 2H), 1.56-1.50 (s, 1H), 1.46 (d, J=6.6 Hz, 6H). LCMS: 521.3

Example 242

2-(1-isopropyl-3-methyl-1H-1,2,4-triazol-5-yl)-9-(1-isopropylpiperidin-4-ylsulfinyl)-5,6-dihydrobenzo[f]imidazo[1,2-d][1,4]oxazepine 242

To an ice-cooled solution of 2-(2-isopropyl-5-methyl-2H-[1,2,4]triazol-3-yl)-8-(1-isopropylpiperidin-4-ylsulfanyl)-4,5-dihydro-6-oxa-1,3a-diazabenzo[e]azulene from Example 49 (102 mg, 0.219 mmol) in DCM (10 mL) was added TFA (84 µL, 1.09 mmol) followed by a solution of m-CPBA (42 mg, 0.241 mmol) in DCM (2 mL). The resulting mixture was stirred for 15 min at 0° C. then volatiles were removed under reduced pressure. The crude material was purified by column chromatography (C$_{18}$, gradient 20-45% MeOH in 0.5% TFA/H$_2$O) and then loaded onto an Isolute® SCX-2 cartridge. The cartridge was washed with MeOH and the product eluted with 0.5M NH$_3$ in MeOH affording 242 as a colorless solid (92 mg, 87%). LCMS: R$_T$ 2.54 min [M+H]$^+$ 483.1. $^1$H NMR (DMSO, 400 MHz): δ 8.58 (1H, d, J=8.39 Hz), 7.96 (1H, s), 7.36 (1H, dd, J=8.39, 1.75 Hz), 7.26 (1H, d, J=1.72 Hz), 5.86-5.73 (1H, m), 4.57 (4H, s), 2.90-2.59 (4H, m), 2.26 (3H, s), 2.17-2.02 (2H, m), 1.84 (1H, bd, J=12.25 Hz), 1.58-1.38 (9H, m), 0.92 (6H, dd, J=6.52, 1.72 Hz)

Example 243

2-(1-isopropyl-3-methyl-1H-1,2,4-triazol-5-yl)-10-(1-isopropylpiperidin-4-ylsulfonyl)-9-methyl-5,6-dihydrobenzo[f]imidazo[1,2-d][1,4]oxazepine 243

To an ice-cooled solution of 2-(2-isopropyl-5-methyl-2H-[1,2,4]triazol-3-yl)-9-(1-isopropylpiperidine-4-sulfinyl)-8-methyl-4,5-dihydro-6-oxa-1,3a-diazabenzo[e]azulene 225 (30 mg, 0.061 mmol) in DCM (3 mL) was added TFA (24 µL, 0.306 mmol) followed by a solution of m-CPBA (14 mg, 0.0796 mmol) in DCM (1 mL). The resulting mixture was stirred for 3 h at 0° C. then volatiles were removed under reduced pressure. The crude material was purified by column chromatography (C$_{18}$, gradient 20-50% MeOH in 0.5% TFA/H$_2$O) and then loaded onto an Isolute® SCX-2 cartridge. The cartridge was washed with MeOH and the product eluted with 0.5M NH$_3$ in MeOH. The basic fractions were combined and concentrated in vacuo and the resulting residue was purified by column chromatography (Si-PCC, gradient 3-15% MeOH in DCM) affording 243 as a white solid (14 mg, 44%). LCMS: $R_T$ 2.83 min [M+H]$^+$ 513.1. $^1$H NMR (CD$_3$OD, 400 MHz): δ 9.08 (1H, s), 7.76 (1H, s), 7.10 (1H, s), 5.93-5.80 (1H, m), 4.63-4.53 (4H, m), 3.21-3.10 (1H, m), 3.00 (2H, bd, J=11.56 Hz), 2.77-2.67 (1H, m), 2.64 (3H, s), 2.37 (3H, s), 2.24 (2H, t, J=12.17 Hz), 1.97 (2H, d, J=12.67 Hz), 1.87-1.74 (2H, m), 1.56 (6H, d, J=6.65 Hz), 1.04 (6H, d, J=6.56 Hz)

Example 244

2-(1-isopropyl-3-methyl-1H-1,2,4-triazol-5-yl)-9-(1-isopropylpiperidin-4-ylsulfonyl)-5,6-dihydrobenzo[f]imidazo[1,2-d][1,4]oxazepine 244

To an ice-cooled solution of 2-(2-isopropyl-5-methyl-2H-[1,2,4]triazol-3-yl)-8-(1-isopropylpiperidine-4-sulfinyl)-4,5-dihydro-6-oxa-1,3a-diazabenzo[e]azulene 242 (38 mg, 0.078 mmol) in DCM (4 mL) was added TFA (30 µL, 0.39 mmol) followed by a solution of m-CPBA (18 mg, 0.101 mmol) in DCM (1 mL). The resulting mixture was stirred for 3 h at 0° C. then volatiles were removed under reduced pressure. The crude material was purified by column chromatography (C$_{18}$, gradient 20-50% MeOH in 0.5% TFA/H$_2$O) and then loaded onto an Isolute® SCX-2 cartridge. The cartridge was washed with MeOH and the product eluted with 0.5M NH$_3$ in MeOH. The basic fractions were combined and concentrated in vacuo and the resulting residue was purified by column chromatography (Si-PCC, gradient 3-15% MeOH in DCM) affording 244 as a white solid (31 mg, 81%). LCMS: $R_T$ 2.77 min [M+H]$^+$ 499.1. $^1$H NMR (CD$_3$OD, 400 MHz): δ 8.73 (1H, d, J=8.46 Hz), 7.84 (1H, s), 7.60 (1H, dd, J=8.47, 1.85 Hz), 7.55 (1H, d, J=1.82 Hz), 5.95-5.82 (1H, m), 4.65-4.57 (4H, m), 3.22-3.11 (1H, m), 2.99 (2H, bd, J=11.61 Hz), 2.77-2.64 (1H, m), 2.37 (3H, s), 2.20 (2H, t, J=11.89 Hz), 2.01 (2H, d, J=12.72 Hz), 1.73 (2H, td, J=12.41, 3.93 Hz), 1.55 (6H, d, J=6.65 Hz), 1.03 (6H, d, J=6.56 Hz)

Example 246

2-(1-isopropyl-3-methyl-1H-1,2,4-triazol-5-yl)-9-(1-methyl-5-(1-methylpiperidin-3-yl)-1H-pyrazol-4-yl)-5,6-dihydrobenzo[f]imidazo[1,2-d][1,4]oxazepine 246

To a solution of 4-[3-methyl-1-(propan-2-yl)-1H-1,2,4-triazol-5-yl]-12-[1-methyl-5-(piperidin-3-yl)-1H-pyrazol-4-yl]-9-oxa-3,6-diazatricyclo[8.4.0.0$^{2,6}$]tetradeca1 (14),2,4,10,12-pentaene, also named as 2-(1-isopropyl-3-methyl-1H-1,2,4-triazol-5-yl)-9-(1-methyl-5-(piperidin-3-yl)-1H-pyrazol-4-yl)-5,6-dihydrobenzo[f]imidazo[1,2-d][1,4]oxazepine (220 mg, 0.39 mmol) in dry THF (5.0 mL), was added LiAlH$_4$ (59.3 mg, 1.56 mmol) in small portions at room temperature. The resultant mixture was heated to reflux for 1 h. Water (2.0 mL) was added to quench the reaction. The organic layer was dried over Na$_2$SO$_4$ and concentrated. The residue was purified by prep-HPLC (Gilson GX 281, Shim-pack PRC-ODS 250 mm×20 mm×2, gradient: CH$_3$CN/10 mm/L NH$_4$HCO$_3$, 17 min) to give racemic 246 (150 mg, 79% yield), which was separated by chiral SFC (Cellulose-2 column, 0.1% DEA in MeOH isocratic) to give: 5.5 mg of one enantiomer and 70 mg of the other (39% total yield). LCMS (ESI): $R_T$=4.96 min, m/z: 487.4 [M+H]$^+$. $^1$H NMR (500 MHz, DMSO-d$_6$) δ 8.42 (d, J=2.0 Hz, 1H), 7.91 (s, 1H), 7.43 (s, 1H), 7.09-7.06 (m, 1H), 6.93 (d, J=1.5 Hz, 1H), 5.87-5.84 (m, 1H), 4.54 (d, J=6.0 Hz, 4H), 3.90 (s, 3H), 3.17 (s, 1H), 2.78-2.74 (m, 2H), 2.26 (s, 3H), 2.18-2.13 (m, 3H), 1.64-1.48 (m, 5H), 1.45 (d, J=7.0 Hz, 6H)

Example 248

2-(3-(4-(2-(1-isopropyl-3-methyl-1H-1,2,4-triazol-5-yl)-5,6-dihydrobenzo[f]imidazo[1,2-d][1,4]oxazepin-9-yl)-1-methyl-1H-pyrazol-5-yl)piperidin-1-yl)-2-methylpropan-1-ol 248

Step 1: Ethyl 2-methyl-2-[3-(1-methyl-4-{4-[3-methyl-1-(propan-2-yl)-1H-1,2,4-triazol-5-yl]-9-oxa-3,6-diazatricyclo[8.4.0.0$^{2,6}$]tetradeca1(14),2,4,10,12-pentaen-12-yl}-1H-pyrazol-5-yl)piperidin-1-yl]propanoate

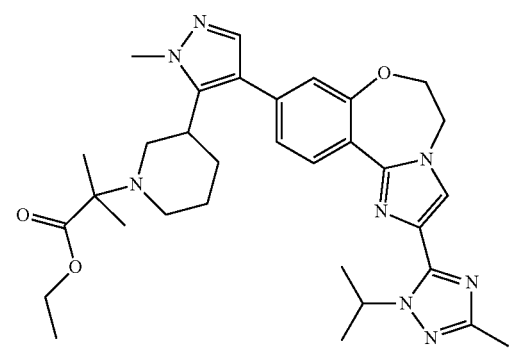 [SMILES: CCOC(=O)C(C)(C)N1CCCC(c2c(-c3ccc4c(c3)OCCn3cc(-c5nc(C)nn5C(C)C)nc3-4)cnn2C)C1]

A mixture of 4-[3-methyl-1-(propan-2-yl)-1H-1,2,4-triazol-5-yl]-12-[1-methyl-5-(piperidin-3-yl)-1H-pyrazol-4-yl]-9-oxa-3,6-diazatricyclo[8.4.0.0$^{2,6}$]tetradeca1 (14),2,4,10,12-pentaene (60 mg, 0.127 mmol), ethyl 2-bromo-2-methylpropanoate (247.65 mg, 1.27 mmol), Ag$_2$O (294 mg, 1.27 mmol), H$_2$O (0.1 ml) and CH$_3$CN (1.5 ml) in a seal tube was heated at 60° C. for 8 h. The solid was filtered off and the filtrate was purified by Combiflash eluting with a 0-70% gradient of CH$_3$CN in 0.3% NH$_4$HCO$_3$ to afford ethyl 2-methyl-2-[3-(1-methyl-4-{4-[3-methyl-1-(propan-2-yl)-1H-1,2,4-triazol-5-yl]-9-oxa-3,6-diazatricyclo[8.4.0.0$^{2,6}$]tetradeca1(14),2,4,10,12-pentaen-12-yl}-1H-pyrazol-5-yl)piperidin-1-yl]propanoate (35 mg, 47% yield). LCMS (ESI) m/z: 589.3 [M+H]$^+$]

Step 2

To a solution of ethyl 2-methyl-2-[3-(1-methyl-4-{4-[3-methyl-1-(propan-2-yl)-1H-1,2,4-triazol-5-yl]-9-oxa-3,6-diazatricyclo[8.4.0.0$^{2,6}$]tetradeca1(14),2,4,10,12-pentaen-12-yl}-1H-pyrazol-5-yl)piperidin-1-yl]propanoate (35 mg, 0.060 mmol) in dry THF (2 ml), was added LiAlH$_4$ (11.4 mg, 0.300 mmol) in small portions at room temperature. The resulting mixture was heated to reflux for 1 h. Water (1 mL) was added to quench the reaction. The organic layer was separated, dried over Na$_2$SO$_4$, and concentrated. The residue was purified by prep-HPLC (Gilson GX 281, Shim-pack PRC-ODS 250 mm×20 mm×2, gradient: CH$_3$CN/10 mm/L NH$_4$HCO$_3$, 17 min) to afford 248 (10 mg, 31% yield). LCMS (ESI): $R_T$=4.72 min, m/z: 545.4 [M+H]$^+$. $^1$H NMR (500 MHz, DMSO-d$_6$) δ 8.39 (d, J=8.5 Hz, 1H), 7.91 (s, 1H), 7.43 (s, 1H), 7.09-7.08 (m, 1H), 6.93 (d, J=1.5 Hz, 1H), 5.86-5.83 (m, 1H), 4.53 (d, J=6.0 Hz, 4H), 4.27-4.25 (m, 1H), 3.89 (s, 3H), 3.28-3.25 (m, 2H), 2.99-2.96 (m, 3H), 2.44-2.40 (m, 2H), 2.26 (s, 3H), 2.08-2.06 (m, 1H), 1.58-1.70 (m, 3H), 1.47-1.45 (m, 6H), 0.93-0.91 (m, 6H)

Example 249

2-(1-isopropyl-3-methyl-1H-1,2,4-triazol-5-yl)-9-(2-(1-methylpiperidin-4-yl)pyrrolidin-1-yl)-5,6-dihydroimidazo[1,2-d]pyrido[3,4-f][1,4]oxazepine 249

Step 1: 12-Chloro-4-[3-methyl-1-(propan-2-yl)-1H-1,2,4-triazol-5-yl]-9-oxa-3,6,13-triazatricyclo[8.4.0.0$^{2,6}$]tetradeca-1(14),2,4,10,12-pentaene

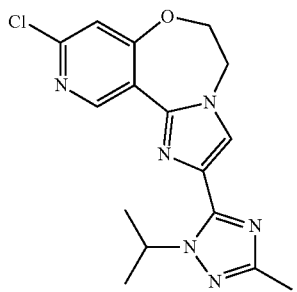 [SMILES: Cc1nc(-c2cn3c(n2)-c2cnc(Cl)cc2OCC3)n(C(C)C)n1]

To a solution of 12-chloro-4-iodo-9-oxa-3,6,13-triazatricyclo[8.4.0.0$^{2,6}$]tetradeca-1(14),2,4,10,12-pentaene (2.0 g, 5.8 mmol) in dry DMF (20 mL) was added hydrochloric acetimidamide (595 mg, 6.30 mmol), Pd(OAc)$_2$ (130 mg, 0.580 mmol), and Xantphos (695 mg, 1.2 mmol). The mixture was stirred at 40° C. for 3 h under carbon monoxide atmosphere. LCMS indicated complete conversion. Acetic acid (40 mL) and hydrochloric (2-methoxypropyl)hydrazine (1.3 g, 12 mmol) were added. The resultant mixture was stirred at 100° C. for 1 h. After concentration, the residue was purified by silica gel chromatography eluting with DCM/methanol (100:1) to give 12-chloro-4-[3-methyl-1-(propan-2-yl)-1H-1,2,4-triazol-5-yl]-9-oxa-3,6,13-triazatricyclo[8.4.0.0$^{2,6}$]tetra-deca1(14),2,4,10,12-pentaene (1.4 g, 71% yield) as a white solid. LCMS (ESI) m/z: 345.3 [M+H$^+$].

Step 2

A 10 mL microwave vial was charged with 12-chloro-4-[3-methyl-1-(propan-2-yl)-1H-1,2,4-triazol-5-yl]-9-oxa-3,6,13-triazatricyclo[8.4.0.0$^{2,6}$]tetradeca1(14), 2,4,10,12-Pentaene (160 mg, 0.470 mmol), toluene (4 mL), 1-methyl-4-(pyrrolidin-2-yl)piperidine (156 mg, 0.94 mmol), Pd(P$^t$Bu$_3$)$_2$(27 mg, 0.047 mmol), NaO$^t$Bu (135 mg, 1.40 mmol). The vial was sealed and degassed with N$_2$ for three times. The resulting mixture was stirred at 110° C. for 1 h. After concentration, the residue was purified by reverse phase Combiflash eluting with a 0-50% gradient of CH$_3$CN in 0.3% NH$_4$HCO$_3$ to give 249, which was separated by chiral HPLC (AD column, 30% EtOH (0.1% DEA) in n-hexane isocratic) to give: 9 mg of one enantiomer and 6 mg of the other (7% total yield)

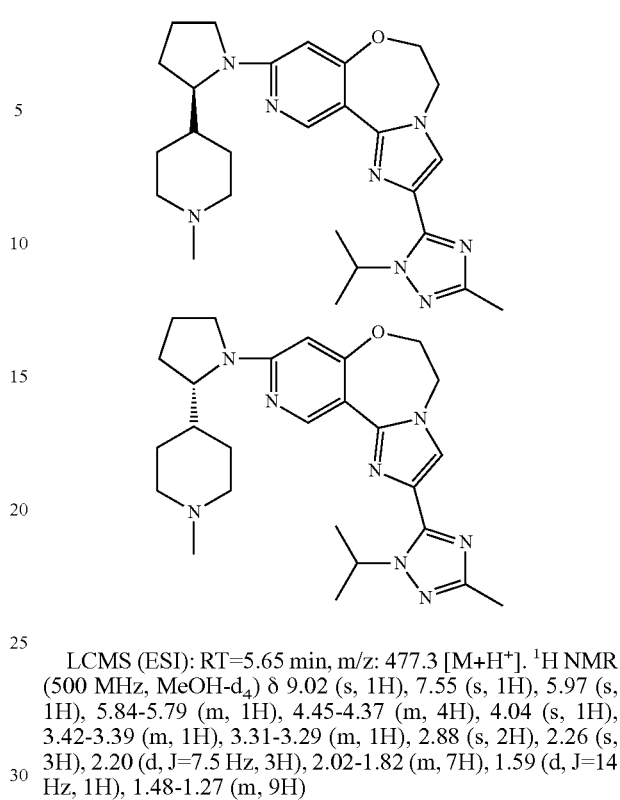

LCMS (ESI): RT=5.65 min, m/z: 477.3 [M+H$^+$]. $^1$H NMR (500 MHz, MeOH-d$_4$) δ 9.02 (s, 1H), 7.55 (s, 1H), 5.97 (s, 1H), 5.84-5.79 (m, 1H), 4.45-4.37 (m, 4H), 4.04 (s, 1H), 3.42-3.39 (m, 1H), 3.31-3.29 (m, 1H), 2.88 (s, 2H), 2.26 (s, 3H), 2.20 (d, J=7.5 Hz, 3H), 2.02-1.82 (m, 7H), 1.59 (d, J=14 Hz, 1H), 1.48-1.27 (m, 9H)

Example 250

2-(2-(1-isopropyl-3-methyl-1H-1,2,4-triazol-5-yl)-5,6-dihydrobenzo[f]imidazo[1,2-d][1,4]oxazepin-9-yloxy)-2-methyl-1-(4-methylpiperazin-1-yl)propan-1-one 250

To a suspension of 2-[2-(2-isopropyl-5-methyl-2H-[1,2,4]triazol-3-yl)-4,5-dihydro-6-oxa-1,3a-diazabenzo[e]azulen-8-yloxy]-2-methylpropionic acid from Example 45 (0.0922 mmol) in DMF (2 mL) were added DIPEA (47 ul, 0.277 mmol), 1-methylpiperazine (31 uL, 0.277 mmol), HOBt (19 mg, 0.138 mmol) and EDCI (27 mg, 0.138 mmol) and the reaction mixture was stirred at RT for 2 h. Additional EDCI (50 mg) was added and the reaction mixture was stirred at RT for 18 h. The mixture was then partitioned between EtOAc and water. The aqueous layer was further extracted with EtOAc and the combined organic layers were washed with water, followed by brine, then dried (Na$_2$SO$_4$) and concentrated in vacuo. The resulting residue was purified by column chromatography (Si-PCC, gradient 2-8% MeOH in DCM) affording 250 as a white solid (28 mg, 60% over three steps). LCMS: R$_T$ 2.92 min [M+H]$^+$ 494.1. $^1$H NMR (DMSO, 400 MHz): δ 8.29 (1H, d, J=8.97 Hz), 7.83 (1H, s), 6.64 (1H, dd, J=8.98, 2.60 Hz), 6.42 (1H, d, J=2.57 Hz), 5.88-5.76 (1H, m), 4.47 (4H, s), 3.75-3.44 (4H, m), 2.24 (3H, s), 2.19 (2H, s), 2.06-1.94 (5H, m), 1.58 (6H, s), 1.44 (6H, d, J=6.59 Hz)

Example 252

2-(3-(4-(2-(1-isopropyl-3-methyl-1H-1,2,4-triazol-5-yl)-5,6-dihydrobenzo[f]imidazo[1,2-d][1,4]oxazepin-9-yl)-1-methyl-1H-pyrazol-5-yl)piperidin-1-yl)-2-methylpropanamide 252

A mixture of 4-[3-methyl-1-(propan-2-yl)-1H-1,2,4-triazol-5-yl]-12-[1-methyl-5-(piperidin-3-yl)-1H-pyrazol-4-yl]-

9-oxa-3,6-diazatricyclo[8.4.0.0²,⁶]tetradeca1(14),2,4,10,12-pentaene (100 mg, 0.21 mmol), ethyl 2-bromo-2-methylpropanoate (348.6 mg, 2.100 mmol), Ag₂O (487.2 mg, 2.100 mmol), H₂O (0.5 mL), and CH₃CN (1.5 mL) in a seal tube was heated at 60° C. for 8 h. The solid was filtered off and the filtrate was purified by Combiflash eluting with a 0-70% gradient of CH₃CN in 0.3% NH₄HCO₃ to afford racemic 252 (35 mg, 30% yield), which was separated by chiral SFC (AS-H column, 0.1% DEA in MeOH isocratic) to give: 5.0 mg of one enantiomer and 3 mg of the other (7% total yield). LCMS (ESI): RT=5.19 min, m/z: 558.3 [M+H⁺]. ¹H NMR (500 MHz, DMSO-d₆) δ 8.42 (d, J=8.0 Hz, 1H), 7.91 (s, 1H), 7.09-7.07 (m, 1H), 7.02-6.94 (m, 3H), 5.86-5.83 (m, 1H), 4.52 (s, 4H), 3.89 (s, 3H), 2.74-2.63 (m, 2H), 2.37-2.32 (m, 2H), 2.26 (s, 3H), 2.00 (s, 1H), 1.75-1.60 (m, 3H), 1.47-1.45 (m, 6H), 1.02-0.97 (m, 7H)

Example 253

2-(3-methyl-1-(2,2,2-trifluoroethyl)-1H-1,2,4-triazol-5-yl)-9-(2-(1-methylpiperidin-4-yl)pyrrolidin-1-yl)-5,6-dihydroimidazo[1,2-d]pyrido[3,4-f][1,4]oxazepine 253

Step 1: (E)-tert-Butyl 2-(2,2,2-trifluoroethylidene)hydrazine-carboxylate

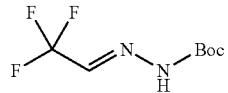

A mixture of 2,2,2-trifluoroacetaldehyde (10.0 g, 76.5 mmol) and NH₂NH₂Boc (10.0 g, 75.7 mmol) in DCM (100 mL) was stirred at 50° C. for 16 h. The solid was filtered off and the filtrate was evaporated. The residue was purified by silica gel chromatography eluting with EtOAc/petroleum ether (1:100) to afford (E)-t ert-butyl 2-(2,2,2-trifluoroethylidene) hydrazinecarboxylate (4.0 g, 28% yield) as pale yellow oil. LCMS (ESI) m/z: 157.1 [M-56+H⁺].

Step 2: tert-Butyl 2-(2,2,2-trifluoroethyl)hydrazinecarboxylate

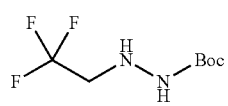

A mixture of (E)-tert-butyl 2-(2,2,2-trifluoroethylidene) hydrazinecarboxylate (4.00 g, 18.9 mmol) and 20% Pd/C (2.00 g) in MeOH (20.0 mL) was stirred under H₂ atmosphere at 25° C. for 16 h. The solid was filtered off and the filtrate was evaporated to give the crude product, which was purified by silica gel chromatography eluting with EtOAc/petroleum ether (1:100) to afford tert-butyl 2-(2,2,2-trifluoroethyl)hydrazinecarboxylate (1.32 g, 33% yield) as pale yellow oil. LCMS (ESI) m/z: 159.3 [M-56+H⁺].

Step 3: (2,2,2-Trifluoroethyl)hydrazine hydrochloride

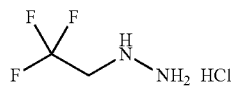

A mixture of tert-butyl 2-(2,2,2-trifluoroethyl)hydrazinecarboxylate (1.30 g, 6.07 mmol) in sat. HCl/EtOAc solution (20.0 mL) was stirred at 25° C. for 16 h. The solvent was evaporated to give (2,2,2-trifluoroethyl)hydrazine hydrochloride (860 mg, 94% yield) as solid, which was used in the next step without further purification.

Step 4: 12-Chloro-4-[3-methyl-1-(2,2,2-trifluoroethyl)-1H-1,2,4-triazol-5-yl]-9-oxa-3,6,13-triazatricyclo[8.4.0.0²,⁶]tetradeca1(14),2,4,10,12-pentaene

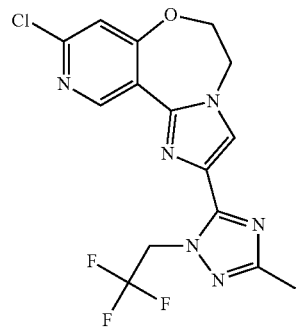 [SMILES: Cc1nc(-c2cn3c(n2)-c2cnc(Cl)cc2OCC3)n(CC(F)(F)F)n1]

A mixture of 12-chloro-4-iodo-9-oxa-3,6,13-triazatricyclo [8.4.0.0²,⁶]tetradeca1 (14),2,4,10,12-pentaene (1.60 g, 4.60 mmol) and acetamidine hydrochloride (481 g, 5.06 mmol), Et₃N (4.00 mL), 4,5-bis(diphenylphosphino)-9,9-dimethylxanthene (Xantphos, 532 mg, 0.920 mmol), and Pd(OAc)₂ (103 mg, 0.460 mmol) in DMF (20.0 mL) was heated under carbon monoxide atmosphere at 40° C. for 3 h. After cooling to room temperature, a solution of (2,2,2-trifluoroethyl)hydrazine hydrochloride (800 mg, 5.32 mmol) in acetic acid (15.0 mL) was added. The resultant mixture was further heated at 65° C. for 3 h. After concentratin, the residue was extracted with ethyl acetate, washed with brine, dried over MgSO₄, filtered, and evaporated. The crude product was purified by reverse phase Combiflash eluting with a 0-40% gradient of CH₃CN in 0.5% NH₄HCO₃ to give 12-chloro-4-[3-methyl-1-(2,2,2-trifluoroethyl)-1H-1,2,4-triazol-5-yl]-9-oxa-3,6,13-triazatricyclo[8.4.0.0²,⁶]tetradeca1(14),2,4,10, 12-pentaene (1.35 mg, 76% yield) as pale yellow solid. LCMS (ESI) m/z: 385.1 [M+H⁺].

Step 5

A mixture of 12-chloro-4-[3-methyl-1-(2,2,2-trifluoroethyl)-1H-1,2,4-triazol-5-yl]-9-oxa-3,6,13-triazatricyclo [8.4.0.0²,⁶]tetradeca1(14),2,4,10,12-pentaene (50.0 mg, 0.130 mmol), 1-methyl-4-(pyrrolidin-2-yl)piperidine (30.0 mg, 0.178 mmol), Pd(P-t-Bu₃)₂ (6.00 mg, 0.0120 mmol), and NaOt-Bu (40.0 mg, 0.412 mmol) in toluene (20.0 mL) in a seal tube was stirred at 110° C. for 3 h. After concentration, the residue was purified by reverse phase Combiflash eluting with a 0-40% gradient of CH₃CN in 0.5% NH₄HCO₃ to afford 253 (8 mg, 12% yield) as white solid. LCMS (ESI): RT=4.70 min, m/z: 517.3 [M+H⁺]. ¹H-NMR (500 MHz, DMSO-d₆) δ 9.03 (s, 1H), 7.66 (s, 1H), 5.85 (s, 1H), 5.70 (dd, J=8.5 Hz, J=23.5 Hz, 2H), 4.46-4.43 (m, 4H), 4.06 (s, 1H), 3.38 (s, 1H), 3.26 (s, 1H), 2.09 (s, 3H), 1.95 (s, 9H), 1.84-1.72 (m, 2H), 1.52-1.34 (m, 3H), 1.19-1.12 (m, 2H)

Example 254

2-(1-isopropyl-3-methyl-1H-1,2,4-triazol-5-yl)-9-(2-(1-(tetrahydro-2H-pyran-4-yl)piperidin-4-yl)pyrrolidin-1-yl)-5,6-dihydrobenzo[f]imidazo[1,2-d][1,4]oxazepine 254

A mixture of 9-bromo-2-(1-isopropyl-3-methyl-1H-1,2,4-triazol-5-yl)-5,6-dihydrobenzo[f]imidazo[1,2-d][1,4]oxazepine (200 mg, 0.516 mmol), 4-(pyrrolidin-2-yl)-1-(tetrahydro-2H-pyran-4-yl)piperidine hydrochloride (354 mg, 1.29 mmol), Pd(P^tBu₃)₂ (20 mg, 0.04 mmol), Na₂O^tBu (148 mg, 1.55 mmol) in toluene (5.0 ml) in a seal tube was degassed with N₂ for three times. The mixture was stirred at 110° C. for 120 min. The solid was filtered through Celite. The filtrate was concentrated to give the crude product, which was purified by prep-HPLC (Gilson GX 281, Shim-pack PRC-ODS 250 mm×20 mm×2, gradient: CH₃CN/1% formic acid, 17 min) to give racemic 254 (13 mg, 4.6% yield). LCMS (ESI): RT=2.00 min, m/z: 546.4 [M+H⁺]. ¹H NMR (500 MHz, CDCl₃): δ 8.33 (d, J=8.5 Hz, 1H), 7.53 (s, 1H), 6.47 (dd, J=9.5 Hz, 2.5 Hz, 1H), 6.18 (d, J=2.5 Hz, 1H), 5.95-5.92 (m, 1H), 4.48-4.36 (m, 4H), 4.05 (d, J=8.5 Hz, 1H), 3.85-3.75 (m, 1H), 3.41-3.24 (m, 6H), 2.41 (s, 4H), 2.02-1.74 (m, 14H), 1.56 (d, J=6.5 Hz, 7H)

Example 255

2-(1-isopropyl-3-methyl-1H-1,2,4-triazol-5-yl)-9-(1-(1-methylpiperidin-4-yl)-1H-1,2,4-triazol-5-yl)-5,6-dihydrobenzo[f]imidazo[1,2-d][1,4]oxazepine 255

Step 1: 4-[3-Methyl-1-(propan-2-yl)-1H-1,2,4-triazol-5-yl]-9-oxa-3,6-diazatricyclo[8.4.0.0²,⁶]tetradeca1(14),2,4,10,12-pentaene-12-carboxamide

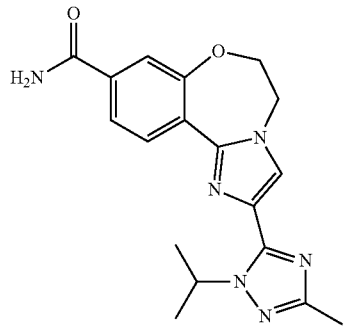 [SMILES: Cc1nc(-c2cn3c(n2)-c2ccc(C(N)=O)cc2OCC3)n(C(C)C)n1]

A mixture of 12-bromo-4-[3-methyl-1-(propan-2-yl)-1H-1,2,4-triazol-5-yl]-9-oxa-3,6-diazatricyclo[8.4.0.0²,⁶]tetradeca1(14),2,4,10,12-pentaene (1.0 g, 2.6 mmol), hexamethyldisilazane (3.0 mL, 14 mmol), and Pd(PPh₃)₂Cl₂ (0.09 g, 0.13 mmol) in dry DMF (10 mL) was heated under CO atmosphere at 80° C. overnight. Most of the solvent was removed and water (20 mL) was added. The solid was collected by filtration, washed with water, and dried in vacuo to afford 4-[3-methyl-1-(propan-2-yl)-1H-1,2,4-triazol-5-yl]-9-oxa-3,6-diazatricyclo[8.4.0.0²,⁶]tetradeca1(14),2,4,10,12-pentaene-12-carboxamide (1.3 g, 95% yield) as a gray solid. LCMS (ESI) m/z: 353.3 [M+H⁺].

Step 2: N-[(1E)-(Dimethylamino)methylidene]-4-[3-methyl-1-(propan-2-yl)-1H-1,2,4-triazol-5-yl]-9-oxa-3,6-diazatricyclo[8.4.0.0²,⁶]tetradeca1(14),2,4,10,12-pentaene-12-carboxamide

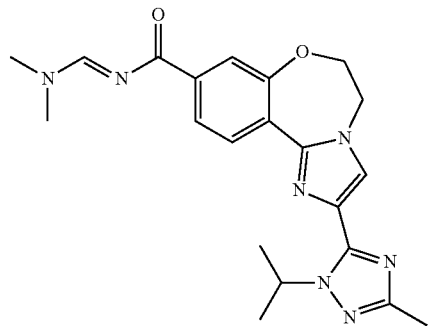

To a solution of 4-[3-methyl-1-(propan-2-yl)-1H-1,2,4-triazol-5-yl]-9-oxa-3,6-diazatricyclo[8.4.0.0²,⁶]tetradeca1(14),2,4,10,12-pentaene-12-carboxamide (200 mg, 0.568 mmol) in dioxane (20 mL) was added DMF-DMA (0.2 mL, 1.7 mmol). The reaction mixture was heated at 100° C. for 1 h. The solvent was removed under reduce pressure and the resultant residue was triturated with hot diethyl ether. The solid was collected by filtration, washed with diethyl ether, and dried in vacuo to afford N-[(1E)-(dimethylamino)methylidene]-4-[3-methyl-1-(propan-2-yl)-1H-1,2,4-triazol-5-yl]-9-oxa-3,6-diazatricyclo[8.4.0.0²,⁶]tetradeca1(14),2,4,10,12-pentaene-12-carboxamide (180 mg, 78% yield) as a brown solid. LCMS (ESI) m/z: 408.3 [M+H⁺].

Step 3: tert-Butyl 2-(1-methylpiperidin-4-ylidene)hydrazinecarboxylate

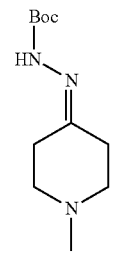

To a solution of 1-methylpiperidin-4-one (3.0 g, 27 mmol) in DCM (60 mL) was added MgSO4 (6.5 g, 54 mmol) and tert-butyl hydrazinecarboxylate (2.9 g, 22 mmol). The reaction mixture was heated to reflux overnight. The solid was filtered off and the filtrate was concentrated. The residue was purified by silica gel chromatography eluting with EtOAc/petroleum ether (1:20) to give tert-butyl 2-(1-methylpiperidin-4-yl)hydrazinecarboxylate (3.2 g, 53% yield) as a colorless oil. LCMS (ESI) m/z: 228.3 [M+H+].

Step 4: tert-Butyl 2-(1-methylpiperidin-4-yl)hydrazinecarboxylate

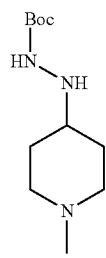

To a solution of tert-butyl 2-(1-methylpiperidin-4-ylidene) hydrazinecarboxylate (500 mg, 2.20 mmol) in THF (50 mL) was added DIBAl-H (22 mL, 22 mmol) under nitrogen atmosphere. The resulting mixture was stirred at 25° C. overnight. Methanol (5 mL) was added to quench the reaction at −78° C. After being stirred at room temperature for 1 h, water (10 mL) was added. The solid was filtered off and washed with EtOAc. The combined filtrate was partitioned and extracted with EtOAc (3×50 mL), dried over $Na_2SO_4$, and concentrated. The residue was purified by silica gel chromatography eluting with EtOAc/petroleum ether (1:10) to give tert-butyl 2-(1-methylpiperidin-4-yl)hydrazinecarboxylate (350 mg, 69% yield) as a colorless oil. LCMS (ESI) m/z: 230.4 [M+H+].

Step 5: 4-Hydrazinyl-1-methylpiperidine hydrochloride

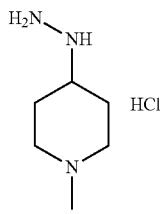

A mixture of tert-butyl 2-(1-methylpiperidin-4-yl)hydrazinecarboxylate (350 mg, 1.53 mmol) in sat. HCl/EtOAc solution (20 mL) was stirred at room temperature overnight. The solvent was removed under reduce pressure to afford 4-hydrazinyl-1-methylpiperidine hydrochloride (253 mg, 100% yield), which was used in the next step without further purification. LCMS (ESI) m/z: 130.3 [M+H+].

Step 6

A mixture of N-[(1E)-(dimethylamino)methylidene]-4-[3-methyl-1-(propan-2-yl)-1H-1,2,4-triazol-5-yl]-9-oxa-3,6-diazatricyclo[8.4.0.0$^{2,6}$]tetradeca1(14),2,4,10,12-pentaene-12-carboxamide (100 mg, 0.246 mmol) and 4-hydrazinyl-1-methylpiperidine hydrochloride (81 mg, 0.49 mmol) in acetic acid (10 mL) was heated at 100° C. for 1 h. The solvent was removed under reduce pressure, and the residue was purified by prep-HPLC (Gilson GX 281, Shim-pack PRC-ODS 250 mm×20 mm×2, gradient: $CH_3CN$/10 mm/L $NH_4HCO_3$, 17 min) to afford 255 (40 mg, 34% yield) as a white solid. LCMS (ESI): RT=4.28 min, m/z: 474.3 [M+H+]. $^1$H NMR (500 MHz, DMSO-d$_6$) δ 8.58-8.57 (d, J=8.0 Hz, 1H), 8.08 (s, 1H), 7.99 (s, 1H), 7.44-7.42 (dd, J=8.0, 1.5 Hz, 1H), 7.31 (d, J=1.5 Hz, 1H), 5.86 (m, 1H), 4.58 (s, 4H), 4.31 (m, 1H), 2.86-2.84 (m, 2H), 2.26 (s, 3H), 2.18 (s, 3H), 2.13-2.07 (m, 2H), 2.01-1.96 (m, 2H), 1.91-1.89 (m, 2H), 1.47 (d, J=6.5 Hz, 6H)

Example 257

2-(5-(9-(1-(1-methylpiperidin-4-yl)-1H-pyrazol-5-yl)-5,6-dihydrobenzo[f]imidazo[1,2-d][1,4]oxazepin-2-yl)-1H-1,2,4-triazol-1-yl)ethanol 257

Step 1: 2-{5-[12-(1-Ethoxyethenyl)-9-oxa-3,6-diazatricyclo[8.4.0.0$^{2,6}$]tetradeca1(14),2,4,10,12-pentaen-4-yl]-1H-1,2,4-triazol-1-yl}ethan-1-ol

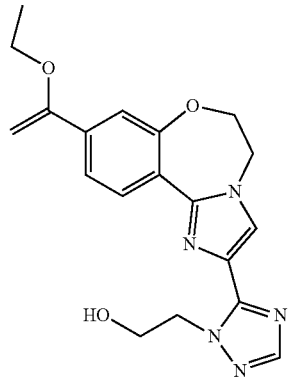 [SMILES: C=C(OCC)c1ccc2c(c1)OCCn1cc(-c3ncnn3CCO)nc1-2]

A mixture of 2-(5-{12-bromo-9-oxa-3,6-diazatricyclo[8.4.0.0$^{2,6}$]tetradeca1 (14),2,4,10,12-pentaen-4-yl-1H-1,2,4-triazol-1-yl)ethan-1-ol (290 mg, 0.770 mmol), tributyl(1-ethoxyvinyl)stannane (0.5 mL), Pd(PPh$_3$)$_4$ (27 mg, 0.023 mmol), LiCl (97 mg, 2.3 mmol) in dry THF (10 mL) was stirred at 70° C. for 48 h under nitrogen atmosphere. The reaction was then treated with KF (40 mL, 0.16 M) and stirred at room temperature for 1 h. The solid was filtered off, the filtrate was concentrated. The residue was purified by reverse phase Combiflash eluting with a 0-50% gradient of $CH_3CN$ in 0.3% $NH_4HCO_3$ to give 2-{5-[12-(1-ethoxyethenyl)-9-oxa-3,6-diazatricyclo[8.4.0.0$^{2,6}$]tetradeca-1(14),2,4,10,12-pentaen-4-yl]-1H-1,2,4-triazol-1-yl}ethan-1-ol (160 mg, 55% yield). LCMS (ESI) m/z: 368.3 [M+H+].

Step 2: 1-{4-[1-(2-Hydroxyethyl)-1H-1,2,4-triazol-5-yl]-9-oxa-3,6-diazatricyclo[8.4.0.0$^{2,6}$]tetradeca1 (14),2,4,10,12-pentaen-12-yl}ethan-1-one

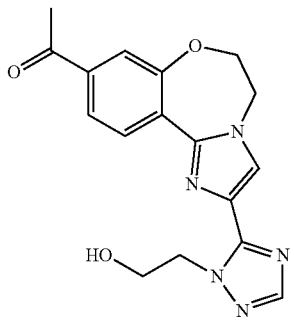 [SMILES: CC(=O)c1ccc2c(c1)OCCn1cc(-c3ncnn3CCO)nc1-2]

A mixture of 2-{5-[12-(1-ethoxyethenyl)-9-oxa-3,6-diazatricyclo[8.4.0.0$^{2,6}$]tetradeca-1(14),2,4,10,12-pentaen-4-yl]-1H-1,2,4-triazol-1-yl}ethan-1-ol (160 mg, 0.440 mmol)

and p-toluenesulfonic acid (7.5 mg, 0.044 mmol) in acetone (10 mL) was stirred at 60° C. for 75 minute. The solid was filtered off, the filtrate was purified by reverse phase Combi-flash eluting with a 0-40% gradient of CH$_3$CN in 0.3% NH$_4$HCO$_3$ to give 1-{4-[1-(2-hydroxyethyl)-1H-1,2,4-tria-zol-5-yl]-9-oxa-3,6-diazatricyclo[8.4.0.0$^{2,6}$]tetradeca-1(14),2,4,10,12-pentaen-12-yl}ethan-1-one (120 mg, 81% yield). LCMS (ESI) m/z: 340.3 [M+H$^+$].

Step 3: (2E)-3-(Dimethylamino)-1-{4-[1-(2-hydroxyethyl)-1H-1,2,4-triazol-5-yl]-9-oxa-3,6-diaza-tricyclo[8.4.0.0$^{2,6}$]tetradeca1(14),2,4,10,12-pentaen-12-yl}prop-2-en-1-one

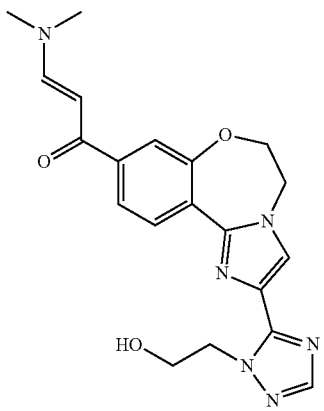 [SMILES: CN(C)/C=C/C(=O)c1ccc2c(c1)OCCn1cc(-c3ncnn3CCO)nc1-2]

A mixture of 1-{4-[1-(2-hydroxyethyl)-1H-1,2,4-triazol-5-yl]-9-oxa-3,6-diazatricyclo[8.4.0.0$^{2,6}$]tetradeca1(14),2,4,10,12-pentaen-12-yl}ethan-1-one (115 mg, 0.290 mmol) and DMF-DMA (69 mg, 0.58 mmol) in xylenes (10 mL) was stirred at 130° C. for 48 h under nitrogen atmosphere. The mixture was then concentrated under reduced pressure, the residue was purified by reverse phase Combiflash eluting with a 0-40% gradient of CH$_3$CN in 0.3% NH$_4$HCO$_3$ to give (2E)-3-(dimethylamino)-1-{4-[1-(2-hydroxyethyl)-1H-1,2,4-triazol-5-yl]-9-oxa-3,6-diazatricyclo[8.4.0.0$^{2,6}$]tetradeca1(14),2,4,10,12-pentaen-12-yl}prop-2-en-1-one (120 mg, 90% yield). LCMS (ESI) m/z: 395.1 [M+H$^+$].

Step 4

To a solution of (2E)-3-(dimethylamino)-1-{4-[1-(2-hydroxyethyl)-1H-1,2,4-triazol-5-yl]-9-oxa-3,6-diazatricyclo[8.4.0.0$^{2,6}$]tetradeca-1(14),2,4,10,12-pentaen-12-yl}prop-2-en-1-one (105 mg, 0.270 mmol) in acetic acid (2.0 mL) was added hydrochloric 4-hydrazinyl-1-methylpiperidine (53 mg, 0.32 mmol). The mixture was stirred at 100° C. for 1 hour under nitrogen atmosphere. After concentration, the residue was purified by preparative HPLC (Gilson GX 281, Shim-pack PRC-ODS 250 mm×20 mm×2, gradient: CH$_3$CN/10 mm/L NH$_4$HCO$_3$, 17 min) to give 257 (17 mg, 13% yield). LCMS (ESI): RT=4.05 min, m/z: 461.2 [M+H$^+$]. $^1$H NMR (500 MHz, DMSO-d$_6$) δ 8.55 (d, J=8.5 Hz, 1H), 8.10 (s, 1H), 7.94 (s, 1H), 7.55 (d, J=1.5 Hz, 1H), 7.23 (d, J=9 Hz, 1H), 7.11 (s, 1H), 6.40 (d, J=1.5 Hz, 1H), 4.98 (t, J=10.5, 1H), 4.84 (t, J=12, 2H), 4.58 (s, 4H), 4.16 (t, J=23 Hz, 1H), 3.88-3.86 (m, 2H), 2.85 (d, J=10 Hz, 2H), 2.15-2.13 (m, 5H), 1.94 (s, 2H), 1.81 (d, J=11.5, 2H)

Example 258

9-(1-(1-tert-butylpiperidin-4-yl)-1H-1,2,4-triazol-5-yl)-2-(1-isopropyl-3-methyl-1H-1,2,4-triazol-5-yl)-5,6-dihydrobenzo[f]imidazo[1,2-d][1,4]oxazepine 258

Step 1: tert-Butyl 2-(1-tert-butylpiperidin-4-ylidene)hydrazinecarboxylate

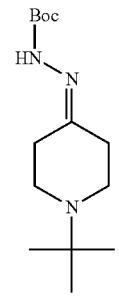

To a solution of 1-tert-butylpiperidin-4-one (1.0 g, 6.5 mmol) in DCM (20 mL) was added MgSO$_4$ (1.5 g, 13 mmol) and tert-butyl hydrazinecarboxylate (0.7 g, 5.3 mmol). The reaction mixture was heated to reflux overnight. The solid was filtered off and the filtrate was concentrated. The residue was purified by silica gel chromatography eluting with EtOAc/petroleum ether (1:20) to give tert-butyl 2-(1-tert-butylpiperidin-4-ylidene)hydrazinecarboxylate (1.2 g, 84% yield) as a colorless oil. LCMS (ESI) m/z: 270.3 [M+H$^+$].

Step 2: tert-Butyl 2-(1-tert-butylpiperidin-4-yl)hydrazinecarboxylate

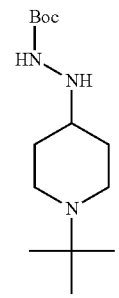

To a solution of tert-butyl 2-(1-tert-butylpiperidin-4-ylidene)hydrazinecarboxylate (400 mg, 1.49 mmol) in THF (40 mL) was added DIBAl-H (15 mL, 15 mmol) under nitrogen atmosphere. The resulting mixture was stirred at 25° C. overnight. Methanol (5 mL) was added at −78° C. After being stirred at room temperature for 1 h, water (10 mL) was added. The solid was filtered off and washed with EtOAc. The combined filtrate was partitioned and extracted with EtOAc (3×50 mL), dried over Na$_2$SO$_4$, and concentrated. The residue was purified by silica gel chromatography eluting with EtOAc/petroleum ether (1:10) to give tert-butyl 2-(1-tert-butylpiperidin-4-yl)hydrazinecarboxylate (350 mg, 87% yield) as colorless oil. LCMS (ESI) m/z: 272.4 [M+H+].

Step 3: 1-tert-Butyl-4-hydrazinylpiperidine hydrochloride

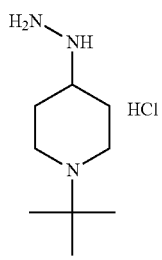

A mixture of tert-butyl 2-(1-tert-butylpiperidin-4-yl)hydrazinecarboxylate (350 mg, 1.29 mmol) in sat. HCl/EtOAc solution (20 mL) was stirred at room temperature overnight. The solvent was removed under reduce pressure to afford 1-tert-butyl-4-hydrazinylpiperidine hydrochloride (268 mg, 100% yield), which was used in the next step without further purification. LCMS (ESI) m/z: 172.3 [M+H$^+$].

Step 4

A mixture of N-[(1E)-(dimethylamino)methylidene]-4-[3-methyl-1-(propan-2-yl)-1H-1,2,4-triazol-5-yl]-9-oxa-3,6-diazatricyclo[8.4.0.0$^{2,6}$]tetradeca-1(14),2,4,10,12-pentaene-12-carboxamide (50 mg, 0.12 mmol) and 1-tert-butyl-4-hydrazinylpiperidine hydrochloride (51 mg, 0.25 mmol) in AcOH (10 mL) was heated at 100° C. for 1 h. The solvent was removed under reduce pressure, and the residue was purified by prep-HPLC (Gilson GX 281, Shim-pack PRC-ODS 250 mm×20 mm×2, gradient: CH$_3$CN/10 mm/L NH$_4$HCO$_3$, 17 min) to afford 258 (30 mg, 48% yield) as a white solid. LCMS (ESI): RT=4.77 min, m/z: 516.4 [M+H$^+$]. $^1$H NMR (500 MHz, DMSO-d$_6$) δ 8.58-8.57 (d, J=8.0 Hz, 1H), 8.07 (s, 1H), 7.99 (s, 1H), 7.43-7.41 (dd, J=8.5, 2.0 Hz, 1H), 7.30 (d, J=1.5 Hz, 1H), 5.86 (m, 1H), 4.58 (s, 4H), 4.29 (m, 1H), 3.08-3.06 (m, 2H), 2.26 (s, 3H), 2.13-2.02 (m, 6H), 1.48-1.47 (d, J=6.5 Hz, 6H), 1.02 (s, 9H)

Example 259

2-(1-isopropyl-3-methyl-1H-1,2,4-triazol-5-yl)-9-(1-((4-methylpiperazin-1-yl)methyl)cyclopropoxy)-5,6-dihydrobenzo[f]imidazo[1,2-d][1,4]oxazepine 259

To an ice-cooled solution of {1-[2-(2-isopropyl-5-methyl-2H-[1,2,4]triazol-3-yl)-4,5-dihydro-6-oxa-1,3a-diazabenzo[e]azulen-8-yloxy]cyclopropyl}-(4-methylpiperazin-1-yl)methanone from Example 50 (90 mg, 0.18 mmol) in THF (5 mL) was added LiAlH$_4$ (1.0M in THF, 0.18 mL) and the mixture was stirred at 0° C. for 2 h. The reaction mixture was quenched by addition of 1N NaOH and then was partitioned between water and EtOAc. The aqueous phase was extracted with EtOAc (×3) and the combined organic layers were washed with brine, dried (MgSO$_4$) and concentrated under reduced pressure. The resulting residue was purified by HPLC (Phenomenex Gemini 5 μm C18 on a 25 min gradient 0-60% 0.1% HCO$_2$H in acetonitrile/water) affording 259 (41 mg, 48%). LCMS: R$_T$ 2.73 min [M+H]$^+$ 478.1. $^1$H NMR (DMSO, 400 MHz): δ 8.30 (1H, d, J=8.96 Hz), 8.18 (1H, s), 7.82 (1H, s), 6.82 (1H, dd, J=8.97, 2.49 Hz), 6.63 (1H, d, J=2.47 Hz), 5.89-5.76 (1H, m), 4.48 (4H, s), 2.69 (2H, s), 2.52-2.41 (3H, m), 2.38-2.21 (7H, s), 2.15 (3H, s), 1.45 (6H, d, J=6.60 Hz), 0.96-0.84 (4H, m)

Example 260

2-(1-isopropyl-3-methyl-1H-1,2,4-triazol-5-yl)-9-(1-isopropyl-5-methylpiperidin-3-yloxy)-5,6-dihydrobenzo[f]imidazo[1,2-d][1,4]oxazepine 260

A solution of methanesulfonic acid 4-[2-(2-isopropyl-5-methyl-2H-[1,2,4]triazol-3-yl)-4,5-dihydro-6-oxa-1,3a-diazabenzo[e]azulen-8-yloxy]-5-methanesulfonyloxy-2-methylpentyl ester from Example 52 (0.2038 mmol) in isopropylamine (0.7 mL) was heated at 90° C. for 1 h in a sealed vial and then at 140° C. for 1 h using microwave irradiation. After cooling to RT, the crude reaction mixture was purified by column chromatography (C$_{18}$, gradient 20-55% MeOH in 0.5% TFA/H$_2$O) and then loaded onto an Isolute® SCX-2 cartridge. The cartridge was washed with MeOH and the diastereomers of 260 eluted with 0.5M NH$_3$/MeOH affording:

cis 8-((3R,5S and 3S,5R)-1-isopropyl-5-methylpiperidin-3-yloxy)-2-(2-isopropyl-5-methyl-2H-[1,2,4]triazol-3-yl)-4,5-dihydro-6-oxa-1,3a-diazabenzo[e]azulene (36 mg, 38% over two steps). LCMS: R$_T$ 3.06 min [M+H]$^+$ 465.2. $^1$H NMR (CD$_3$OD, 400 MHz): δ 8.34 (1H, d, J=8.97 Hz), 7.66 (1H, s), 6.73 (1H, dd, J=8.99, 2.52 Hz), 6.59 (1H, d, J=2.50 Hz), 5.94-5.81 (1H, m), 4.51-4.36 (5H, m), 3.18 (1H, bd, J=10.59 Hz), 2.90-2.76 (2H, m), 2.36 (3H, s), 2.21 (1H, bd, J=12.20 Hz), 2.07 (1H, t, J=10.30 Hz), 1.88-1.74 (2H, m), 1.53 (6H, d, J=6.65 Hz), 1.09 (6H, d, J=6.60 Hz), 1.04-0.94 (4H, m); and trans 8-((3R,5R and 3S,5S)-1-Isopropyl-5-methylpiperidin-3-yloxy)-2-(2-isopropyl-5-methyl-2H-[1,2,4]triazol-3-yl)-4,5-dihydro-6-oxa-1,3a-diazabenzo[e]azulene as a colorless foam (22 mg, 23% over two steps). LCMS: R$_T$ 2.88 min [M+H]$^+$ 465.1. $^1$H NMR (CD$_3$OD, 400 MHz): δ 8.34 (1H, d, J=8.99 Hz), 7.67 (1H, s), 6.80 (1H, dd, J=9.00, 2.55 Hz), 6.64 (1H, d, J=2.52 Hz), 5.94-5.81 (1H, m), 4.69-4.66 (1H, m), 4.52-4.45 (4H, m), 3.09 (1H, bd, J=12.11 Hz), 2.89-2.71 (2H, m), 2.42 (1H, d, J=12.35 Hz), 2.36 (3H, s), 2.16-1.91 (3H, m), 1.53 (6H, d, J=6.65 Hz), 1.31-1.21 (1H, m), 1.11-1.02 (6H, m), 0.92 (3H, d, J=6.55 Hz)

Example 261

2-(1-isopropyl-3-methyl-1H-1,2,4-triazol-5-yl)-9-(1-isopropyl-3-methylpyrrolidin-3-yloxy)-5,6-dihydrobenzo[f]imidazo[1,2-d][1,4]oxazepine 261

A solution of methanesulfonic acid 3-[2-(2-isopropyl-5-methyl-2H-[1,2,4]triazol-3-yl)-4,5-dihydro-6-oxa-1,3a-diazabenzo[e]azulen-8-yloxy]-4-methanesulfonyloxy-3-methylbutyl ester from Example 51 (0.0318 mmol) in isopropylamine (0.7 mL) was heated at 90° C. for 1 h in a sealed vial and then at 130° C. for 2 h using microwave irradiation. After cooling to RT, the crude reaction mixture was purified by column chromatography (C$_{18}$, gradient 20-50% MeOH in 0.5% TFA/H$_2$O) and then loaded onto an Isolute® SCX-2 cartridge. The cartridge was washed with MeOH and the product eluted with 0.5M NH$_3$/MeOH affording 261 as a colorless gum (10 mg, 69% over two steps). LCMS: R$_T$ 2.80 min [M+H]$^+$ 451.1. $^1$H NMR (CD$_3$OD, 400 MHz): δ 8.33 (1H, d, J=8.96 Hz), 7.68 (1H, s), 6.75 (1H, dd, J=8.96, 2.51 Hz), 6.60 (1H, d, J=2.49 Hz), 5.93-5.82 (1H, m), 4.49 (4H, s), 3.24 (1H, bd, J=10.84 Hz), 2.99-2.89 (1H, m), 2.76 (1H, bd, J=10.76 Hz), 2.73-2.64 (1H, m), 2.53-2.37 (2H, m), 2.36 (3H, s), 2.11-2.02 (1H, m), 1.60 (3H, s), 1.53 (6H, d, J=6.65 Hz), 1.14 (6H, d, J=6.35 Hz)

Example 262

9-(1-(1-benzylpiperidin-3-yl)-1H-pyrazol-5-yl)-2-(1-isopropyl-3-methyl-1H-1,2,4-triazol-5-yl)-5,6-dihydrobenzo[f]imidazo[1,2-d][1,4]oxazepine 262

Following the procedures in Example 266, 262 was prepared. $^1$H NMR (400 MHz, DMSO) δ 8.49 (d, J=8.3 Hz, 1H), 7.95 (s, 1H), 7.51 (d, J=1.6 Hz, 1H), 7.36-7.16 (m, 5H), 7.10 (dd, J=8.3, 1.6 Hz, 1H), 7.03 (d, J=1.5 Hz, 1H), 6.37 (d, J=1.7 Hz, 1H), 5.88 (dt, J=13.2, 6.6 Hz, 1H), 4.57 (s, 4H), 4.44-4.12 (m, 1H), 3.51 (dd, J=39.5, 13.3 Hz, 2H), 2.97-2.73 (m, 2H), 2.34 (t, J=10.6 Hz, 1H), 2.27 (s, 3H), 2.04-1.86 (m, 3H), 1.83-1.69 (m, 1H), 1.49 (d, J=6.6 Hz, 6H). LCMS: 549.3

Example 263

(R)-2-(1-isopropyl-3-methyl-1H-1,2,4-triazol-5-yl)-9-(2-(1-isopropylpiperidin-4-yl)pyrrolidin-1-yl)-5,6-dihydrobenzo[f]imidazo[1,2-d][1,4]oxazepine 263

Step 1: tert-Butyl 2-(1-isopropylpiperidin-4-yl)pyrrolidine-1-carboxylate

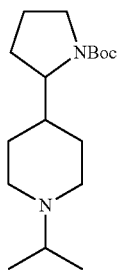 [SMILES: CC(C)N1CCC(C2CCCN2C(=O)OC(C)(C)C)CC1]

To a solution of tert-butyl 2-(piperidin-4-yl)pyrrolidine-1-carboxylate (400 mg, 1.57 mmol) in dry DMF (2.0 mL) at 0° C., was added NaH (132 mg, 3.30 mmol, 60% in mineral oil) in small portions. The reaction mixture was then warmed to room temperature with stirring for another 1 h. 2-iodopropane (2.0 mL) was added. The resulting mixture was stirred at room temperature for 24 h and then poured into the ice-water (20 mL). The resultant mixture was extracted with EtOAc (2×50 mL). The combined organic layers were dried over Na$_2$SO$_4$ and evaporated to dryness. The residue was purified by silica gel chromatography using 5-10% MeOH in DCM as eluant to afford the desired product (302 mg, 65% yield). LCMS m/z [M+H]$^+$ 297.2.

Step 2: 1-Isopropyl-4-(pyrrolidin-2-yl)piperidine hydrochloride

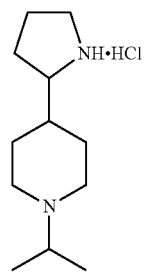

A solution of tert-butyl 2-(1-isopropylpiperidin-4-yl)pyrrolidine-1-carboxylate (302 mg, 1.02 mmol) in 4N HCl/dioxane (5 mL) was stirred at room temperature for 8 h. Removal of the solvent gave the desired product (232 mg, 100% yield) as a yellow solid. LCMS m/z [M+H]$^+$ 197.2

Step 3

A mixture of 12-bromo-4-[3-methyl-1-(propan-2-yl)-1H-1,2,4-triazol-5-yl]-9-oxa-3,6-diazatricyclo[8.4.0.0$^{2,6}$]tetradeca-1(14),2,4,10,12-pentaene (also named as: 9-bromo-2-(1-isopropyl-3-methyl-1H-1,2,4-triazol-5-yl)-5,6-dihydrobenzo[f]imidazo[1,2-d][1,4]oxazepine) (180 mg, 0.464 mmol), 1-isopropyl-4-(pyrrolidin-2-yl)piperidine hydrochloride (270 mg, 1.16 mmol), Pd(P$^t$Bu$_3$)$_2$(20 mg, 0.040 mmol), NaO$^t$Bu (134 mg, 1.39 mmol) in toluene (4.0 ml) in a seal tube was degassed with N$_2$ for three times. The resulting mixture was stirred at 110° C. for 120 min. The solid was filtered off via Celite. The filtrate was concentrated to give the crude product, which was purified by prep-HPLC (Gilson GX 281, Shim-pack PRC-ODS 250 mm×20 mm×2, gradient: CH$_3$CN/1% formic acid, 17 min) to afford the racemic product (48 mg, 21% yield), which was further separated by chiral HPLC (AY-H column, 10% EtOH (0.1% DEA) in hexane isocratic) to give the two enantiomers 263 and 265.

263: First eluting peak, 6.6 mg, 2.8% yield. >99% ee (7.72 min, AY-H, 10% EtOH (0.1% DEA) in hexane isocratic, 15 min). $^1$H NMR (500 MHz, DMSO-d$_6$) δ 8.17 (d, J=9.5 Hz, 1H), 7.74 (s, 1H), 6.49 (dd, J=8.5 Hz, 2.0 Hz, 1H), 6.13 (d, J=2.5 Hz, 1H), 5.87 (m, 1H), 4.45-4.39 (m, 4H), 3.74 (m, 1H), 3.43 (m, 1H), 3.13 (m, 1H), 2.90-2.76 (m, 3H), 2.24-2.17 (m, 4H), 2.07 (m, 1H), 1.93-1.83 (m, 4H), 170-1.60 (m, 2H), 1.45-1.43 (m, 6H), 1.35-1.30 (m, 3H), 0.97 (d, J=7.0 Hz, 6H). LCMS m/z [M+H]$^+$ 540.4. LCMS 10 MIN CAD GRADIENT, 1.2 ml/min on Agilent 1200/G6110 System. Purity is 97% by UV 215.

Example 264

2-(1-isopropyl-1H-1,2,4-triazol-5-yl)-10-methyl-9-(1-(1-methylpiperidin-4-yl)-1H-pyrazol-5-yl)-5,6-dihydrobenzo[f]imidazo[1,2-d][1,4]oxazepine 264

Step 1: 12-(1-Ethoxyethenyl)-13-methyl-4-[1-(propan-2-yl)-1H-1,2,4-triazol-5-yl]-9-oxa-3,6-diazatricyclo[8.4.0.0$^{2,6}$]tetradeca1(14),2,4,10,12-pentaene

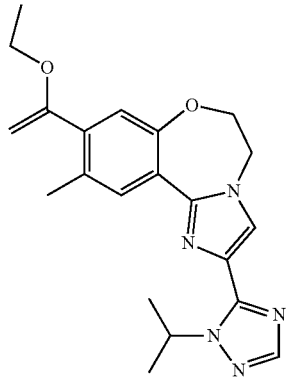 [SMILES: C=C(OCC)c1cc2c(cc1C)-c1nc(-c3ncnn3C(C)C)cn1CCO2]

A mixture of 12-bromo-13-methyl-4-[1-(propan-2-yl)-1H-1,2,4-triazol-5-yl]-9-oxa-3,6-diazatricyclo[8.4.0.0$^{2,6}$]tetradeca1(14),2,4,10,12-pentaene (1.0 g, 2.6 mmol), tributyl (1-ethoxyvinyl)stannane (1.2 mL), Pd(PPh$_3$)$_4$ (90 mg, 7.8 mmol), and LiCl (328 mg, 7.8 mmol) in dry THF (10 mL) was stirred at 70° C. for 48 h under nitrogen atmosphere. KF (100 mL, 0.16 M) was added and the mixture was further stirred at room temperature for 1 h. The solid was filtered off. The filtrate was concentrated to give the crude product, which was purified by reverse phase Combiflash eluting with a 0-50% gradient of CH$_3$CN in 0.3% NH$_4$HCO$_3$ to afford 12-(1-ethoxyethenyl)-13-methyl-4-[1-(propan-2-yl)-1H-1,2,4-triazol-5-yl]-9-oxa-3,6-diazatricyclo[8.4.0.0$^{2,6}$]tetradeca1(14),2,4,10,12-pentaene (660 mg, 68% yield). LCMS (ESI) m/z: 380.2 [M+H$^+$].

Step 2: 1-{13-Methyl-4-[1-(propan-2-yl)-1H-1,2,4-triazol-5-yl]-9-oxa-3,6-diazatricyclo[8.4.0.0$^{2,6}$]tetradeca-1(14),2,4,10,12-pentaen-12-yl}ethan-1-one

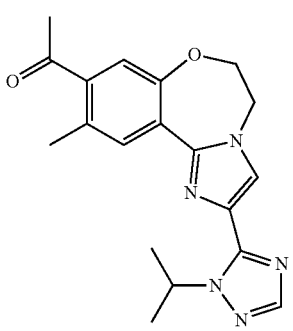 [SMILES: CC(=O)c1cc2c(cc1C)-c1nc(-c3ncnn3C(C)C)cn1CCO2]

A mixture of 12-(1-ethoxyethenyl)-13-methyl-4-[1-(propan-2-yl)-1H-1,2,4-triazol-5-yl]-9-oxa-3,6-diazatricyclo[8.4.0.0$^{2,6}$]tetradeca1(14),2,4,10,12-pentaene (160 mg, 0.440 mmol) and p-toluenesulfonic acid (7.5 mg, 0.044 mmol) in acetone (10 mL) was stirred at 60° C. for 75 min. The solid was filtered off and the filtrate was concentrated. The residue was purified by reverse phase Combiflash eluting with a 0-40% gradient of CH$_3$CN in 0.3% NH$_4$HCO$_3$ to afford 1-{13-methyl-4-[1-(propan-2-yl)-1H-1,2,4-triazol-5-yl]-9-oxa-3,6-diazatricyclo[8.4.0.0$^{2,6}$]tetradeca1(14),2,4,10,12-pentaen-12-yl}ethan-1-one (120 mg, 81% yield). LCMS (ESI) m/z: 352.2 [M+H$^+$].

Step 3: (2E)-3-(Dimethylamino)-1-{13-methyl-4-[1-(propan-2-yl)-1H-1,2,4-triazol-5-yl]-9-oxa-3,6-diazatricyclo[8.4.0.0$^{2,6}$]tetradeca1(14),2,4,10,12-pentaen-12-yl}prop-2-en-1-one

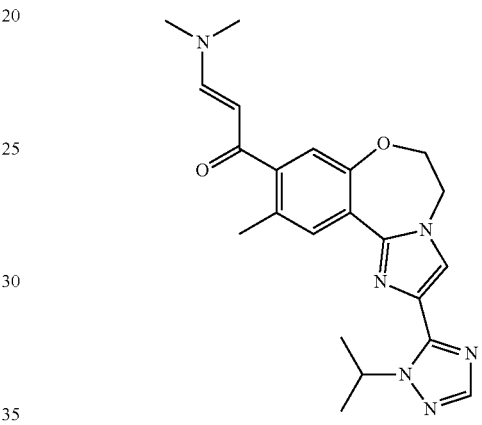

A mixture of 1-{13-methyl-4-[1-(propan-2-yl)-1H-1,2,4-triazol-5-yl]-9-oxa-3,6-diazatricyclo[8.4.0.0$^{2,6}$]tetradeca1(14),2,4,10,12-pentaen-12-yl}ethan-1-one (250 mg, 0.720 mmol) and DMF-DMA (170 mg, 1.44 mmol) in xylenes (10 mL) was stirred at 130° C. for 48 h under nitrogen atmosphere. After concentration, the residue was purified by reverse phase combiflash eluting with a 0-40% gradient of CH$_3$CN in 0.3% NH$_4$HCO$_3$ to afford (2E)-3-(dimethylamino)-1-{13-methyl-4-[1-(propan-2-yl)-1H-1,2,4-triazol-5-yl]-9-oxa-3,6-diazatricyclo[8.4.0.0$^{2,6}$]tetradeca-1(14),2,4,10,12-pentaen-12-yl}prop-2-en-1-one (240 mg, 77% yield). LCMS (ESI) m/z: 407.3 [M+H$^+$].

Step 4

A mixture of (2E)-3-(dimethylamino)-1-{13-methyl-4-[1-(propan-2-yl)-1H-1,2,4-triazol-5-yl]-9-oxa-3,6-diazatricyclo[8.4.0.0$^{2,6}$]tetradeca-1(14),2,4,10,12-pentaen-12-yl}prop-2-en-1-one (110 mg, 0.30 mmol) and 4-hydrazinyl-1-methylpiperidine hydrochloride (42 mg, 0.24 mmol) in acetic acid (2.0 mL) was stirred at 100° C. for 1 hour under nitrogen atmosphere. After concentration, the residue was purified by preparative HPLC (Gilson GX 281, Shim-pack PRC-ODS 250 mm×20 mm×2, gradient: CH$_3$CN/10 mm/L NH$_4$HCO$_3$, 17 min) to afford 264 (30 mg, 21% yield). LCMS (ESI): RT=5.04 min, m/z: 473.3 [M+H$^+$]. $^1$H NMR (500 MHz, DMSO-d$_6$) δ 8.35 (s, 1H), 8.00 (s, 1H), 7.94 (s, 1H), 7.58 (d, J=1.5 Hz, 1H), 6.92 (s, 1H), 6.27-6.26 (m, 1H), 5.85

(t, J=13 Hz, 1H), 4.55 (t, J=20 Hz, 4H), 3.76 (s, 1H), 2.86 (s, 2H), 2.19-2.11 (m, 8H), 1.78 (s, 2H), 1.74 (d, J=14.5 Hz, 2H), 4.51 (d, J=7 Hz, 6H)

Example 265

(S)-2-(1-isopropyl-3-methyl-1H-1,2,4-triazol-5-yl)-9-(2-(1-isopropylpiperidin-4-yl)pyrrolidin-1-yl)-5,6-dihydrobenzo[f]imidazo[1,2-d][1,4]oxazepine 265

Following the procedures of Example 263, 265 was prepared.

265: Second eluting peak, 2.8 mg, 1.2% yield. >96% ee (9.63 min, AY-H, 10% EtOH (0.1% DEA) in hexane isocratic, 15 min). $^1$H NMR (500 MHz, DMSO-d$_6$) δ 8.17 (d, J=9.5 Hz, 1H), 7.74 (s, 1H), 6.49 (dd, J=8.5 Hz, 2.0 Hz, 1H), 6.13 (d, J=2.5 Hz, 1H), 5.87 (m, 1H), 4.45-4.39 (m, 4H), 3.74 (m, 1H), 3.43 (m, 1H), 3.13 (m, 1H), 2.90-2.76 (m, 3H), 2.24-2.17 (m, 4H), 2.07 (m, 1H), 1.93-1.83 (m, 4H), 170-1.60 (m, 2H), 1.45-1.43 (m, 6H), 1.35-1.30 (m, 3H), 0.97 (d, J=7.0 Hz, 6H). LCMS m/z [M+H]$^+$ 540.4. LCMS 10 MIN CAD GRADIENT, 1.2 ml/min on Agilent 1200/G6110 System. Purity is 97% by UV 215

Example 266

2-(3-(5-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)piperidin-1-yl)-2-methylpropan-1-ol 266

Step 1: 1-benzyl-3-hydrazinylpiperidine

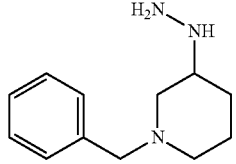 [SMILES: NNC1CCCN(Cc2ccccc2)C1]

To a solution of 1-benzylpiperidin-3-one (2.0 g, 0.0089 mol), and tert-Butyl carbazate (1.17 g, 0.00886 mol) in Methanol (31 mL, 0.78 mol) was added Sodium cyanoborohydride (1.11 g, 0.0177 mol) portionwise at 0° C. The mixture was stirred at room temperature overnight. The reaction mixture was basified with 1N NaOH solution and a white precipitate crashed out of solution. The reaction mixture was filtered and the white solid was allowed to air dry to give 1-benzyl-3-hydrazinylpiperidine.

1-benzyl-3-hydrazinylpiperidine (4.27 g, 0.0122 mol) was dissolved in Methylene chloride (20 mL, 0.3 mol). Trifluoroacetic Acid (10 mL, 0.1 mol) was added and the mixture was stirred at room temperature for 3 hours. The reaction was complete by LCMS. The reaction mixture was concentrated to dryness and carried on without further purification.

Step 2: 2-(1-isopropyl-3-methyl-1H-1,2,4-triazol-5-yl)-5,6-dihydrobenzo[f]imidazo[1,2-d][1,4]oxazepine-9-carboxylic acid

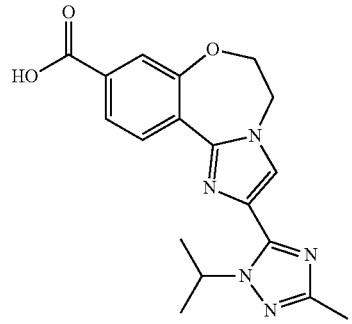 [SMILES: Cc1nc(-c2cn3c(n2)-c2ccc(C(=O)O)cc2OCC3)n(C(C)C)n1]

To a solution of methyl 2-(2-isopropyl-5-methyl-1,2,4-triazol-3-yl)-5,6-dihydroimidazo[1,2-d][1,4]benzoxazepine-9-carboxylate; (4.50 g, 12.2 mmol) in Tetrahydrofurane; (100 mL) was added a slurry of Lithium Hydroxide (880 mg, 36.7 mmol) in water (20 mL). The reaction mixture was stirred at room temperature for 1 hour. LC-MS analysis of the reaction mixture showed no more starting material. The solvent was removed and the residue was used in the next step without further purification.

Step 3: 2-(1-isopropyl-3-methyl-1H-1,2,4-triazol-5-yl)-N-methoxy-N-methyl-5,6-dihydrobenzo[f]imidazo[1,2-d][1,4]oxazepine-9-carboxamide

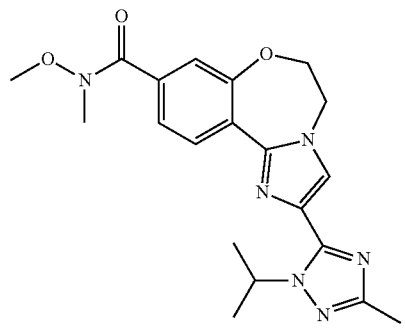

To a solution of 2-(1-isopropyl-3-methyl-1H-1,2,4-triazol-5-yl)-5,6-dihydrobenzo[f]imidazo[1,2-d][1,4]oxazepine-9-carboxylic acid (4.00 g, 11.3 mmol) and N-methoxymethanamine hydrochloride (1.32 g, 13.6 mmol) in N,N-Dimethylformamide (100 mL) was added N-Ethyldiisopropylamine 7.9 mL, 45.3 mmol) followed by HBTU (4.72 g, 12.5 mmol). The reaction mixture was stirred at room temperature for 1 hour. LC-MS analysis of the reaction mixture showed no more starting material. The solvent was removed and the residue was diluted with DCM, washed with NaHCO3 sat. aq., dried over Na2SO4, filtered and concentrated. The resulting oil was purified on silica gel (0→10% MeOH/DCM) to give 2-(1-isopropyl-3-methyl-1H-1,2,4- triazol-5-yl)-N-methoxy-N-methyl-5,6-dihydrobenzo[f]imidazo[1,2-d][1,4]oxazepine-9-carboxamide Step 4: 1-(2-(1-isopropyl-3-methyl-1H-1,2,4-triazol-5-yl)-5,6-dihydrobenzo[f]imidazo[1,2-d][1,4]oxazepin-9-yl)ethanone

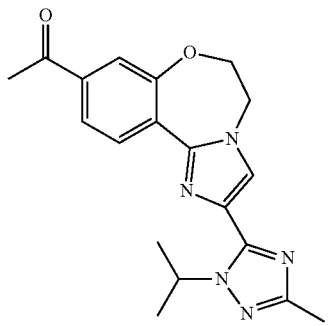 [SMILES: CC(=O)c1ccc2c(c1)OCCn1cc(-c3nc(C)nn3C(C)C)nc1-2]

2-(1-isopropyl-3-methyl-1H-1,2,4-triazol-5-yl)-N-methoxy-N-methyl-5,6-dihydrobenzo[f]imidazo[1,2-d][1,4]oxazepine-9-carboxamide (2.0 g, 0.0050 mol) was dissolved in Tetrahydrofuran (20 mL, 0.3 mol). The reaction was cooled at 0° C. 3.0 M of Methylmagnesium bromide in Ether was added dropwise. The reaction was allowed to warm to room temperature over a 1 hour period. LCMS shows complete conversion to desired product. The reaction was cooled back to 0° C. and quenched with saturated aqueous ammonium chloride. The reaction mixture was diluted with H₂O and the crude product was extracted with Ethyl Acetate The organic extracts were combined, dried over Na₂SO₄, filtered and concentrated to dryness. The crude was purified on silica gel (0→10% MeOH/DCM) to yield 1-(2-(1-isopropyl-3-methyl-1H-1,2,4-triazol-5-yl)-5,6-dihydrobenzo[f]imidazo[1,2-d][1,4]oxazepin-9-yl)ethanone as an orange solid.

Step 5: (E)-3-(dimethylamino)-1-(2-(1-isopropyl-3-methyl-1H-1,2,4-triazol-5-yl)-5,6-dihydrobenzo[f]imidazo[1,2-d][1,4]oxazepin-9-yl)prop-2-en-1-one

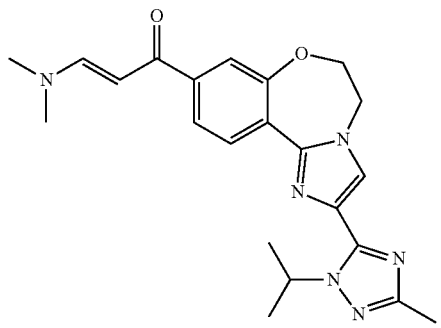

1-(2-(1-isopropyl-3-methyl-1H-1,2,4-triazol-5-yl)-5,6-dihydrobenzo[f]imidazo[1,2-d][1,4]oxazepin-9-yl)ethanone (2.6 g, 0.0074 mol) and 1,1-Dimethoxy-N,N-dimethylmethanamine (0.98 mL, 0.0074 mol) was mixed in Xylenes (30 mL, 0.07 mol) and was heated to reflux and stirred overnight. LCMS showed complete conversion to desired product. The solvent was removed and (E)-3-(dimethylamino)-1-(2-(1-isopropyl-3-methyl-1H-1,2,4-triazol-5-yl)-5,6-dihydrobenzo[f]imidazo[1,2-d][1,4]oxazepin-9-yl)prop-2-en-1-one was used in the next step without further purification.

Step 6: 9-(1-(1-benzylpiperidin-3-yl)-1H-pyrazol-5-yl)-2-(1-isopropyl-3-methyl-1H-1,2,4-triazol-5-yl)-5,6-dihydrobenzo[f]imidazo[1,2-d][1,4]oxazepine

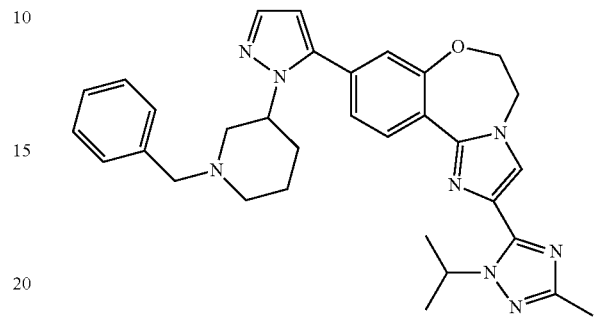

(E)-3-(dimethylamino)-1-(2-(1-isopropyl-3-methyl-1H-1,2,4-triazol-5-yl)-5,6-dihydrobenzo[f]imidazo[1,2-d][1,4]oxazepin-9-yl)prop-2-en-1-one (0.366 g, 0.000901 mol), 1-benzyl-3-hydrazinylpiperidine trifluoroacetic acid salt (0.376 g, 0.00135 mol), and N,N-Diisopropylethylamine (0.392 mL, 0.00225 mol) was mixed in Ethanol (9 mL, 0.2 mol). The reaction mixture was heated to reflux and was stirred overnight. LCMS showed complete conversion to desired product. The reaction mixture was cooled to room temperature and concentrated to dryness and purified by rHPLC to give 9-(1-(1-benzylpiperidin-3-yl)-1H-pyrazol-5-yl)-2-(1-isopropyl-3-methyl-1H-1,2,4-triazol-5-yl)-5,6-dihydrobenzo[f]imidazo[1,2-d][1,4]oxazepine Step 7: 2-(1-isopropyl-3-methyl-1H-1,2,4-triazol-5-yl)-9-(1-(piperidin-3-yl)-1H-pyrazol-5-yl)-5,6-dihydrobenzo[f]imidazo[1,2-d][1,4]oxazepine

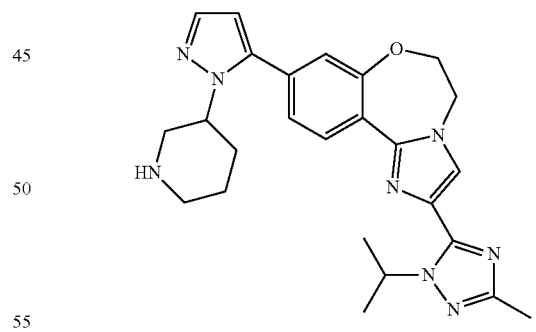

9-(1-(1-benzylpiperidin-3-yl)-1H-pyrazol-5-yl)-2-(1-isopropyl-3-methyl-1H-1,2,4-triazol-5-yl)-5,6-dihydrobenzo[f]imidazo[1,2-d][1,4]oxazepine (500 mg, 0.0009 mol) was dissolved in Methanol (10 mL). 4.0 M of Hydrogen chloride in 1,4-Dioxane (0.5 mL, 0.002 mol) was added. 10% Palladium on Carbon (0.1:0.9, Palladium: carbon black, 120 mg, 0.00011 mol) was added under a stream of Nitrogen. The reaction mixture was vac/flushed with H₂ (balloon) and stirred overnight at room temperature. LCMS show reaction is complete. The reaction mixture was filtered and concentrated to dryness to give 2-(1-isopropyl-3-methyl-1H-1,2,4- triazol-5-yl)-9-(1-(piperidin-3-yl)-1H-pyrazol-5-yl)-5,6-dihydrobenzo[f]imidazo[1,2-d][1,4]oxazepine Step 8: ethyl 2-(3-(5-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)piperidin-1-yl)-2-methylpropanoate

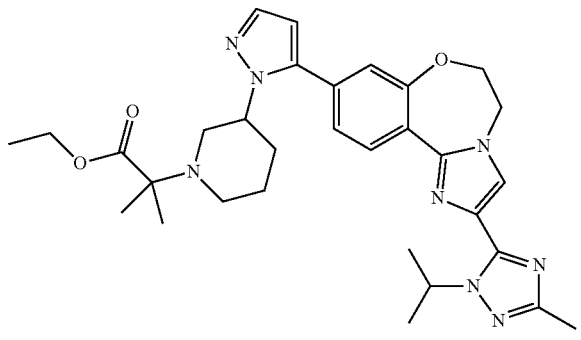

To a solution of 2-(2-isopropyl-5-methyl-1,2,4-triazol-3-yl)-9-[2-(3-piperidyl)pyrazol-3-yl]-5,6-dihydroimidazo[1,2-d][1,4]benzoxazepine; I; 100 mass % in N,N-Dimethylformamide; 100 mass % was added Cesium Carbonate; 2.00 equiv.; 1.090 mmol; 100 mass % followed by ethyl 2-bromo-2-methyl-propanoate; G; 3.00 equiv.; 1.635 mmol; 100 mass %. The reaction mixture was heated to 90° C. and was stirred for 12 hours. LC-MS analysis of the reaction mixture showed almost complete conversion to the desired product. The solvent was removed and the residue was purified on silica gel (0→10% MeOH/DCM) to yield ethyl 2-(3-(5-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)piperidin-1-yl)-2-methylpropanoate as a light yellow foam.

Step 9

To a solution of ethyl 2-(3-(5-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)piperidin-1-yl)-2-methylpropanoate (150 mg, 0.26 mmol) in Tetrahydrofuran (2.00 mL) at 0° C. was added Lithium Aluminum Hydride (1 mol/L) in THF (0.52 mL, 0.5238 mmol) dropwise. The reaction mixture was slowly allowed to warm up to room temperature and was stirred for 2 hours. LC-MS analysis of the reaction mixture showed no more starting material and the formation of the desired product. The reaction mixture was quenched by the addition of MeOH, filtered and the concentrated. The resulting oil was purified by rHPLC to give 266. $^1$H NMR (400 MHz, DMSO) δ 8.51 (d, J=8.3 Hz, 1H), 7.98-7.86 (m, 1H), 7.52 (d, J=1.5 Hz, 1H), 7.22 (dd, J=8.3, 1.4 Hz, 1H), 7.09 (s, 1H), 6.39 (t, J=6.8 Hz, 1H), 5.83 (dt, J=13.2, 6.6 Hz, 1H), 4.54 (d, J=15.0 Hz, 4H), 4.36-4.15 (m, 2H), 3.24 (d, J=4.9 Hz, 2H), 3.08 (d, J=8.5 Hz, 1H), 2.93 (t, J=15.9 Hz, 1H), 2.62-2.52 (m, 2H), 2.26 (s, 3H), 2.11 (t, J=10.8 Hz, 1H), 1.92 (s, 2H), 1.73 (d, J=13.1 Hz, 1H), 1.57-1.42 (m, 6H), 0.91 (s, 6H). LCMS: 531.3

Example 267

2-(1-(2-methoxypropyl)-1H-1,2,4-triazol-5-yl)-9-(1-(1-methylpiperidin-4-yl)-1H-pyrazol-5-yl)-5,6-dihydrobenzo[f]imidazo[1,2-d][1,4]oxazepine 267

Step 1: 12-Bromo-4-[1-(2-methoxypropyl)-1H-1,2,4-triazol-5-yl]-9-oxa-3,6-diazatricyclo[8.4.0.0$^{2,6}$]tetradeca1(14),2,4,10,12-pentaene

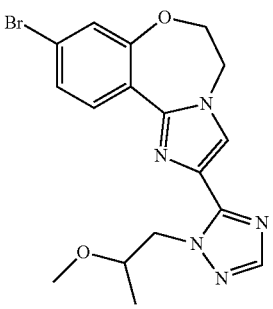 [SMILES: COC(C)Cn1ncnc1-c1cn2c(n1)-c1ccc(Br)cc1OCC2]

To a solution of 12-bromo-N-[(1E)-(dimethylamino)methylidene]-9-oxa-3,6-diazatricyclo[8.4.0.0$^{2,6}$]tetradeca1(14),2,4,10,12-pentaene-4-carboxamide (0.25 mmol, 80 mg) in acetic acid (3 ml) was added hydrochloric (1-methoxyethyl)hydrazine (0.5 mmol, 63 mg). The mixture was stirred at 100° C. for 1 h under nitrogen atmosphere. After concentration, the residue was purified by reverse phase Combiflash eluting with a 0-50% gradient of CH$_3$CN in 0.3% NH$_4$HCO$_3$ to give 12-bromo-4-[1-(2-methoxypropyl)-1H-1,2,4-triazol-5-yl]-9-oxa-3,6-diazatricyclo[8.4.0.0$^{2,6}$]tetradeca1(14),2,4,10,12-pentaene (68 mg, 73% yield). LCMS (ESI) m/z: 391.3 [M+H$^+$].

Step 2: 12-(1-Ethoxyethenyl)-4-[1-(2-methoxypropyl)-1H-1,2,4-triazol-5-yl]-9-oxa-3,6-diazatricyclo[8.4.0.0$^{2,6}$]tetradeca1(14),2,4,10,12-pentaene

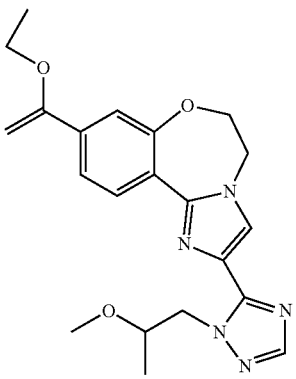 [SMILES: C=C(OCC)c1ccc2c(c1)OCCn1cc(-c3ncnn3CC(C)OC)nc1-2]

A mixture of 12-bromo-4-[1-(2-methoxypropyl)-1H-1,2,4-triazol-5-yl]-9-oxa-3,6-diazatricyclo[8.4.0.0$^{2,6}$]tetradeca1(14),2,4,10,12-pentaene (290 mg, 0.720 mmol), tributyl(1-ethoxyvinyl)stannane (0.5 mL), Pd(PPh$_3$)$_4$ (27 mg, 0.023 mmol), and LiCl (97 mg, 2.3 mmol) in dry THF (10 mL) was stirred at 70° C. for 48 h under nitrogen atmosphere. KF (40 mL, 0.16 M) was added and the mixture was further stirred at room temperature for 1 h. The solid was filtered off. The filtrate was concentrated to give the crude product, which was purified by reverse phase Combiflash eluting with a 0-50% gradient of CH$_3$CN in 0.3% NH$_4$HCO$_3$ to afford 12-(1-ethoxyethenyl)-4-[1-(2-methoxypropyl)-1H-1,2,4-triazol-5-yl]-9-oxa-3,6-diazatricyclo[8.4.0.0$^{2,6}$]tetradeca-1(14),2,4,10,12-pentaene (195 mg, 66% yield). LCMS (ESI) m/z: 396.3 [M+H$^+$].

Step 3: 1-{4-[1-(2-Methoxypropyl)-1H-1,2,4-triazol-5-yl]-9-oxa-3,6-diazatricyclo[8.4.0.0$^{2,6}$]tetradeca-1(14),2,4,10,12-pentaen-12-yl}ethan-1-one

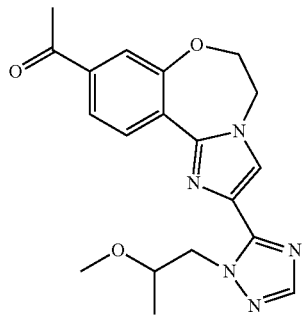 [SMILES: COC(C)Cn1ncnc1-c1cn2c(n1)-c1ccc(C(C)=O)cc1OCC2]

A mixture of 12-(1-ethoxyethenyl)-4-[1-(2-methoxypropyl)-1H-1,2,4-triazol-5-yl]-9-oxa-3,6-diazatricyclo[8.4.0.0$^{2,6}$]tetradeca-1(14),2,4,10,12-pentaene (190 mg, 0.480 mmol) and p-toluenesulfonic acid (11 mg, 0.060 mmol) in acetone (10 mL) was stirred at 60° C. for 75 min. The solid was filtered off and the filtrate was concentrated. The residue was purified by reverse phase Combiflash eluting with a 0-40% gradient of CH$_3$CN in 0.3% NH$_4$HCO$_3$ to afford 1-{4-[1-(2-methoxypropyl)-1H-1,2,4-triazol-5-yl]-9-oxa-3,6-diazatricyclo[8.4.0.0$^{2,6}$]tetradeca1(14),2,4,10,12-pentaen-12-yl}ethan-1-one (160 mg, 91% yield). LCMS (ESI) m/z: 368.1 [M+H$^+$]

Step 4: (2E)-3-(Dimethylamino)-1-{4-[1-(2-methoxypropyl)-1H-1,2,4-triazol-5-yl]-9-oxa-3,6-diazatricyclo[8.4.0.0$^{2,6}$]tetradeca1(14),2,4,10,12-pentaen-12-yl}prop-2-en-1-one

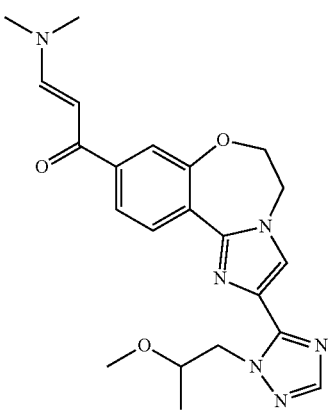 [SMILES: COC(C)Cn1ncnc1-c1cn2c(n1)-c1ccc(C(=O)/C=C/N(C)C)cc1OCC2]

A mixture of 1-{4-[1-(2-methoxypropyl)-1H-1,2,4-triazol-5-yl]-9-oxa-3,6-diazatricyclo[8.4.0.0$^{2,6}$]tetradeca1(14),2,4,10,12-pentaen-12-yl}ethan-1-one (163 mg, 0.44 mmol) and DMF-DMA (112 mg, 0.88 mmol) in xylenes (10 mL) was stirred at 130° C. for 48 h under nitrogen atmosphere. After concentration, the residue was purified by reverse phase Combiflash eluting with a 0-40% gradient of CH$_3$CN in 0.3% NH$_4$HCO$_3$ to afford (2E)-3-(dimethylamino)-1-{4-[1-(2-methoxypropyl)-1H-1,2,4-triazol-5-yl]-9-oxa-3,6-diazatricyclo[8.4.0.0$^{2,6}$]tetradeca1(14),2,4,10,12-pentaen-12-yl}prop-2-en-1-one (120 mg, 90% yield). LCMS (ESI) m/z: 422.1 [M+H$^+$].

Step 5: 1-tert-Butyl-6-(5-{4-[1-(2-methoxypropyl)-1H-1,2,4-triazol-5-yl]-9-oxa-3,6-diazatricyclo[8.4.0.0$^{2,6}$]tetradeca1(14),2,4,10,12-pentaen-12-yl}-1H-pyrazol-1-yl)-1λ$^3$,3-oxazocan-2-one

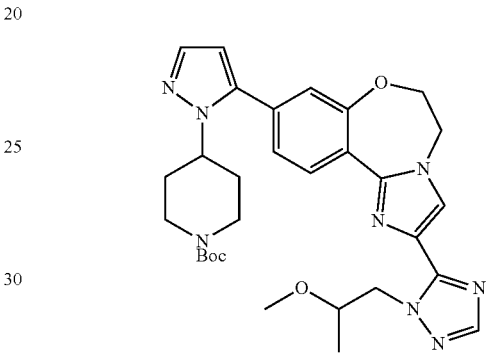

A mixture of (2E)-3-(dimethylamino)-1-{4-[1-(2-methoxypropyl)-1H-1,2,4-triazol-5-yl]-9-oxa-3,6-diazatricyclo[8.4.0.0$^{2,6}$]tetradeca1(14),2,4,10,12-pentaen-12-yl}prop-2-en-1-one (105 mg, 0.250 mmol), tert-butyl 4-hydrazinylpiperidine-1-carboxylate (108 mg, 0.500 mmol), and DIPEA (60 mg, 0.50 mmol) in ethanol (10 mL) was stirred at 80° C. for 48 h under nitrogen atmosphere. After concentration, the residue was purified by reverse phase Combiflash eluting with a 0-40% gradient of CH$_3$CN in 0.3% NH$_4$HCO$_3$ to give 1-tert-butyl-6-(5-{4-[1-(2-methoxypropyl)-1H-1,2,4-triazol-5-yl]-9-oxa-3,6-diazatricyclo[8.4.0.0$^{2,6}$]tetradeca1(14),2,4,10,12-pentaen-12-yl}-1H-pyrazol-1-yl)-1λ$^3$,3-oxazocan-2-one (105 mg, 67% yield). LCMS (ESI) m/z: 422.1 [M+H$^+$].

Step 6

A mixture of 1-tert-butyl-6-(5-{4-[1-(2-methoxypropyl)-1H-1,2,4-triazol-5-yl]-9-oxa-3,6-diazatricyclo[8.4.0.0$^{2,6}$]tetradeca-1(14),2,4,10,12-pentaen-12-yl}-1H-pyrazol-1-yl)-1λ$^3$,3-oxazocan-2-one (105 mg, 0.250 mmol) and LiAlH$_4$ (51 mg, 1.3 mmol) in THF (5 mL) was refluxed for 1 hr. MeOH was added to quench reaction and the solid was filtered off. The filtrate was evaporated to afford the crude product, which was purified by preparative HPLC (Gilson GX 281, Shimpack PRC-ODS 250 mm×20 mm×2, gradient: CH$_3$CN/10 mm/L NH$_4$HCO$_3$, 17 min) to give 267 (17 mg, 13% yield). LCMS (ESI): RT=4.80 min, m/z: 489.3 [M+H$^+$]. $^1$H NMR (500 MHz, DMSO-d$_6$) δ 8.52 (d, J=8.5 Hz, 1H), 8.01 (s, 1H), 7.95 (s, 1H), 7.55 (d, J=1.5 Hz, 1H), 7.26-7.24 (m, 1H), 7.10 (d, J=1.5 Hz, 1H), 6.39 (d, J=1.5 Hz, 1H), 5.01-4.97 (m, 1H), 4.71-4.69 (m, 1H), 4.58 (t, J=13.5, 4H), 4.17-4.13 (m, 1H), 3.91-3.87 (m, 1H), 3.19 (s, 3H), 2.83 (d, J=12 Hz, 2H), 2.16-2.09 (m, 5H), 1.90 (t, J=53 Hz, 2H), 1.80 (d, J=11.5, 2H), 1.12 (d, J=6.5, 3H)

Example 268

2-(1-isopropyl-3-methyl-1H-1,2,4-triazol-5-yl)-9-(5-(1-isopropylpiperidin-3-yl)-1-methyl-1H-pyrazol-4-yl)-5,6-dihydrobenzo[f]imidazo[1,2-d][1,4]oxazepine 268

To a solution of 4-[3-methyl-1-(propan-2-yl)-1H-1,2,4-triazol-5-yl]-12-[1-methyl-5-(piperidin-3-yl)-1H-pyrazol-4-yl]-9-oxa-3,6-diazatricyclo[8.4.0.0$^{2,6}$]tetradeca1(14), 2,4,10,12-pentaene (140 mg, 0.300 mmol) and acetone (174 mg, 3.0 mmol) in ethanol (10 mL) was added Ti(Oi-Pr)$_4$ (171 mg, 0.60 mmol). After being stirred at 20° C. for 20 min, NaBH$_3$CN (37 mg, 0.60 mmol) was added and stirred at 20° C. for 24 h. The solvent was removed and several drops of water were added. The solid was filtered off and the filtrate was evaporated to afford the crude product, which was purified prep-HPLC (Gilson GX 281, Shim-pack PRC-ODS 250 mm×20 mm×2, gradient: CH$_3$CN/1% formic acid, 17 min) to give racemic 268 (45 mg, 29% yield). LCMS (ESI): RT=5.41 min, m/z: 515.3 [M+H$^+$]. $^1$H NMR (500 MHz, DMSO-d$_6$) δ 8.40 (d, J=8.0 Hz, 1H), 7.91 (s, 1H), 7.43 (s, 1H), 7.09 (dd, J=8.5, 1.5 Hz, 1H), 6.94 (s, 1H), 5.90-5.82 (m, 1H), 4.53 (s, 4H), 3.90 (s, 3H), 3.11 (m, 1H), 3.10-2.66 (m, 3H), 2.50 (t, J=2.0 Hz, 1H), 2.26 (s, 3H), 2.08 (m, 1H), 1.80-1.20 (m, 10H), 0.95-0.92 (m, 6H)

Example 271

2-(2-isopropyl-5-methyl-1,2,4-triazol-3-yl)-9-(3-methylazetidin-3-yl)oxy-5,6-dihydroimidazo[1,2-d][1,4]benzoxazepine 271

Step 1: 2-[2-(2-Isopropyl-5-methyl-2H-[1,2,4]triazol-3-yl)-4,5-dihydro-6-oxa-1,3a-diazabenzo[e]azulen-8-yloxy]-2-methylmalonic acid diethyl ester

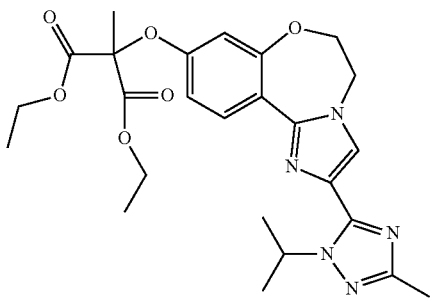 [SMILES: CCOC(=O)C(C)(Oc1ccc2c(c1)OCCn1cc(-c3nc(C)nn3C(C)C)nc1-2)C(=O)OCC]

To a suspension of 2-(2-isopropyl-5-methyl-2H-[1,2,4]triazol-3-yl)-4,5-dihydro-6-oxa-1,3a-diazabenzo[e]azulen-8-ol from Example 4 (100 mg, 0.307 mmol) in DMF (2 mL) was added sodium hydride (12.3 mg, 60% in oil, 0.307 mmol). The mixture was stirred at RT (room temperature) for 15 min, then 2-bromo-2-methylmalonic acid diethyl ester (88 μL, 0.461 mmol) was added. The reaction mixture was stirred at RT for 45 min, and then partitioned between water and EtOAc. The aqueous phase was extracted with EtOAc and the combined organic layers were washed with water, followed by brine, then dried (Na$_2$SO$_4$) and concentrated in vacuo. The resulting residue was purified by column chromatography (Si-PCC, gradient 2-8% MeOH in DCM) affording the title compound as a colourless gum (148 mg, 97%). LCMS (Method B): R$_T$ 3.46 min [M+H]$^+$ 498.

Step 2: 2-[2-(2-Isopropyl-5-methyl-2H-[1,2,4]triazol-3-yl)-4,5-dihydro-6-oxa-1,3a-diazabenzo[e]azulen-8-yloxy]-2-methylpropane-1,3-diol

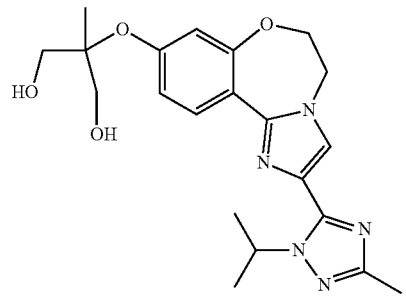 [SMILES: Cc1nc(-c2cn3c(n2)-c2ccc(OC(C)(CO)CO)cc2OCC3)n(C(C)C)n1]

To an ice-cooled suspension of LiAlH$_4$ (34 mg, 0.892 mmol) in THF (3 mL) was added a solution of 2-[2-(2-isopropyl-5-methyl-2H-[1,2,4]triazol-3-yl)-4,5-dihydro-6-oxa-1,3a-diazabenzo[e]azulen-8-yloxy]-2-methylmalonic acid diethyl ester (148 mg, 0.297 mmol) in THF (2 mL). The ice bath was removed and stirring at RT was continued for 1.5 h. To the reaction mixture was added EtOAc (5 mL) and stirring was continued for 10 min. An aqueous solution of Rochelle's salt was then added and stirring continued for a further 30 min. The mixture was filtered through a Celite® pad and the aqueous phase was extracted with EtOAc. The combined organic phases were washed with brine, then dried (Na$_2$SO$_4$) and concentrated in vacuo. The resulting residue was purified by column chromatography (Si-PCC, gradient 2-12% MeOH in DCM) affording the title compound (79.4 mg, 65%). LCMS (Method B): R$_T$ 2.32 min [M+H]$^+$ 414.

Step 3: Methanesulfonic acid 2-[2-(2-isopropyl-5-methyl-2H-[1,2,4]triazol-3-yl)-4,5-dihydro-6-oxa-1,3a-diazabenzo[e]azulen-8-yloxy]-3-methanesulfonyloxy-2-methylpropyl ester

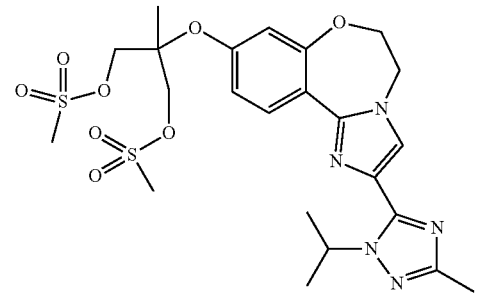 [SMILES: Cc1nc(-c2cn3c(n2)-c2ccc(OC(C)(COS(C)(=O)=O)COS(C)(=O)=O)cc2OCC3)n(C(C)C)n1]

To a solution of 2-[2-(2-isopropyl-5-methyl-2H-[1,2,4]triazol-3-yl)-4,5-dihydro-6-oxa-1,3a-diazabenzo[e]azulen-8-yloxy]-2-methylpropane-1,3-diol (79.4 mg, 0.192 mmol) and Et$_3$N (80 uL, 0.574 mmol) in DCM (10 mL) cooled at 0° C. was added methanesulfonyl chloride (37.4 uL, 0.48 mmol) and stirring at RT was continued for 1.5 h. The mixture was diluted with DCM, washed with a saturated solution of NaHCO$_3$, followed by water, then dried (Na$_2$SO$_4$) and concentrated in vacuo affording the title compound as a colourless gum (quantitative). LCMS (Method J): R$_T$ 2.98 min [M+H]$^+$ 570.

Step 4: 8-(1-Benzyl-3-methylazetidin-3-yloxy)-2-(2-isopropyl-5-methyl-2H-[1,2,4]triazol-3-yl)-4,5-dihydro-6-oxa-1,3a-diazabenzo[e]azulene

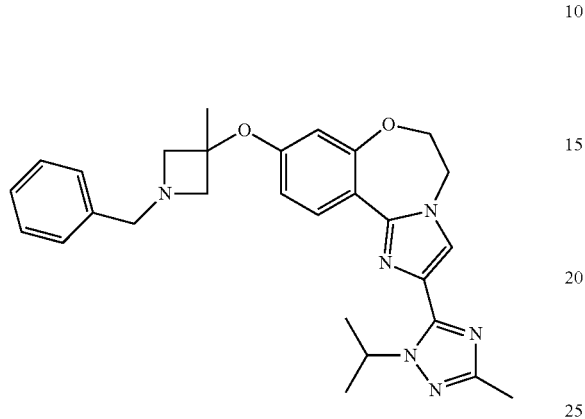

A solution of methanesulfonic acid 2-[2-(2-isopropyl-5-methyl-2H-[1,2,4]triazol-3-yl)-4,5-dihydro-6-oxa-1,3a-diazabenzo[e]azulen-8-yloxy]-3-methanesulfonyloxy-2-methylpropyl ester (0.096 mmol) in benzylamine (0.5 mL) was heated at 150° C. for 1 h and then 180° C. for a further 1 h using microwave irradiation. After cooling to RT, the crude reaction mixture was purified by column chromatography (C$_{18}$, gradient 15-55% MeOH in 0.5% TFA/H$_2$O) and then loaded onto an Isolute® SCX-2 cartridge. The cartridge was washed with MeOH and the product eluted with 0.5M NH$_3$/MeOH affording the title compound as a colourless gum (31 mg, 67% over two steps). LCMS (Method B): R$_T$ 2.40 min [M+H]$^+$ 485

Step 5

To a solution of 8-(1-benzyl-3-methylazetidin-3-yloxy)-2-(2-isopropyl-5-methyl-2H-[1,2,4]triazol-3-yl)-4,5-dihydro-6-oxa-1,3a-diazabenzo[e]azulene (31 mg, 0.064 mmol) in IMS (5 mL) was added Pd(OH)$_2$/C (11 mg) and the reaction mixture was stirred at RT under a hydrogen atmosphere for 16 h. The suspension was then filtered through a pad of Celite® and the filtrate was concentrated in vacuo. The resulting residue was purified by column chromatography (C$_{18}$, gradient 15-50% MeOH in 0.5% TFA/H$_2$O) and then loaded onto an Isolute® SCX-2 cartridge. The cartridge was washed with MeOH and the product eluted with 0.5M NH$_3$/MeOH. Further purifications by column chromatography (Si-PCC, gradient 2-12% 2M NH$_3$/MeOH in DCM) and then (Si-PCC, gradient 3-33% MeOH in DCM) afforded 271 as a colourless gum (5.3 mg, 21%). LCMS (Method K): R$_T$ 2.57 min [M+H]$^+$ 395.1. $^1$H NMR (CD$_3$OD, 400 MHz): δ 8.33 (1H, d, J=9.0 Hz), 7.67 (1H, s), 6.55 (1H, dd, J=9.0, 2.6 Hz), 6.35 (1H, d, J=2.5 Hz), 5.87 (1H, septet, J=6.7 Hz), 4.48 (4H, s), 3.95 (2H, d, J=9.4 Hz), 3.60 (2H, d, J=9.4 Hz), 2.35 (3H, s), 1.70 (3H, s), 1.52 (6H, d, J=6.6 Hz)

Example 275

2-(2-isopropyl-5-methyl-1,2,4-triazol-3-yl)-9-(1-isopropyl-3-phenyl-azetidin-3-yl)oxy-5,6-dihydroimidazo[1,2-d][1,4]benzoxazepine 275

Step 1: 2-Bromo-2-phenylmalonic acid diethyl ester

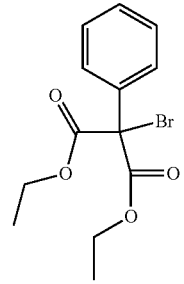 [SMILES: CCOC(=O)C(Br)(C(=O)OCC)c1ccccc1]

To an ice-cooled solution of diethyl phenylmalonate (3.0 g, 12.7 mmol) in THF (90 mL) was added portionwise sodium hydride (1.015 g, 60% in oil, 25.4 mmol). The mixture was stirred in the ice bath for 30 min and NBS (2.486 g, 14 mmol) was added. The mixture was stirred in the ice bath for 10 min, and then at RT for 20 min. The reaction mixture was filtered through Celite® and the filtrate concentrated in vacuo. The residue was dissolved in DCM, then dried (Na$_2$SO$_4$) and concentrated in vacuo. The resulting residue was purified by column chromatography (Si-PCC, gradient 2-8% EtOAc in cyclohexane) affording the title compound as a colourless oil (3.418 g, 85%). $^1$H NMR (CDCl$_3$, 300 MHz): δ 7.60-7.56 (2H, m), 7.39-7.32 (3H, m), 4.33 (2H, q, J=7.1 Hz), 4.32 (2H, q, J=7.1 Hz), 1.30 (6H, d, J=7.1 Hz).

Step 2: 2-[2-(2-Isopropyl-5-methyl-2H-[1,2,4]triazol-3-yl)-4,5-dihydro-6-oxa-1,3a-diazabenzo[e]azulen-8-yloxy]-2-phenylmalonic acid diethyl ester

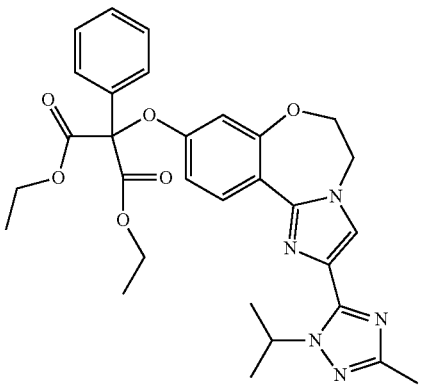 [SMILES: CCOC(=O)C(Oc1ccc2c(c1)OCCn1cc(-c3nc(C)nn3C(C)C)nc1-2)(C(=O)OCC)c1ccccc1]

To a suspension of 2-(2-isopropyl-5-methyl-2H-[1,2,4]triazol-3-yl)-4,5-dihydro-6-oxa-1,3a-diazabenzo[e]azulen-8-ol from Example 4 (300 mg, 0.922 mmol) in DMF (3 mL) was added sodium hydride (37 mg, 60% in oil, 0.925 mmol). The mixture was stirred at RT for 15 min, then a solution of 2-bromo-2-phenylmalonic acid diethyl ester (435 mg, 1.38 mmol) in DMF (0.5 mL) was added. The reaction mixture was stirred at RT for 30 min, and then at 90° C. for 2 h. The cooled reaction mixture was partitioned between water and EtOAc. The aqueous phase was extracted with EtOAc and the combined organic layers were washed with water, followed by brine, then dried ($Na_2SO_4$) and concentrated in vacuo. The resulting residue was purified by column chromatography (Si-PCC, gradient 2-10% MeOH in DCM) affording the title compound as a colourless gum (0.3933 g, 76%). LCMS (Method J): $R_T$ 3.73 min $[M+H]^+$ 560

Step 3: 2-[2-(2-Isopropyl-5-methyl-2H-[1,2,4]triazol-3-yl)-4,5-dihydro-6-oxa-1,3a-diazabenzo[e]azulen-8-yloxy]-2-phenylpropane-1,3-diol

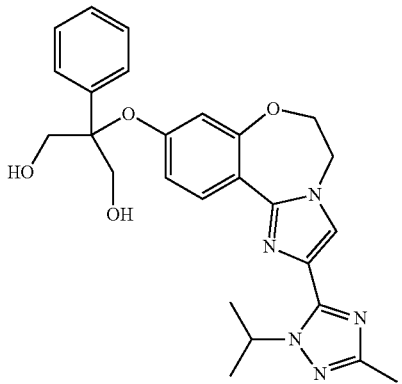 [SMILES: Cc1nc(-c2cn3c(n2)-c2ccc(OC(CO)(CO)c4ccccc4)cc2OCC3)n(C(C)C)n1]

To a suspension of $LiAlH_4$ (15 mg, 0.389 mmol) in THF (2 mL) was added a solution of 2-[2-(2-isopropyl-5-methyl-2H-[1,2,4]triazol-3-yl)-4,5-dihydro-6-oxa-1,3a-diazabenzo[e]azulen-8-yloxy]-2-phenylmalonic acid diethyl ester (72.5 mg, 0.13 mmol) in THF (1 mL). The mixture was stirred at RT for 2 h, then EtOAc (5 mL) was added and stirring was continued for 10 min. An aqueous solution of Rochelle's salt was then added and stirring continued for a further 30 min. The mixture was filtered through a Celite® pad and the aqueous phase was extracted with EtOAc. The combined organic phases were washed with brine, then dried ($Na_2SO_4$) and concentrated in vacuo. The resulting residue was purified by column chromatography (Si-PCC, gradient 4-12% MeOH in DCM) affording the title compound (28.1 mg, 46%). LCMS (Method B): $R_T$ 2.75 min $[M+H]^+$ 476

Step 4: Methanesulfonic acid 2-[2-(2-isopropyl-5-methyl-2H-[1,2,4]triazol-3-yl)-4,5-dihydro-6-oxa-1,3a-diazabenzo[e]azulen-8-yloxy]-3-methanesulfonyloxy-2-phenylpropylester

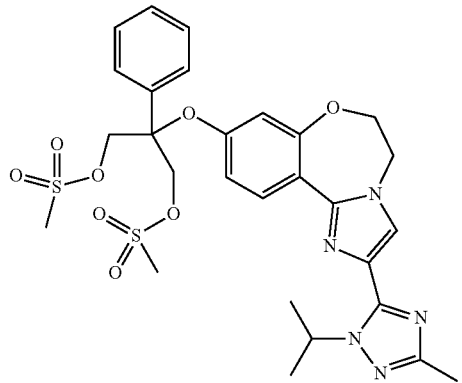 [SMILES: Cc1nc(-c2cn3c(n2)-c2ccc(OC(COS(C)(=O)=O)(COS(C)(=O)=O)c4ccccc4)cc2OCC3)n(C(C)C)n1]

To a solution of 2-[2-(2-isopropyl-5-methyl-2H-[1,2,4]triazol-3-yl)-4,5-dihydro-6-oxa-1,3a-diazabenzo[e]azulen-8-yloxy]-2-phenylpropane-1,3-diol (115 mg, 0.242 mmol) and $Et_3N$ (101 µL, 0.725 mmol) in DCM (15 mL) cooled at 0° C. was added methanesulfonyl chloride (47 µL, 0.605 mmol) and stirring at RT was continued for 1.5 h. The mixture was diluted with DCM, washed with a saturated solution of $NaHCO_3$, followed by water, then dried ($Na_2SO_4$) and concentrated in vacuo The resulting residue was purified by column chromatography (Si-PCC, gradient 2-8% MeOH in DCM) affording the title compound (124.5 mg, 81%) as a colourless gum. LCMS (Method J): $R_T$ 3.26 min $[M+H]^+$ 632

Step 5

A solution of methanesulfonic acid 2-[2-(2-isopropyl-5-methyl-2H-[1,2,4]triazol-3-yl)-4,5-dihydro-6-oxa-1,3a-diazabenzo[e]azulen-8-yloxy]-3-methanesulfonyloxy-2-phenylpropylester (41.5 mg, 0.0657 mmol) in isopropylamine (0.7 mL) was heated at 140° C. for 12 h using microwave irradiation. After cooling to RT, the crude reaction mixture was evaporated and then purified by column chromatography ($C_{18}$, gradient 20-50% MeOH in 0.5% $TFA/H_2O$) and then loaded onto an Isolute® SCX-2 cartridge. The cartridge was washed with MeOH and the product eluted with 0.5M $NH_3$/MeOH. Further purification by column chromatography (Si-PCC, gradient 2-10% MeOH in DCM) affording 275 as a colourless gum (11.7 mg, 36%). LCMS (Method K): $R_T$ 3.17 min $[M+H]^+$ 499.1. $^1$H NMR ($CD_3OD$, 400 MHz): δ 8.22 (1H, d, J=9.0 Hz), 7.62 (1H, s), 7.59-7.57 (2H, m), 7.40-7.36 (2H, m), 7.31-7.27 (1H, m), 6.47 (1H, dd, J=9.0, 2.5 Hz), 6.21 (1H, d, J=2.5 Hz), 5.82 (1H, septet, J=6.7 Hz), 4.43-4.38 (4H, m), 3.88 (2H, d, J=9.2 Hz), 3.67 (2H, d, J=9.2 Hz), 2.58 (1H, septet, J=6.2 Hz), 2.34 (3H, s), 1.49 (6H, d, J=6.7 Hz), 1.02 (6H, d, J=6.2 Hz)

Example 283

9-[3-(cyclopropylmethyl)-1-isopropyl-azetidin-3-yl]oxy-2-(2-isopropyl-5-methyl-1,2,4-triazol-3-yl)-5,6-dihydroimidazo[1,2-d][1,4]benzoxazepine 283

Step 1: 2-Cyclopropylmethylmalonic acid diethyl ester

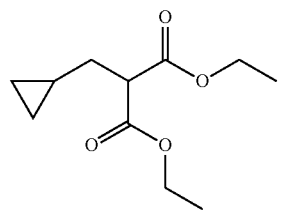

To an ice-cooled solution of diethyl malonate (3.0 g, 18.7 mmol) in THF (30 mL) was added, portionwise over 15 min, sodium hydride (0.824 g, 60% in oil, 20.6 mmol). The mixture was stirred at RT for 30 min, and then cooled in an ice bath. Cyclopropylmethyl bromide (2.36 mL, 24.3 mmol) was added and the reaction mixture stirred at RT for 1 h and then refluxed for 6 h. The cooled mixture was concentrated in vacuo, the residue was partitioned between diethyl ether and dilute aqueous $NH_4Cl$; and the aqueous phase was extracted with diethyl ether. The combined organic phases were washed with brine, then dried ($Na_2SO_4$) and concentrated in vacuo. The resulting residue was purified by column chromatography (Si-PCC, gradient 2-8% EtOAc in cyclohexane) affording a mixture of the title compound and 2-but-3-enylmalonic acid diethyl ester (3.24 g, 10:1 ratio respectively). This mixture was dissolved in DCM (150 mL) and a solution of mCPBA (0.77 g, 4.46 mmol) in DCM (5 mL) added. The reaction mixture was stirred at RT for 16 h, and then washed with a saturated solution of NaHCO₃, dried (Na₂SO₄) and concentrated in vacuo. The resulting residue was purified by column chromatography (Si-PCC, gradient 2-8% EtOAc in cyclohexane) affording the title compound as a colourless oil (2.68 g, 67%). ¹H NMR (CDCl₃, 300 MHz): δ 4.20 (4H, q, J=7.1 Hz), 3.44 (1H, t, J=7.5 Hz), 1.81 (2H, t, J=7.3 Hz), 1.27 (6H, t, J=7.1 Hz), 0.80-0.67 (1H, m), 0.48-0.42 (2H, m), 0.12-0.07 (2H, m).

Step 2: 2-Bromo-2-cyclopropylmethylmalonic acid diethyl ester

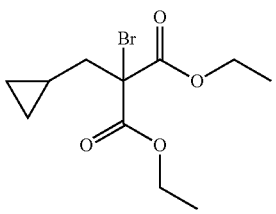 [SMILES: CCOC(=O)C(Br)(CC1CC1)C(=O)OCC]

To an ice-cooled solution of 2-cyclopropylmethylmalonic acid diethyl ester (1.3 g, 6.067 mmol) in THF (45 mL) was added, portionwise, sodium hydride (0.485 g, 60% in oil, 12.13 mmol). The mixture was stirred in the ice bath for 15 min, and then at RT for 15 min. The suspension was re-cooled in the ice bath and NBS (1.19 g, 6.67 mmol) was added over 5 min. The mixture was stirred in the ice bath for 10 min, and then at RT for 30 min. The reaction mixture was filtered through Celite® and the filtrate concentrated in vacuo. The resulting residue was purified by column chromatography (Si-PCC, gradient 2-8% EtOAc in cyclohexane) affording the title compound as a colourless oil (1.55 g, 87%). ¹H NMR (CDCl₃, 300 MHz): δ 4.33-4.22 (4H, m), 2.24 (2H, d, J=6.6 Hz) 1.30 (6H, d, J=7.1 Hz) 1.01-0.88 (1H, m), 0.54-0.48 (2H, m), 0.17-0.12 (2H, m).

Step 3: 2-Cyclopropylmethyl-2-[2-(2-isopropyl-5-methyl-2H-[1,2,4]triazol-3-yl)-4,5-dihydro-6-oxa-1,3a-diazabenzo[e]azulen-8-yloxy]malonic acid diethyl ester

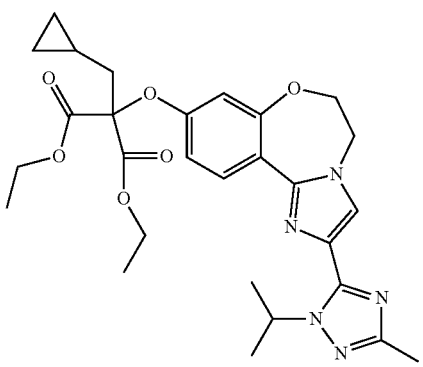 [SMILES: CCOC(=O)C(CC1CC1)(Oc1ccc2c(c1)OCCn1cc(-c3nc(C)nn3C(C)C)nc1-2)C(=O)OCC]

To a suspension of 2-(2-isopropyl-5-methyl-2H-[1,2,4]triazol-3-yl)-4,5-dihydro-6-oxa-1,3a-diazabenzo[e]azulen-8-ol from Example 4 (100 mg, 0.307 mmol) in DMF (2 mL) was added sodium hydride (12.3 mg, 60% in oil, 0.307 mmol). The mixture was stirred at RT for 15 min, then 2-bromo-2-cyclopropylmethylmalonic acid diethyl ester (135 mg, 0.46 mmol) was added. The reaction mixture was stirred at RT for 1 h, and then at 70° C. for 6 h. The reaction was repeated with 2-(2-isopropyl-5-methyl-2H-[1,2,4]triazol-3-yl)-4,5-dihydro-6-oxa-1,3a-diazabenzo[e]azulen-8-ol from Example 4 (400 mg, 1.23 mmol), DMF (8 mL), sodium hydride (49.2 mg, 1.23 mmol) and 2-bromo-2-cyclopropylmethylmalonic acid diethyl ester (540 mg, 1.84 mmol). The cooled reaction mixtures were combined and partitioned between water and EtOAc. The aqueous phase was extracted with EtOAc. The combined organic phases were washed with water, followed by brine, then dried (Na₂SO₄) and concentrated in vacuo. The resulting residue was purified by column chromatography (Si-PCC, gradient 2-10% MeOH in DCM) affording the title compound (0.309 g, 37%). LCMS (Method B): R_T 3.77 min [M+H]⁺ 538.

Step 4: 2-Cyclopropylmethyl-2-[2-(2-isopropyl-5-methyl-2H-[1,2,4]triazol-3-yl)-4,5-dihydro-6-oxa-1,3a-diazabenzo[e]azulen-8-yloxy]-propane-1,3-diol

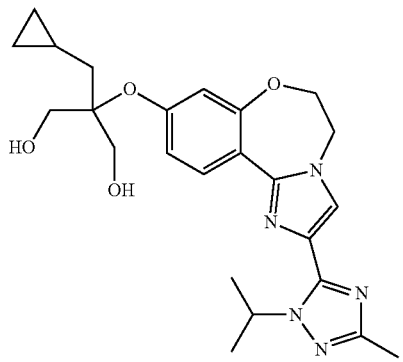 [SMILES: Cc1nc(-c2cn3c(n2)-c2ccc(OC(CO)(CO)CC4CC4)cc2OCC3)n(C(C)C)n1]

To a suspension of LiAlH₄ (65.5 mg, 1.724 mmol) in THF (7 mL) cooled to 10° C. was added a solution of 2-cyclopropylmethyl-2-[2-(2-isopropyl-5-methyl-2H-[1,2,4]triazol-3-yl)-4,5-dihydro-6-oxa-1,3a-diazabenzo[e]azulen-8-yloxy]-malonic acid diethyl ester (309 mg, 0.575 mmol) in THF (5 mL). The reaction mixture was stirred at RT for 1.5 h. To the reaction mixture was added EtOAc (1 mL) and stirring was continued for 10 min. An aqueous solution of Rochelle salt was then added and stirring continued for a further 1.5 h. EtOAc was added and the mixture was filtered through a Celite® pad and the aqueous phase was extracted with EtOAc. The combined organic phases were washed with brine, then dried (Na₂SO₄) and concentrated in vacuo. The resulting residue was purified by column chromatography (Si-PCC, gradient 4-12% MeOH in DCM) affording the title compound as a colourless foam (0.20 g, 77%). LCMS (Method B): R_T 2.72 min [M+H]⁺ 454.

Step 5: Methanesulfonic acid 2-cyclopropylmethyl-2-[2-(2-isopropyl-5-methyl-2H-[1,2,4]triazol-3-yl)-4,5-dihydro-6-oxa-1,3a-diazabenzo[e]azulen-8-yloxy]-3-methanesulfonyloxypropyl ester

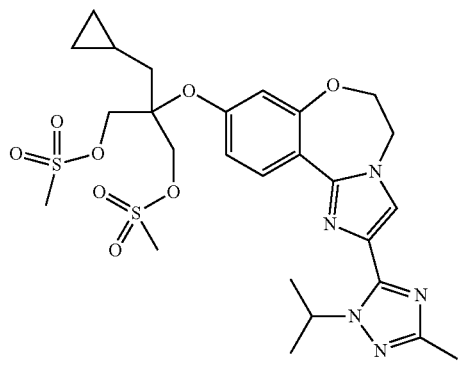 [SMILES: Cc1nc(-c2cn3c(n2)-c2ccc(OC(COS(C)(=O)=O)(COS(C)(=O)=O)CC4CC4)cc2OCC3)n(C(C)C)n1]

To a solution of 2-cyclopropylmethyl-2-[2-(2-isopropyl-5-methyl-2H-[1,2,4]triazol-3-yl)-4,5-dihydro-6-oxa-1,3a-diazabenzo[e]azulen-8-yloxy]-propane-1,3-diol (200 mg, 0.441 mmol) and $Et_3N$ (184 µL, 1.32 mmol) in DCM (20 mL) cooled at 0° C. was added methanesulfonyl chloride (86 µL, 1.10 mmol) and stirring at RT was continued for 1.5 h. The mixture was diluted with DCM, washed with a saturated solution of $NaHCO_3$, followed by water, then dried ($Na_2SO_4$) and concentrated in vacuo affording the title compound as a colourless solid (264 mg, 98%). LCMS (Method B): $R_T$ 3.34 min [M+H]$^+$ 610

Step 6

A solution of methanesulfonic acid 2-cyclopropylmethyl-2-[2-(2-isopropyl-5-methyl-2H-[1,2,4]triazol-3-yl)-4,5-dihydro-6-oxa-1,3a-diazabenzo[e]azulen-8-yloxy]-3-methanesulfonyloxypropyl ester (87 mg, 0.1427 mmol) in isopropylamine (1.2 mL) was heated at 150° C. for 28 h using microwave irradiation. After cooling to RT, the crude reaction mixture was evaporated and then purified by column chromatography ($C_{18}$, gradient 25-55% MeOH in 0.5% TFA/$H_2O$) and then loaded onto an Isolute® SCX-2 cartridge. The cartridge was washed with MeOH and the product eluted with 0.5M $NH_3$/MeOH affording 283 as a colourless foam (43.1 mg, 63%). LCMS (Method K): $R_T$ 3.15 min [M+H]$^+$ 477.2. $^1$H NMR (CD$_3$OD, 400 MHz): δ 8.33 (1H, d, J=9.0 Hz), 7.67 (1H, s), 6.57 (1H, dd, J=9.0, 2.6 Hz), 6.36 (1H, d, J=2.5 Hz), 5.87 (1H, septet, J=6.7 Hz), 4.48 (4H, s), 3.72-3.69 (2H, m), 3.38-3.35 (2H, m), 2.49 (1H, septet, J=6.3 Hz), 2.35 (3H, s), 2.04 (2H, d, J=6.6 Hz), 1.52 (6H, d, J=6.6 Hz), 0.99 (6H, d, J=6.3 Hz), 0.80-0.70 (1H, m), 0.45-0.41 (2H, m), 0.03-0.00 (2H, m)

Example 284

9-[3-(cyclopropylmethyl)azetidin-3-yl]oxy-2-(2-isopropyl-5-methyl-1,2,4-triazol-3-yl)-5,6-dihydroimidazo[1,2-d][1,4]benzoxazepine 284

Step 1: 8-(1-Benzyl-3-cyclopropylmethylazetidin-3-yloxy)-2-(2-isopropyl-5-methyl-2H-[1,2,4]triazol-3-yl)-4,5-dihydro-6-oxa-1,3a-diazabenzo[e]azulene

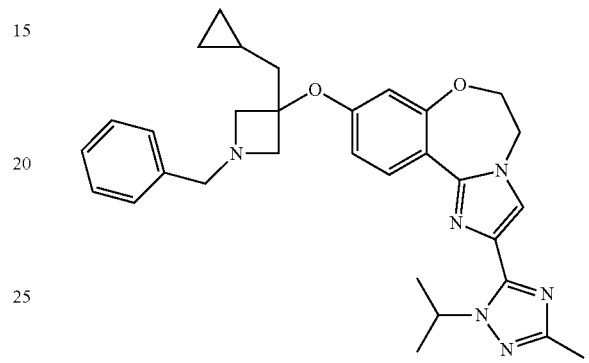

A solution of methanesulfonic acid 2-cyclopropylmethyl-2-[2-(2-isopropyl-5-methyl-2H-[1,2,4]triazol-3-yl)-4,5-dihydro-6-oxa-1,3a-diazabenzo[e]azulen-8-yloxy]-3-methanesulfonyloxypropyl ester from Example 283 (90 mg, 0.1476 mmol) in benzylamine (1 mL) was heated at 180° C. for 2.5 h using microwave irradiation. After cooling to RT, the crude reaction mixture was purified by column chromatography ($C_{18}$, gradient 30-65% MeOH in 0.5% TFA/$H_2O$) and then loaded onto an Isolute® SCX-2 cartridge. The cartridge was washed with MeOH and the product eluted with 0.5M $NH_3$/MeOH affording the title compound as a colourless gum (65 mg, 84%). LCMS (Method B): $R_T$ 2.66 min [M+H]$^+$ 525

Step 2

To a solution of 8-(1-benzyl-3-cyclopropylmethylazetidin-3-yloxy)-2-(2-isopropyl-5-methyl-2H-[1,2,4]triazol-3-yl)-4,5-dihydro-6-oxa-1,3a-diazabenzo[e]azulene (65 mg, 0.124 mmol) in IMS (8 mL) was added Pd(OH)$_2$/C (20 mg) and the reaction mixture was stirred at RT under a hydrogen atmosphere for 16 h. The suspension was then filtered through a pad of Celite® and Pd(OH)$_2$/C (30 mg) was added to the filtrate which was stirred at RT under a hydrogen atmosphere for a further 10 h. The suspension was then filtered through a pad of Celite® and the filtrate was concentrated in vacuo. The resulting residue was purified by column chromatography ($C_{18}$, gradient 20-55% MeOH in 0.5% TFA/$H_2O$) and then loaded onto an Isolute® SCX-2 cartridge. The cartridge was washed with MeOH and the product eluted with 0.5M $NH_3$/MeOH. Further purification by column chromatography (Si-PCC, gradient 3-12% MeOH in DCM then 10-15% 2M $NH_3$/MeOH in DCM) afforded 284 as a colourless foam (10.4 mg, 19%). LCMS (Method K): $R_T$ 2.96 min [M+H]$^+$ 435.1. $^1$H NMR (CD$_3$OD, 400 MHz): δ 8.33 (1H, d, J=9.0 Hz), 7.67 (1H, s), 6.55 (1H, dd, J=8.9, 2.5 Hz), 6.34 (1H, d, J=2.5 Hz), 5.87 (1H, septet, J=6.7 Hz), 4.48 (4H, s), 3.94 (2H, d, J=10.0

Hz), 3.80 (2H, d, J=10.0 Hz), 2.36 (3H, s), 2.06 (2H, d, J=6.6 Hz), 1.52 (6H, d, J=6.6 Hz), 0.83-0.73 (1H, m), 0.48-0.43 (2H, m), 0.06-0.02 (2H, m)

Example 294

(R)-10-(1-(4-tert-butylpiperazin-1-yl)ethyl)-9-fluoro-2-(1-isopropyl-3-methyl-1H-1,2,4-triazol-5-yl)-5,6-dihydrobenzo[f]imidazo[1,2-d][1,4]oxazepine 294

Step 1: 13-Bromo-12-fluoro-4-[3-methyl-1-(propan-2-yl)-1H-1,2,4-triazol-5-yl]-9-oxa-3,6-diazatricyclo[8.4.0.0$^{2,6}$]tetradeca1(14),2,4,10,12-pentaene

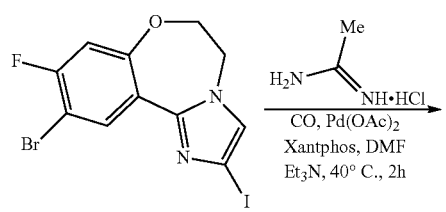

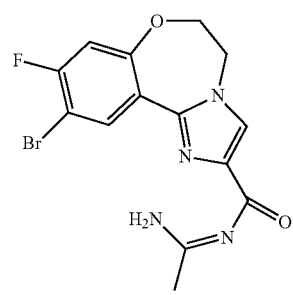

A solution of 13-bromo-4-iodo-12-fluoro-9-oxa-3,6-diazatricyclo[8.4.0.0$^{2,6}$]tetradeca-1(14),2,4,10,12-pentaene (10.0 g, 24.4 mmol) and acetamidine hydrochloride (2.63 g, 26.9 mmol) in triethylamine (6.90 mL, 49.4 mmol) and N,N-dimethylformamide (32.0 mL) was thoroughly degassed with N$_2$. Palladium acetate (276 mg, 1.22 mmol) and 4,5-bis(diphenylphosphino)-9,9-dimethylxanthene (1.40 g, 2.44 mmol) were added and the solution was degassed with CO for 1 minute. A CO balloon was attached to the flask and the reaction was heated to 40° C. for 2 h. After being cooled to room temperature, the mixture was further treated with isopropylhydrazine hydrochloride (4.05 g, 36.6 mmol) and acetic acid (15 mL). The resulting mixture was heated again to 80° C. for 1 h. After cooling to room temperature, the mixture was diluted with H$_2$O (400 mL). The resulting solid was collected by filtration and purified by silica gel chromatography using 15-50% EtOAc in petroleum ether as eluant to give the title compound (4.9 g, 50% yield). LCMS m/z [M+H]$^+$ 406.0.

Step 2: 13-(1-Ethoxyethenyl)-12-fluoro-4-[3-methyl-1-(propan-2-yl)-1H-1,2,4-triazol-5-yl]-9-oxa-3,6-diazatricyclo[8.4.0.0$^{2,6}$]tetradeca1(14),2,4,10,12-pentaene

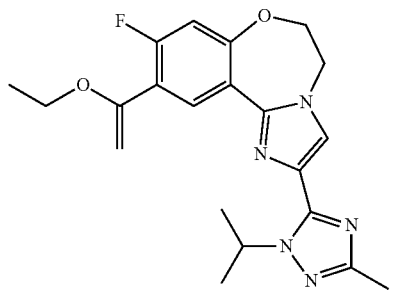 [SMILES: C=C(OCC)c1cc2c(cc1F)OCCn1cc(-c3nc(C)nn3C(C)C)nc1-2]

To a suspension of 13-bromo-12-fluoro-4-[3-methyl-1-(propan-2-yl)-1H-1,2,4-triazol-5-yl]-9-oxa-3,6-diazatricyclo[8.4.0.0$^{2,6}$]tetradeca1(14),2,4,10,12-pentaene (2.00 g, 4.93 mmol) and LiCl (620 mg, 14.8 mmol) in dry THF (15 mL), was added tri-n-butyl(1-ethoxyvinyl)tin (1.78 g, 4.93 mmol) and tetrakis(triphenylphosphine) palladium (185 mg, 0.160 mmol) under nitrogen at room temperature. The resultant mixture was heated under 80° C. for 24 h in a seal tube. After cooling down, the mixture was diluted with THF, treated with an aqueous 0.16 M potassium fluoride solution (20 ml), and stirred at ambient temperature for 1 h. The precipitated tri-nbutylstannyl fluoride was removed by filtration. The filtrate was evaporated under reduced pressure to give an aqueous suspension, which was extracted with ethyl acetate. The combined organic layers were washed with water and evaporated in vacuo to give the crude product (1.97 g, over 100% yield) a yellow solid, which was used directly in the next step without further purification. LCMS m/z [M+H]$^+$ 398.1

Step 3: 1-{12-Fluoro-4-[3-methyl-1-(propan-2-yl)-1H-1,2,4-triazol-5-yl]-9-oxa-3,6-diazatricyclo[8.4.0.0$^{2,6}$]tetradeca1(14),2,4,10,12-pentaen-13-yl}ethan-1-one

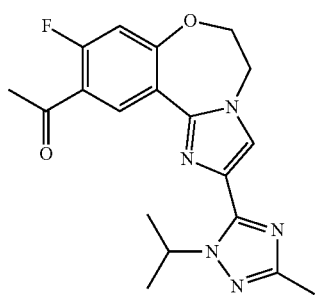 [SMILES: CC(=O)c1cc2c(cc1F)OCCn1cc(-c3nc(C)nn3C(C)C)nc1-2]

A mixture of the above crude 13-(1-ethoxyethenyl)-12-fluoro-4-[3-methyl-1-(propan-2-yl)-1H-1,2,4-triazol-5-yl]-9-oxa-3,6-diazatricyclo[8.4.0.0$^{2,6}$]tetradeca1(14),2,4,10,12-pentaene (1.97 g, 4.93 mmol) and p-toluenesulfonic acid (90 mg, 0.50 mmol) in acetone (10.0 ml) was heated under reflux for 30 min. Evaporation under reduced pressure gave a yellow solid, which was purified using flash chromatography on silica gel using 4% dichloromethane in methanol as eluant to afford the title compound (1.55 g, 85% yield for two steps). LCMS m/z [M+H]+ 370.1

Step 4: 1-{12-Fluoro-4-[3-methyl-1-(propan-2-yl)-1H-1,2,4-triazol-5-yl]-9-oxa-3,6-diazatricyclo[8.4.0.0$^{2,6}$]tetradeca1(14),2,4,10,12-pentaen-13-yl}ethan-1-ol

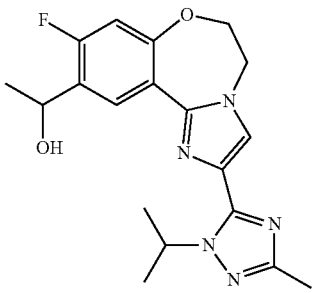 [SMILES: Cc1nc(-c2cn3c(n2)-c2cc(C(C)O)c(F)cc2OCC3)n(C(C)C)n1]

To a stirred suspension of NaBH$_4$ (638 mg, 16.8 mmol) in MeOH (15 mL), was added a solution of 1-{12-fluoro-4-[3-methyl-1-(propan-2-yl)-1H-1,2,4-triazol-5-yl]-9-oxa-3,6-diazatricyclo[8.4.0.0$^{2,6}$]tetradeca1(14),2,4,10,12-pentaen-13-yl}ethan-1-one (1.55 g, 4.20 mmol) in MeOH (15 mL) at 0° C. under a nitrogen atmosphere. After the addition was completed, the cooling bath was removed and the mixture was stirred at room temperature for 1 h. After removal of the solvent, the residue was purified by silica gel chromatography using 5% dichloromethane in methanol as eluant to give the title compound (1.5 g, 96% yield) as a white solid. LCMS m/z [M+H]+ 372.1

Step 5: 1-{12-Fluoro-4-[3-methyl-1-(propan-2-yl)-1H-1,2,4-triazol-5-yl]-9-oxa-3,6-diazatricyclo[8.4.0.0$^{2,6}$]tetradeca1(14),2,4,10,12-pentaen-13-yl}ethyl methanesulfonate

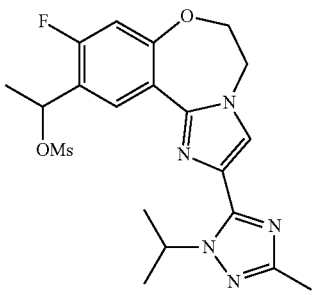

To a solution of 1-{12-fluoro-4-[3-methyl-1-(propan-2-yl)-1H-1,2,4-triazol-5-yl]-9-oxa-3,6-diazatricyclo[8.4.0.0$^{2,6}$]tetradeca1(14),2,4,10,12-pentaen-13-yl}ethan-1-ol (300 mg, 0.810 mmol) in DCM (15 mL) at 0° C., was added Et$_3$N (0.245 mL, 2.43 mmol) dropwise. After stirring for 10 min, methanesulfonyl chloride (185 mg, 1.62 mmol) was added. After being stirred for another 3 h, the reaction mixture was then treated with saturated aqueous sodium hydrogen carbonate (20 mL), water (20 mL), brine (50 mL), and dried over Na$_2$SO$_4$. The organic phase was concentrated in vacuo to afford the crude, racemic mesylate (375 mg), which was used directly in the next step without further purification Step 6

To a solution of 1-{12-fluoro-4-[3-methyl-1-(propan-2-yl)-1H-1,2,4-triazol-5-yl]-9-oxa-3,6-diazatricyclo[8.4.0.0$^{2,6}$]tetradeca-1(14),2,4,10,12-pentaen-13-yl}ethyl methanesulfonate (123 mg, 0.274 mmol) in dioxane (15 mL) was added 4-tert-butylpiperidine (386 mg, 2.74 mmol). The mixture was heated at 90° C. overnight. The solvent was removed and the residue was purified by Combi-flash eluting with a 5-95% gradient of CH$_3$CN in 0.3% NH$_4$HCO$_3$ to give racemic 10-(1-(4-tert-butylpiperazin-1-yl)ethyl)-9-fluoro-2-(1-isopropyl-3-methyl-1H-1,2,4-triazol-5-yl)-5,6-dihydrobenzo[f]imidazo[1,2-d][1,4]oxazepine. The isolated solid was further separated by chiral SFC (OD-H column, 15% EtOH isocratic) to give the two enantiomers 294 and 297.

294: First eluting peak, 26 mg, 19% yield. >95% ee (4.95 min, OZ—H, 20% EtOH (0.1% DEA) in n-hexane (0.1% DEA) isocratic, 15 min). II-NMR (500 MHz, CD$_3$OD) δ 8.58 (d, J=8.5 Hz, 1H), 7.73 (s, 1H), 6.82 (d, J=11 Hz, 1H), 5.85 (m, 1H), 4.54-4.53 (m, 4H), 3.91 (m, 1H), 2.73-2.57 (m, 8H), 2.38 (s, 3H), 1.57 (d, J=6.5 Hz, 6H), 1.47 (d, J=7.0 Hz, 3H), 1.09 (s, 9H). LCMS m/z [M+H]+ 496.3. LCMS 10 MIN CAD GRADIENT, 1.2 ml/min on Agilent 1200/G6110 System. Purity is 100% by UV 254.

Example 297

(S)-10-(1-(4-tert-butylpiperazin-1-yl)ethyl)-9-fluoro-2-(1-isopropyl-3-methyl-1H-1,2,4-triazol-5-yl)-5,6-dihydrobenzo[f]imidazo[1,2-d][1,4]oxazepine 297

Following the procedures of Example 294, 297 was prepared.

297: Second eluting peak, 26 mg, 19% yield. >95% ee (6.63 min, OZ—H, 20% EtOH (0.1% DEA) in n-hexane (0.1% DEA) isocratic, 15 min). II-NMR (500 MHz, CD$_3$OD) δ 8.58 (d, J=8.5 Hz, 1H), 7.73 (s, 1H), 6.82 (d, J=11 Hz, 1H), 5.85 (m, 1H), 4.54-4.53 (m, 4H), 3.91 (m, 1H), 2.73-2.57 (m, 8H), 2.38 (s, 3H), 1.57 (d, J=6.5 Hz, 6H), 1.47 (d, J=7.0 Hz, 3H), 1.09 (s, 9H). LCMS m/z [M+H]+ 496.3. LCMS 10 MIN CAD GRADIENT, 1.2 ml/min on Agilent 1200/G6110 System. Purity is 100% by UV 254.

Example 299

(R)-10-(1-(4-tert-butylpiperazin-1-yl)ethyl)-2-(1-isopropyl-3-methyl-1H-1,2,4-triazol-5-yl)-9-methyl-5,6-dihydrobenzo[f]imidazo[1,2-d][1,4]oxazepine 299

Step 1: 13-Bromo-12-methyl-4-[3-methyl-1-(propan-2-yl)-1H-1,2,4-triazol-5-yl]-9-oxa-3,6-diazatricyclo[8.4.0.0$^{2,6}$]tetradeca-1(14),2,4,10,12-pentaene

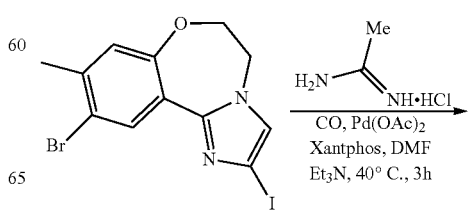

-continued

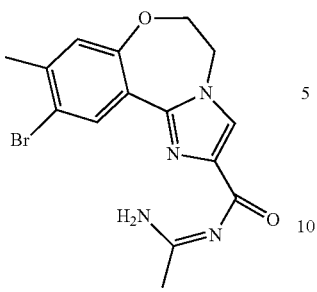

A mixture of 13-bromo-4-iodo-12-methyl-9-oxa-3,6-diazatricyclo[8.4.0.0²,⁶]tetradeca-1(14),2,4,10,12-pentaene (5.00 g, 12.3 mmol), acetamidine hydrochloride (1.29 g, 13.6 mmol), Pd(OAc)₂ (277 mg, 1.24 mmol), and Xantphos (1.43 g, 2.47 mmol) in DMF (20.0 mL) and TEA (5.0 mL) was heated at 40° C. under CO (1 atm) for 3 hrs. To above cooled solution was added isopropylhydrazine hydrochloride (1.64 g, 14.8 mmol) and AcOH (20.0 mL). The resulting mixture was heated to 65° C. and stirred at this temperature for 1 hr. At the end of reaction, solvents were removed and the residue was poured into water (2000 mL). The solid was collected by filtration and washed with acetone to give the desired product (4.90 g, 85% yield) as a pale yellow solid. ¹H NMR (500 MHz, DMSO-d6) δ 8.48 (s, 1H), 7.91 (s, 1H), 7.08 (s, 1H), 5.67 (m, 1H), 4.52-4.49 (m, 4H), 2.33 (s, 3H), 2.25 (s, 3H), 1.46 (s, 6H). LCMS m/z [M+H]⁺ 402.2.

Step 2: 13-(1-Ethoxyethenyl)-12-methyl-4-[3-methyl-1-(propan-2-yl)-1H-1,2,4-triazol-5-yl]-9-oxa-3,6-diazatricyclo[8.4.0.0²,⁶]tetradeca-1(14),2,4,10,12-pentaene

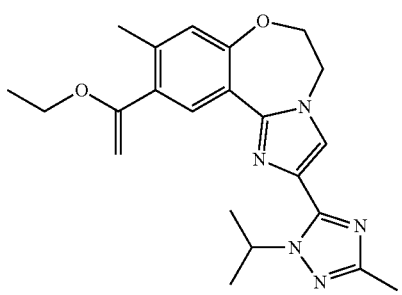 [SMILES: C=C(OCC)c1cc2c(cc1C)OCCn1cc(-c3nc(C)nn3C(C)C)nc1-2]

A mixture of 13-bromo-12-methyl-4-[3-methyl-1-(propan-2-yl)-1H-1,2,4-triazol-5-yl]-9-oxa-3,6-diazatricyclo[8.4.0.0²,⁶]tetradeca-1(14),2,4,10,12-pentaene (1.50 g, 3.73 mmol), tributyl(1-ethoxyvinyl)stannane (1.35 g, 3.74 mmol), LiCl (472 mg, 11.2 mmol), Pd(PPh₃)₄ (130 mg, 0.120 mmol) in THF (30 mL) was stirred at 80° C. for 16 hrs under N₂ atmosphere in a sealed tube. After being cooled to room temperature, the mixture was treated with aq. KF (2.0 M, 50.0 mL). The resulting mixture was stirred at room temperature for 1 h and then filtered. The filtrate was extracted with ethyl acetate (5×50 mL). The combined organic layer was washed with brine and dried over MgSO₄. Removal of the solvent gave the crude product (2.0 g, over 100% yield) as pale yellow oil, which was used directly in the next step without further purification. LCMS m/z [M+H]⁺ 395.3.

Step 3: 1-{12-Methyl-4-[3-methyl-1-(propan-2-yl)-1H-1,2,4-triazol-5-yl]-9-oxa-3,6-diazatricyclo[8.4.0.0²,⁶]tetradeca-1(14),2,4,10,12-pentaen-13-yl}ethan-1-one

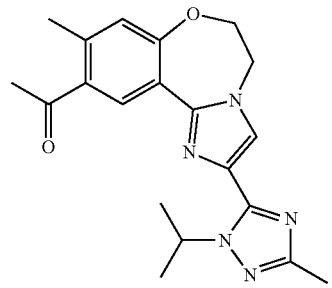 [SMILES: CC(=O)c1cc2c(cc1C)OCCn1cc(-c3nc(C)nn3C(C)C)nc1-2]

A mixture of 13-(1-ethoxyethenyl)-12-methyl-4-[3-methyl-1-(propan-2-yl)-1H-1,2,4-triazol-5-yl]-9-oxa-3,6-diazatricyclo[8.4.0.0²,⁶]tetradeca-1(14),2,4,10,12-pentaene (2.0 g) and 4-methylbenzenesulfonic acid (438 mg, 2.54 mmol) in acetone (20.0 mL) was stirred at 60° C. for 75 min. The solvent was removed to give the desired compound (2.20 g, over 100% yield) as yellow oil, which was used directly in the next step without further purification. LCMS m/z [M+H]⁺ 366.2

Step 4: 1-{12-Methyl-4-[3-methyl-1-(propan-2-yl)-1H-1,2,4-triazol-5-yl]-9-oxa-3,6-diazatricyclo[8.4.0.0²,⁶]tetradeca-1(14),2,4,10,12-pentaen-13-yl}ethan-1-ol

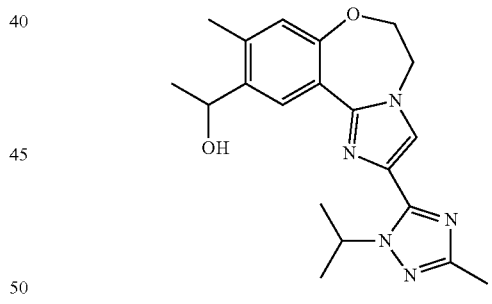

To a solution of 1-{12-methyl-4-[3-methyl-1-(propan-2-yl)-1H-1,2,4-triazol-5-yl]-9-oxa-3,6-diazatricyclo[8.4.0.0²,⁶]tetradeca-1(14),2,4,10,12-pentaen-13-yl}ethan-1-one (2.20 g) in MeOH (50.0 mL) was added NaBH₄ (920 mg, 24.2 mmol). The mixture was stirred at room temperature for 2 hrs. Water was added to quench the reaction. The mixture was extracted with ethyl acetate (5×50 mL). The combined organic layers were washed with brine and dried over MgSO₄. Removal of the solvent gave the crude product, which was purified by reverse phase Combi-flash eluting with a 25-30% gradient of CH₃CN in 0.3% NH₄HCO₃ to afford the racemic product (800 mg, 58% yield for three steps). ¹H NMR (500 MHz, DMSO-d₆) δ 8.50 (s, 1H), 7.85 (s, 1H), 6.81 (s, 1H), 5.74 (m, 1H), 5.07 (s, 1H), 4.87 (s, 1H), 4.48-4.44 (m, 4H), 2.28 (s, 3H), 2.25 (s, 3H), 1.46 (s, 6H), 1.33 (s, 3H). LCMS m/z [M+H]⁺ 368.2

Step 5

To a solution of 1-{12-methyl-4-[3-methyl-1-(propan-2-yl)-1H-1,2,4-triazol-5-yl]-9-oxa-3,6-iazatricyclo[8.4.0.0²,⁶]tetradeca-1(14),2,4,10,12-pentaen-13-yl}ethan-1-ol (300 mg, 0.820 mmol) in DCM (10.0 mL) and TEA (248 mg, 2.45 mmol) was added MsCl (140 mg, 1.23 mmol) dropwise at 0° C. The resulting mixture was stirred at this temperature for 3 hrs. The mixture was then poured into sat. NaHCO₃. The resulting aqueous layers were extracted with DCM (3×50 mL). The combined DCM layers were washed with brine and dried over MgSO₄. Removal of the solvent gave the crude racemic mesylate (400 mg), which was used directly in next step.

A mixture of 1-{12-methyl-4-[3-methyl-1-(propan-2-yl)-1H-1,2,4-triazol-5-yl]-9-oxa-3,6-diazatricyclo[8.4.0.0²,⁶]tetradeca-1(14),2,4,10,12-pentaen-13-yl}ethyl methanesulfonate (400 mg) and 1-tert-butylpiperazine (348 mg, 2.45 mmol) in dioxane (10.0 mL) was stirred at 100° C. for 16 hrs under N₂ atmosphere. After solvents were removed, the residue was purified by reverse phase Combi-flash eluting with a 25-29% gradient of CH₃CN in 0.3% NH₄HCO₃ to give the desired racemic product. The isolated solid was further separated by chiral SFC (OZ—H column, MeOH (0.1% DEA) isocratic) to give the two enantiomers 299 and 300.

299: First eluting peak, 25 mg, 6.0% yield. >98% ee (3.84 min, OZ—H, SFC with CH₃OH/0.1% DEA as co-solvent, 8 min). ¹H NMR (500 MHz, DMSO-d₆) δ 8.48 (s, 1H), 7.84 (s, 1H), 6.82 (s, 1H), 5.82 (brs, 1H), 4.47-4.43 (m, 4H), 3.51 (s, 1H), 2.38-2.35 (m, 8H), 2.29 (s, 3H), 2.25 (s, 3H), 1.50 (s, 3H), 1.46 (s, 3H), 1.21 (s, 3H), 0.97 (s, 9H). LCMS m/z [M+H]⁺ 492.3. LCMS 10 MIN CAD GRADIENT, 1.2 ml/min on Agilent 1200/G6110 System. Purity is 100% by UV 215.

Example 300

(S)-10-(1-(4-tert-butylpiperazin-1-yl)ethyl)-2-(1-isopropyl-3-methyl-1H-1,2,4-triazol-5-yl)-9-methyl-5,6-dihydrobenzo[f]imidazo[1,2-d][1,4]oxazepine Following the procedures of Example 299, 300 was prepared.

300: Second eluting peak, 35 mg, 9.0% yield. >98% ee (4.36 min, OZ—H, SFC with CH₃OH/0.1% DEA as co-solvent, 8 min). ¹H NMR (500 MHz, DMSO-d₆) δ 8.48 (s, 1H), 7.84 (s, 1H), 6.82 (s, 1H), 5.82 (brs, 1H), 4.47-4.43 (m, 4H), 3.51 (s, 1H), 2.38-2.35 (m, 8H), 2.29 (s, 3H), 2.25 (s, 3H), 1.50 (s, 3H), 1.46 (s, 3H), 1.21 (s, 3H), 0.97 (s, 9H). LCMS m/z [M+H]⁺ 492.3. LCMS 10 MIN CAD GRADIENT, 1.2 ml/min on Agilent 1200/G6110 System. Purity is 99% by UV 215

Example 301

9-(3-isobutyl-1-isopropyl-azetidin-3-yl)oxy-2-(2-isopropyl-5-methyl-1,2,4-triazol-3-yl)-5,6-dihydroimidazo[1,2-d][1,4]benzoxazepine 301

Step 1: 2-Bromo-2-isobutylmalonic acid diethyl ester

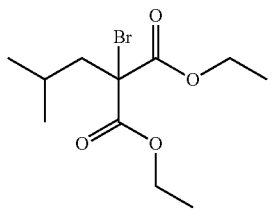 [SMILES: CCOC(=O)C(Br)(CC(C)C)C(=O)OCC]

To an ice-cooled solution of 2-isobutylmalonic acid diethyl ester (3.21 g, 14.8 mmol) in THF (50 mL) was added portionwise sodium hydride (1.19 g, 60% in oil, 29.7 mmol). The mixture was stirred in the ice bath for 15 min, and then at RT for 15 min. The suspension was re-cooled in the ice bath and NBS (2.9 g, 16.3 mmol) was added over 5 min. The mixture was stirred in the ice bath for 10 min, and then at RT for 30 min. The reaction mixture was filtered through Celite® and the filtrate concentrated in vacuo. The resulting residue was purified by column chromatography (Si-PCC, gradient 2-6% EtOAc in cyclohexane) affording the title compound as a colourless oil (3.828 g, 88%). ¹H NMR (CDCl₃, 300 MHz): δ 4.27 & 4.26 (4H, 2 q, J=7.1 Hz), 2.26 (2H, d, J=6.2 Hz) 1.95 (1H, nonet, J=6.5 Hz), 1.29 (6H, t, J=7.1 Hz), 0.94 (6H, d, J=6.7 Hz).

Step 2: 2-Isobutyl-2-[2-(2-isopropyl-5-methyl-2H-[1,2,4]triazol-3-yl)-4,5-dihydro-6-oxa-1,3a-diazabenzo[e]azulen-8-yloxy]malonic acid diethyl ester

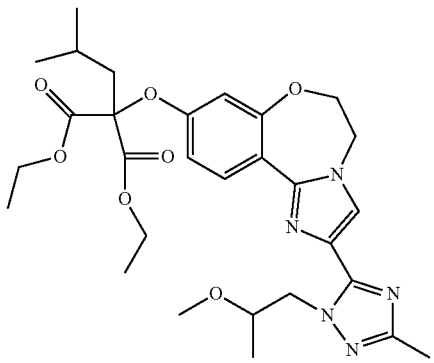 [SMILES: CCOC(=O)C(CC(C)C)(Oc1ccc2c(c1)OCCn1cc(-c3nc(C)nn3CC(C)OC)nc1-2)C(=O)OCC]

To a suspension of 2-(2-isopropyl-5-methyl-2H-[1,2,4]triazol-3-yl)-4,5-dihydro-6-oxa-1,3a-diazabenzo[e]azulen-8-ol from Example 4 (465 mg, 1.429 mmol) in DMF (8 mL) was added sodium hydride (57.2 mg, 60% in oil, 1.429 mmol). The mixture was stirred at RT for 15 min, then a solution of 2-bromo-2-isobutylmalonic acid diethyl ester (633 mg, 2.14 mmol) in DMF (1 mL) was added. The reaction mixture was stirred at 70° C. for 4 h. The cooled reaction mixture was partitioned between water and EtOAc. The aqueous phase was extracted with EtOAc. The combined organic phases were washed with water, followed by brine, then dried (Na₂SO₄) and concentrated in vacuo. The resulting residue was purified by column chromatography (Si-PCC, gradient 2-10% MeOH in DCM) affording the title compound (0.39 g, 51%). LCMS (Method B): R_T 3.96 min [M+H]⁺ 540.

Step 3: 2-Isobutyl-2-[2-(2-isopropyl-5-methyl-2H-[1,2,4]triazol-3-yl)-4,5-dihydro-6-oxa-1,3a-diazabenzo[e]azulen-8-yloxy]-propane-1,3-diol

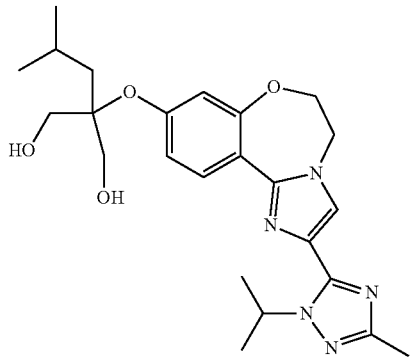 [SMILES: Cc1nc(-c2cn3c(n2)-c2ccc(OC(CO)(CO)CC(C)C)cc2OCC3)n(C(C)C)n1]

To an ice-cooled suspension of LiAlH₄ (41.3 mg, 1.09 mmol) in THF (3 mL) was added a solution of 2-isobutyl-2-[2-(2-isopropyl-5-methyl-2H-[1,2,4]triazol-3-yl)-4,5-dihydro-6-oxa-1,3a-diazabenzo[e]azulen-8-yloxy]malonic acid diethyl ester (195 mg, 0.362 mmol) in THF (2 mL). The reaction mixture was stirred at RT for 1.5 h. To the reaction mixture was added EtOAc (1 mL) and stirring was continued for 10 min. An aqueous solution of Rochelle salt's and EtOAc were then added and stirring continued for a further 1 h. The mixture was filtered through a Celite® pad and the aqueous phase was extracted with EtOAc. The combined organic phases were washed with brine, then dried (Na₂SO₄) and concentrated in vacuo. The resulting residue was purified by column chromatography (Si-PCC, gradient 4-14% MeOH in DCM) affording the title compound as a colourless gum (88.6 mg, 54%). LCMS (Method B): $R_T$ 2.87 min [M+H]⁺ 456.

Step 4: Methanesulfonic acid 2-[2-(2-isopropyl-5-methyl-2H-[1,2,4]triazol-3-yl)-4,5-dihydro-6-oxa-1,3a-diazabenzo[e]azulen-8-yloxy]-2-methanesulfonyloxymethyl-4-methylpentyl ester

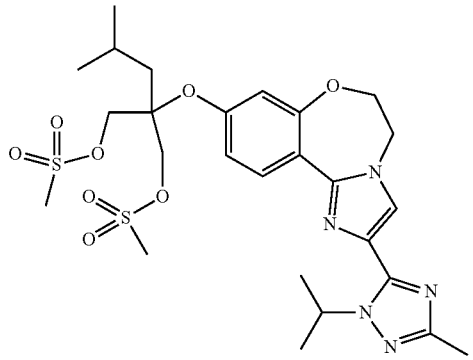 [SMILES: Cc1nc(-c2cn3c(n2)-c2ccc(OC(COS(C)(=O)=O)(COS(C)(=O)=O)CC(C)C)cc2OCC3)n(C(C)C)n1]

To a solution of 2-isobutyl-2-[2-(2-isopropyl-5-methyl-2H-[1,2,4]triazol-3-yl)-4,5-dihydro-6-oxa-1,3a-diazabenzo[e]azulen-8-yloxy]-propane-1,3-diol (88.6 mg, 0.194 mmol) and Et₃N (81.1 µL, 0.582 mmol) in DCM (10 mL) cooled at 0° C. was added methanesulfonyl chloride (37.9 µL, 0.485 mmol) and stirring at RT was continued for 1.5 h. The mixture was diluted with DCM, washed with a saturated solution of NaHCO₃, followed by water, then dried (Na₂SO₄) and concentrated in vacuo affording the title compound as a colourless gum (quantitative). LCMS (Method B): $R_T$ 3.46 min [M+H]⁺ 612.

Step 5

A solution of methanesulfonic acid 2-[2-(2-isopropyl-5-methyl-2H-[1,2,4]triazol-3-yl)-4,5-dihydro-6-oxa-1,3a-diazabenzo[e]azulen-8-yloxy]-2-methanesulfonyloxymethyl-4-methylpentyl ester (194 mmol) in isopropylamine (2 mL) was heated at 150° C. for 33 h using microwave irradiation. After cooling to RT, the crude reaction mixture was evaporated and then purified by column chromatography (C₁₈, gradient 30-55% MeOH in 0.5% TFA/H₂O) and then loaded onto an Isolute® SCX-2 cartridge. The cartridge was washed with MeOH and the product eluted with 0.5M NH₃/MeOH affording 301 as a colourless foam (95 mg, 100% over 2 steps). LCMS (Method K): $R_T$ 3.29 min [M+H]⁺ 479.2. ¹H NMR (CD₃OD, 400 MHz): δ 8.41 (1H, d, J=9.0 Hz), 7.69 (1H, s), 6.67 (1H, bd, J=9.0 Hz), 6.51 (1H, bs), 5.84 (1H, septet, J=6.6 Hz), 4.51 (4H, s), 4.44-4.37 (4H, m), 3.49-3.42 (1H, m), 2.36 (3H, s), 2.17 (2H, d, J=6.9 Hz), 1.72 (1H, nonet, J=6.8 Hz), 1.52 (6H, d, J=6.6 Hz), 1.25 (6H, d, J=6.5 Hz), 0.92 (6H, d, J=6.8 Hz)

Example 303

(S)-10-(1-(4-tert-butylpiperazin-1-yl)ethyl)-2-(1-isopropyl-3-methyl-1H-1,2,4-triazol-5-yl)-5,6-dihydroimidazo[1,2-d]pyrido[4,3-f][1,4]oxazepine 303

Step 1: 13-Chloro-4-[3-methyl-1-(propan-2-yl)-1H-1,2,4-triazol-5-yl]-9-oxa-3,6,12-triazatricyclo[8.4.0.0²,⁶]tetradeca-1(14),2,4,10,12-pentaene

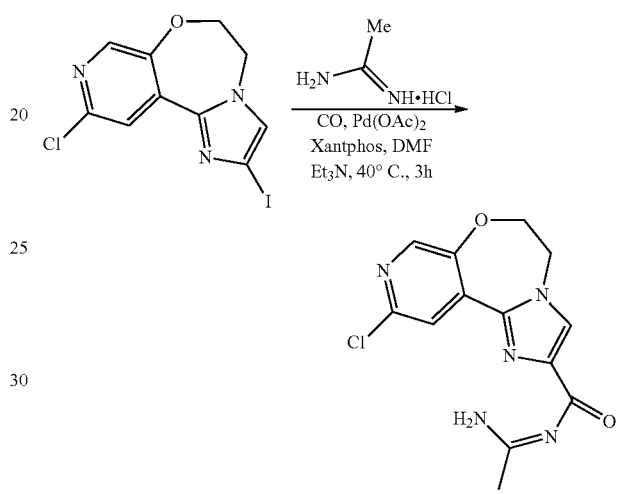

A mixture of 13-chloro-4-iodo-9-oxa-3,6,12-triazatricyclo[8.4.0.0²,⁶]tetradeca-1(14),2,4,10,12-pentaene (3.00 g, 8.63 mmol), acetamidine hydrochloride (984 mg, 10.4 mmol), Pd(OAc)₂ (194 mg, 0.870 mmol), and Xantphos (998 mg, 1.73 mmol) in DMF (20.0 mL) and TEA (5.0 mL) was heated at 40° C. under CO (1 atm) for 3 hrs. After cooling down, isopropylhydrazine hydrochloride (1.05 g, 9.50 mmol) and acetic acid (20.0 mL) were added. The resulting mixture was heated to 65° C. and stirred at this temperature for 1 hr. At the end of reaction, solvents were removed and the residue was poured into water (2000 mL). The solid was collected and washed with acetone to give the desired product (2.23 g, 73% yield) as a yellow solid. LCMS m/z [M+H]⁺ 345.2.

Step 2: 13-(1-Ethoxyethenyl)-4-[3-methyl-1-(propan-2-yl)-1H-1,2,4-triazol-5-yl]-9-oxa-3,6,12-triazatricyclo[8.4.0.0²,⁶]tetradeca-1(14),2,4,10,12-pentaene

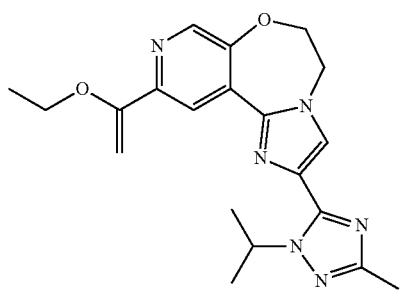 [SMILES: C=C(OCC)c1cc2c(cn1)OCCn1cc(-c3nc(C)nn3C(C)C)nc1-2]

A mixture of 13-chloro-4-[3-methyl-1-(propan-2-yl)-1H-1,2,4-triazol-5-yl]-9-oxa-3,6,12-triazatricyclo[8.4.0.0²,⁶]tetradeca-1(14),2,4,10,12-pentaene (1.60 g, 4.64 mmol), tributyl(1-ethoxyvinyl)stannane (1.70 g, 4.71 mmol), LiCl (585 mg, 13.9 mmol), and Pd(PPh$_3$)$_4$ (537 mg, 0.460 mmol) in THF (30 mL) in a sealed tube was stirred at 80° C. for 48 hrs under N$_2$ atmosphere. After being cooled to room temperature, aq. KF (2.0 M, 50 mL) was added. The resulting mixture was stirred at room temperature for 1 h and then filtered. The filtrate was extracted with ethyl acetate (5×50 mL). The combined organic layers were washed brine and dried over MgSO$_4$. Removal of the solvent gave the desired product (900 mg, 51% yield) as a yellow solid. $^1$H NMR (500 MHz, DMSO-d$_6$) δ 8.63 (s, 1H), 8.35 (s, 1H), 8.04 (s, 1H), 5.90 (m, 1H), 5.30 (s, 1H), 4.64-4.60 (m, 4H), 4.39 (s, 1H), 3.95-3.94 (m, 2H), 2.27 (s, 3H), 1.51-1.48 (m, 6H), 1.42-1.39 (m, 3H). LCMS m/z [M+H]$^+$ 381.3

Step 3: 1-{4-[3-Methyl-1-(propan-2-yl)-1H-1,2,4-triazol-5-yl]-9-oxa-3,6,12-triazatricyclo[8.4.0.0$^{2,6}$]tetradeca-1(14),2,4,10,12-pentaen-13-yl}ethan-1-one

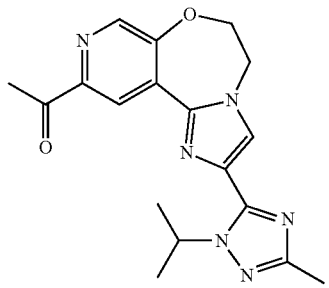 [SMILES: CC(=O)c1cc2c(cn1)OCCn1cc(-c3nc(C)nn3C(C)C)nc1-2]

A mixture of 13-(1-ethoxyethenyl)-4-[3-methyl-1-(propan-2-yl)-1H-1,2,4-triazol-5-yl]-9-oxa-3,6,12-triazatricyclo[8.4.0.0$^{2,6}$]tetradeca-1(14),2,4,10,12-pentaene (900 mg, 2.36 mmol) and 4-methylbenzenesulfonic acid (204 mg, 1.18 mmol) in acetone (20 mL) was stirred at 60° C. for 75 min. After removal of the solvent, the residue was purified by reverse phase Combi-flash eluting with a 23-27% gradient of CH$_3$CN in 0.3% NH$_4$HCO$_3$ to give the desired product (650 mg, 74% yield) as a pale yellow solid. $^1$H NMR (500 MHz, DMSO-d$_6$) δ 8.85 (s, 1H), 8.49 (s, 1H), 8.07 (s, 1H), 5.69 (m, 1H), 4.68-4.59 (m, 4H), 2.63 (s, 3H), 2.29 (s, 3H), 1.49 (s, 6H). LCMS m/z [M+H]$^+$ 353.3

Step 4: 1-{4-[3-Methyl-1-(propan-2-yl)-1H-1,2,4-triazol-5-yl]-9-oxa-3,6,12-triazatricyclo[8.4.0.0$^{2,6}$]tetradeca-(14),2,4,10,12-pentaen-13-yl}ethan-1-ol

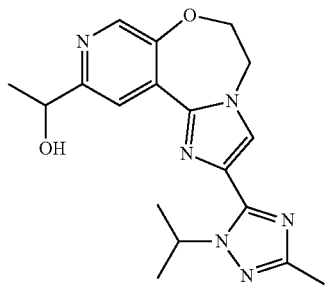 [SMILES: Cc1nc(-c2cn3c(n2)-c2cc(C(C)O)ncc2OCC3)n(C(C)C)n1]

To a solution of 1-{4-[3-methyl-1-(propan-2-yl)-1H-1,2,4-triazol-5-yl]-9-oxa-3,6,12-triazatricyclo[8.4.0.0$^{2,6}$]tetradeca-1(14),2,4,10,12-pentaen-13-yl}ethan-1-one (400 mg, 1.14 mmol) in MeOH (20.0 mL) was added NaBH$_4$ (173 mg, 4.55 mmol). The mixture was stirred at room temperature for 2 hrs. Water was added to quench the reaction. The resulting mixture was extracted with ethyl acetate (3×50 mL). The combined organic layers were washed with brine and dried over MgSO$_4$. After removal of the solvent, the residue was purified by reverse phase Combi-flash eluting with a 20-25% gradient of CH$_3$CN in 0.3% NH$_4$HCO$_3$ to give the desired racemic product (175 mg, 44% yield). $^1$H NMR (500 MHz, CD$_3$OD) δ 8.52 (s, 1H), 8.27 (s, 1H), 7.84 (s, 1H), 5.89 (m, 1H), 4.85 (m, 1H), 4.61-4.55 (m, 4H), 2.36 (s, 3H), 1.54 (dd, J=4.5 Hz, 6.0 Hz, 6H), 1.48 (d, J=6.0 Hz, 3H). LCMS m/z [M+H]$^+$ 355.3

Step 5

To a solution of 1-{4-[3-methyl-1-(propan-2-yl)-1H-1,2,4-triazol-5-yl]-9-oxa-3,6,12-triazatricyclo[8.4.0.0$^{2,6}$]tetradeca-(14),2,4,10,12-pentaen-13-yl}ethan-1-ol (175 mg, 0.490 mmol) and TEA (150 mg, 1.48 mmol) in DCM (10.0 mL) was added MsCl (85.0 mg, 0.740 mmol) dropwise at 0° C. After being stirred at this temperature for another 3 hrs, the mixture was poured into sat. NaHCO$_3$. The organic layer was further washed with sat. NaHCO$_3$ (3×30 mL). The aqueous layers were combined and extracted with DCM (3×50 mL). The combined DCM layers were washed with brine and then dried over MgSO$_4$. Removal of the solvent gave the crude, racemic mesylate (240 mg). which was used in the next step without purification.

Step 6

A mixture of 1-{4-[3-methyl-1-(propan-2-yl)-1H-1,2,4-triazol-5-yl]-9-oxa-3,6,12-triazatricyclo[8.4.0.0$^{2,6}$]tetradeca-1(14),2,4,10,12-pentaen-13-yl}ethyl methanesulfonate (240 mg) and 1-tert-butylpiperazine (281 mg, 1.97 mmol) in dioxane (5.00 mL) was stirred at 100° C. for 16 hrs under N$_2$ atmosphere. After removal of the solvents, the residue was purified with reverse phase Combi-flash eluting with a 20-28% gradient of CH$_3$CN in 0.3% NH$_4$HCO$_3$ to afford the desired product. The isolated solid was further separated by chiral SFC (AD-H column, EtOH (0.1% DEA) isocratic) to give the two enantiomers 303 and 305.

303: First eluting peak, 31 mg, 13% yield. >95% ee (5.08 min, AD-H, SFC with EtOH/0.1% DEA as co-solvent, 8 min). $^1$H NMR (500 MHz, DMSO-d$_6$) δ 8.35 (s, 1H), 8.30 (s, 1H), 8.01 (s, 1H), 5.77 (m, 1H), 4.59-4.55 (m, 4H), 3.58 (s, 1H), 2.50-2.42 (m, 8H), 2.26 (s, 3H), 1.51-1.47 (m, 6H), 1.30-1.28 (m, 3H), 0.96 (s, 9H). LCMS m/z [M+H]$^+$ 479.3. LCMS 10 MIN CAD GRADIENT, 1.2 ml/min on Agilent 1200/G6110 System. Purity is 100% by UV 215.

Example 305

(R)-10-(1-(4-tert-butylpiperazin-1-yl)ethyl)-2-(1-isopropyl-3-methyl-1H-1,2,4-triazol-5-yl)-5,6-dihydroimidazo[1,2-d]pyrido[4,3-f][1,4]oxazepine 305

Following the procedures of Example 303, 305 was prepared.

305: Second eluting peak, 25 mg, pale yellow solid, 11% yield. >95% ee (5.65 min, AD-H, SFC with EtOH/0.1% DEA as co-solvent, 8 min). $^1$H NMR (500 MHz, DMSO-d$_6$) δ 8.35 (s, 1H), 8.30 (s, 1H), 8.01 (s, 1H), 5.77 (m, 1H), 4.59-4.55 (m, 4H), 3.58 (s, 1H), 2.50-2.42 (m, 8H), 2.26 (s, 3H), 1.51-1.47 (m, 6H), 1.30-1.28 (m, 3H), 0.96 (s, 9H). LCMS m/z [M+H]$^+$ 479.3. LCMS 10 MIN CAD GRADIENT, 1.2 ml/min on Agilent 1200/G6110 System. Purity is 97% by UV 215

Example 342

2-(1-isopropyl-3-methyl-1H-1,2,4-triazol-5-yl)-9-(2-((R)-1-isopropylpiperidin-3-yl)azetidin-1-yl)-5,6-dihydrobenzo[f]imidazo[1,2-d][1,4]oxazepine 342

Step 1: (S)-34(E)-2-Ethoxycarbonylvinyl)piperidine-1-carboxylic acid benzyl ester

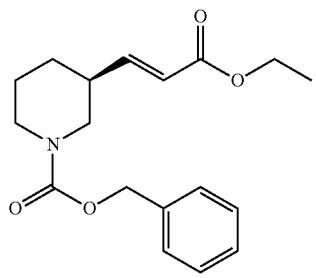 [SMILES: CCOC(=O)/C=C/[C@@H]1CCCN(C(=O)OCc2ccccc2)C1]

To a stirred mixture of triethyl phosphonoacetate (0.481 mL, 2.43 mmol), lithium chloride (0.103 g, 2.43 mmol) and DIPEA (0.346 mL, 2.02 mmol) in CH$_3$CN (20 mL) was added a solution of (R)-3-formylpiperidine-1-carboxylic acid benzyl ester (WO 2002/046157) (0.50 g, 2.02 mmol) in CH$_3$CN (2 mL). Stirring was continued for 2.5 h and then the mixture was concentrated in vacuo. The residue was partitioned between 1M sodium hydrogen sulfate and EtOAc. The aqueous phase was extracted with EtOAc. The combined organic phases were washed with water, followed by brine, then dried (Na$_2$SO$_4$) and concentrated in vacuo. The resulting residue was purified by column chromatography (Si-PCC, gradient 10-30% EtOAc in cyclohexane) affording the title compound (0.4656 g, 73%) as a colourless oil. LCMS (Method B): R$_T$ 3.81 min [M+H]$^+$ 318.

Step 2: (R)-3-(1-Allylamino-2-ethoxycarbonylethyl)piperidine-1-carboxylic acid benzyl ester

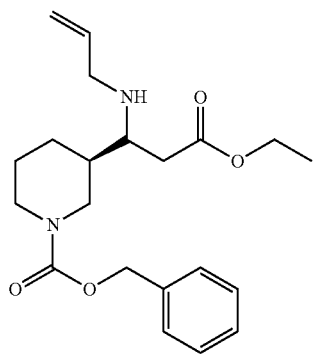 [SMILES: C=CCNC(CC(=O)OCC)[C@@H]1CCCN(C(=O)OCc2ccccc2)C1]

A mixture of (S)-34(E)-2-ethoxycarbonylvinyl)piperidine-1-carboxylic acid benzyl ester (0.391 g, 1.23 mmol) and allylamine (3.0 mL) was stirred at RT for 3 days and then evaporated under a nitrogen stream. The residue was purified by column chromatography (Si-PCC, gradient 1-3% 2M NH$_3$/MeOH in DCM) affording the title compound (0.4431 g, 96%) as a colourless oil. LCMS (Method B): R$_T$ 2.34 min [M+H]$^+$ 375.

Step 3: (R)-3-(1-Allylamino-3-hydroxypropyl)piperidine-1-carboxylic acid benzyl ester

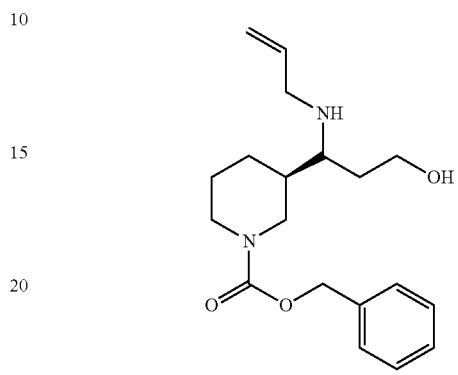

To a solution of (R)-3-(1-allylamino-2-ethoxycarbonylethyl)piperidine-1-carboxylic acid benzyl ester (0.427 g, 1.14 mmol) in THF (20 mL) was added a solution of lithium borohydride in THF (2M, 5.7 mL, 11.4 mmol). The mixture was stirred at RT for 10 min then at 40° C. for 22 h. After cooling to RT, water was added with initial caution. The mixture was extracted twice with EtOAc, and the combined organic phases were washed with water, followed by brine, then dried (Na$_2$SO$_4$) and concentrated in vacuo. The resulting residue was purified by column chromatography (Si-PCC, gradient 2-8% 2M NH$_3$/MeOH in DCM) affording the title compound (0.264 g, 70%) as a colourless gum. LCMS (Method B): R$_T$ 2.00 min [M+H]$^+$ 333.

Step 4: (R)-3-(1-Allylamino-3-methanesulfonyloxypropyl)piperidine-1-carboxylic acid benzyl ester

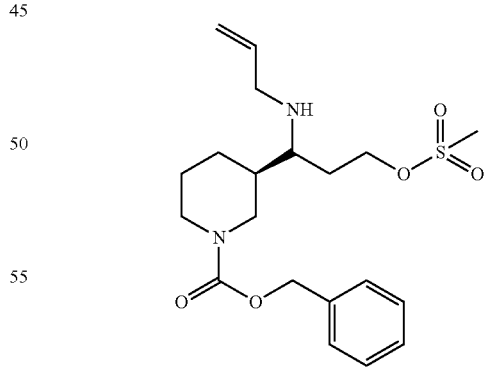

To a solution of (R)-3-(1-allylamino-3-hydroxypropyl)piperidine-1-carboxylic acid benzyl ester (0.264 g, 0.794 mmol) in DCM (15 mL) cooled at 0° C. was added successively methanesulfonyl chloride (68 μL, 0.873 mmol) and Et$_3$N (0.133 mL, 0.953 mmol). The mixture was stirred at RT for 1.5 h, and then diluted with DCM, washed with a saturated solution of NaHCO$_3$, followed by water, then dried (Na$_2$SO$_4$)

and concentrated in vacuo affording the title compound as a colourless gum (quantitative). LCMS (Method B): $R_T$ 2.14 min [M+H]$^+$ 411.

Step 5: (R)-3-(1-Allylazetidin-2-yl)piperidine-1-carboxylic acid benzyl ester

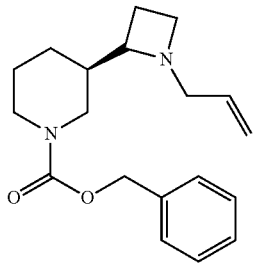 [SMILES: C=CCN1CCC1[C@@H]1CCCN(C(=O)OCc2ccccc2)C1]

A solution of (R)-3-(1-allylamino-3-methanesulfonyloxypropyl)piperidine-1-carboxylic acid benzyl ester (326 mg, 0.794 mmol) in CH$_3$CN (12 mL) was heated at 100° C. for 1 h using microwave irradiation. After cooling to RT, the reaction mixture was concentrated in vacuo. The residue was partitioned between 2M sodium carbonate and EtOAc. The aqueous phase was extracted with EtOAc. The combined organic phases were washed with brine, then dried (Na$_2$SO$_4$) and concentrated in vacuo. The resulting residue was purified by column chromatography (Si-PCC, gradient 2-5% 2M NH$_3$/MeOH in DCM) affording the title compound (0.2127 g, 85%, 2 steps) as a colourless gum. LCMS (Method B): $R_T$ 2.03 min [M+H]$^+$ 315.

Step 6: (R)-3-Azetidin-2-ylpiperidine-1-carboxylic acid benzyl ester

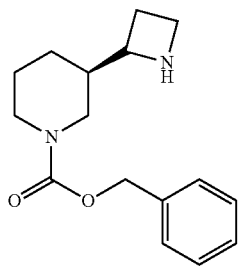 [SMILES: O=C(OCc1ccccc1)N1CCC[C@@H](C2CCN2)C1]

To a solution of (R)-3-(1-allylazetidin-2-yl)piperidine-1-carboxylic acid benzyl ester (163 mg, 0.518 mmol) in DCM (10 mL) was added 1,3-dimethylbarbituric acid (243 mg, 1.56 mmol) and Pd(PPh$_3$)$_4$ (60 mg, 0.052 mmol). The mixture was stirred at RT for 64 h, then diluted with MeOH and loaded onto an Isolute® SCX-2 cartridge. The cartridge was washed with MeOH and the product eluted with 0.5M NH$_3$/MeOH. Further purification by column chromatography (Si-PCC, gradient 3-15% 2M NH$_3$/MeOH in DCM) afforded the title compound (126.5 mg, 89%) as a colourless oil. LCMS (Method B): $R_T$ 1.99 & 2.07 min [M+H]$^+$ 275.

Step 7: (R)-3-{1-[2-(2-Isopropyl-5-methyl-2H-[1,2,4]triazol-3-yl)-4,5-dihydro-6-oxa-1,3a-diazabenzo[e]azulen-8-yl]azetidin-2-yl}piperidine-1-carboxylic acid benzyl ester and 2-(2-Isopropyl-5-methyl-2H-[1,2,4]triazol-3-yl)-84(R)-2-piperidin-3-ylazetidin-1-yl)-4,5-dihydro-6-oxa-1,3a-diazabenzo[e]azulene

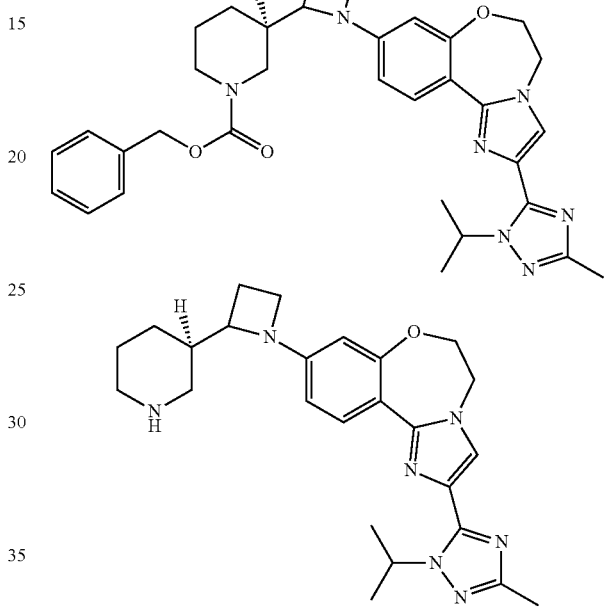

A mixture of (R)-3-azetidin-2-ylpiperidine-1-carboxylic acid benzyl ester (103 mg, 0.375 mmol), 9-bromo-2-(2-isopropyl-2H-[1,2,4]triazol-3-yl)-4,5-dihydro-6-oxa-1,3a-diazabenzo[e]azulene (97.3 mg, 0.25 mmol), bis(tri-tert-butylphosphine)palladium(0) (6.5 mg, 0.0125 mmol), sodium tert-butoxide (72 mg, 0.75 mmol) and dioxane (3 mL) was heated in a sealed vial at 100° C. for 16 h. The cooled reaction mixture was partitioned between water and EtOAc. The aqueous phase was extracted with EtOAc. The combined organic phases were washed with water, followed by brine, then dried (Na$_2$SO$_4$) and concentrated in vacuo. The resulting residue was purified by column chromatography (Si-PCC, gradient 2-8% MeOH in DCM, then 8-15% 2M NH$_3$/MeOH in DCM). The earlier eluting component, (R)-3-{1-[2-(2-Isopropyl-5-methyl-2H-[1,2,4]triazol-3-yl)-4,5-dihydro-6-oxa-1,3a-diazabenzo[e]azulen-8-yl]azetidin-2-yl}piperidine-1-carboxylic acid benzyl ester (66.8 mg, 46%), was obtained as a colourless gum. LCMS (Method B): $R_T$ 3.77 & 3.81 min [M+H]$^+$ 582. The later eluting component, 2-(2-Isopropyl-5-methyl-2H-[1,2,4]triazol-3-yl)-84(R)-2-piperidin-3-ylazetidin-1-yl)-4,5-dihydro-6-oxa-1,3a-diazabenzo[e]azulene (64.3 mg, 57%), was obtained as a colourless gum and carried forward to Step 8. LCMS (Method B): $R_T$ 2.03 & 2.08 min [M+H]$^+$ 448

Step 8

To a solution of 2-(2-isopropyl-5-methyl-2H-[1,2,4]triazol-3-yl)-8-((R)-2-piperidin-3-ylazetidin-1-yl)-4,5-dihydro- 6-oxa-1,3a-diazabenzo[e]azulene (64.3 mg, 0.1436 mmol) in a mixture of IMS (5 mL) and acetone (1 mL) was added Pd/C (10%, 15 mg). The mixture was stirred at RT under a balloon of hydrogen for 16 h, then filtered through a celite pad. The filtrate was concentrated in vacuo. The resulting residue was purified by column chromatography (Si-PCC, gradient 2-15% 2M NH$_3$/MeOH in DCM), then C$_{18}$, gradient 20-60% MeOH in 0.5% TFA/H$_2$O) and then loaded in MeOH onto an Isolute® SCX-2 cartridge. The cartridge was washed with MeOH and the product eluted with 0.5M NH$_3$/MeOH, affording 342 as a colourless foam (28 mg, 40%). LCMS (method K): R$_T$ 2.97 min [M+H]$^+$ 490.2. $^1$H NMR (CD$_3$OD, 400 MHz): δ 8.21 (1H, dd, J=8.7, 2.0 Hz), 7.61 (1H, s), 6.36-6.32 (1H, m), 6.13 (1H, dd, J=5.5, 2.3 Hz), 5.85 (1H, septet, J=6.6 Hz), 4.43 (4H, s), 4.10-3.91 (2H, m), 3.64 (1H, quintet, J=7.9 Hz), 3.06-2.87 (2H, m), 2.75 (1H, septet, J=6.4 Hz), 2.35 (3H, s), 2.33-2.08 (5H, m), 1.85-1.56 (3H, m), 1.51 (6H, d, J=6.6 Hz), 1.98 (0.5H, d, J=10.8 Hz), 1.25-1.11 (1H, m), 1.09 & 1.07 (6H, 2d, J=6.6 Hz)

Example 356

(R)-10-(1-(4-tert-butylpiperazin-1-yl)ethyl)-2-(1-isopropyl-3-methyl-1H-1,2,4-triazol-5-yl)-9-methoxy-5,6-dihydrobenzo[f]imidazo[1,2-d][1,4]oxazepine 356

Step 1: 12-(Benzyloxy)-13-bromo-4-[3-methyl-1-(propan-2-yl)-1H-1,2,4-triazol-5-yl]-9-oxa-3,6-diazatricyclo[8.4.0.0$^{2,6}$]tetradeca-1(14),2,4,10,12-pentaene

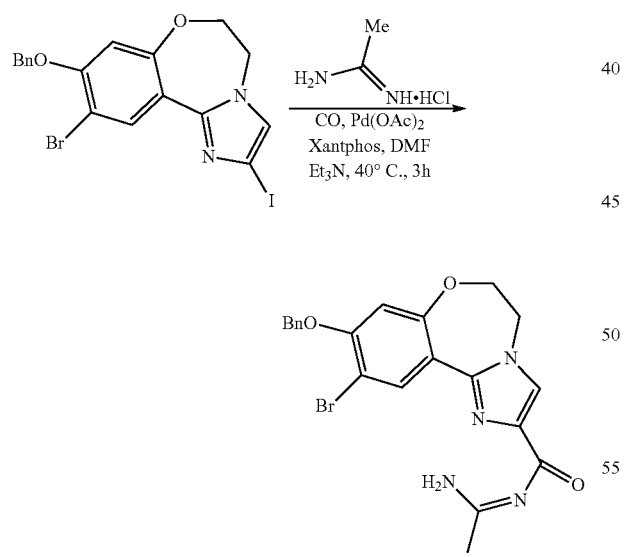

A mixture of 12-(benzyloxy)-13-bromo-4-iodo-9-oxa-3,6-diazatricyclo[8.4.0.0$^{2,6}$]tetradeca-1(14),2,4,10,12-pentaene (6.13 g, 12.3 mmol), acetamidine hydrochloride (1.29 g, 13.6 mmol), Pd(OAc)$_2$ (277 mg, 1.24 mmol), and Xantphos (1.43 g, 2.47 mmol) in DMF (20.0 mL) and TEA (5.0 mL) was heated at 40° C. under CO (1 atm) for 3 hrs. After cooling down, isopropylhydrazine hydrochloride (1.64 g, 14.8 mmol) and acetic acid (20.0 mL) were added. The resulting mixture was heated to 65° C. and stirred at this temperature for 1 hr. After removal of the solvent, the residue was poured into water (2000 mL). The solid was collected by filtration and washed with acetone to give the desired product (5.5 g, 90% yield) as a yellow solid. LCMS m/z [M+H]$^+$ 494.1.

Step 2: 13-Bromo-4-[3-methyl-1-(propan-2-yl)-1H-1,2,4-triazol-5-yl]-9-oxa-3,6-diazatricyclo[8.4.0.0$^{2,6}$]tetradeca-1(14),2,4,10,12-pentaen-12-ol

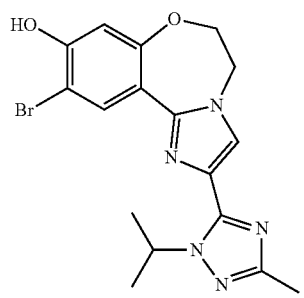 [SMILES: Cc1nc(-c2cn3c(n2)-c2cc(Br)c(O)cc2OCC3)n(C(C)C)n1]

A solution of 12-(benzyloxy)-13-bromo-4-[3-methyl-1-(propan-2-yl)-1H-1,2,4-triazol-5-yl]-9-oxa-3,6-diazatricyclo[8.4.0.0$^{2,6}$]tetradeca-1(14),2,4,10,12-pentaene (5.50 g, 11.1 mmol) in trifluoroacetic acid (20 mL) was heated to reflux for 1 h. After cooling down, the mixture was concentrated to give the crude product (5.5 g), which was used directly in the next step without further purification. LCMS m/z [M+H]$^+$ 404.1.

Step 3: 13-Bromo-12-methoxy-4-[3-methyl-1-(propan-2-yl)-1H-1,2,4-triazol-5-yl]-9-oxa-3,6-diazatricyclo[8.4.0.0$^{2,6}$]tetradeca-1(14),2,4,10,12-pentaene

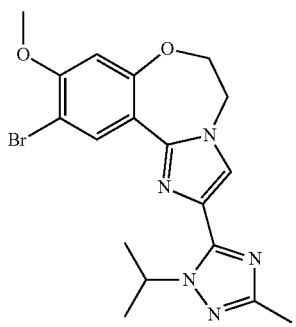 [SMILES: COc1cc2c(cc1Br)-c1nc(-c3nc(C)nn3C(C)C)cn1CCO2]

To a solution of 13-bromo-4-[3-methyl-1-(propan-2-yl)-1H-1,2,4-triazol-5-yl]-9-oxa-3,6-diazatricyclo[8.4.0.0$^{2,6}$]tetradeca-1(14),2,4,10,12-pentaen-12-ol (5.5 g) in acetone (30 mL) was added K$_2$CO$_3$ (3.03 g, 22.0 mmol) and methyl iodide (1.87 g, 13.1 mmol). The mixture was stirred at room temperature for 16 h. The mixture was concentrated and diluted with ethyl acetate (50 mL). After removal of the solvent, the residue was purified by silica gel chromatography using 1-10% MeOH in DCM as eluant to afford the desired product (3.0 g, 65% yield for two steps). LCMS m/z [M+H]+ 418.1.

Step 4: 13-(1-Ethoxyethenyl)-12-methoxy-4-[3-methyl-1-(propan-2-yl)-1H-1,2,4-triazol-5-yl]-9-oxa-3,6-diazatricyclo[8.4.0.0²,⁶]tetradeca-1(14),2,4,10,12-pentaene

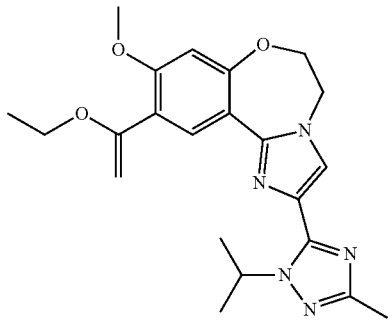 [SMILES: C=C(OCC)c1cc2c(cc1OC)OCCn1cc(-c3nc(C)nn3C(C)C)nc1-2]

A mixture of 13-bromo-12-methoxy-4-[3-methyl-1-(propan-2-yl)-1H-1,2,4-triazol-5-yl]-9-oxa-3,6-diazatricyclo[8.4.0.0²,⁶]tetradeca-1(14),2,4,10,12-pentaen (1.55 g, 3.73 mmol), tributyl(1-ethoxyvinyl)stannane (1.35 g, 3.74 mmol), LiCl (472 mg, 11.2 mmol), and Pd(PPh₃)₄ (130 mg, 0.120 mmol) in THF (30 mL) in a sealed tube was stirred at 80° C. for 16 hrs under N₂ atmosphere. After cooling to room temperature, aq. KF (2.0 M, 50.0 mL) was added. The resulting mixture was stirred at room temperature for 1 h and then filtered. The filtrate was extracted with ethyl acetate (5×50 mL). The combined organic layers were washed with brine and dried over MgSO₄. Removal of the solvent gave the desired product (2.0 g) as pale yellow oil. LCMS m/z [M+H]+ 410.3

Step 5: 1-{12-Methoxy-4-[3-methyl-1-(propan-2-yl)-1H-1,2,4-triazol-5-yl]-9-oxa-3,6-diazatricyclo[8.4.0.0²,⁶]tetradeca-1(14),2,4,10,12-pentaen-13-yl}ethan-1-one

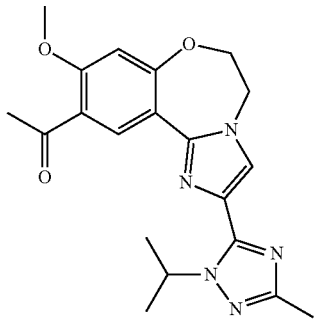 [SMILES: COc1cc2c(cc1C(C)=O)-c1nc(-c3nc(C)nn3C(C)C)cn1CCO2]

A mixture of 13-(1-ethoxyethenyl)-12-methoxy-4-[3-methyl-1-(propan-2-yl)-1H-1,2,4-triazol-5-yl]-9-oxa-3,6-diazatricyclo[8.4.0.0²,⁶]tetradeca-1(14),2,4,10,12-pentaene (2.00 g) and 4-methylbenzenesulfonic acid (438 mg, 2.54 mmol) in acetone (20.0 mL) was stirred at 60° C. for 75 min. After removal of the solvent, the residue was purified by silica gel chromatography using 1-10% MeOH in DCM as eluant to afford the desired product (1.14 g, 80% yield for two steps). LCMS m/z [M+H]+ 382.3

Step 6: Rₛ—N-[(1E)-1-{12-Methoxy-4-[3-methyl-1-(propan-2-yl)-1H-1,2,4-triazol-5-yl]-9-oxa-3,6-diazatricyclo[8.4.0.0²,⁶]tetradeca-1(14),2,4,10,12-pentaen-13-yl}ethylidene]-2-methylpropane-2-sulfinamide

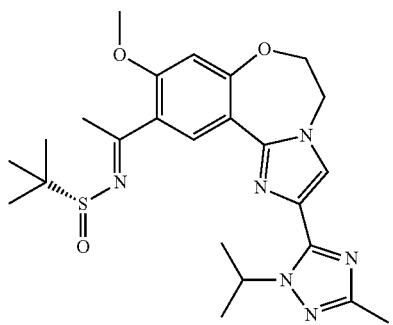 [SMILES: COc1cc2c(cc1/C(C)=N/[S@](=O)C(C)(C)C)-c1nc(-c3nc(C)nn3C(C)C)cn1CCO2]

To a solution of 1-{12-methoxy-4-[3-methyl-1-(propan-2-yl)-1H-1,2,4-triazol-5-yl]-9-oxa-3,6-diazatricyclo[8.4.0.0²,⁶]tetradeca-1(14),2,4,10,12-pentaen-13-yl}ethan-1-one (92 mg, 0.24 mmol) and R-tert-butanesulfinamide (44 mg, 0.36 mmol) in anhydrous toluene (1.0 mL), was added Ti(OEt)₄ (0.20 mL, 0.96 mmol). The mixture was heated at 100° C. for 16 h under an argon atmosphere. Water (2.5 mL) was then added with rapid stirring. The resulting mixture was filtered through a pad of Celite and the filter cake was washed with CH₂Cl₂. The organic phase was washed with brine, dried over Na₂SO₄, and concentrated. The residue was purified by silica gel column chromatography using 3% MeOH in CH₂Cl₂ as eluant to give the desired product (80 mg, 69% yield) as a pale yellow solid. LCMS m/z [M+H]+ 485.3

Step 7: Rₛ—N-[(1R)-1-{12-Methoxy-4-[3-methyl-1-(propan-2-yl)-1H-1,2,4-triazol-5-yl]-9-oxa-3,6-diazatricyclo[8.4.0.0²,⁶]tetradeca-1(14),2,4,10,12-pentaen-13-yl}ethyl]-2-methylpropane-2-sulfinamide

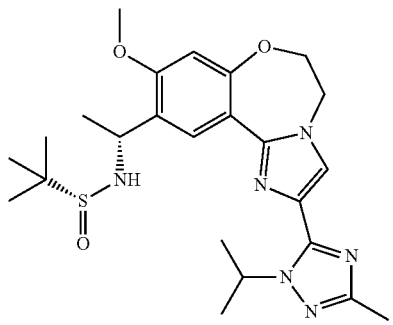 [SMILES: COc1cc2c(cc1[C@@H](C)N[S@](=O)C(C)(C)C)-c1nc(-c3nc(C)nn3C(C)C)cn1CCO2]

To a solution of Rs-N-[(1E)-1-{12-methoxy-4-[3-methyl-1-(propan-2-yl)-1H-1,2,4-triazol-5-yl]-9-oxa-3,6-diazatricyclo[8.4.0.0²,⁶]tetradeca-1(14),2,4,10,12-pentaen-13-yl}ethylidene]-2-methylpropane-2-sulfinamide (80 mg, 0.16 mmol) in THF (1.0 mL) under an argon atmosphere at −78° C., was added a solution of DIBAL-H (1 M solution in hexane, 0.48 mL, 0.48 mmol) in THF (0.5 mL). The reaction mixture was stirred at −78° C. for 2.5 h and then allowed it warm to room temperature. After removal of the solvent, the residue was treated with 10% NaOH (6 mL) and extracted three times with ethyl ether. The combined organic extracts were dried over Na$_2$SO$_4$ and concentrated. The crude product was purified by reverse phase Combi-flash eluting with a 0-50% gradient CH$_3$CN in 0.5% NH$_4$HCO$_3$ to give the desired product (60 mg, 75% yield) as a white solid. LCMS m/z [M+H]$^+$ 487.2

Step 8: 1R-1-{12-Methoxy-4-[3-methyl-1-(propan-2-yl)-1H-1,2,4-triazol-5-yl]-9-oxa-3,6-diazatricyclo[8.4.0.0$^{2,6}$]tetradeca-1(14),2,4,10,12-pentaen-13-yl}ethan-1-amine hydrochloride

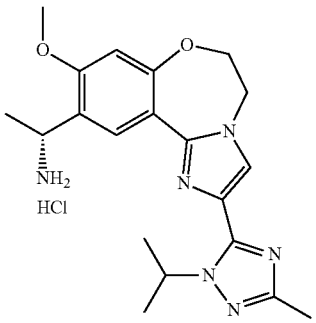 [SMILES: COc1cc2c(cc1[C@@H](C)N)-c1nc(-c3nc(C)nn3C(C)C)cn1CCO2 ; Cl]

To a solution of Rs-N-[(1R)-1-{12-methoxy-4-[3-methyl-1-(propan-2-yl)-1H-1,2,4-triazol-5-yl]-9-oxa-3,6-diazatricyclo[8.4.0.0$^{2,6}$]tetradeca-1(14),2,4,10,12-pentaen-13-yl}ethyl]-2-methylpropane-2-sulfinamide (60 mg, 0.12 mmol) in MeOH (0.50 mL) was added HCl/MeOH (4.0 M, 0.50 mL). The mixture was stirred at room temperature for 8 h and then concentrated to afford the desired product (50 mg) as a pale yellow solid, which was used directly in the next step without further purification. LCMS m/z [M+H]$^+$ 383.2

Step 9

To a mixture of the above crude 1R-1-{12-methoxy-4-[3-methyl-1-(propan-2-yl)-1H-1,2,4-triazol-5-yl]-9-oxa-3,6-diazatricyclo[8.4.0.0$^{2,6}$]tetradeca-1(14),2,4,10,12-pentaen-13-yl}ethan-1-amine hydrochloride (50 mg), K$_2$CO$_3$ (166 mg, 1.20 mmol), and KI (2.0 mg, 0.010 mmol) in acetonitrile (5 mL), was N,N-bis(2-chloroethyl)-2-methylpropan-2-amine hydrochloride (28 mg, 0.12 mmol). The resultant mixture was refluxed for 8 h. After cooling to room temperature, the inorganic materials were filtered off and the filtrate was concentrated under reduced pressure. The residue was purified by reverse phase Combi-flash eluting with a 0-50% gradient CH$_3$CN in 0.5% NH$_4$HCO$_3$ to give 356 (15 mg, 25% yield for two steps) as a white solid. >98% ee (2.48 min, OJ-H, SFC with EtOH/0.1% DEA as co-solvent, 5 min). $^1$H NMR (500 MHz, CD$_3$OD) δ 8.48 (s, 1H), 7.69 (s, 1H), 6.66 (s, 1H), 5.90 (m, 1H), 4.51 (s, 4H), 4.07 (m, 1H), 3.86 (s, 3H), 2.75-2.50 (m, 7H), 2.38 (s, 3H), 1.56 (dd, J=6.5, 2.0 Hz, 6H), 1.41 (d, J=6.5 Hz, 3H), 1.10 (m, 1H), 1.09 (s, 9H). LCMS m/z [M+H]$^+$ 508.3. LCMS 10 MIN CAD GRADIENT, 1.2 ml/min on Agilent 1200/G6110 System. Purity is 100% by UV 215

Example 357

(S)-10-(1-(4-tert-butylpiperazin-1-yl)ethyl)-2-(1-isopropyl-3-methyl-1H-1,2,4-triazol-5-yl)-9-methoxy-5,6-dihydrobenzo[f]imidazo[1,2-d][1,4]oxazepine Step 1: R$_s$—N-[(1S)-1-{12-Methoxy-4-[3-methyl-1-(propan-2-yl)-1H-1,2,4-triazol-5-yl]-9-oxa-3,6-diazatricyclo[8.4.0.0$^{2,6}$]tetradeca-1(14),2,4,10,12-pentaen-13-yl}ethyl]-2-methylpropane-2-sulfinamide

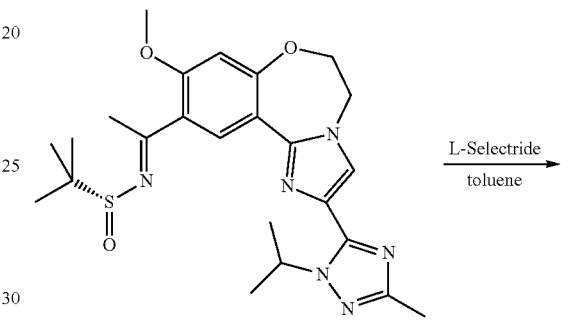

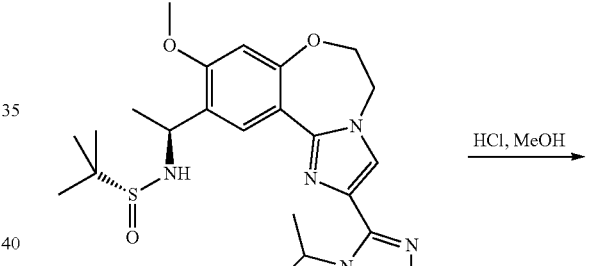

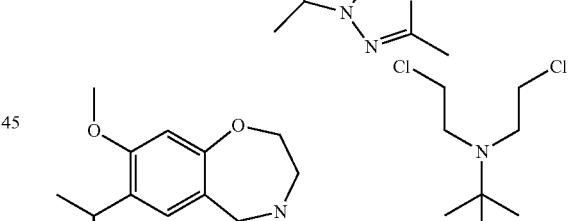

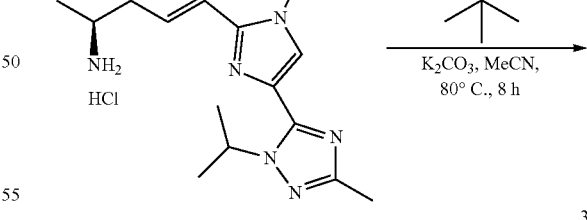

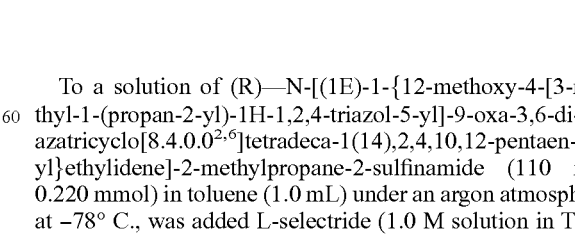

357

To a solution of (R)—N-[(1E)-1-{12-methoxy-4-[3-methyl-1-(propan-2-yl)-1H-1,2,4-triazol-5-yl]-9-oxa-3,6-diazatricyclo[8.4.0.0$^{2,6}$]tetradeca-1(14),2,4,10,12-pentaen-13-yl}ethylidene]-2-methylpropane-2-sulfinamide (110 mg, 0.220 mmol) in toluene (1.0 mL) under an argon atmosphere at −78° C., was added L-selectride (1.0 M solution in THF, 0.66 mL, 0.66 mmol). The reaction mixture was stirred at −78° C. for 2.5 h and then treated with saturated NaHCO$_3$ (1.0 mL). The mixture was extracted with ethyl acetate (3×10 mL). The combined organic extracts were dried over Na$_2$SO$_4$. After removal of the solvent, the residue was purified by reverse phase Combi-flash eluting with a 0-50% gradient CH$_3$CN in 0.5% NH$_4$HCO$_3$ to give the desired product (54 mg, 50% yield) as a white solid. LCMS m/z [M+H]$^+$ 487.2

Step 2: 1S-1-{12-Methoxy-4-[3-methyl-1-(propan-2-yl)-1H-1,2,4-triazol-5-yl]-9-oxa-3,6-diazatricyclo[8.4.0.0$^{2,6}$]tetradeca-1(14),2,4,10,12-pentaen-13-yl}ethan-1-amine hydrochloride To a solution of R$_s$—N-[(1S)-1-{12-methoxy-4-[3-methyl-1-(propan-2-yl)-1H-1,2,4-triazol-5-yl]-9-oxa-3,6-diazatricyclo[8.4.0.0$^{2,6}$]tetradeca-1(14),2,4,10,12-pentaen-13-yl}ethyl]-2-methylpropane-2-sulfinamide (54 mg, 0.11 mmol) in MeOH (0.5 mL) was added HCl/MeOH (4M, 0.4 mL). The mixture was stirred at room temperature for 8 h and then concentrated to afford the desired product (50 mg) as a pale yellow solid, which was used directly in the next step without further purification. LCMS m/z [M+H]$^+$ 383.2.

Step 3

To a mixture of the above crude 1S-1-{12-methoxy-4-[3-methyl-1-(propan-2-yl)-1H-1,2,4-triazol-5-yl]-9-oxa-3,6-diazatricyclo[8.4.0.0$^{2,6}$]tetradeca-1(14),2,4,10,12-pentaen-13-yl}ethan-1-amine hydrochloride (50 mg), K$_2$CO$_3$ (193 mg, 1.40 mmol), and KI (2.0 mg, 0.010 mmol) in acetonitrile (5.0 mL), was added N,N-bis(2-chloroethyl)-2-methylpropan-2-amine hydrochloride (33 mg, 0.14 mmol). The mixture was refluxed for 8 h. After cooling to room temperature, the inorganic materials were filtered off and the filtrate was concentrated under reduced pressure. The residue was purified by reverse phase Combi-flash eluting with a 0-50% gradient CH$_3$CN in 0.5% NH$_4$HCO$_3$ to give 357 (15 mg, 27% yield for two steps) as a white solid. $^1$H NMR (500 MHz, CD$_3$OD) δ 8.48 (s, 1H), 7.69 (s, 1H), 6.66 (s, 1H), 5.90 (m, 1H), 4.51 (s, 4H), 4.07 (m, 1H), 3.86 (s, 3H), 2.75-2.50 (m, 7H), 2.38 (s, 3H), 1.56 (dd, J=6.5, 2.0 Hz, 6H), 1.41 (d, J=6.5 Hz, 3H), 1.10 (m, 1H), 1.09 (s, 9H). LCMS m/z [M+H]$^+$ 508.3. LCMS 10 MIN CAD GRADIENT, 1.2 ml/min on Agilent 1200/G6110 System. Purity is 100% by UV 215

Example 373

9-fluoro-2-(2-isopropyl-5-methyl-1,2,4-triazol-3-yl)-10-[1-(4-methylpiperazin-1-yl)ethyl]-5,6-dihydroimidazo[1,2-d][1,4]benzoxazepine 373

A solution of 9-(1-bromoethyl)-8-fluoro-2-(2-isopropyl-5-methyl-2H-[1,2,4]triazol-3-yl)-4,5-dihydro-6-oxa-1,3a-diazabenzo[e]azulene from Example 374 (99 mg, 0.23 mmol), N-methylpiperazine (28 μL, 0.25 mmol) and DIPEA (60 μL, 0.35 mmol) in dioxane (1 mL) was stirred at RT for 72 h. The reaction mixture was concentrated in vacuo and the residue was purified by column chromatography (Si-PPC, gradient 0-8% 2 M NH$_3$/MeOH in DCM) to give 66 mg of a pale yellow oil. The compound was further purified by reverse phase column chromatography (C$_{18}$, gradient 2-50% MeOH in 1% TFA/H$_2$O) and then loaded in MeOH onto an Isolute® SCX-2 cartridge. The cartridge was washed with MeOH and the product eluted with 2 M NH$_3$ in MeOH. The basic fraction was concentrated in vacuo to afford 373 (47 mg, 40% over 2 steps) as a white solid. LCMS (Method K): R$_T$ 2.70 min [M+H]$^+$ 454.2. $^1$H NMR (CD$_3$OD, 400 MHz): δ 8.54 (1H, d, J=8.6 Hz), 7.68 (1H, s), 6.76 (1H, d, J=11.0 Hz), 5.83 (1H, sept., J=6.7 Hz), 4.49 (4H, br s), 3.84 (1H, q, J=6.8 Hz), 2.47 (8H, br s), 2.33 (3H, s), 2.22 (3H, s), 1.53 (3H, d, J=6.7 Hz), 1.52 (3H, d, J=6.7 Hz), 1.40 (3H, d, J=6.8 Hz)

Example 374

10-[1-(4-ethylpiperazin-1-yl)ethyl]-9-fluoro-2-(2-isopropyl-5-methyl-1,2,4-triazol-3-yl)-5,6-dihydroimidazo[1,2-d][1,4]benzoxazepine 374

Step 1: 8-Fluoro-2-(2-isopropyl-5-methyl-2H-[1,2,4]triazol-3-yl)-9-vinyl-4,5-dihydro-6-oxa-1,3a-diazabenzo[e]azulene

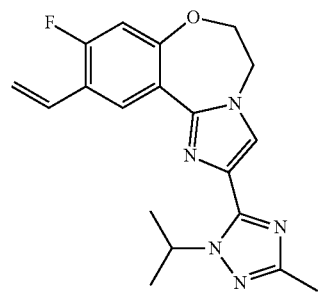 [SMILES: C=Cc1cc2c(cc1F)OCCn1cc(-c3nc(C)nn3C(C)C)nc1-2]

A degassed solution of 9-bromo-8-fluoro-2-(2-isopropyl-5-methyl-2H-[1,2,4]triazol-3-yl)-4,5-dihydro-6-oxa-1,3a-diazabenzo[e]azulene from Example 8 (5.0 g, 12.31 mmol), potassium vinyltrifluoroborate (2.47 g, 18.46 mmol), [1,1'-bis(diphenylphosphino)ferrocene]dichloropalladium (II) (1.01 g, 1.23 mmol) and triethylamine (8.58 mL, 61.55 mmol) in $^n$PrOH (50 mL) was heated to 100° C. for 2 h. The reaction mixture was concentrated in vacuo; the residue was taken up in EtOAc and filtered through celite. Organics were washed with water and brine, dried (Na$_2$SO$_4$) and concentrated in vacuo to give the title compound (3.82 g, 10.81 mmol, 88%) as a peach solid. The product was taken on without further purification. LCMS (Method J): R$_T$=3.35 min, [M+H]$^+$ =354.

Step 2: 8-Fluoro-2-(2-isopropyl-5-methyl-2H-[1,2,4]triazol-3-yl)-4,5-dihydro-6-oxa-1,3a-diazabenzo[e]azulene-9-carbaldehyde

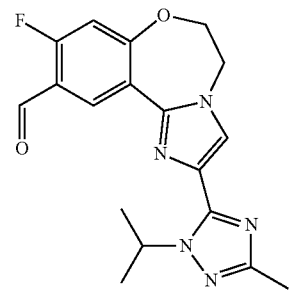 [SMILES: Cc1nc(-c2cn3c(n2)-c2cc(C=O)c(F)cc2OCC3)n(C(C)C)n1]

Osmium tetraoxide (1.8 mL of a 2.5% solution in $^t$BuOH) and sodium periodate (1.51 g, 7.08 mmol) were added to a solution of 8-fluoro-2-(2-isopropyl-5-methyl-2H-[1,2,4]triazol-3-yl)-9-vinyl-4,5-dihydro-6-oxa-1,3a-diazabenzo[e]azulene (1.0 g, 2.83 mmol) in an acetone-water mixture (5:1, 60 mL). The reaction mixture was stirred vigorously for 24 h at RT. The mixture was diluted with EtOAc (100 mL), washed with water and brine, dried (Na₂SO₄) and concentrated in vacuo to give the title compound (968 mg, 2.72 mmol, 96%) as a pale yellow oil. The product was taken on without further purification. LCMS (Method J): R_T=2.78 min, [M+H]⁺ =356

Step 3: 1-[8-Fluoro-2-(2-isopropyl-5-methyl-2H-[1,2,4]triazol-3-yl)-4,5-dihydro-6-oxa-1,3a-diazabenzo[e]azulen-9-yl]ethanol

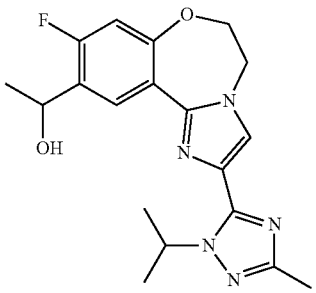 [SMILES: Cc1nc(-c2cn3c(n2)-c2cc(C(C)O)c(F)cc2OCC3)n(C(C)C)n1]

Methylmagnesium bromide (10.1 mL of a 1.4 M solution in THF/PhMe) was added to a solution of 8-fluoro-2-(2-isopropyl-5-methyl-2H-[1,2,4]triazol-3-yl)-4,5-dihydro-6-oxa-1,3a-diazabenzo[e]azulene-9-carbaldehyde (968 mg, 2.83 mmol) in THF (20 mL) at 0° C. The reaction mixture was stirred at 0° C. for 1 h and then quenched by addition of sat. NH₄Cl (10 mL). The mixture was extracted with EtOAc (3×25 mL) and the combined organics were washed (brine), dried (Na₂SO₄) and concentrated in vacuo. Compound purified by column chromatography (Si-PPC, gradient 0-5% MeOH in DCM) to give the title compound (361 mg, 0.97 mmol, 34%) as a pale brown solid. LCMS (Method J): R_T=2.53 min, [M+H]⁺=372

Step 4: 9-(1-Bromoethyl)-8-fluoro-2-(2-isopropyl-5-methyl-2H-[1,2,4]triazol-3-yl)-4,5-dihydro-6-oxa-1,3a-diazabenzo[e]azulene

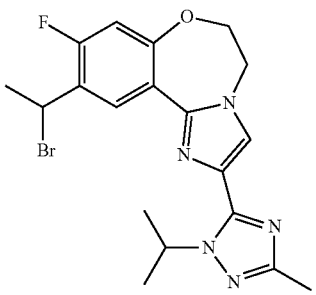 [SMILES: Cc1nc(-c2cn3c(n2)-c2cc(C(C)Br)c(F)cc2OCC3)n(C(C)C)n1]

Phosphorus tribromide (0.53 mL of a 1.0 M solution in DCM) was added to a solution of 1-[8-fluoro-2-(2-isopropyl-5-methyl-2H-[1,2,4]triazol-3-yl)-4,5-dihydro-6-oxa-1,3a-diazabenzo[e]azulen-9-yl]ethanol (98 mg, 0.26 mmol) in DCM (1 mL) at 0° C. The mixture was warmed to RT and stirred for 20 h. Water (2 mL) and sat. NaHCO₃ (2 mL) were added and the mixture was extracted with DCM. The combined organics were washed (brine), dried (Na₂SO₄) and concentrated in vacuo to give the title compound (100 mg, 0.23 mmol, 88%) as a pale yellow solid. The product was taken on without further purification. ¹H NMR (CDCl₃, 300 MHz): δ 8.72 (1H, d, J=8.7 Hz), 7.60 (1H, s), 6.75 (1H, d, J=11.0 Hz), 5.82 (1H, sept., J=6.6 Hz), 5.45 (1H, q, J=7.0 Hz), 4.52-4.49 (2H, m), 4.44-4.41 (2H, m), 2.42 (3H, s), 2.11 (3H, d, J=7.0 Hz), 1.60 (6H, d, J=6.6 Hz)

Step 5: A solution of 9-(1-bromoethyl)-8-fluoro-2-(2-isopropyl-5-methyl-2H-[1,2,4]triazol-3-yl)-4,5-dihydro-6-oxa-1,3a-diazabenzo[e]azulene (85 mg, 0.20 mmol), N-ethylpiperazine (27 μL, 0.22 mmol) and DIPEA (54 μL, 0.30 mmol) in dioxane (2 mL) was stirred at RT for 24 h. The reaction mixture was concentrated in vacuo and the residue was purified by column chromatography (Si-PPC, gradient 0-10% 2 M NH₃/MeOH in DCM) to give 374 (61 mg, 0.13 mmol, 65% over 2 steps) as a white solid. LCMS (Method K): R_T 2.74 min [M+H]⁺ 468.2. ¹H NMR (CD₃OD, 400 MHz): δ 8.55 (1H, d, J=8.2 Hz), 7.68 (1H, s), 6.76 (1H, d, J=11.1 Hz), 5.83 (1H, sept., J=6.7 Hz), 4.48 (4H, br s), 3.84 (1H, q, J=6.8 Hz), 2.50 (8H, br s), 2.38 (2H, q, J=7.4 Hz), 2.33 (3H, s), 1.53 (3H, d, J=6.7 Hz), 1.52 (3H, d, J=6.7 Hz), 1.40 (3H, d, J=6.8 Hz), 1.03 (3H, t, J=7.4 Hz)

Example 901

PI3K Isoform Inhibition Assay (p110 alpha, beta, gamma, delta: α, β, γ, δ)

PI3K enzymatic activity was assayed by measuring the amount of product phosphatidylinositol 3,4,5-phosphate (PIP3) formed from substrate 4,5 phosphatidylinositol 4,5-phosphate (PIP2) using a fluorescence polarization displacement assay. The decrease in fluorescence polarization of a fluorescent PIP₃ probe is measured as it is displaced from a PIP₃-binding protein GRP-1 detector by PI3K-catalyzed product. Assays were conducted in 384-well black Proxiplates in the presence of 10 mM Tris (pH 7.5), 50 mM NaCl, 4 mM MgCl₂, 5% glycerol, 25 μM ATP, 10 μM PIP₂ (Echelon Biosciences), 0.05% 3-[(3-cholamidopropyl)dimethylammonio]-1-propanesulfonate, 1 mM dithiothreitol, and 2% DMSO. The kinase reactions were initiated by the addition of 40 ng/mL p110α/p85α, 300 ng/mL p110β/p85α, 40 ng/mL p110γ, or 40 ng/mL p110δ/p85α (Upstate Group, Millipore; Dundee, UK), and 10 μM PIP₂ (Echelon Biosciences) to the wells. The reactions were stopped at timepoints that yielded a fixed change in fluorescence polarization consistent with initial rate conditions (typically 30 minutes), by the addition of 12.5 mM EDTA, 100 nM GRP-1 detector, and 5 nM tetramethylrhodamine-labeled PIP₃ (TAMRA-PIP₃; Echelon Biosciences). After 60 minutes of incubation at room temperature to allow equilibration of labeled and unlabeled PIP3 binding, the parallel and perpendicular components of the fluorescence emissions from each sample were measured at an excitation wavelength of 530 nm and an emission wavelength of 590 nm using an Envision fluorescent plate reader with a rhodamine filter (PerkinElmer Life and Analytical Sciences; Wellesley, Mass.). The assay is capable of detecting 0.1-2.0 μM PIP₃ product. The IC₅₀ values were obtained by fitting the dose-dependent inhibition data to a 4-parameter equation using Assay Explorer software (MDL, San Ramon, Calif.).

Alternatively, inhibition of PI3K was determined in a radiometric assay using purified, recombinant enzyme and ATP at a concentration of 1 uM. The Formula I compound was serially diluted in 100% DMSO. The kinase reaction was incubated for 1 h at room temperature, and the reaction was terminated by the addition of PBS. IC₅₀ values were subsequently determined using sigmoidal dose-response curve fit (variable slope).

The same protocol may be used to establish IC$_{50}$ values for p110α (alpha) PI3K binding.

Recombinant PI3K p110 isoforms alpha, beta, and delta may be prepared and purified according to US 2008/0275067 from recombinant PI3K heterodimeric complexes consisting of a p110 catalytic subunit and a p85 regulatory subunit overexpressed using the BAC-TO-BAC® HT baculovirus expression system (GIBCO/BRL), and then purified for use in biochemical assays. The four Class I PI 3-kinases are cloned into baculovirus vectors as follows:

p110 delta: A FLAG™-tagged (Eastman Kodak Co., U.S. Pat. No. 4,703,004; U.S. Pat. No. 4,782,137; U.S. Pat. No. 4,851,341) version of human p110.delta (Chantry et al., J. Biol. Chem. (1997) 272:19236-41) is subcloned using standard recombinant DNA techniques into the BamHI-XbaI site of the insect cell expression vector pFastbac HTb (Life Technologies, Gaithersburg, Md.), such that the clone is in frame with the His tag of the vector.

p110 alpha: Similar to the method used for p110 delta, described above, a FLAG™-tagged version of p110 alpha (Volinia et al (1994) Genomics, 24(3):427-77) was subcloned in BamH1-HindIII sites of pFastbac HTb (Life Technologies) such that the clone was in frame with the His tag of the vector.

p110 beta: A p110 beta (see Hu et al (1993) Mol. Cell. Biol., 13:7677-88) clone was amplified from the human MARATHON™ Ready spleen cDNA library (Clontech, Palo Alto Calif.) according to the manufacturer's protocol using the specified primers.

The p110 delta binding IC$_{50}$ values and delta/alpha selectivity of selected compounds are listed in Table 1 and Table 2.

Example 902

Collagen Induced Arthritis Efficacy Test

The efficacy of Formula I compound inhibitors of PI3K delta to inhibit the induction and/or progression of collagen induced arthritis was tested in mice. DBA1/J male mice (Jackson Labs; 5-6 weeks of age) are acclimatized for one week and are then injected intra-dermally at the base of the tail with 0.1 ml of an emulsion of Bovine Type II Collagen (100 mg) and an equal volume of Complete Freunds Adjuvant (200 mg *Mycobacterium tuberculosis*). Three weeks later, mice are injected intra-dermally at the base of the tail with 0.1 ml of an emulsion of Bovine Type II Collagen (100 mg) and an equal volume of Incomplete Freunds Adjuvant for boost. Dosing generally starts as soon as animals display signs of joint inflammation or clinical score 1-2.

All mice are evaluated 2-3 times a week for arthritis using a macroscopic scoring system for each paw. At the end of the experiment clinical scores are obtained to evaluate the intensity of edema in the four paws. A score of 0 to 4 is assigned to each paw. Animals are scored 0 when no inflammatory signs (swelling and redness) are observed in any of the small joints (intraphalangeal, metacarpophalangeal, metatarsophalangeal) or large joints (wrist/carpus, ankle/tarsus). Animals are scored 1 when very slight to slight inflammation was observed (swelling and/or redness of paw or one digit), 2 moderate edema (swelling in two or more joint), 3 severe edema (gross swelling of the paw with more than two joints involved), and 4 when very severe edema (severe arthritis of the entire paw and digits) is present. The arthritic index for each mouse is evaluated by adding the four scores of the individual paws, giving a maximum score of 16. Plasma and serum samples are taken at 1 hour (orbital bleed) post dose and 24 hrs (cardiac puncture) post dose. Samples are stored at −20° C. until analysis. At termination, the hind paws are transected at the distal tibia, just proximal to the tarsal joint. The left and right hind paws are placed in the histology cassettes individually and fixed in 10% formalin. These paws are sent to histology dept for further process.

Materials: Bovine Type II collagen, immunization grade, 2 mg/ml (5 ml/vial) in 0.05 M acetic acid (solution), store at −20° C., from Chondrex, LLC, Seattle, Wash. Adjuvant complete H37 Ra, 6×10 ml/box, contains 1 mg/ml *Mycobacterium tuberculosis*. For use in animal immunological studies, for laboratory use, store at +4° C., from Difco Laboratories, Detroit, Mich. 48232-7058 USA. Adjuvant Incomplete H37 Ra, 6×10 ml/box: For use in animal immunological studies, for laboratory use, store at +4° C., from Difco Laboratories.

Example 903

CD69 Whole Blood Assay

Human blood is obtained from healthy volunteers, with the following restrictions: 1 week drug-free, non-smokers. Blood (approximately 20 mls to test 8 compounds) is collected by venipuncture into Vacutainer tubes with sodium heparin.

Cynomolgus monkey blood is obtained courtesy of the LAT group from monkeys not previously exposed to, or after a washout period from, chemical dosing. Additional cyno blood draws may be collected during the course of pharmacokinetic or toxicology studies. Blood (25-30 mls for naïve monkeys or 3-4 mls from monkeys on studies requiring repeated draws) is collected by venipuncture into Vacutainer tubes with sodium heparin.

Solutions of Formula I compounds at 1000 or 2000 μM in PBS (20×), are diluted by three-fold serial dilutions in 10% DMSO in PBS for a nine point dose-response curve. An aliquot of 5.5 μl of each compound is added in duplicate to a 2 ml 96-well plate; 5.5 μl of 10% DMSO in PBS is added as control and no-stimulus wells. Human whole blood—HWB (100 μl) is added to each well. After mixing the plates are incubated at 37° C., 5% CO$_2$, 100% humidity for 30 minutes. Goat F(ab')2 anti-human IgM (10 μl of a 500 μg/ml solution, 50 μg/ml final) is added to each well (except the no-stimulus wells) with mixing and the plates are incubated for an additional 20 hours. At the end of the 20 hour incubation, samples are incubated with fluorescent labeled antibodies for 30 minutes, at 37° C., 5% CO$_2$, 100% humidity. Include induced control, unstained and single stains for compensation adjustments and initial voltage settings. Samples are then lysed with Pharmingen Lyse according to the manufacturer's instructions. Samples are then transferred to a 96 well plate suitable to be run on the AMS 96 well system on the BD Calibur FACs machine. Data acquired and Mean Fluorescence Intensity values were obtained using Cell Quest Software. Results are initially analyzed by FACS analysis software (Flow Jo). The IC50 for test compounds is defined as the concentration which decreases by 50% the percent positive of CD69 cells that are also CD20 positive stimulated by anti-IgM (average of 8 control wells, after subtraction of the average of 8 wells for the no-stimulus background). The IC50 values are calculated by ActivityBase using XIfit version 3, equation 201.

The IC50 values of selected compounds from Table 1 in the CD69 Whole Blood Assay include:

| Compound No. | IC50 (micromolar) |
|---|---|
| 108 | 0.0405 |
| 110 | 0.129 |
| 115 | 0.0381 |

-continued

| Compound No. | IC50 (micromolar) |
|---|---|
| 143 | 0.0582 |
| 160 | 0.0459 |
| 248 | 0.0497 |
| 263 | 0.0458 |

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be considered to fall within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

We claim:
1. A compound selected from
2-(3-methyl-1-(2,2,2-trifluoroethyl)-1H-1,2,4-triazol-5-yl)-9-(2-(1-methylpiperidin-2-yl)pyrrolidin-1-yl)-5,6-dihydroimidazo[1,2-d]pyrido[3,4-f][1,4]oxazepine;
(cis)-2-(3-methyl-1-(2,2,2-trifluoroethyl)-1H-1,2,4-triazol-5-yl)-9-(2-(1-methylpiperidin-2-yl)pyrrolidin-1-yl)-5,6-dihydroimidazo[1,2-d]pyrido[3,4-f][1,4]oxazepine;
(trans)-2-(3-methyl-1-(2,2,2-trifluoroethyl)-1H-1,2,4-triazol-5-yl)-9-(2-(1-methylpiperidin-2-yl)pyrrolidin-1-yl)-5,6-dihydroimidazo[1,2-d]pyrido[3,4-f][1,4]oxazepine;
2-(1-isopropyl-1H-1,2,4-triazol-5-yl)-9-(2-(pyrrolidin-1-ylmethyl)pyrrolidin-1-yl)-5,6-dihydroimidazo[1,2-d]pyrido[3,4-f][1,4]oxazepine;
2-(1-isopropyl-1H-1,2,4-triazol-5-yl)-9-(2-(1-methylpiperidin-4-yl)pyrrolidin-1-yl)-5,6-dihydroimidazo[1,2-d]pyrido[3,4-f][1,4]oxazepine;
10-((4-tert-butylpiperazin-1-yl)methyl)-2-(1-isopropyl-1H-1,2,4-triazol-5-yl)-5,6-dihydrobenzo[f]imidazo[1,2-d][1,4]oxazepine;
2-(2-(1-isopropyl-1H-1,2,4-triazol-5-yl)-5,6-dihydrobenzo[f]imidazo[1,2-d][1,4]oxazepin-9-yl)benzenesulfonamide;
(4-tert-butylpiperazin-1-yl)(2-(1-isopropyl-1H-1,2,4-triazol-5-yl)-5,6-dihydrobenzo[f]imidazo[1,2-d][1,4]oxazepin-10-yl)methanone;
9-((S)-2-((S)-1-methylpiperidin-2-yl)pyrrolidin-1-yl)-2-(pyridin-2-yl)-5,6-dihydroimidazo[1,2-d]pyrido[3,4-f][1,4]oxazepine;
2-(1-isopropyl-1H-1,2,4-triazol-5-yl)-9-(2-(piperidin-1-ylmethyl)pyrrolidin-1-yl)-5,6-dihydroimidazo[1,2-d]pyrido[3,4-f][1,4]oxazepine;
2-(1-isopropyl-1H-1,2,4-triazol-5-yl)-9-(2-(1-methylpiperidin-4-yl)pyrrolidin-1-yl)-5,6-dihydroimidazo[1,2-d]pyrido[3,4-f][1,4]oxazepine;
2-(1-isopropyl-1H-1,2,4-triazol-5-yl)-N-phenyl-5,6-dihydrobenzo[f]imidazo[1,2-d][1,4]oxazepine-10-sulfonamide;
2-(2-(1-isopropyl-1H-1,2,4-triazol-5-yl)-5,6-dihydrobenzo[f]imidazo[1,2-d][1,4]oxazepin-10-yl)-N-phenylacetamide;
N-benzyl-2-(2-(1-isopropyl-1H-1,2,4-triazol-5-yl)-5,6-dihydrobenzo[f]imidazo[1,2-d][1,4]oxazepin-10-yl)acetamide;
10-(4-tert-butylpiperazin-1-ylsulfonyl)-2-(1-isopropyl-1H-1,2,4-triazol-5-yl)-5,6-dihydrobenzo[f]imidazo[1,2-d][1,4]oxazepine;
2-(1-isopropyl-1H-1,2,4-triazol-5-yl)-10-(3-morpholinoazetidin-1-ylsulfonyl)-5,6-dihydrobenzo[f]imidazo[1,2-d][1,4]oxazepine;
(S)-2-(1-isopropyl-1H-1,2,4-triazol-5-yl)-10-(2-(pyrrolidin-1-ylmethyl)pyrrolidin-1-ylsulfonyl)-5,6-dihydrobenzo[f]imidazo[1,2-d][1,4]oxazepine;
9-(2-(1-methylpiperidin-3-yl)pyrrolidin-1-yl)-2-(pyridin-2-yl)-5,6-dihydroimidazo[1,2-d]pyrido[3,4-f][1,4]oxazepine;
2-(1-isopropyl-1H-1,2,4-triazol-5-yl)-10-(4-isopropylpiperazin-1-ylsulfonyl)-5,6-dihydrobenzo[f]imidazo[1,2-d][1,4]oxazepine;
9-(2-(piperidin-1-ylmethyl)pyrrolidin-1-yl)-2-(pyridin-2-yl)-5,6-dihydroimidazo[1,2-d]pyrido[3,4-f][1,4]oxazepine;
1-(2-(1-isopropyl-1H-1,2,4-triazol-5-yl)-5,6-dihydrobenzo[f]imidazo[1,2-d][1,4]oxazepin-1-ylsulfonyl)-N,N-dimethylpiperidin-4-amine;
1-(dihydro-1H-pyrido[1,2-a]pyrazin-2(6H,7H,8H,9H,9aH)-ylsulfonyl)-2-(1-isopropyl-1H-1,2,4-triazol-5-yl)-5,6-dihydrobenzo[f]imidazo[1,2-d][1,4]oxazepine;
(S)-2-(1-isopropyl-1H-1,2,4-triazol-5-yl)-9-(2-(pyrrolidin-1-ylmethyl)pyrrolidin-1-yl)-5,6-dihydrobenzo[f]imidazo[1,2-d][1,4]oxazepine;
2-(1-isopropyl-1H-1,2,4-triazol-5-yl)-10-(4-(pentan-3-yl)piperazin-1-ylsulfonyl)-5,6-dihydrobenzo[f]imidazo[1,2-d][1,4]oxazepine;
2-(1-isopropyl-1H-1,2,4-triazol-5-yl)-9-(2-(pyridin-4-yl)pyrrolidin-1-yl)-5,6-dihydroimidazo[1,2-d]pyrido[3,4-f][1,4]oxazepine;
2-(1-isopropyl-1H-1,2,4-triazol-5-yl)-9-((1-methylpiperidin-2-yl)methoxy)-5,6-dihydroimidazo[1,2-d]pyrido[3,4-f][1,4]oxazepine;
2-(4-(2-(1-isopropyl-1H-1,2,4-triazol-5-yl)-5,6-dihydrobenzo[f]imidazo[1,2-d][1,4]oxazepin-10-ylsulfonyl)piperazin-1-yl)-2-methylpropan-1-ol;
10-(1-tert-butylpiperidin-4-ylthio)-2-(1-isopropyl-1H-1,2,4-triazol-5-yl)-5,6-dihydrobenzo[f]imidazo[1,2-d][1,4]oxazepine;
10-(1-tert-butylpiperidin-4-ylsulfinyl)-2-(1-isopropyl-1H-1,2,4-triazol-5-yl)-5,6-dihydrobenzo[f]imidazo[1,2-d][1,4]oxazepine;
2-(1-isopropyl-1H-1,2,4-triazol-5-yl)-9-(2-(1-methylpiperidin-4-yl)pyrrolidin-1-yl)-5,6-dihydrobenzo[f]imidazo[1,2-d][1,4]oxazepine;
10-(1-tert-butylpiperidin-4-ylsulfonyl)-2-(1-isopropyl-1H-1,2,4-triazol-5-yl)-5,6-dihydrobenzo[f]imidazo[1,2-d][1,4]oxazepine;
2-(1-isopropyl-1H-1,2,4-triazol-5-yl)-9-(1-(1-isopropylpiperidin-4-yl)ethoxy)-5,6-dihydrobenzo[f]imidazo[1,2-d][1,4]oxazepine;
(R)-2-(1-isopropyl-1H-1,2,4-triazol-5-yl)-9-(2-(pyrrolidin-1-ylmethyl)pyrrolidin-1-yl)-5,6-dihydrobenzo[f]imidazo[1,2-d][1,4]oxazepine;
1-(1-(2-(1-isopropyl-1H-1,2,4-triazol-5-yl)-5,6-dihydroimidazo[1,2-d]pyrido[3,4-f][1,4]oxazepin-9-yl)pyrrolidin-2-yl)-N,N-dimethylmethanamine;
2-(1-isopropyl-1H-1,2,4-triazol-5-yl)-10-(1-(4-methylpiperazin-1-yl)ethyl)-5,6-dihydrobenzo[f]imidazo[1,2-d][1,4]oxazepine;

2-(1-isopropyl-1H-1,2,4-triazol-5-yl)-10-(1-(4-methylpiperazin-1-yl)ethyl)-5,6-dihydrobenzo[f]imidazo[1,2-d][1,4]oxazepine;
(S)-10-(1-(4-tert-butylpiperazin-1-yl)ethyl)-2-(1-isopropyl-1H-1,2,4-triazol-5-yl)-5,6-dihydrobenzo[f]imidazo[1,2-d][1,4]oxazepine;
(R)-10-(1-(4-tert-butylpiperazin-1-yl)ethyl)-2-(1-isopropyl-1H-1,2,4-triazol-5-yl)-5,6-dihydrobenzo[f]imidazo[1,2-d][1,4]oxazepine;
2-(1-(1-(2-(1-isopropyl-1H-1,2,4-triazol-5-yl)-5,6-dihydrobenzo[f]imidazo[1,2-d][1,4]oxazepin-10-yl)ethyl)piperidin-4-yl)propan-2-ol;
10-(1-tert-butylpiperidin-4-ylthio)-2-(pyridin-3-yl)-5,6-dihydrobenzo[f]imidazo[1,2-d][1,4]oxazepine;
10-(1-tert-butylpiperidin-4-ylthio)-2-(pyridin-2-yl)-5,6-dihydrobenzo[f]imidazo[1,2-d][1,4]oxazepine;
(S)-10-(1-tert-butylpiperidin-4-ylsulfinyl)-2-(1-isopropyl-1H-1,2,4-triazol-5-yl)-5,6-dihydrobenzo[f]imidazo[1,2-d][1,4]oxazepine;
2-(1-isopropyl-1H-1,2,4-triazol-5-yl)-10-(1-(4-(pyrrolidin-1-yl)piperidin-1-yl)ethyl)-5,6-dihydrobenzo[f]imidazo[1,2-d][1,4]oxazepine;
10-(1-tert-butylpiperidin-4-ylthio)-2-(3-methyl-1H-pyrazol-4-yl)-5,6-dihydrobenzo[f]imidazo[1,2-d][1,4]oxazepine;
10-(1-tert-butylpiperidin-4-ylthio)-2-(3-(trifluoromethyl)-1H-pyrazol-4-yl)-5,6-dihydrobenzo[f]imidazo[1,2-d][1,4]oxazepine;
2-(1-isopropyl-1H-1,2,4-triazol-5-yl)-9-(1-(1-methylpiperidin-4-yl)-1H-pyrazol-5-yl)-5,6-dihydrobenzo[f]imidazo[1,2-d][1,4]oxazepine;
2-(1-isopropyl-1H-1,2,4-triazol-5-yl)-10-(2-(1-methylpiperidin-4-yl)pyrrolidin-1-yl)-5,6-dihydrobenzo[f]imidazo[1,2-d][1,4]oxazepine;
2-(1-isopropyl-1H-1,2,4-triazol-5-yl)-10-(1-(3-morpholinoazetidin-1-yl)ethyl)-5,6-dihydrobenzo[f]imidazo[1,2-d][1,4]oxazepine;
2-(1-isopropyl-1H-1,2,4-triazol-5-yl)-9-(1-(1-isopropylazetidin-3-yl)ethoxy)-5,6-dihydrobenzo[f]imidazo[1,2-d][1,4]oxazepine;
9-(1-(3-fluoropyridin-4-yl)ethoxy)-2-(1-isopropyl-3-methyl-1H-1,2,4-triazol-5-yl)-5,6-dihydrobenzo[f]imidazo[1,2-d][1,4]oxazepine;
1-(1-(2-(1-isopropyl-1H-1,2,4-triazol-5-yl)-5,6-dihydrobenzo[f]imidazo[1,2-d][1,4]oxazepin-10-yl)ethyl)-N,N-dimethylazetidin-3-amine;
2-(1-isopropyl-1H-1,2,4-triazol-5-yl)-10-(1-(4-methylpiperazin-1-yl)propyl)-5,6-dihydrobenzo[f]imidazo[1,2-d][1,4]oxazepine;
2-(1-isopropyl-1H-1,2,4-triazol-5-yl)-10-(1-(4-methylpiperazin-1-yl)propyl)-5,6-dihydrobenzo[f]imidazo[1,2-d][1,4]oxazepine;
2-(1-isopropyl-3-methyl-1H-1,2,4-triazol-5-yl)-9-(2-(1-methylpiperidin-4-yl)pyrrolidin-1-yl)-5,6-dihydrobenzo[f]imidazo[1,2-d][1,4]oxazepine;
2-(1-isopropyl-1H-1,2,4-triazol-5-yl)-9-(2-(1-isopropylpiperidin-4-yl)pyrrolidin-1-yl)-5,6-dihydrobenzo[f]imidazo[1,2-d][1,4]oxazepine;
2-(1-isopropyl-1H-1,2,4-triazol-5-yl)-10-(1-isopropylpiperidin-4-ylthio)-5,6-dihydrobenzo[f]imidazo[1,2-d][1,4]oxazepine;
2-(1-isopropyl-1H-1,2,4-triazol-5-yl)-10-(1-isopropylpiperidin-4-ylsulfinyl)-5,6-dihydrobenzo[f]imidazo[1,2-d][1,4]oxazepine;
2-(1-isopropyl-1H-1,2,4-triazol-5-yl)-10-(1-isopropylpiperidin-4-ylsulfonyl)-5,6-dihydrobenzo[f]imidazo[1,2-d][1,4]oxazepine;
1-(4-(2,2,2-trifluoro-1-(2-(1-isopropyl-3-methyl-1H-1,2,4-triazol-5-yl)-5,6-dihydrobenzo[f]imidazo[1,2-d][1,4]oxazepin-9-yloxy)ethyl)piperidin-1-yl)ethanone;
2-(1-isopropyl-1H-1,2,4-triazol-5-yl)-9-(1-(1-isopropylpiperidin-4-yl)ethoxy)-5,6-dihydrobenzo[f]imidazo[1,2-d][1,4]oxazepine;
2-(1-isopropyl-1H-1,2,4-triazol-5-yl)-9-(1-(1-isopropylazetidin-3-yl)ethoxy)-5,6-dihydrobenzo[f]imidazo[1,2-d][1,4]oxazepine;
9-(1-(3-fluoropyridin-4-yl)ethoxy)-2-(1-isopropyl-3-methyl-1H-1,2,4-triazol-5-yl)-5,6-dihydrobenzo[f]imidazo[1,2-d][1,4]oxazepine;
2-(4-(2-(1-isopropyl-1H-1,2,4-triazol-5-yl)-5,6-dihydrobenzo[f]imidazo[1,2-d][1,4]oxazepin-10-ylsulfinyl)piperidin-1-yl)-2-methylpropan-1-ol;
2-(4-(2-(1-isopropyl-1H-1,2,4-triazol-5-yl)-5,6-dihydrobenzo[f]imidazo[1,2-d][1,4]oxazepin-10-ylsulfonyl)piperidin-1-yl)-2-methylpropan-1-ol;
9-(1-(2,4-dimethylthiazol-5-yl)ethoxy)-2-(1-isopropyl-3-methyl-1H-1,2,4-triazol-5-yl)-5,6-dihydrobenzo[f]imidazo[1,2-d][1,4]oxazepine;
10-((4-tert-butylpiperazin-1-yl)methyl)-2-(1-isopropyl-1H-1,2,4-triazol-5-yl)-5,6-dihydroimidazo[1,2-d]pyrido[4,3-f][1,4]oxazepine;
10-((4-tert-butylpiperazin-1-yl)methyl)-2-(1-isopropyl-1H-1,2,4-triazol-5-yl)-9-methyl-5,6-dihydrobenzo[f]imidazo[1,2-d][1,4]oxazepine;
3-(1-(2-(1-isopropyl-3-methyl-1H-1,2,4-triazol-5-yl)-5,6-dihydrobenzo[f]imidazo[1,2-d][1,4]oxazepin-9-yloxy)ethyl)benzonitrile;
2-(4-(2-(1-isopropyl-1H-1,2,4-triazol-5-yl)-5,6-dihydrobenzo[f]imidazo[1,2-d][1,4]oxazepin-10-ylsulfonyl)piperidin-1-yl)-2-methylpropanamide;
2-(4-(2-(1-isopropyl-1H-1,2,4-triazol-5-yl)-5,6-dihydrobenzo[f]imidazo[1,2-d][1,4]oxazepin-10-ylsulfinyl)piperidin-1-yl)-2-methylpropanamide;
2-(1-isopropyl-3-methyl-1H-1,2,4-triazol-5-yl)-9-(1-methyl-5-(1-methylpiperidin-4-yl)-1H-pyrazol-4-yl)-5,6-dihydrobenzo[f]imidazo[1,2-d][1,4]oxazepine;
1-(4-(4-(2-(1-isopropyl-3-methyl-1H-1,2,4-triazol-5-yl)-5,6-dihydrobenzo[f]imidazo[1,2-d][1,4]oxazepin-9-yl)-1-methyl-1H-pyrazol-5-yl)piperidin-1-yl)ethanone;
10-(1-isopropylpiperidin-4-ylthio)-2-(pyridin-2-yl)-5,6-dihydrobenzo[f]imidazo[1,2-d][1,4]oxazepine;
2-methyl-2-(4-(2-(pyridin-2-yl)-5,6-dihydrobenzo[f]imidazo[1,2-d][1,4]oxazepin-10-ylsulfinyl)piperidin-1-yl)propan-1-ol;
10-(1-isopropylpiperidin-4-ylsulfinyl)-2-(pyridin-2-yl)-5,6-dihydrobenzo[f]imidazo[1,2-d][1,4]oxazepine;
2-methyl-2-(4-(2-(pyridin-2-yl)-5,6-dihydrobenzo[f]imidazo[1,2-d][1,4]oxazepin-10-ylsulfonyl)piperidin-1-yl)propan-1-ol;
10-(1-isopropylpiperidin-4-ylsulfonyl)-2-(pyridin-2-yl)-5,6-dihydrobenzo[f]imidazo[1,2-d][1,4]oxazepine;
2-(1-isopropyl-3-methyl-1H-1,2,4-triazol-5-yl)-9-(1-methyl-5-((4-methylpiperazin-1-yl)methyl)-1H-pyrazol-4-yl)-5,6-dihydrobenzo[f]imidazo[1,2-d][1,4]oxazepine;
2-(1-(1-(2-(1-isopropyl-4-methyl-1H-imidazol-2-yl)-5,6-dihydrobenzo[f]imidazo[1,2-d][1,4]oxazepin-10-yl)ethyl)piperidin-4-yl)propan-2-ol;
(4-tert-butylpiperazin-1-yl)(2-(1-isopropyl-1H-1,2,4-triazol-5-yl)-5,6-dihydroimidazo[1,2-d]pyrido[4,3-f][1,4]oxazepin-10-yl)methanone;
10-(1-isopropylpiperidin-4-ylsulfinyl)-2-(3-methylpyridin-2-yl)-5,6-dihydrobenzo[f]imidazo[1,2-d][1,4]oxazepine;

10-(1-isopropylpiperidin-4-ylsulfonyl)-2-(3-methylpyridin-2-yl)-5,6-dihydrobenzo[f]imidazo[1,2-d][1,4]oxazepine;

2-(1-isopropyl-3-methyl-1H-1,2,4-triazol-5-yl)-10-(1-isopropylpiperidin-4-ylsulfinyl)-5,6-dihydrobenzo[f]imidazo[1,2-d][1,4]oxazepine;

2-(1-isopropyl-3-methyl-1H-1,2,4-triazol-5-yl)-9-(1-(1-methylpiperidin-4-yl)-1H-pyrazol-5-yl)-5,6-dihydrobenzo[f]imidazo[1,2-d][1,4]oxazepine;

2-(1-isopropyl-3-methyl-1H-1,2,4-triazol-5-yl)-10-(1-isopropylpiperidin-4-ylsulfonyl)-5,6-dihydrobenzo[f]imidazo[1,2-d][1,4]oxazepine;

9-fluoro-2-(1-isopropyl-3-methyl-1H-1,2,4-triazol-5-yl)-10-(1-isopropylpiperidin-4-ylthio)-5,6-dihydrobenzo[f]imidazo[1,2-d][1,4]oxazepine;

9-fluoro-2-(1-isopropyl-3-methyl-1H-1,2,4-triazol-5-yl)-10-(1-isopropylpiperidin-4-ylsulfinyl)-5,6-dihydrobenzo[f]imidazo[1,2-d][1,4]oxazepine;

9-fluoro-2-(1-isopropyl-3-methyl-1H-1,2,4-triazol-5-yl)-10-(1-isopropylpiperidin-4-ylsulfonyl)-5,6-dihydrobenzo[f]imidazo[1,2-d][1,4]oxazepine;

2-(4-(9-fluoro-2-(1-isopropyl-3-methyl-1H-1,2,4-triazol-5-yl)-5,6-dihydrobenzo[f]imidazo[1,2-d][1,4]oxazepin-10-ylsulfinyl)piperidin-1-yl)-2-methylpropan-1-ol;

2-(1-isopropyl-3-methyl-1H-1,2,4-triazol-5-yl)-9-(1-methyl-5-(1-(oxetan-3-yl)piperidin-3-yl)-1H-pyrazol-4-yl)-5,6-dihydrobenzo[f]imidazo[1,2-d][1,4]oxazepine;

2-(1-isopropyl-3-methyl-1H-1,2,4-triazol-5-yl)-9-(1-methyl-5-(1-(tetrahydro-2H-pyran-4-yl)piperidin-3-yl)-1H-pyrazol-4-yl)-5,6-dihydrobenzo[f]imidazo[1,2-d][1,4]oxazepine;

2-(1-isopropyl-3-methyl-1H-1,2,4-triazol-5-yl)-9-(1'-methyl-2,4'-bipiperidin-1-yl)-5,6-dihydrobenzo[f]imidazo[1,2-d][1,4]oxazepine;

2-(1-isopropyl-3-methyl-1H-1,2,4-triazol-5-yl)-9-(1-(1-isopropylpiperidin-4-yl)ethoxy)-5,6-dihydrobenzo[f]imidazo[1,2-d][1,4]oxazepine;

2-(1-isopropyl-3-methyl-1H-1,2,4-triazol-5-yl)-9-(1-(1-isopropylazepan-4-yl)ethoxy)-5,6-dihydrobenzo[f]imidazo[1,2-d][1,4]oxazepine;

9-(1-isopropylpiperidin-3-yloxy)-2-(pyridin-2-yl)-5,6-dihydrobenzo[f]imidazo[1,2-d][1,4]oxazepine;

2-(4-(9-fluoro-2-(1-isopropyl-3-methyl-1H-1,2,4-triazol-5-yl)-5,6-dihydrobenzo[f]imidazo[1,2-d][1,4]oxazepin-10-ylsulfonyl)piperidin-1-yl)-2-methylpropan-1-ol;

2-(4-(9-fluoro-2-(1-isopropyl-3-methyl-1H-1,2,4-triazol-5-yl)-5,6-dihydrobenzo[f]imidazo[1,2-d][1,4]oxazepin-10-ylsulfinyl)piperidin-1-yl)-2-methylpropanamide;

1-(3-(4-(2-(1-isopropyl-3-methyl-1H-1,2,4-triazol-5-yl)-5,6-dihydrobenzo[f]imidazo[1,2-d][1,4]oxazepin-9-yl)-1-methyl-1H-pyrazol-5-yl)piperidin-1-yl)-2-methylpropan-2-ol;

10-(1-isopropylpiperidin-4-ylsulfinyl)-2-(4-methylpyridin-2-yl)-5,6-dihydrobenzo[f]imidazo[1,2-d][1,4]oxazepine;

10-(1-isopropylpiperidin-4-ylsulfonyl)-2-(4-methylpyridin-2-yl)-5,6-dihydrobenzo[f]imidazo[1,2-d][1,4]oxazepine;

2-(1-isopropyl-3-methyl-1H-1,2,4-triazol-5-yl)-10-(1-isopropylpiperidin-4-ylsulfinyl)-9-methyl-5,6-dihydrobenzo[f]imidazo[1,2-d][1,4]oxazepine;

2-(1-isopropyl-3-methyl-1H-1,2,4-triazol-5-yl)-9-(1-methyl-5-(1-(tetrahydro-2H-pyran-4-yl)piperidin-3-yl)-1H-pyrazol-4-yl)-5,6-dihydrobenzo[f]imidazo[1,2-d][1,4]oxazepine;

2-(1-isopropyl-3-methyl-1H-1,2,4-triazol-5-yl)-9-(1'-methyl-2,4'-bipiperidin-1-yl)-5,6-dihydrobenzo[f]imidazo[1,2-d][1,4]oxazepine;

9-(2-(1-methylpiperidin-4-yl)pyrrolidin-1-yl)-2-(1-(tetrahydrofuran-3-yl)-1H-1,2,4-triazol-5-yl)-5,6-dihydrobenzo[f]imidazo[1,2-d][1,4]oxazepine;

2-(1-(2-methoxypropyl)-3-methyl-1H-1,2,4-triazol-5-yl)-9-(2-(1-methylpiperidin-4-yl)pyrrolidin-1-yl)-5,6-dihydrobenzo[f]imidazo[1,2-d][1,4]oxazepine;

(4-tert-butylpiperazin-1-yl)(2-(1-isopropyl-3-methyl-1H-1,2,4-triazol-5-yl)-5,6-dihydroimidazo[1,2-d]pyrido[4,3-f][1,4]oxazepin-10-yl)methanone;

1-tert-butyl-4-(2-(1-isopropyl-3-methyl-1H-1,2,4-triazol-5-yl)-5,6-dihydroimidazo[1,2-d]pyrido[4,3-f][1,4]oxazepine-10-carbonyl)piperazin-2-one;

9-fluoro-2-(1-isopropyl-3-methyl-1H-1,2,4-triazol-5-yl)-10-(1-isopropylpiperidin-4-ylsulfinyl)-5,6-dihydrobenzo[f]imidazo[1,2-d][1,4]oxazepine;

2-(3-methyl-5-(9-(2-(1-methylpiperidin-4-yl)pyrrolidin-1-yl)-5,6-dihydrobenzo[f]imidazo[1,2-d][1,4]oxazepin-2-yl)-1H-1,2,4-triazol-1-yl)ethanol;

2-(3-(4-(2-(1-isopropyl-3-methyl-1H-1,2,4-triazol-5-yl)-5,6-dihydrobenzo[f]imidazo[1,2-d][1,4]oxazepin-9-yl)-1-methyl-1H-pyrazol-5-yl)pyrrolidin-1-yl)-2-methylpropan-1-ol;

2-(1-isopropyl-3-methyl-1H-1,2,4-triazol-5-yl)-9-(1-methyl-5-(1-methylpiperidin-3-yl)-1H-pyrazol-4-yl)-5,6-dihydrobenzo[f]imidazo[1,2-d][1,4]oxazepine;

2-(1-isopropyl-3-methyl-1H-1,2,4-triazol-5-yl)-9-(1-methyl-5-(1-methylpyrrolidin-3-yl)-1H-pyrazol-4-yl)-5,6-dihydrobenzo[f]imidazo[1,2-d][1,4]oxazepine;

4-(2-(1-isopropyl-3-methyl-1H-1,2,4-triazol-5-yl)-5,6-dihydroimidazo[1,2-d]pyrido[4,3-f][1,4]oxazepine-10-carbonyl)-1-(tetrahydro-2H-pyran-4-yl)piperazin-2-one;

2-(1-isopropyl-3-methyl-1H-1,2,4-triazol-5-yl)-9-(1-isopropylpiperidin-4-ylsulfinyl)-5,6-dihydrobenzo[f]imidazo[1,2-d][1,4]oxazepine;

2-(1-isopropyl-3-methyl-1H-1,2,4-triazol-5-yl)-10-(1-isopropylpiperidin-4-ylsulfonyl)-9-methyl-5,6-dihydrobenzo[f]imidazo[1,2-d][1,4]oxazepine;

2-(1-isopropyl-3-methyl-1H-1,2,4-triazol-5-yl)-9-(1-methyl-5-(1-methylpiperidin-3-yl)-1H-pyrazol-4-yl)-5,6-dihydrobenzo[f]imidazo[1,2-d][1,4]oxazepine;

2-(1-isopropyl-3-methyl-1H-1,2,4-triazol-5-yl)-9-(1-methyl-5-(1-methylpyrrolidin-3-yl)-1H-pyrazol-4-yl)-5,6-dihydrobenzo[f]imidazo[1,2-d][1,4]oxazepine;

2-(3-(4-(2-(1-isopropyl-3-methyl-1H-1,2,4-triazol-5-yl)-5,6-dihydrobenzo[f]imidazo[1,2-d][1,4]oxazepin-9-yl)-1-methyl-1H-pyrazol-5-yl)piperidin-1-yl)-2-methylpropan-1-ol;

2-(1-isopropyl-3-methyl-1H-1,2,4-triazol-5-yl)-9-(2-(1-methylpiperidin-4-yl)pyrrolidin-1-yl)-5,6-dihydroimidazo[1,2-d]pyrido[3,4-f][1,4]oxazepine;

2-(2-(1-isopropyl-3-methyl-1H-1,2,4-triazol-5-yl)-5,6-dihydrobenzo[f]imidazo[1,2-d][1,4]oxazepin-9-yloxy)-2-methyl-1-(4-methylpiperazin-1-yl)propan-1-one;

2-(3-(4-(2-(1-isopropyl-3-methyl-1H-1,2,4-triazol-5-yl)-5,6-dihydrobenzo[f]imidazo[1,2-d][1,4]oxazepin-9-yl)-1-methyl-1H-pyrazol-5-yl)piperidin-1-yl)-2-methylpropanamide;

2-(3-methyl-1-(2,2,2-trifluoroethyl)-1H-1,2,4-triazol-5-yl)-9-(2-(1-methylpiperidin-4-yl)pyrrolidin-1-yl)-5,6-dihydroimidazo[1,2-d]pyrido[3,4-f][1,4]oxazepine;

2-(1-isopropyl-3-methyl-1H-1,2,4-triazol-5-yl)-9-(2-(1-(tetrahydro-2H-pyran-4-yl)piperidin-4-yl)pyrrolidin-1-yl)-5,6-dihydrobenzo[f]imidazo[1,2-d][1,4]oxazepine;

2-(1-isopropyl-3-methyl-1H-1,2,4-triazol-5-yl)-9-(1-(1-methylpiperidin-4-yl)-1H-1,2,4-triazol-5-yl)-5,6-dihydrobenzo[f]imidazo[1,2-d][1,4]oxazepine;

2-(5-(9-(1-(1-methylpiperidin-4-yl)-1H-pyrazol-5-yl)-5,6-dihydrobenzo[f]imidazo[1,2-d][1,4]oxazepin-2-yl)-1H-1,2,4-triazol-1-yl)ethanol;

9-(1-(1-tert-butylpiperidin-4-yl)-1H-1,2,4-triazol-5-yl)-2-(1-isopropyl-3-methyl-1H-1,2,4-triazol-5-yl)-5,6-dihydrobenzo[f]imidazo[1,2-d][1,4]oxazepine;

2-(1-isopropyl-3-methyl-1H-1,2,4-triazol-5-yl)-9-(1-((4-methylpiperazin-1-yl)methyl)cyclopropoxy)-5,6-dihydrobenzo[f]imidazo[1,2-d][1,4]oxazepine;

2-(1-isopropyl-3-methyl-1H-1,2,4-triazol-5-yl)-9-(1-isopropyl-5-methylpiperidin-3-yloxy)-5,6-dihydrobenzo[f]imidazo[1,2-d][1,4]oxazepine;

2-(1-isopropyl-3-methyl-1H-1,2,4-triazol-5-yl)-9-(1-isopropyl-3-methylpyrrolidin-3-yloxy)-5,6-dihydrobenzo[f]imidazo[1,2-d][1,4]oxazepine;

9-(1-(1-benzylpiperidin-3-yl)-1H-pyrazol-5-yl)-2-(1-isopropyl-3-methyl-1H-1,2,4-triazol-5-yl)-5,6-dihydrobenzo[f]imidazo[1,2-d][1,4]oxazepine;

(R)-2-(1-isopropyl-3-methyl-1H-1,2,4-triazol-5-yl)-9-(2-(1-isopropylpiperidin-4-yl)pyrrolidin-1-yl)-5,6-dihydrobenzo[f]imidazo[1,2-d][1,4]oxazepine;

2-(1-isopropyl-1H-1,2,4-triazol-5-yl)-10-methyl-9-(1-(1-methylpiperidin-4-yl)-1H-pyrazol-5-yl)-5,6-dihydrobenzo[f]imidazo[1,2-d][1,4]oxazepine;

(S)-2-(1-isopropyl-3-methyl-1H-1,2,4-triazol-5-yl)-9-(2-(1-isopropylpiperidin-4-yl)pyrrolidin-1-yl)-5,6-dihydrobenzo[f]imidazo[1,2-d][1,4]oxazepine;

2-(3-(5-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)piperidin-1-yl)-2-methylpropan-1-ol;

2-(1-(2-methoxypropyl)-1H-1,2,4-triazol-5-yl)-9-(1-(1-methylpiperidin-4-yl)-1H-pyrazol-5-yl)-5,6-dihydrobenzo[f]imidazo[1,2-d][1,4]oxazepine; and 2-(1-isopropyl-3-methyl-1H-1,2,4-triazol-5-yl)-9-(5-(1-isopropylpiperidin-3-yl)-1-methyl-1H-pyrazol-4-yl)-5,6-dihydrobenzo[f]imidazo[1,2-d][1,4]oxazepine.

2. A compound selected from

9-[2-(1-tert-butyl-4-piperidyl)pyrazol-3-yl]-2-(2-isopropyl-5-methyl-1,2,4-triazol-3-yl)-5,6-dihydroimidazo[1,2-d][1,4]benzoxazepine;

10-(1-tert-butylpiperidin-4-ylsulfinyl)-2-(1-isopropyl-1H-1,2,4-triazol-5-yl)-5,6-dihydrobenzo[f]imidazo[1,2-d][1,4]oxazepine;

2-(2-isopropyl-5-methyl-1,2,4-triazol-3-yl)-9-(3-methylazetidin-3-yl)oxy-5,6-dihydroimidazo[1,2-d][1,4]benzoxazepine;

1-[4-[1-[2-(2-isopropyl-5-methyl-1,2,4-triazol-3-yl)-5,6-dihydroimidazo[1,2-d][1,4]benzoxazepin-9-yl]pyrrolidin-2-yl]-1-piperidyl]-2-methyl-propan-2-ol;

(4-tert-butylpiperazin-1-yl)-[9-fluoro-2-(2-isopropyl-5-methyl-1,2,4-triazol-3-yl)-5,6-dihydroimidazo[1,2-d][1,4]benzoxazepin-10-yl]methanone;

2-(2-isopropyl-5-methyl-1,2,4-triazol-3-yl)-9-(1-isopropyl-3-phenyl-azetidin-3-yl)oxy-5,6-dihydroimidazo[1,2-d][1,4]benzoxazepine;

[2-(2-isopropyl-5-methyl-1,2,4-triazol-3-yl)-5,6-dihydroimidazo[1,2-d][1,4]benzoxazepin-10-yl]-(1-methyl-4-piperidyl)methanol;

9-[5-[(4-tert-butylpiperazin-1-yl)methyl]-1-isopropyl-pyrazol-4-yl]-2-(2-isopropyl-5-methyl-1,2,4-triazol-3-yl)-5,6-dihydroimidazo[1,2-d][1,4]benzoxazepine;

9-[1-isopropyl-5-[(4-methylpiperazin-1-yl)methyl]pyrazol-4-yl]-2-(2-isopropyl-5-methyl-1,2,4-triazol-3-yl)-5,6-dihydroimidazo[1,2-d][1,4]benzoxazepine;

2-(2-isopropyl-5-methyl-1,2,4-triazol-3-yl)-9-[5-(1-isopropyl-3-piperidyl)-1-methyl-pyrazol-4-yl]-5,6-dihydroimidazo[1,2-d][1,4]benzoxazepine;

2-(2-isopropyl-5-methyl-1,2,4-triazol-3-yl)-9-[3-(1-isopropyl-3-piperidyl)-1-methyl-pyrazol-4-yl]-5,6-dihydroimidazo[1,2-d][1,4]benzoxazepine;

[9-fluoro-2-(2-isopropyl-5-methyl-1,2,4-triazol-3-yl)-5,6-dihydroimidazo[1,2-d][1,4]benzoxazepin-10-yl]-[4-(2-hydroxy-1,1-dimethyl-ethyl)piperazin-1-yl]methanone;

2-(2-isopropyl-5-methyl-1,2,4-triazol-3-yl)-9-[2-(1,2,6-trimethyl-4-piperidyl)pyrazol-3-yl]-5,6-dihydroimidazo[1,2-d][1,4]benzoxazepine;

9-[3-(cyclopropylmethyl)-1-isopropyl-azetidin-3-yl]oxy-2-(2-isopropyl-5-methyl-1,2,4-triazol-3-yl)-5,6-dihydroimidazo[1,2-d][1,4]benzoxazepine;

9-[3-(cyclopropylmethyl)azetidin-3-yl]oxy-2-(2-isopropyl-5-methyl-1,2,4-triazol-3-yl)-5,6-dihydroimidazo[1,2-d][1,4]benzoxazepine;

2-(2-isopropyl-5-methyl-1,2,4-triazol-3-yl)-9-[2-[1-(3-methyloxetan-3-yl)-3-piperidyl]pyrazol-3-yl]-5,6-dihydroimidazo[1,2-d][1,4]benzoxazepine;

2-(2-isopropyl-5-methyl-1,2,4-triazol-3-yl)-9-[2-(1-methyl-4-piperidyl)azetidin-1-yl]-5,6-dihydroimidazo[1,2-d][1,4]benzoxazepine;

(R)-2-(3-(5-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)piperidin-1-yl)-2-methylpropan-1-ol;

(S)-2-(3-(5-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)piperidin-1-yl)-2-methylpropan-1-ol;

1-[2-[4-[2-(2-isopropyl-5-methyl-1,2,4-triazol-3-yl)-5,6-dihydroimidazo[1,2-d][1,4]benzoxazepin-9-yl]-2-methyl-pyrazol-3-yl]-1-piperidyl]-2-methyl-propan-2-ol;

[1-isopropyl-5-[9-[2-(1-methyl-4-piperidyl)pyrazol-3-yl]-5,6-dihydroimidazo[1,2-d][1,4]benzoxazepin-2-yl]-1,2,4-triazol-3-yl]methanol;

(R)-2-(1-isopropyl-3-methyl-1H-1,2,4-triazol-5-yl)-9-(5-(1-isopropylpiperidin-3-yl)-1-methyl-1H-pyrazol-4-yl)-5,6-dihydrobenzo[f]imidazo[1,2-d][1,4]oxazepine;

(S)-2-(1-isopropyl-3-methyl-1H-1,2,4-triazol-5-yl)-9-(5-(1-isopropylpiperidin-3-yl)-1-methyl-1H-pyrazol-4-yl)-5,6-dihydrobenzo[f]imidazo[1,2-d][1,4]oxazepine;

2-(2-isopropyl-5-methyl-1,2,4-triazol-3-yl)-9-[2-(1-isopropyl-4-piperidyl)azetidin-1-yl]-5,6-dihydroimidazo[1,2-d][1,4]benzoxazepine;

(R)-10-(1-(4-tert-butylpiperazin-1-yl)ethyl)-9-fluoro-2-(1-isopropyl-3-methyl-1H-1,2,4-triazol-5-yl)-5,6-dihydrobenzo[f]imidazo[1,2-d][1,4]oxazepine;

2-[4-[2-(2-isopropyl-5-methyl-1,2,4-triazol-3-yl)-5,6-dihydroimidazo[1,2-d][,4]benzoxazepin-9-yl]-2-methyl-pyrazol-3-yl]-N,N-dimethyl-tetrahydropyran-4-amine;

2-(2-isopropyl-5-methyl-1,2,4-triazol-3-yl)-9-[2-(1-isopropyl-4-piperidyl)pyrazol-3-yl]-5,6-dihydroimidazo[1,2-d][1,4]benzoxazepine;

(S)-10-(1-(4-tert-butylpiperazin-1-yl)ethyl)-9-fluoro-2-(1-isopropyl-3-methyl-1H-1,2,4-triazol-5-yl)-5,6-dihydrobenzo[f]imidazo[1,2-d][1,4]oxazepine;

1-isopropyl-5-[9-[2-(1-methyl-4-piperidyl)pyrazol-3-yl]-5,6-dihydroimidazo[1,2-d][1,4]benzoxazepin-2-yl]-1,2,4-triazol-3-amine;

(R)-10-(1-(4-tert-butylpiperazin-1-yl)ethyl)-2-(1-isopropyl-3-methyl-1H-1,2,4-triazol-5-yl)-9-methyl-5,6-dihydrobenzo[f]imidazo[1,2-d][1,4]oxazepine;

(S)-10-(1-(4-tert-butylpiperazin-1-yl)ethyl)-2-(1-isopropyl-3-methyl-1H-1,2,4-triazol-5-yl)-9-methyl-5,6-dihydrobenzo[f]imidazo[1,2-d][1,4]oxazepine;

9-(3-isobutyl-1-isopropyl-azetidin-3-yl)oxy-2-(2-isopropyl-5-methyl-1,2,4-triazol-3-yl)-5,6-dihydroimidazo[1,2-d][1,4]benzoxazepine;

(S)-10-(1-(4-tert-butylpiperazin-1-yl)ethyl)-2-(1-isopropyl-3-methyl-1H-1,2,4-triazol-5-yl)-5,6-dihydroimidazo[1,2-d]pyrido[4,3-f][1,4]oxazepine;

9-[2-(1-ethyl-4-piperidyl)pyrrolidin-1-yl]-2-(2-isopropyl-5-methyl-1,2,4-triazol-3-yl)-5,6-dihydroimidazo[1,2-d][1,4]benzoxazepine;

(R)-10-(1-(4-tert-butylpiperazin-1-yl)ethyl)-2-(1-isopropyl-3-methyl-1H-1,2,4-triazol-5-yl)-5,6-dihydroimidazo[1,2-d]pyrido[4,3-f][1,4]oxazepine;

2-(2-isopropyl-5-methyl-1,2,4-triazol-3-yl)-9-[2-(1-methylsulfonyl-4-piperidyl)pyrrolidin-1-yl]-5,6-dihydroimidazo[1,2-d][1,4]benzoxazepine;

2-(2-isopropyl-5-methyl-1,2,4-triazol-3-yl)-9-[2-(1-methyl-4-piperidyl)azetidin-1-yl]-5,6-dihydroimidazo[1,2-d][1,4]benzoxazepine;

2-[3-[4-[2-(2-isopropyl-5-methyl-1,2,4-triazol-3-yl)-5,6-dihydroimidazo[1,2-d][1,4]benzoxazepin-9-yl]-2-methyl-pyrazol-3-yl]-1-piperidyl]-2-methyl-propan-1-ol;

2-(2-isopropyl-5-methyl-1,2,4-triazol-3-yl)-9-[2-(1-methyl-3-piperidyl)pyrrolidin-1-yl]-5,6-dihydroimidazo[1,2-d][1,4]benzoxazepine;

2-[4-[2-(2-isopropyl-5-methyl-1,2,4-triazol-3-yl)-5,6-dihydroimidazo[1,2-d][,4]benzoxazepin-9-yl]-2-methyl-pyrazol-3-yl]-N,N-dimethyl-tetrahydropyran-4-amine;

2-(2-isopropyl-5-methyl-1,2,4-triazol-3-yl)-9-(7-methyl-1,7-diazaspiro[4.5]decan-1-yl)-5,6-dihydroimidazo[1,2-d][1,4]benzoxazepine;

(R)-9-fluoro-2-(1-isopropyl-3-methyl-1H-1,2,4-triazol-5-yl)-10-(1-(1-isopropylpiperidin-3-yl)-1H-pyrazol-5-yl)-5,6-dihydrobenzo[f]imidazo[1,2-d][1,4]oxazepine;

(S)-9-fluoro-2-(1-isopropyl-3-methyl-1H-1,2,4-triazol-5-yl)-10-(1-(1-isopropylpiperidin-3-yl)-1H-pyrazol-5-yl)-5,6-dihydrobenzo[f]imidazo[1,2-d][1,4]oxazepine;

2-(2-isopropyl-5-methyl-1,2,4-triazol-3-yl)-9-[3-(1-isopropyl-3-piperidyl)-2-methyl-imidazol-4-yl]-5,6-dihydroimidazo[1,2-d][1,4]benzoxazepine;

2-(2-isopropyl-5-methyl-1,2,4-triazol-3-yl)-9-[2-(1-methyl-2-piperidyl)pyrrolidin-1-yl]-5,6-dihydroimidazo[1,2-d][1,4]benzoxazepine;

(S)-2-(1-isopropyl-3-methyl-1H-1,2,4-triazol-5-yl)-9-(2-(pyrrolidin-1-ylmethyl)pyrrolidin-1-yl)-5,6-dihydrobenzo[f]imidazo[1,2-d][1,4]oxazepine;

(R)-2-(1-isopropyl-3-methyl-1H-1,2,4-triazol-5-yl)-9-(2-(pyrrolidin-1-ylmethyl)pyrrolidin-1-yl)-5,6-dihydrobenzo[f]imidazo[1,2-d][1,4]oxazepine;

5-[9-[2-(1-tert-butyl-4-piperidyl)pyrazol-3-yl]-5,6-dihydroimidazo[1,2-d][1,4]benzoxazepin-2-yl]-1-isopropyl-1,2,4-triazol-3-amine;

10-[1-(4-tert-butylpiperazin-1-yl)ethyl]-9-fluoro-2-(2-isopropyl-5-methyl-1,2,4-triazol-3-yl)-5,6-dihydroimidazo[1,2-d][1,4]benzoxazepine;

2-[4-[2-(2-isopropyl-5-methyl-1,2,4-triazol-3-yl)-5,6-dihydroimidazo[1,2-d][,4]benzoxazepin-9-yl]-2-methyl-pyrazol-3-yl]-N,N-dimethyl-tetrahydropyran-4-amine;

(R)-2-(1-isopropyl-3-methyl-1H-1,2,4-triazol-5-yl)-10-(1-(4-isopropylpiperazin-1-yl)ethyl)-9-methyl-5,6-dihydrobenzo[f]imidazo[1,2-d][1,4]oxazepine;

(S)-2-(1-isopropyl-3-methyl-1H-1,2,4-triazol-5-yl)-10-(1-(4-isopropylpiperazin-1-yl)ethyl)-9-methyl-5,6-dihydrobenzo[f]imidazo[1,2-d][1,4]oxazepine;

N,N-diethyl-2-[4-[2-(2-isopropyl-5-methyl-1,2,4-triazol-3-yl)-5,6-dihydroimidazo[1,2-d][1,4]benzoxazepin-9-yl]-2-methyl-pyrazol-3-yl]tetrahydropyran-4-amine;

(R)-1-(4-(1-(9-fluoro-2-(1-isopropyl-3-methyl-1H-1,2,4-triazol-5-yl)-5,6-dihydrobenzo[f]imidazo[1,2-d][1,4]oxazepin-10-yl)ethyl)piperazin-1-yl)-2-methylpropan-2-ol;

N-isopropyl-2-[4-[2-(2-isopropyl-5-methyl-1,2,4-triazol-3-yl)-5,6-dihydroimidazo[1,2-d][1,4]benzoxazepin-9-yl]-2-methyl-pyrazol-3-yl]-N-methyl-tetrahydropyran-4-amine;

(S)-1-(4-(1-(9-fluoro-2-(1-isopropyl-3-methyl-1H-1,2,4-triazol-5-yl)-5,6-dihydrobenzo[f]imidazo[1,2-d][1,4]oxazepin-10-yl)ethyl)piperazin-1-yl)-2-methylpropan-2-ol;

9-(7-isopropyl-1,7-diazaspiro[4.5]decan-1-yl)-2-(2-isopropyl-5-methyl-1,2,4-triazol-3-yl)-5,6-dihydroimidazo[1,2-d][1,4]benzoxazepine;

(R)-9-fluoro-2-(1-isopropyl-3-methyl-1H-1,2,4-triazol-5-yl)-10-(1-(4-isopropylpiperazin-1-yl)ethyl)-5,6-dihydrobenzo[f]imidazo[1,2-d][1,4]oxazepine;

(S)-9-fluoro-2-(1-isopropyl-3-methyl-1H-1,2,4-triazol-5-yl)-10-(1-(4-isopropylpiperazin-1-yl)ethyl)-5,6-dihydrobenzo[f]imidazo[1,2-d][1,4]oxazepine;

2-(1-isopropyl-3-methyl-1H-1,2,4-triazol-5-yl)-9-(2-((R)-1-isopropylpiperidin-3-yl)azetidin-1-yl)-5,6-dihydrobenzo[f]imidazo[1,2-d][1,4]oxazepine;

N-isopropyl-2-[4-[2-(2-isopropyl-5-methyl-1,2,4-triazol-3-yl)-5,6-dihydroimidazo[1,2-d][1,4]benzoxazepin-9-yl]-2-methyl-pyrazol-3-yl]-N-methyl-tetrahydropyran-4-amine;

2-(2-isopropyl-5-methyl-1,2,4-triazol-3-yl)-9-methyl-10-[1-[4-(oxetan-3-yl)piperazin-1-yl]ethyl]-5,6-dihydroimidazo[1,2-d][1,4]benzoxazepine;

1-[1-[2-(2-isopropyl-5-methyl-1,2,4-triazol-3-yl)-5,6-dihydroimidazo[1,2-d][1,4]benzoxazepin-9-yl]pyrrolidin-2-yl]-N,N-dimethyl-methanamine;

(R)-2-(4-(1-(9-fluoro-2-(1-isopropyl-3-methyl-1H-1,2,4-triazol-5-yl)-5,6-dihydrobenzo[f]imidazo[1,2-d][1,4]oxazepin-10-yl)ethyl)piperazin-1-yl)-2-methylpropan-1-ol;

1-[4-[1-[2-(2-isopropyl-5-methyl-1,2,4-triazol-3-yl)-9-methyl-5,6-dihydroimidazo[1,2-d][1,4]benzoxazepin-10-yl]ethyl]piperazin-1-yl]-2-methyl-propan-2-ol;

(S)-2-(4-(1-(9-fluoro-2-(1-isopropyl-3-methyl-1H-1,2,4-triazol-5-yl)-5,6-dihydrobenzo[f]imidazo[1,2-d][1,4]oxazepin-10-yl)ethyl)piperazin-1-yl)-2-methylpropan-1-ol;

(R)-9-fluoro-2-(1-isopropyl-3-methyl-1H-1,2,4-triazol-5-yl)-10-(1-(1-(oxetan-3-yl)piperidin-3-yl)-1H-pyrazol-5-yl)-5,6-dihydrobenzo[f]imidazo[12-d][1,4]oxazepine;

(S)-9-fluoro-2-(1-isopropyl-3-methyl-1H-1,2,4-triazol-5-yl)-10-(1-(1-(oxetan-3-yl)piperidin-3-yl)-1H-pyrazol-5-yl)-5,6-dihydrobenzo[f]imidazo[12-d][1,4]oxazepine;

(R)-2-(3-(5-(9-fluoro-2-(1-isopropyl-3-methyl-1H-1,2,4-triazol-5-yl)-5,6-dihydrobenzo[f]imidazo[1,2-d][1,4]oxazepin-10-yl)-1H-pyrazol-1-yl)piperidin-1-yl)-2-methylpropan-1-ol;

2-[4-[9-fluoro-2-(2-isopropyl-5-methyl-1,2,4-triazol-3-yl]-5,6-dihydroimidazo[1,2-d][1,4]benzoxazepin-10-yl]-2-methyl-pyrazol-3-yl]-N,N-dimethyl-tetrahydropyran-4-amine;

(R)-10-(1-(4-tert-butylpiperazin-1-yl)ethyl)-2-(1-isopropyl-3-methyl-1H-1,2,4-triazol-5-yl)-9-methoxy-5,6-dihydrobenzo[f]imidazo[1,2-d][1,4]oxazepine;

(S)-10-(1-(4-tert-butylpiperazin-1-yl)ethyl)-2-(1-isopropyl-3-methyl-1H-1,2,4-triazol-5-yl)-9-methoxy-5,6-dihydrobenzo[f]imidazo[1,2-d][1,4]oxazepine;

9-fluoro-2-(2-isopropyl-5-methyl-1,2,4-triazol-3-yl)-10-[5-(1-isopropyl-3-piperidyl)-1-methyl-pyrazol-4-yl]-5,6-dihydroimidazo[1,2-d][1,4]benzoxazepine 2-(2-isopropyl-5-methyl-1,2,4-triazol-3-yl)-9-[5-(1-isopropyl-3-piperidyl)-1H-pyrazol-4-yl]-5,6-dihydroimidazo[1,2-d][1,4]benzoxazepine;

2-[4-[2-(2-isopropyl-5-methyl-1,2,4-triazol-3-yl)-5,6-dihydroimidazo[1,2-d][,4]benzoxazepin-9-yl]-2-methyl-pyrazol-3-yl]-N,N-dimethyl-tetrahydropyran-4-amine;

(S)-2-(4-(1-(2-(1-isopropyl-3-methyl-1H-1,2,4-triazol-5-yl)-5,6-dihydroimidazo[1,2-d]pyrido[4,3-f][1,4]oxazepin-10-yl)ethyl)piperazin-1-yl)-2-methylpropan-1-ol;

(R)-2-(4-(1-(2-(1-isopropyl-3-methyl-1H-1,2,4-triazol-5-yl)-5,6-dihydroimidazo[1,2-d]pyrido[4,3-f][1,4]oxazepin-10-yl)ethyl)piperazin-1-yl)-2-methylpropan-1-ol 9-[5-(4-isopropyl-1-methyl-piperazin-2-yl]-1-methyl-pyrazol-4-yl]-2-(2-isopropyl-5-methyl-1,2,4-triazol-3-yl)-5,6-dihydroimidazo[1,2-d][1,4]benzoxazepine;

9-[5-[(3R)-3-isopropyl-4-methyl-piperazin-1-yl]-1-methyl-pyrazol-4-yl]-2-(2-isopropyl-5-methyl-1,2,4-triazol-3-yl)-5,6-dihydroimidazo[1,2-d][1,4]benzoxazepine;

10-[(1R)-1-(4-tert-butylpiperazin-1-yl)ethyl]-2-(2-isopropyl-5-methyl-1,2,4-triazol-3-yl)-9-methoxy-5,6-dihydroimidazo[1,2-d][1,4]benzoxazepine;

2-(2-isopropyl-5-methyl-1,2,4-triazol-3-yl)-9-[2-(1-isopropyl-3-piperidyl)imidazol-1-yl]-5,6-dihydroimidazo[1,2-d][1,4]benzoxazepine;

2-(1-isopropyl-3-methyl-1H-1,2,4-triazol-5-yl)-9-(5-(1-isopropylpiperidin-3-yl)-1-methyl-1H-pyrazol-4-yl)-5,6-dihydroimidazo[1,2-d]pyrido[3,4-f][1,4]oxazepine;

10-[(1S)-1-(4-tert-butylpiperazin-1-yl)ethyl]-2-(2-isopropyl-5-methyl-1,2,4-triazol-3-yl)-9-methoxy-5,6-dihydroimidazo[1,2-d][1,4]benzoxazepine;

2-(2-isopropyl-5-methyl-1,2,4-triazol-3-yl)-9-[5-(4-isopropylmorpholin-2-yl)-1-methyl-pyrazol-4-yl]-5,6-dihydroimidazo[1,2-d][1,4]benzoxazepine;

9-fluoro-2-(2-isopropyl-5-methyl-1,2,4-triazol-3-yl)-10-[1-(4-methylpiperazin-1-yl)ethyl]-5,6-dihydroimidazo[1,2-d][1,4]benzoxazepine; and 10-[1-(4-ethylpiperazin-1-yl)ethyl]-9-fluoro-2-(2-isopropyl-5-methyl-1,2,4-triazol-3-yl)-5,6-dihydroimidazo[1,2-d][1,4]benzoxazepine.

3. A pharmaceutical composition comprised of a compound of claim 1 or 2 and a pharmaceutically acceptable carrier, glidant, diluent, or excipient.

4. A process for making a pharmaceutical composition which comprises combining a compound of claim 1 or 2 with a pharmaceutically acceptable carrier.

5. A method of treating an immune disorder comprising administering a therapeutically effective amount of a compound of claim 1 or 2 to a patient with an immune disorder selected from systemic and local inflammation, arthritis, inflammation related to immune suppression, organ transplant rejection, allergies, ulcerative colitis, Crohn's disease, dermatitis, asthma, systemic lupus erythematosus, Sjogren's Syndrome, multiple sclerosis, scleroderma/systemic sclerosis, idiopathic thrombocytopenic purpura (ITP), anti-neutrophil cytoplasmic antibodies (ANCA) vasculitis, chronic obstructive pulmonary disease (COPD), and psoriasis.

6. The method of claim 5 wherein the immune disorder is rheumatoid arthritis.

\* \* \* \* \*